US011166951B2

(12) United States Patent
Hamdy et al.

(10) Patent No.: US 11,166,951 B2
(45) Date of Patent: Nov. 9, 2021

(54) THERAPEUTIC COMBINATIONS OF A BTK INHIBITOR, A PI3K INHIBITOR, A JAK-2 INHIBITOR, AND/OR A BCL-2 INHIBITOR

(71) Applicant: Acerta Pharma B.V., Oss (NL)

(72) Inventors: Ahmed Hamdy, Santa Cruz, CA (US); Wayne Rothbaum, Delray Beach, FL (US); Raquel Izumi, San Carlos, CA (US); Brian Lannutti, Solana Beach, CA (US); Todd Covey, San Carlos, CA (US); Roger Ulrich, Sammamish, WA (US); Dave Johnson, Aptos, CA (US); Tjeerd Barf, Ravenstein (NL); Allard Kaptein, Zaltbommel (NL)

(73) Assignee: Acerta Pharma B.V., Oss (NL)

( * ) Notice: Subject to any disclaimer, the term of this patent is extended or adjusted under 35 U.S.C. 154(b) by 0 days.

(21) Appl. No.: 15/982,525

(22) Filed: May 17, 2018

(65) Prior Publication Data
US 2018/0250298 A1 Sep. 6, 2018

Related U.S. Application Data

(63) Continuation of application No. 15/503,217, filed as application No. PCT/IB2015/056126 on Aug. 11, 2015, now abandoned.

(60) Provisional application No. 62/035,795, filed on Aug. 11, 2014, provisional application No. 62/088,240, filed on Dec. 5, 2014, provisional application No. 62/115,497, filed on Feb. 12, 2015, provisional application No. 62/181,160, filed on Jun. 17, 2015.

(51) Int. Cl.
| A61K 31/4985 | (2006.01) |
| A61K 31/519 | (2006.01) |
| A61K 31/4468 | (2006.01) |
| A61K 45/06 | (2006.01) |
| A61K 31/675 | (2006.01) |
| A61K 31/437 | (2006.01) |
| A61P 35/00 | (2006.01) |
| A61K 31/454 | (2006.01) |
| A61K 31/52 | (2006.01) |
| A61K 31/635 | (2006.01) |

(52) U.S. Cl.
CPC ........ *A61K 31/4985* (2013.01); *A61K 31/437* (2013.01); *A61K 31/4468* (2013.01); *A61K 31/454* (2013.01); *A61K 31/519* (2013.01); *A61K 31/52* (2013.01); *A61K 31/675* (2013.01); *A61K 45/06* (2013.01); *A61P 35/00* (2018.01)

(58) Field of Classification Search
CPC .............. A61K 31/437; A61K 31/4468; A61K 31/519; A61K 31/675; A61K 31/454; A61K 31/4985; A61K 31/52; A61K 31/635; A61K 39/3955; A61K 45/06; A61P 35/00; A61P 35/02
See application file for complete search history.

(56) References Cited

U.S. PATENT DOCUMENTS

| 7,459,554 | B2 | 12/2008 | Dong et al. | |
| 7,825,118 | B2 | 11/2010 | Honigberg et al. | |
| 7,960,396 | B2 | 6/2011 | Honigberg et al. | |
| 8,377,946 | B1 | 2/2013 | Chen et al. | |
| 8,546,399 | B2 * | 10/2013 | Bruncko | C07D 471/04 514/252.18 |
| 8,658,794 | B2 | 2/2014 | deMan et al. | |
| 9,290,504 | B2 * | 3/2016 | Barf | C07D 519/00 |
| 9,717,745 | B2 * | 8/2017 | He | A61K 31/52 |
| 9,718,828 | B2 | 8/2017 | De Man et al. | |
| 9,758,524 | B2 | 9/2017 | Barf et al. | |
| 9,790,226 | B2 | 10/2017 | Bart et al. | |
| 9,796,721 | B2 * | 10/2017 | Blatter | C07D 487/04 |
| 9,949,971 | B2 * | 4/2018 | Hamdy | A61K 45/06 |
| 10,239,883 | B2 | 3/2019 | Barf et al. | |
| 10,328,080 | B2 * | 6/2019 | Hamdy | A61K 45/06 |
| 2006/0084654 | A1 | 4/2006 | Beck et al. | |
| 2008/0076921 | A1 | 3/2008 | Honigberg et al. | |
| 2008/0227788 | A9 | 9/2008 | Beck et al. | |
| 2011/0257203 | A1 | 10/2011 | Honigberg et al. | |
| 2012/0053189 | A1 | 3/2012 | Loury | |
| 2012/0095026 | A1 | 4/2012 | Honigberg et al. | |

(Continued)

FOREIGN PATENT DOCUMENTS

| EP | 2548877 | 1/2013 |
| WO | 2000017203 A1 | 3/2000 |

(Continued)

OTHER PUBLICATIONS

Souers et al., "ABT-199, a potent and selective BCL-2 inhibitor, achieves antitumor activity while sparing platelets", 2013, Nature Medicine, 19(2), pp. 202-208. (Year: 2013).*

(Continued)

*Primary Examiner* — My-Chau T. Tran
(74) *Attorney, Agent, or Firm* — Morgan, Lewis & Bockius LLP

(57) ABSTRACT

Therapeutic combinations of a phosphoinositide 3-kinase (PI3K) inhibitor, including PI3K inhibitors selective for the γ- and δ-isoforms and selective for both γ- and δ-isoforms (PI3K-γ,δ, PI3K-γ, and PI3K-δ), a Janus kinase-2 (JAK-2) inhibitor, a Bruton's tyrosine kinase (BTK) inhibitor, and/or a B-cell lymphoma-2 (BCL-2) inhibitor are described. In some embodiments, the invention provides therapeutic combinations of a PI3K-δ inhibitor and a BTK inhibitor, a JAK-2 and a BTK inhibitor, and a BCL-2 and BTK inhibitor.

18 Claims, 157 Drawing Sheets

Specification includes a Sequence Listing.

(56) References Cited

U.S. PATENT DOCUMENTS

| | | | |
|---|---|---|---|
| 2012/0129821 A1 | 5/2012 | Honigberg et al. | |
| 2012/0135944 A1 | 5/2012 | Honigberg et al. | |
| 2012/0165328 A1 | 6/2012 | Honigberg et al. | |
| 2013/0018032 A1 | 1/2013 | Chen et al. | |
| 2013/0079327 A1 | 3/2013 | Yamamoto et al. | |
| 2014/0073593 A1 | 3/2014 | Conklin et al. | |
| 2014/0206681 A1 | 7/2014 | Kim et al. | |
| 2014/0212425 A1 | 7/2014 | Chang et al. | |
| 2014/0377258 A1* | 12/2014 | Stern | A61K 31/519 424/133.1 |
| 2016/0287592 A1* | 10/2016 | Chang | A61K 31/704 |
| 2017/0136014 A1 | 5/2017 | Hamdy et al. | |
| 2017/0224819 A1 | 8/2017 | Hamdy et al. | |
| 2017/0231995 A1* | 8/2017 | Hamdy | A61K 31/4439 514/249 |
| 2017/0239351 A1* | 8/2017 | Hamdy | A61K 39/39558 |
| 2017/0266191 A1 | 9/2017 | Hamdy et al. | |
| 2018/0250400 A1* | 9/2018 | Hamdy | A61K 45/06 |
| 2019/0201409 A1* | 7/2019 | Gold | A61K 31/496 |
| 2019/0209591 A1* | 7/2019 | Lannutti | A61K 31/69 |
| 2019/0376971 A1* | 12/2019 | Barf | C07D 495/04 |

FOREIGN PATENT DOCUMENTS

| | | |
|---|---|---|
| WO | 2001019828 | 3/2001 |
| WO | 2007064993 | 6/2001 |
| WO | 2002080926 | 10/2002 |
| WO | 2003065995 | 8/2003 |
| WO | 2005014599 A1 | 2/2005 |
| WO | 2005037836 | 4/2005 |
| WO | 2005097800 | 10/2005 |
| WO | 2007061737 | 5/2007 |
| WO | 2007064883 | 6/2007 |
| WO | 2007106503 | 9/2007 |
| WO | 2008121742 | 10/2008 |
| WO | 2009076170 | 6/2009 |
| WO | 2010126960 | 11/2010 |
| WO | 2011095556 | 8/2011 |
| WO | 2011119663 | 9/2011 |
| WO | 2011152351 | 12/2011 |
| WO | 2011153514 | 12/2011 |
| WO | 2012158843 | 11/2012 |
| WO | 2013003629 | 1/2013 |
| WO | 2013010380 | 1/2013 |
| WO | 2013010868 | 1/2013 |
| WO | 2013010869 | 1/2013 |
| WO | 2013059738 | 4/2013 |
| WO | 2014143807 | 9/2014 |
| WO | 2014159745 | 10/2014 |
| WO | 2014168975 | 10/2014 |
| WO | 2015018522 | 2/2015 |
| WO | 2015061752 | 4/2015 |
| WO | 2016022853 A1 | 2/2016 |
| WO | 2016024232 A1 | 2/2016 |

OTHER PUBLICATIONS

Greene & Wuts, Protective Groups in Organic Synthesis, 2d edition (1991).
Higuchi et al. (eds.), Pro-drugs as Novel Delivery Systems, 14 A.C.S. Symposium Series (1975).
Roch (ed.), Bioreversible Carriers in Drug Design, Pergamon Press (1987).
Translation of Office Action dated Mar. 20, 2020 for Chinese Patent Application No. 201680050713.6, 8 pages.
Translation of Search Report dated Dec. 31, 2019 for Russian Patent Application No. 2018103913, 2 pages.
Office Action dated Nov. 27, 2019 for Chilean Patent Application No. 201703445, 6 pages.
Communication dated Apr. 29, 2019 for European Patent Application 16735945, 5 pages.
Communication Pursuant to Rules 161(1) and 162 from the European Patent Office dated Feb. 14, 2018.
Examination Report dated Nov. 25, 2019 for Australian Patent Application No. 2016286548, 4 pages.
Guidance for Industry, ANDAs: Pharmaceutical Solid Polymorphism, Chemistry, Manufacturing, and Controls 34 Information; U.S. Department of Health and Human Services, Food and Drug Administration, Center for Drug Evaluation and Research (GOER); Jul. 2007, 13 pages.
Examination Report dated Oct. 30, 2019 for Singapore Patent Application No. 11201710679U, 4 pages.
Communication dated Apr. 3, 2020 for European Patent Application No. 15757002, 4 pages.
Communication dated Mar. 26, 2018 for European Patent Application No. 15757002, 7 pages.
Communication dated Mar. 21, 2019 for European Patent Application No. 15757002, 4 pages.
Berge et al. "Pharmaceutical salts" 66(1) J. Pharm. Sci. 1-19 (1977).
Bingham et al., "Over one hundred solvates of sulfathlazole" Chem. Commun. 603-04 (2001).
Caira et al., "Preparation and Crystal Characterization of a Polymorph, a Monohydrate, and an Ethyl Acetate Solvate of the Antifungal Fluconazole," 93(3) J. Pharma. Sci. 601-11 (2004).
Davis et al., "Chronic active B-cell-receptor signaling in diffuse large B-cell lymphoma," 463 Nature 88-92 (2010).
Dhar et al., "Synthesis and SAR of p38a MAP kinase inhibitors based on heterobicyclic scaffolds," 17 Bioorg. & Med. Chem. Lett. 5019-24 (2007).
Gaudet et al., "A Homogeneous Fluorescence Polarization Assay Adaptable for a Range of Protein Serine/Threonine and Tyrosine Kinases," 8(2) J. Biomol. Screening 164-75 (2003).
Gilfillan et al., "The tyrosine kinase network regulating mast cell activation," 288 Immun. Rev. 149-69 (2009).
Gould "Salt selection for basic drugs" 33 Int'l J. Pharmaceutics 201-217 (1986).
Harder et al., "Gain- and Loss-of-Function Lyn Mutant Mice Define a Critical Inhibitory Role for Lyn in the Myeloid Lineage" 15 immunity 603-15 (2001).
Hartz et al., "Synthesis and Evaluation of imidazo[1,5-a]pyrazines as Corticotrophin Releasing Hormone Receptor Ligands," 12 Bioorg. & Med Chem. Lett 291-94 (2002).
Ji et al., "A novel, potent, and selective insulin-like growth factor-I receptor kinase inhibitor blocks insulin-like growth factor-I receptor signaling in vitro and inhibits insulin-like growth factor-Ireceptor-dependent tumor growth in vivo," 6(8) Mol. Cancer Ther. 2158-67 (2007).
King et al., "Nucleofugality effects in the pyridine promoted formation of esters from 2-substituted ethanesulfonyl chlorides," 66 Can. J. Chem. 1109-16 (1988).
Klinghoffer et al., "Src family kinases are required for integrin but not PDGFR signal transduction," 18(9) EMBO J. 2459-71 (1999).
Lim et al., "Anti-CD20 monoclonal antibodies: historical and future perspectives," 95(1) Haematologica 135-43 (2010).
Lowell et al., "Deficiency of the Hck and Src Tyrosine Kinases Results in Extreme Levels of Extramedullary Hematopoiesis," 87(5) Blood 1780-92 (1996).
Mitchell et al., "Synthesis of C-nucleoside isosteres of 9-(2-hydroxyethoxymethyl)guanine (acyclovir)," 21 (3) J. Heterocyclic Chem. 697-99 (1984).
Mukaiyama et al., "Synthesis and c-Src inhibitory activity of imidazo[1,5-a]pyrazine derivatives as an agent for treatment of acute ischemic stroke," 15 Bioorg. & Med. Chem. 868-85 (2007).
Mulvihill et al., "1,3-Disubstituted-imidazo[1,5-a]pyrazines as insulin-like growth-factor-I receptor (IGF-IR) inhibitors", 17 Bioorg. & Med. Chem. Lett. 1091-97 (2007).
Mulvihill et al., "Novel 2-phenylquinolin-7-yl-derived imidazo[1,5-a]pyrazines as potent insulin-growth factor-I receptor (IGF-IR) inhibitors", 16 Bioorg. & Med. Chem. 1359-75 (2008).
Odom et al., "Negative Regulation of immunoglobulin E-dependent Allergic Responses by Lyn Kinase," 199(11) J. Exp. Med. 1491-1502 (2004).
Pan et al., "Discovery of Selective Irreversible Inhibitors for Burton's Tyrosine Kinase," 2 ChemMedChem 58-61 (2007).
Roby et al., "Alterations in Reproductive Function in Src Tyrosine Kinase Knockout Mice", 26 Endocrine 169-76 (2005).

(56) References Cited

OTHER PUBLICATIONS

Shinohara et al., "Tyrosine Kinases Btk and Tec Regulate Osteoclast Differentiation by Linking RANK and ITAM Signals" 132 Cell 794-806 (2008).
Van Tonder et al., "Preparation and Physicochemical Characterization of 5 Niclosamide Solvates and 1 Hemisolvate", 5(1) AAPS PharmSciTech Article 12 (2004).
Written Opinion dated Aug. 10, 2016 relating to PCT/IB2016/053988.
International Search Report dated Aug. 10, 2016 relating to PCT/IB2016/053988.
Chen et al., "Rapamycin Enhances the Anti-Cancer Effect of Dasatinib by Suppressing Src/PI3K/mTOR Pathway in NSCLC Cells", PLoS ONE, vol. 10, No. 6, 20 pages (2015).
Chiron et al., "Cell Cycle Reprogramming for PI3K Inhibition Overrides Relapse-Specific C481S BTK Mutation Revealed by Longitudinal Functional Genomics in Mantle Cell Lymphoma", Cancer Discov., vol. 4, No. 9, pp. 1022-1035 (2014).
D'Cruz et al., "Novel Burton's tyrosine kinase inhibitors currently in development", OncoTargets and Therapy, vol. 6, pp. 161-176 (2013).
Girotti et al., "No longer an untreatable disease: How targeted and immunotherapies have changed the management of melanoma patients", Molecular Oncology, vol. 8, pp. 1140-1158 (2014).
Griner et al., "High-throughput combinatorial screening identifies drugs that cooperate with ibrutinib to kill activated B-cell-like diffuse large B-cell lymphoma cells", PNAS, vol. 111, No. 6, pp. 2349-2354 (2014).
Grisafi et al., "Ibrutinib: from bench side to clinical implications", Med Oncol, vol. 32, 225 (10 pages) (2015).
Hantschel, "Targeting BCR-ABL and JAK2 in Ph+ ALL", Blood, vol. 125, No. 9, pp. 1362-1363 (2015).
Klyuchnikov et al., "Allogeneic hematopoietic cell transplantion for diffuse large B cell lymphoma: who, when and how?", Bone Marrow Transplantation, vol. 49, pp. 1-7 (2014).
Liu et al., Design and synthesis of carbazole carboxamides as promising inhibitors of Bruton's tyrosine kinase (BTK) and Janus kinase 2 (JAK2), Bioorganic & Medicinal Chemistry Letters, vol. 25, pp. 4265-4269 (2015).

Park et al., "Dasatinib synergizes with both cytotoxic and signal transduction inhibitors in heterogeneous breast cancer cell lines—lessons for design of combination targeted therapy", Cancer Lett., vol. 320, pp. 104-110 (2012).
Philips et al., "Therapeutic uses of anti-PD-1 and anti-PD-L1 antibodies", International Immunology, vol. 27, No. 1, pp. 39-46 (2014).
Sagiv-Barfi et al., "Therapeutic antitumor immunity by checkpoint blockade is enhanced by ibrutinib, an inhibitor of both BTK and ITK", PNAS, pp. E966-E972 (2015).
Schwamb et al., "B-cell receptor triggers drug sensitivity of primary CLL cells by controlling glucosylation of ceramides", Blood, vol. 120, No. 19, pp. 3978-3985 (2012).
Songdej et al., "GIST Treatment Options after Tyrosine Kinase Inhibitors", Current Treatment Options in Oncology, vol. 15, pp. 496-506 (2014).
Stephens et al., "Changing the Treatment Paradigm for Previously Treated Chronic Lymphocytic Leukemia Patients with Del(17p) Karyotype", Blood, vol. 122, No. 21, p. 2872 (2013).
Van Den Akker et al., "The Btk inhibitor LFM-A13 is a potent inhibitor of Jak2 kinase activity", Biol. Chem., vol. 385, pp. 409-413 (2004).
Yori et al., "Abstract LB-221: Inhibition of rapamycin-induced feedback activation of AKT with dasatinib induces complete tumor regression in a preclinical model of breast cancer" Cancer Research, vol. 73, No. 8, Suppl. 1, p. LB-221 (2013).
Zhang et al., Effect of PI3K Inhibitor CAL-101 on myeloma cell lines and preliminary study of synergistic effects with other new drugs, Zhonghua Xue Ye XUE Za Zhi=Zhonghua Xueyexue Zazhi, vol. 35, No. 10, pp. 926-930 (2014) Abstract Only.
Written Opinion for PCT/IB2015/056126 dated Feb. 18, 2016.
International Search Report for PCT/IB2015/056126 dated Oct. 19, 2015.
Wu et al., "Acalabrutinib (ACP-196): a selective second generation BTK inhibitor", 2016, Journal of Hematology & Oncology, 9:21, pp. 1-4. (Year: 2016).
National Center for Biotechnology Information. PubChem Compound Database; CID=49846579, https://pubchem.ncbi.nlm.nih.gov/compound/49846579 (accessed Jan. 8, 2018). (Year: 2018).
National Center for Biotechnology Information. PubChem Compound Database; CID=71226662, https://pubchem.ncbi.nlm.nih.gov/compound/71226662 (accessed Jan. 10, 2018). (Year: 2018).
Sennaro ed., Remington: The Science and Practice of Pharmac , 20th edition 2000.

* cited by examiner x Inh.1+Inh.4
− Inh.1
o Inh.4

FIG. 106

SEQUENCE LISTING

```
<160> NUMBER OF SEQ ID NOS: 14

<210> SEQ ID NO 1
<211> LENGTH: 451
<212> TYPE: PRT
<213> ORGANISM: Artificial Sequence
<220> FEATURE:
<223> OTHER INFORMATION: Heavy chain amino acid sequence of the anti-
      CD20 monoclonal antibody rituximab.

<400> SEQUENCE: 1
```

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Light chain amino acid sequence of the anti-
      CD20 monoclonal antibody rituximab.

<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
            85                  90                  95

Phe Gly Gly Gly Thr Lys Leu Glu Ile Lys Arg Thr Val Ala Ala Pro
        100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 3
<211> LENGTH: 449
<212> TYPE: PRT
<213> ORGANISM: Artificial Sequence
<220> FEATURE:
<223> OTHER INFORMATION: Heavy chain amino acid sequence of the anti-
      CD20 monoclonal antibody obinutuzumab.

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser

```
                        245                 250                 255
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 4
<211> LENGTH: 219
<212> TYPE: PRT
<213> ORGANISM: Artificial Sequence
<220> FEATURE:
<223> OTHER INFORMATION: Light chain amino acid sequence of the anti-
      CD20 monoclonal antibody obinutuzumab.

<400> SEQUENCE: 4

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
```

```
                145                 150                 155                 160
Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                    180                 185                 190

Lys His Lys Val Tyr Ala Cys Glu Val Thr His Gln Gly Leu Ser Ser
                    195                 200                 205

Pro Val Thr Lys Ser Phe Asn Arg Gly Glu Cys
                    210                 215

<210> SEQ ID NO 5
<211> LENGTH: 122
<212> TYPE: PRT
<213> ORGANISM: Artificial Sequence
<220> FEATURE:
<223> OTHER INFORMATION: Variable heavy chain amino acid sequence of the
      anti-CD20 monoclonal antibody ofatumumab.

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
        50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 6
<211> LENGTH: 107
<212> TYPE: PRT
<213> ORGANISM: Artificial Sequence
<220> FEATURE:
<223> OTHER INFORMATION: Variable light chain amino acid sequence of the
      anti-CD20 monoclonal antibody ofatumumab.

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
```

100                 105

<210> SEQ ID NO 7
<211> LENGTH: 222
<212> TYPE: PRT
<213> ORGANISM: Artificial Sequence
<220> FEATURE:
<223> OTHER INFORMATION: Fab fragment of heavy chain amino acid sequence
      of the anti-CD20 monoclonal antibody ofatumumab.

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Gly Ser Ser Lys Ser Thr Ser Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro
    210                 215                 220

<210> SEQ ID NO 8
<211> LENGTH: 211
<212> TYPE: PRT
<213> ORGANISM: Artificial Sequence
<220> FEATURE:
<223> OTHER INFORMATION: Fab fragment of light chain amino acid sequence
      of the anti-CD20 monoclonal antibody ofatumumab.

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro

```
                    65                  70                  75                  80
        Glu Asp Phe Ala Val Tyr Tyr Cys Gln Gln Arg Ser Asn Trp Pro Ile
                            85                  90                  95

Thr Phe Gly Gln Gly Thr Arg Leu Glu Ile Lys Arg Thr Val Ala Ala
                        100                 105                 110

Pro Ser Val Phe Ile Phe Pro Pro Ser Asp Glu Gln Leu Lys Ser Gly
                    115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                195                 200                 205

Phe Asn Arg
            210

<210> SEQ ID NO 9
<211> LENGTH: 451
<212> TYPE: PRT
<213> ORGANISM: Artificial Sequence
<220> FEATURE:
<223> OTHER INFORMATION: Heavy chain amino acid sequence of the anti-
      CD20 monoclonal antibody veltuzumab.

<400> SEQUENCE: 9

Gln Val Gln Leu Gln Gln Ser Gly Ala Glu Val Lys Lys Pro Gly Ser
        1               5                   10                  15

Ser Val Lys Val Ser Cys Lys Ala Ser Gly Tyr Thr Phe Thr Ser Tyr
                    20                  25                  30

Asn Met His Trp Val Lys Gln Ala Pro Gly Gln Gly Leu Glu Trp Ile
                35                  40                  45

Gly Ala Ile Tyr Pro Gly Met Gly Asp Thr Ser Tyr Asn Gln Lys Phe
            50                  55                  60

Lys Gly Lys Ala Thr Leu Thr Ala Asp Glu Ser Thr Asn Thr Ala Tyr
        65                  70                  75                  80

Met Glu Leu Ser Ser Leu Arg Ser Glu Asp Thr Ala Phe Tyr Tyr Cys
                        85                  90                  95

Ala Arg Ser Thr Tyr Tyr Gly Gly Asp Trp Tyr Phe Asp Val Trp Gly
                    100                 105                 110

Gln Gly Thr Thr Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
        145                 150                 155                 160

Ser Trp Asn Ser Gly Ala Leu Thr Ser Gly Val His Thr Phe Pro Ala
                        165                 170                 175

Val Leu Gln Ser Ser Gly Leu Tyr Ser Leu Ser Ser Val Val Thr Val
                    180                 185                 190

Pro Ser Ser Ser Leu Gly Thr Gln Thr Tyr Ile Cys Asn Val Asn His
                195                 200                 205
```

```
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 10
<211> LENGTH: 213
<212> TYPE: PRT
<213> ORGANISM: Artificial Sequence
<220> FEATURE:
<223> OTHER INFORMATION: Light chain amino acid sequence of the anti-
      CD20 monoclonal antibody veltuzumab.

<400> SEQUENCE: 10

Asp Ile Gln Leu Thr Gln Ser Pro Ser Ser Leu Ser Ala Ser Val Gly
1               5                   10                  15
Asp Arg Val Thr Met Thr Cys Arg Ala Ser Ser Val Ser Tyr Ile
            20                  25                  30
His Trp Phe Gln Gln Lys Pro Gly Lys Ala Pro Lys Pro Trp Ile Tyr
        35                  40                  45
Ala Thr Ser Asn Leu Ala Ser Gly Val Pro Val Arg Phe Ser Gly Ser
    50                  55                  60
Gly Ser Gly Thr Asp Tyr Thr Phe Thr Ile Ser Ser Leu Gln Pro Glu
65                  70                  75                  80
Asp Ile Ala Thr Tyr Tyr Cys Gln Gln Trp Thr Ser Asn Pro Pro Thr
                85                  90                  95
Phe Gly Gly Gly Thr Lys Leu Glu Ile Lys Arg Thr Val Ala Ala Pro
            100                 105                 110
```

```
Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 11
<211> LENGTH: 447
<212> TYPE: PRT
<213> ORGANISM: Artificial Sequence
<220> FEATURE:
<223> OTHER INFORMATION: Heavy chain amino acid sequence of the anti-
      CD20 monoclonal antibody tositumomab.

<400> SEQUENCE: 11

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
                        245                 250                 255
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 12
<211> LENGTH: 210
<212> TYPE: PRT
<213> ORGANISM: Artificial Sequence
<220> FEATURE:
<223> OTHER INFORMATION: Light chain amino acid sequence of the anti-
      CD20 monoclonal antibody tositumomab.

<400> SEQUENCE: 12

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg
    210

<210> SEQ ID NO 13
<211> LENGTH: 443
<212> TYPE: PRT
<213> ORGANISM: Artificial Sequence
<220> FEATURE:
<223> OTHER INFORMATION: Heavy chain amino acid sequence of the anti-
      CD20 monoclonal antibody ibritumomab.

<400> SEQUENCE: 13

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300
```

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
            325                 330                 335

Ser Lys Pro Lys Gly Ser Val Arg Ala Pro Gln Val Tyr Val Leu Pro
            340                 345                 350

Pro Pro Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg
        435                 440

<210> SEQ ID NO 14
<211> LENGTH: 209
<212> TYPE: PRT
<213> ORGANISM: Artificial Sequence
<220> FEATURE:
<223> OTHER INFORMATION: Light chain amino acid sequence of the anti-
      CD20 monoclonal antibody ibritumomab.

<400> SEQUENCE: 14

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Ala Asp Ala Ala Pro
            100                 105                 110

Thr Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

```
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
            195                 200                 205
Asn
```

THERAPEUTIC COMBINATIONS OF A BTK INHIBITOR, A PI3K INHIBITOR, A JAK-2 INHIBITOR, AND/OR A BCL-2 INHIBITOR

CROSS-REFERENCE TO RELATED APPLICATIONS

This application claims the benefit of U.S. Provisional Application No. 62/035,795 filed on Aug. 11, 2014; U.S. Provisional Application No. 62/088,240 filed on Dec. 5, 2014; U.S. Provisional Application No. 62/115,497 filed on Feb. 12, 2015; and U.S. Provisional Application No. 62/181,160 filed on Jun. 17, 2015, all of which are herein incorporated by reference in their entireties.

FIELD OF THE INVENTION

Therapeutic combinations of a Bruton's tyrosine kinase (BTK) inhibitor, a B-cell lymphoma-2 (BCL-2) inhibitor, a phosphoinositide 3-kinase (PI3K) inhibitor, and/or a Janus kinase-2 (JAK-2) inhibitor, and uses of the therapeutic combinations, are disclosed herein. In particular, a combination of a BCL-2 inhibitor and a BTK inhibitor and uses thereof are disclosed.

BACKGROUND OF THE INVENTION

PI3K kinases are members of a unique and conserved family of intracellular lipid kinases that phosphorylate the 3'-OH group on phosphatidylinositols or phosphoinositides. PI3K kinases are key signaling enzymes that relay signals from cell surface receptors to downstream effectors. The PI3K family comprises 15 kinases with distinct substrate specificities, expression patterns, and modes of regulation. The class I PI3K kinases (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases.

The PI3K signaling pathway is known to be one of the most highly mutated in human cancers. PI3K signaling is also a key factor in disease states including hematologic malignancies, non-Hodgkin lymphoma (such as diffuse large B-cell lymphoma), allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome. The role of PI3K in cancer has been discussed, for example, in Engleman, Nat. Rev. Cancer 2009, 9, 550-562. The PI3K-δ and PI3K-γ isoforms are preferentially expressed in normal and malignant leukocytes.

The delta (δ) isoform of class I PI3K (PI3K-δ) is involved in mammalian immune system functions such as T-cell function, B-cell activation, mast cell activation, dendritic cell function, and neutrophil activity. Due to its role in immune system function, PI3K-δ is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. The gamma (γ) isoform of class I PI3K (PI3K-γ) is also involved in immune system functions and plays a role in leukocyte signaling and has been implicated in inflammation, rheumatoid arthritis, and autoimmune diseases such as lupus.

Downstream mediators of the PI3K signal transduction pathway include Akt and mammalian target of rapamycin (mTOR). One important function of Akt is to augment the activity of mTOR, through phosphorylation of TSC2 and other mechanisms. mTOR is a serine-threonine kinase related to the lipid kinases of the PI3K family and has been implicated in a wide range of biological processes including cell growth, cell proliferation, cell motility and survival. Disregulation of the mTOR pathway has been reported in various types of cancer.

In view of the above, PI3K inhibitors are prime targets for drug development, as described in Kurt and Ray-Coquard, Anticancer Res. 2012, 32, 2463-70. Several PI3K inhibitors are known, including those that are PI3K-δ inhibitors, PI3K-γ inhibitors, and PI3K-δ,γ inhibitors.

Bruton's Tyrosine Kinase (BTK) is a Tec family non-receptor protein kinase expressed in B cells and myeloid cells. The function of BTK in signaling pathways activated by the engagement of the B cell receptor (BCR) and FCER1 on mast cells is well established. Functional mutations in BTK in humans result in a primary immunodeficiency disease characterized by a defect in B cell development with a block between pro- and pre-B cell stages. The result is an almost complete absence of B lymphocytes, causing a pronounced reduction of serum immunoglobulin of all classes. These findings support a key role for BTK in the regulation of the production of auto-antibodies in autoimmune diseases.

Other diseases with an important role for dysfunctional B cells are B cell malignancies. The reported role for BTK in the regulation of proliferation and apoptosis of B cells indicates the potential for BTK inhibitors in the treatment of B cell lymphomas. BTK inhibitors have thus been developed as potential therapies, as described in D'Cruz and Uckun, OncoTargets and Therapy 2013, 6, 161-176.

JAK-2 is an enzyme that is a member of the Janus kinase family of four cytoplasmic tyrosine kinases that also includes JAK-1, JAK-3, and Tyk2 (tyrosine kinase 2). The Janus kinase family transduces cytokine-mediated signals as part of the JAK-STAT signalling pathway (where STAT is an acronym for "signal transducer and activator of transcription"), as described in K. Ghoreschi, A. Laurence, J. J. O'Shea, Janus kinases in immune cell signaling. Immunol. Rev. 2009, 228, 273-287. The JAK-STAT pathway is commonly expressed in leukocytes. The Janus kinase family of enzymes is required for signaling by cytokine and growth factor receptors that lack intrinsic kinase activity. JAK-2 is implicated in signaling processes by members of the type II cytokine receptor family (such as interferon receptors), the GM-CSF receptor family (IL-3R, IL-5R and GM-CSF-R), the gp130 receptor family (e.g. IL-6R), and the single chain receptors (e.g. Epo-R, Tpo-R, GH-R, PRL-R), as described in U.S. Patent Application Publication No. 2012/0157500, the disclosure of which is incorporated herein by reference. JAK-2 signaling is activated downstream from the prolactin receptor. JAK-2 inhibitors were developed after discovery of an activating tyrosine kinase mutation (the V617F mutation) in myeloproliferative cancers. JAK-2 inhibitors have been developed as potential therapies for myeloproliferative neoplasms, polycythemia vera, essential thrombocythemia, and primary myelofibrosis, as discussed in S. Verstovsek, Therapeutic potential of JAK2 inhibitors, Hematology (American Society of Hematology Education Book), 2009, 636-642.

B-cell lymphoma-2 (BCL-2) is the prototype of a family of mammalian genes and the proteins they produce, which govern mitochondrial outer membrane permeabilisation, and which can be either anti-apoptotic (e.g., BCL-2 proper, BCL-xL, and BCL-w) or pro-apoptotic (e.g., BAX, BAD, BAK and BOK).

The BCL-2 family has a general structure consisting of a hydrophobic helix surrounded by amphipathic helices. BCL-2 is a pro-survival protein that can share up to four highly conserved domains known as BH1, BH2, BH3 and BH4. These domains form the basis for protein-protein interaction sites between members of the BCL-2 family of proteins. The BH domains are known to be crucial for function, since deletion of these domains affects apoptosis rates. In anti-apoptotic BCL-2 proteins, all four BH domains are conserved.

The site of action for the BCL-2 family is mostly on the outer mitochondrial membrane. Within the mitochondria are pro-apoptotic factors (e.g., cytochrome C) that if released, activate caspases which are key proteins in the apoptotic cascade. Depending on their function, once activated, BCL-2 proteins either promote the release of these factors (directly via multidomain, pro-apoptotic BCL-2 proteins), or keep them sequestered (by the binding of anti-apoptotic BCL-2 proteins) in the mitochondria.

The BCL-2 gene may be linked to a number of cancers, including melanoma, breast, prostate, and lung cancer. Research has shown that the overexpression of BCL-2 family proteins can be associated with tumor progression, poor prognosis and resistance to chemotherapy (Stauffer, Curr. Top. Med. Chem. 2007, 7, 961-965). Development of therapies to inhibit BCL-2 proteins may prove to be beneficial in cancer and other proliferative disorders.

Targeted BCL-2 therapies, specifically, antagonism of the protein-protein interactions of BCL-2 family proteins (including BCL-2 and BCL-xL) are considered extremely important points for drug intervention in cancer. Small molecule BCL-2 inhibitors are increasingly being developed as new anticancer agents capable of overcoming apoptosis resistance. Furthermore, efforts are also being directed to developing new and more efficacious combinations of anticancer drugs which include BCL-2 inhibitors.

In many solid tumors, the supportive microenvironment (which may make up the majority of the tumor mass) is a dynamic force that enables tumor survival. The tumor microenvironment is generally defined as a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz et al., Cancer Res., 2012, 72, 2473. Although tumors express antigens that should be recognized by T cells, tumor clearance by the immune system is rare because of immune suppression by the microenvironment. Addressing the tumor cells themselves with e.g. chemotherapy has also proven to be insufficient to overcome the protective effects of the microenvironment. New approaches are thus urgently needed for more effective treatment of solid tumors that take into account the role of the microenvironment.

The present invention includes the unexpected discovery that combinations of a PI3K inhibitor, a JAK-2 inhibitor, a BTK inhibitor, and/or a BCL-2 inhibitor are effective in the treatment of any of several types of cancers such as leukemia, lymphoma and solid tumor cancers. The present invention further provides the unexpected discovery that a combination of a BCL-2 inhibitor and a BTK inhibitor is effective in the treatment of any of several types of cancers such as leukemia, lymphoma and solid tumor cancers. The present invention also provides the unexpected discovery that a combination of a PI3K inhibitor and a BTK inhibitor is effective in the treatment of any of several types of cancers such as leukemia, lymphoma and solid tumor cancers. The present invention also provides the unexpected discovery that a combination of a JAK-2 inhibitor and a BTK inhibitor is effective in the treatment of any of several types of cancers such as leukemia, lymphoma and solid tumor cancers. The present invention further provides the unexpected discovery that a combination of a JAK-2 inhibitor, a PI3K inhibitor, a BTK inhibitor, and/or a BCL-2 inhibitor is effective in the treatment of any of several types of cancers such as leukemia, lymphoma and solid tumor cancers. Embodiments of the invention are also useful in the discovery and/or development of pharmaceutical products for the treatment of any of several types of cancers such as leukemia, lymphoma and solid tumor cancers.

SUMMARY OF THE INVENTION

In an embodiment, the invention provides combinations of a Bruton's tyrosine kinase (BTK) inhibitor, a B-cell lymphoma-2 (BCL-2) inhibitor, a phosphoinositide 3-kinase (PI3K) inhibitor, and/or a Janus kinase-2 (JAK-2) inhibitor.

In an embodiment, the invention provides a combination comprising two or more ingredients selected from a BTK inhibitor, a BCL-2 inhibitor, PI3K inhibitor, and a JAK-2 inhibitor. The combination is typically a pharmaceutical combination. The ingredients are typically pharmaceutically acceptable. The ingredient may be a BTK inhibitor, a BCL-2 inhibitor, a PI3K inhibitor, or JAK-2 inhibitor or a pharmaceutically acceptable salt, solvate, hydrate, cocrystal, or prodrug thereof. Examples of a BTK inhibitor, a BCL-2 inhibitor, a PI3K inhibitor, or JAK-2 inhibitor or a pharmaceutically acceptable salt, solvate, hydrate, cocrystal, or prodrug thereof are described herein.

In an embodiment, the invention provides a combination comprising (1) a BTK inhibitor or a pharmaceutically acceptable salt, solvate, hydrate, cocrystal, or prodrug thereof and (2) an ingredient selected from a BCL-2 inhibitor, a PI3K inhibitor, and a JAK-2 inhibitor or a pharmaceutically acceptable salt, solvate, hydrate, cocrystal, or prodrug thereof. The combination is typically a pharmaceutical combination.

In an embodiment, the invention provides a combination comprising (1) a BCL-2 inhibitor or a pharmaceutically acceptable salt, solvate, hydrate, cocrystal, or prodrug thereof and (2) an ingredient selected from a BTK inhibitor, a PI3K inhibitor, and a JAK-2 inhibitor or a pharmaceutically acceptable salt, solvate, hydrate, cocrystal, or prodrug thereof. The combination is typically a pharmaceutical combination.

In an embodiment, the invention provides a combination comprising (1) a BCL-2 inhibitor or a pharmaceutically acceptable salt, solvate, hydrate, cocrystal, or prodrug thereof; and (2) a BTK inhibitor or a pharmaceutically acceptable salt, solvate, hydrate, cocrystal, or prodrug thereof. This combination is typically a pharmaceutical combination.

In an embodiment, the invention provides a combination comprising (1) a BCL-2 inhibitor or a pharmaceutically acceptable salt, solvate, bination hydrate, cocrystal, or prodrug thereof; (2) a BTK inhibitor or a pharmaceutically acceptable salt, solvate, hydrate, cocrystal, or prodrug thereof; and (3) a phosphoinositide 3-kinase (PI3K) inhibitor or a pharmaceutically acceptable salt, solvate, hydrate, cocrystal, or prodrug thereof. This combination is typically a pharmaceutical combination.

In an embodiment, the invention provides a combination comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a PI3K-δ inhibitor or a pharmaceutically acceptable salt, solvate, hydrate, cocrystal, or prodrug thereof. This combination is typically a pharmaceutical combination.

In an embodiment, the invention provides a combination comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) an anti-coagulant or antiplatelet active pharmaceutical ingredient. This combination is typically a pharmaceutical combination.

In an embodiment, the invention provides a combination comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a phosphoinositide 3-kinase (PI3K) inhibitor or a pharmaceutically acceptable salt, solvate, hydrate, cocrystal, or prodrug thereof and (4) an anti-coagulant or antiplatelet active pharmaceutical ingredient. This combination is typically a pharmaceutical combination.

In an embodiment, the invention provides a combination comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a PI3K-δ inhibitor or a pharmaceutically acceptable salt, solvate, hydrate, cocrystal, or prodrug thereof; and (4) an anti-coagulant or antiplatelet active pharmaceutical ingredient. This combination is typically a pharmaceutical combination.

In an embodiment, the invention provides a combination comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a JAK-2 inhibitor or a pharmaceutically acceptable salt, solvate, hydrate, cocrystal, or prodrug thereof. This combination is typically a pharmaceutical combination.

In an embodiment, the invention provides a combination comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a PI3K-δ inhibitor or a pharmaceutically acceptable salt, solvate, hydrate, cocrystal, or prodrug thereof; and (4) a JAK-2 inhibitor or a pharmaceutically acceptable salt, solvate, hydrate, cocrystal, or prodrug thereof. This combination is typically a pharmaceutical combination.

In an embodiment, the invention provides a combination comprising (1) a BTK inhibitor or a pharmaceutically acceptable salt, solvate, hydrate, cocrystal, or prodrug thereof; and (2) a PI3K inhibitor or a pharmaceutically acceptable salt, solvate, hydrate, cocrystal, or prodrug thereof. This combination is typically a pharmaceutical combination.

In an embodiment, the invention provides a combination comprising (1) a BTK inhibitor or a pharmaceutically acceptable salt, solvate, hydrate, cocrystal, or prodrug thereof; and (2) a JAK-2 inhibitor or a pharmaceutically acceptable salt, solvate, hydrate, cocrystal, or prodrug thereof. This combination is typically a pharmaceutical combination.

In an embodiment, the invention provides a composition comprising two or more ingredients selected from a Bruton's tyrosine kinase (BTK) inhibitor, a B-cell lymphoma-2 (BCL-2) inhibitor, a phosphoinositide 3-kinase (PI3K) inhibitor, and a Janus kinase-2 (JAK-2) inhibitor. The composition is typically a pharmaceutical composition. The ingredients are typically pharmaceutically acceptable. The ingredient may be a BTK inhibitor, a BCL-2 inhibitor, a PI3K inhibitor, or JAK-2 inhibitor or a pharmaceutically acceptable salt, solvate, hydrate, cocrystal, or prodrug thereof. Examples of a BTK inhibitor, a BCL-2 inhibitor, a PI3K inhibitor, or JAK-2 inhibitor or a pharmaceutically acceptable salt, solvate, hydrate, cocrystal, or prodrug thereof are described herein.

In an embodiment, the invention provides a composition comprising (1) a BTK inhibitor or a pharmaceutically acceptable salt, solvate, hydrate, cocrystal, or prodrug thereof and (2) an ingredient selected from a BCL-2 inhibitor, a PI3K inhibitor, and a JAK-2 inhibitor or a pharmaceutically acceptable salt, solvate, hydrate, cocrystal, or prodrug thereof. The composition is typically a pharmaceutical composition.

In an embodiment the invention provides a composition comprising (1) a BCL-2 inhibitor or a pharmaceutically acceptable salt, solvate, hydrate, cocrystal, or prodrug thereof and (2) an ingredient selected from a BTK inhibitor, a PI3K inhibitor, and a JAK-2 inhibitor or a pharmaceutically acceptable salt, solvate, hydrate, cocrystal, or prodrug thereof. The composition is typically a pharmaceutical composition.

In an embodiment, the invention provides a composition comprising (1) a BCL-2 inhibitor or a pharmaceutically acceptable salt, solvate, hydrate, cocrystal, or prodrug thereof; and (2) a BTK inhibitor or a pharmaceutically acceptable salt, solvate, hydrate, cocrystal, or prodrug thereof. This composition is typically a pharmaceutical composition.

In an embodiment, the invention provides a composition comprising (1) a BCL-2 inhibitor or a pharmaceutically acceptable salt, solvate, hydrate, cocrystal, or prodrug thereof (2) a BTK inhibitor or a pharmaceutically acceptable salt, solvate, hydrate, cocrystal, or prodrug thereof and (3) a phosphoinositide 3-kinase (PI3K) inhibitor or a pharmaceutically acceptable salt, solvate, hydrate, cocrystal, or prodrug thereof. This composition is typically a pharmaceutical composition.

In an embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a PI3K-δ inhibitor or a pharmaceutically acceptable salt, solvate, hydrate, cocrystal, or prodrug thereof. This composition is typically a pharmaceutical composition.

In an embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) an anti-coagulant or antiplatelet active pharmaceutical ingredient. This composition is typically a pharmaceutical composition.

In an embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a phosphoinositide 3-kinase (PI3K) inhibitor or a pharmaceutically acceptable salt, solvate, hydrate, cocrystal, or prodrug thereof and (4) an anti-coagulant or antiplatelet active pharmaceutical ingredient. This composition is typically a pharmaceutical composition.

In an embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a PI3K-δ inhibitor or a pharmaceutically acceptable salt, solvate, hydrate, cocrystal, or prodrug thereof; and (4) an anti-coagulant or antiplatelet active pharmaceutical ingredient. This composition is typically a pharmaceutical composition.

In an embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a JAK-2 inhibitor or a pharmaceutically acceptable salt, solvate, hydrate, cocrystal, or prodrug thereof. This composition is typically a pharmaceutical composition.

In an embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a PI3K-δ inhibitor or a pharmaceutically acceptable salt, solvate, hydrate, cocrystal, or prodrug thereof; and (4) a JAK-2 inhibitor or a pharmaceutically acceptable salt, solvate, hydrate, cocrystal, or prodrug thereof. This composition is typically a pharmaceutical composition.

In an embodiment, the invention provides a composition comprising (1) a BTK inhibitor or a pharmaceutically acceptable salt, solvate, hydrate, cocrystal, or prodrug thereof; and (2) a PI3K inhibitor or a pharmaceutically acceptable salt, solvate, hydrate, cocrystal, or prodrug thereof. This composition is typically a pharmaceutical composition.

In an embodiment, the invention provides a composition comprising (1) a BTK inhibitor or a pharmaceutically acceptable salt, solvate, hydrate, cocrystal, or prodrug thereof; and (2) a JAK-2 inhibitor or a pharmaceutically acceptable salt, solvate, hydrate, cocrystal, or prodrug thereof. This composition is typically a pharmaceutical composition.

The anti-coagulant or the anti-platelet active pharmaceutical ingredient in some specific embodiments is a compound selected from the group consisting of acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, and combinations thereof.

In an embodiment, the invention provides a kit comprising two or more compositions and optionally a package insert or label providing directions for administering the compositions simultaneously, separately or sequentially. Each composition comprises at least one of a BTK inhibitor, a BCL-2 inhibitor, a PI3K inhibitor or a JAK-2 inhibitor or a pharmaceutically acceptable salt, solvate, hydrate, cocrystal, or prodrug thereof wherein the two or more compositions together comprise two or more ingredients selected from a BTK inhibitor, a BCL-2 inhibitor, a PI3K inhibitor and a JAK-2 inhibitor or a pharmaceutically acceptable salt, solvate, hydrate, cocrystal, or prodrug thereof. Each composition is typically a pharmaceutical composition.

In an embodiment, the invention provides a kit comprising (1) a composition comprising a BCL-2 inhibitor or a pharmaceutically acceptable salt, solvate, hydrate, cocrystal, or prodrug thereof; and (2) a composition comprising a BTK inhibitor or a pharmaceutically acceptable salt, solvate, hydrate, cocrystal, or prodrug thereof. These compositions are typically pharmaceutical compositions. The kit is for co-administration of a BCL-2 inhibitor and a BTK inhibitor, either simultaneously or separately.

In an embodiment, the invention provides a kit comprising (1) a composition comprising a BCL-2 inhibitor or a pharmaceutically acceptable salt, solvate, hydrate, cocrystal, or prodrug thereof; (2) a composition comprising a BTK inhibitor or a pharmaceutically acceptable salt, solvate, hydrate, cocrystal, or prodrug thereof; and (3) a composition comprising a PI3K inhibitor or a pharmaceutically acceptable salt, solvate, hydrate, cocrystal, or prodrug thereof. These compositions are typically pharmaceutical compositions. The kit is for co-administration of a BCL-2 inhibitor, a BTK inhibitor, and a PI3K inhibitor, either simultaneously or separately.

In an embodiment, the invention provides a kit comprising (1) a composition comprising BCL-2 inhibitor or a pharmaceutically acceptable salt, solvate, hydrate, cocrystal, or prodrug thereof (2) a composition comprising a BTK inhibitor or a pharmaceutically acceptable salt, solvate, hydrate, cocrystal, or prodrug thereof; and (3) a composition comprising a PI3K-δ inhibitor or a pharmaceutically acceptable salt, solvate, hydrate, cocrystal, or prodrug thereof. These compositions are typically pharmaceutical compositions. The kit is for co-administration of a BCL-2 inhibitor, a BTK inhibitor, and an anti-coagulant or antiplatelet active pharmaceutical ingredient, either simultaneously or separately.

In an embodiment, the invention provides a kit comprising (1) a composition comprising a BCL-2 inhibitor or a pharmaceutically acceptable salt, solvate, hydrate, cocrystal, or prodrug thereof; (2) a composition comprising a BTK inhibitor or a pharmaceutically acceptable salt, solvate, hydrate, cocrystal, or prodrug thereof; and (3) an anti-coagulant or antiplatelet active pharmaceutical ingredient. These compositions are typically pharmaceutical compositions. The kit is for co-administration of a BCL-2 inhibitor, a BTK inhibitor, and an anti-coagulant or antiplatelet active pharmaceutical ingredient, either simultaneously or separately.

In an embodiment, the invention provides a kit comprising (1) a composition comprising a BCL-2 inhibitor or a pharmaceutically acceptable salt, solvate, hydrate, cocrystal, or prodrug thereof; (2) a composition comprising a BTK inhibitor or a pharmaceutically acceptable salt, solvate, hydrate, cocrystal, or prodrug thereof; and (3) a composition comprising a PI3K inhibitor or a pharmaceutically acceptable salt, solvate, hydrate, cocrystal, or prodrug thereof; and (4) an anti-coagulant or antiplatelet active pharmaceutical ingredient. These compositions are typically pharmaceutical compositions. The kit is for co-administration of a PI3K-δ inhibitor and an anti-coagulant or antiplatelet active pharmaceutical ingredient, either simultaneously or separately.

In an embodiment, the invention provides a kit comprising (1) a composition comprising a BCL-2 inhibitor or a pharmaceutically acceptable salt, solvate, hydrate, cocrystal, or prodrug thereof; (2) a composition comprising a BTK inhibitor or a pharmaceutically acceptable salt, solvate, hydrate, cocrystal, or prodrug thereof; and (3) a composition comprising a PI3K-δ inhibitor or a pharmaceutically acceptable salt, solvate, hydrate, cocrystal, or prodrug thereof; and (4) an anti-coagulant or antiplatelet active pharmaceutical ingredient. These compositions are typically pharmaceutical compositions. The kit is for co-administration of a BCL-2 inhibitor, a BTK inhibitor, a PI3K-δ inhibitor, and an anti-coagulant or antiplatelet active pharmaceutical ingredient, either simultaneously or separately.

In an embodiment, the invention provides a kit comprising (1) a composition comprising a BCL-2 inhibitor or a pharmaceutically acceptable salt, solvate, hydrate, cocrystal, or prodrug thereof; (2) a composition comprising a BTK inhibitor or a pharmaceutically acceptable salt, solvate, hydrate, cocrystal, or prodrug thereof; and (3) a composition comprising a JAK-2 inhibitor or a pharmaceutically acceptable salt, solvate, hydrate, cocrystal, or prodrug thereof. The compositions are typically pharmaceutical compositions.

In an embodiment, the invention provides a kit comprising (1) a composition comprising a BCL-2 inhibitor or a pharmaceutically acceptable salt, solvate, hydrate, cocrystal, or prodrug thereof; (2) a composition comprising a BTK inhibitor or a pharmaceutically acceptable salt, solvate, hydrate, cocrystal, or prodrug thereof; and (3) a composition comprising a PI3K-δ inhibitor or a pharmaceutically acceptable salt, solvate, hydrate, cocrystal, or prodrug thereof and (4) a composition comprising a JAK-2 inhibitor or a pharmaceutically acceptable salt, solvate, hydrate, cocrystal, or prodrug thereof. The compositions are typically pharmaceutical compositions.

In an embodiment, the invention provides a kit comprising (1) a composition comprising a BTK inhibitor or a pharmaceutically acceptable salt, solvate, hydrate, cocrystal, or prodrug thereof; and (2) a composition comprising a PI3K inhibitor or a pharmaceutically acceptable salt, solvate, hydrate, cocrystal, or prodrug thereof. The compositions are typically pharmaceutical compositions.

In an embodiment, the invention provides a kit comprising (1) a composition comprising a BTK inhibitor or a pharmaceutically acceptable salt, solvate, hydrate, cocrystal, or prodrug thereof; and (2) a composition comprising a JAK-2 inhibitor or a pharmaceutically acceptable salt, solvate, hydrate, cocrystal, or prodrug thereof. The compositions are typically pharmaceutical compositions.

In preferred embodiments, the combinations, the compositions and the kits disclosed herein are for use in treating cancer, for example leukemia, lymphoma and/or solid tumor cancer. In some specific embodiments, the combinations, the compositions and the kits disclosed herein are for use in treating cancer selected from the group consisting of a B cell hematological malignancy selected from the hematological malignancy is selected from the group consisting of chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, or myelofibrosis.

In some specific embodiments, the combinations, the compositions and the kits disclosed herein are for use in treating a cancer selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, glioma, esophageal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, primary central nervous system lymphoma, and Burkitt's lymphoma.

In other specific embodiments, the combinations, the compositions and the kits disclosed herein are for use in treating a solid tumor cancer selected from the group consisting of bladder cancer, non-small cell lung cancer, cervical cancer, anal cancer, pancreatic cancer, squamous cell carcinoma including head and neck cancer, renal cell carcinoma, melanoma, ovarian cancer, small cell lung cancer, glioblastoma, gastrointestinal stromal tumor, breast cancer, lung cancer, colorectal cancer, thyroid cancer, bone sarcoma, stomach cancer, oral cavity cancer, oropharyngeal cancer, gastric cancer, kidney cancer, liver cancer, prostate cancer, colorectal cancer, esophageal cancer, testicular cancer, gynecological cancer, thyroid cancer, colon cancer, and brain cancer.

In some preferred embodiments, the combinations, the compositions and the kits disclosed herein are for use in treating a solid tumor cancer, wherein the active ingredients are in a dosage that is effective in inhibiting signaling between the cells of the solid tumor cancer and at least one tumor microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts.

In some preferred embodiments, the combinations, the compositions and the kits disclosed herein are for use in treating a solid tumor cancer, wherein the active ingredients are in a dosage that is effective in increasing immune system recognition and rejection of the solid tumor by the human body receiving the treatment.

In some preferred embodiments, the combination, the compositions and the kits disclosed herein are for use in treating cancer, wherein the BCL-2 inhibitor is administered before administration of the BTK inhibitor.

In some preferred embodiments, the combinations, the compositions and the kits disclosed herein are for use in treating cancer, wherein the BCL-2 inhibitor is administered concurrently with the administration of the BTK inhibitor.

In some preferred embodiments, the combinations, the compositions and the kits disclosed herein are for use in treating cancer, wherein the BCL-2 inhibitor is administered to the subject after administration of the BTK inhibitor.

In some preferred embodiments, the combinations, the compositions and the kits disclosed herein are for use in discovery and/or development of pharmaceutical products for therapeutic treatment, such as treating cancer. The combinations, the compositions and/or the kits may be used as research tools in the discovery and/or development of pharmaceutical products for therapeutic treatment, for example for the treatment of hyperproliferative disease such as cancer.

In some preferred embodiments, the invention provides a method of treating cancer, for example leukemia, lymphoma and/or a solid tumor cancer in a subject, comprising administering to a mammal in need thereof a combination or composition of the invention.

In an embodiment, the invention provides a method of treating leukemia, lymphoma or a solid tumor cancer in a subject, comprising co-administering to a mammal in need thereof a therapeutically effective amount of a BCL-2 inhibitor and a BTK inhibitor.

In an embodiment, the invention provides a method of treating leukemia, lymphoma or a solid tumor cancer in a subject, comprising co-administering to a mammal in need thereof a therapeutically effective amount of a BCL-2 inhibitor, a JAK-2 inhibitor, and a BTK inhibitor.

In an embodiment, the invention provides a method of treating leukemia, lymphoma or a solid tumor cancer in a subject, comprising co-administering to a mammal in need thereof a therapeutically effective amount of a PI3K inhibitor, a BCL-2 inhibitor, and a BTK inhibitor.

In an embodiment, the invention provides a method of treating leukemia, lymphoma or a solid tumor cancer in a subject, comprising co-administering to a mammal in need thereof a therapeutically effective amount of a PI3K-γ inhibitor, a BCL-2 inhibitor, and a BTK inhibitor.

In an embodiment, the invention provides a method of treating leukemia, lymphoma or a solid tumor cancer in a subject, comprising co-administering to a mammal in need thereof a therapeutically effective amount of a PI3K-δ inhibitor, a BCL-2 inhibitor, and a BTK inhibitor.

In an embodiment, the invention provides a method of treating leukemia, lymphoma or a solid tumor cancer in a subject, comprising co-administering to a mammal in need thereof a therapeutically effective amount of a PI3K-γ,δ inhibitor, a BCL-2 inhibitor, and a BTK inhibitor.

In an embodiment, the invention provides a method of treating leukemia, lymphoma or a solid tumor cancer in a subject, comprising co-administering to a mammal in need thereof a therapeutically effective amount of a PI3K inhibitor, a JAK-2 inhibitor, a BCL-2 inhibitor, and a BTK inhibitor.

In an embodiment, the invention provides a method of treating leukemia, lymphoma or a solid tumor cancer in a subject, comprising co-administering to a mammal in need thereof a therapeutically effective amount of a PI3K-γ inhibitor, a JAK-2 inhibitor, a BCL-2 inhibitor, and a BTK inhibitor.

In an embodiment, the invention provides a method of treating leukemia, lymphoma or a solid tumor cancer in a subject, comprising co-administering to a mammal in need thereof a therapeutically effective amount of a PI3K-δ inhibitor, a JAK-2 inhibitor, a BCL-2 inhibitor, and a BTK inhibitor.

In an embodiment, the invention provides a method of treating leukemia, lymphoma or a solid tumor cancer in a subject, comprising co-administering to a mammal in need thereof a therapeutically effective amount of a PI3K-γ,δ inhibitor, a JAK-2 inhibitor, a BCL-2 inhibitor, and a BTK inhibitor.

In an embodiment, the invention provides a method of treating leukemia, lymphoma or a solid tumor cancer in a subject, comprising co-administering to a mammal in need thereof a therapeutically effective amount of a PI3K inhibitor and a BTK inhibitor.

In an embodiment, the invention provides a method of treating leukemia, lymphoma or a solid tumor cancer in a subject, comprising co-administering to a mammal in need thereof a therapeutically effective amount of a PI3K-γ inhibitor and a BTK inhibitor.

In an embodiment, the invention provides a method of treating leukemia, lymphoma or a solid tumor cancer in a subject, comprising co-administering to a mammal in need thereof a therapeutically effective amount of a PI3K-δ inhibitor and a BTK inhibitor.

In an embodiment, the invention provides a method of treating leukemia, lymphoma or a solid tumor cancer in a subject, comprising co-administering to a mammal in need thereof a therapeutically effective amount of a PI3K-γ,δ inhibitor and a BTK inhibitor.

In an embodiment, the invention provides a method of treating leukemia, lymphoma or a solid tumor cancer in a subject, comprising co-administering to a mammal in need thereof a therapeutically effective amount of a JAK-2 inhibitor and a BTK inhibitor.

BRIEF DESCRIPTION OF THE DRAWINGS

The foregoing summary, as well as the following detailed description of the invention, will be better understood when read in conjunction with the appended drawings.

(leukemia, myeloid, and/or chronic myelogenous leukemia). The dose-effect curves for these cell lines are given in FIG. 58, FIG. 59, and FIG. 60.

Figure 58:
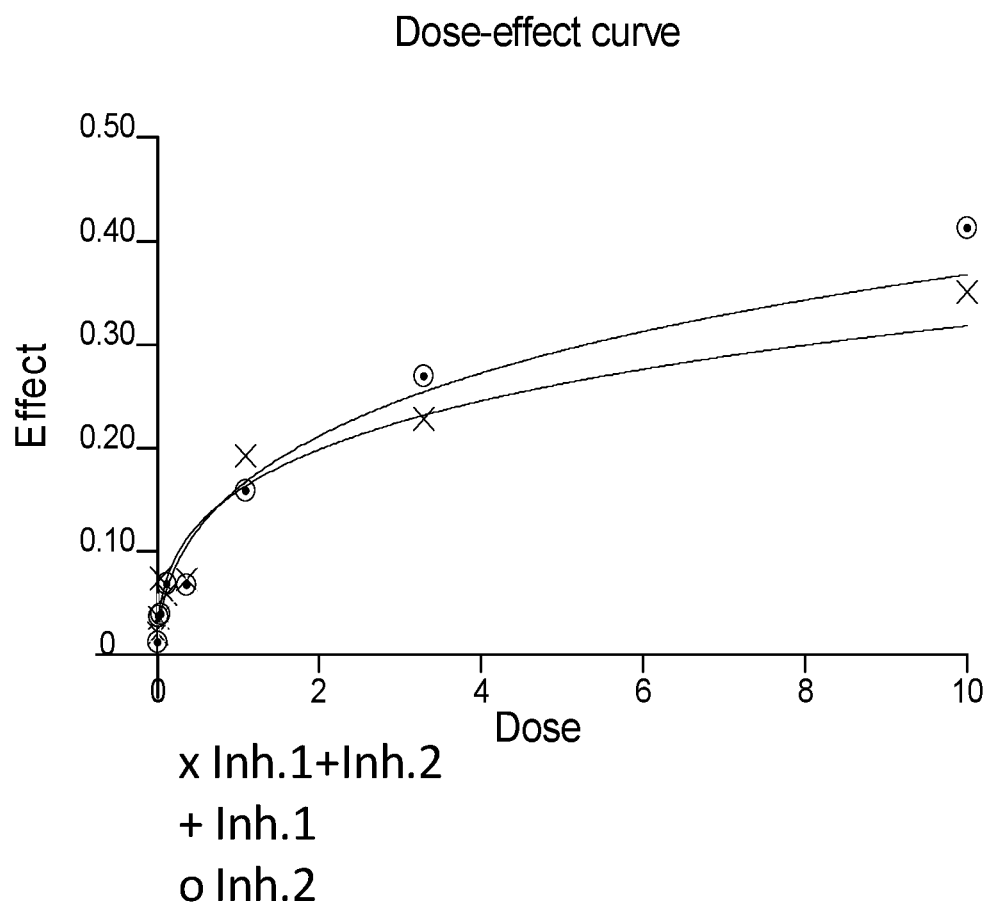

FIG. 58 illustrates the dose-effect curves obtained for the tested U937 cell line (histiocytic lymphoma) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.

Figure 59:
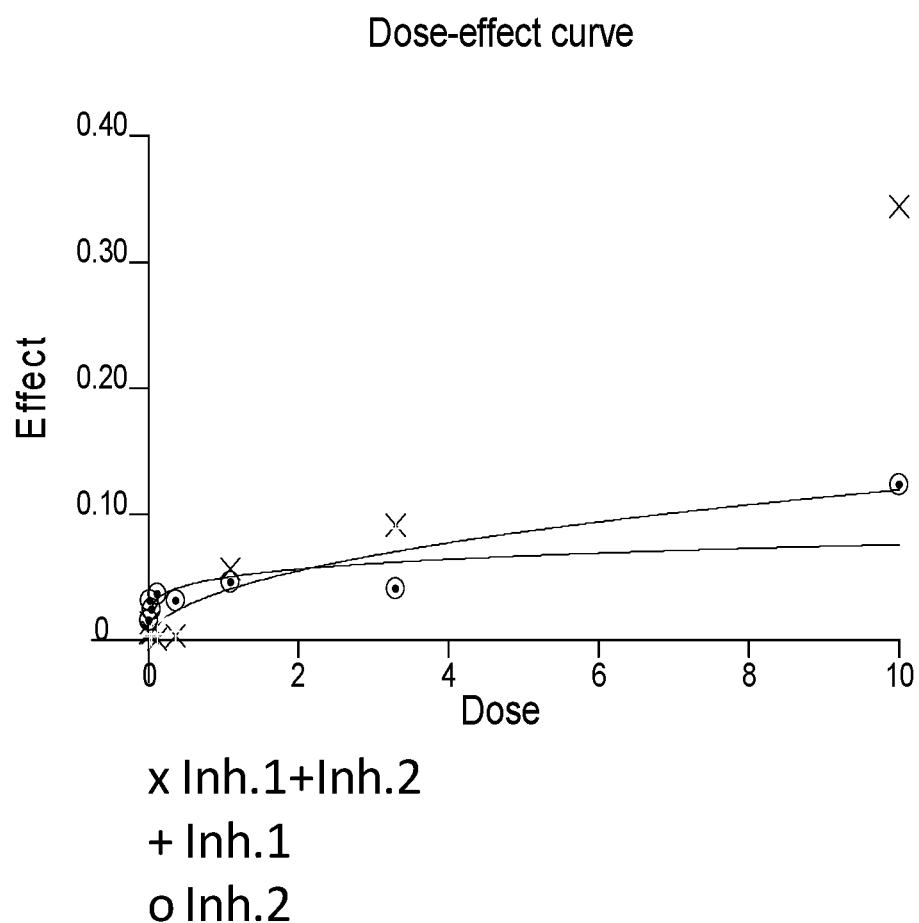

FIG. 59 illustrates the dose-effect curves obtained for the tested Daudi cell line (human Burkitt's lymphoma) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.

Figure 60:
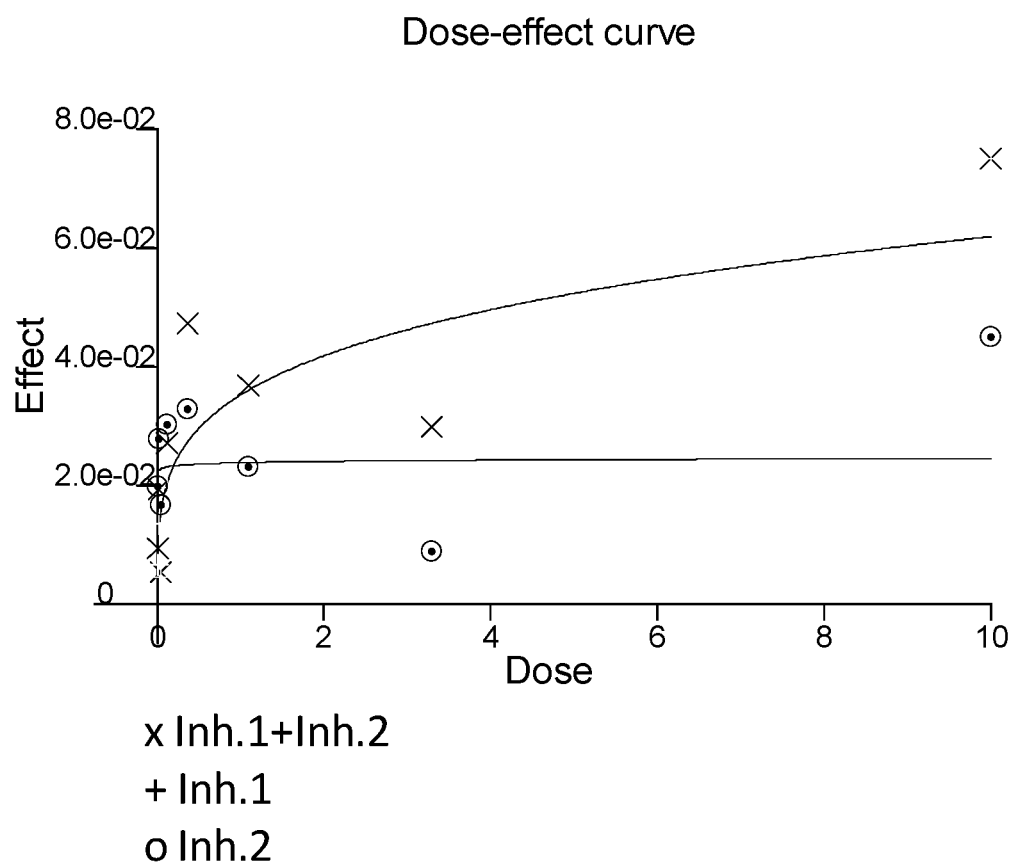

FIG. 60 illustrates the dose-effect curves obtained for the tested K562 cell line (leukemia, myeloid, and/or chronic myelogenous leukemia) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.

Figure 61:
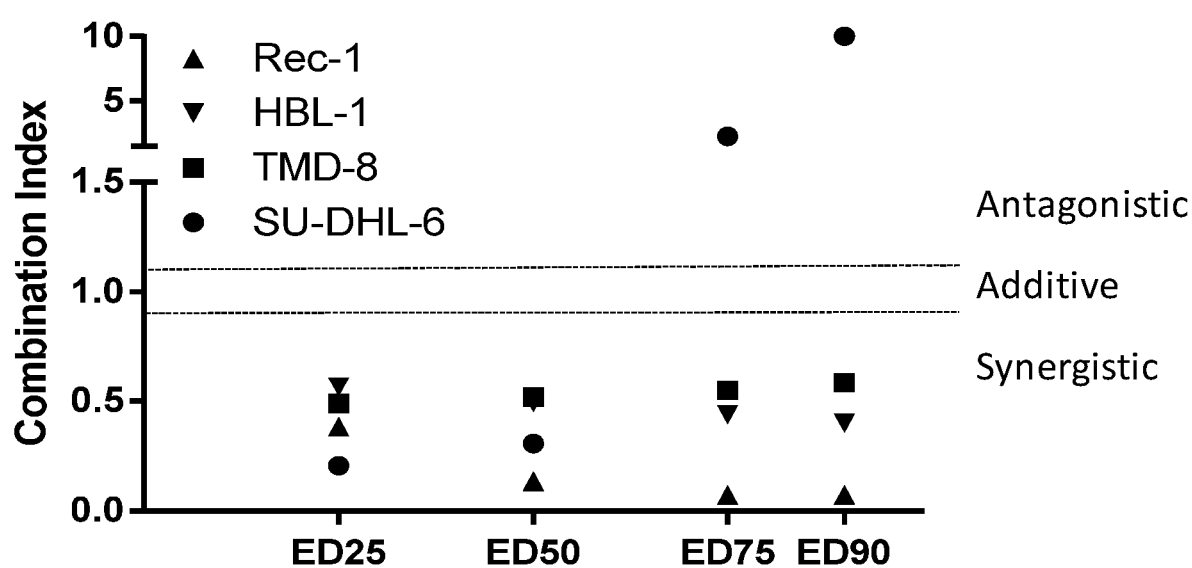

FIG. 61 illustrates the synergy observed in certain cell lines when the BTK inhibitor of Formula XVIII and the JAK-2 inhibitor of Formula XXX (ruxolitinib) are combined. The tested cell lines include SU-DHL-6 (DLBCL-GCB or PTCL), TMD-8 (DLBCL-ABC), HBL-1 (DLBCL-ABC), and Rec-1 (follicular lymphoma). The dose-effect curves for these cell lines are given in FIG. 62, FIG. 63, FIG. 64, and FIG. 65.

Figure 62:
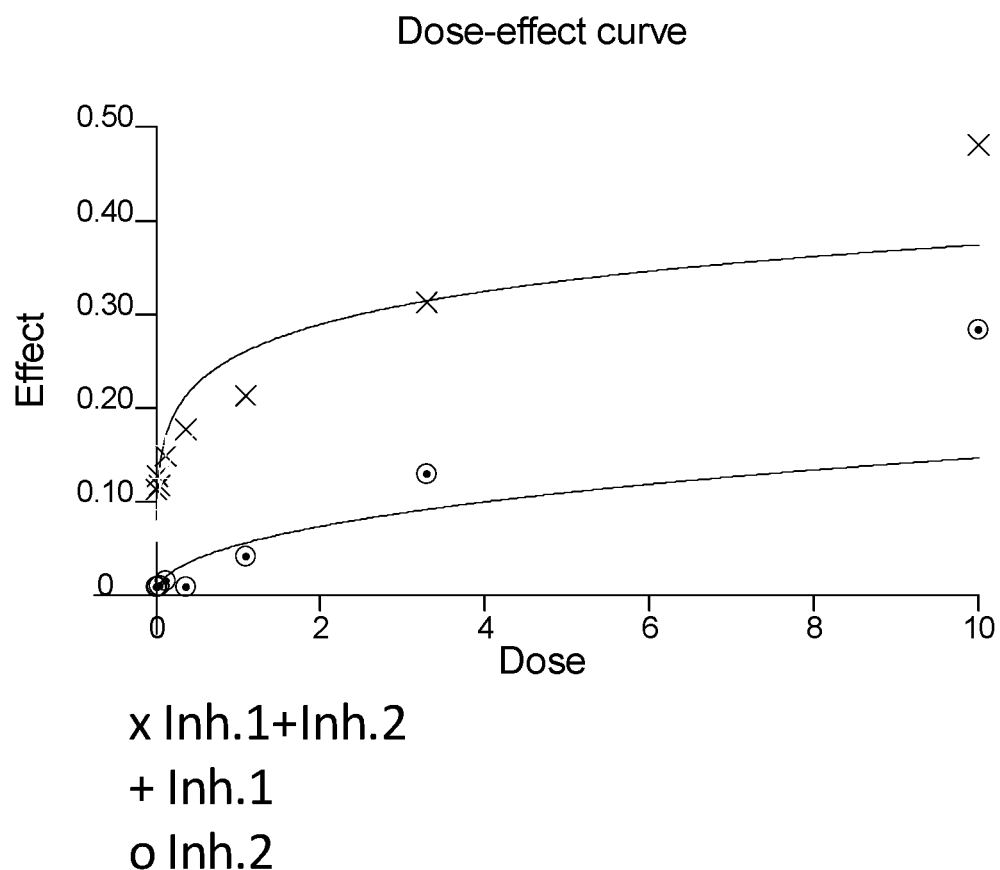

FIG. 62 illustrates the dose-effect curves obtained for the tested SU-DHL-6 cell line (DLBCL-GCB or PTCL) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.

Figure 63:
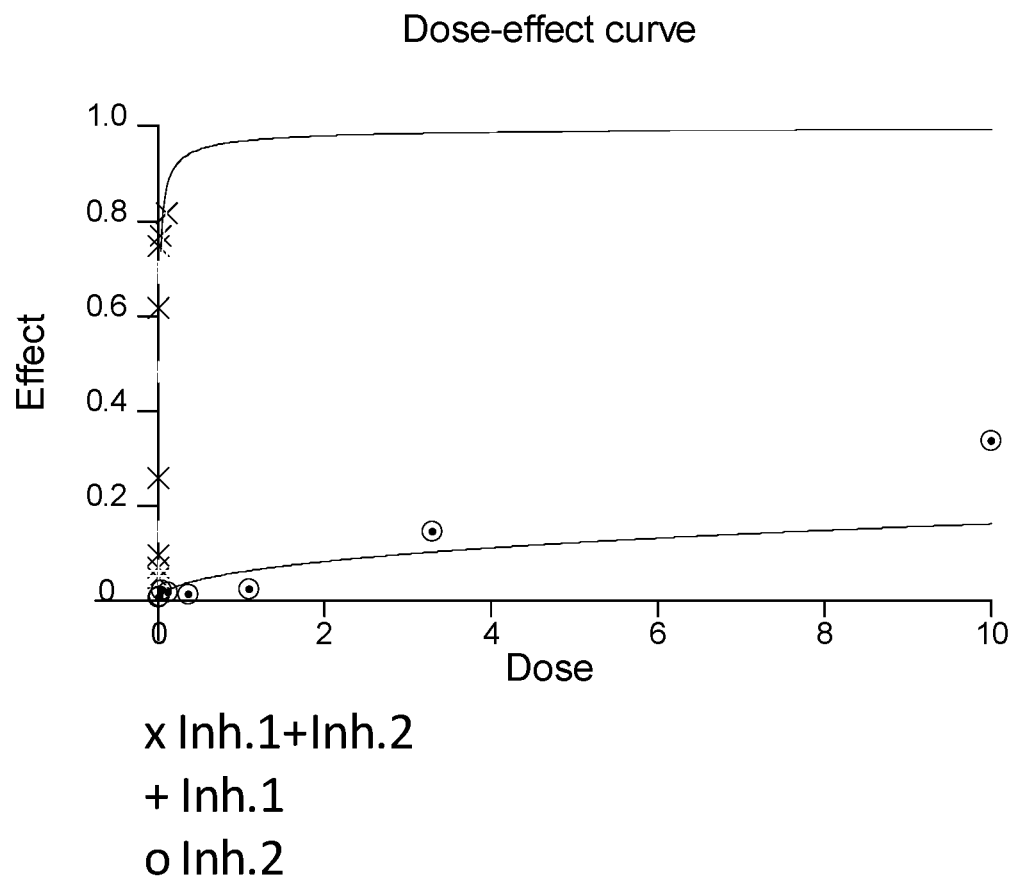

FIG. 63 illustrates the dose-effect curves obtained for the tested TMD-8 cell line (DLBCL-ABC) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.

Figure 64:
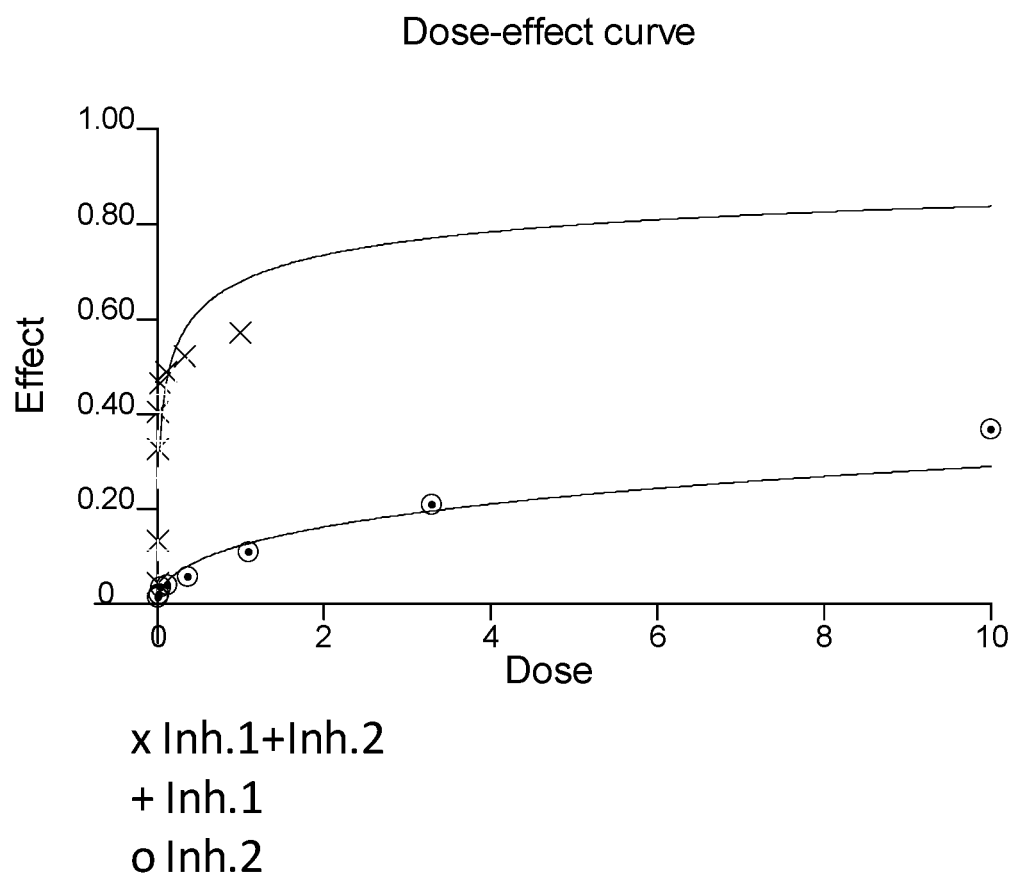

FIG. 64 illustrates the dose-effect curves obtained for the tested HBL-1 cell line (DLBCL-ABC) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.

Figure 65:
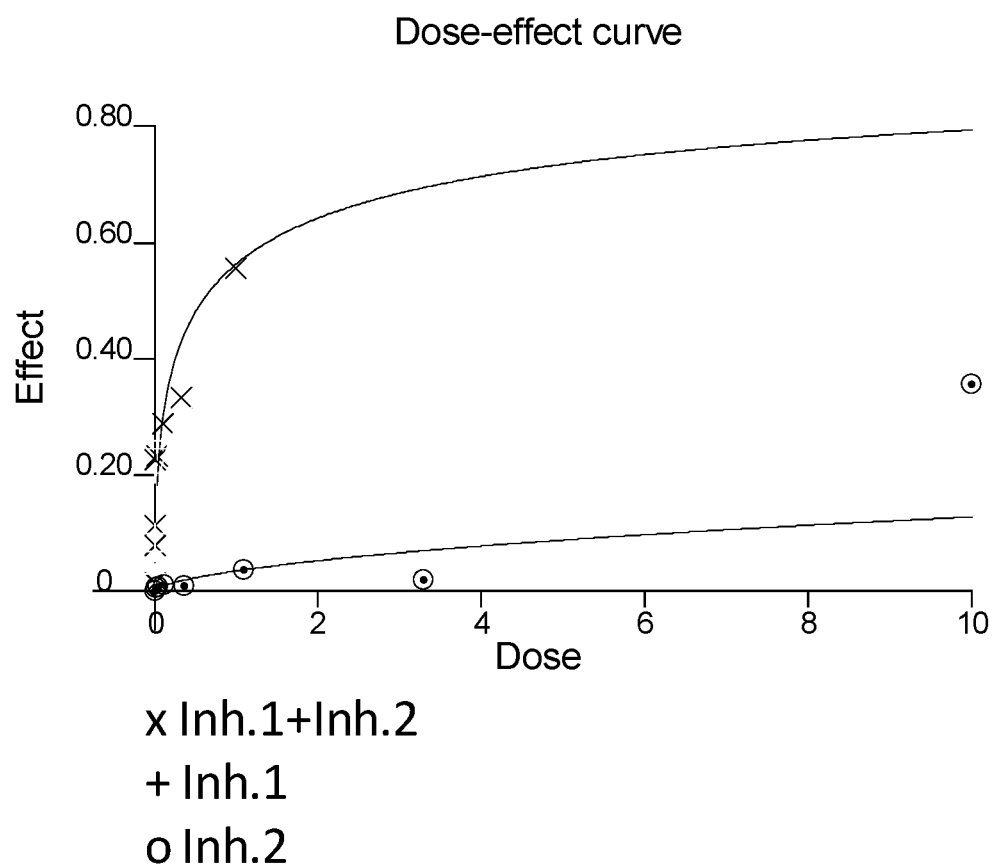

FIG. 65 illustrates the dose-effect curves obtained for the tested Rec-1 cell line (follicular lymphoma) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.

Figure 66:
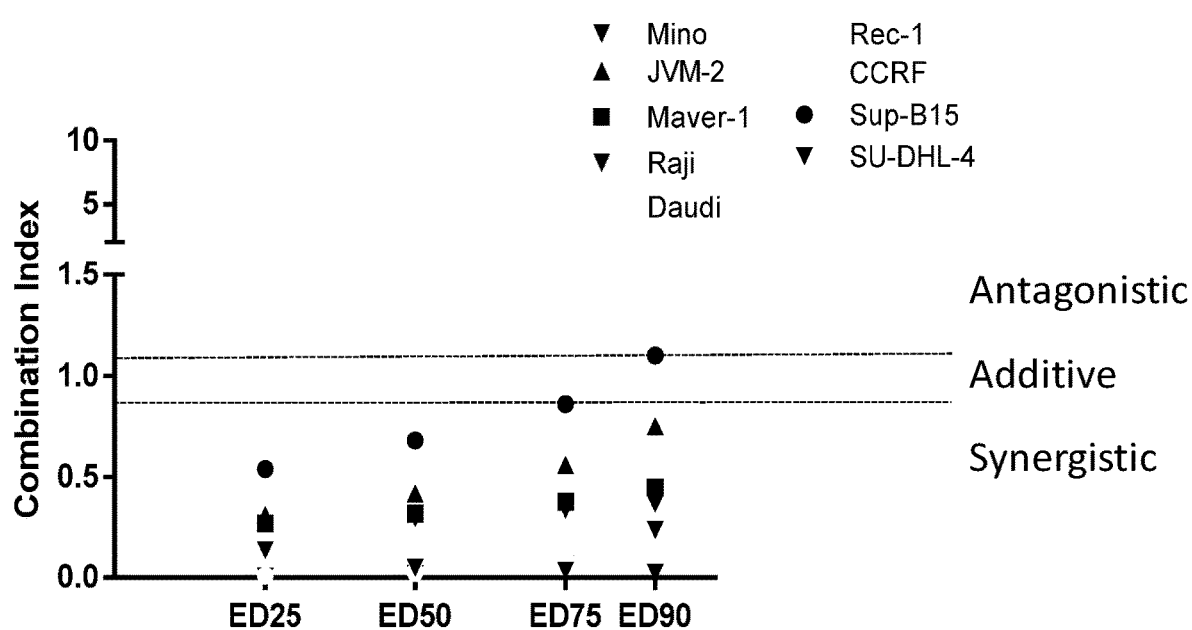

FIG. 66 illustrates the synergy observed in certain cell lines when the BTK inhibitor of Formula (XVIII) and the JAK-2 inhibitor of Formula LIV (pacritinib) are combined. The tested cell lines include Mino (mantle cell lymphoma), Maver-1 (B cell lymphoma, mantle cell lymophoma), Raji (B lymphocyte, Burkitt's lymphoma), JVM-2 (prolymphocytic leukemia), Daudi (Human Burkitt's lymphoma), Rec-1 (follicular lymphoma), SUP-B15 (B lymphoblast, acute lymphoblastic leukemia), CCRF (B lymphoblast, acute lymphoblastic leukemia), and SU-DHL-4 (DLBCL-ABC). The dose-effect curves for these cell lines are given in FIG. 67, FIG. 68, FIG. 69, FIG. 70, FIG. 71, FIG. 72, FIG. 73, FIG. 74, and FIG. 75.

Figure 67:
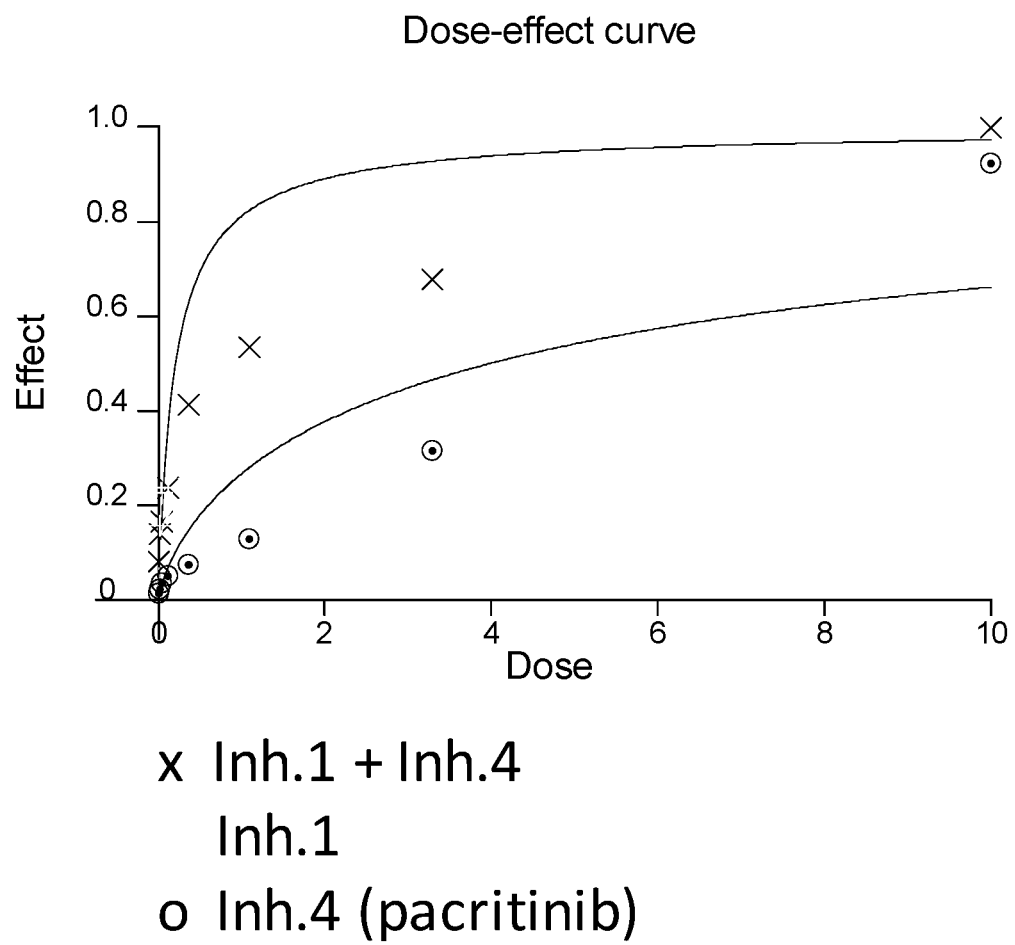

FIG. 67 illustrates the dose-effect curves obtained for the tested Mino cell line (mantle cell lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 68:
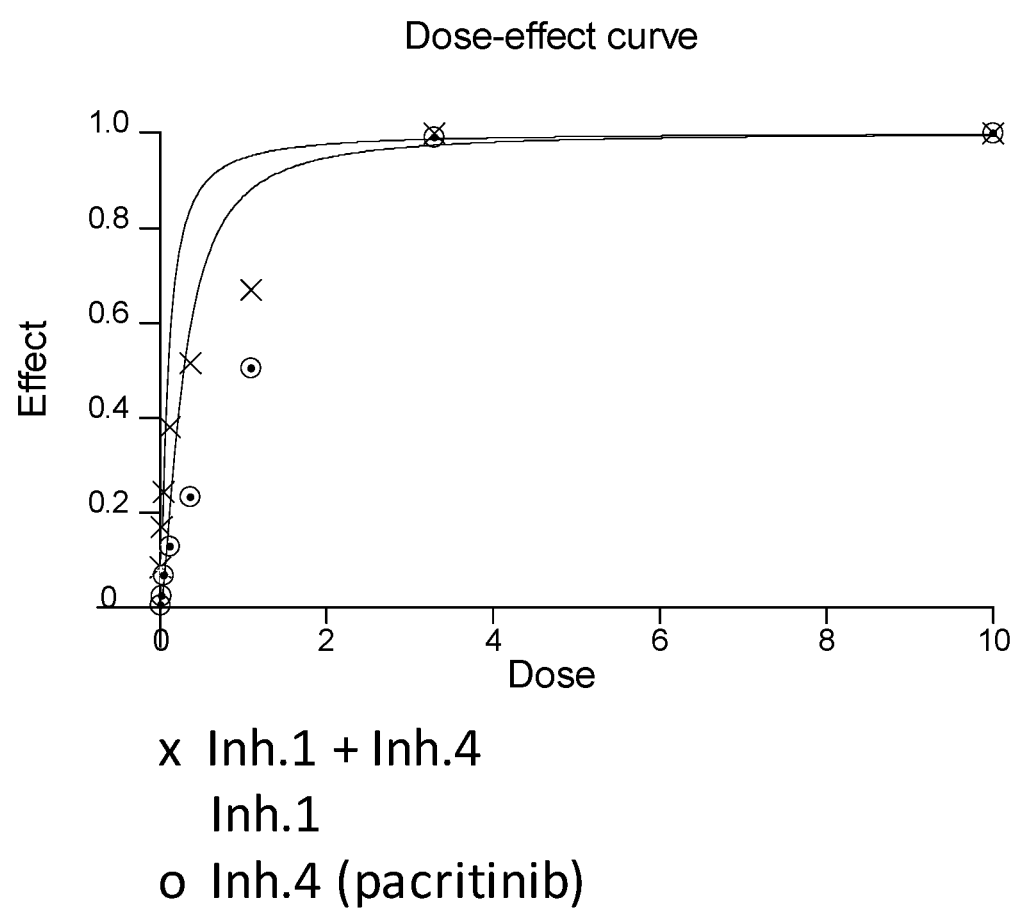

FIG. 68 illustrates the dose-effect curves obtained for the tested Maver-1 cell line (B cell lymphoma, mantle cell lymophoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 69:
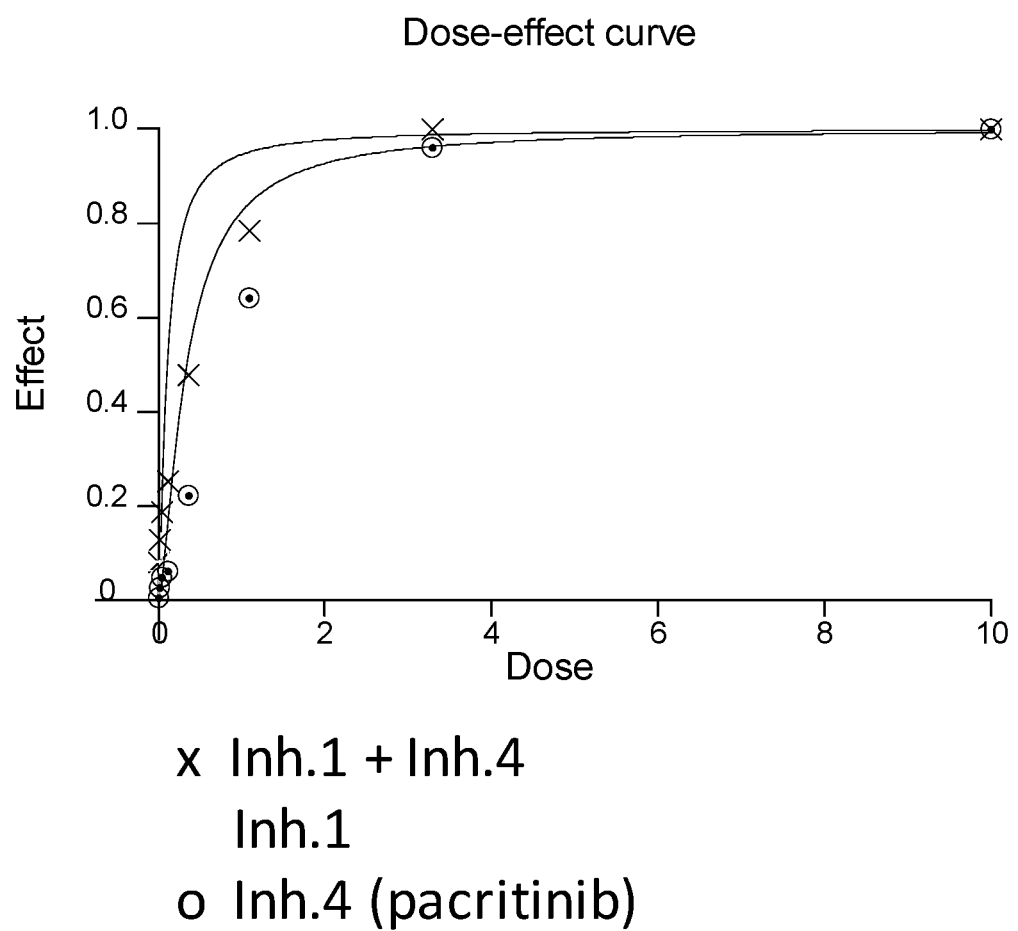

FIG. 69 illustrates the dose-effect curves obtained for the tested Raji cell line (B lymphocyte, Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 70:
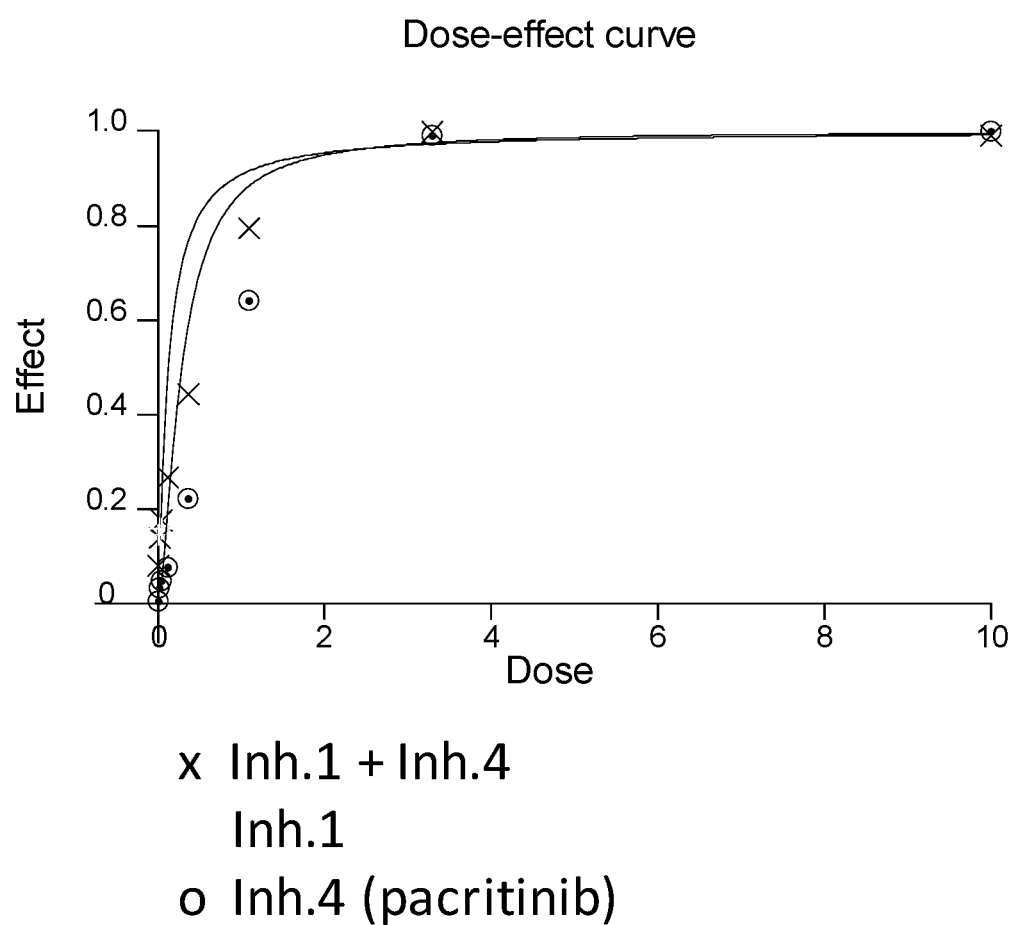

FIG. 70 illustrates the dose-effect curves obtained for the tested JVM-2 cell line (prolymphocytic leukemia) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 71:
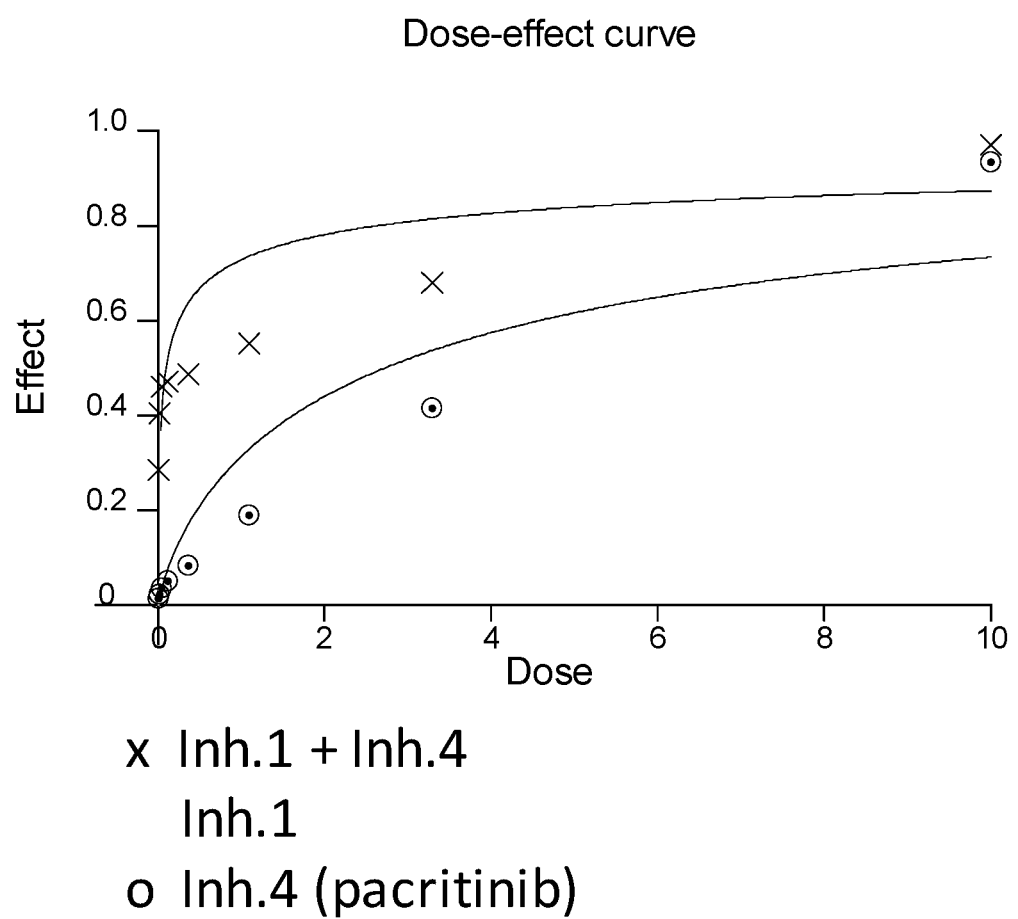

FIG. 71 illustrates the dose-effect curves obtained for the tested Daudi cell line (Human Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 72:
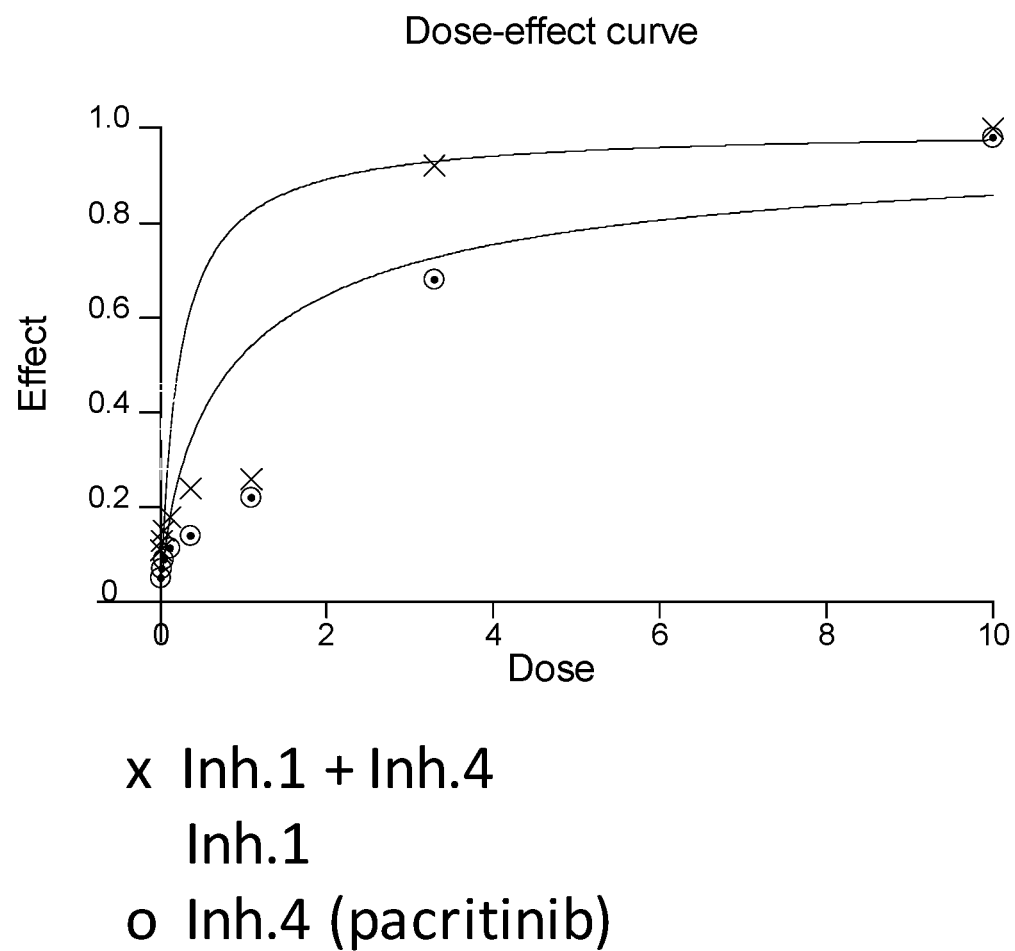

FIG. 72 illustrates the dose-effect curves obtained for the tested Rec-1 cell line (follicular lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 73:
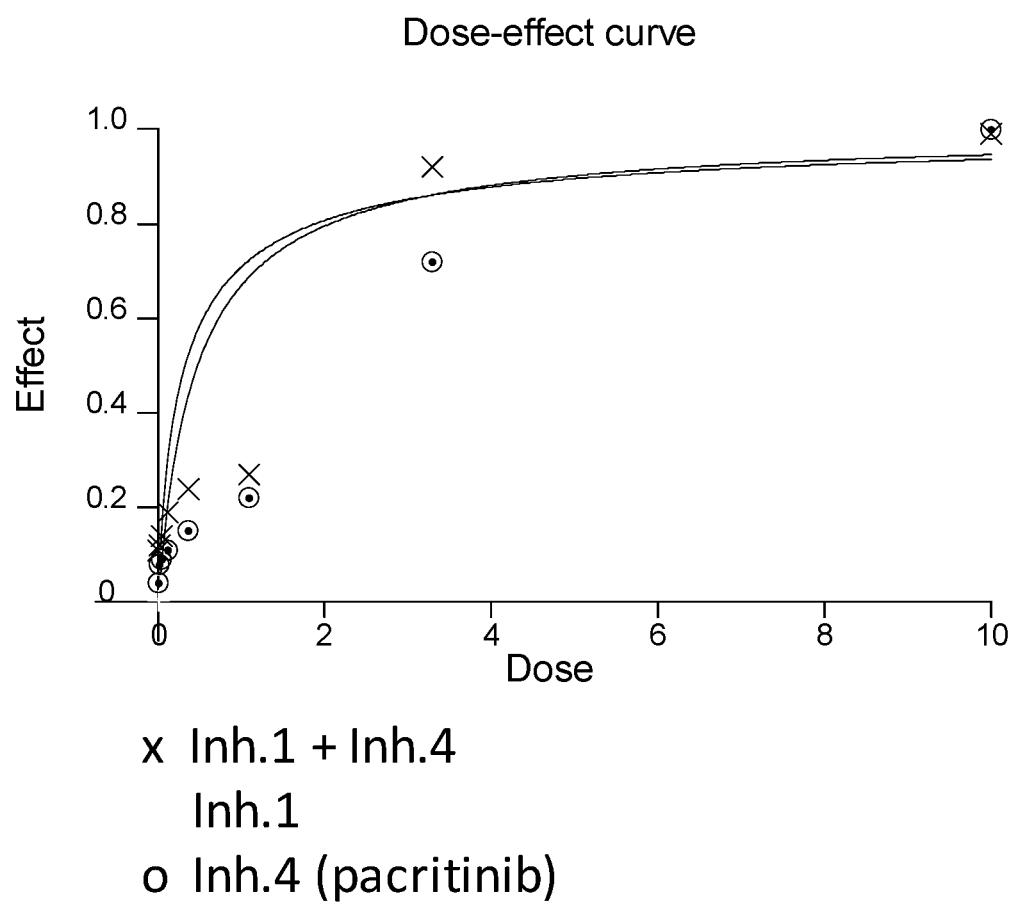

FIG. 73 illustrates the dose-effect curves obtained for the tested SUP-B15 cell line (B lymphoblast, acute lymphoblastic leukemia) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 74:
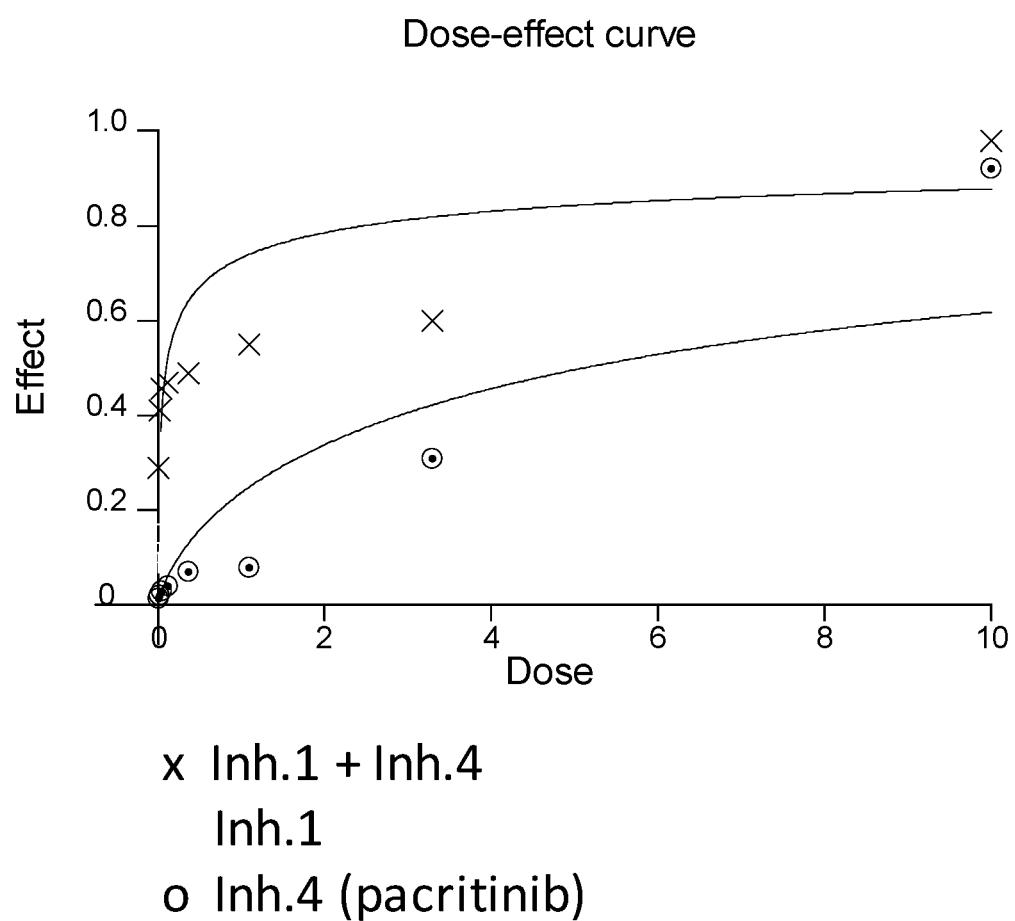

FIG. 74 illustrates the dose-effect curves obtained for the tested CCRF cell line (B lymphoblast, acute lymphoblastic leukemia) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of µM.

Figure 75:
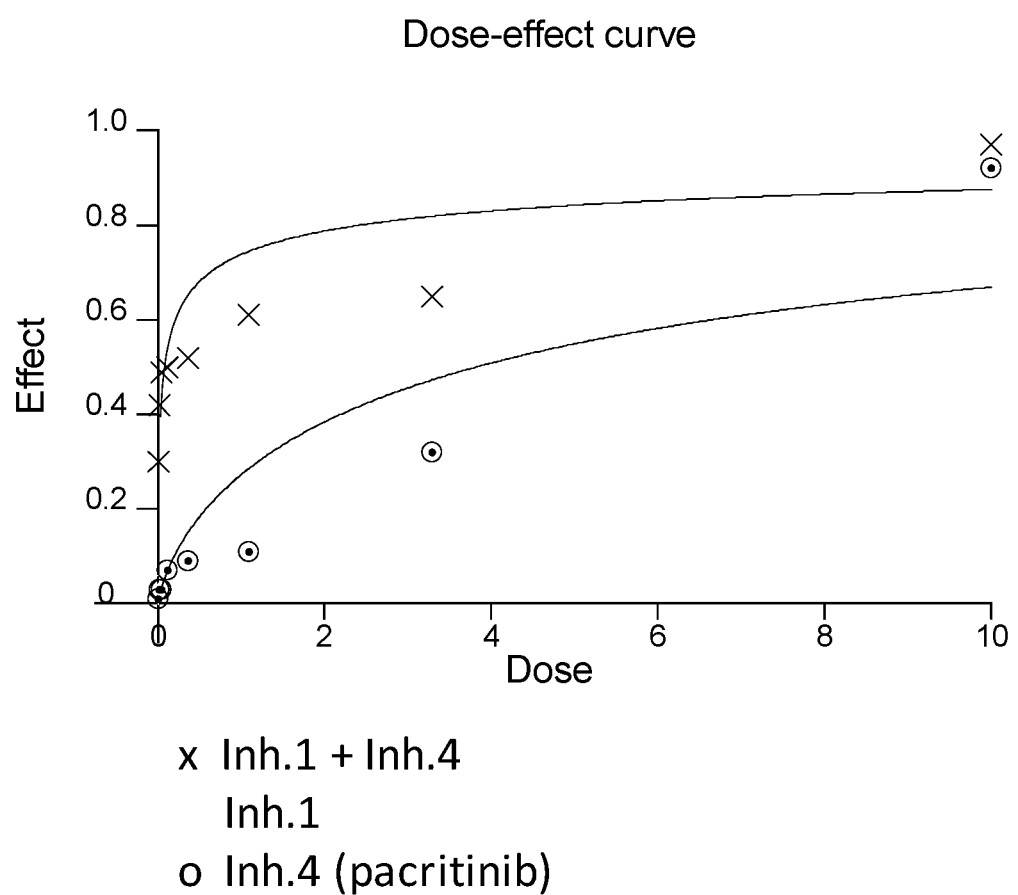

FIG. 75 illustrates the dose-effect curves obtained for the tested SU-DHL-4 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 76:
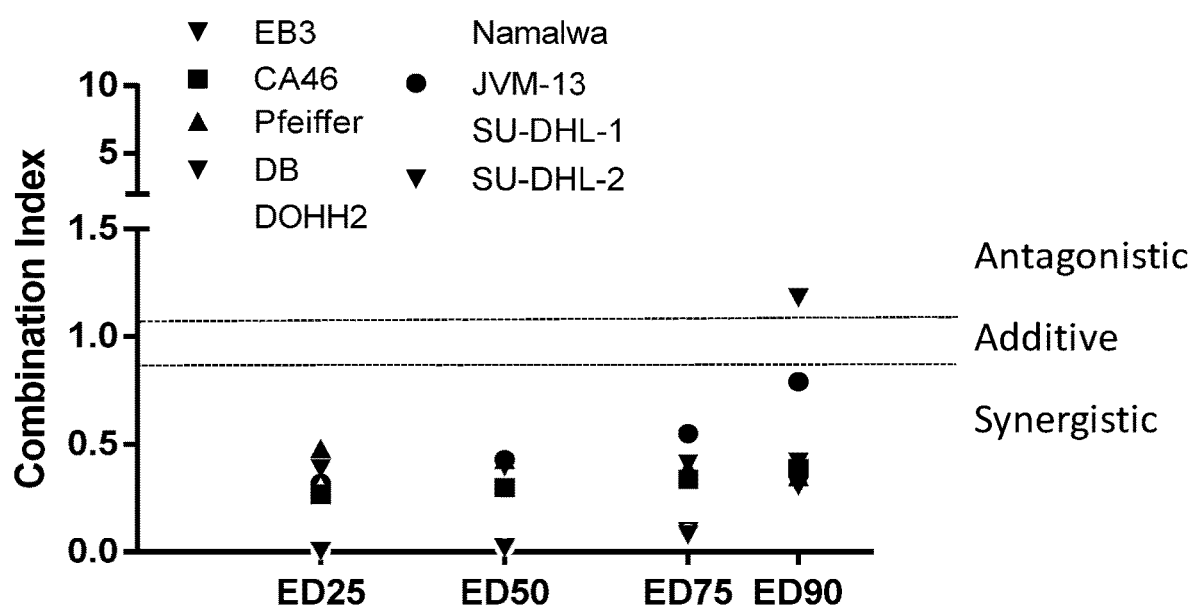

FIG. 76 illustrates the synergy observed in certain cell lines when the BTK inhibitor of Formula (XVIII) and the JAK-2 inhibitor of Formula LIV (pacritinib) are combined. The tested cell lines include EB3 (B lymphocyte, Burkitt's lymphoma), CA46 (B lymphocyte, Burkitt's lymphoma), DB (B cell lymphoma, mantle cell lymphoma), Pfeiffer (follicular lymphoma), DOHH2 (follicular lymphoma), Namalwa (B lymphocyte, Burkitt's lymphoma), JVM-13 (B cell lymphoma, mantle cell lymphoma), SU-DHL-1 (DLBCL-ABC), and SU-DHL-2 (DLBCL-ABC). The dose-effect curves for these cell lines are given in FIG. 77, FIG. 78, FIG. 79, FIG. 80, FIG. 81, FIG. 82, FIG. 83, FIG. 84, and FIG. 85.

Figure 77:
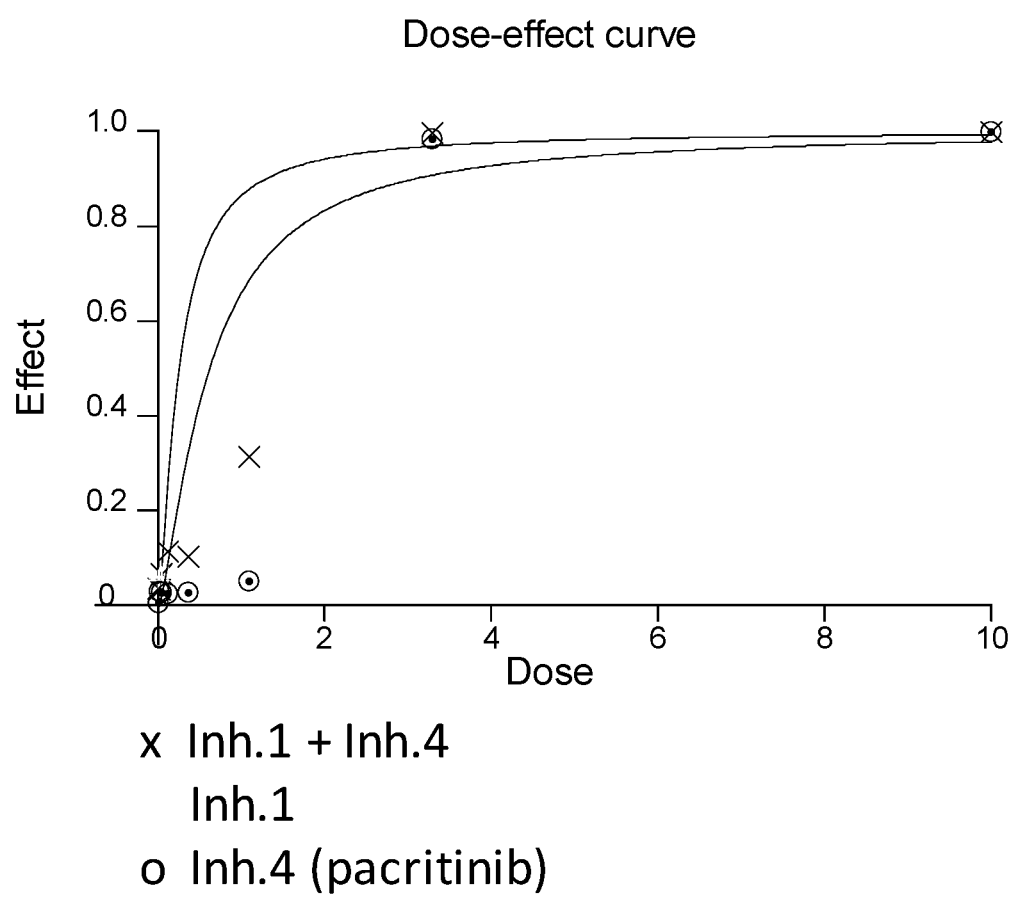

FIG. 77 illustrates the dose-effect curves obtained for the tested EB3 cell line (B lymphocyte, Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 78:
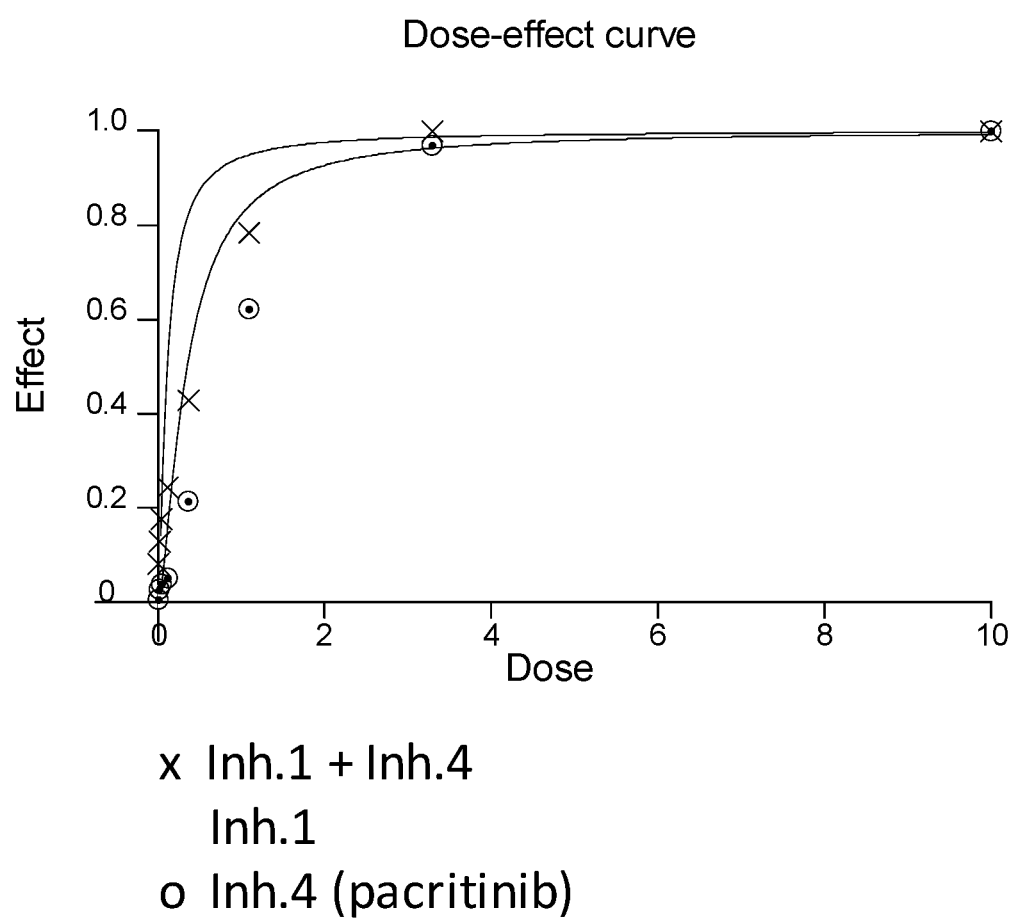

FIG. 78 illustrates the dose-effect curves obtained for the tested CA46 cell line (B lymphocyte, Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 79:
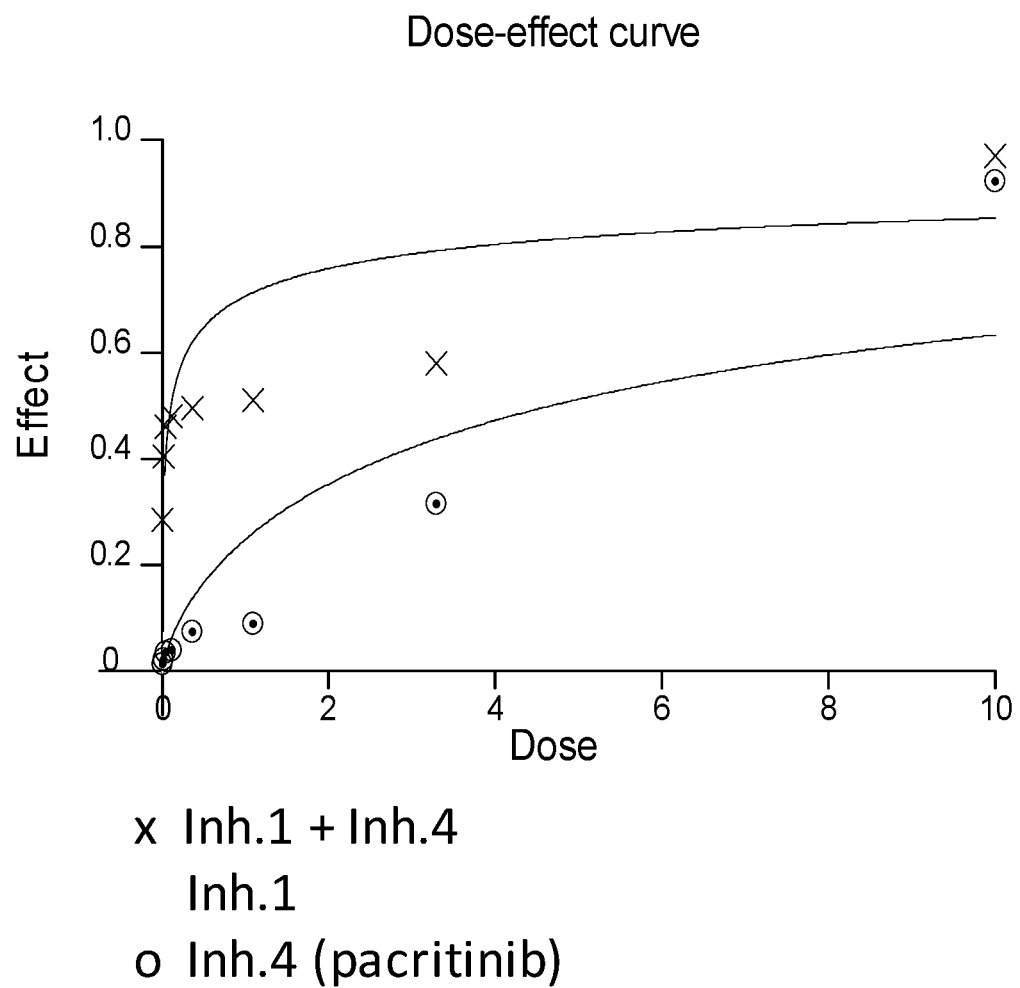

FIG. 79 illustrates the dose-effect curves obtained for the tested DB cell line (B cell lymphoma, mantle cell lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 80:
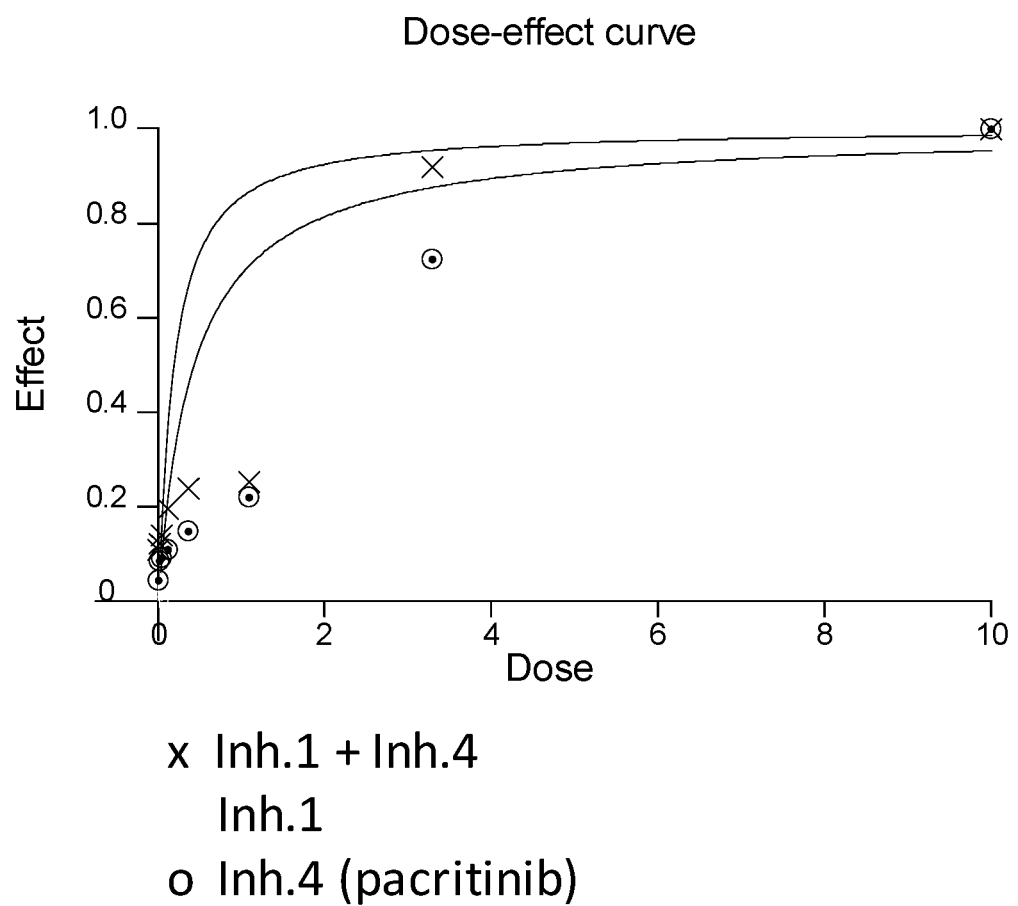

FIG. 80 illustrates the dose-effect curves obtained for the tested Pfeiffer cell line (follicular lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 81:
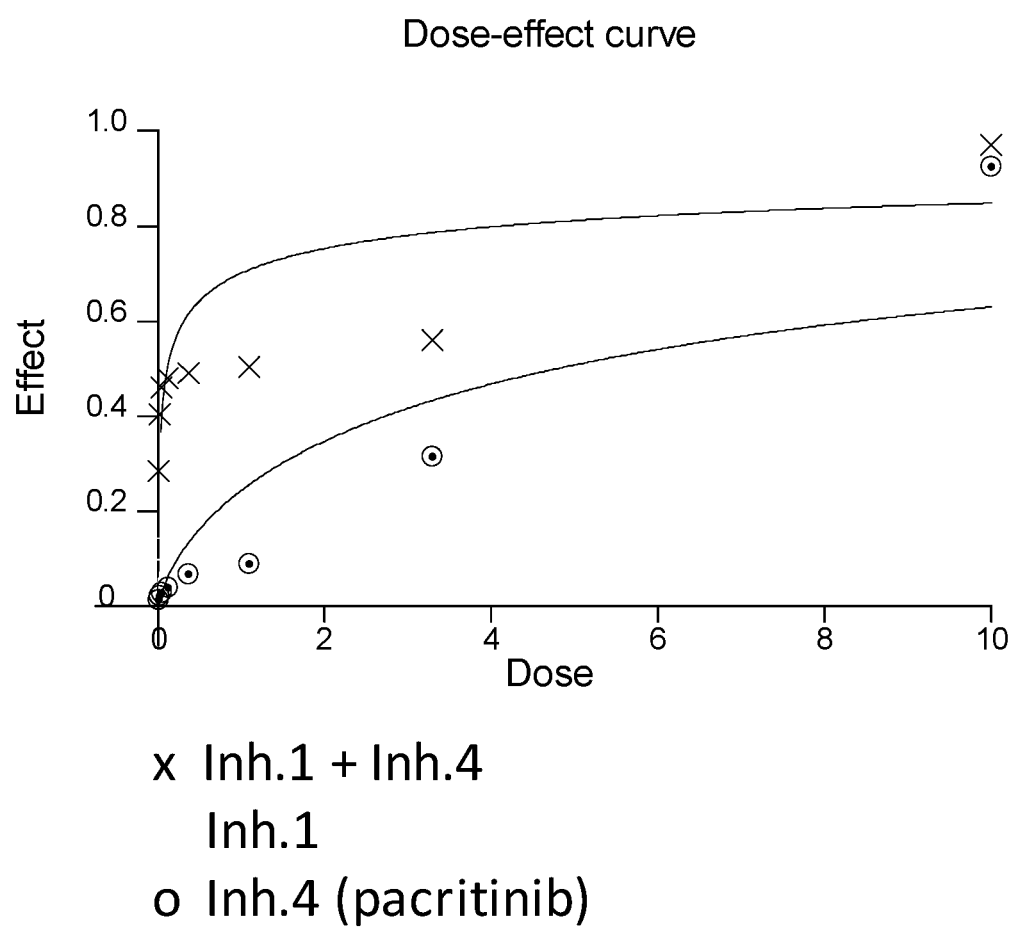

FIG. 81 illustrates the dose-effect curves obtained for the tested DOHH2 cell line (follicular lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 82:
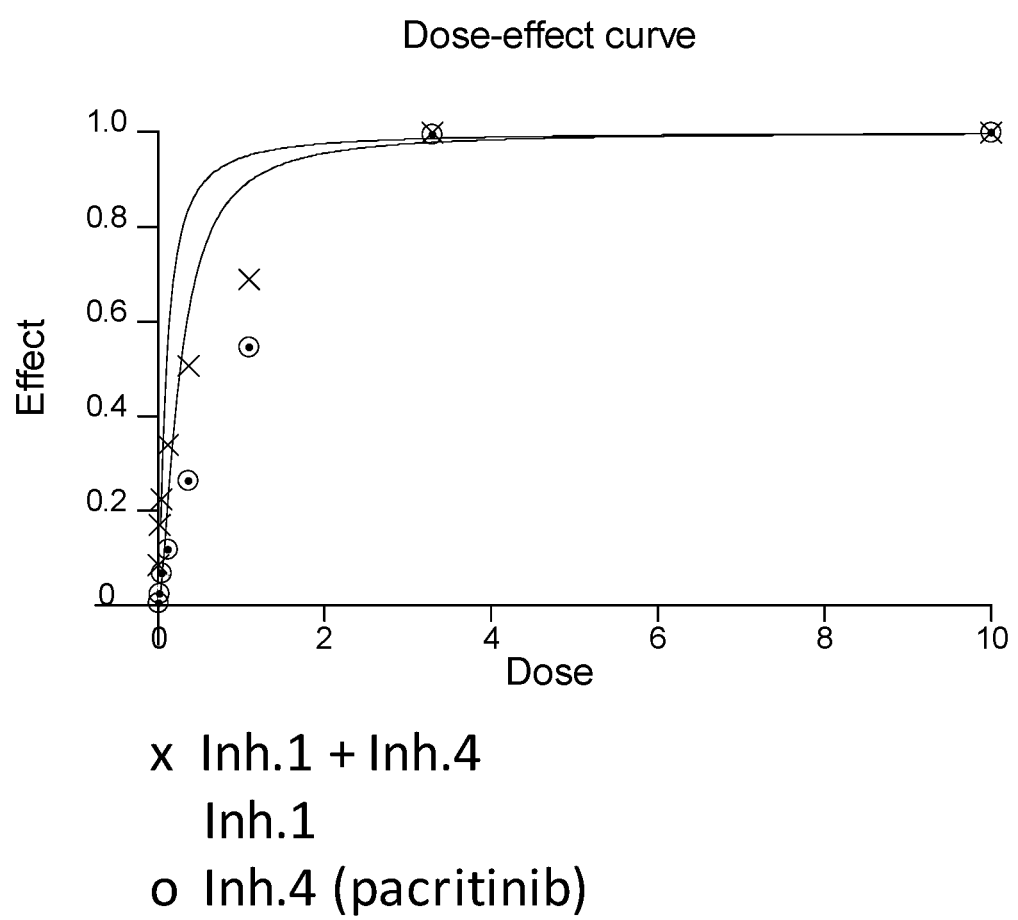

FIG. 82 illustrates the dose-effect curves obtained for the tested Namalwa cell line (B lymphocyte, Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 83:
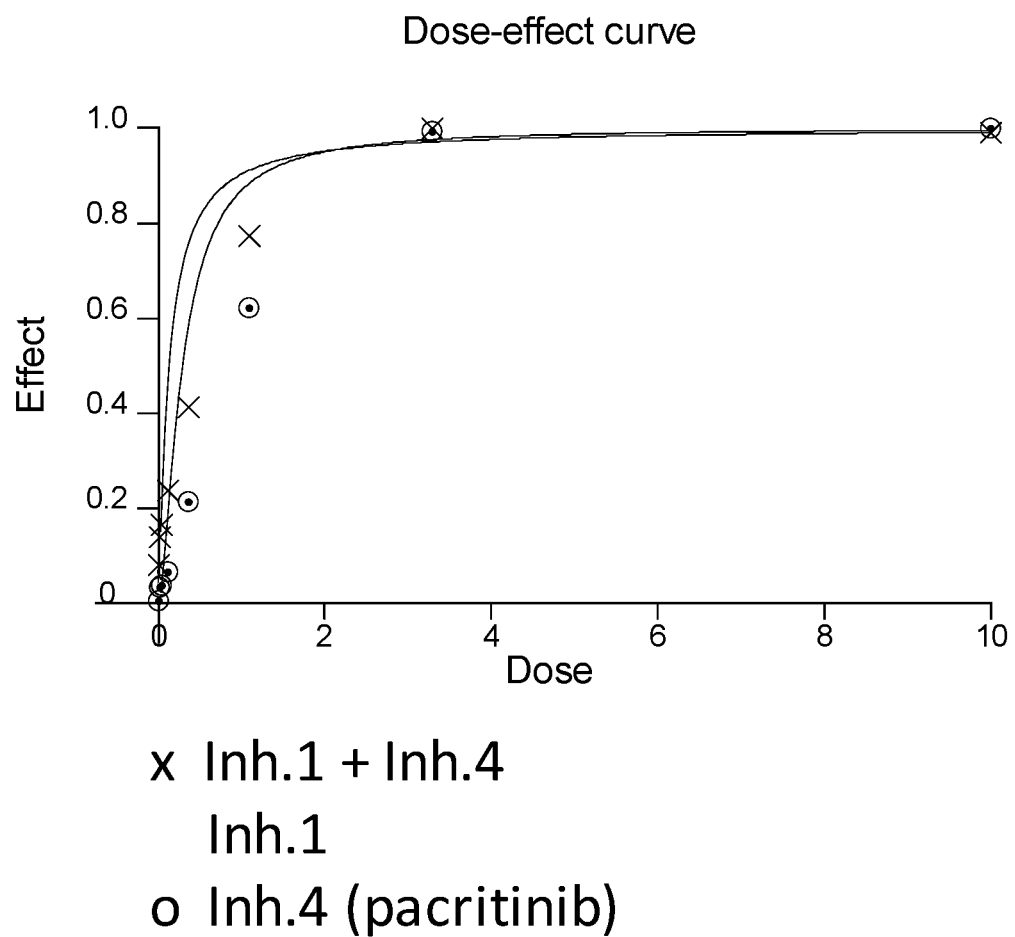

FIG. 83 illustrates the dose-effect curves obtained for the tested JVM-13 cell line (B cell lymphoma, mantle cell lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 84:
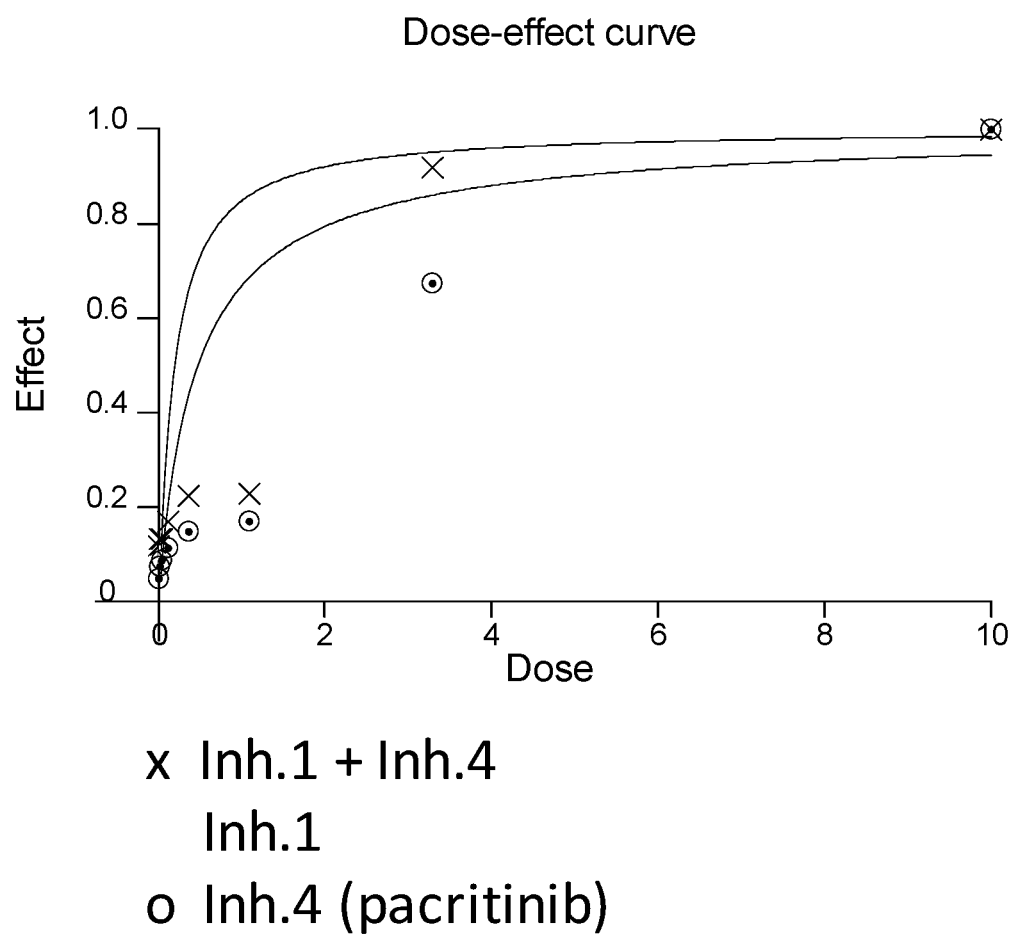

FIG. 84 illustrates the dose-effect curves obtained for the tested SU-DHL-1 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 85:
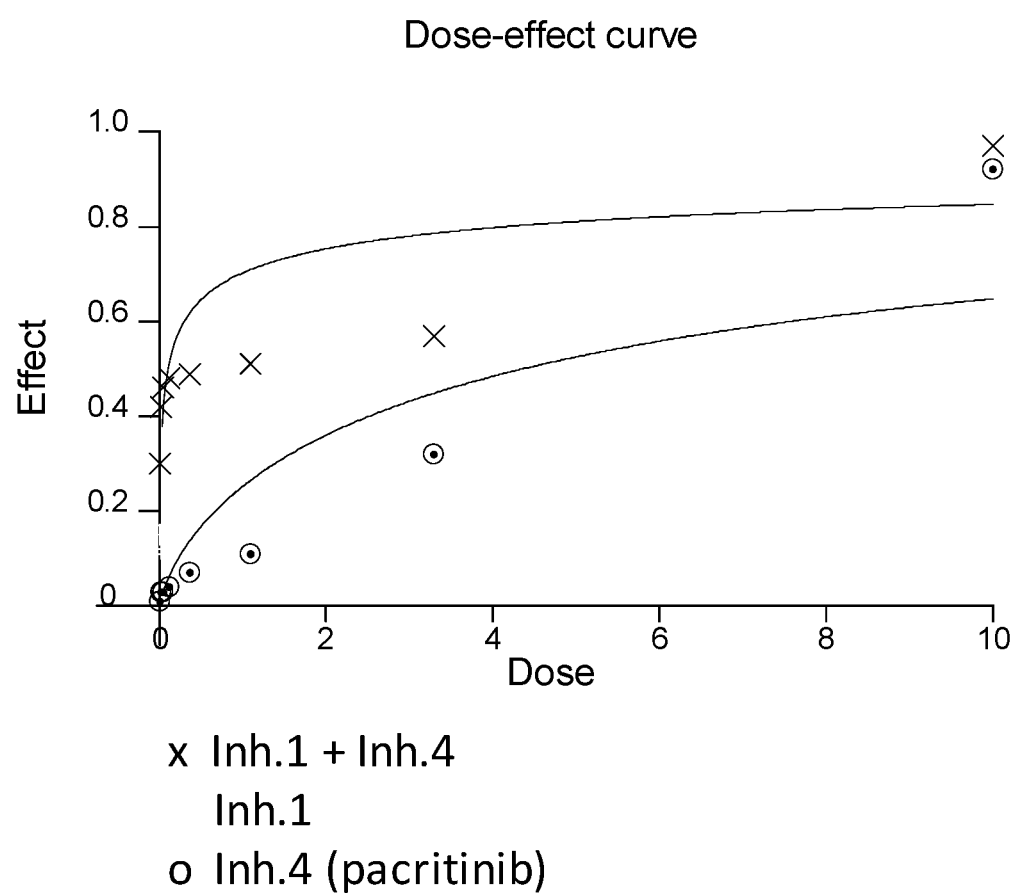

FIG. 85 illustrates the dose-effect curves obtained for the tested SU-DHL-2 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 86:
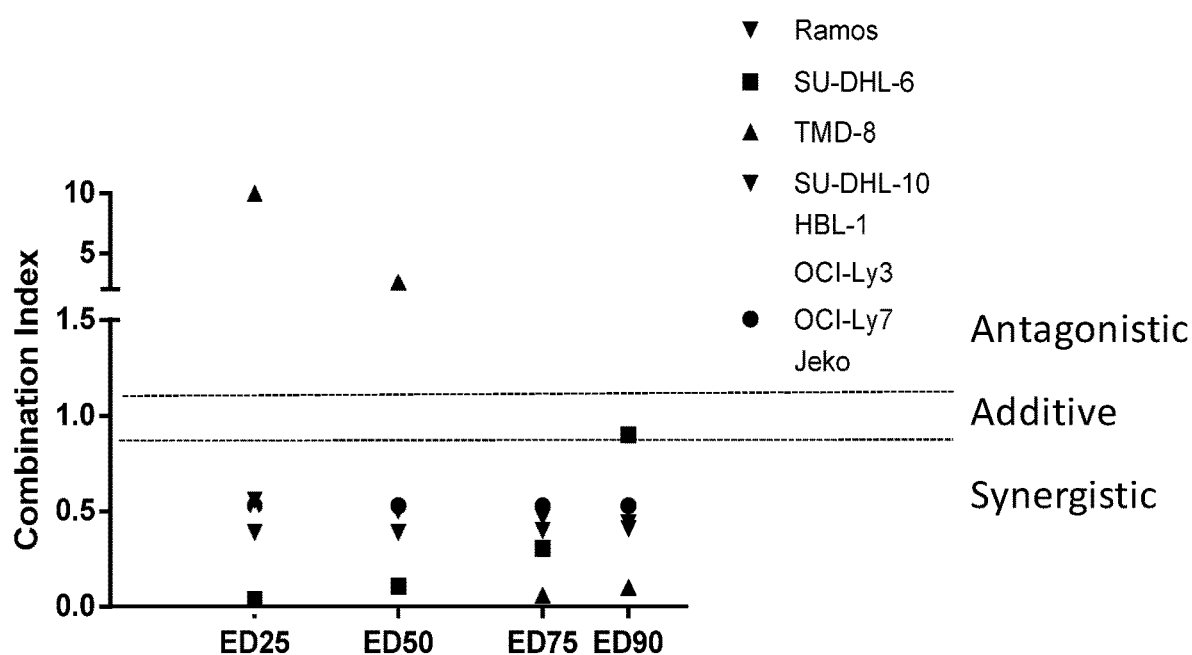

FIG. 86 illustrates the synergy observed in certain cell lines when the BTK inhibitor of Formula (XVIII) and the JAK-2 inhibitor of Formula LIV (pacritinib) are combined. The tested cell lines include Jeko (B cell lymphoma, mantle cell lymphoma), TMD-8 (DLBCL-ABC), SU-DHL6 (DLBCL-GCB), Ramos (human Burkitt's lymphoma), HBL-1 (DLBCL-ABC), SU-DHL-10 (DLBCL-GCB), OCI-Ly7 (DLBCL-ABC), and OCI-Ly3 (DLBCL-ABC). The dose-effect curves for these cell lines are given in FIG. 87, FIG. 88, FIG. 89, FIG. 90, FIG. 91, FIG. 92, FIG. 93, and FIG. 94.

Figure 87:
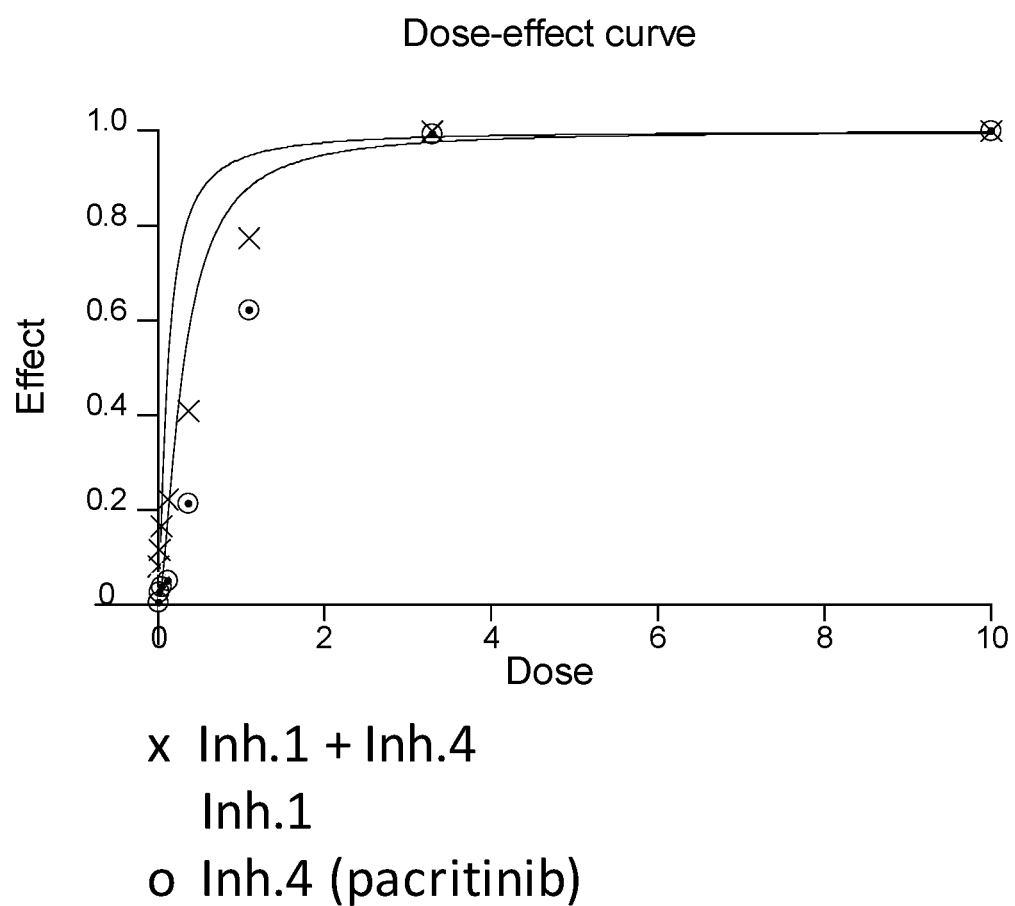

FIG. 87 illustrates the dose-effect curves obtained for the tested Jeko cell line (B cell lymphoma, mantle cell lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 88:
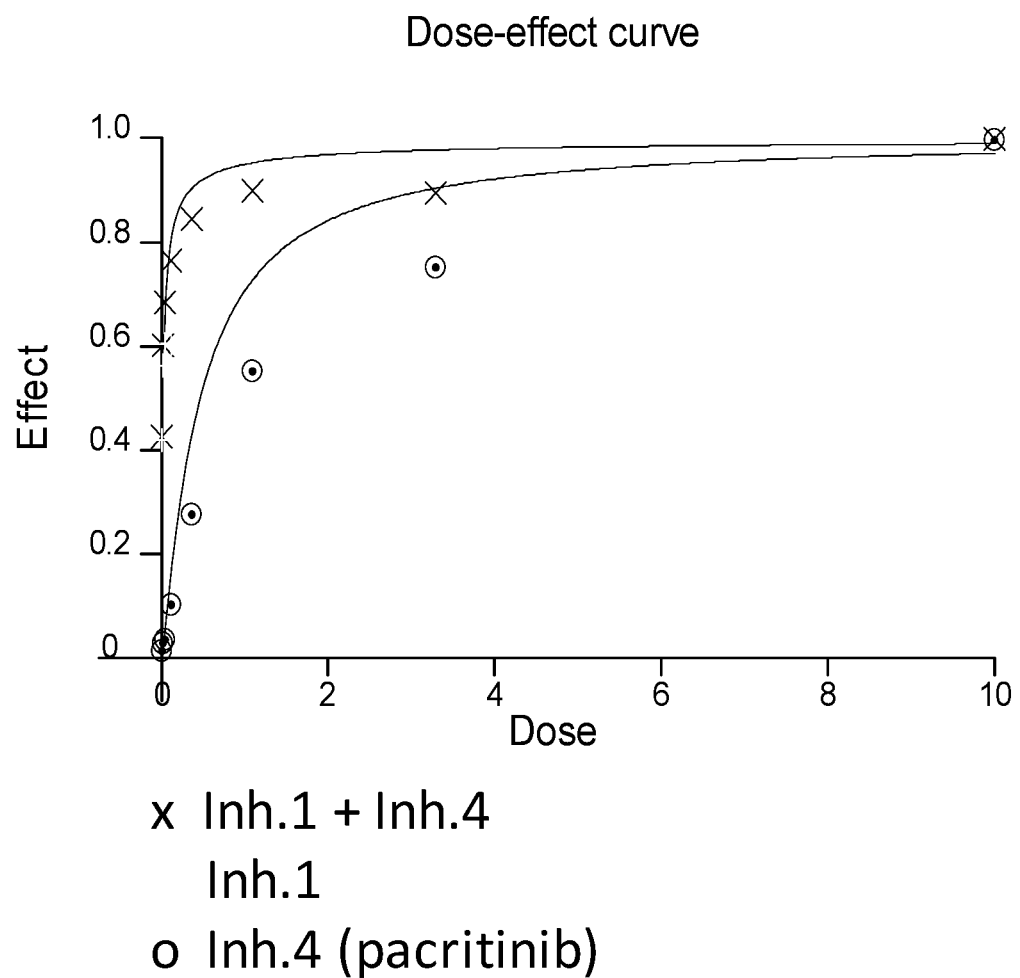

FIG. 88 illustrates the dose-effect curves obtained for the tested TMD-8 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 89:
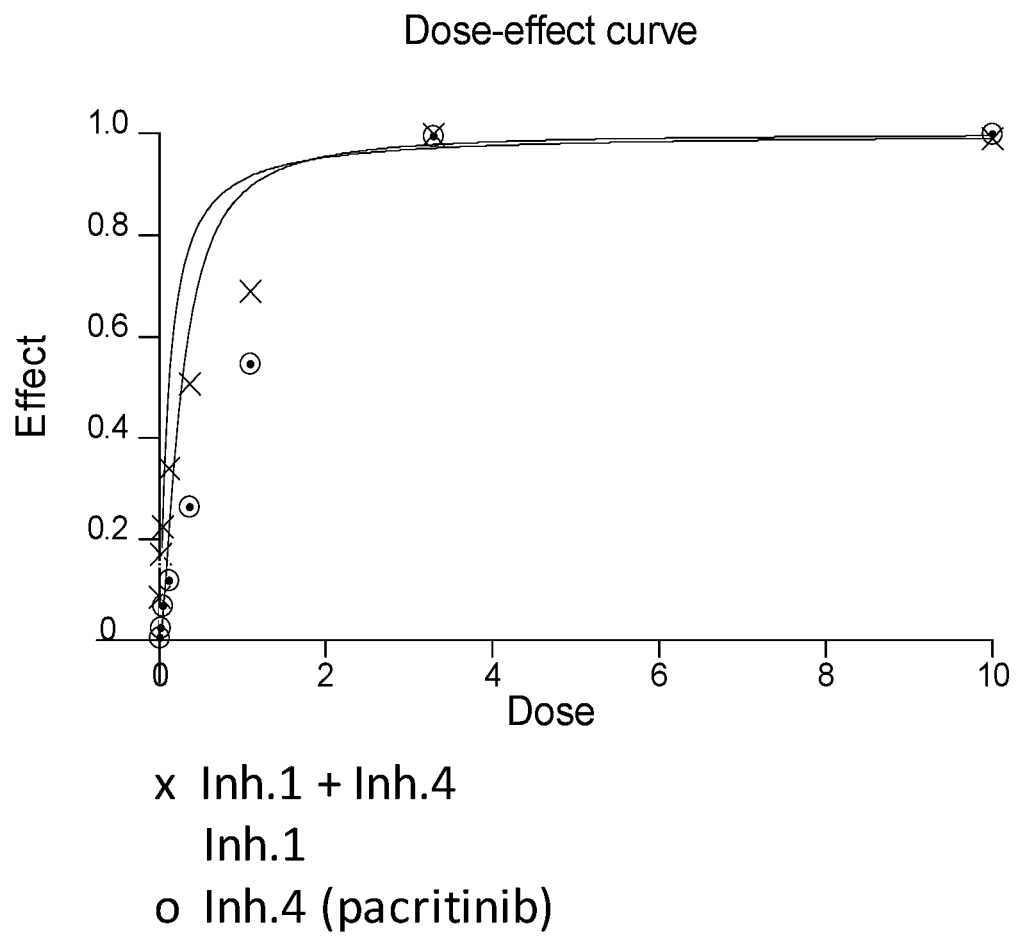

FIG. 89 illustrates the dose-effect curves obtained for the tested SU-DHL6 cell line (DLBCL-GCB) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 90:
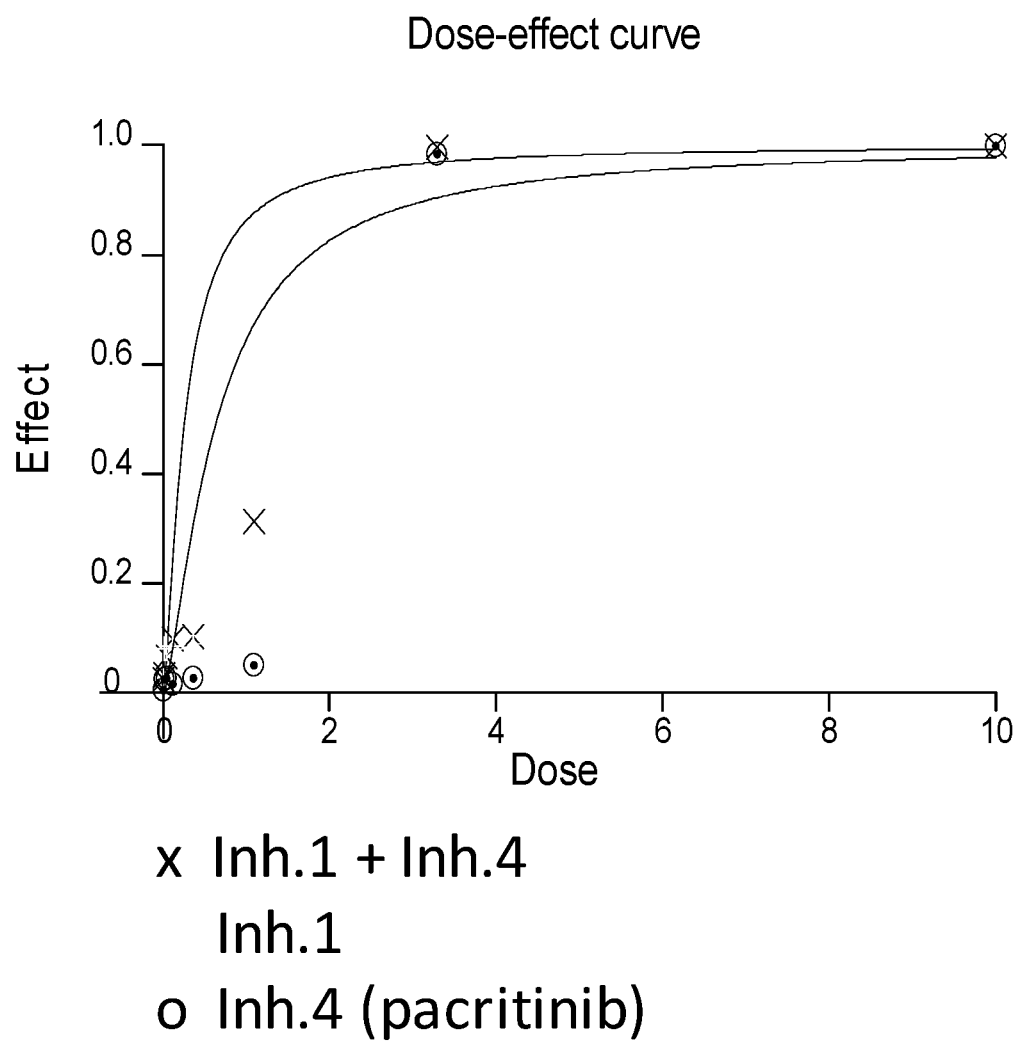

FIG. 90 illustrates the dose-effect curves obtained for the tested Ramos cell line (human Burkitt's lymphoma) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 91:
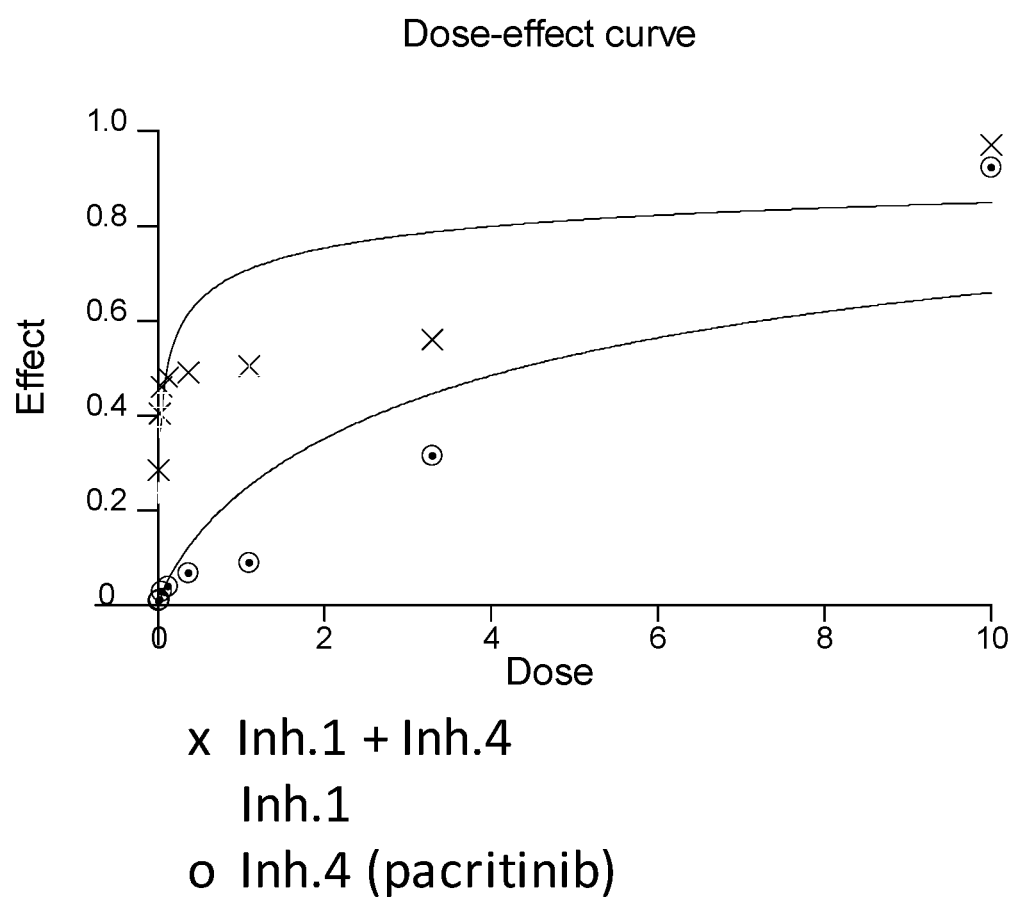

FIG. 91 illustrates the dose-effect curves obtained for the tested HBL-1 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 92:
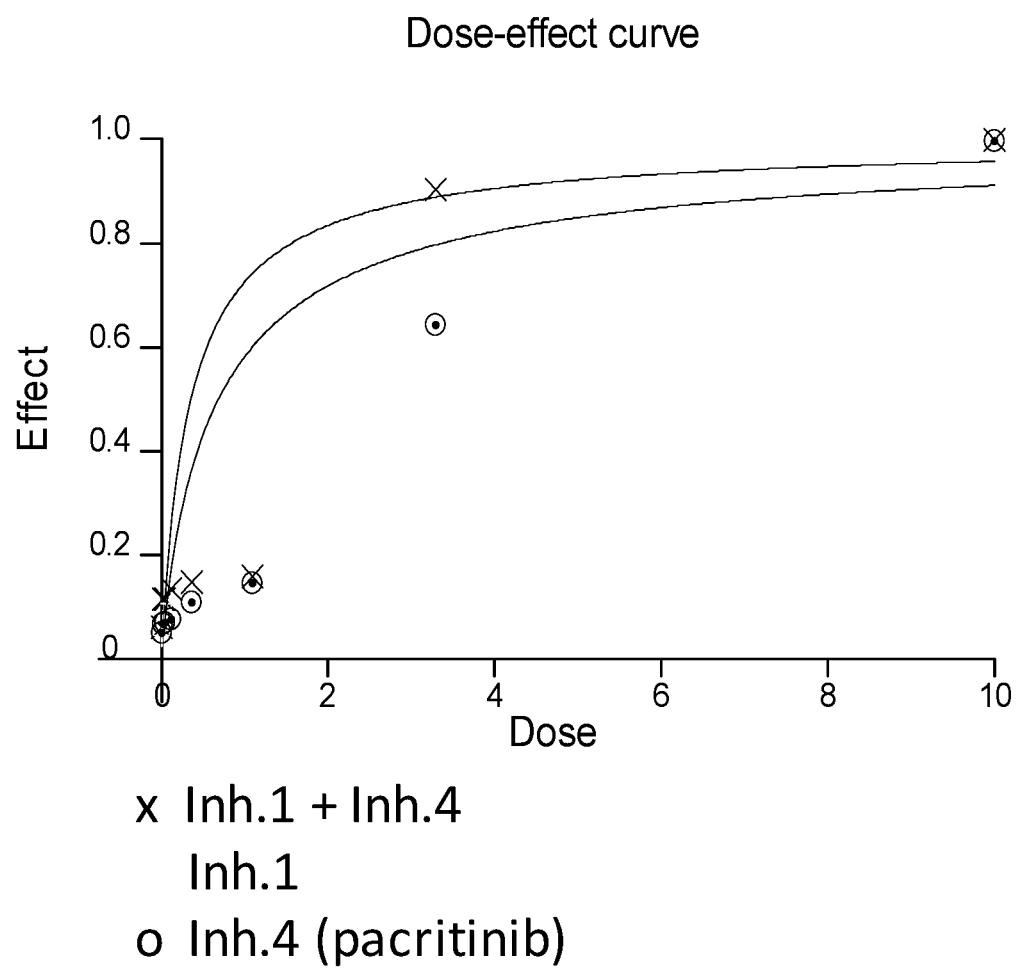

FIG. 92 illustrates the dose-effect curves obtained for the tested SU-DHL-10 cell line (DLBCL-GCB) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 93:
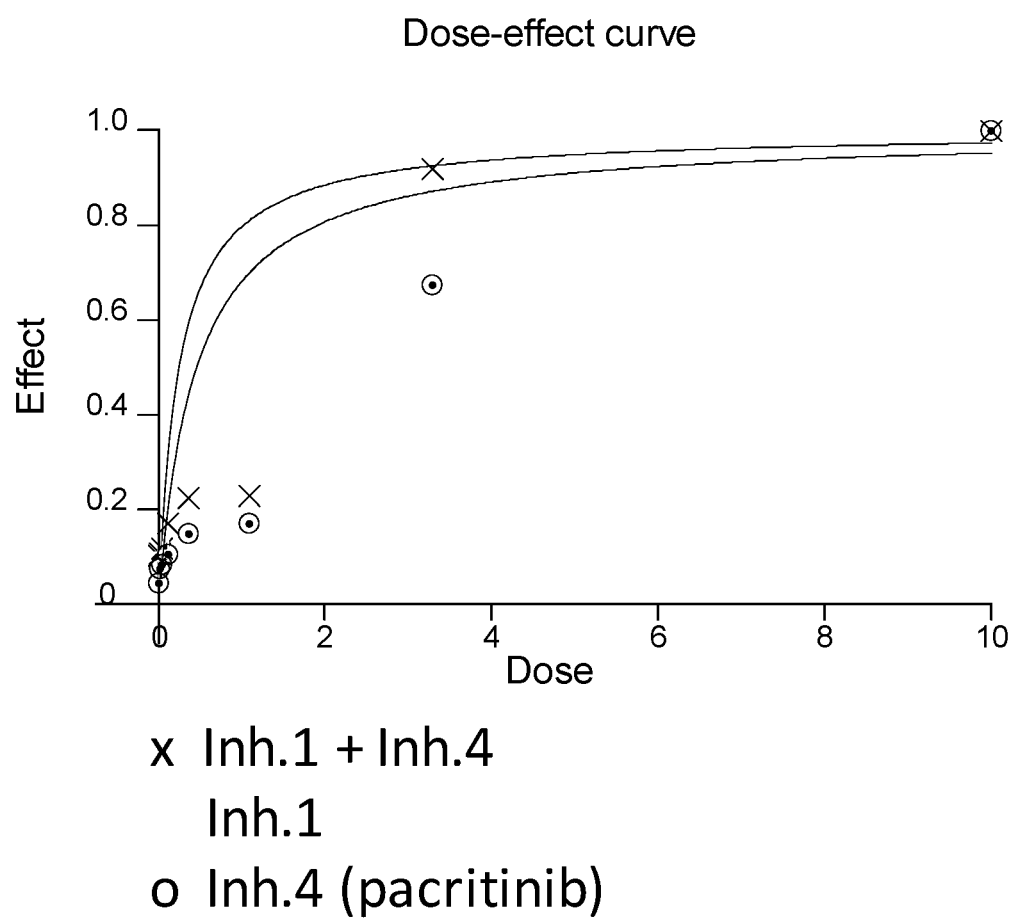

FIG. 93 illustrates the dose-effect curves obtained for the tested OCI-Ly7 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 94:
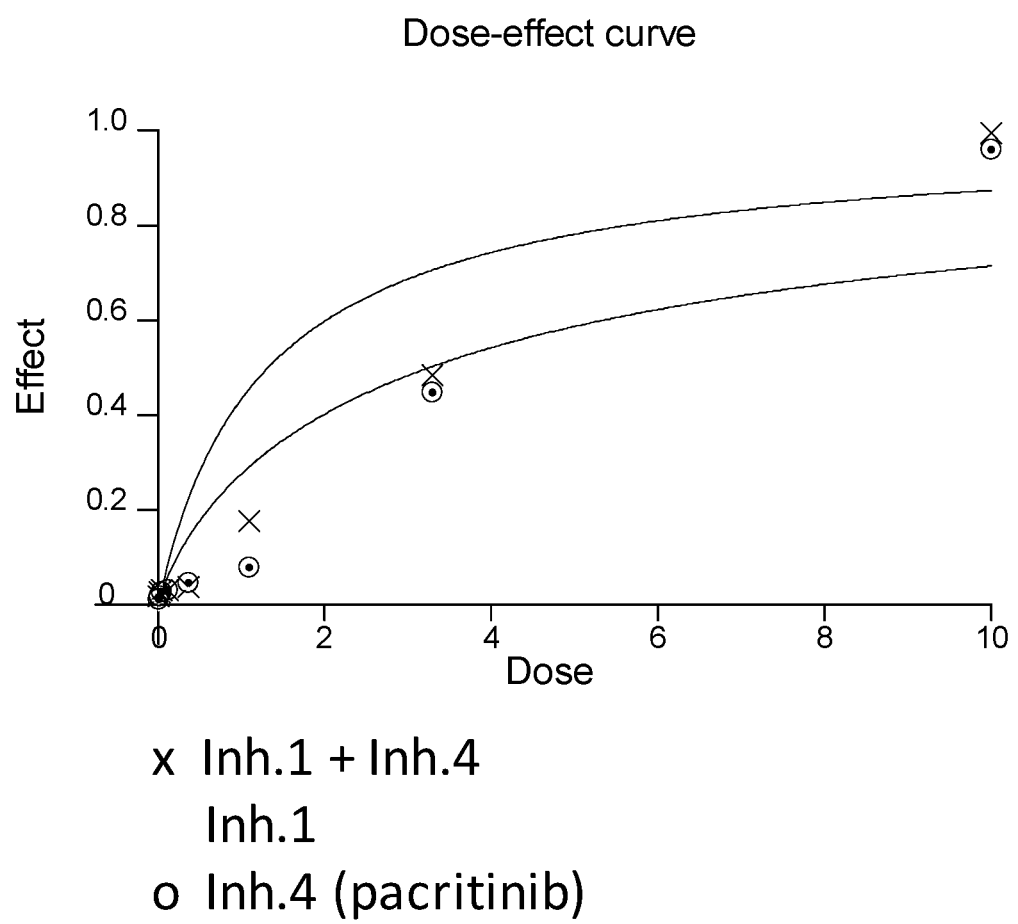

FIG. 94 illustrates the dose-effect curves obtained for the tested OCI-Ly3 cell line (DLBCL-ABC) using combined dosing of the BTK inhibitor of Formula (XVIII) ("Inh.1") and the JAK-2 inhibitor of Formula LIV ("Inh.4") (pacritinib). The y-axis ("Effect") is given in units of Fa (fraction affected) and the x-axis ("Dose") is given in linear units of μM.

Figure 95:
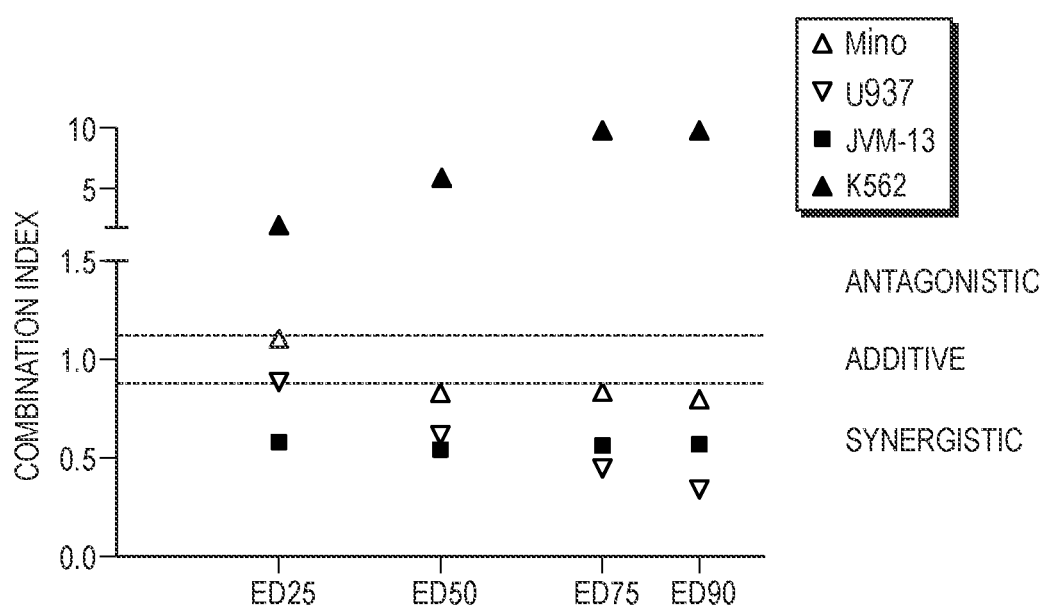

FIG. 95 illustrates the synergy observed in certain cell lines when the BTK inhibitor of Formula XVIII and the BCL-2 inhibitor of Formula (LXVI) (venetoclax) are combined. The tested cell lines include Mino (mantle cell lymphoma), U937 (histiocytic lymphoma and/or myeloid), JVM-13 (cell lymphoma, mantle), and K562 (leukemia, myeloid, and/or chronic myelogenous leukemia). The dose-effect curves for these cell lines are given in FIG. 96, FIG. 97, FIG. 69, and FIG. 70.

Figure 96:
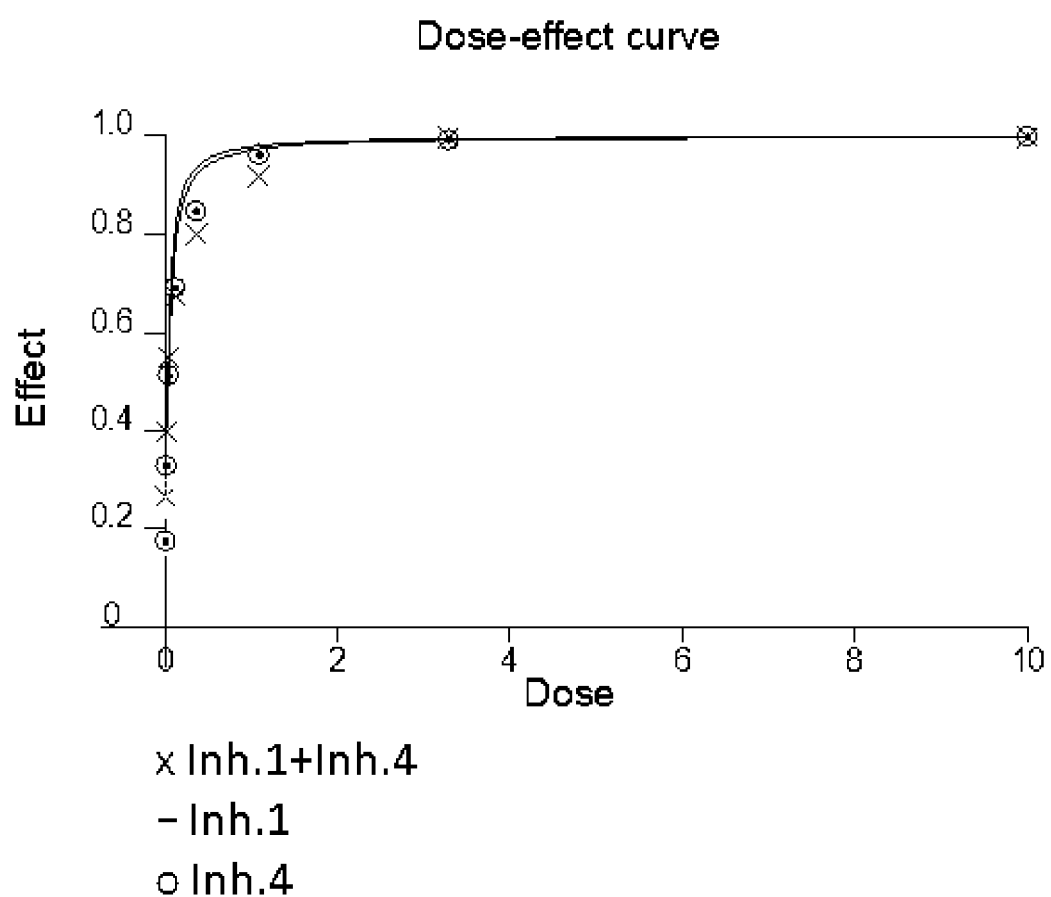

FIG. 96 illustrates the dose-effect curves obtained for the tested Mino cell line (mantle cell lymphoma) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 97:
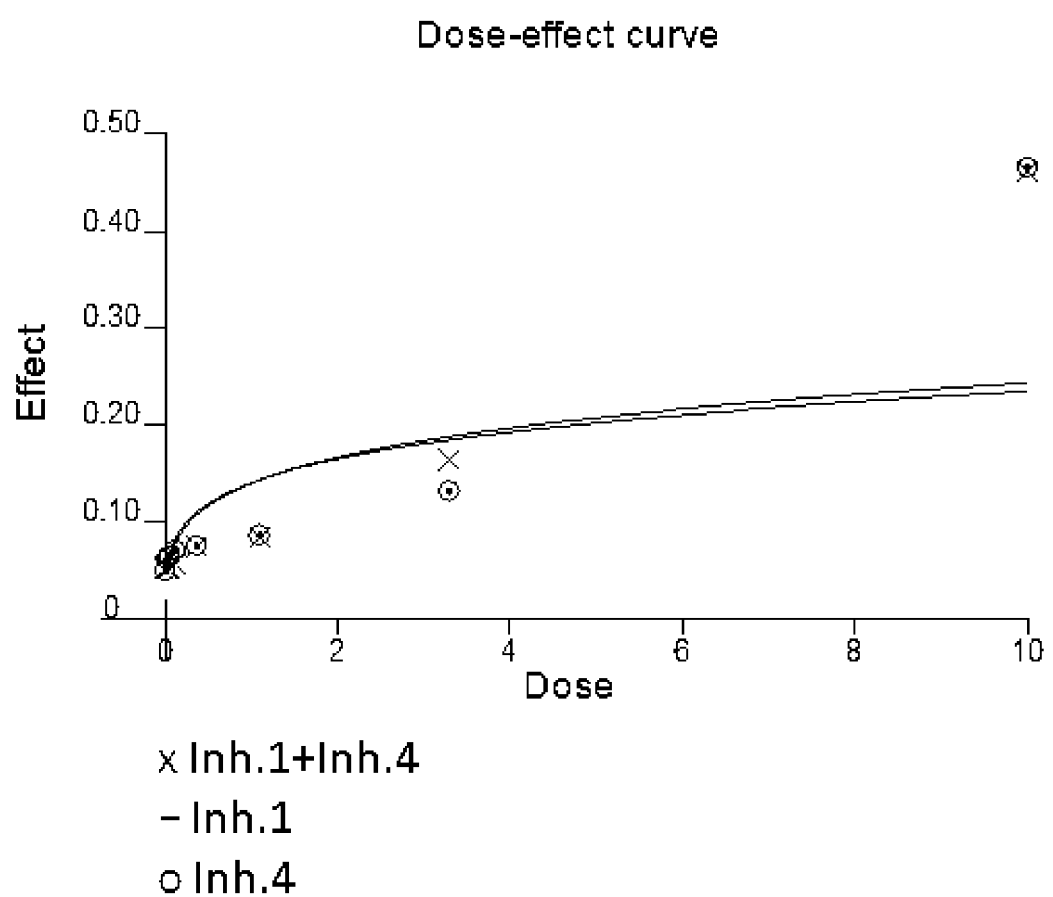

FIG. 97 illustrates the dose-effect curves obtained for the tested U937 cell line (histiocytic lymphoma and/or myeloid) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 98:
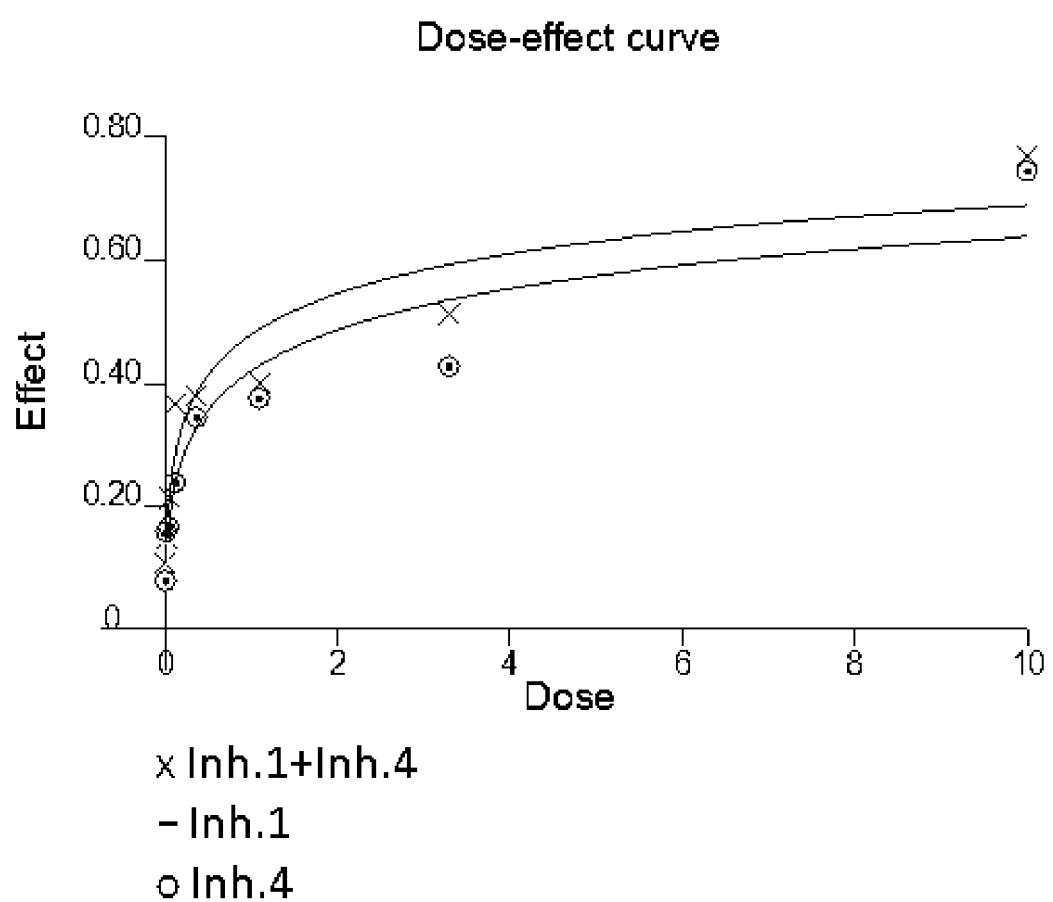

FIG. 98 illustrates the dose-effect curves obtained for the tested JVM-13 cell line (cell lymphoma, mantle) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 99:
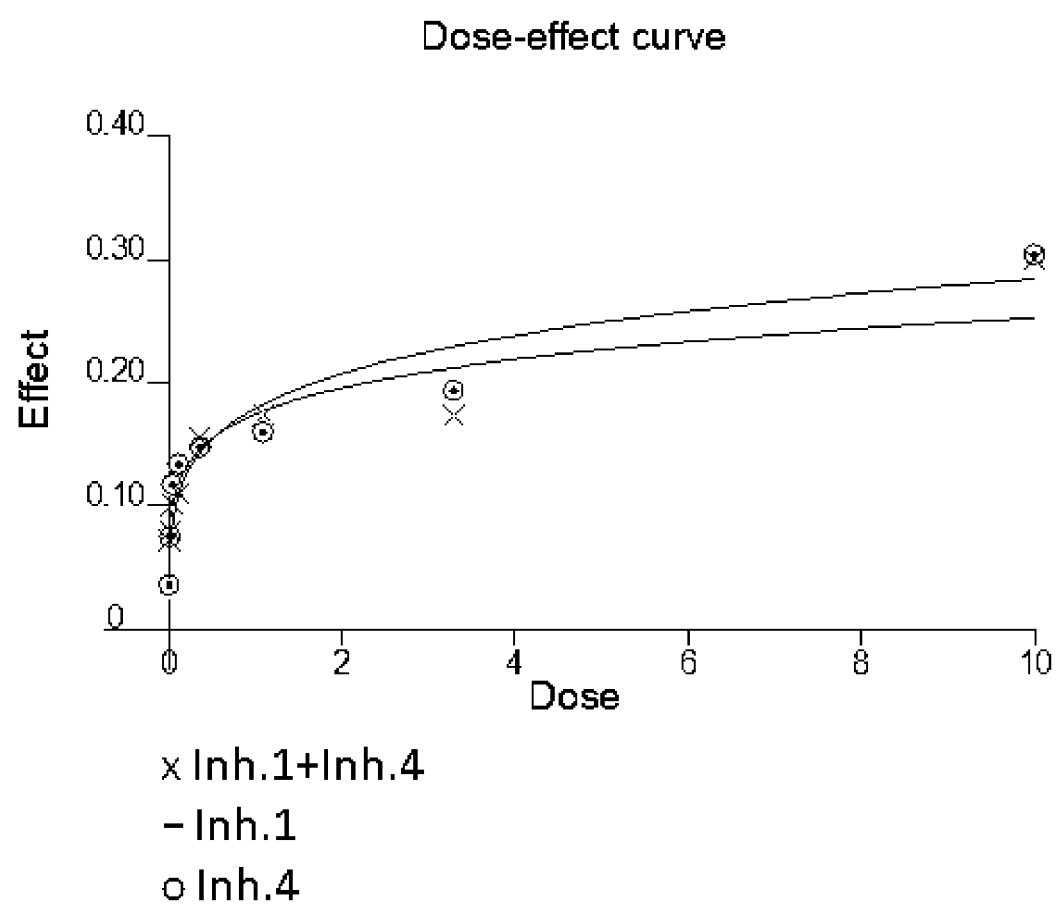

FIG. 99 illustrates the dose-effect curves obtained for the tested K562 cell line (leukemia, myeloid, and/or chronic myelogenous leukemia) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 100:
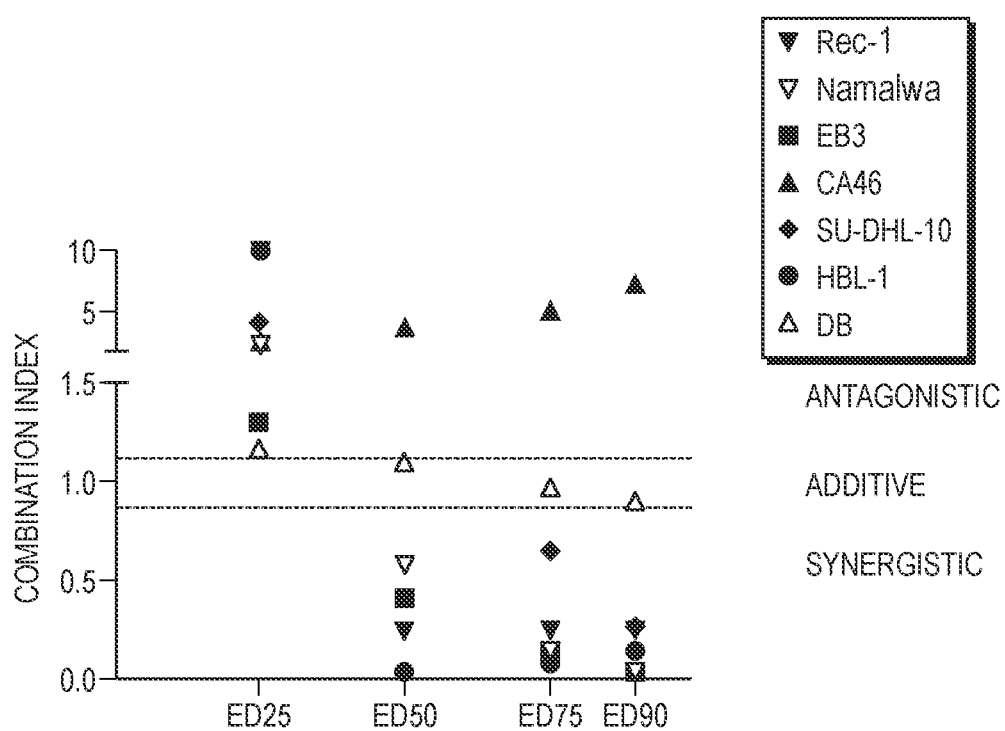

FIG. 100 illustrates the synergy observed in certain cell lines when the BTK inhibitor of Formula XVIII and the BCL-2 inhibitor of Formula (LXVI) (venetoclax) are combined. The tested cell lines include Rec-1 (follicular lymphoma), EB3 (B lymphocyte, Burkitt's lymphoma), CA46 (B lymphocyte, Burkitt's lymphoma), DB (cell lymphoma, mantle), Namalwa (B lymphocyte, Burkitt's lymphoma), HBL-1 (DLBCL-ABC), and SU-DHL-10 (DLBCL-GCB). The dose-effect curves for these cell lines are given in FIG. 101, FIG. 102, FIG. 103, FIG. 104, FIG. 105, FIG. 106, and FIG. 107.

Figure 101:
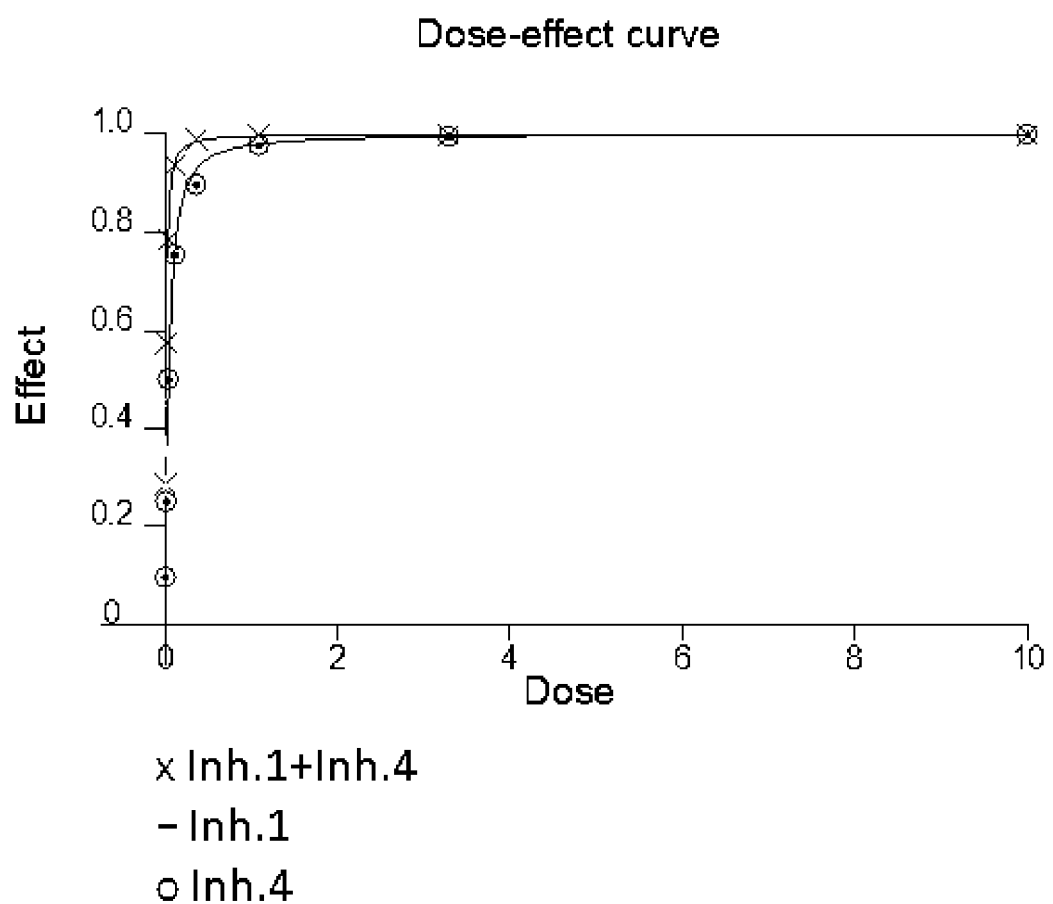

FIG. 101 illustrates the dose-effect curves obtained for the tested Rec-1 cell line (follicular lymphoma) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 102:
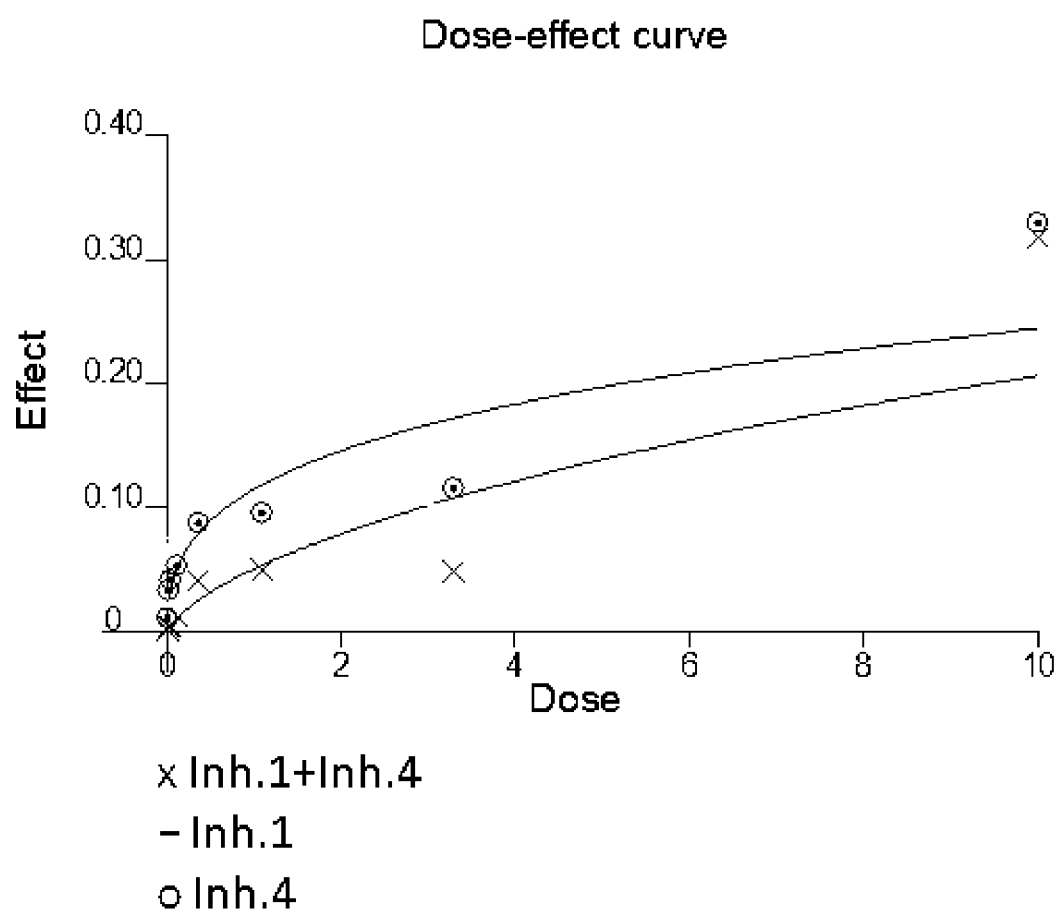

FIG. 102 illustrates the dose-effect curves obtained for the tested EB3 cell line (B lymphocyte, Burkitt's lymphoma) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 103:
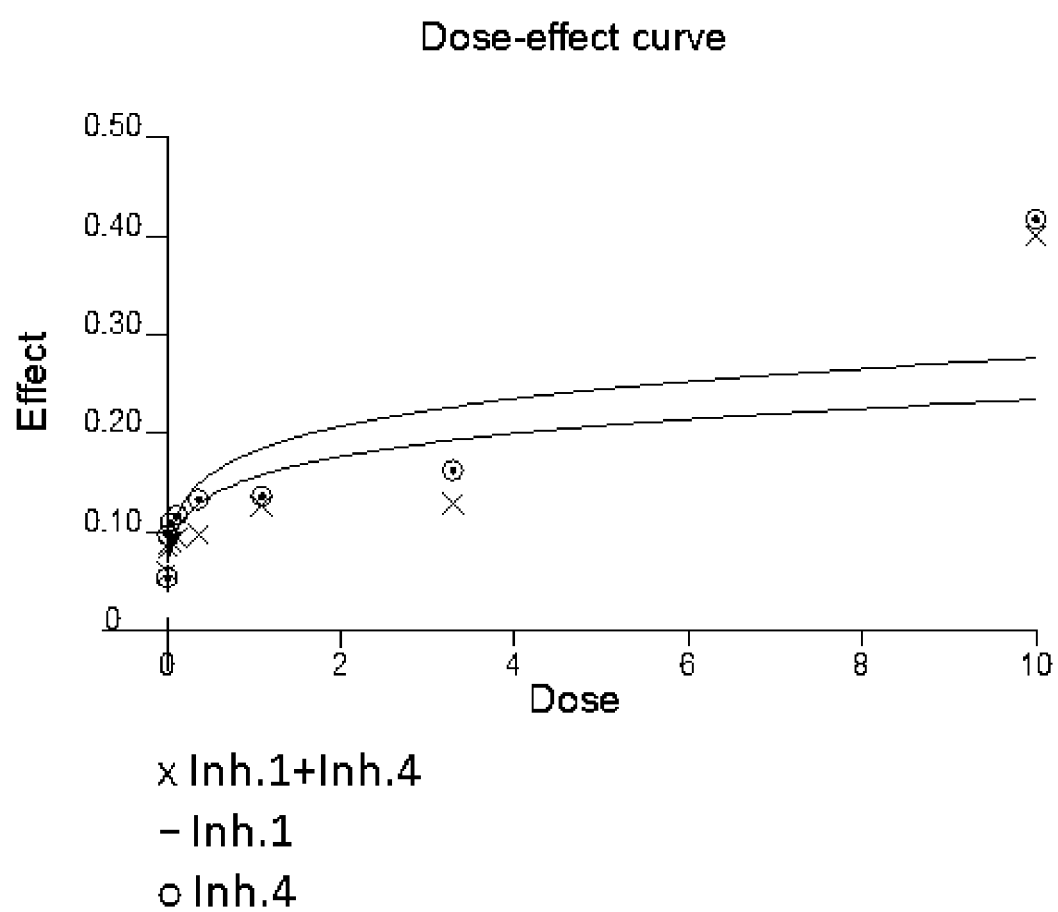

FIG. 103 illustrates the dose-effect curves obtained for the tested CA46 cell line (B lymphocyte, Burkitt's lymphoma) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 104:
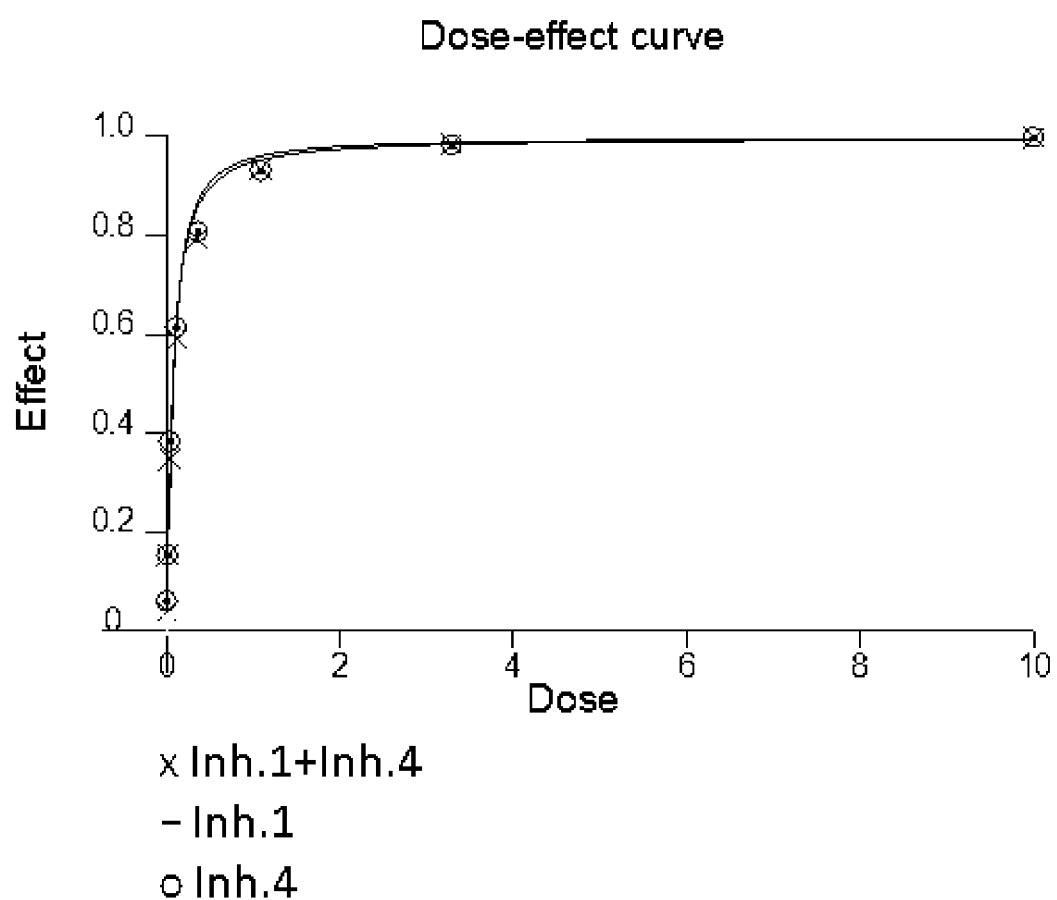

FIG. 104 illustrates the dose-effect curves obtained for the tested DB cell line (cell lymphoma, mantle) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 105:
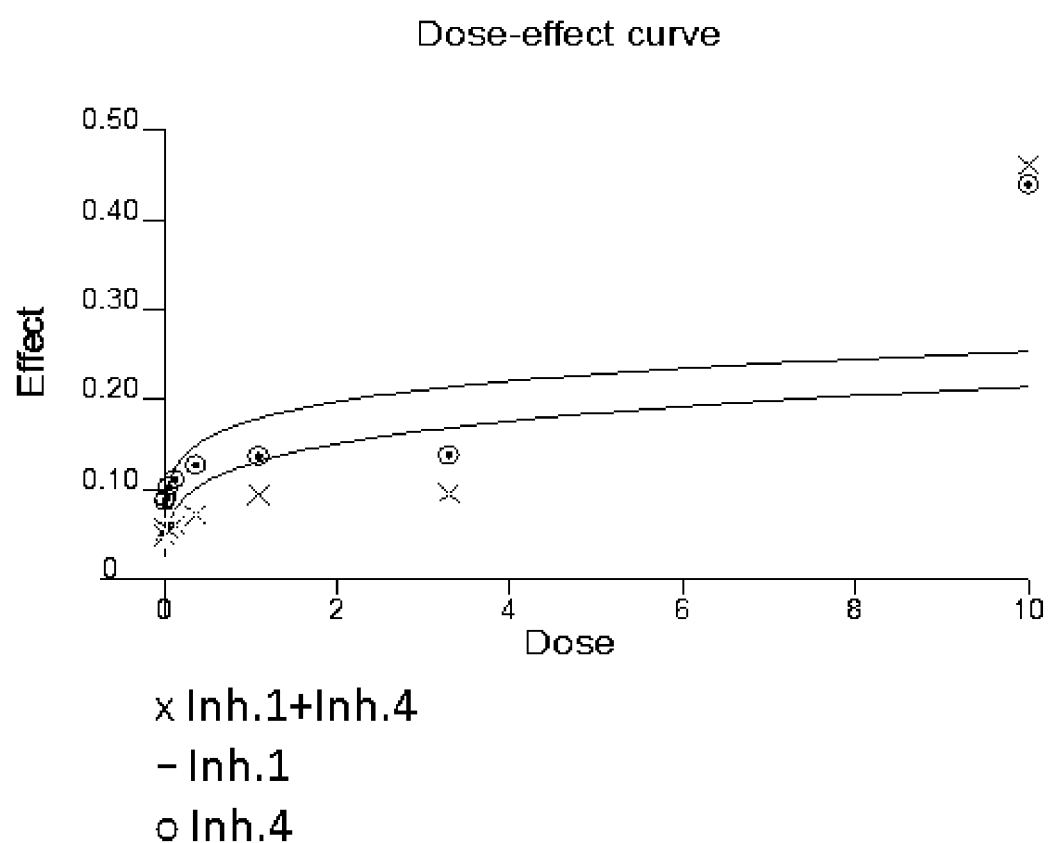

FIG. 105 illustrates the dose-effect curves obtained for the tested Namalwa cell line (B lymphocyte, Burkitt's lymphoma) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 106:
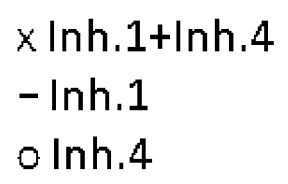

FIG. 106 illustrates the dose-effect curves obtained for the tested HBL-1 cell line (DLBCL-ABC) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 107:
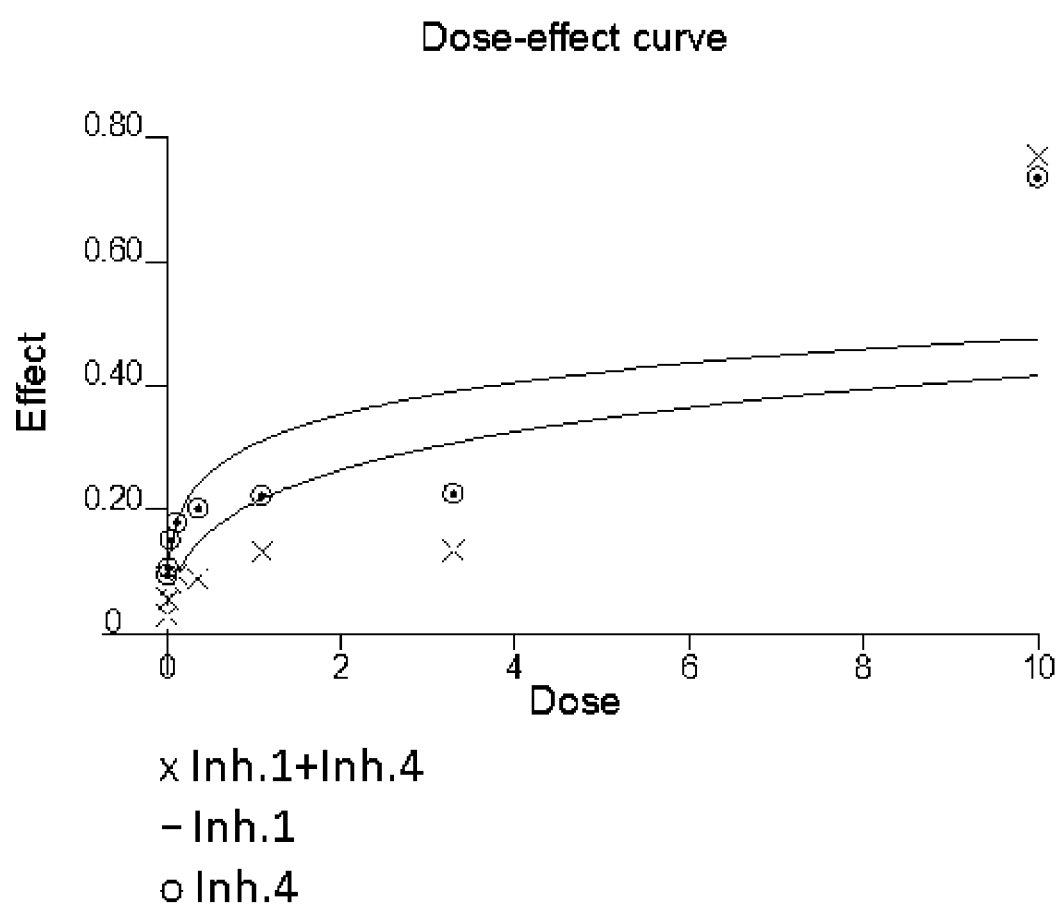

FIG. 107 illustrates the dose-effect curves obtained for the tested SU-DHL-10 cell line (DLBCL-GCB) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 108:
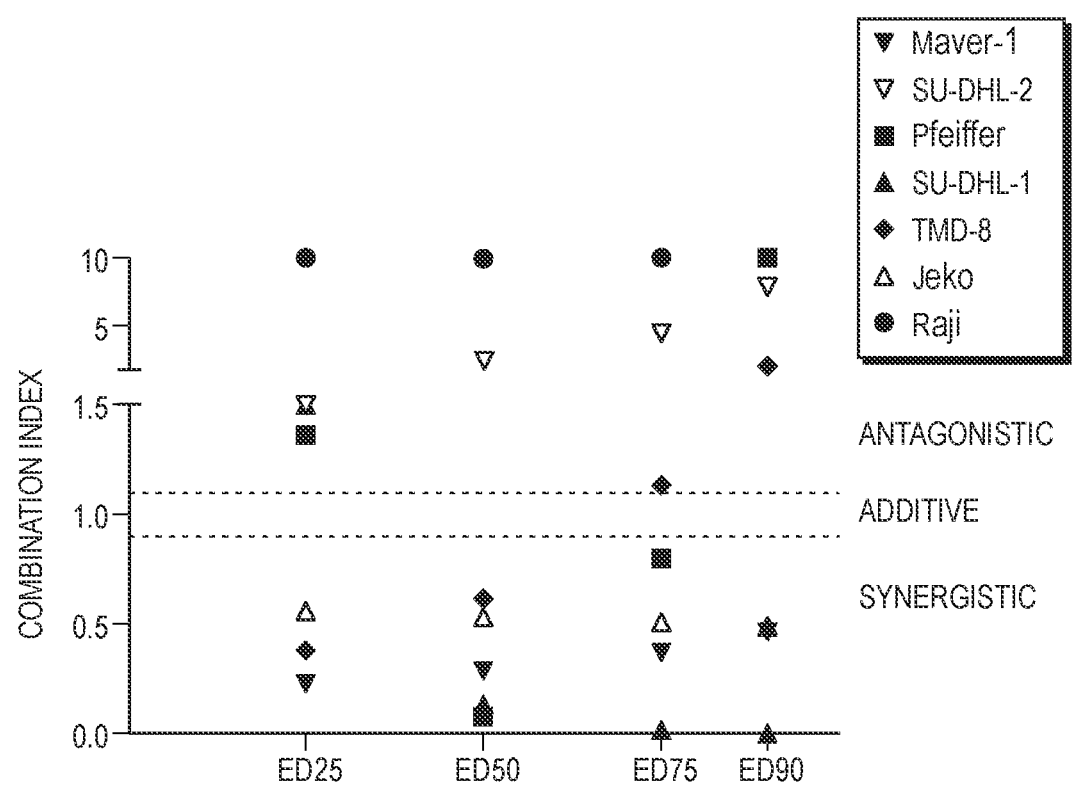

FIG. 108 illustrates the synergy observed in certain cell lines when the BTK inhibitor of Formula XVIII and the BCL-2 inhibitor of Formula (LXVI) (venetoclax) are combined. The tested cell lines include Maver-1 (B cell lymphoma, mantle), SU-DHL-1 (DLBCL-ABC), Pfeiffer (follicular lymphoma), SU-DHL-2 (DLBCL-ABC), TMD-8 (DLBCL-ABC), Raji (B lymphocyte, Burkitt's lymphoma), and Jeko (B cell lymphoma, mantle). The dose-effect curves for these cell lines are given in FIG. 109, FIG. 110, FIG. 111, FIG. 112, FIG. 113, FIG. 114, and FIG. 115.

Figure 109:
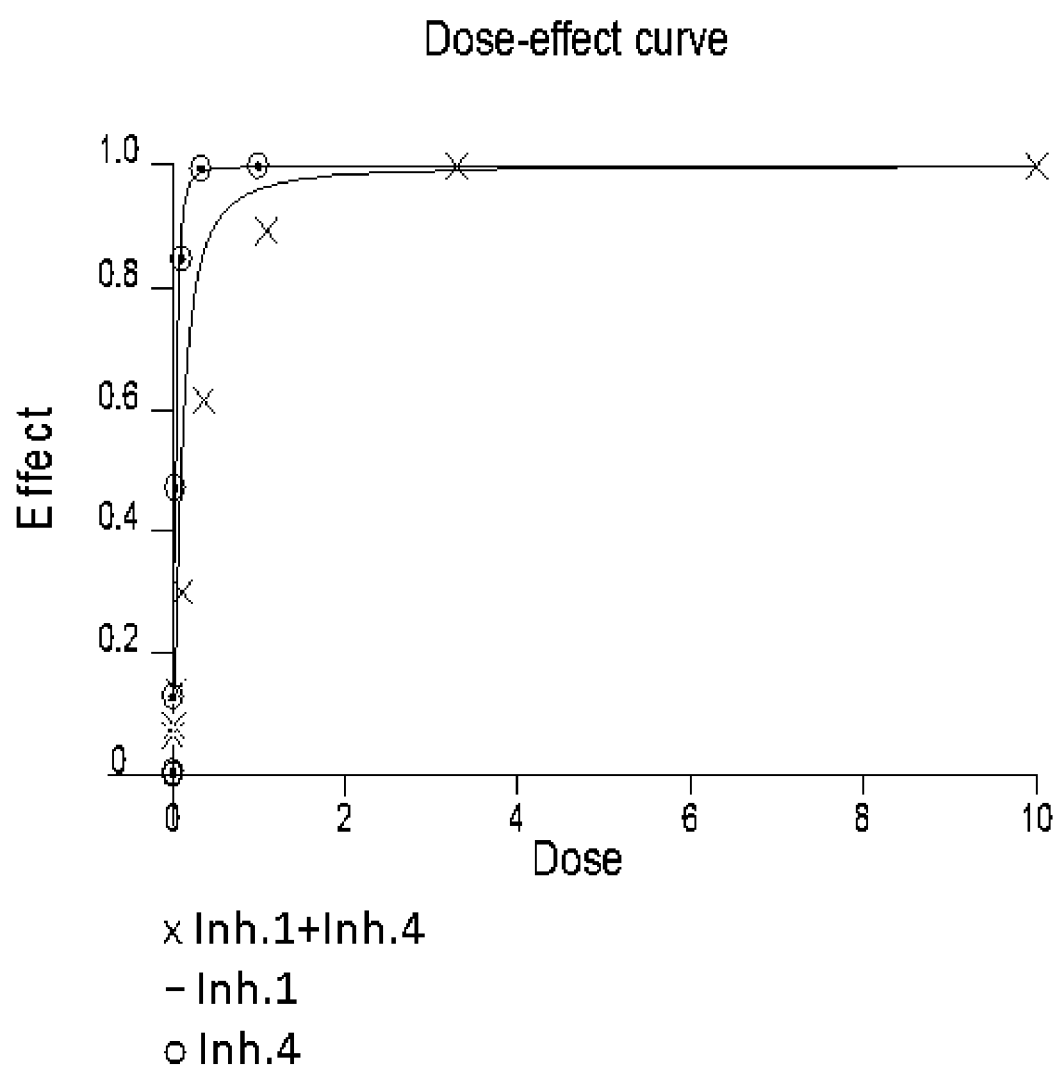

FIG. 109 illustrates the dose-effect curves obtained for the tested Maver-1 cell line (B cell lymphoma, mantle) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 110:
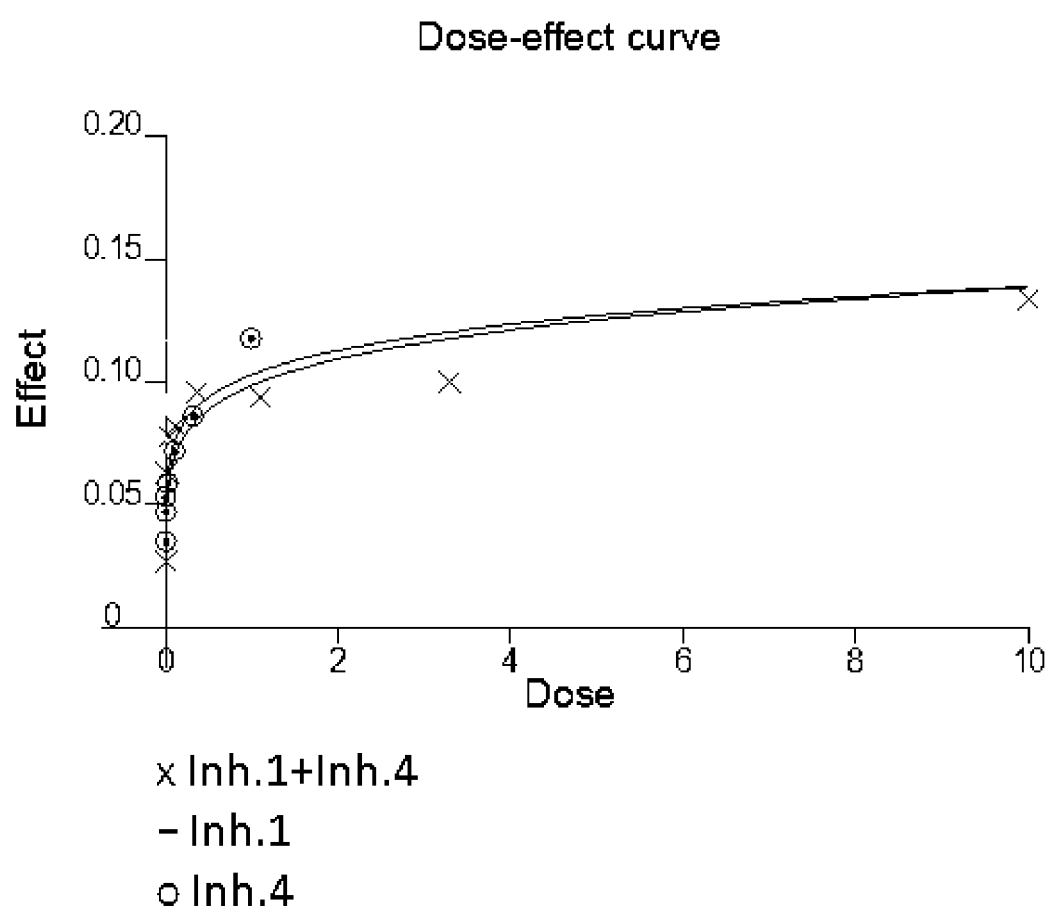

FIG. 110 illustrates the dose-effect curves obtained for the tested SU-DHL-1 cell line (DLBCL-ABC) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of μM.

Figure 111:
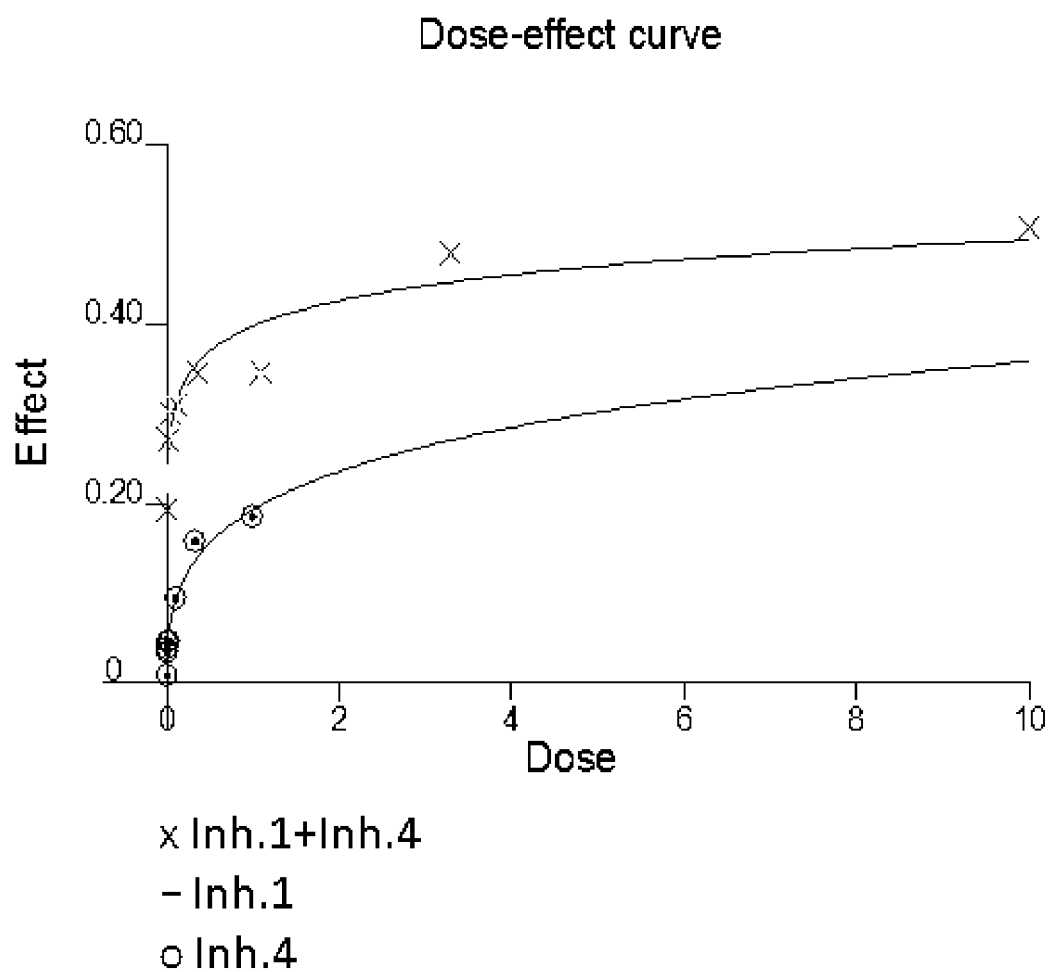

FIG. 111 illustrates the dose-effect curves obtained for the tested Pfeiffer cell line (follicular lymphoma) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of µM.

Figure 112:
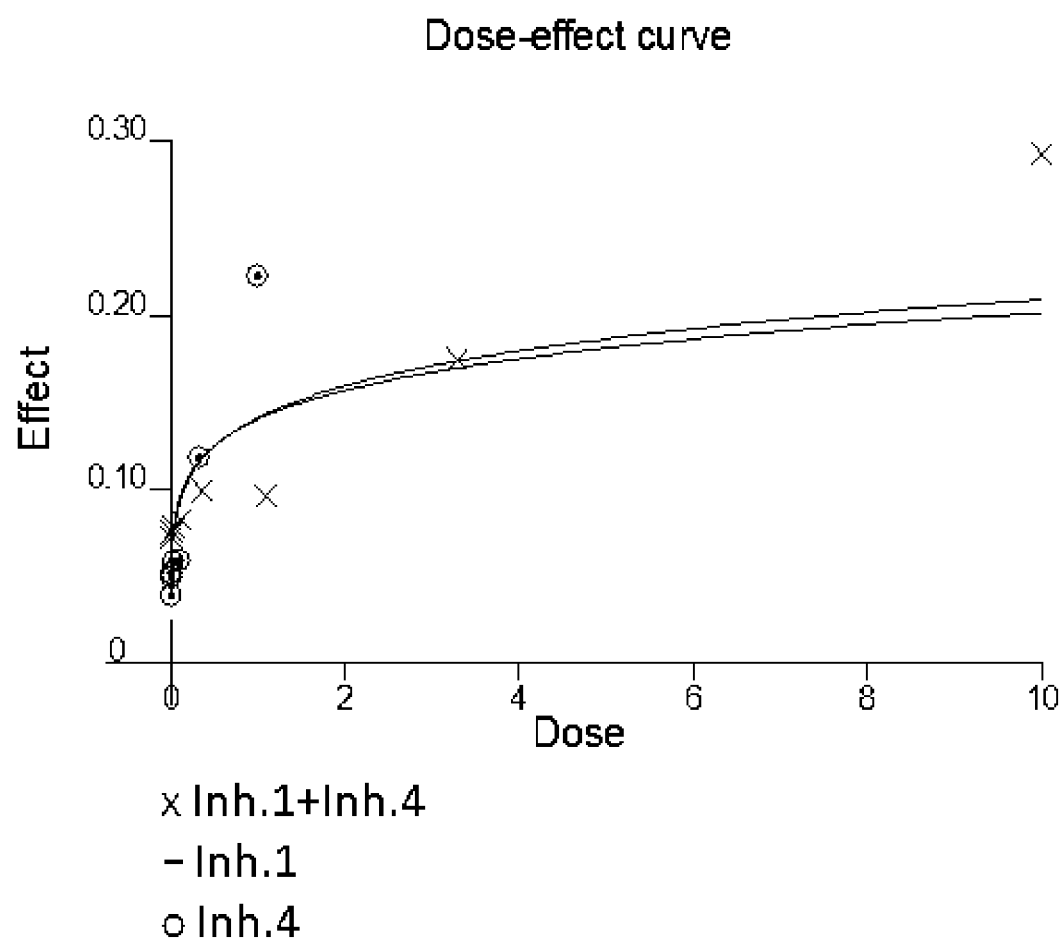

FIG. 112 illustrates the dose-effect curves obtained for the tested SU-DHL-2 cell line (DLBCL-ABC) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of µM.

Figure 113:
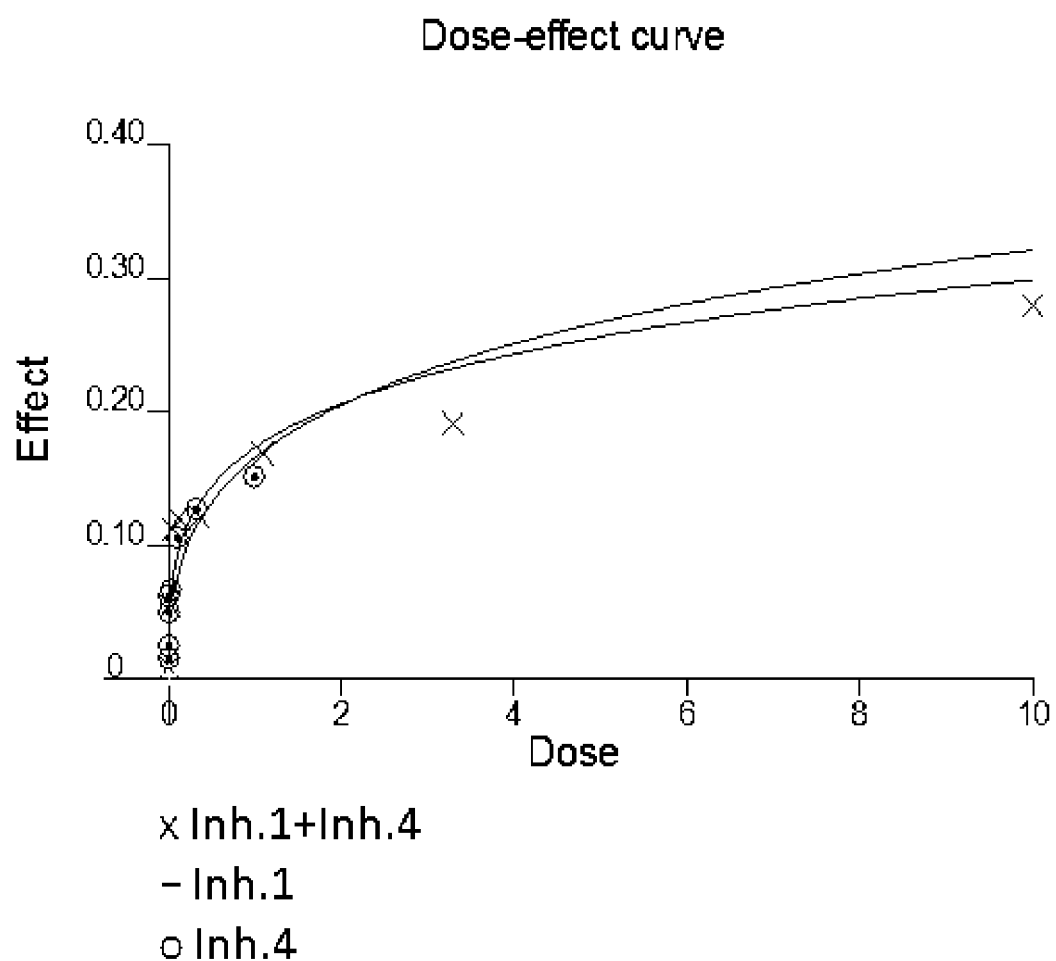

FIG. 113 illustrates the dose-effect curves obtained for the tested TMD-8 cell line (DLBCL-ABC) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of µM.

Figure 114:
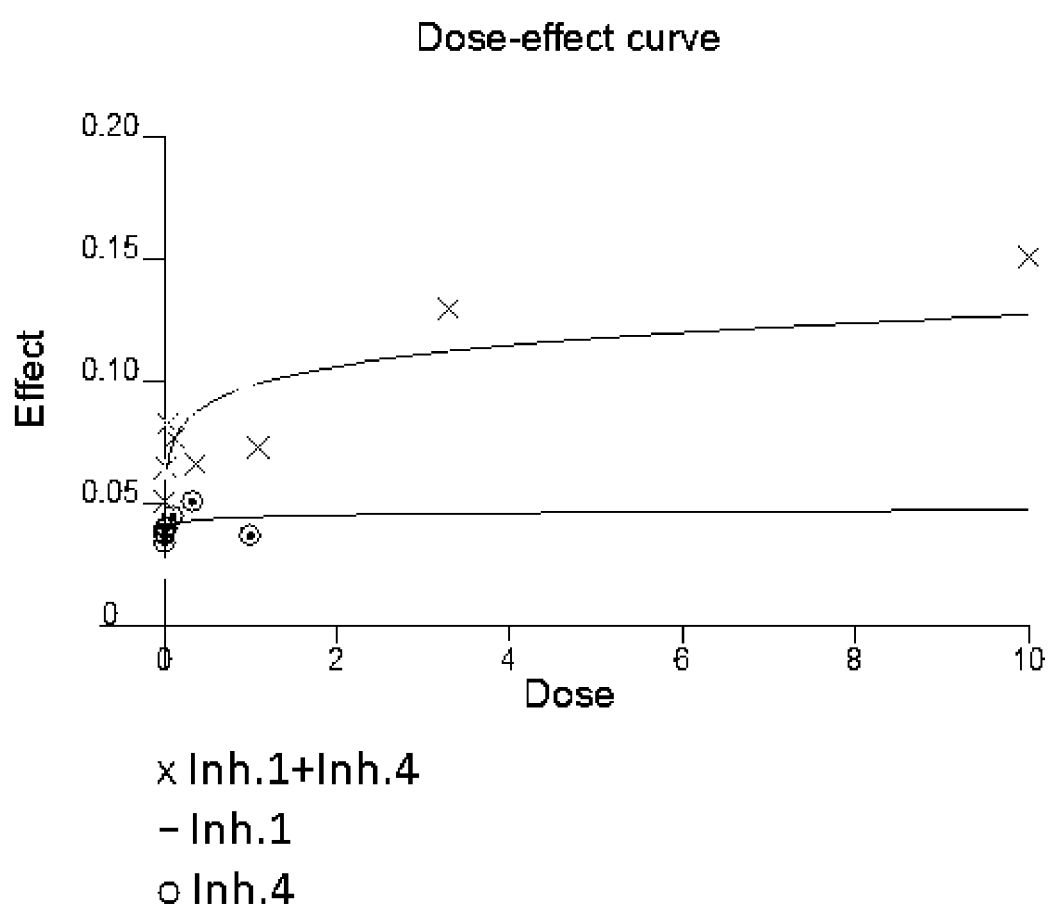

FIG. 114 illustrates the dose-effect curves obtained for the tested Raji cell line (B lymphocyte, Burkitt's lymphoma) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of µM.

Figure 115:
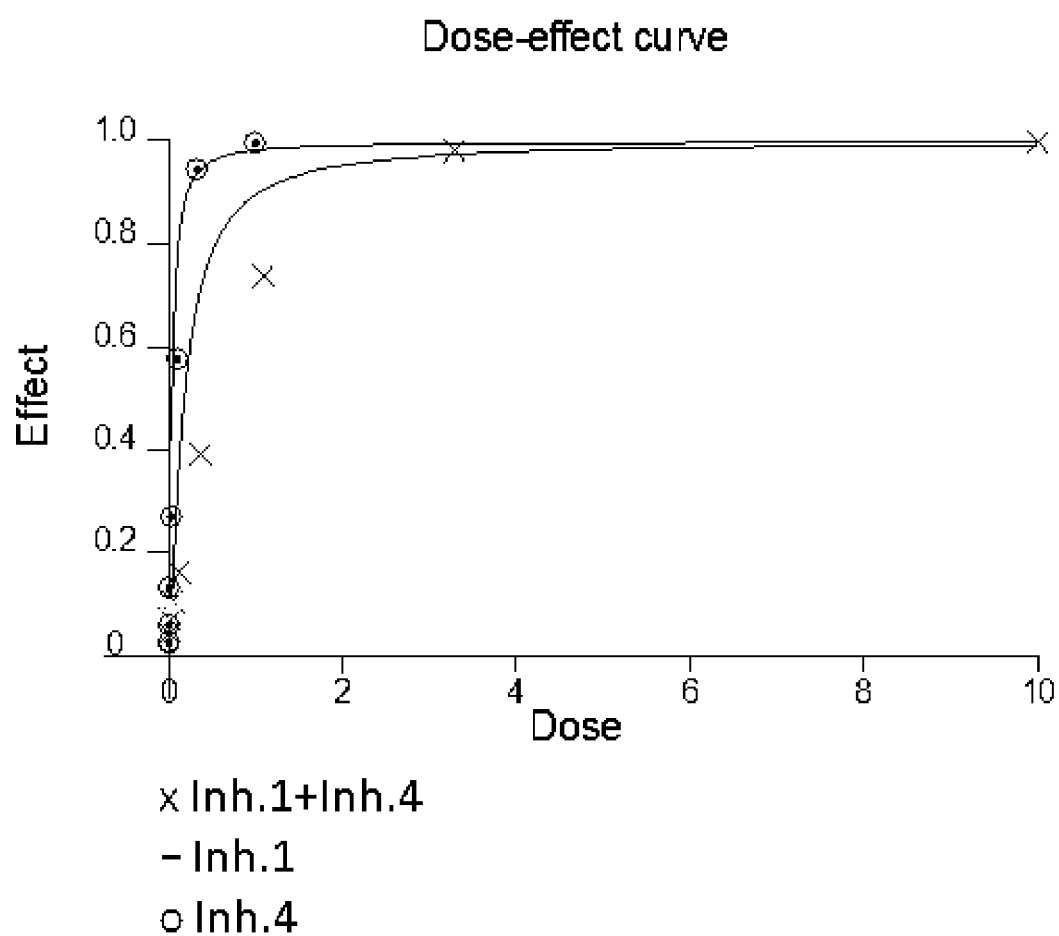

FIG. 115 illustrates the dose-effect curves obtained for the tested Jeko cell line (B cell lymphoma, mantle) using combined dosing of the BTK inhibitor of Formula XVIII ("Inh.1") and the BCL-2 inhibitor of Formula (LXVI) ("Inh.4") (venetoclax). The y-axis ("Effect") is given in units of Fa (fraction affected) and the x-axis ("Dose") is given in linear units of µM.

Figure 116:
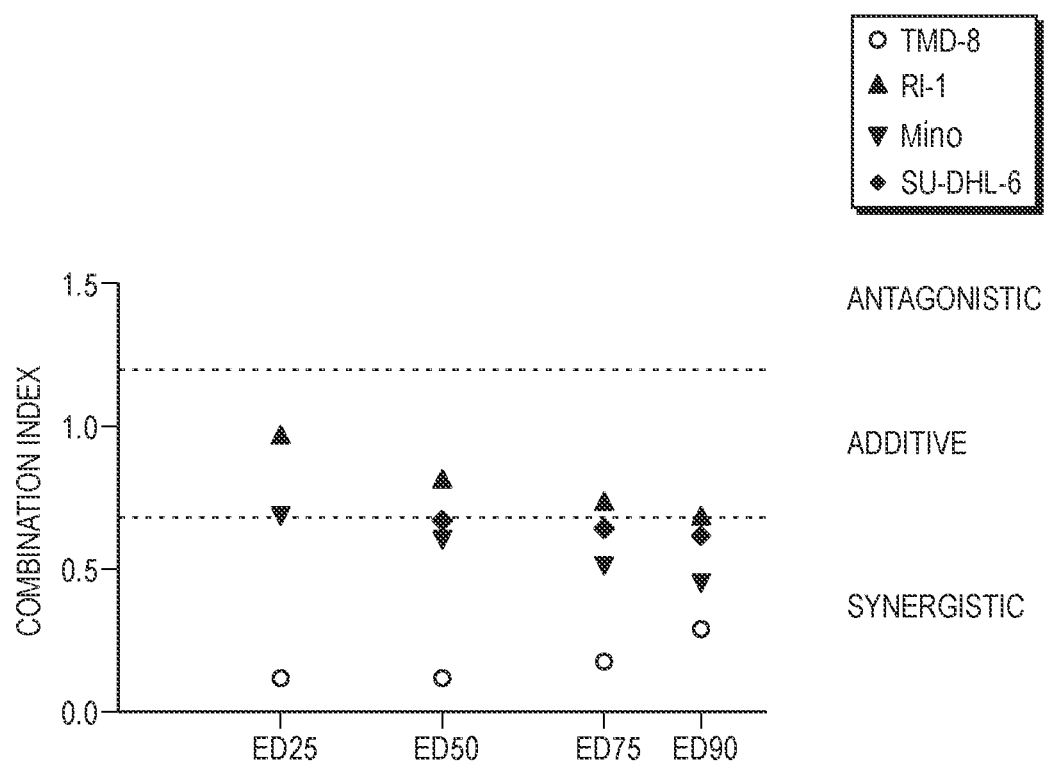

FIG. 116 illustrates the synergy observed in certain cell lines when the BTK inhibitor of Formula (XX-A) ("Inh.5") (ibrutinib) and the BCL-2 inhibitor of Formula (LXVI) ("Inh.4") (venetoclax) are combined. The tested cell lines include TMD-8 (DLBCL-ABC), RI-1 (NHL), Mino (MCL), and SU-DHL-6 (DLBCL-GCB). The dose-effect curves for these cell lines are given in FIG. 117, FIG. 118, FIG. 119, and FIG. 120.

Figure 117:
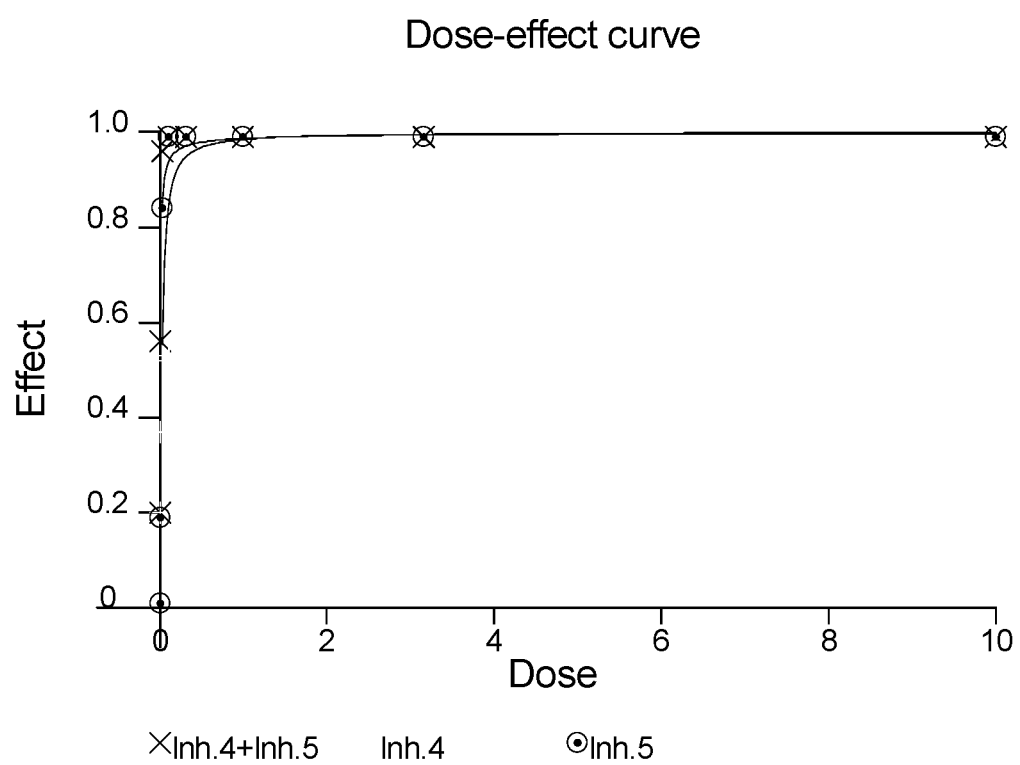

FIG. 117 illustrates the dose-effect curves obtained for the tested TMD-8 cell line (DLBCL-ABC) using combined dosing of the BTK inhibitor of Formula (XX-A) ("Inh.5") (ibrutinib) and the BCL-2 inhibitor of Formula (LXVI) ("Inh.4") (venetoclax). The y-axis ("Effect") is given in units of Fa (fraction affected) and the x-axis ("Dose") is given in linear units of µM.

Figure 118:
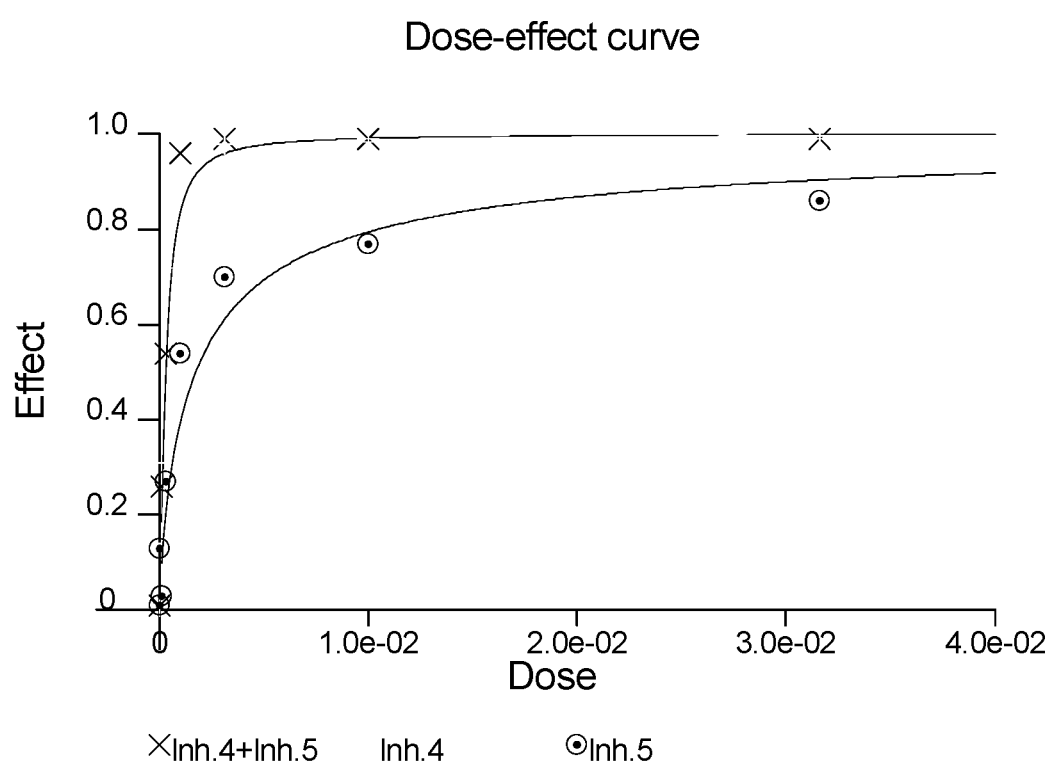

FIG. 118 illustrates the dose-effect curves obtained for the tested RI-1 cell line (NHL) using combined dosing of the BTK inhibitor of Formula (XX-A) ("Inh.5") (ibrutinib) and the BCL-2 inhibitor of Formula (LXVI) ("Inh.4") (venetoclax). The y-axis ("Effect") is given in units of Fa (fraction affected) and the x-axis ("Dose") is given in linear units of µM.

Figure 119:
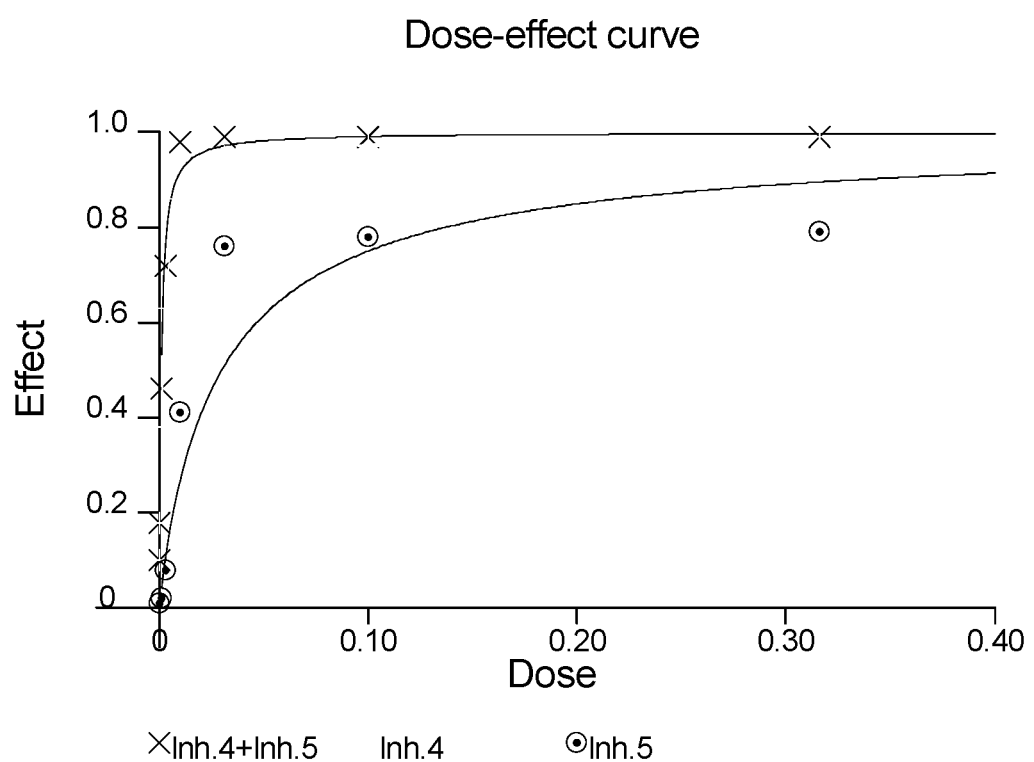

FIG. 119 illustrates the dose-effect curves obtained for the tested Mino cell line (MCL) using combined dosing of the BTK inhibitor of Formula (XX-A) ("Inh.5") (ibrutinib) and the BCL-2 inhibitor of Formula (LXVI) ("Inh.4") (venetoclax). The y-axis ("Effect") is given in units of Fa (fraction affected) and the x-axis ("Dose") is given in linear units of µM.

Figure 120:
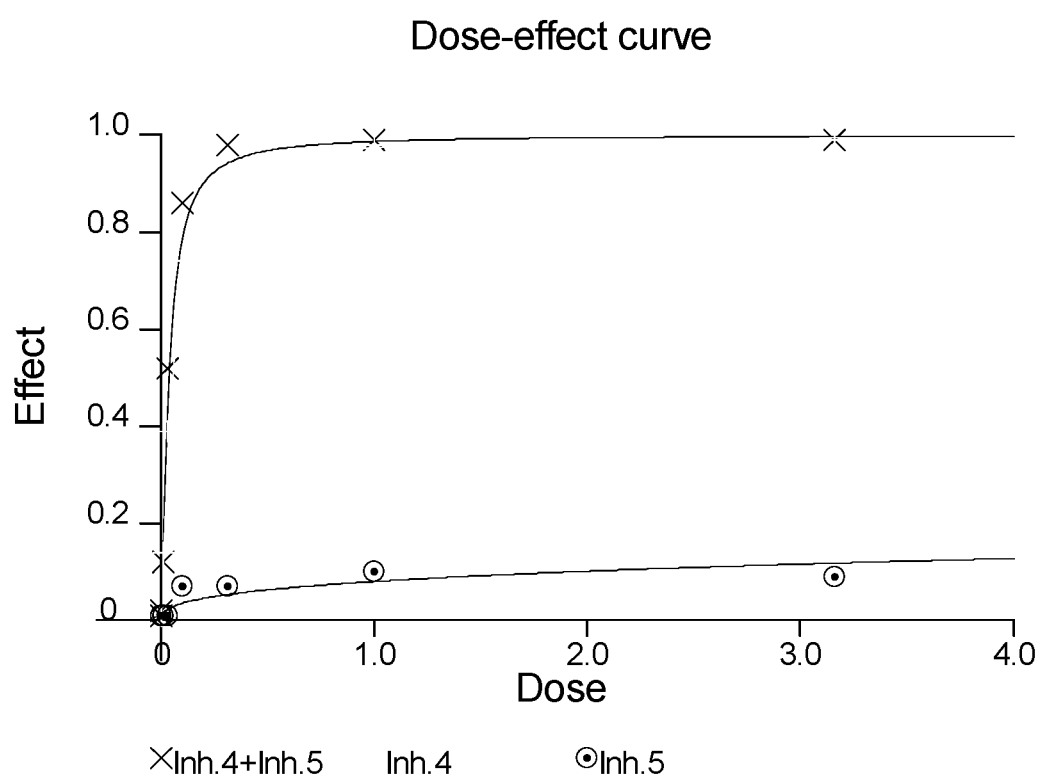

FIG. 120 illustrates the dose-effect curves obtained for the tested SU-DHL-6 cell line (DLBCL-GCB) using combined dosing of the BTK inhibitor of Formula (XX-A) ("Inh.5") (ibrutinib) and the BCL-2 inhibitor of Formula (LXVI) ("Inh.4") (venetoclax). The y-axis ("Effect") is given in units of Fa (fraction affected) and the x-axis ("Dose") is given in linear units of µM.

Figure 121:
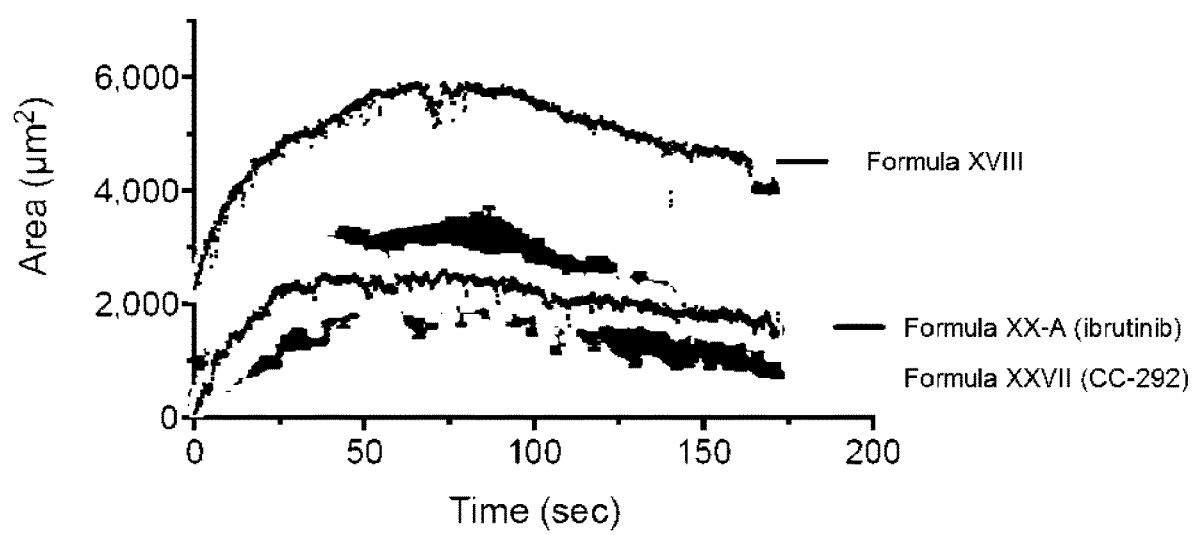

FIG. 121 illustrates a quantitative comparison obtained by in vivo analysis of early thrombus dynamics in a humanized mouse laser injury model using three BTK inhibitors at a concentration 1 µM.

Figure 122:
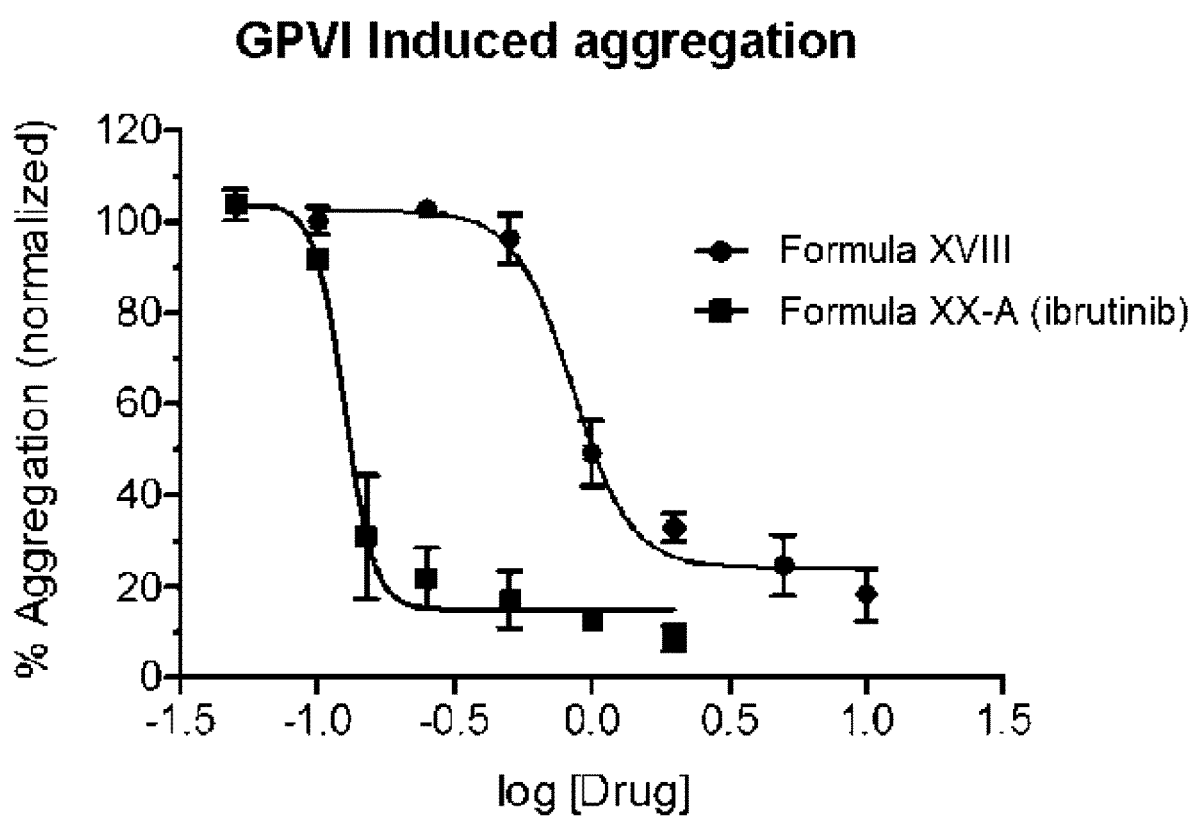

FIG. 122 illustrates the results of GPVI platelet aggregation studies of Formula XVIII (IC50=1.15 µM) and Formula (XX-A) (ibrutinib, IC50=0.13 µM).

Figure 123:
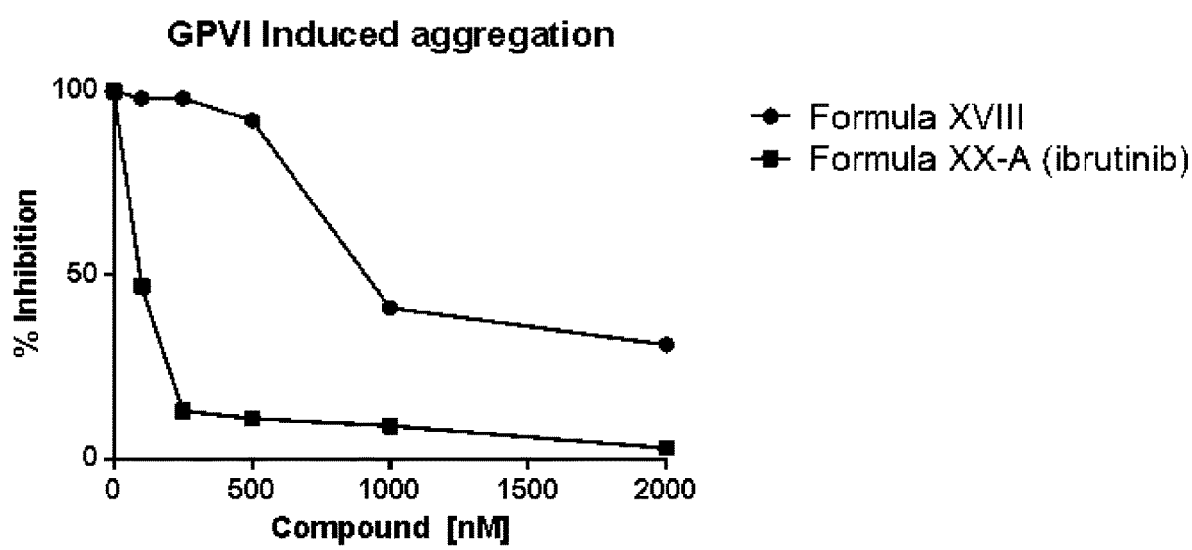

FIG. 123 illustrates the results of GPVI platelet aggregation studies of Formula XVIII and Formula (XX-A) (ibrutinib).

Figure 124:
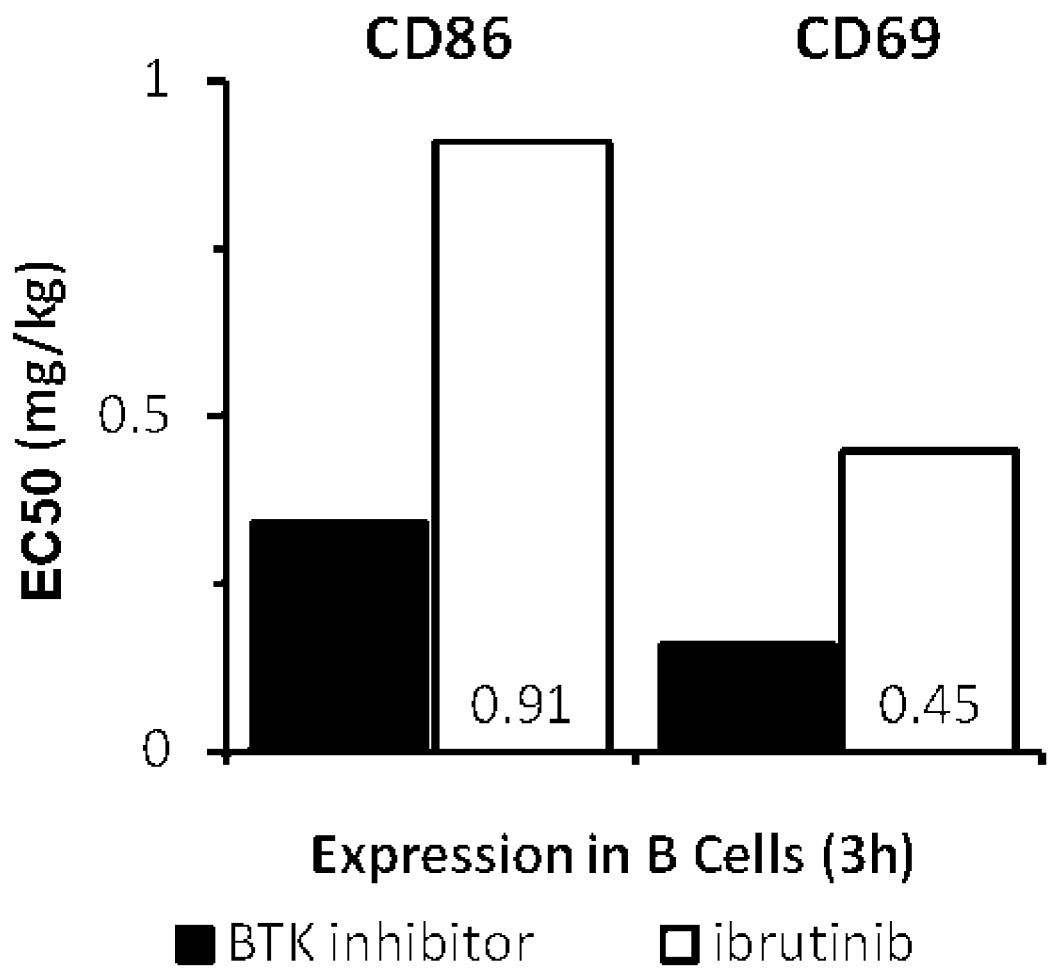

FIG. 124 illustrates in vivo potency of Formula (XVIII) (labeled "BTK inhibitor") and ibrutinib. Mice were gavaged at increasing drug concentration and sacrificed at one time point (3 h post-dose). BCR is stimulated with IgM and the expression of activation markers CD69 and CD86 are monitored by flow cytometry to determine $EC_{50}$'s. The results show that Formula (XVIII) is more potent at inhibiting expression of activation makers than ibrutinib.

Figure 1:
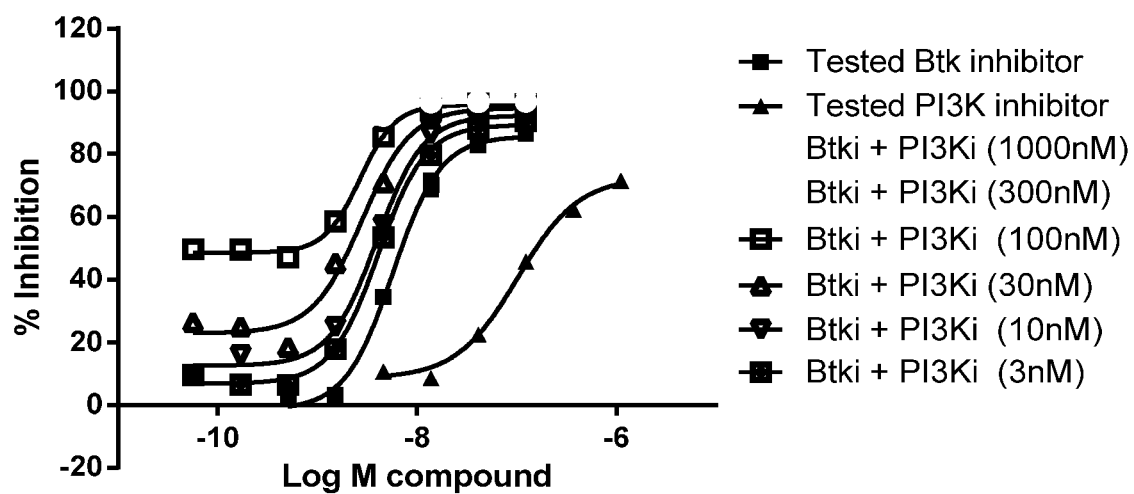
FIG. 1 illustrates the sensitivity of the TMD8 diffuse large B cell lymphoma (DLBCL) cell line to individual treatment with the BTK inhibitor of Formula XVIII ("Tested Btk Inhibitor") and the PI3K inhibitor of Formula IX ("Tested PI3K Inhibitor") and combined treatment with Formula XVIII and Formula IX ("Btki+PI3Ki") at different concentrations. The concentration of the first agent in the combination (the BTK inhibitor) and the concentration of the individual agents is given on the x-axis, and the concentration of the added PI3K inhibitor in combination with the BTK inhibitor is given in the legend.
Figure 2:
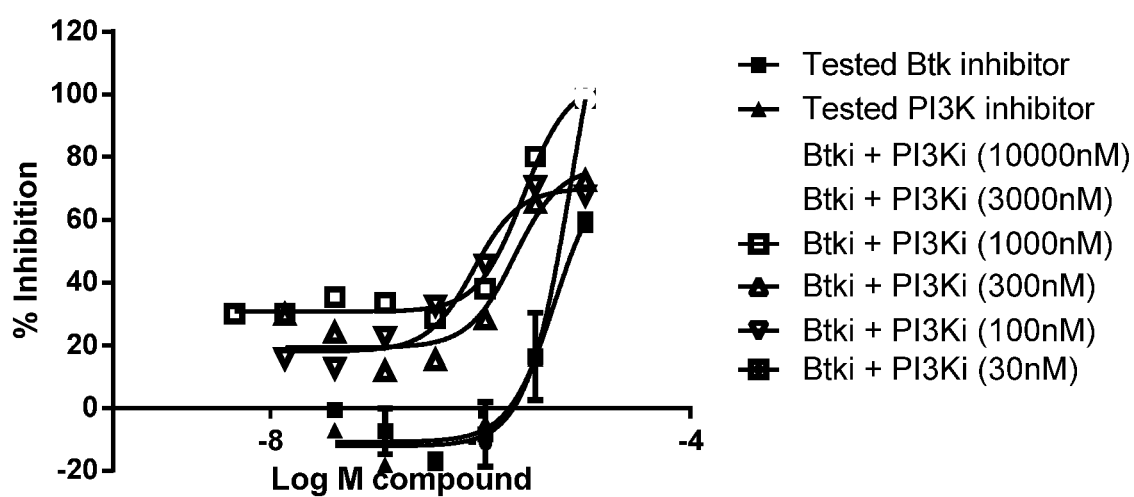
FIG. 2 illustrates the sensitivity of the MINO mantle cell lymphoma cell to individual treatment with the BTK inhibitor of Formula XVIII ("Tested Btk Inhibitor") and the PI3K inhibitor of Formula IX ("Tested PI3K Inhibitor") and combined treatment with Formula XVIII and Formula IX ("Btki+PI3Ki") at different concentrations. The concentration of the first agent in the combination (the BTK inhibitor) and the concentration of the individual agents is given on the x-axis, and the concentration of the added PI3K inhibitor in combination with the BTK inhibitor is given in the legend.
Figure 3:
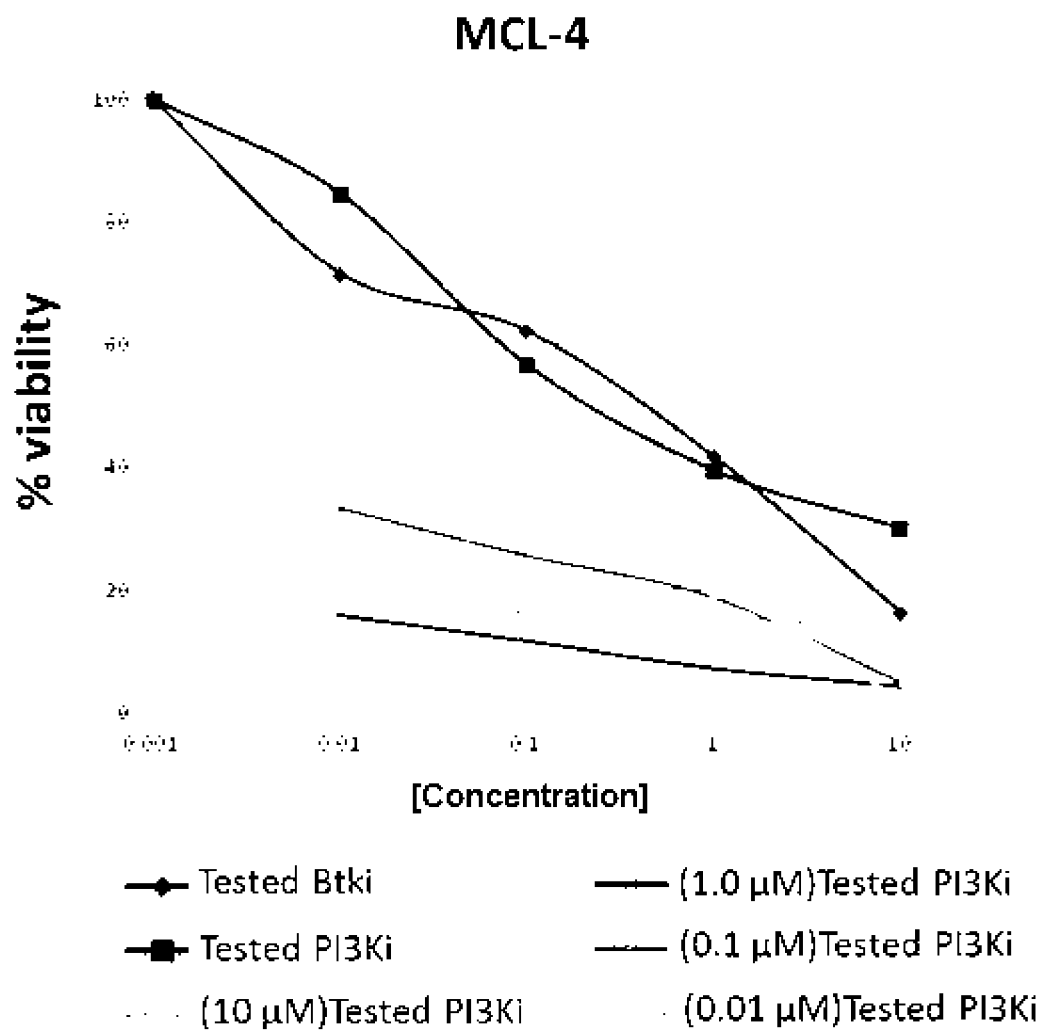
FIG. 3 illustrates the proproliferative activity in primary mantle cell lymphoma cells of Formula XVIII ("Tested Btki") and Formula IX ("Tested PI3Ki"). The percentage viability of cells ("% viability", y-axis) is plotted versus the concentration of the agent or agents. Single-agent BTK ("Tested Btki") and PI3K inhibitors ("Tested PI3Ki") are compared to four combinations of Formula XVIII and Formula IX ("(10 µM) Tested PI3Ki", "1.0 µM Tested PI3Ki," "0.1 µM Tested PI3Ki," "0.01 µM Tested PI3Ki").
Figure 4:
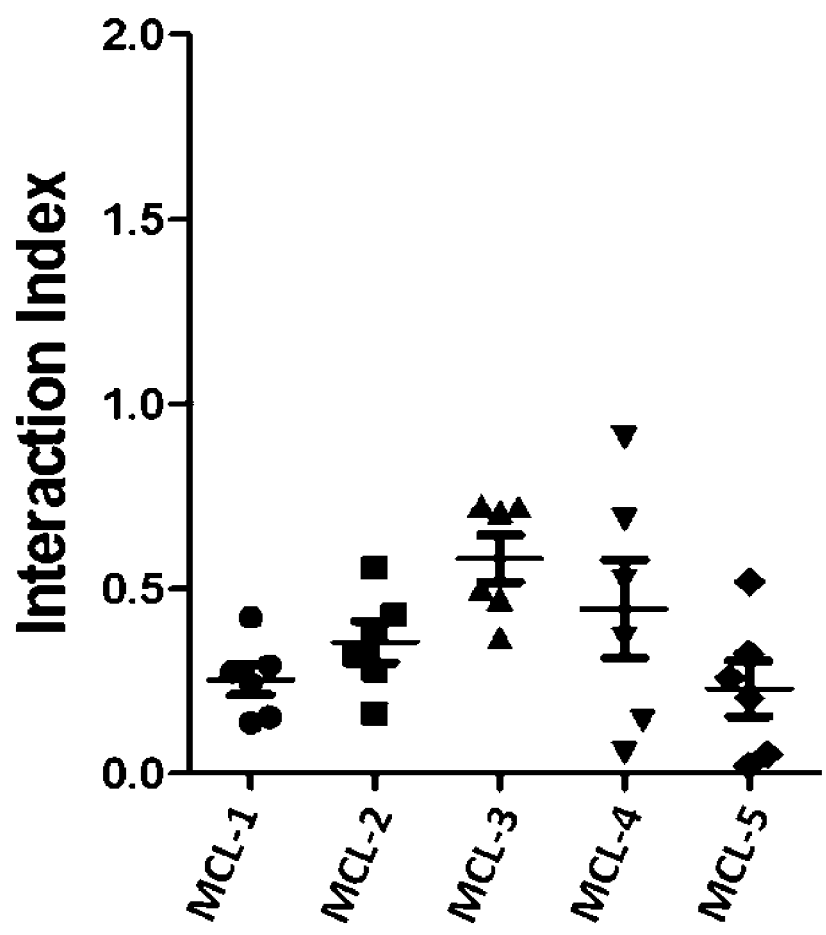
FIG. 4 illustrates the interaction index of the combination of the BTK inhibitor of Formula XVIII and the PI3K inhibitor of Formula IX in primary mantle cell lymphoma cells from different patients (MCL-1 to MCL-5). Each symbol represents a concentration from 10 uM to 0.0001 uM.
Figure 5:
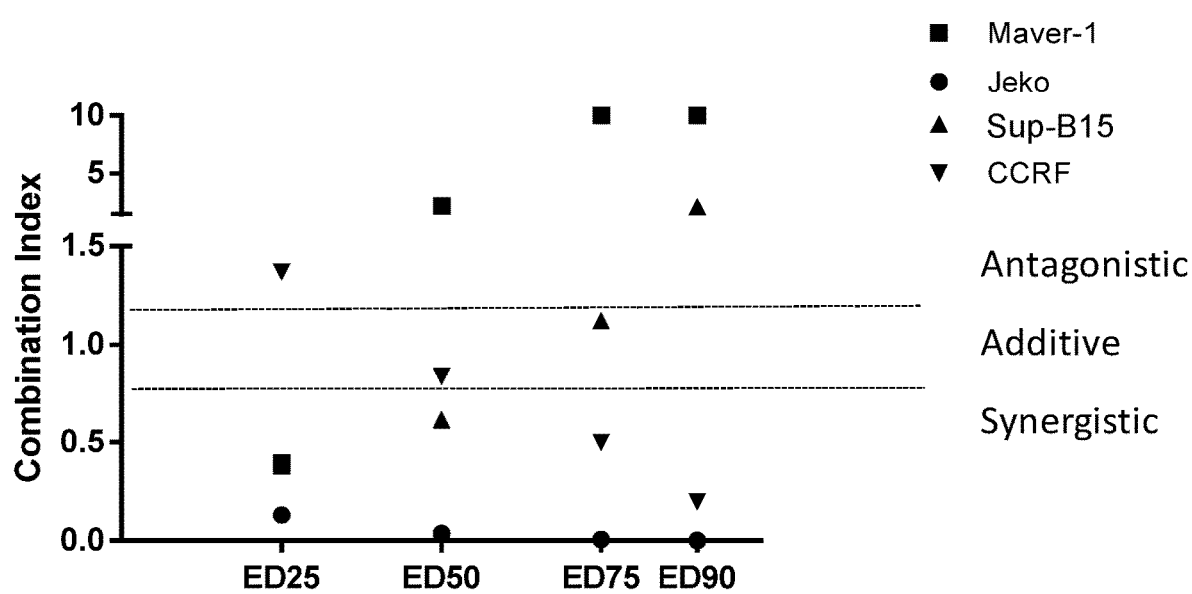
FIG. 5 illustrates the synergy observed in certain cell lines when the BTK inhibitor of Formula XVIII and the PI3K-δ inhibitor of Formula IX are combined. The tested cell lines include Maver-1 (B cell lymphoma, mantle), Jeko (B cell lymphoma, mantle), CCRF (B lymphoblast, acute lymphoblastic leukemia), and SUP-B15 (B lymphoblast, acute lymphoblastic leukemia). The dose-effect curves for these cell lines are given in FIG. 6, FIG. 7, FIG. 8, and FIG. 9. ED25, ED50, ED75, and ED90 refer to the effective doses causing 25%, 50%, 75%, and 90% of the maximum biological effect (proliferation).
Figure 6:
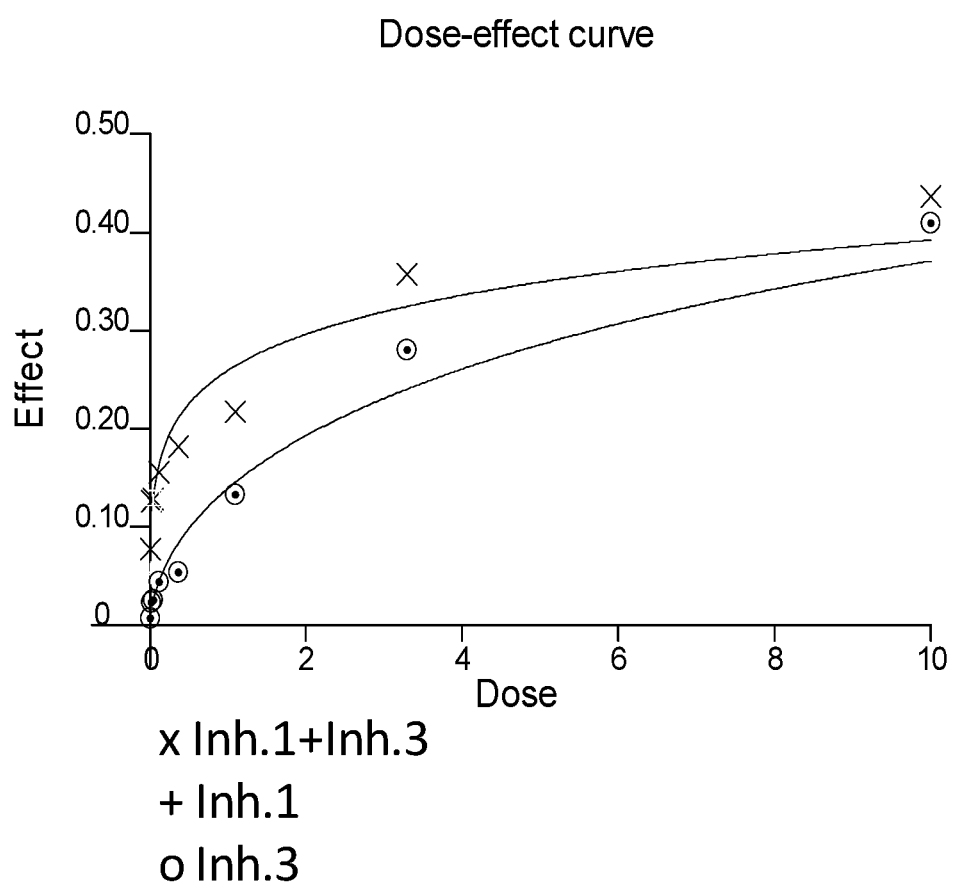
FIG. 6 illustrates the dose-effect curves obtained for the tested Maver-1 cell line (B cell lymphoma, mantle) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 7:
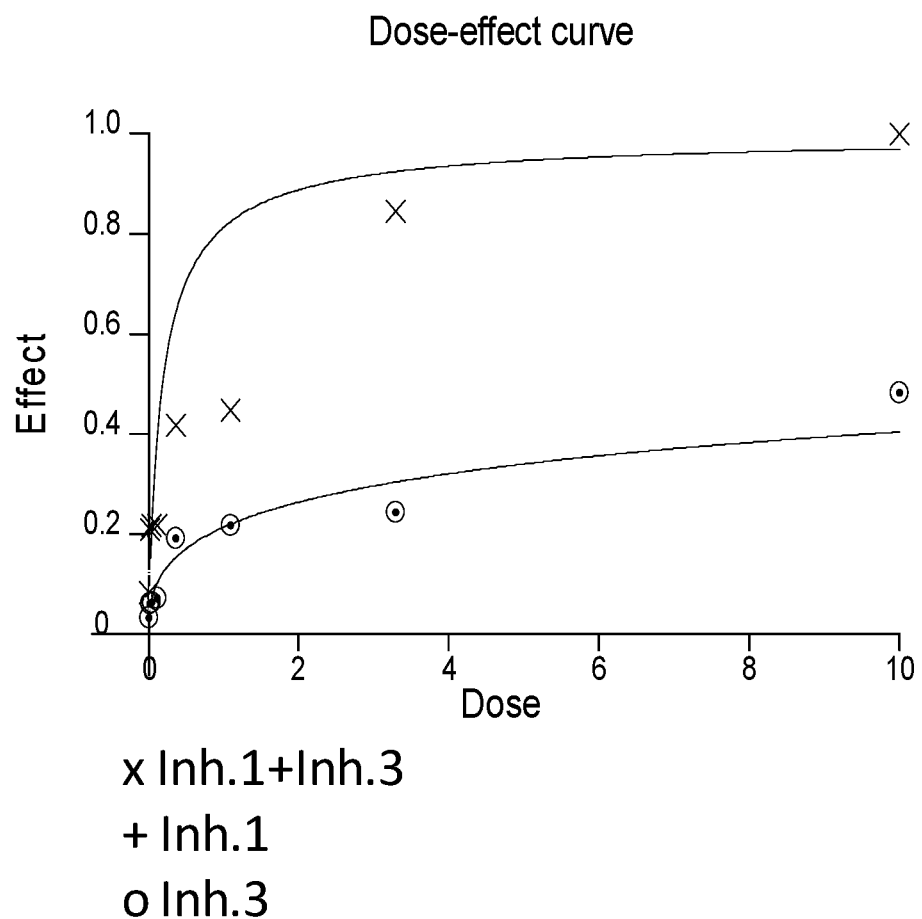
FIG. 7 illustrates the dose-effect curves obtained for the tested Jeko cell line (B cell lymphoma, mantle) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 8:
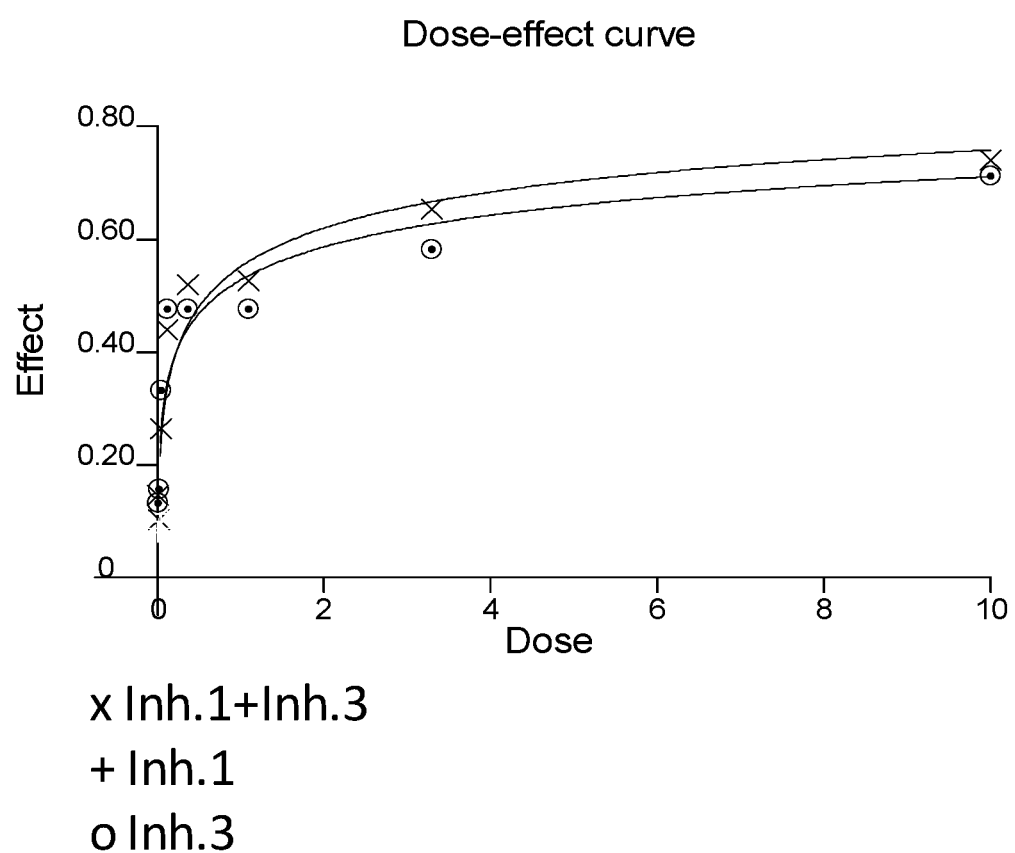
FIG. 8 illustrates the dose-effect curves obtained for the tested CCRF cell line (B lymphoblast, acute lymphoblastic leukemia) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 9:
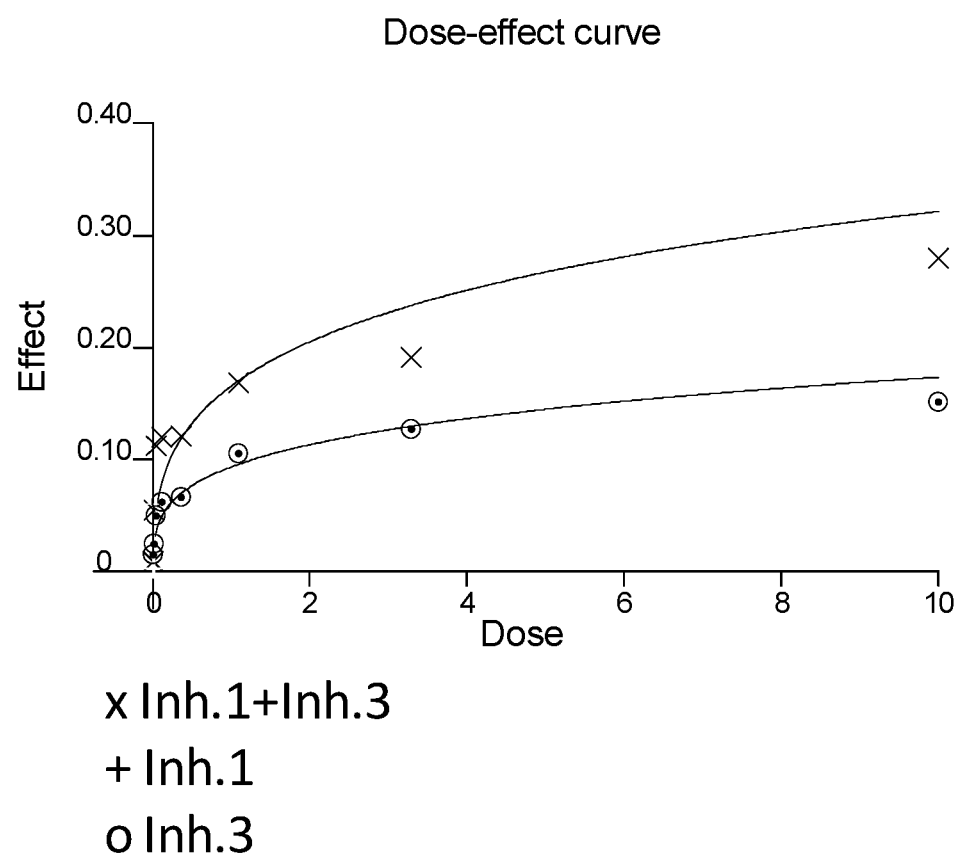
FIG. 9 illustrates the dose-effect curves obtained for the tested SUP-B15 cell line (B lymphoblast, acute lymphoblastic leukemia) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 10:
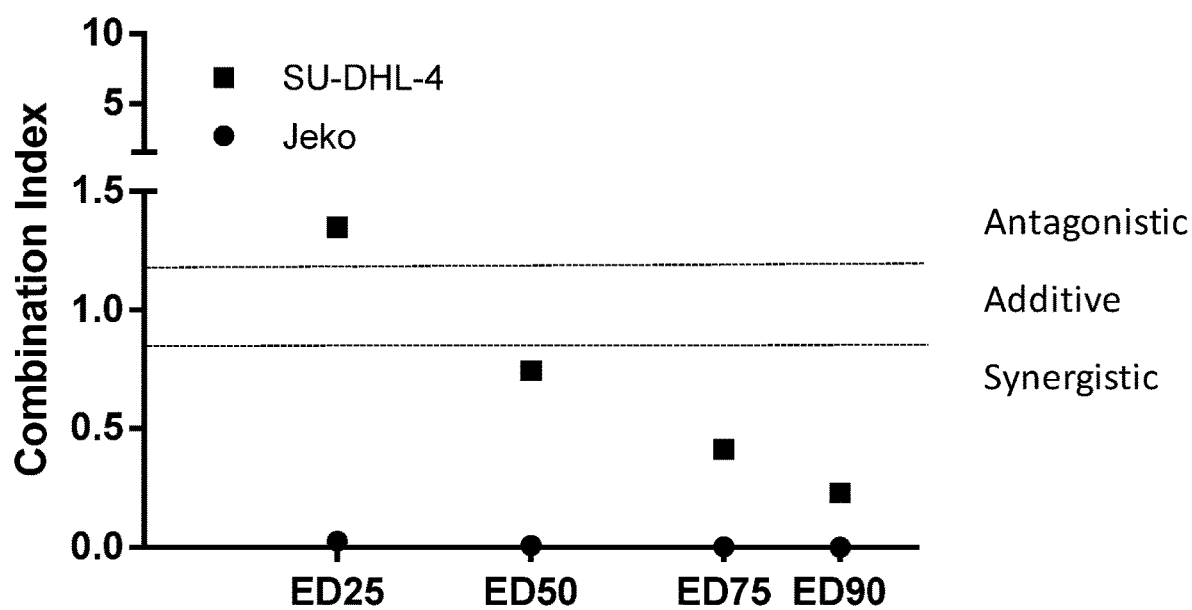
FIG. 10 illustrates the synergy observed in certain cell lines when the BTK inhibitor of Formula XVIII and the PI3K-δ inhibitor of Formula IX are combined. The tested cell lines include Jeko (B cell lymphoma, mantle) and SU-DHL-4 (diffuse large B cell lymphoma, ABC). The dose-effect curves for these cell lines are given in FIG. 11 and FIG. 12.
Figure 11:
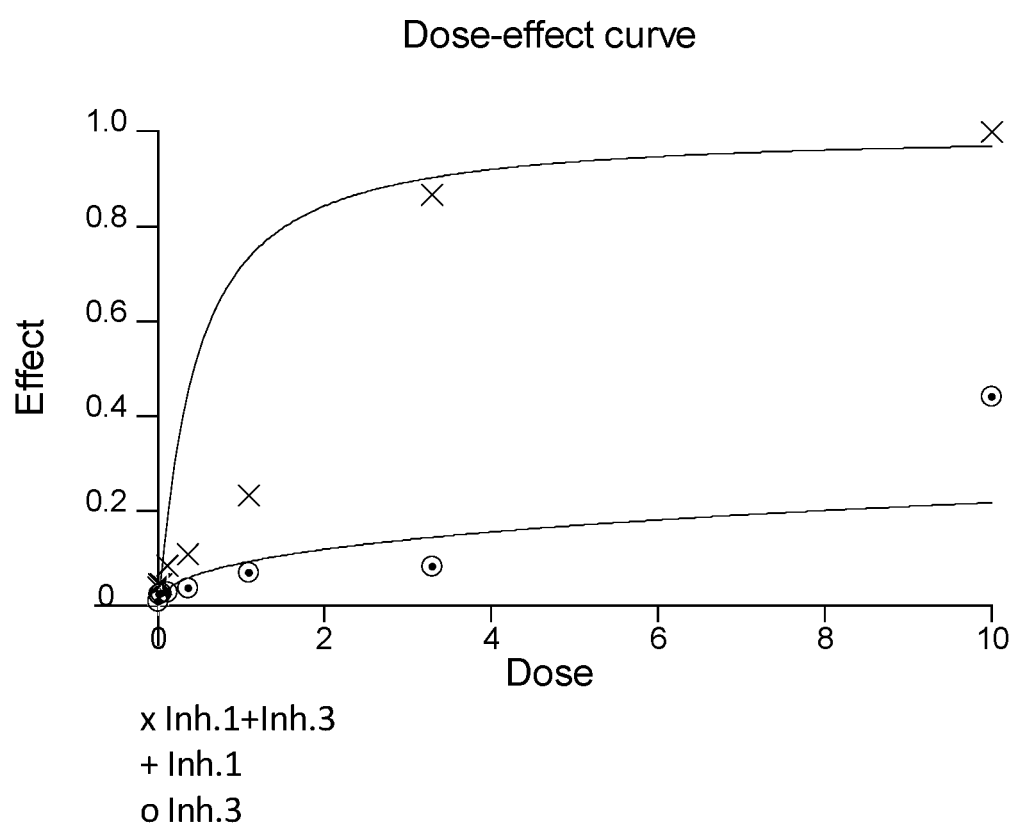
FIG. 11 illustrates the dose-effect curves obtained for the tested Jeko cell line (B cell lymphoma, mantle) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 12:
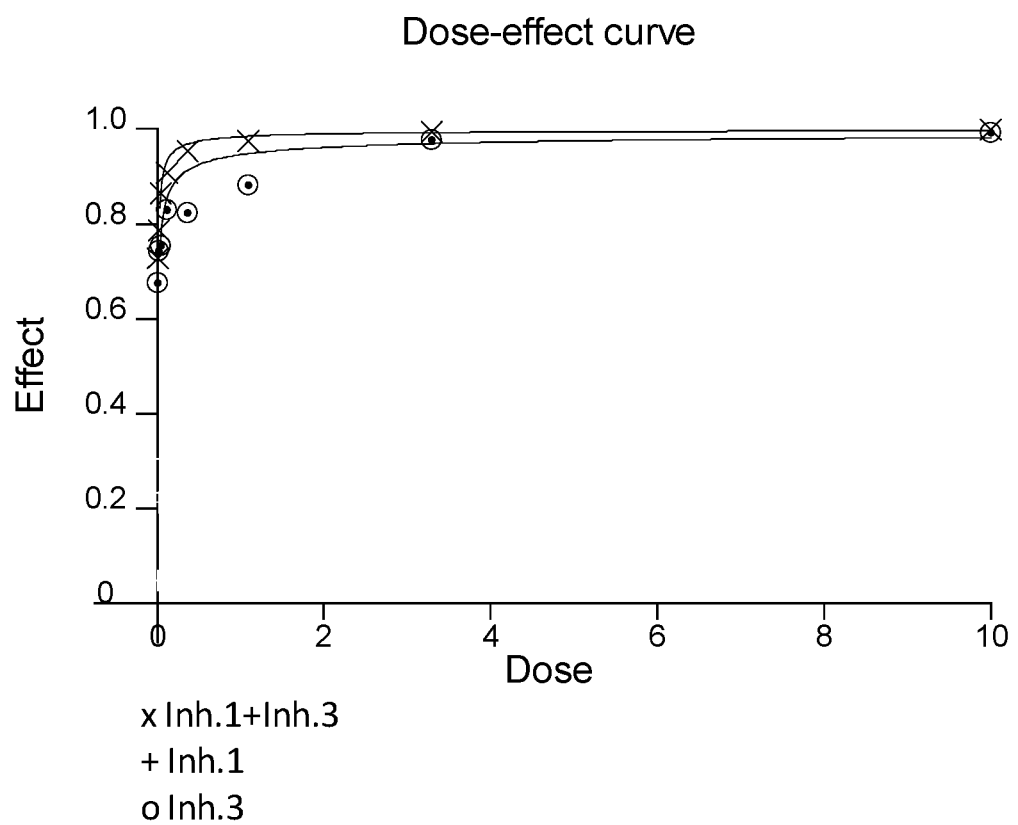
FIG. 12 illustrates the dose-effect curves obtained for the tested SU-DHL-4 cell line (diffuse large B cell lymphoma, ABC) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 13:
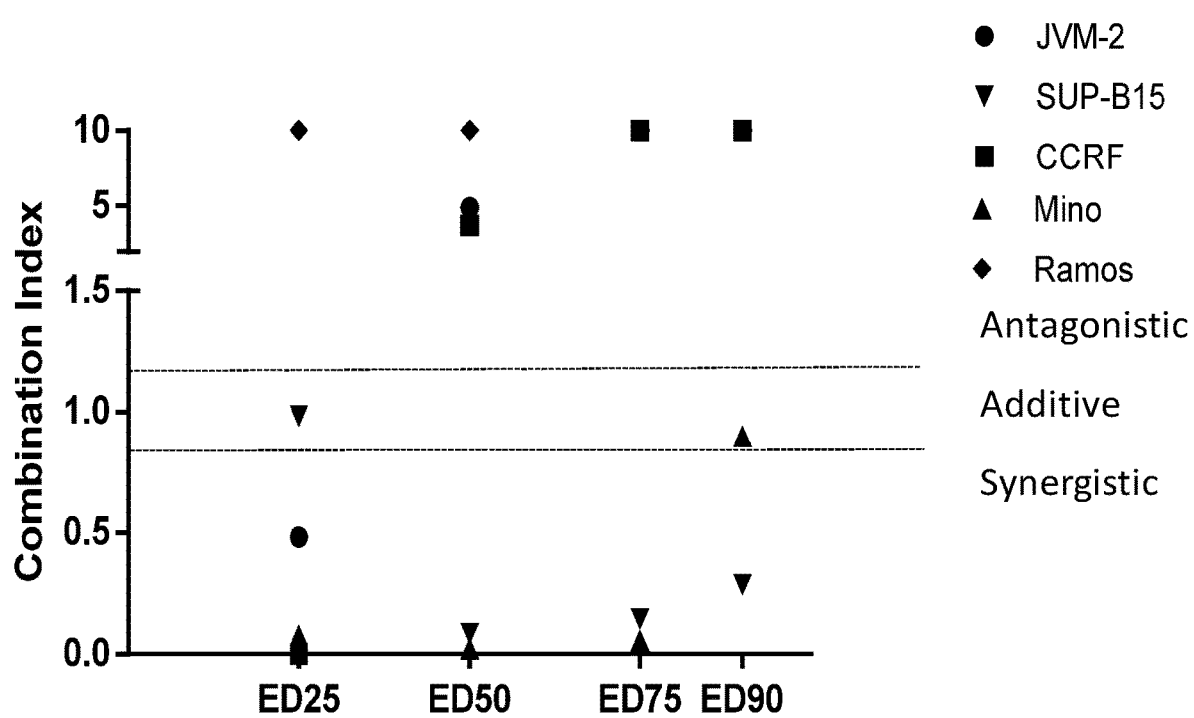
FIG. 13 illustrates the synergy observed in certain cell lines when the BTK inhibitor of Formula XVIII and the PI3K-δ inhibitor of Formula IX are combined. The tested cell lines include CCRF (B lymphoblast, acute lymphoblastic leukemia), SUP-B15 (B lymphoblast, acute lymphoblastic leukemia), JVM-2 (prolymphocytic leukemia), Ramos (Burkitt's lymphoma), and Mino (mantle cell lymphoma). The dose-effect curves for these cell lines are given in FIG. 14, FIG. 15, FIG. 16, and FIG. 17. No dose-effect curve is given for Ramos (Burkitt's lymphoma) because of negative slope.
Figure 14:
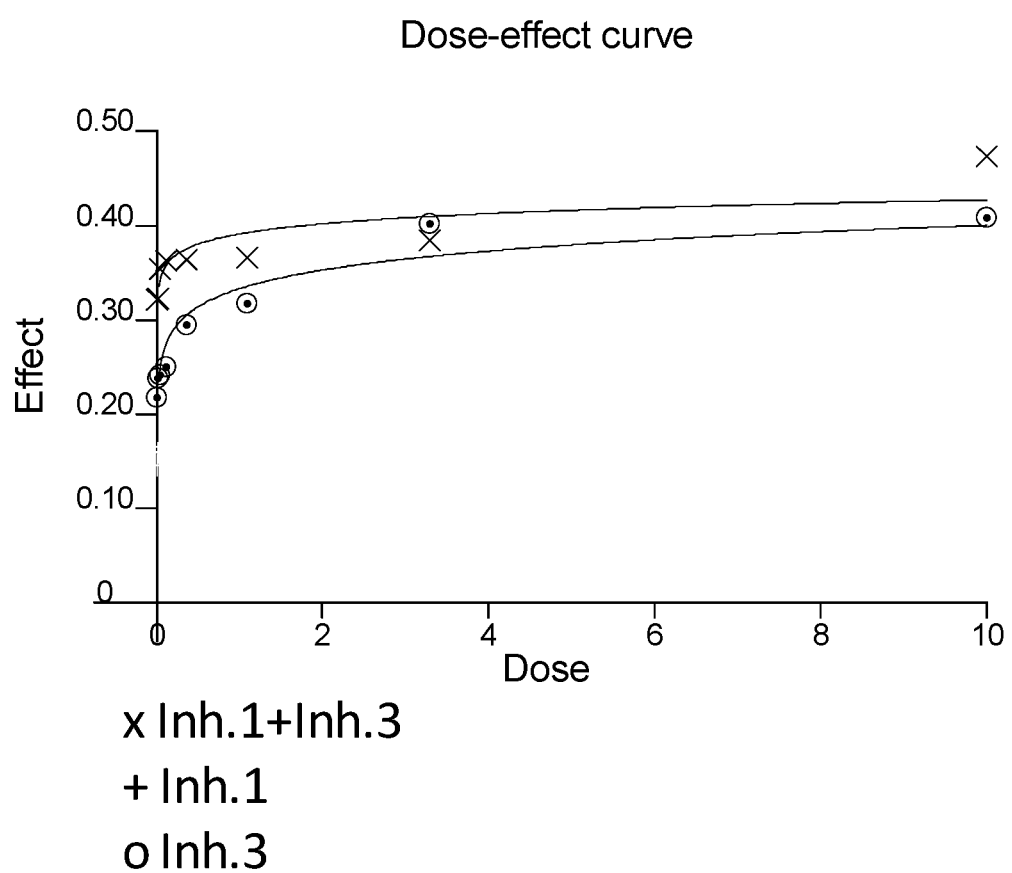
FIG. 14 illustrates the dose-effect curves obtained for the tested CCRF cell line (B lymphoblast, acute lymphoblastic leukemia) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 15:
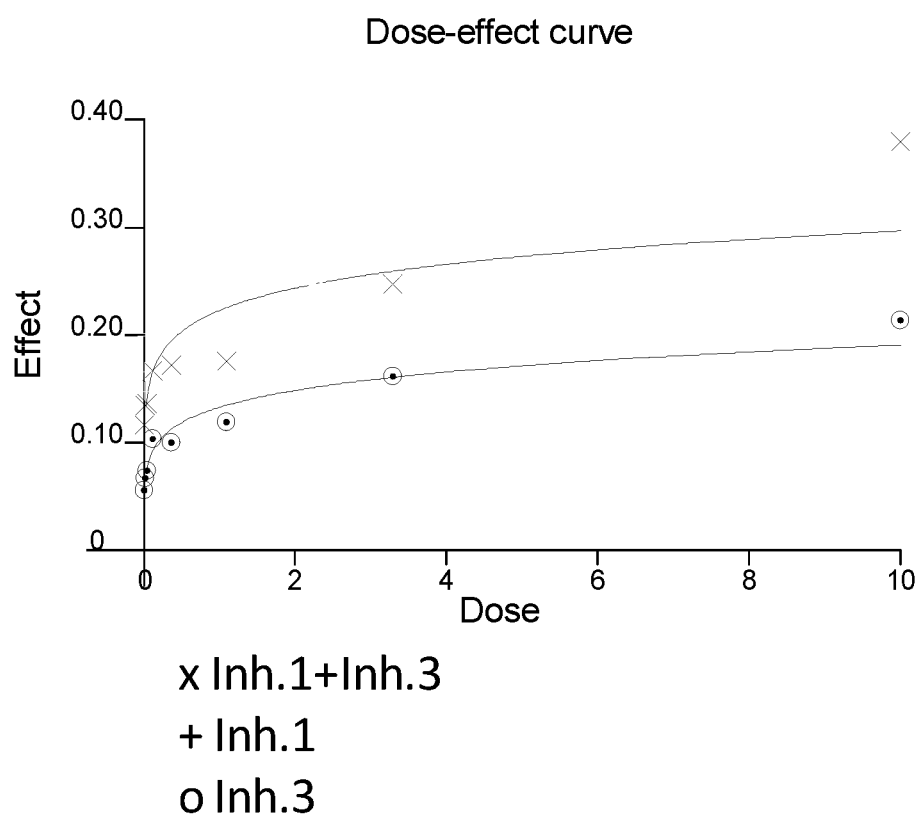
FIG. 15 illustrates the dose-effect curves obtained for the tested SUP-B15 cell line (B lymphoblast, acute lymphoblastic leukemia) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 16:
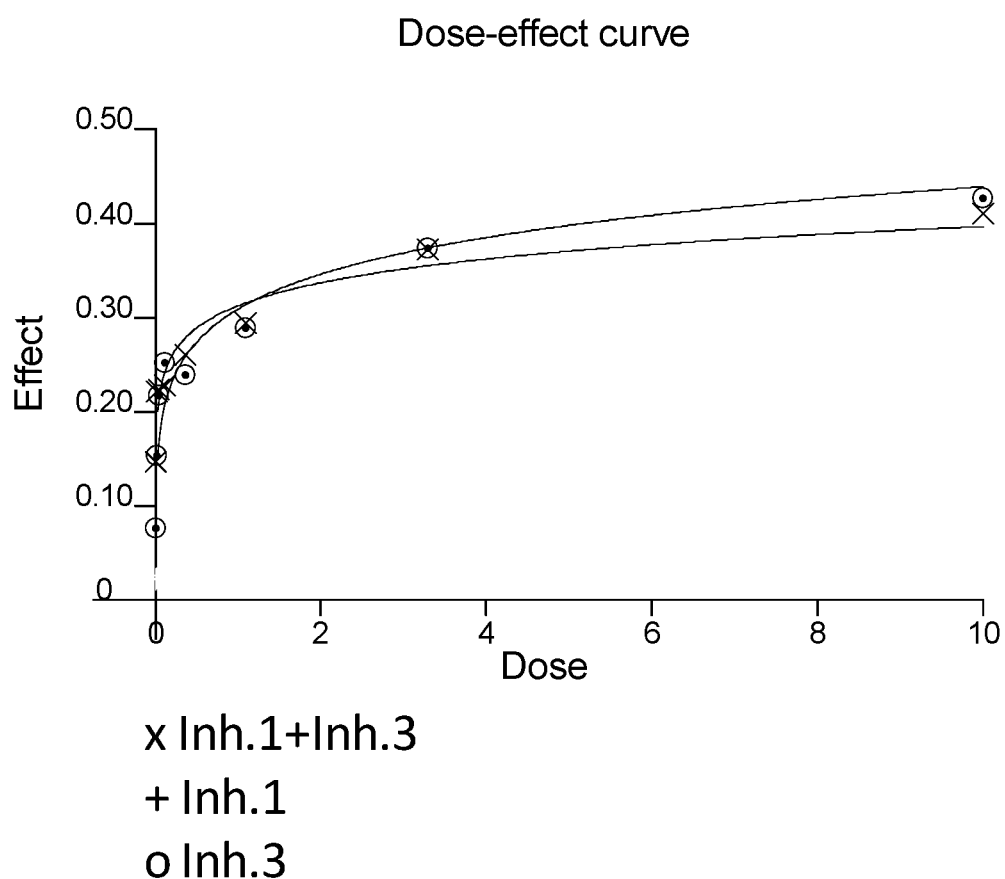
FIG. 16 illustrates the dose-effect curves obtained for the tested JVM-2 cell line (prolymphocytic leukemia) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 17:
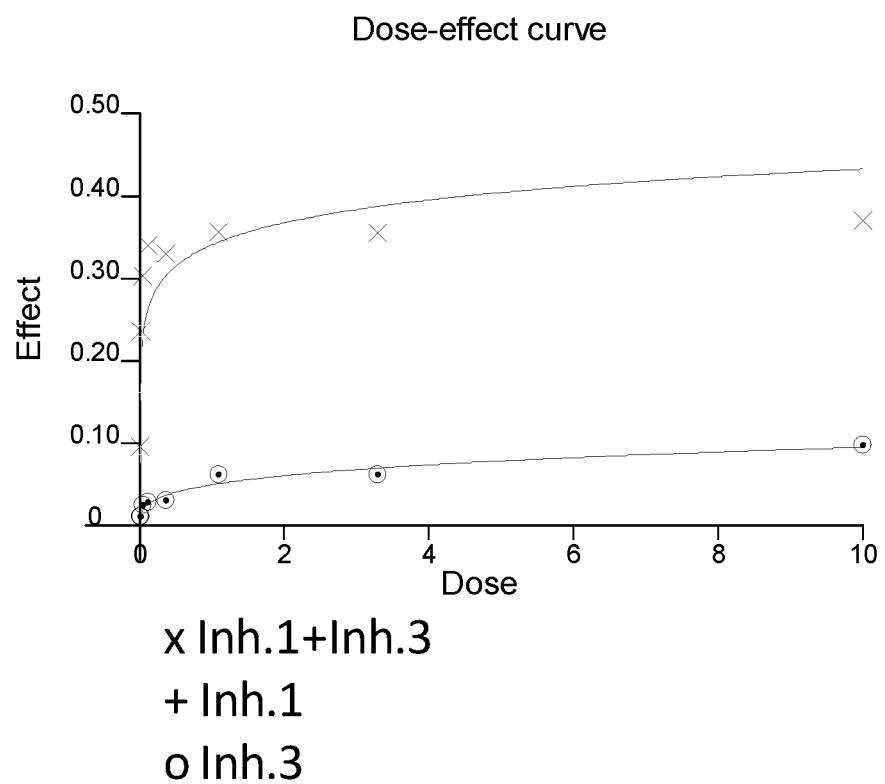
FIG. 17 illustrates the dose-effect curves obtained for the tested Mino cell line (mantle cell lymphoma) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 18:
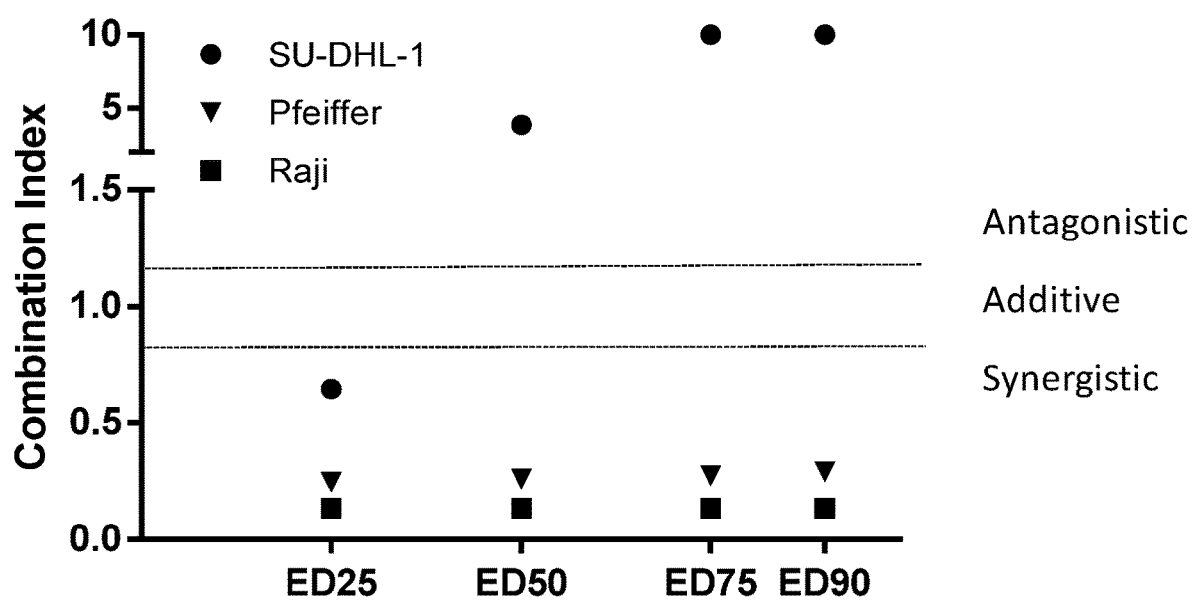
FIG. 18 illustrates the synergy observed in certain cell lines when the BTK inhibitor of Formula XVIII and the PI3K-δ inhibitor of Formula IX are combined. The tested cell lines include Raji (B lymphocyte, Burkitt's lymphoma), SU-DHL-1 (diffuse large B cell lymphoma-activated B cell, DLBCL-ABC), and Pfeiffer (follicular lymphoma). The dose-effect curves for these cell lines are given in FIG. 19, FIG. 20, and FIG. 21.
Figure 19:
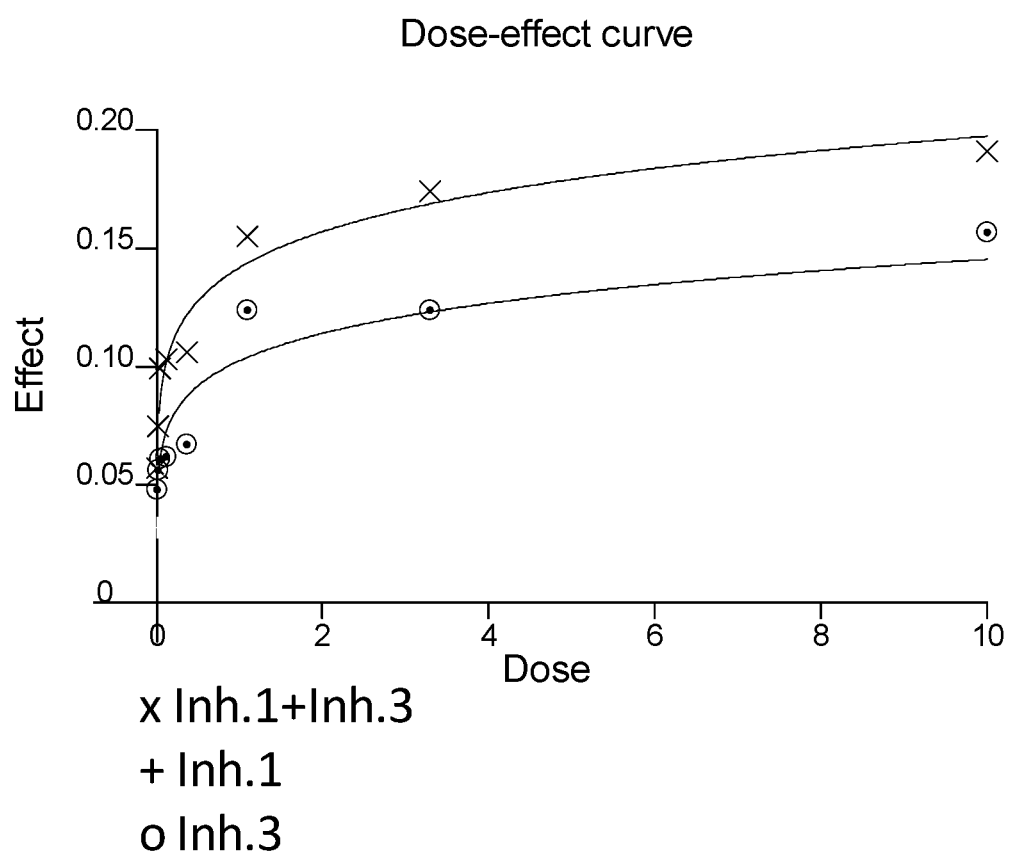
FIG. 19 illustrates the dose-effect curves obtained for the tested Raji cell line (B lymphocyte, Burkitt's lymphoma) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of µM.
Figure 20:
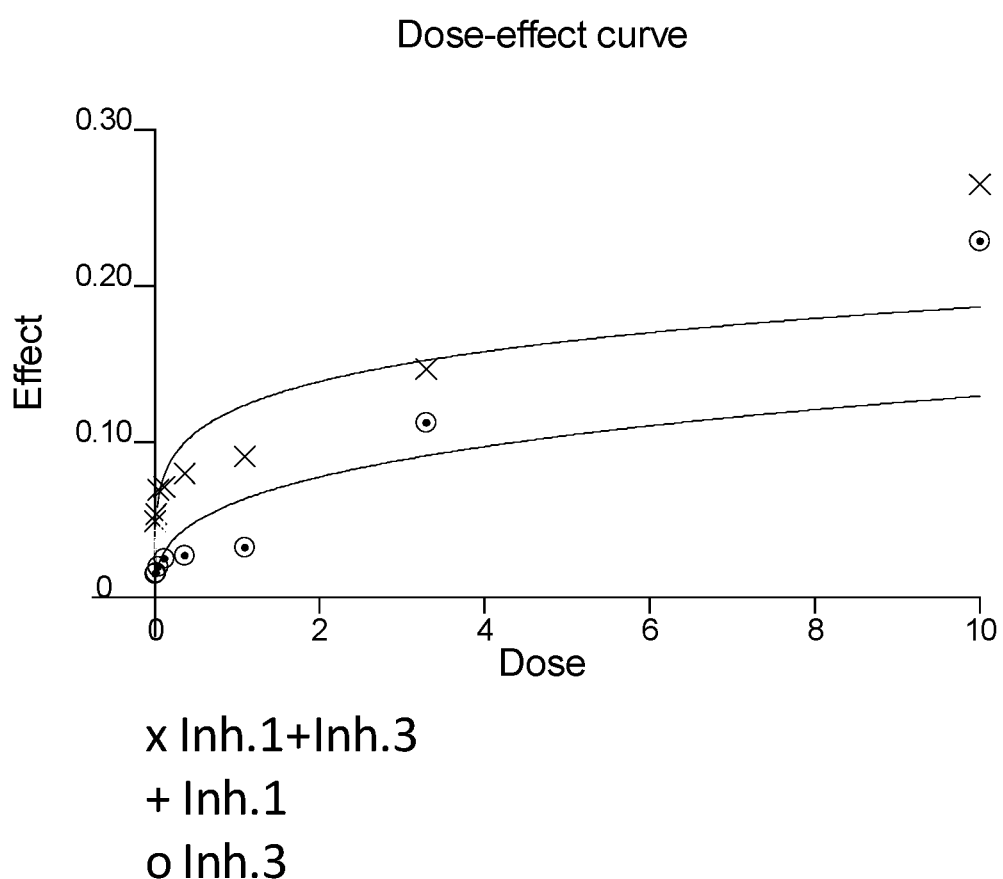
FIG. 20 illustrates the dose-effect curves obtained for the tested SU-DHL-1 cell line (DLBCL-ABC) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 21:
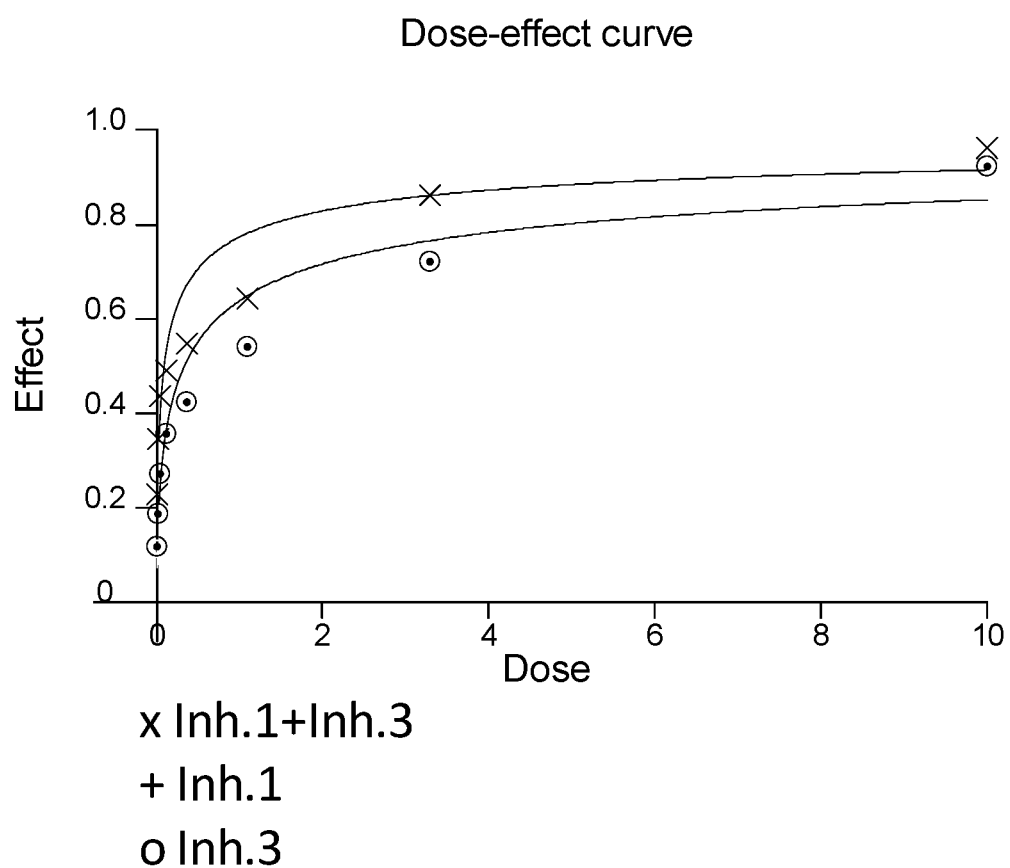
FIG. 21 illustrates the dose-effect curves obtained for the tested Pfeiffer cell line (follicular lymphoma) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 22:
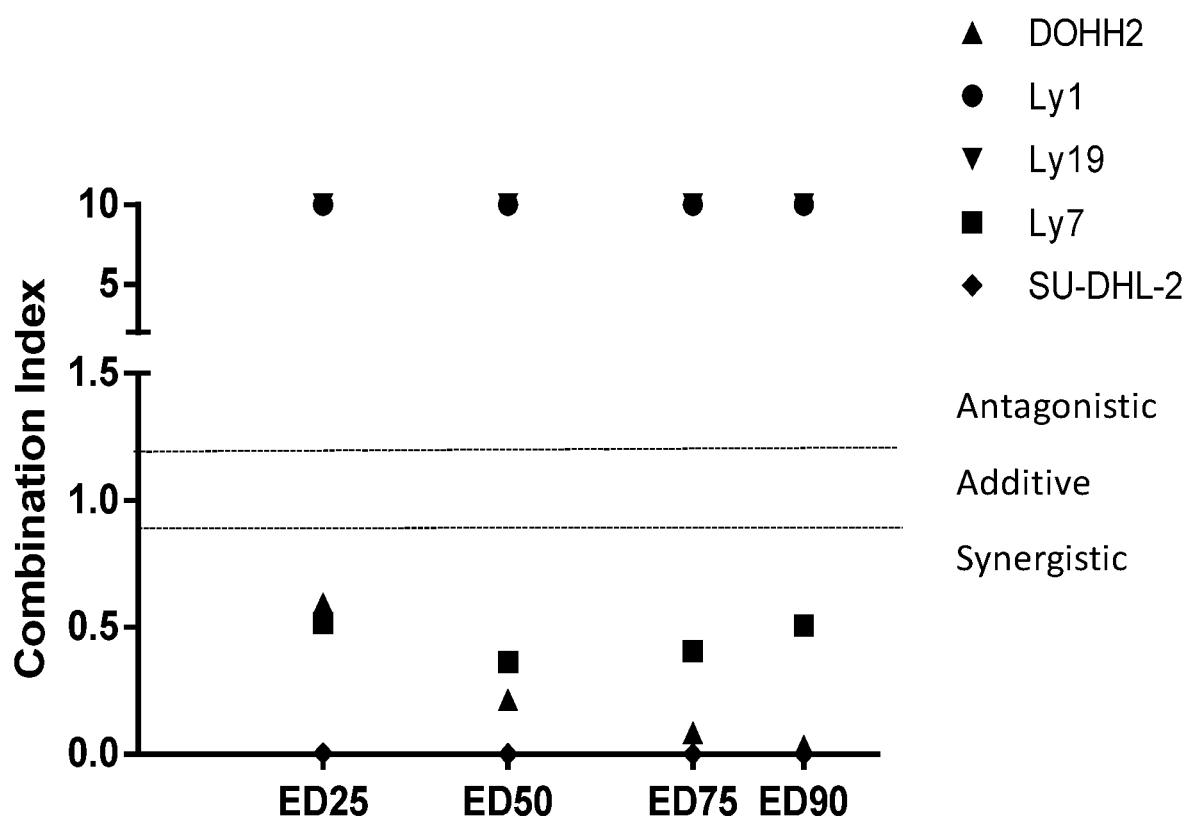
FIG. 22 illustrates the synergy observed in certain cell lines when the BTK inhibitor of Formula XVIII and the PI3K-δ inhibitor of Formula IX are combined. The tested cell lines include Ly1 (Germinal center B-cell like diffuse large B-cell lymphoma, DLBCL-GCB), Ly7 (DLBCL-GCB), Ly19 (DLBCL-GCB), SU-DHL-2 (Activated B-cell like diffuse large B-cell lymphoma, DLBCL-ABC), and DOHH2 (follicular lymophoma, FL). The dose-effect curves for these cell lines are given in FIG. 23, FIG. 24, FIG. 25, and FIG. 26, except for the Ly19 cell line, which is not graphed because of a negative slope.
Figure 23:
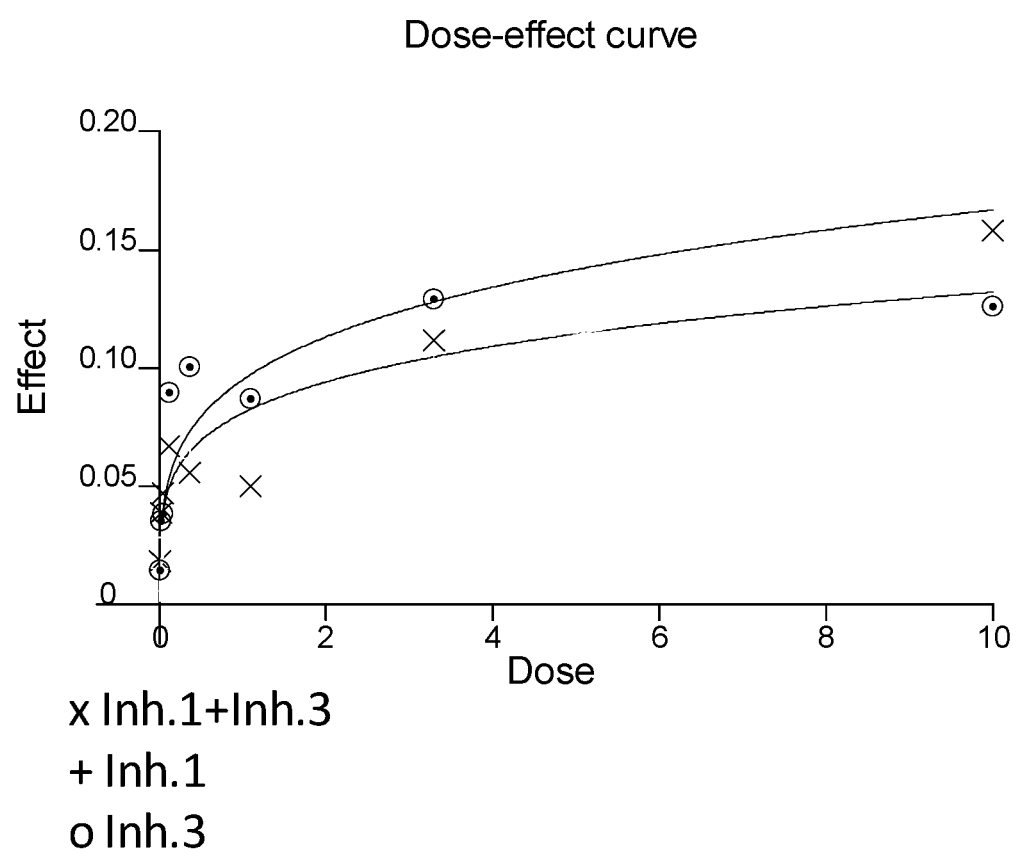
FIG. 23 illustrates the dose-effect curves obtained for the tested Ly1 cell line (DLBCL-GCB) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 24:
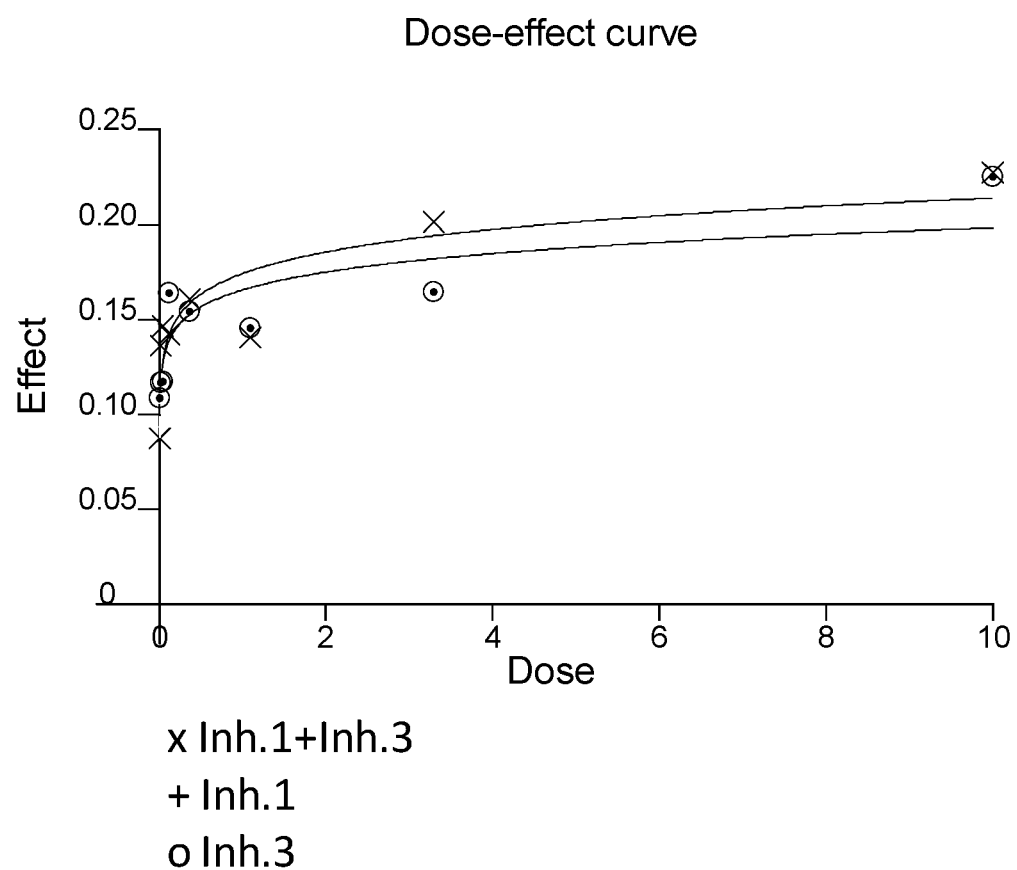
FIG. 24 illustrates the dose-effect curves obtained for the tested Ly7 cell line (DLBCL-GCB) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 25:
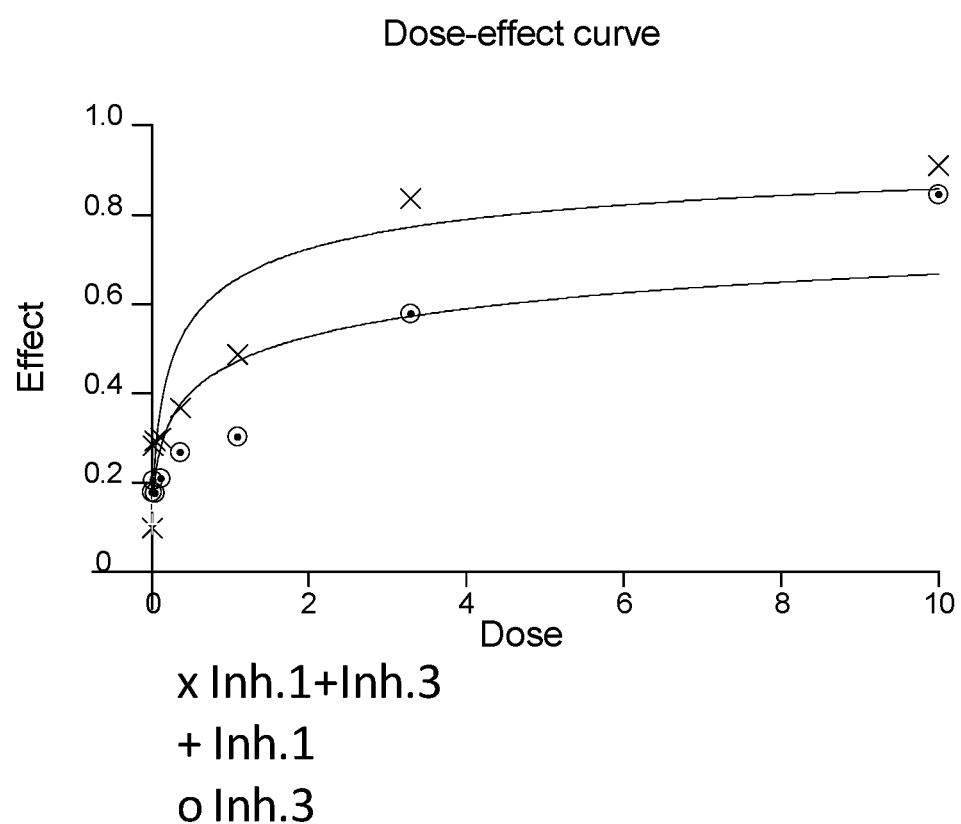
FIG. 25 illustrates the dose-effect curves obtained for the tested DOHH2 cell line (FL) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 26:
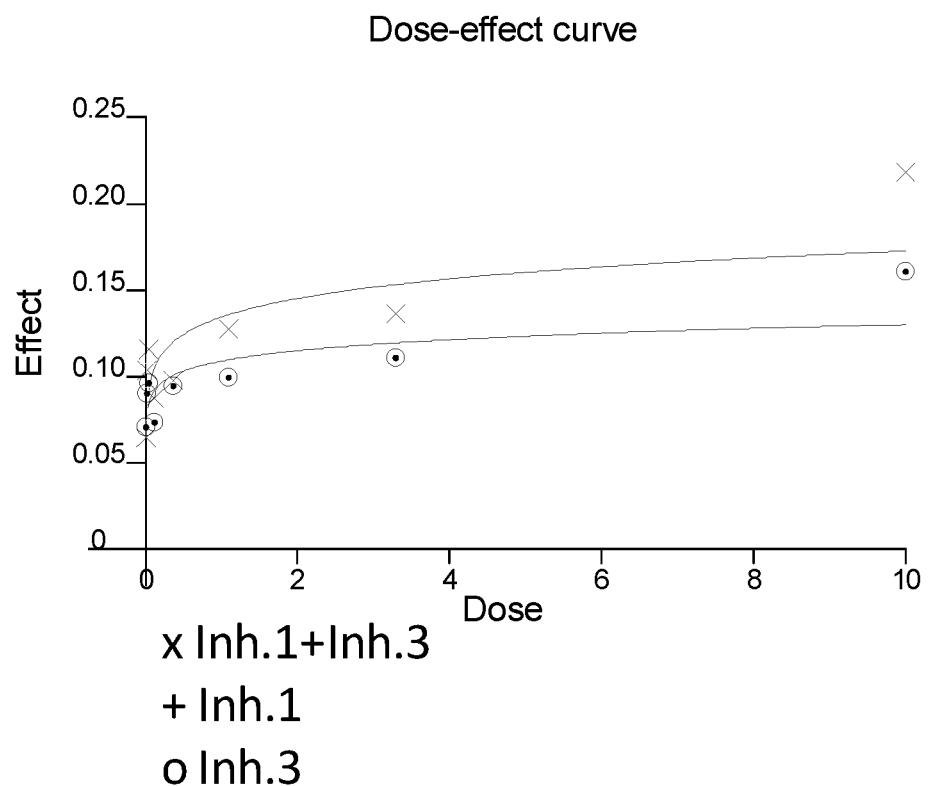
FIG. 26 illustrates the dose-effect curves obtained for the tested SU-DHL-2 cell line (DLBCL-ABC) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 27:
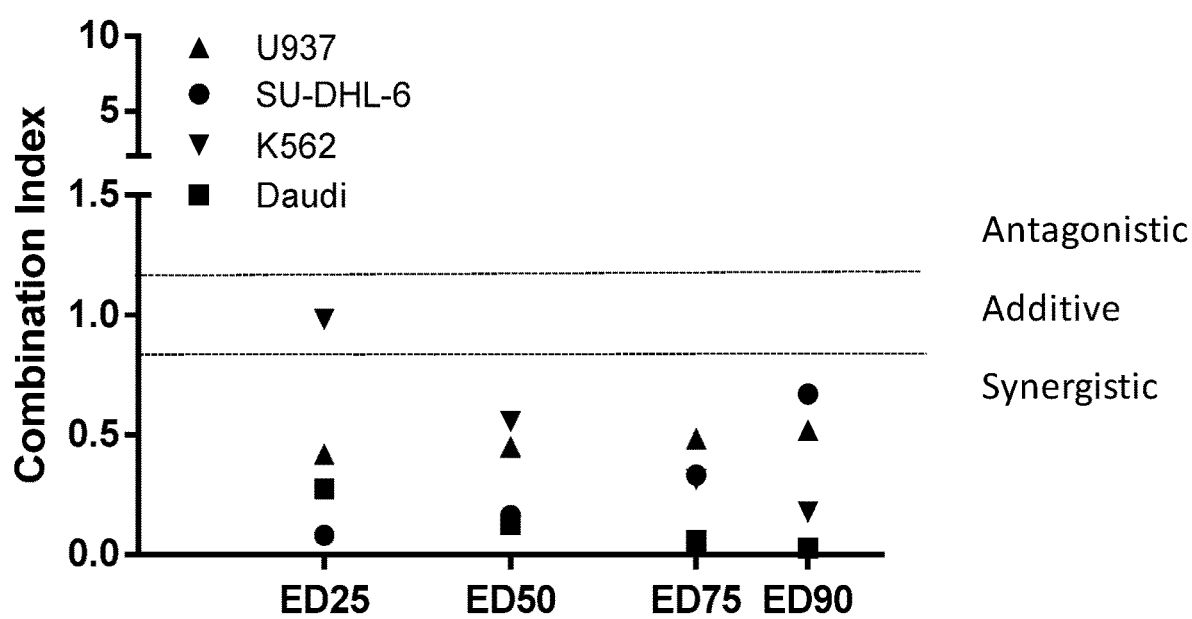
FIG. 27 illustrates the synergy observed in certain cell lines when Formula XVIII and Formula IX are combined. The tested cell lines include U937 (histiocytic lymphoma and/or myeloid), K562 (leukemia, myeloid, and/or chronic myelogenous leukemia), Daudi (human Burkitt's lymphoma), and SU-DHL-6 (DLBCL-GCB and/or peripheral T-cell lymphoma, PTCL). The dose-effect curves for these cell lines are given in FIG. 28, FIG. 29, FIG. 30, and FIG. 31.
Figure 28:
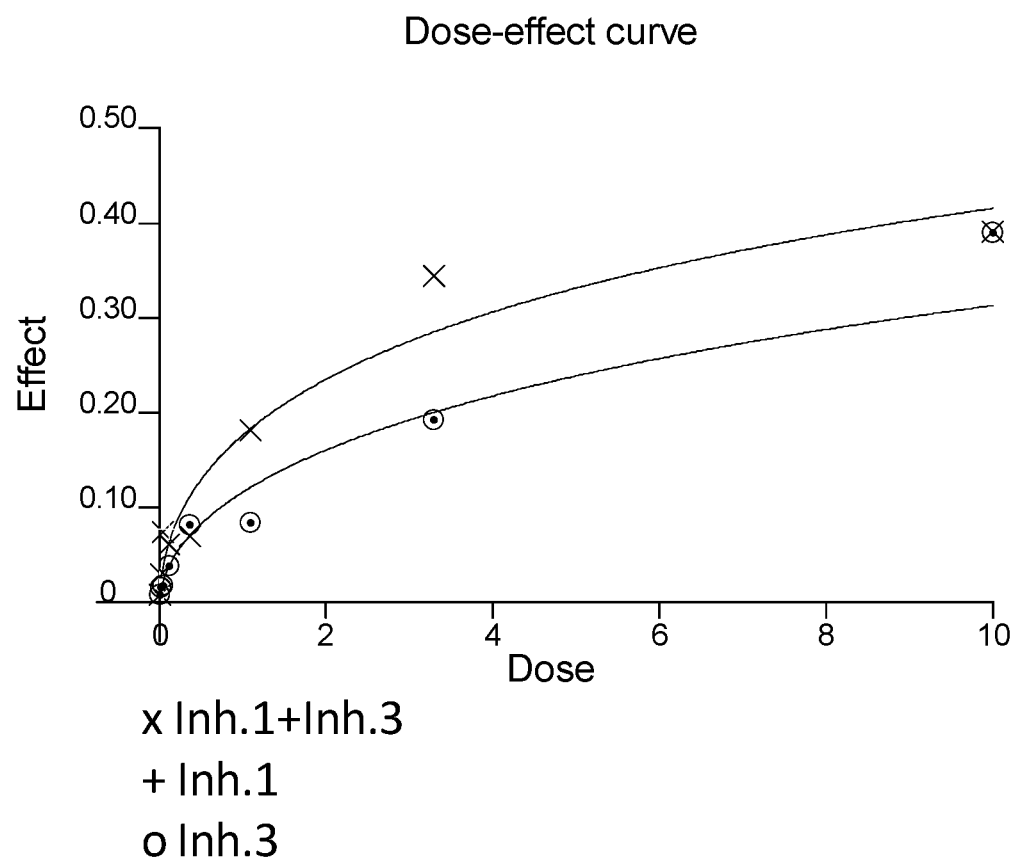
FIG. 28 illustrates the dose-effect curves obtained for the tested U937 cell line (histiocytic lymphoma and/or myeloid) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 29:
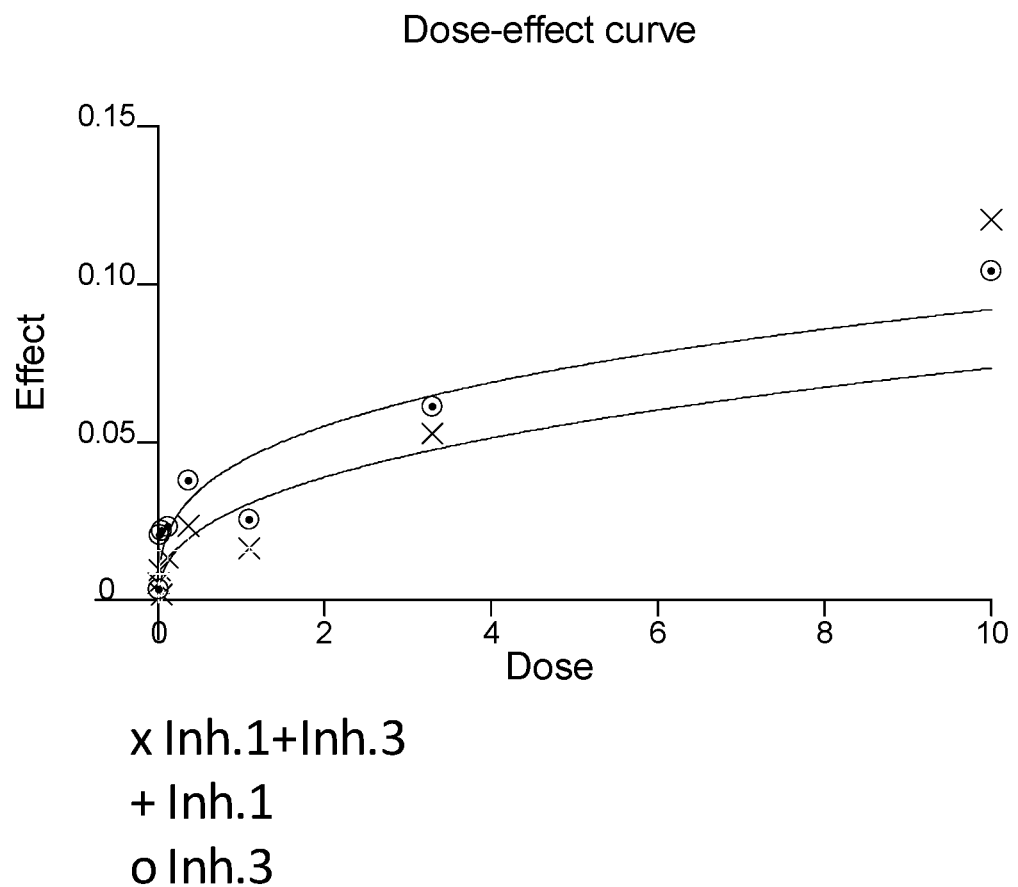
FIG. 29 illustrates the dose-effect curves obtained for the tested K562 cell line (leukemia, myeloid, and/or chronic myelogenous leukemia) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 30:
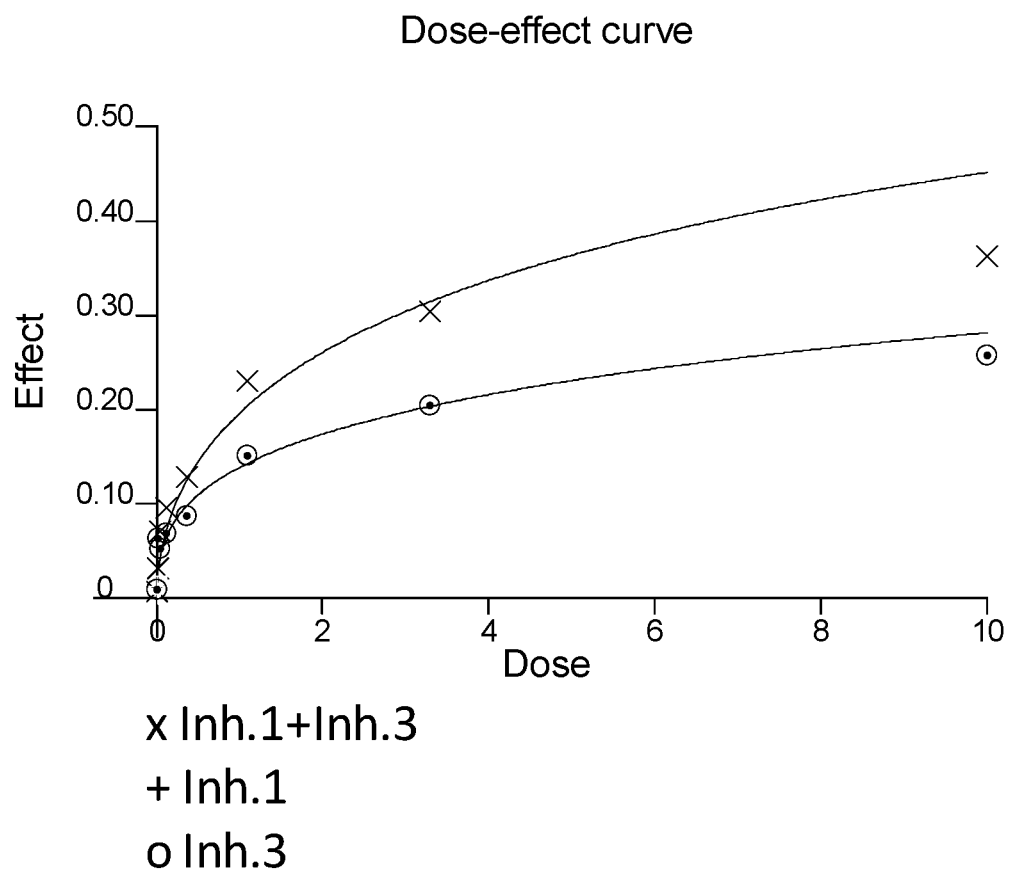
FIG. 30 illustrates the dose-effect curves obtained for the tested Daudi cell line (human Burkitt's lymphoma) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 31:
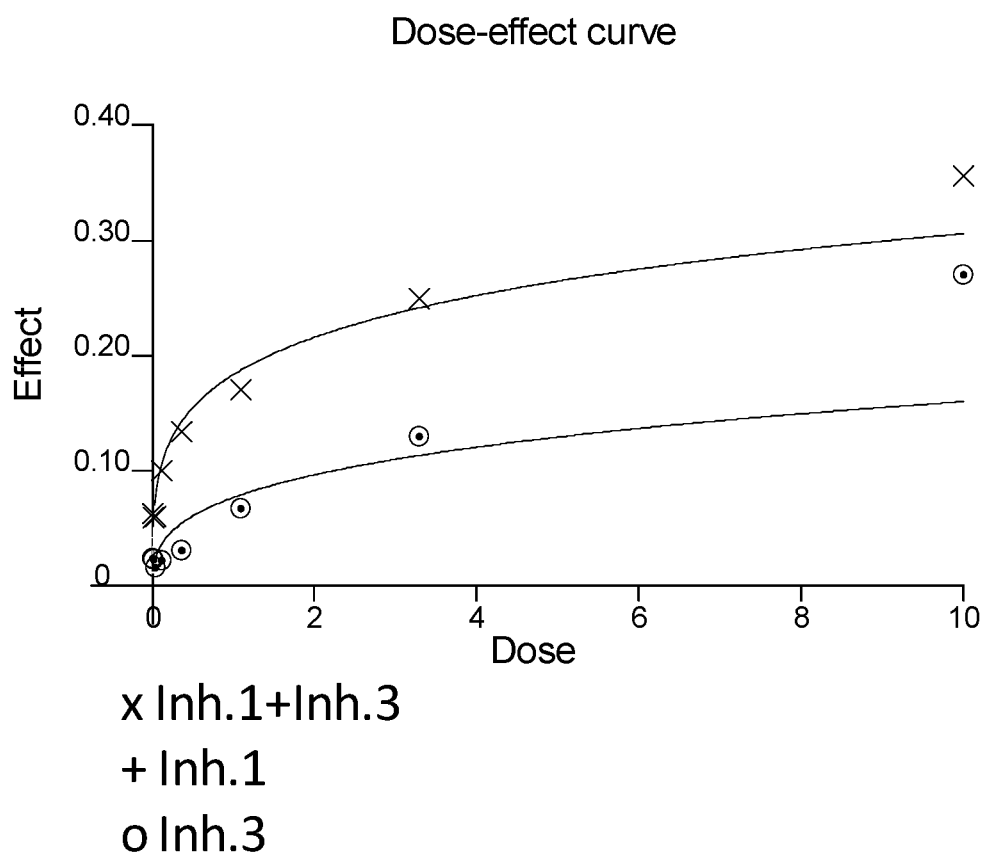
FIG. 31 illustrates the dose-effect curves obtained for the tested SU-DHL-6 cell line (DLBCL-GCB and/or PTCL) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 32:
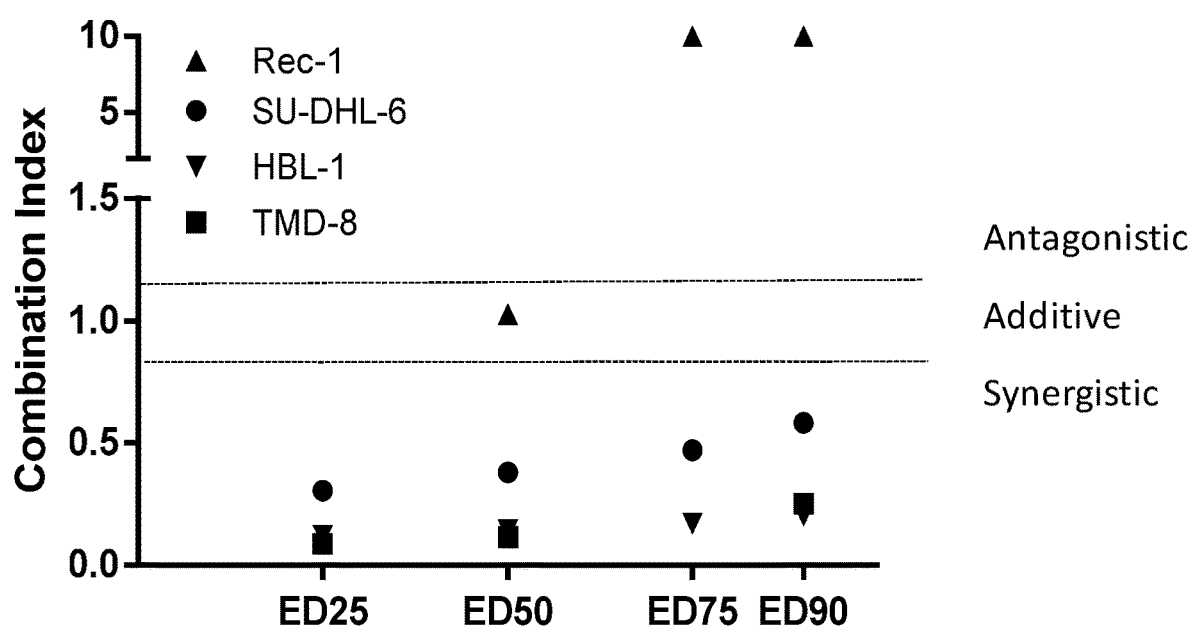
FIG. 32 illustrates the synergy observed in certain cell lines when the BTK inhibitor of Formula XVIII and the PI3K-δ inhibitor of Formula IX are combined. The tested cell lines include SU-DHL-6 (DLBCL-GCB or PTCL), TMD-8 (DLBCL-ABC), HBL-1 (DLBCL-ABC), and Rec-1 (follicular lymphoma). The dose-effect curves for these cell lines are given in FIG. 34, FIG. 35, FIG. 36, and FIG. 37.
Figure 33:
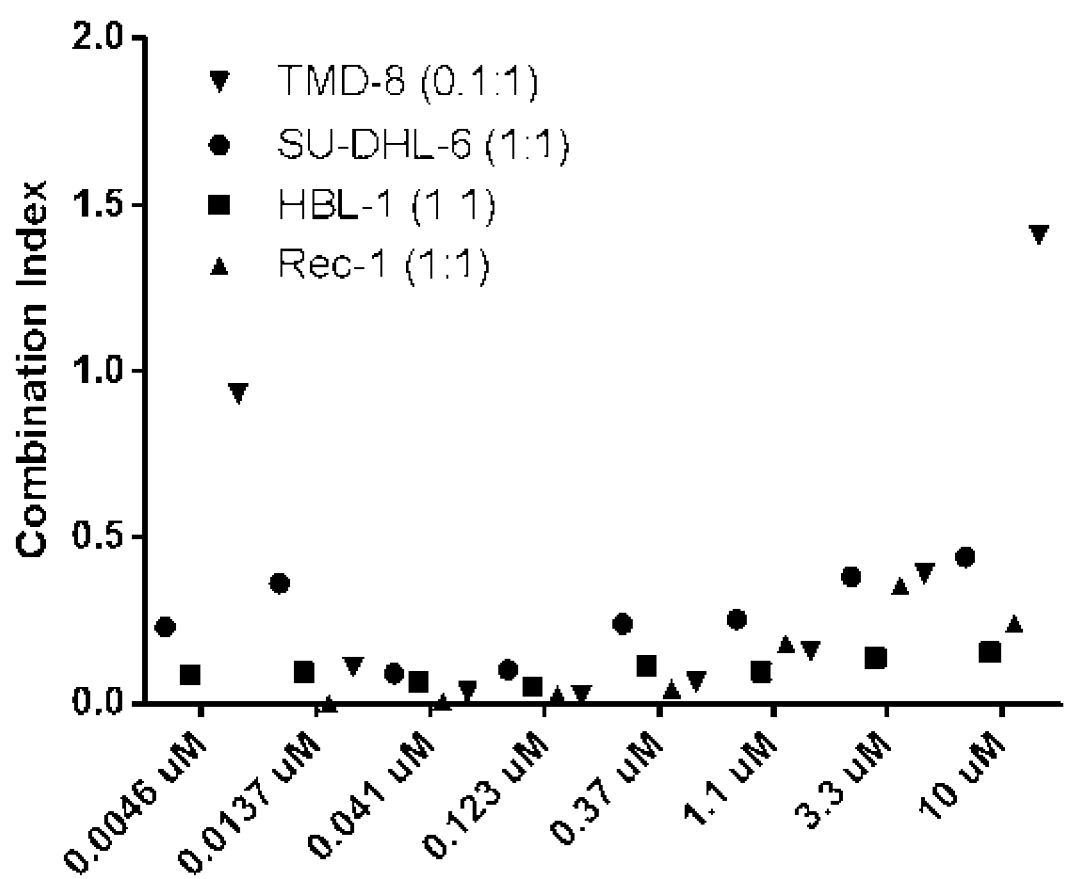
FIG. 33 illustrates the synergy observed in certain cell lines when the BTK inhibitor of Formula XVIII and the PI3K-δ inhibitor of Formula IX are combined. The tested cell lines include SU-DHL-6 (DLBCL-GCB or PTCL), TMD-8 (DLBCL-ABC), HBL-1 (DLBCL-ABC), and Rec-1 (follicular lymphoma). All corresponding CIs are shown for each of the combinations tested as listed on the x axis.
Figure 34:
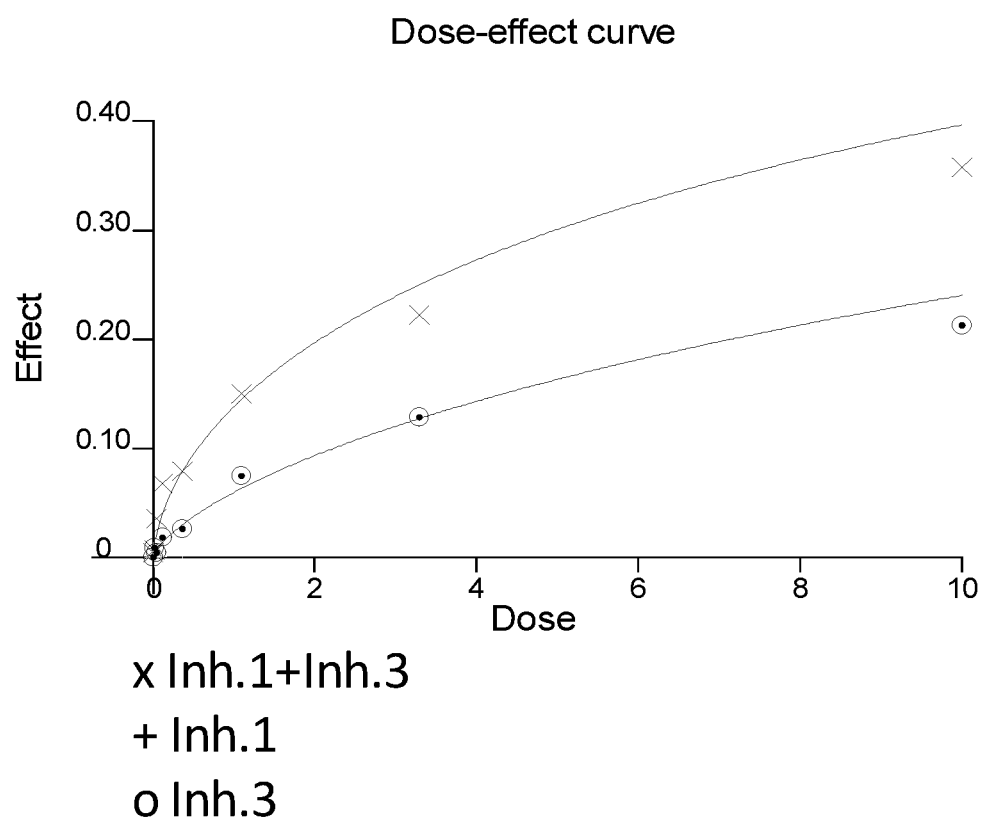
FIG. 34 illustrates the dose-effect curves obtained for the tested SU-DHL-6 cell line (DLBCL-GCB or PTCL) cell line using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 35:
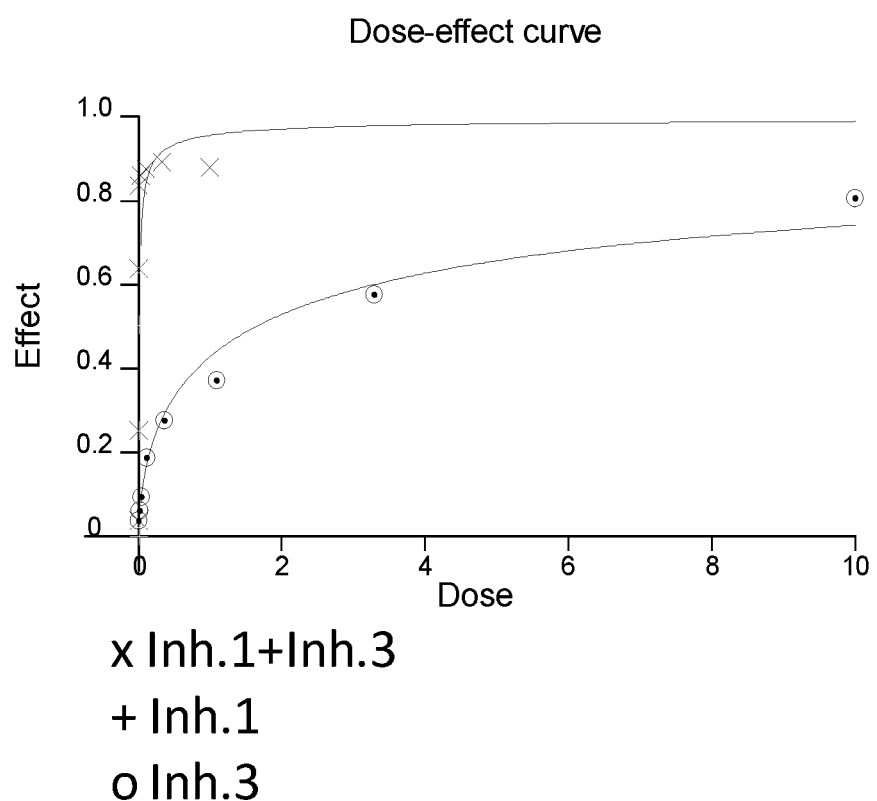
FIG. 35 illustrates the dose-effect curves obtained for the tested TMD-8 cell line (DLBCL-ABC) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 36:
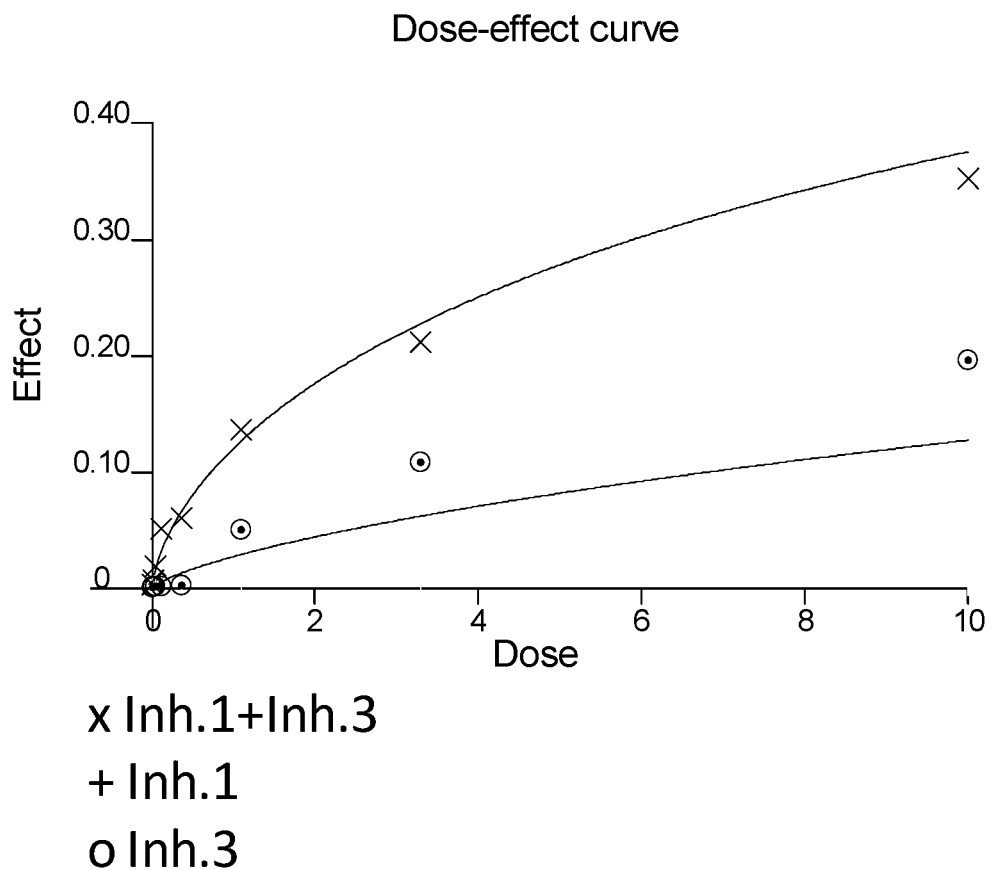
FIG. 36 illustrates the dose-effect curves obtained for the tested HBL-1 cell line (DLBCL-ABC) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 37:
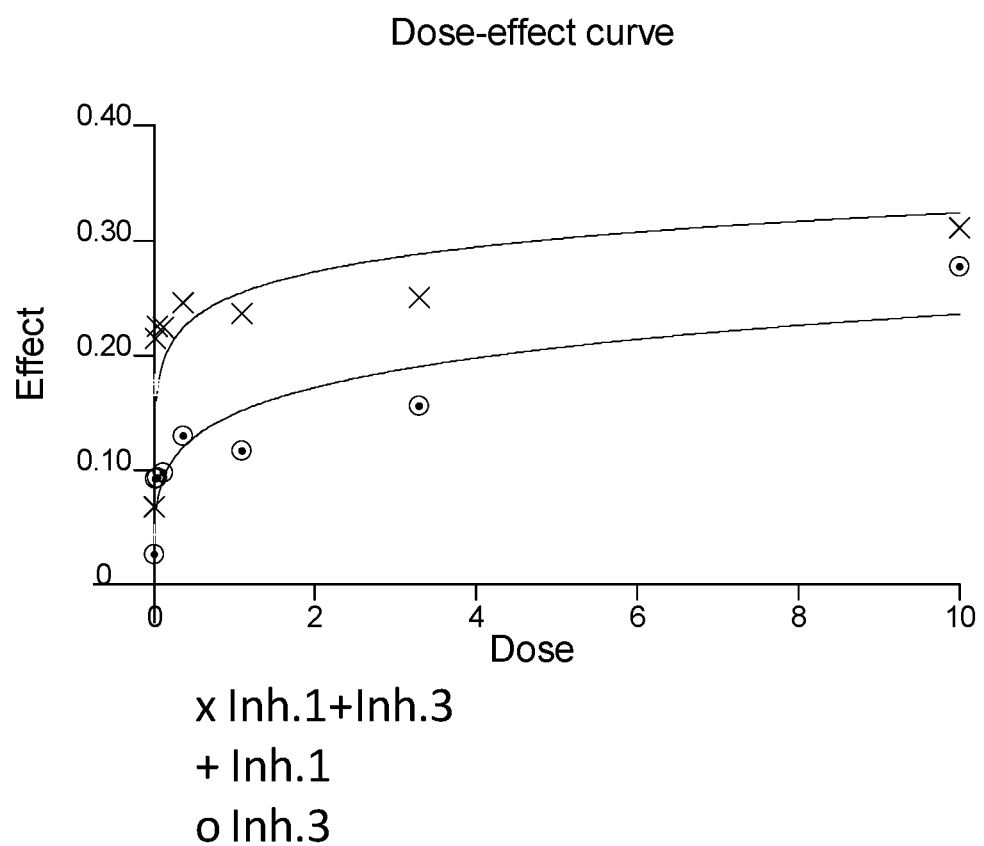
FIG. 37 illustrates the dose-effect curves obtained for the tested Rec-1 cell line (follicular lymphoma) using combined dosing of the BTK inhibitor of Formula XVIII ("Inh.1") and the PI3K-δ inhibitor of Formula IX ("Inh.3"). The y-axis ("Effect") is given in units of Fa (fraction affected) and the x-axis ("Dose") is given in linear units of μM.
Figure 38:
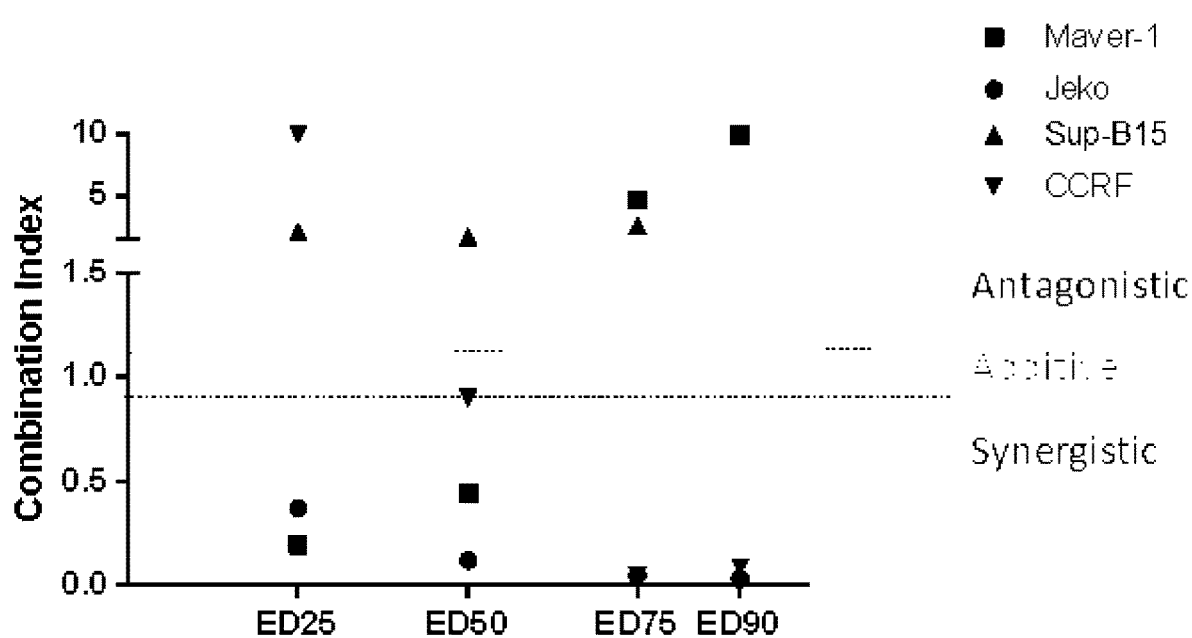
FIG. 38 illustrates the synergy observed in certain cell lines when the BTK inhibitor of Formula XVIII and the JAK-2 inhibitor of Formula XXX (ruxolitinib) are combined. The tested cell lines included Maver-1 (B cell lymphoma, mantle), Jeko (B cell lymphoma, mantle), SUP-B15 (B lymphoblast, acute lymphoblastic leukemia), and CCRF (B lymphoblast, acute lymphoblastic leukemia). The dose-effect curves for these cell lines are given in FIG. 39, FIG. 40, FIG. 41, and FIG. 42.
Figure 39:
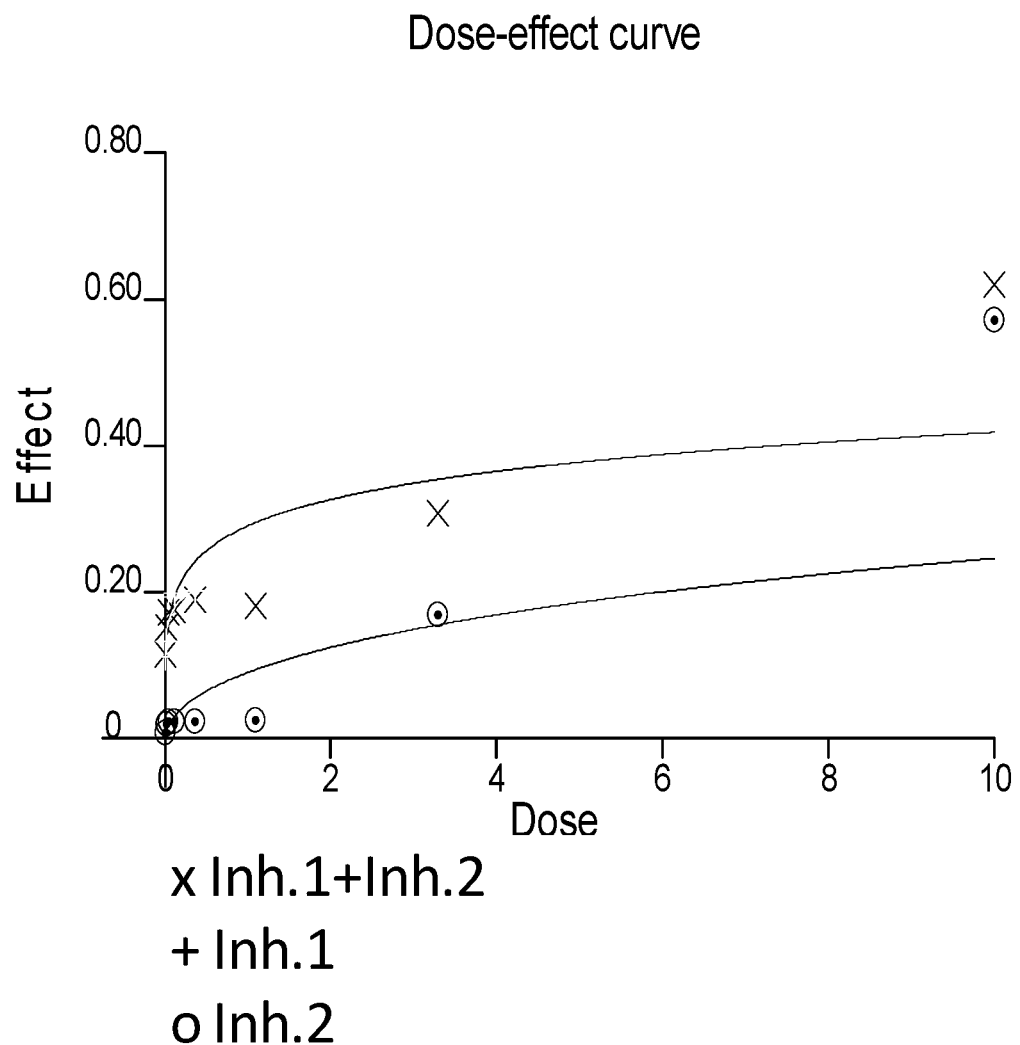
FIG. 39 illustrates the dose-effect curves obtained for the tested Maver-1 cell line (B cell lymphoma, mantle) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 40:
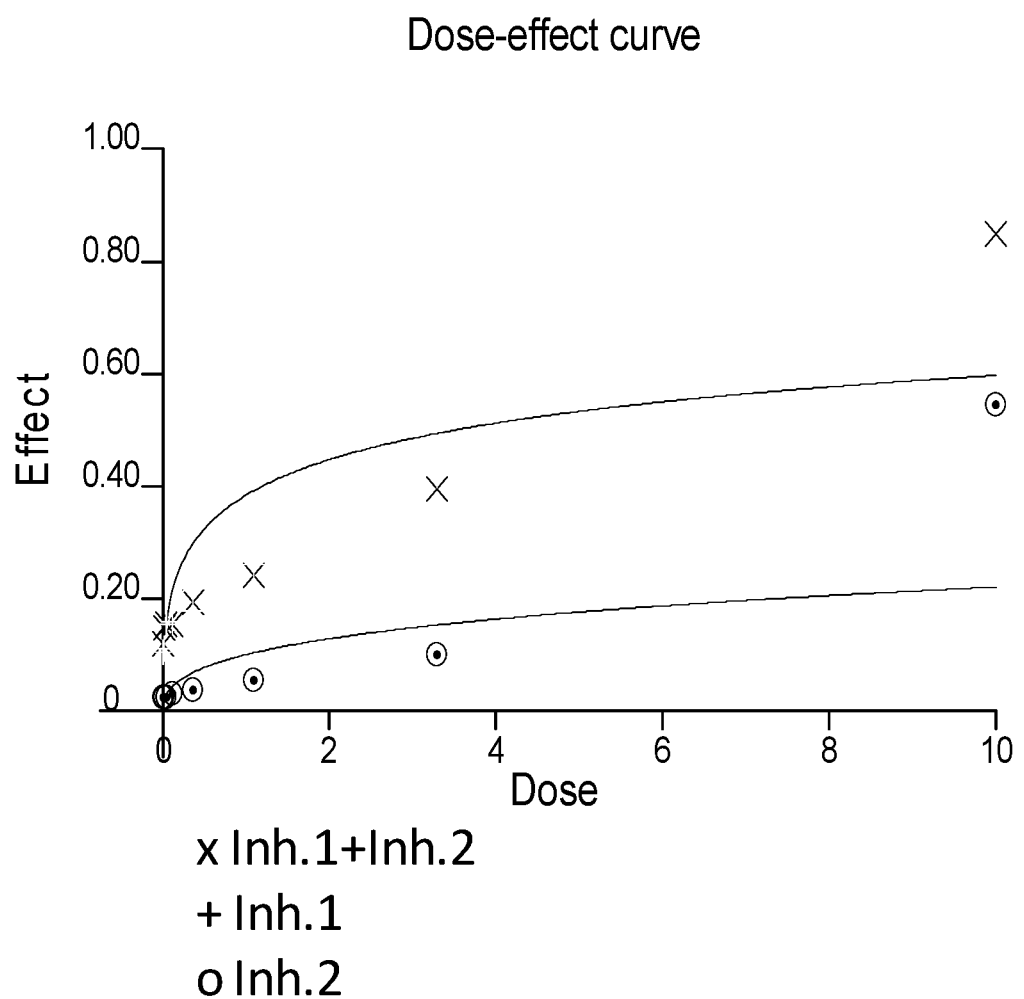
FIG. 40 illustrates the dose-effect curves obtained for the tested Jeko cell line (B cell lymphoma, mantle) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 41:
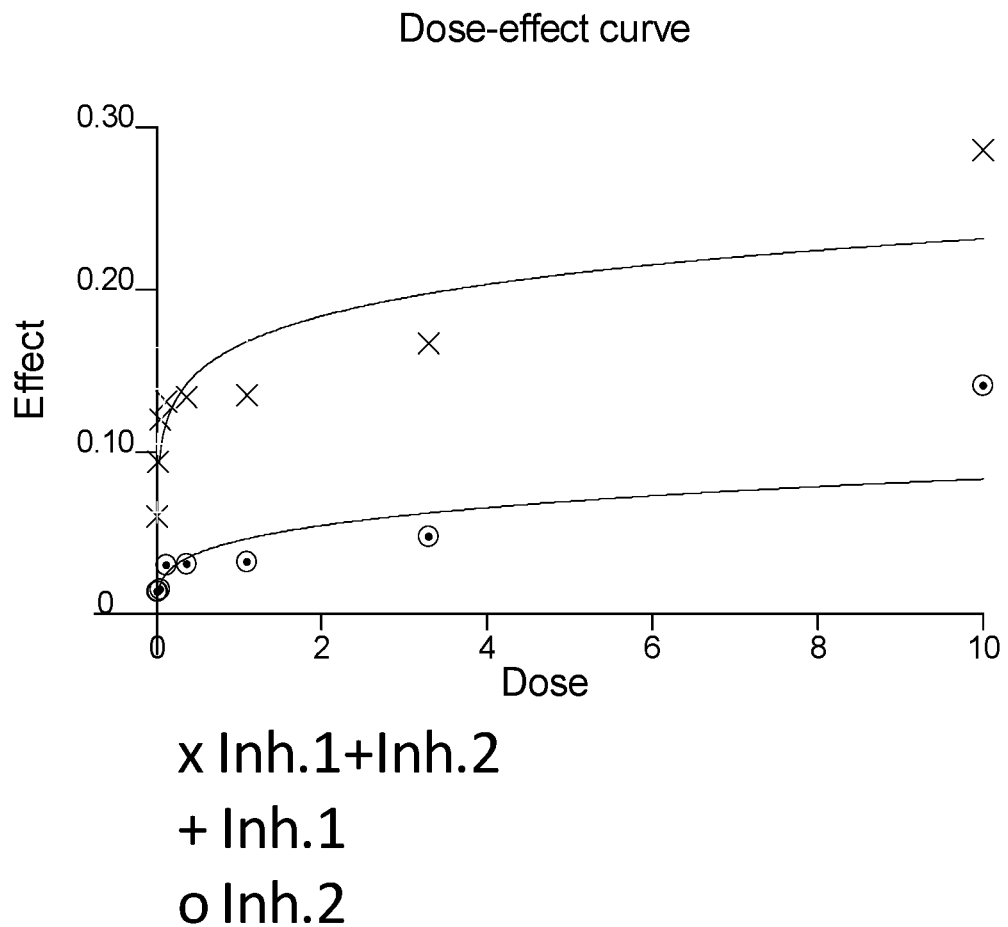
FIG. 41 illustrates the dose-effect curves obtained for the tested SUP-B15 cell line (B lymphoblast, acute lymphoblastic leukemia) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 42:
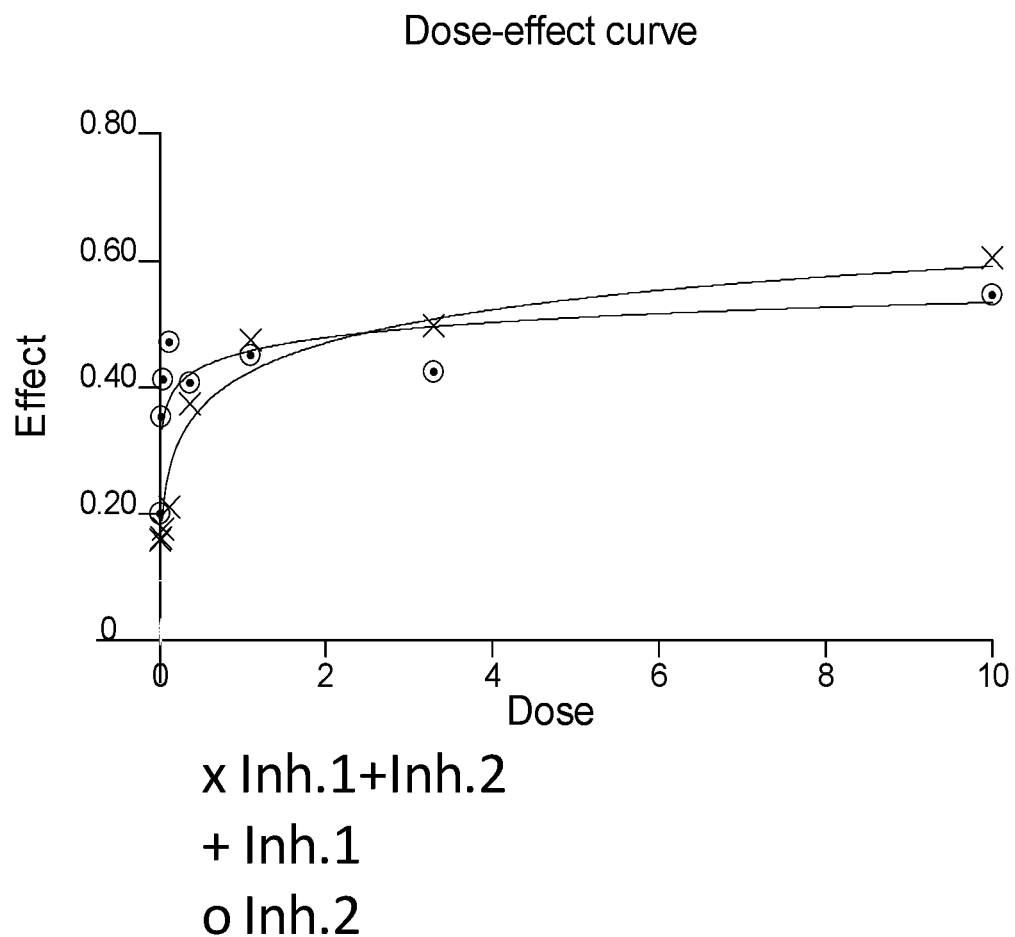
FIG. 42 illustrates the dose-effect curves obtained for the tested CCRF cell line (B lymphoblast, acute lymphoblastic leukemia) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 43:
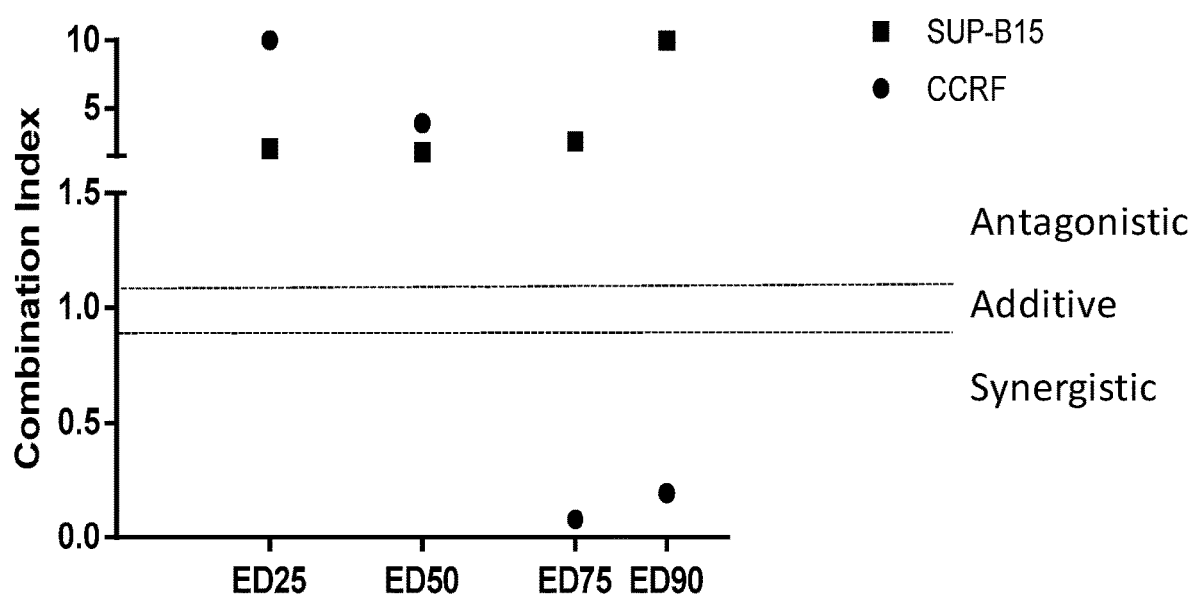
FIG. 43 illustrates the synergy observed in certain cell lines when the BTK inhibitor of Formula XVIII and the JAK-2 inhibitor of Formula XXX (ruxolitinib) are combined. Repeat experiments for two of the cell lines previously shown in FIG. 38 are shown, including SUP-B15 (B lymphoblast, acute lymphoblastic leukemia) and CCRF (B lymphoblast, acute lymphoblastic leukemia).
Figure 44:
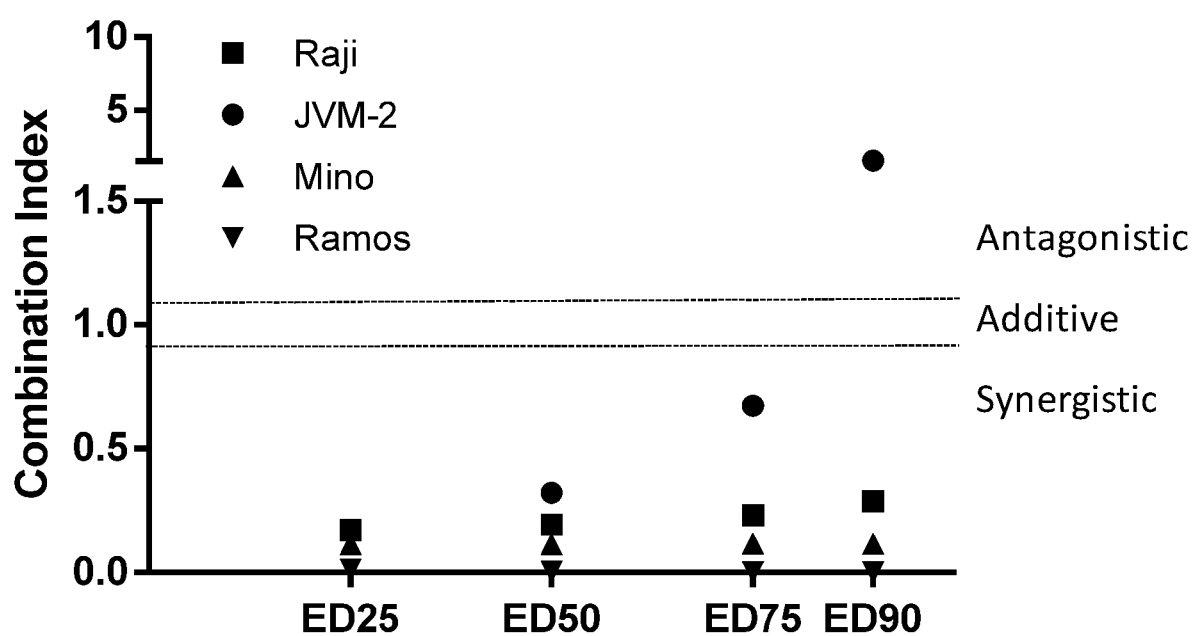
FIG. 44 illustrates the synergy observed in certain cell lines when the BTK inhibitor of Formula XVIII and the JAK-2 inhibitor of Formula XXX (ruxolitinib) are combined. The tested cell lines included JVM-2 (prolymphocytic leukemia), Raji (B lymphocyte, Burkitt's lymphoma), Ramos (B lymphocyte, Burkitt's lymphoma), and Mino (mantle cell lymphoma). The dose-effect curves for these cell lines are given in FIG. 45, FIG. 46, FIG. 47, and FIG. 48.
Figure 45:
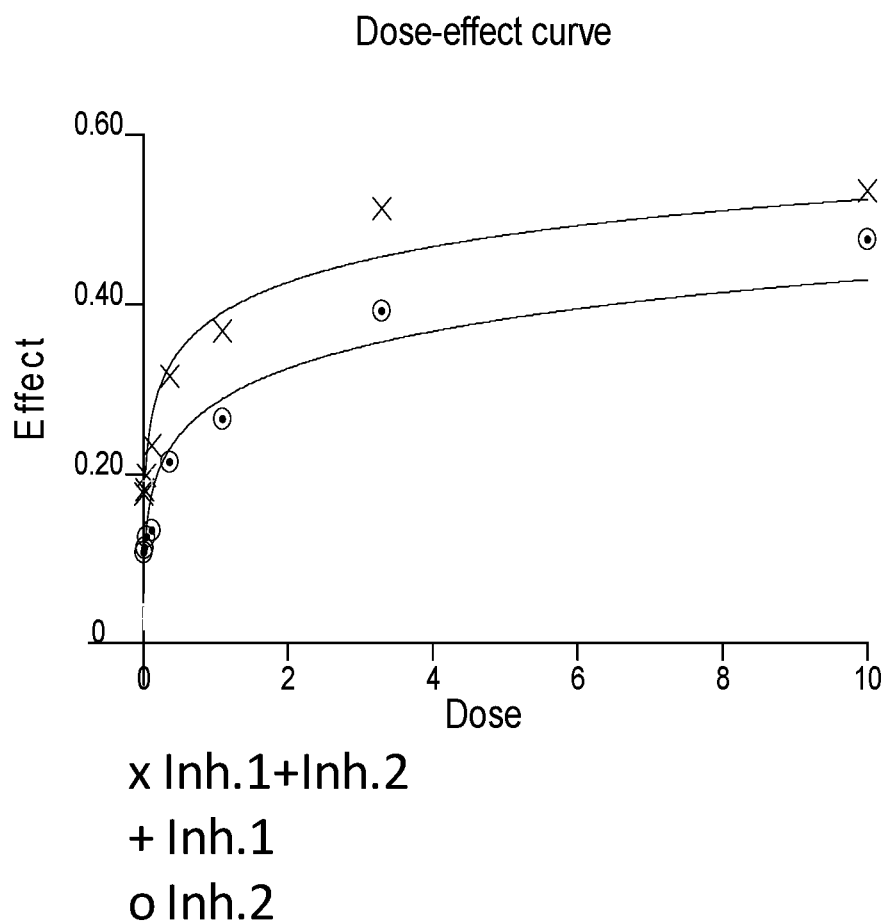
FIG. 45 illustrates the dose-effect curves obtained for the tested JVM-2 cell line (prolymphocytic leukemia) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 46:
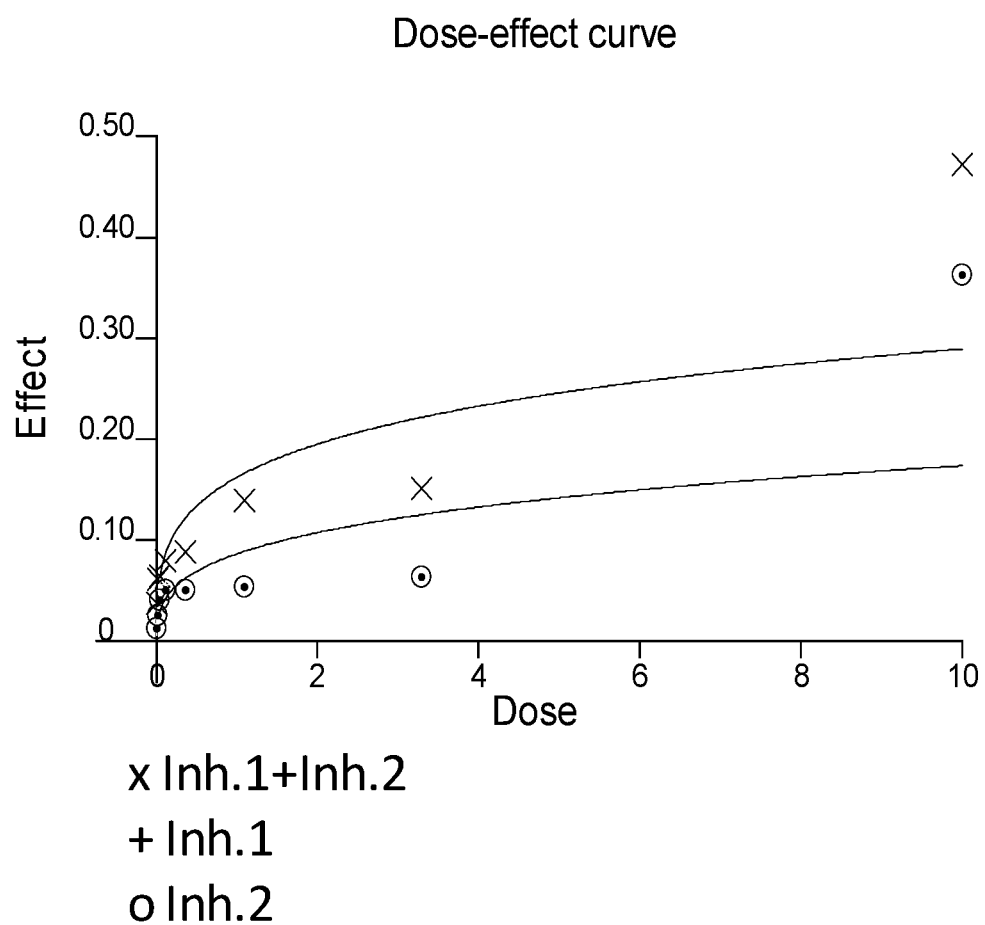
FIG. 46 illustrates the dose-effect curves obtained for the tested Raji cell line (B lymphocyte, Burkitt's lymphoma) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 47:
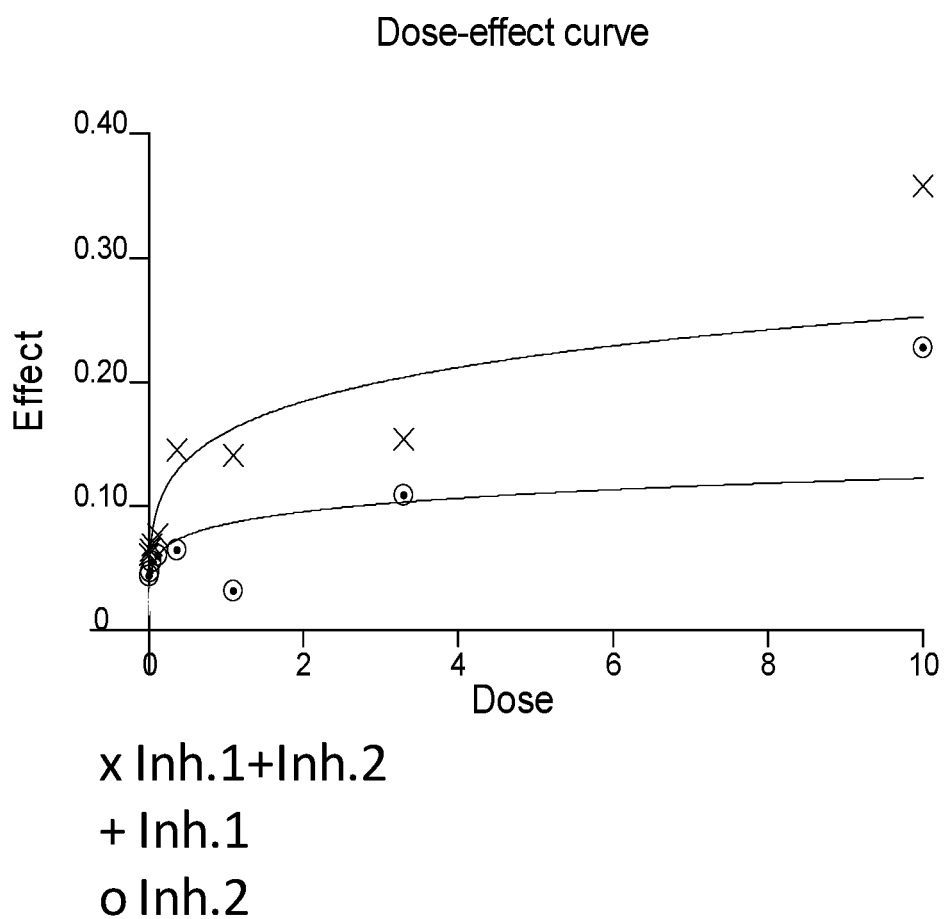
FIG. 47 illustrates the dose-effect curves obtained for the tested Ramos cell line (B lymphocyte, Burkitt's lymphoma) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 48:
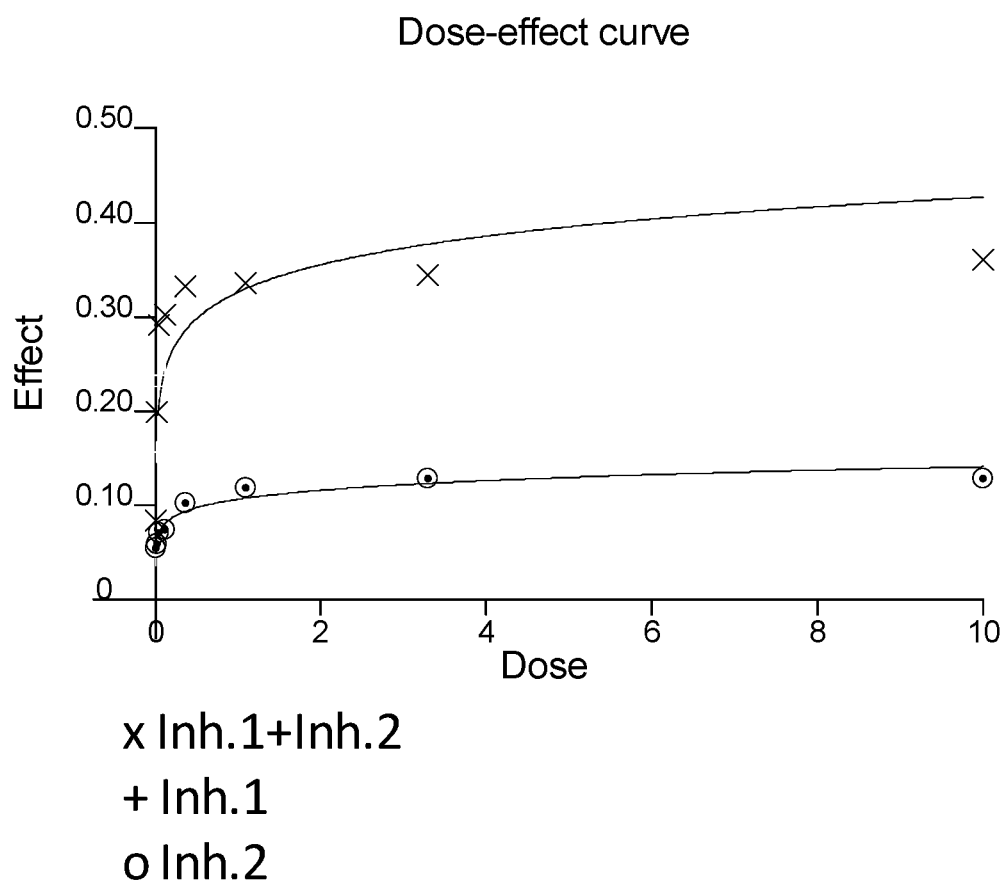
FIG. 48 illustrates the dose-effect curves obtained for the tested Mino cell line (mantle cell lymphoma) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 49:
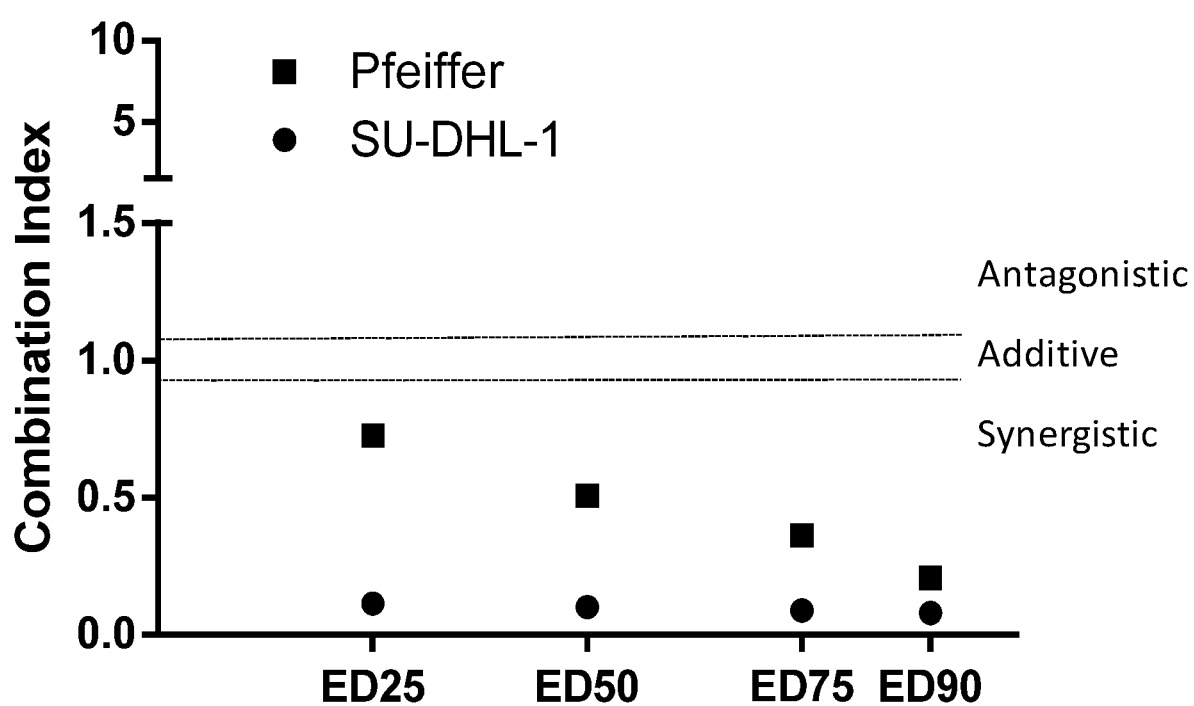
FIG. 49 illustrates the synergy observed in certain cell lines when the BTK inhibitor of Formula XVIII and the JAK-2 inhibitor of Formula XXX (ruxolitinib) are combined. The tested cell lines included Pfeiffer (follicular lymphoma) and SU-DHL-1 (DLBCL-ABC). The dose-effect curves for these cell lines are given in FIG. 50 and FIG. 51.
Figure 50:
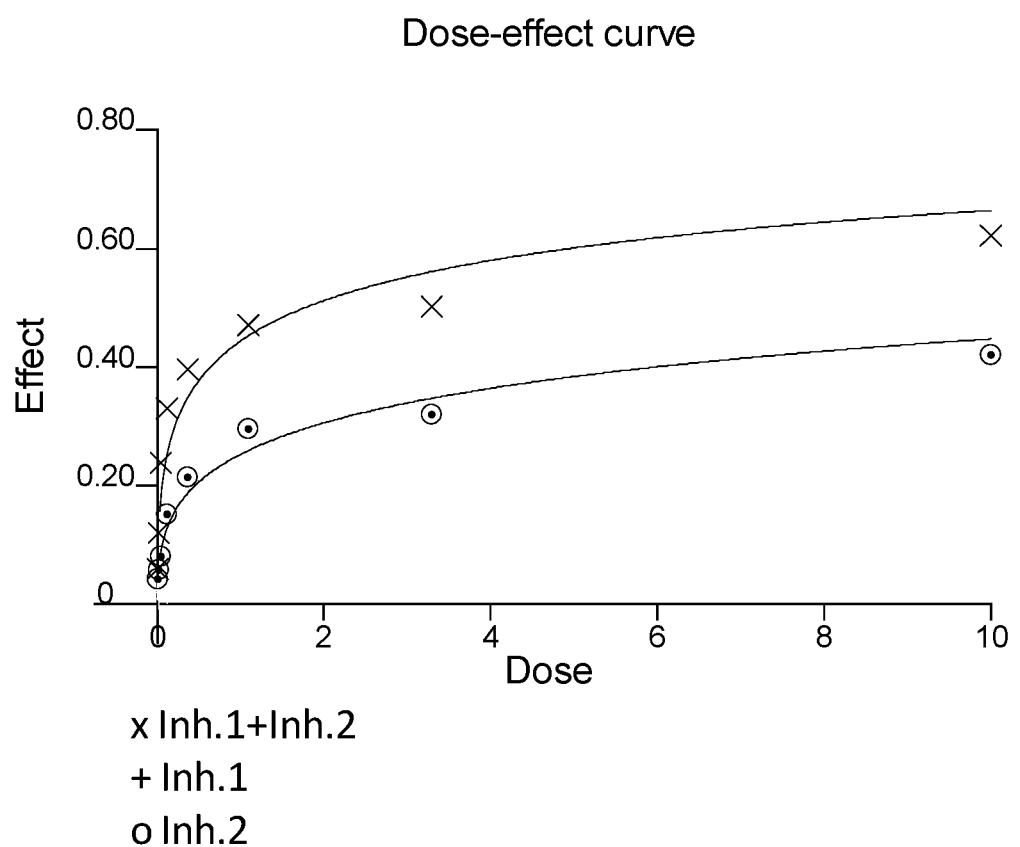
FIG. 50 illustrates the dose-effect curves obtained for the tested Pfeiffer cell line (follicular lymphoma) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 51:
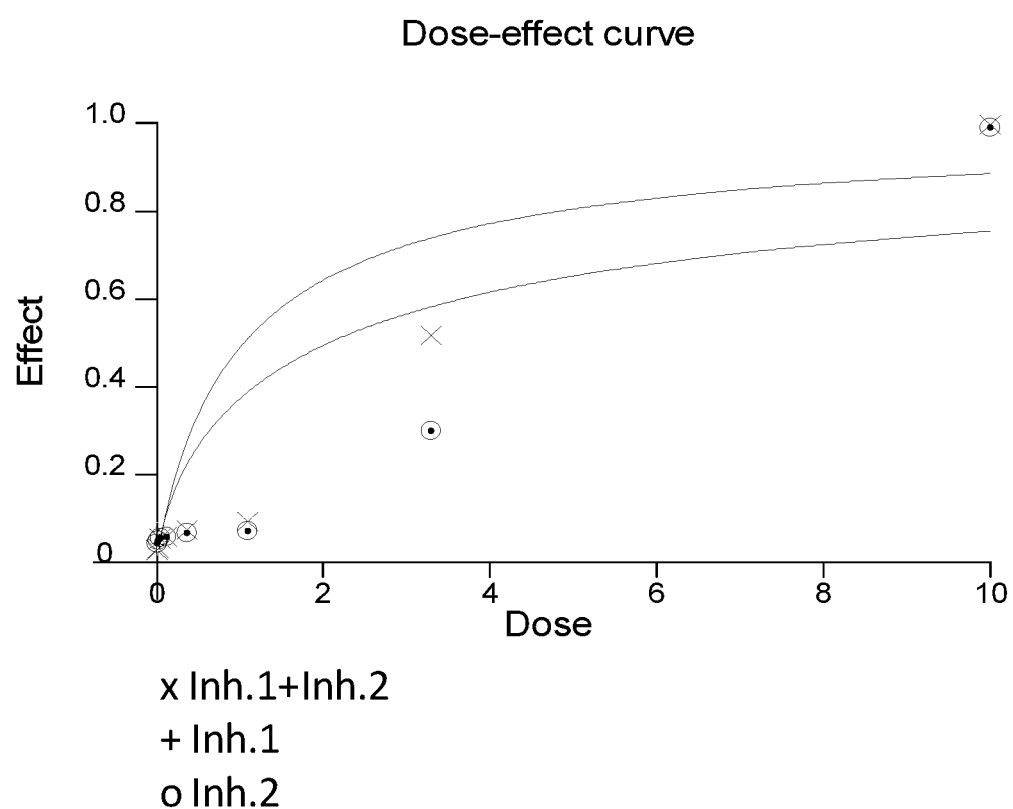
FIG. 51 illustrates the dose-effect curves obtained for the tested SU-DHL-1 cell line (follicular lymphoma) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 52:
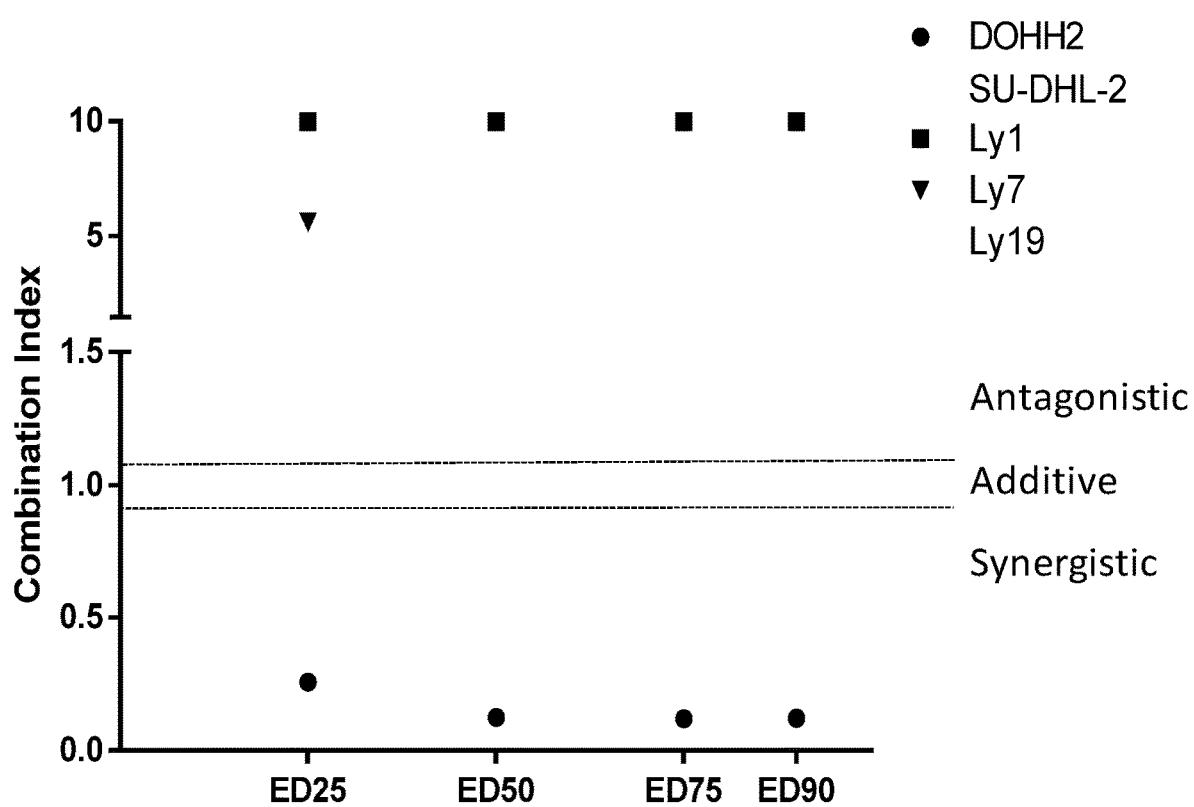
FIG. 52 illustrates the synergy observed in certain cell lines when the BTK inhibitor of Formula XVIII and the JAK-2 inhibitor of Formula XXX (ruxolitinib) are combined. The tested cell lines included DOHH2 (follicular lymphoma), SU-DHL-1 (DLBCL-ABC), Ly1 (DLBCL-GCB), Ly7 (DLBCL-GCB), and Ly19 (DLBCL-GCB). The dose-effect curves for these cell lines are given in FIG. 53, FIG. 54, FIG. 55, and FIG. 56, except for the Ly19 cell line, which is not graphed because of a negative slope.
Figure 53:
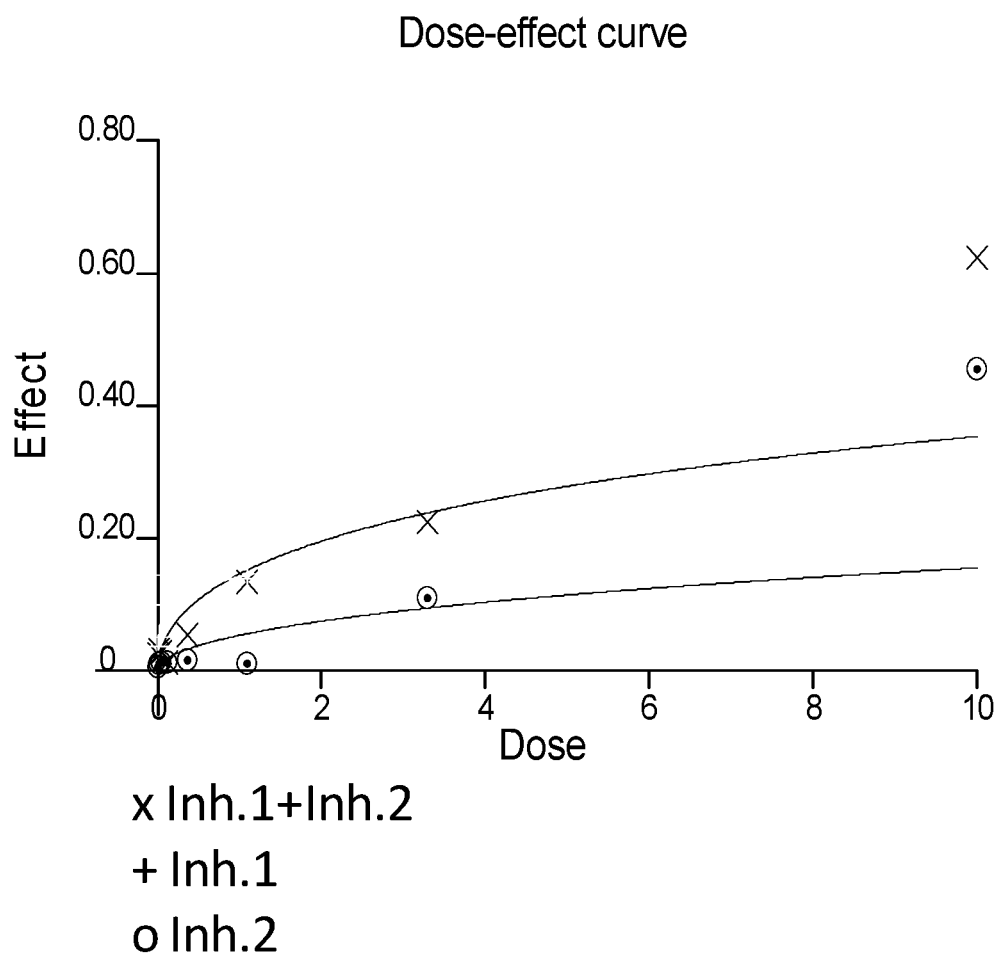
FIG. 53 illustrates the dose-effect curves obtained for the tested DOHH2 cell line (follicular lymphoma) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 54:
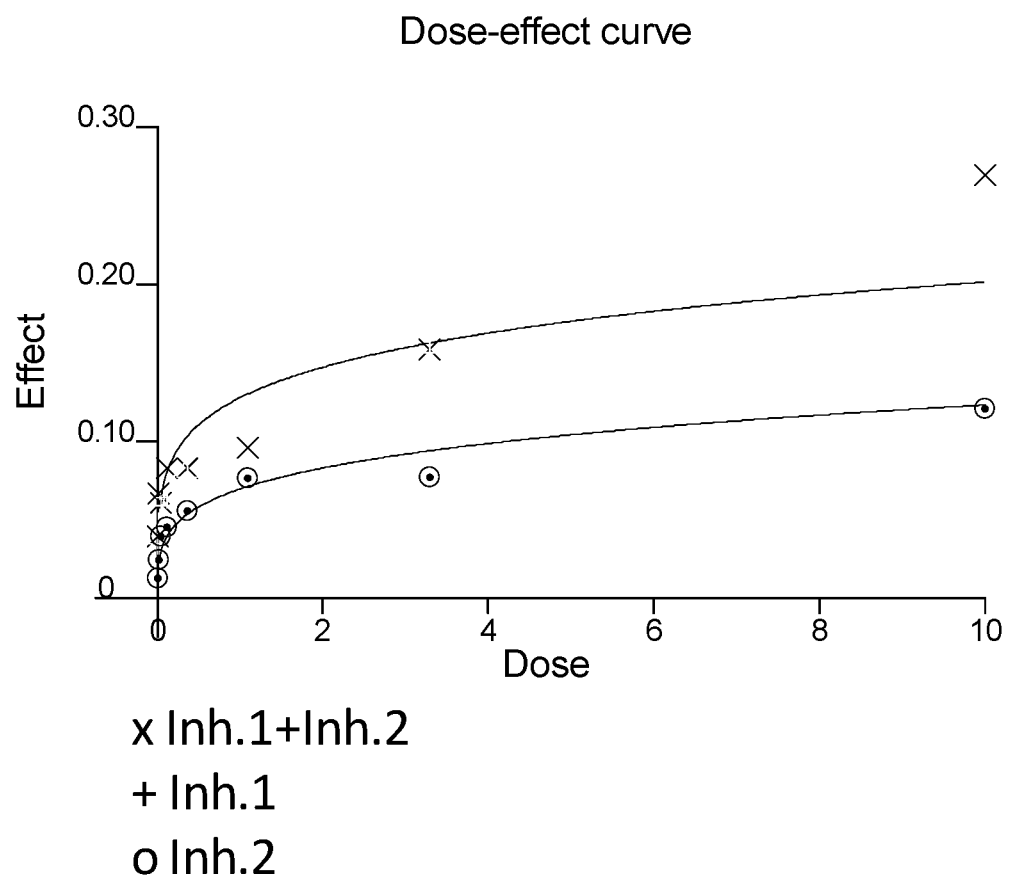
FIG. 54 illustrates the dose-effect curves obtained for the tested SU-DHL-1 cell line (DLBCL-ABC) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 55:
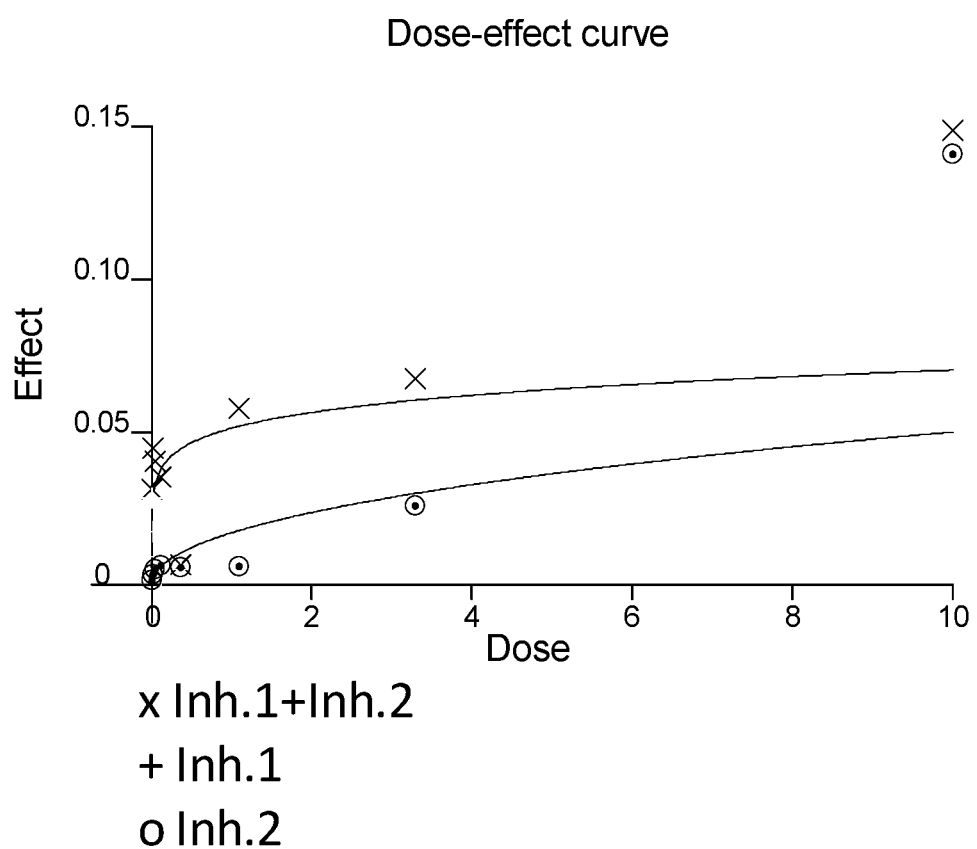
FIG. 55 illustrates the dose-effect curves obtained for the tested Ly1 cell line (DLBCL-GCB) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 56:
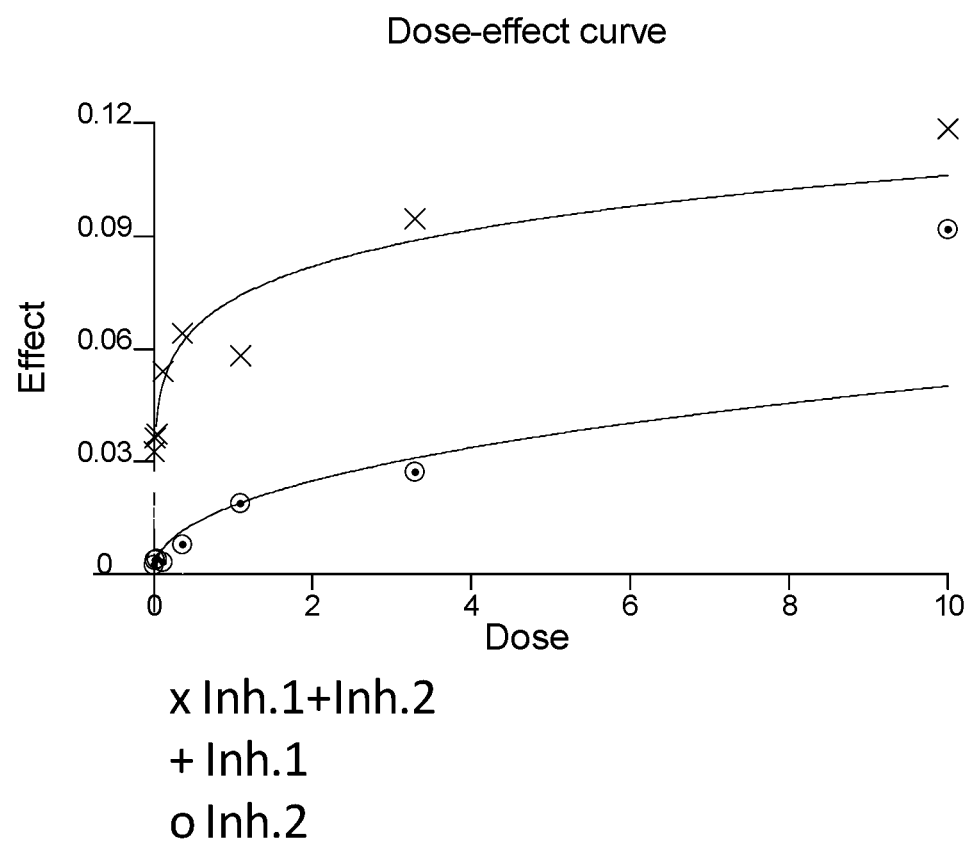
FIG. 56 illustrates the dose-effect curves obtained for the tested Ly7 cell line (DLBCL-GCB) using combined dosing of the BTK inhibitor of Formula XVIII ("Inh.1") and the JAK-2 inhibitor of Formula XXX ("Inh.2") (ruxolitinib). The y-axis ("Effect") is given in units of Fa (fraction affected) and the x-axis ("Dose") is given in linear units of µM.
Figure 57:
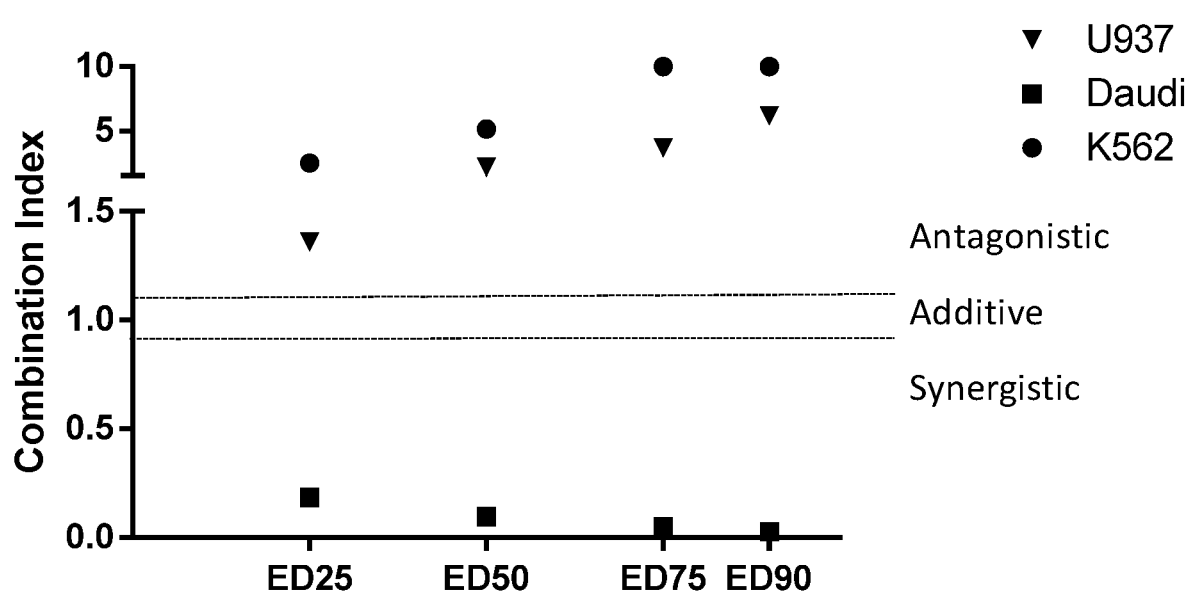
FIG. 57 illustrates the synergy observed in certain cell lines when the BTK inhibitor of Formula XVIII and the JAK-2 inhibitor of Formula XXX (ruxolitinib) are combined. The tested cell lines included U937 (histiocytic lymphoma), Daudi (human Burkitt's lymphoma), and K562
Figure 125:
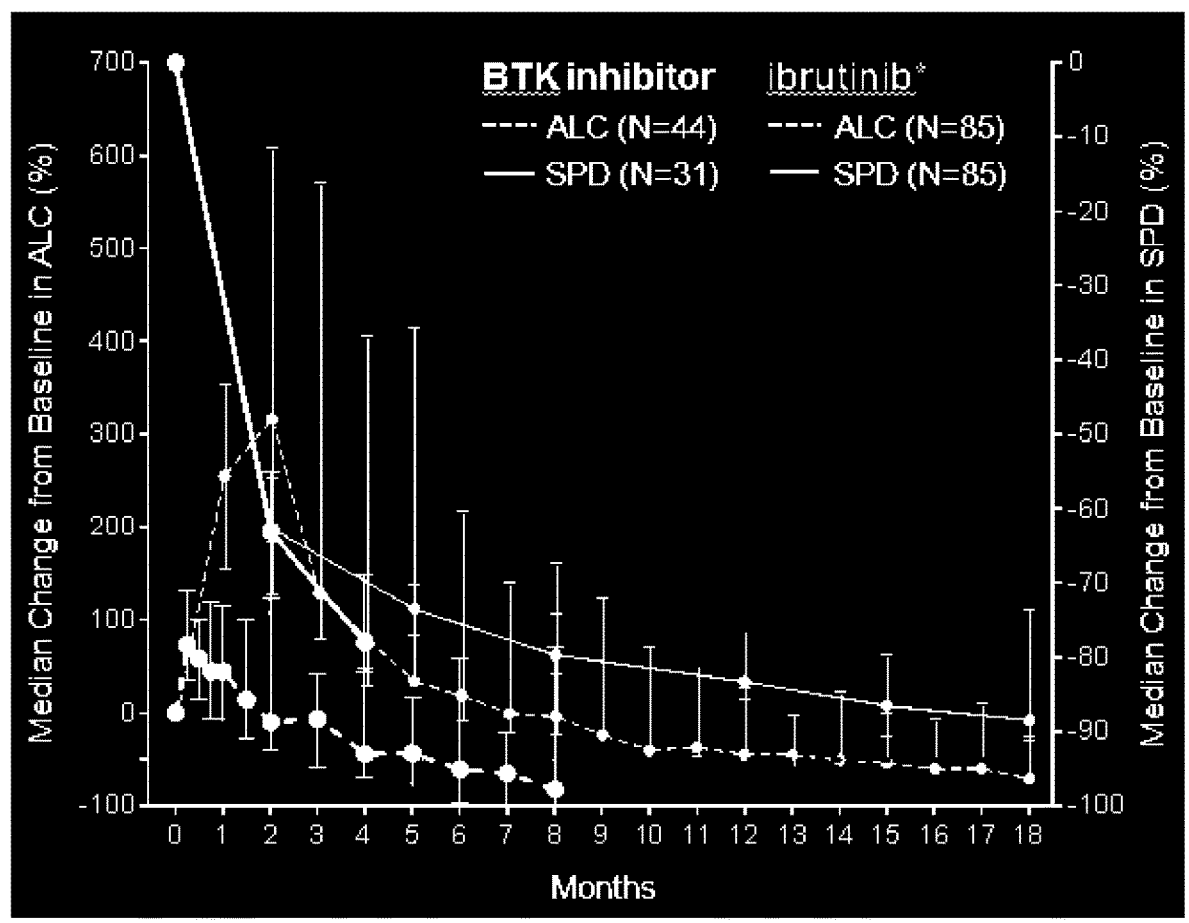

FIG. 125 illustrates the results of the clinical study of Formula (XVIII) (labeled "BTK inhibitor") in CLL, which are shown in comparison to the results reported for ibrutinib in FIG. 1A of Byrd, et al., *N. Engl. J. Med.* 2013, 369, 32-42. The results show that the BTK inhibitor of Formula (XVIII) causes a much smaller relative increase and much faster decrease in absolute lymphocyte count (ALC) relative to the BTK inhibitor ibrutinib. The sum of the product of greatest diameters (SPD) also decreases more rapidly during treatment with the BTK inhibitor than with the BTK inhibitor ibrutinib.

Figure 126:
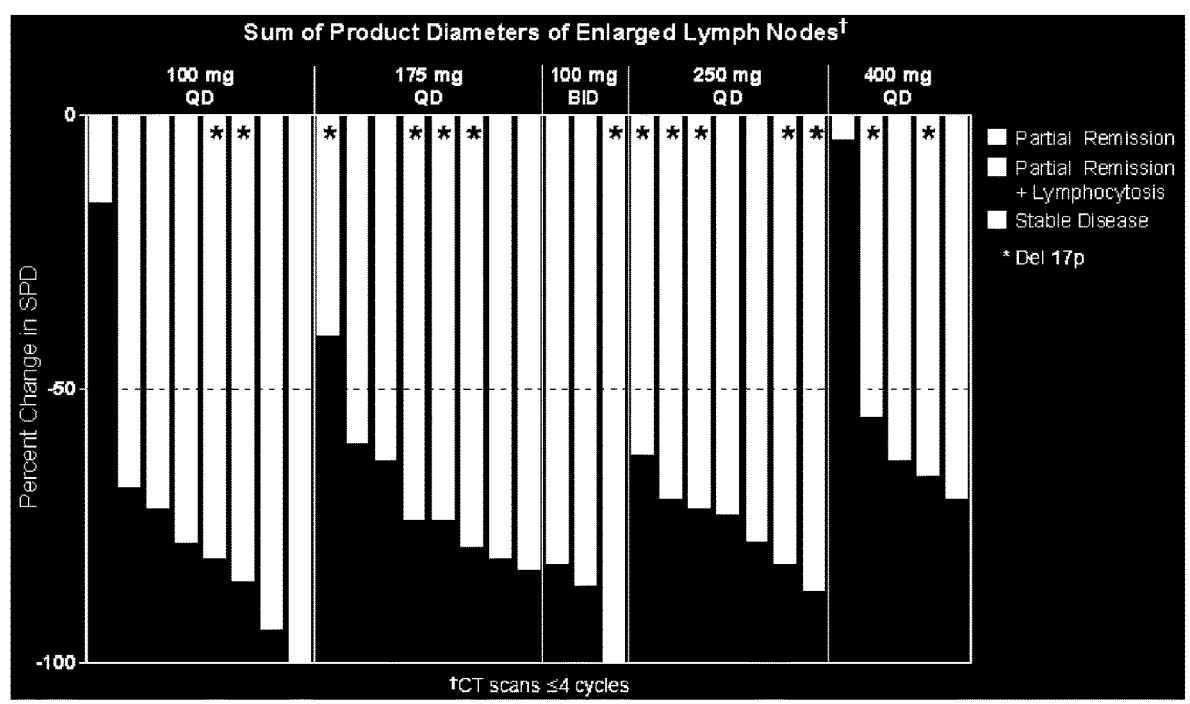

FIG. 126 shows overall response data shown by SPD of enlarged lymph nodes in CLL patients as a function of dose of the BTK inhibitor of Formula (XVIII).

Figure 127:
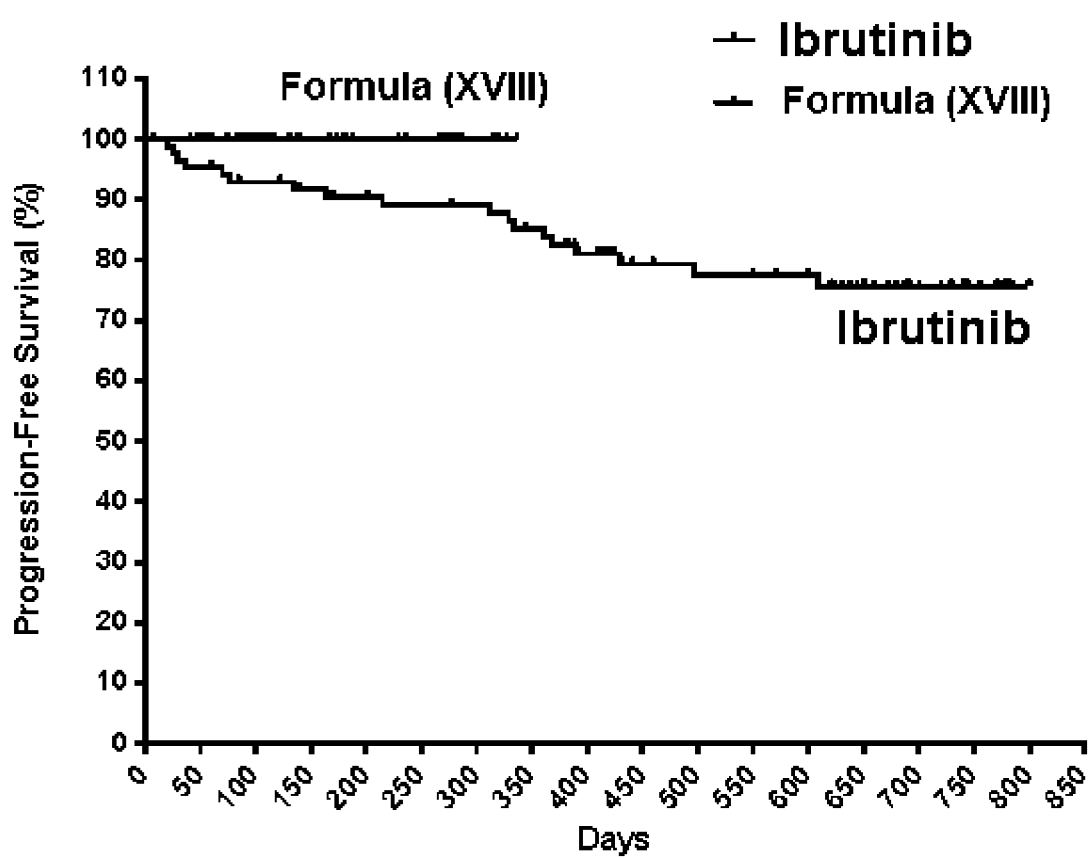

FIG. 127 shows a comparison of progression-free survival (PFS) in CLL patients treated with the BTK inhibitor ibrutinib or the BTK inhibitor of Formula (XVIII). The ibrutinib data is taken from Byrd, et al., *N. Engl. J. Med.* 2013, 369, 32-42. CLL patients treated with Formula (XVIII) for at least 8 days are included.

Figure 128:
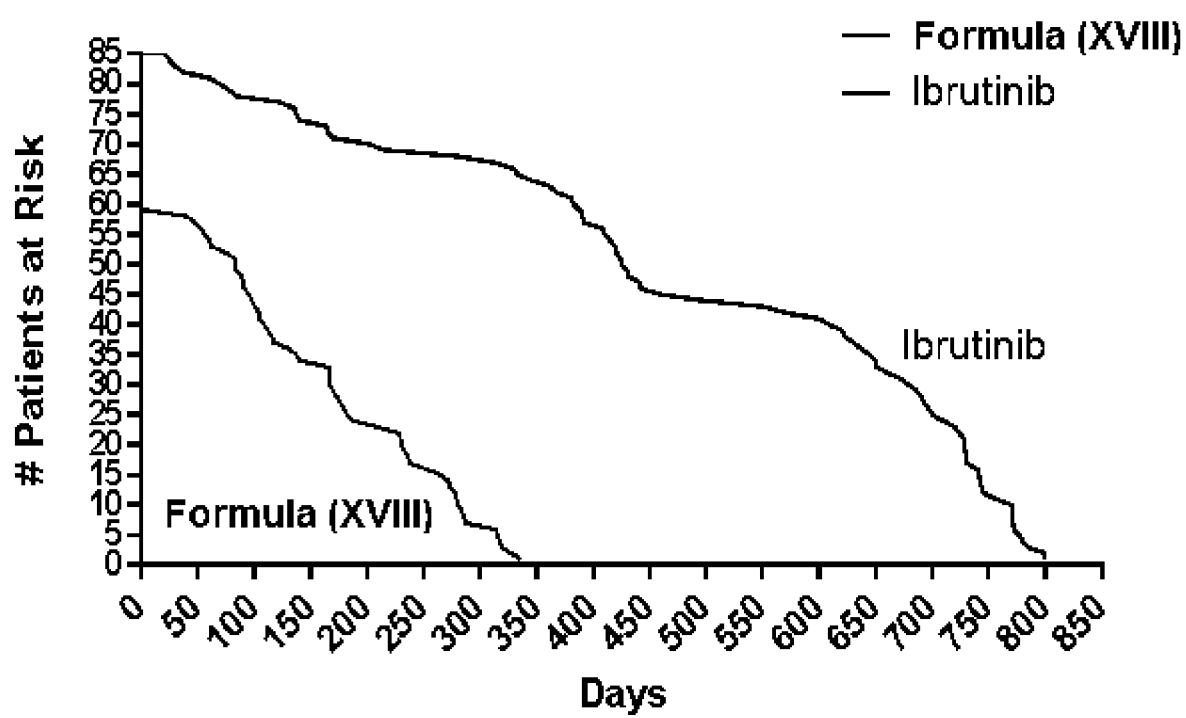

FIG. 128 shows a comparison of number of patients at risk in CLL patients treated with the BTK inhibitor ibrutinib or the BTK inhibitor of Formula (XVIII). CLL patients treated with Formula (XVIII) for at least 8 days are included.

Figure 129:
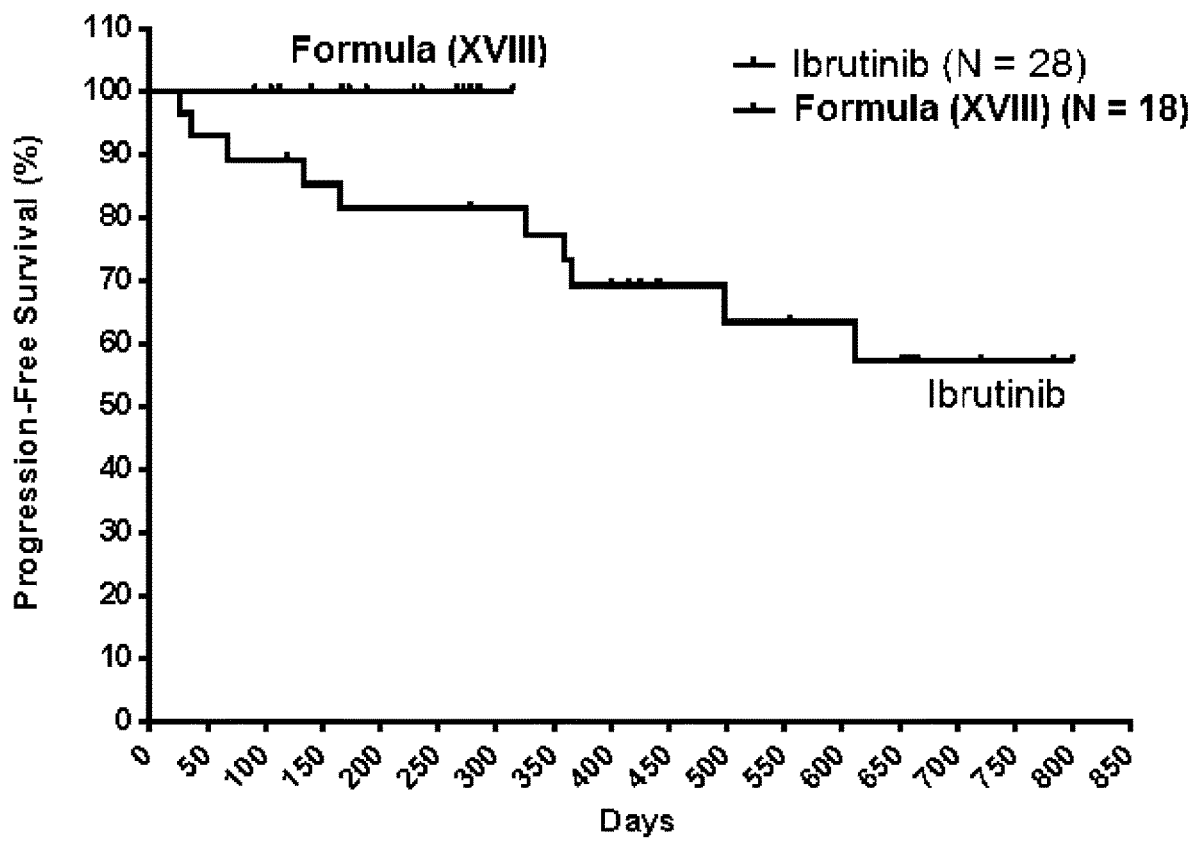

FIG. 129 shows a comparison of progression-free survival (PFS) in CLL patients exhibiting the 17p deletion and treated with the BTK inhibitor ibrutinib or the BTK inhibitor of Formula (XVIII). The ibrutinib data is taken from Byrd, et al., *N. Engl. J. Med.* 2013, 369, 32-42.

Figure 130:
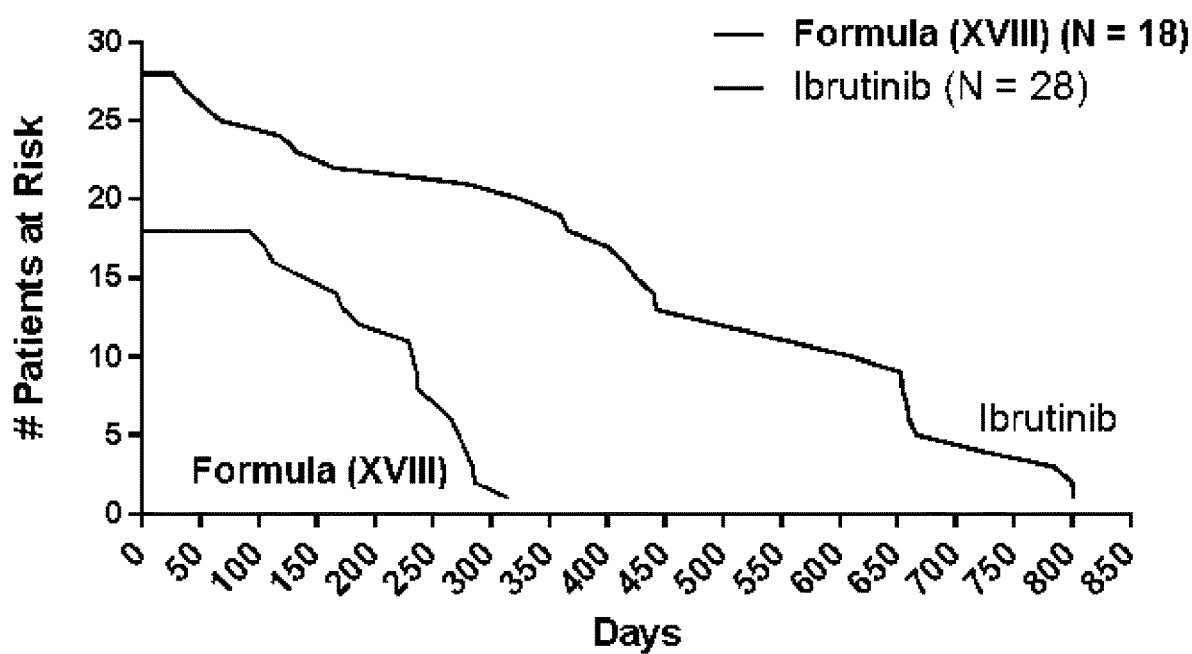

FIG. 130 shows a comparison of number of patients at risk in CLL patients exhibiting the 17p deletion and treated with the BTK inhibitor ibrutinib or the BTK inhibitor of Formula (XVIII). The ibrutinib data is taken from Byrd, et al., *N. Engl. J. Med.* 2013, 369, 32-42. CLL patients treated with Formula (XVIII) for at least 8 days are included.

Figure 131:
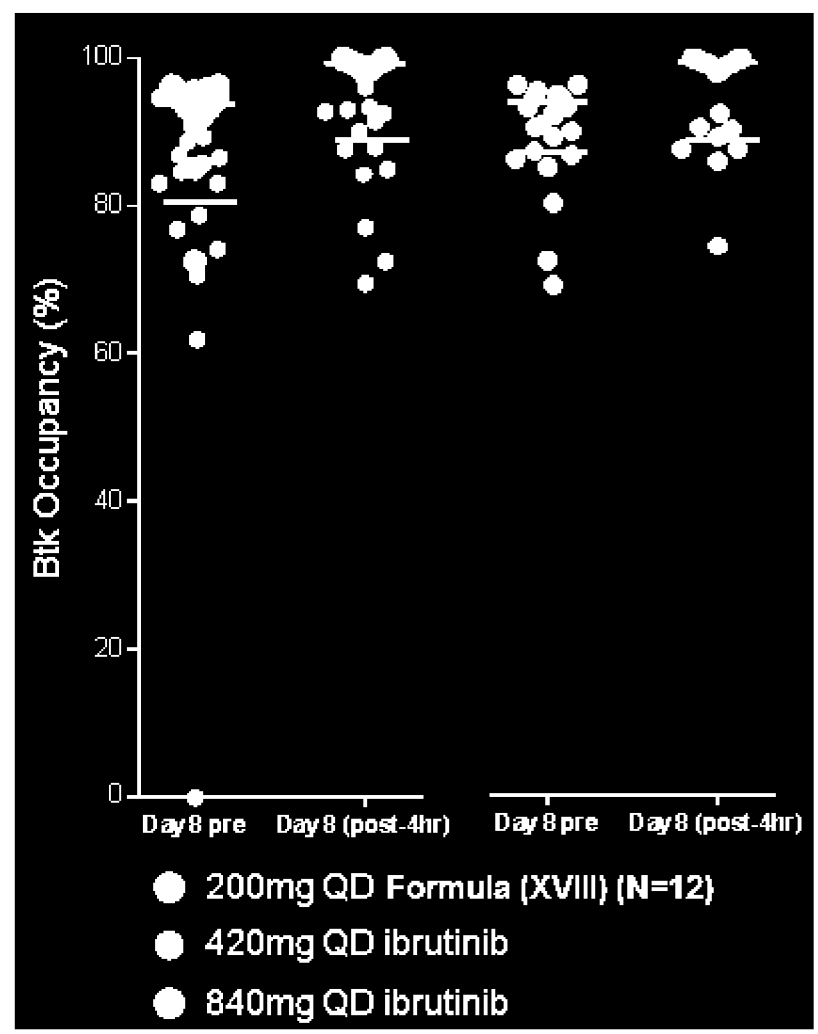

FIG. 131 shows improved BTK target occupancy of Formula (XVIII) at lower dosage versus ibrutinib in relapsed/refractory CLL patients.

Figure 132:
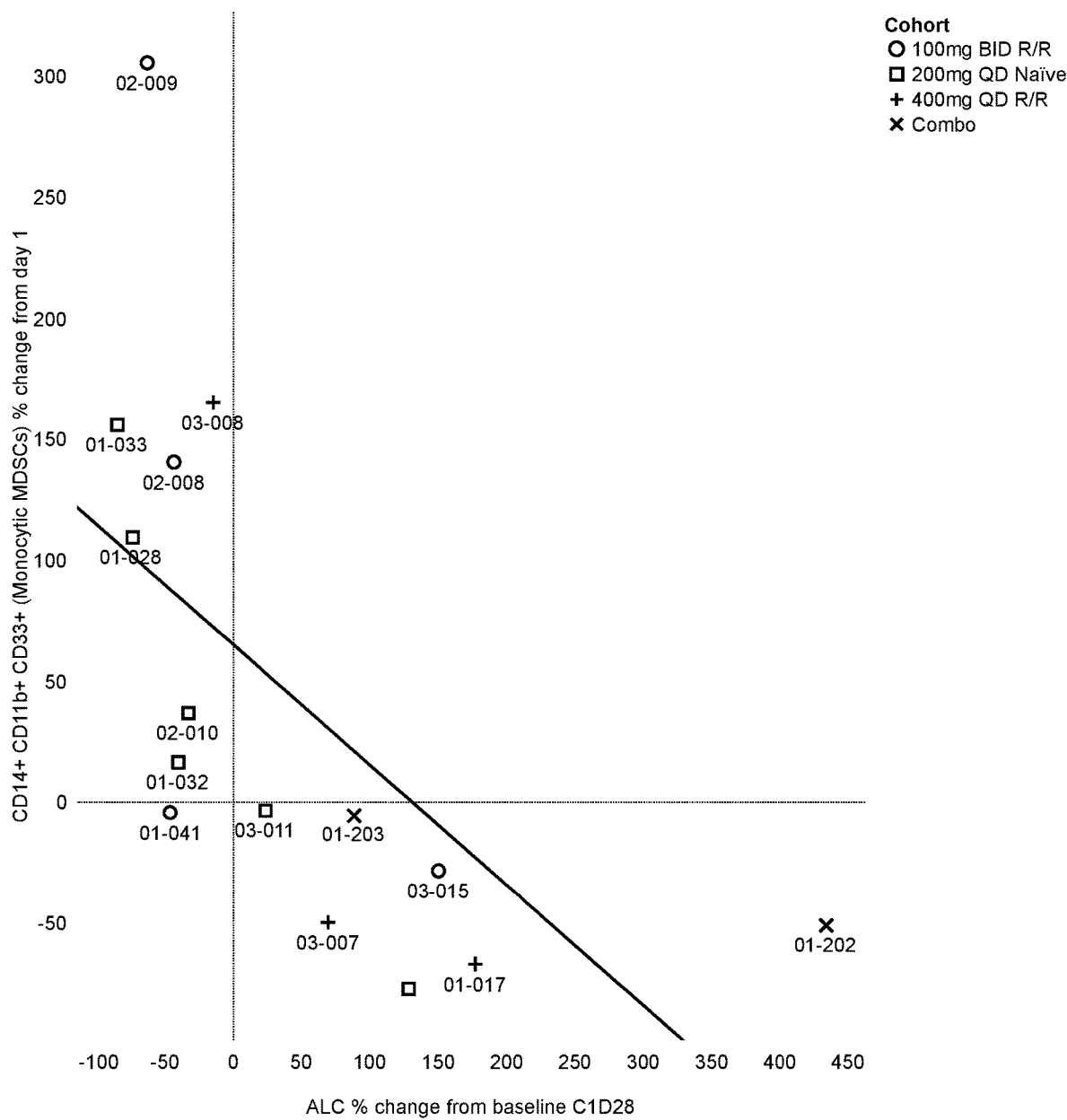

FIG. 132 shows the % change in myeloid-derived suppressor cell (MDSC) (monocytic) level over 28 days versus % ALC change at Cycle 1, day 28 (C1D28) with trendlines.

Figure 133:
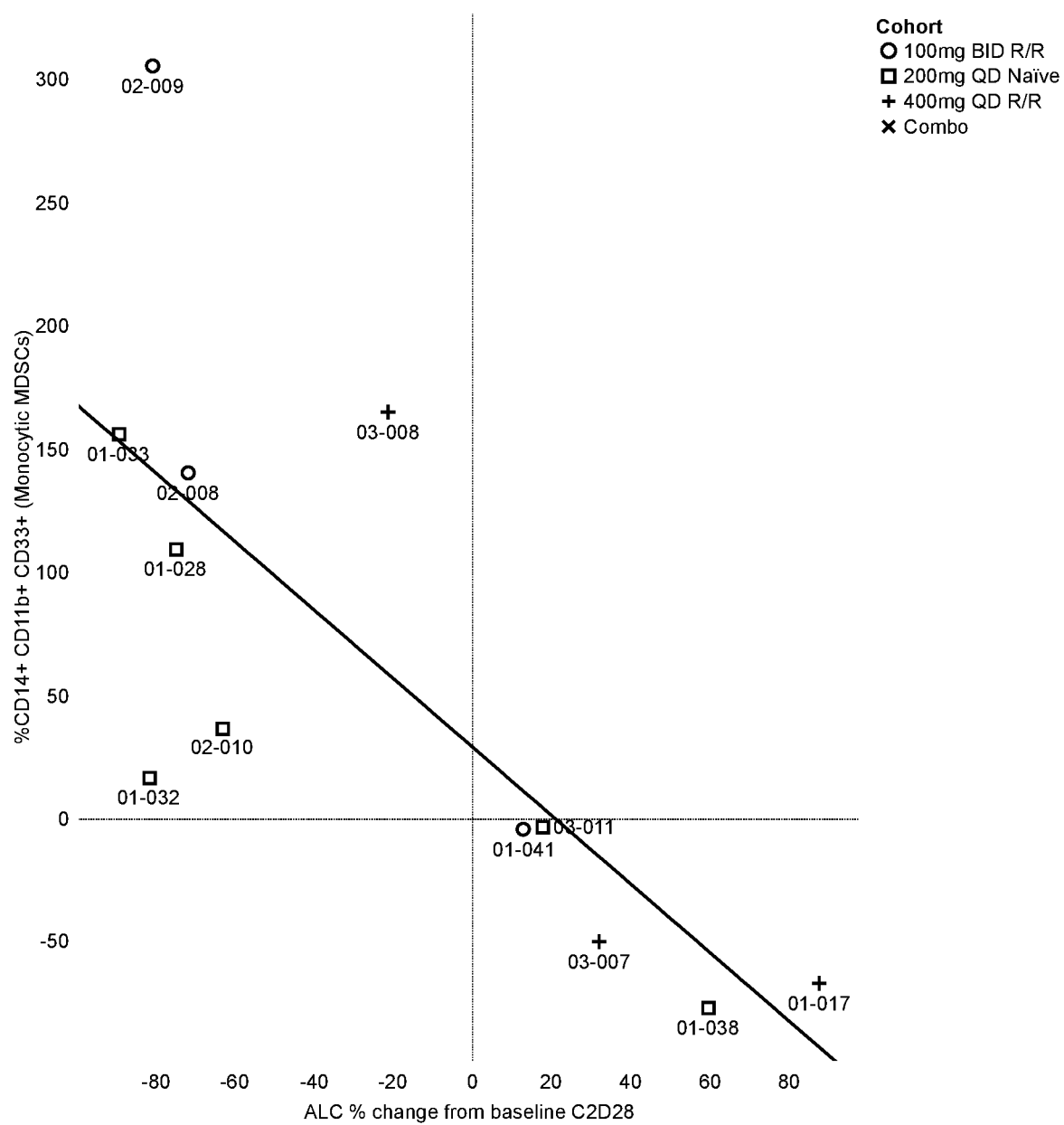

FIG. 133 shows the % change in MDSC (monocytic) level over 28 days versus % ALC change at Cycle 2, day 28 (C2D28) with trendlines.

Figure 134:
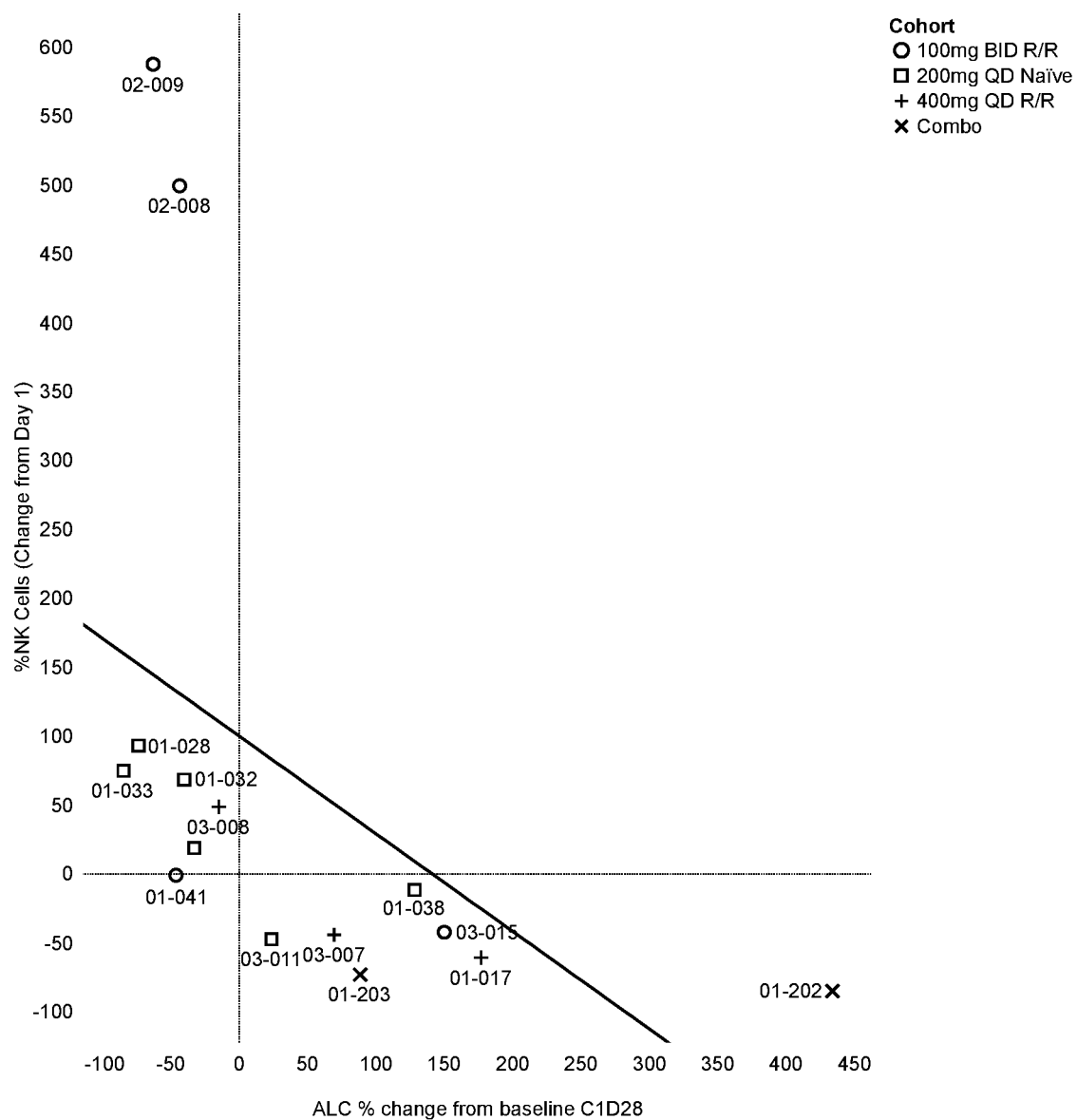

FIG. 134 shows the % change in natural killer (NK) cell level over 28 days versus % ALC change at Cycle 1, day 28 (C2D28) with trendlines.

Figure 135:
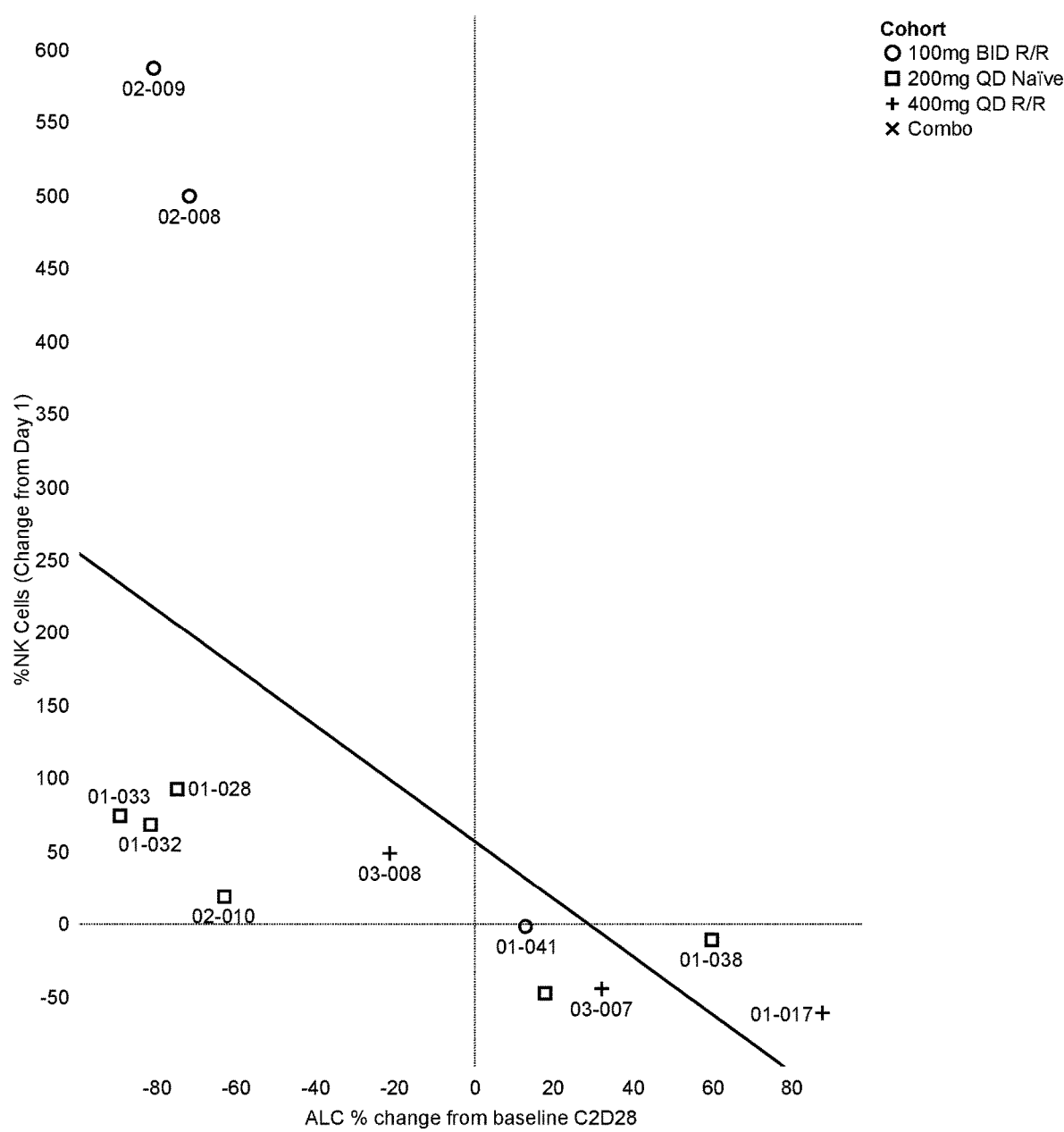

FIG. 135 shows the % change in NK cell level over 28 days versus % ALC change at Cycle 2, day 28 (C2D28) with trendlines.

Figure 136:
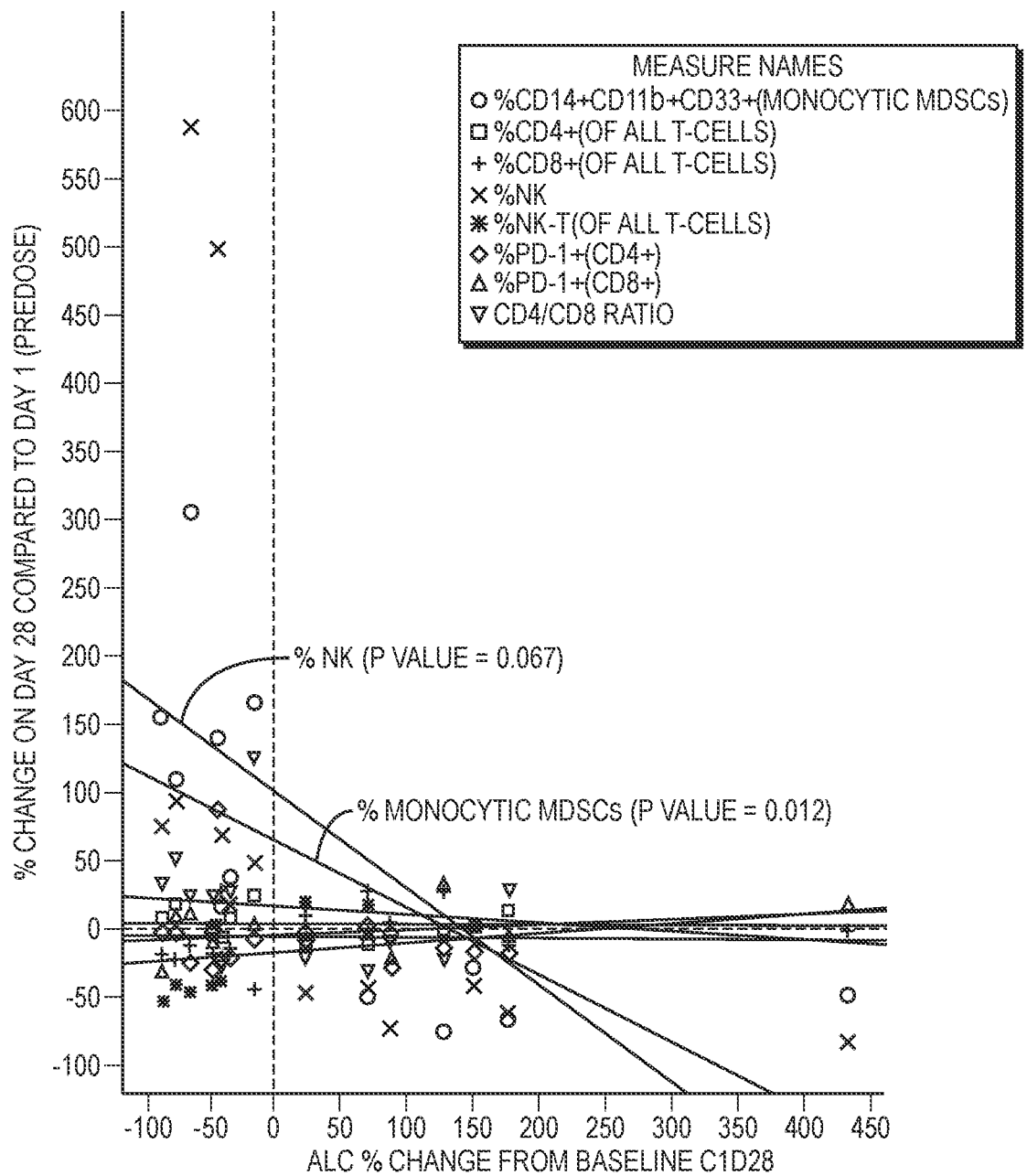

FIG. 136 compares the % change in MDSC (monocytic) level and % change in NK cell level over 28 days versus % ALC change with the % change in level of CD4+ T cells, CD8+ T cells, CD4+/CD8+ T cell ratio, NK-T cells, PD-1+ CD4+ T cells, and PD-1+CD8+ T cells, also versus % ALC change, at Cycle 1 day 28 (C1D28). Trendlines are shown for % change in MDSC (monocytic) level and % change in NK cell level.

Figure 137:
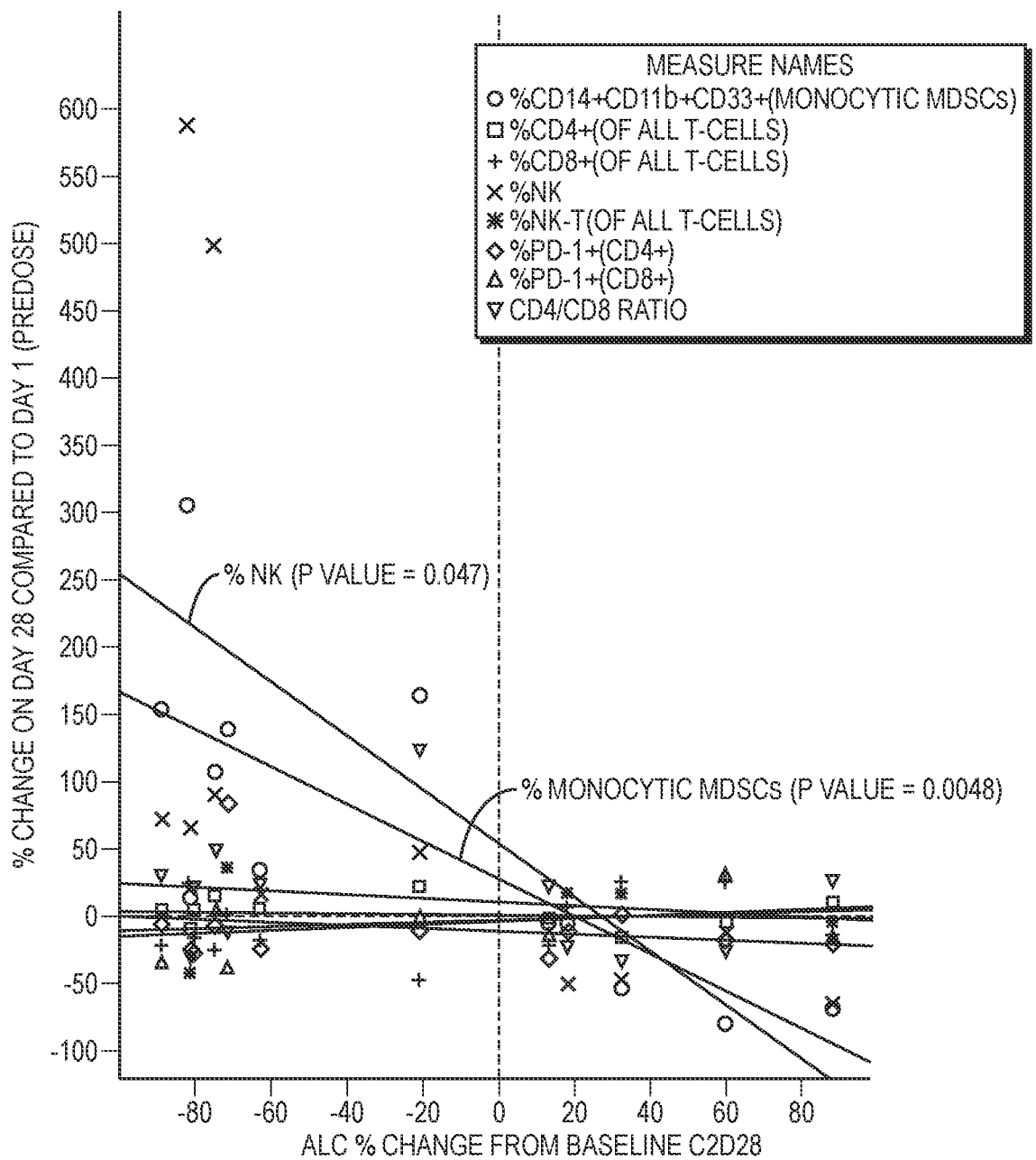

FIG. 137 compares the % change in MDSC (monocytic) level and % change in NK cell level over 28 days versus % ALC change with the % change in level of CD4+ T cells, CD8+ T cells, CD4+/CD8+ T cell ratio, NK-T cells, PD-1+ CD4+ T cells, and PD-1+CD8+ T cells, also versus % ALC change, at Cycle 2 day 28 (C2D28). Trendlines are shown for % change in MDSC (monocytic) level and % change in NK cell level.

Figure 138:
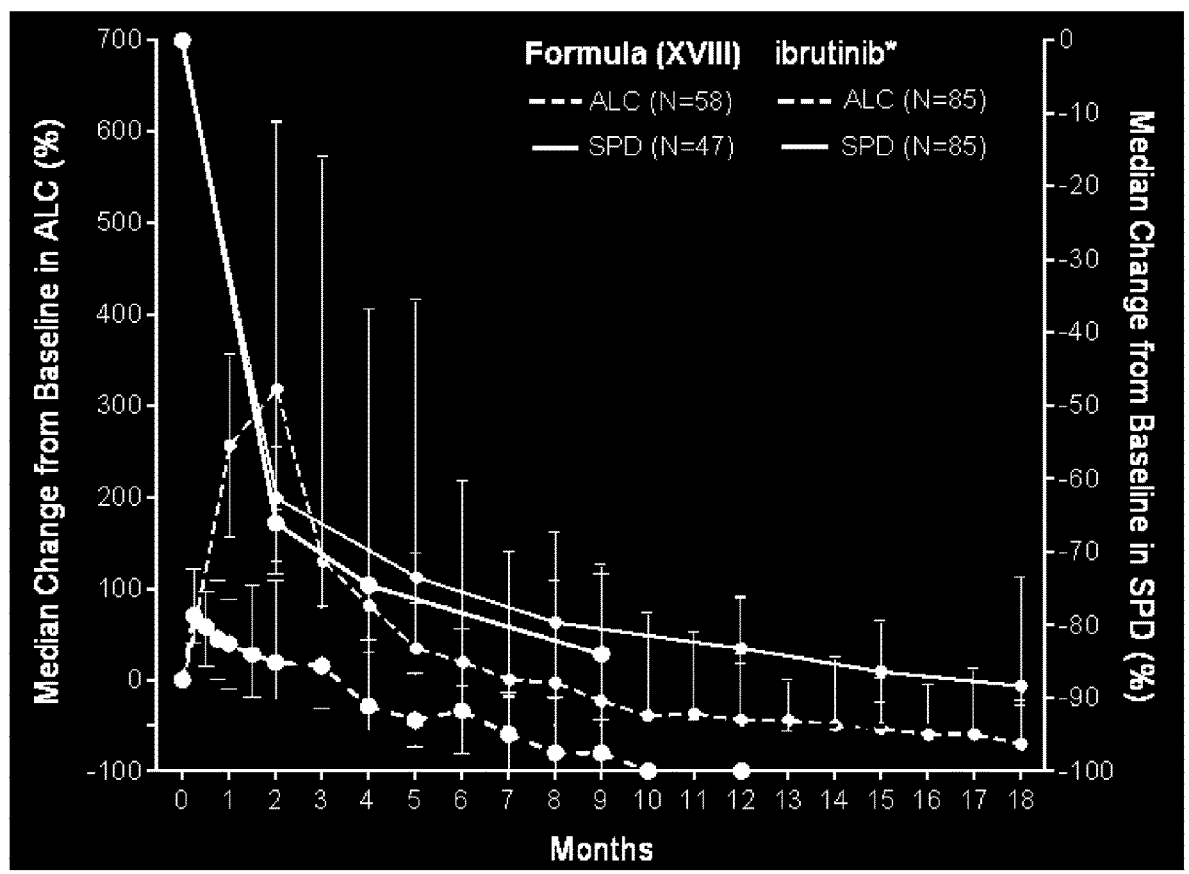

FIG. 138 shows additional data related to that presented in FIG. 125.

Figure 139:
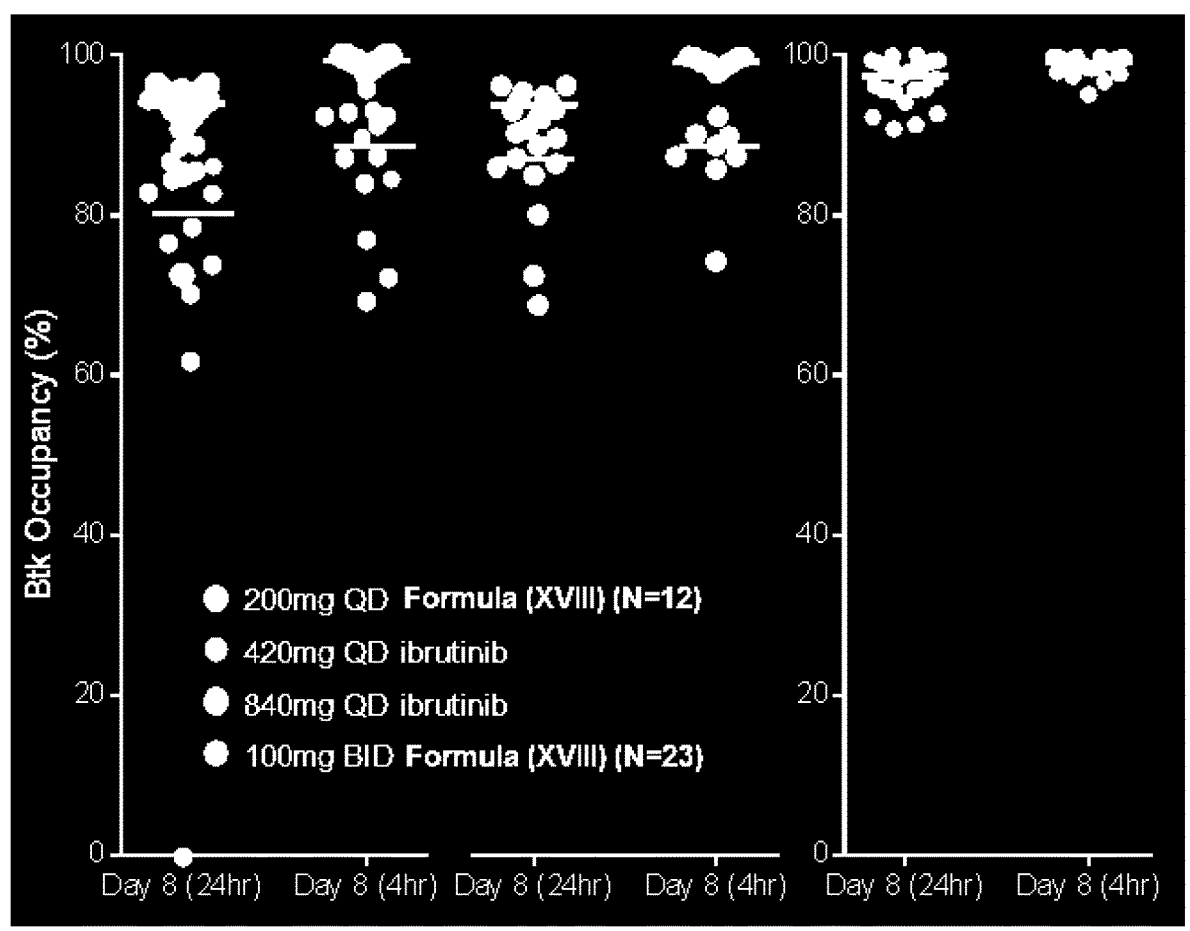

FIG. 139 shows additional data related to that presented in FIG. 131, and includes BID dosing results.

Figure 140:
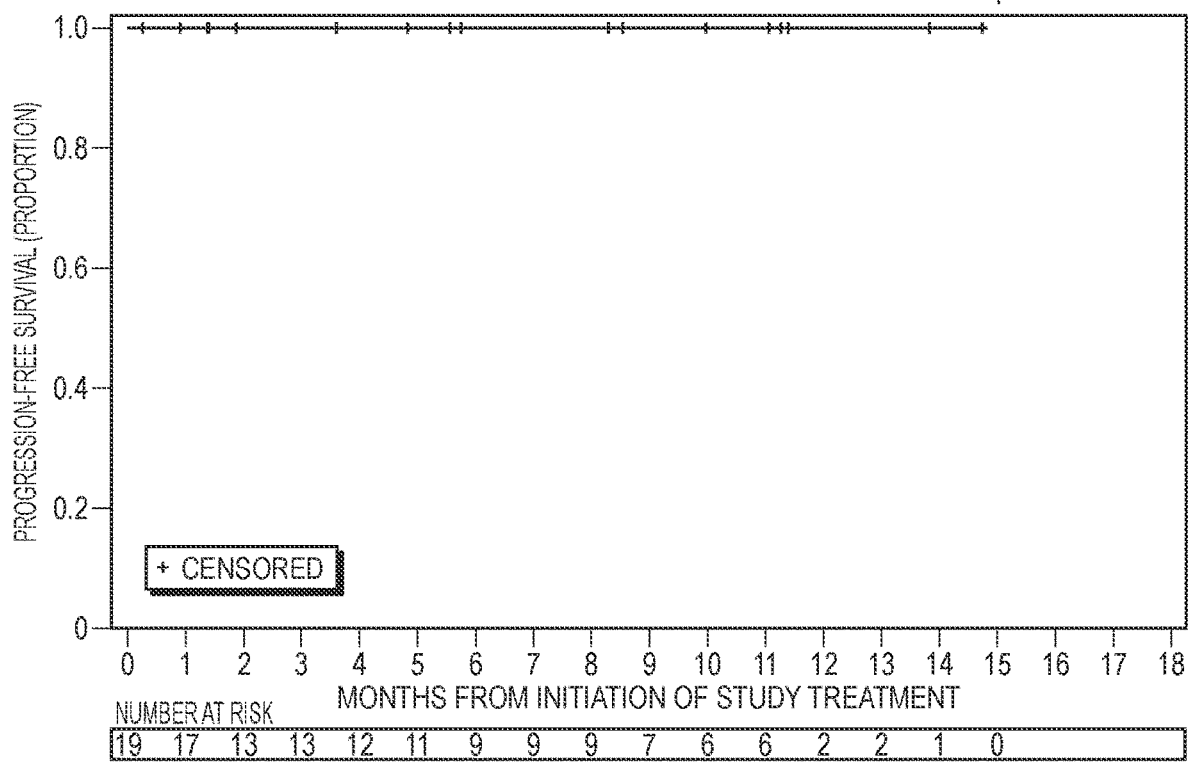

FIG. 140 illustrates PFS for patients with 17p deletion.

Figure 141:
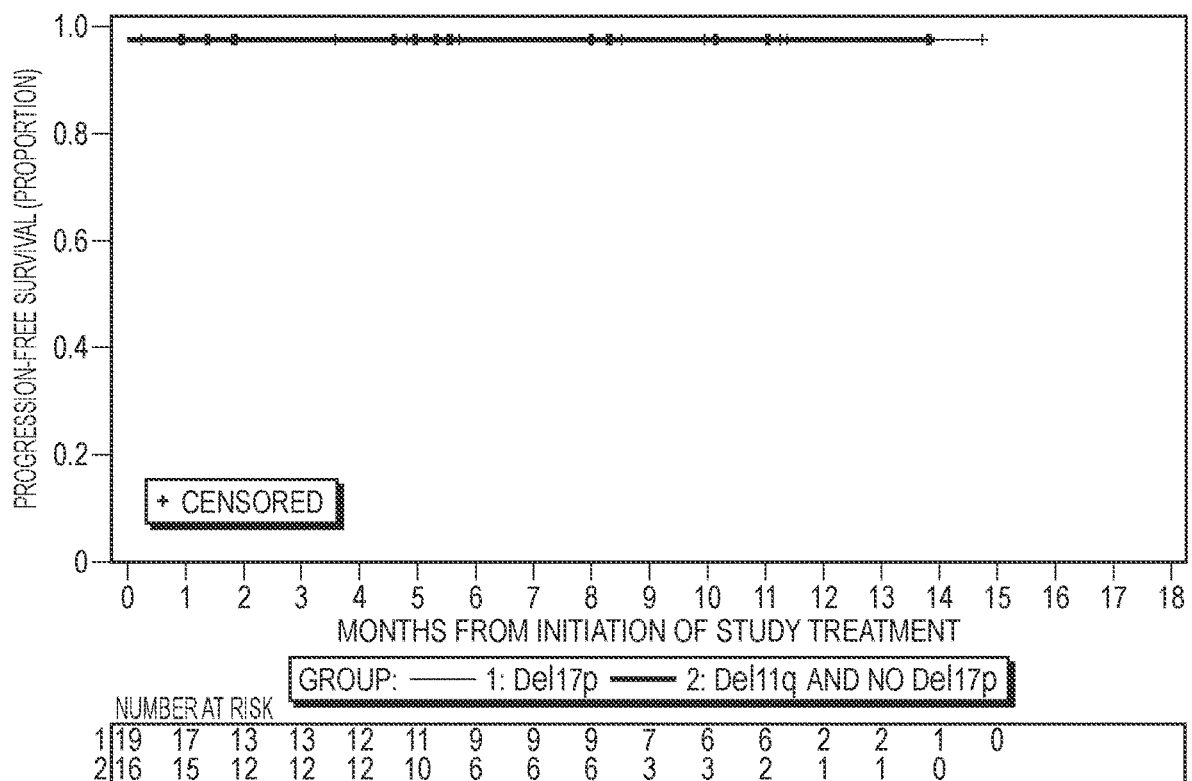

FIG. 141 illustrates PFS across relapsed/refractory patients with 17p deletion and with 11q deletion and no 17p deletion.

Figure 142:
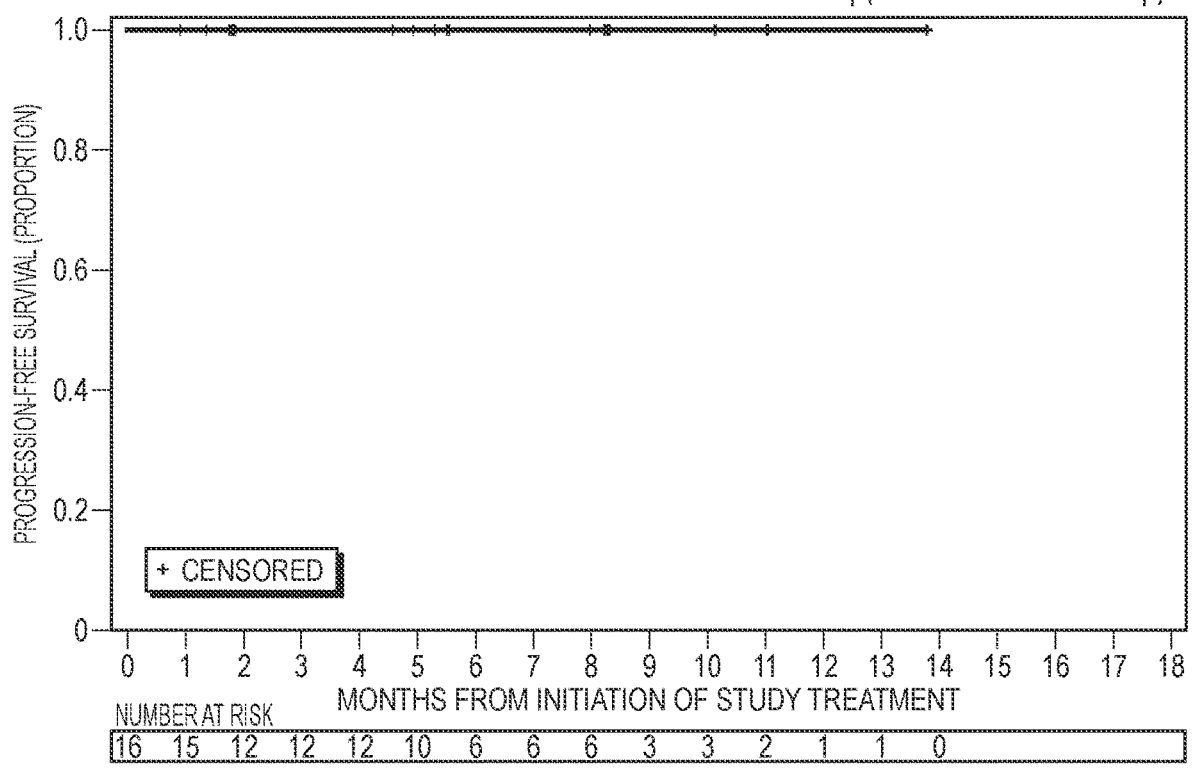

FIG. 142 illustrates PFS for patients with 11q deletion and no 17p deletion.

Figure 143:
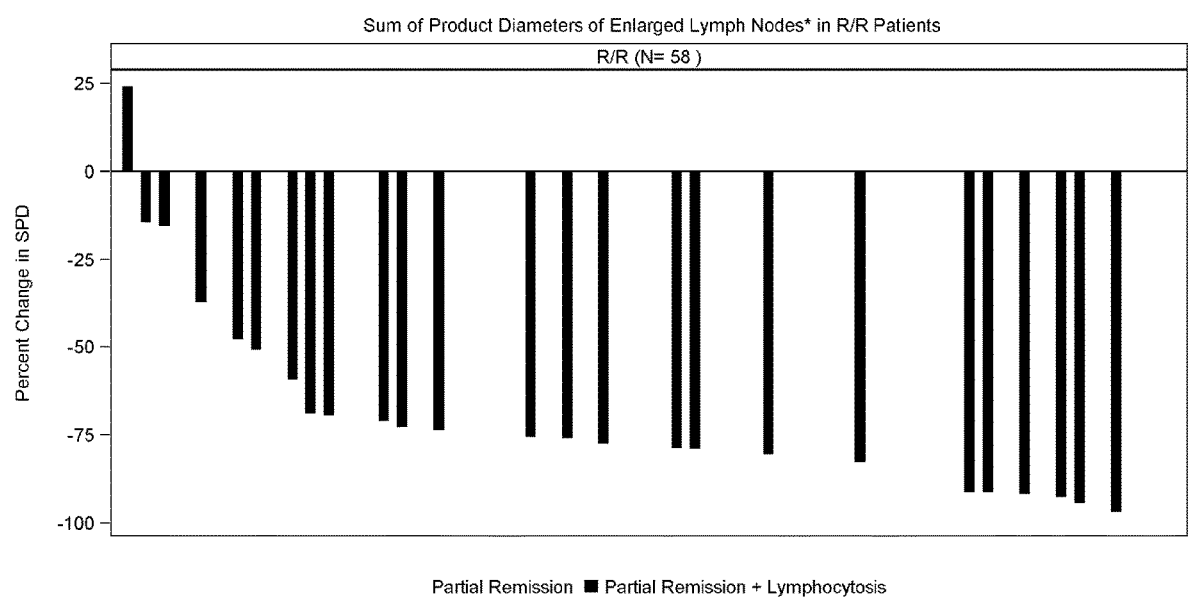

FIG. 143 illustrates additional SPD results from the clinical study of Formula (XVIII) in relapsed/refractory CLL patients.

Figure 144:
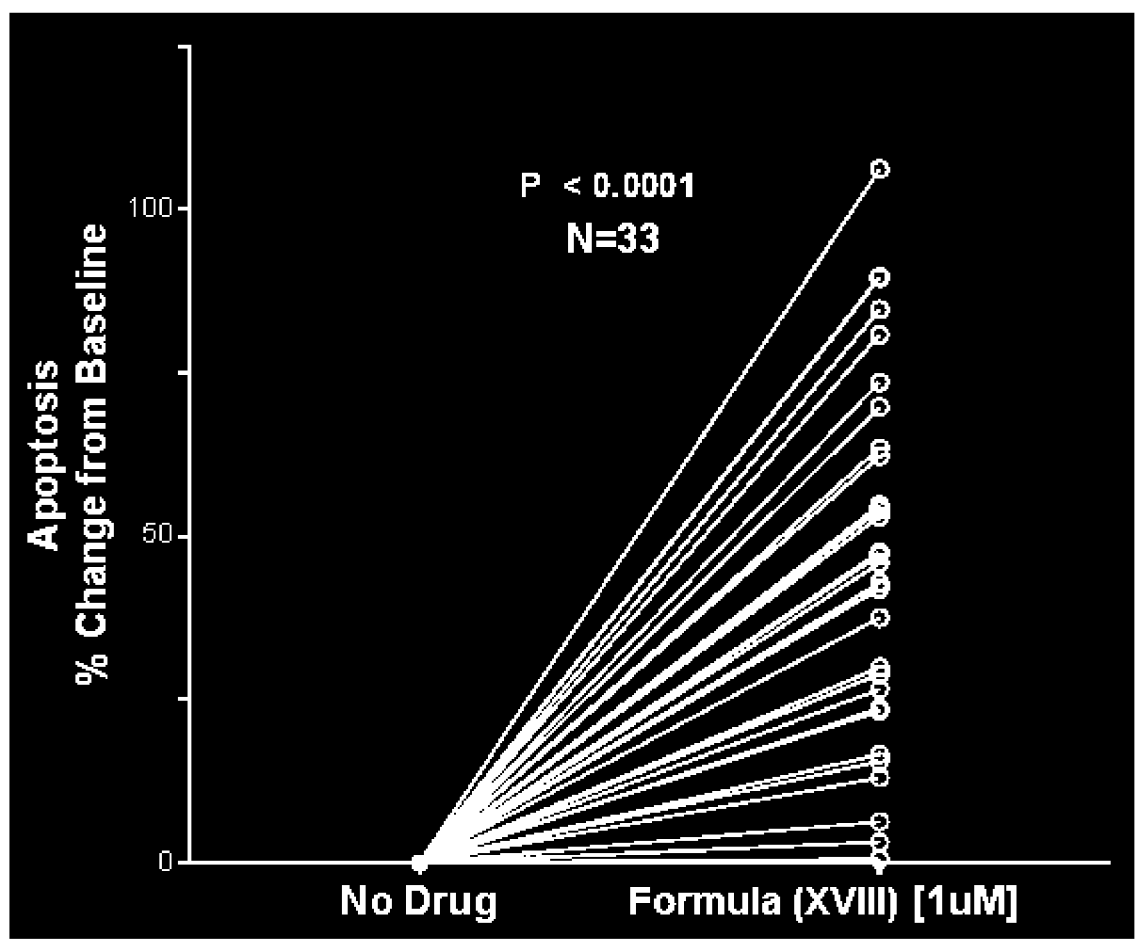

FIG. 144 illustrates that treatment of CLL patients with Formula (XVIII) resulted in increased apoptosis.

Figure 145:
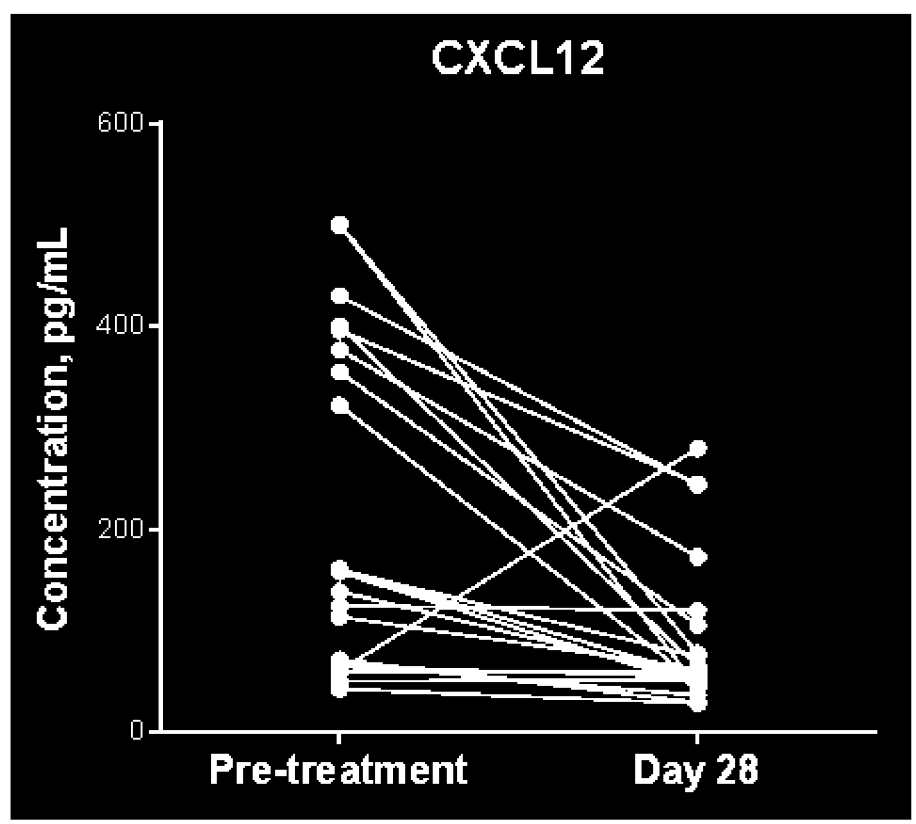

FIG. 145 illustrates a decrease in CXCL12 levels observed in patients treated with Formula (XVIII).

Figure 146:
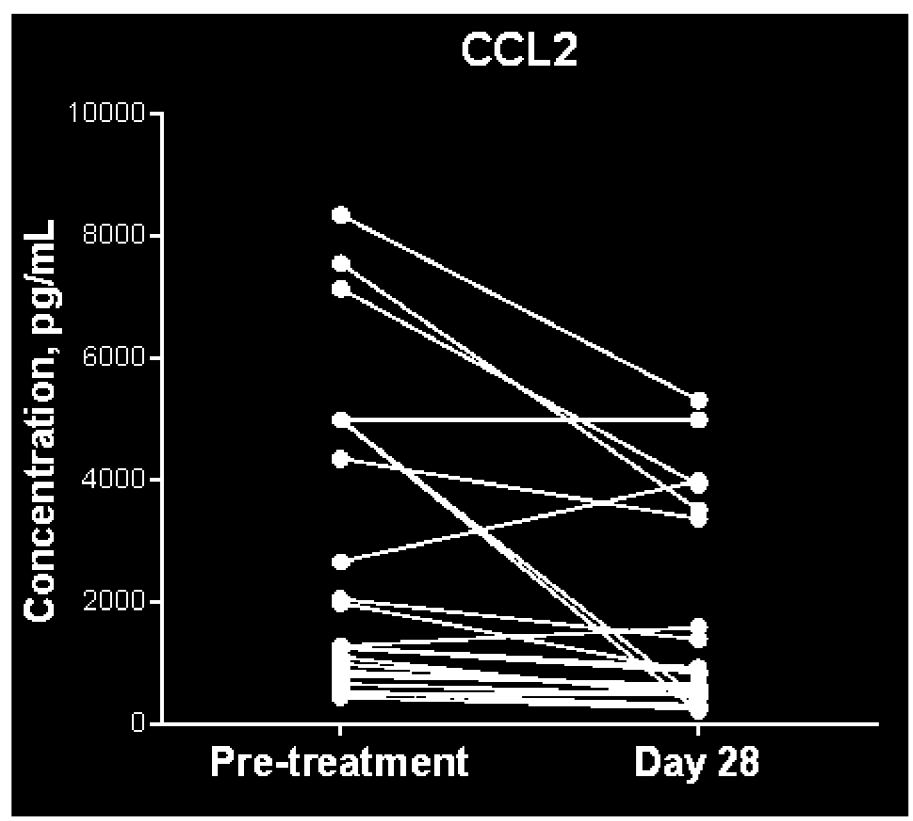

FIG. 146 illustrates a decrease in CCL2 levels observed in patients treated with Formula (XVIII).

Figure 147:
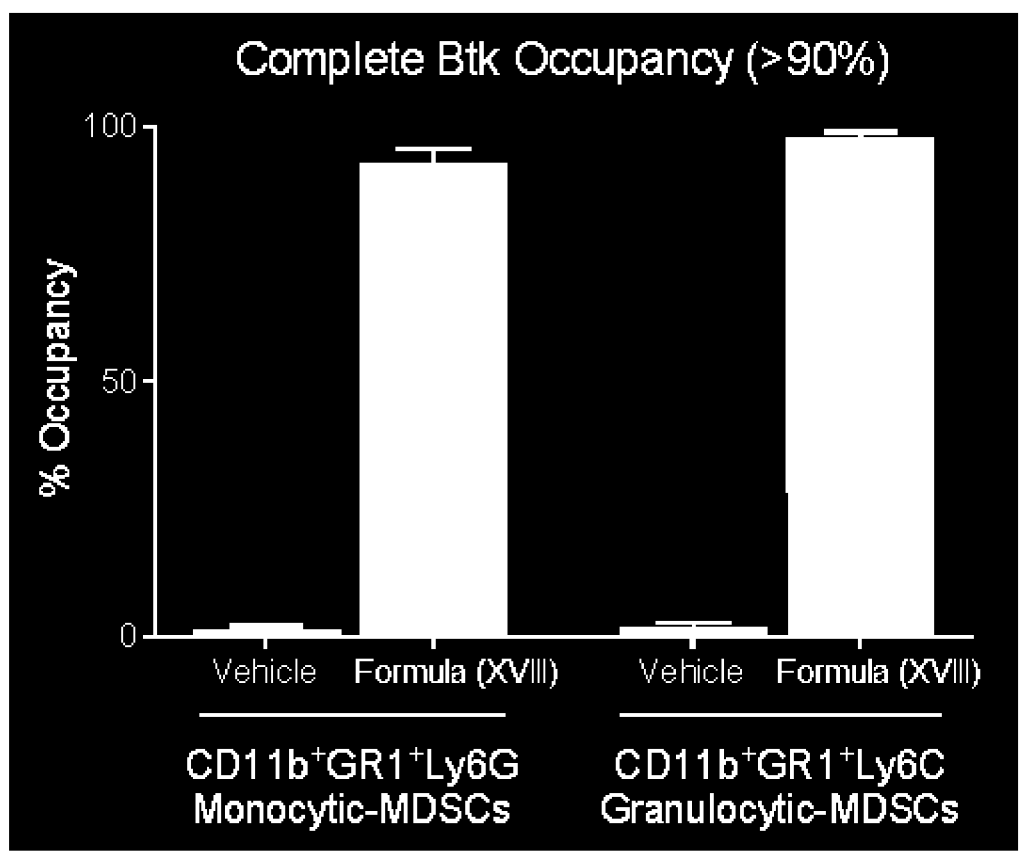

FIG. 147 illustrates BTK inhibitory effects on MDSCs.

Figure 148:
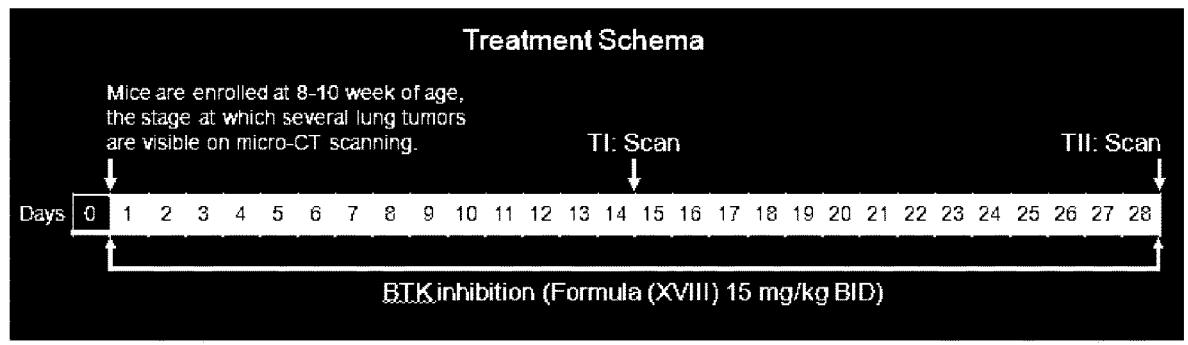

FIG. 148 illustrates the dosing schema used with the KrasLA2 non-small cell lung cancer (NSCLC) model.

Figure 149:
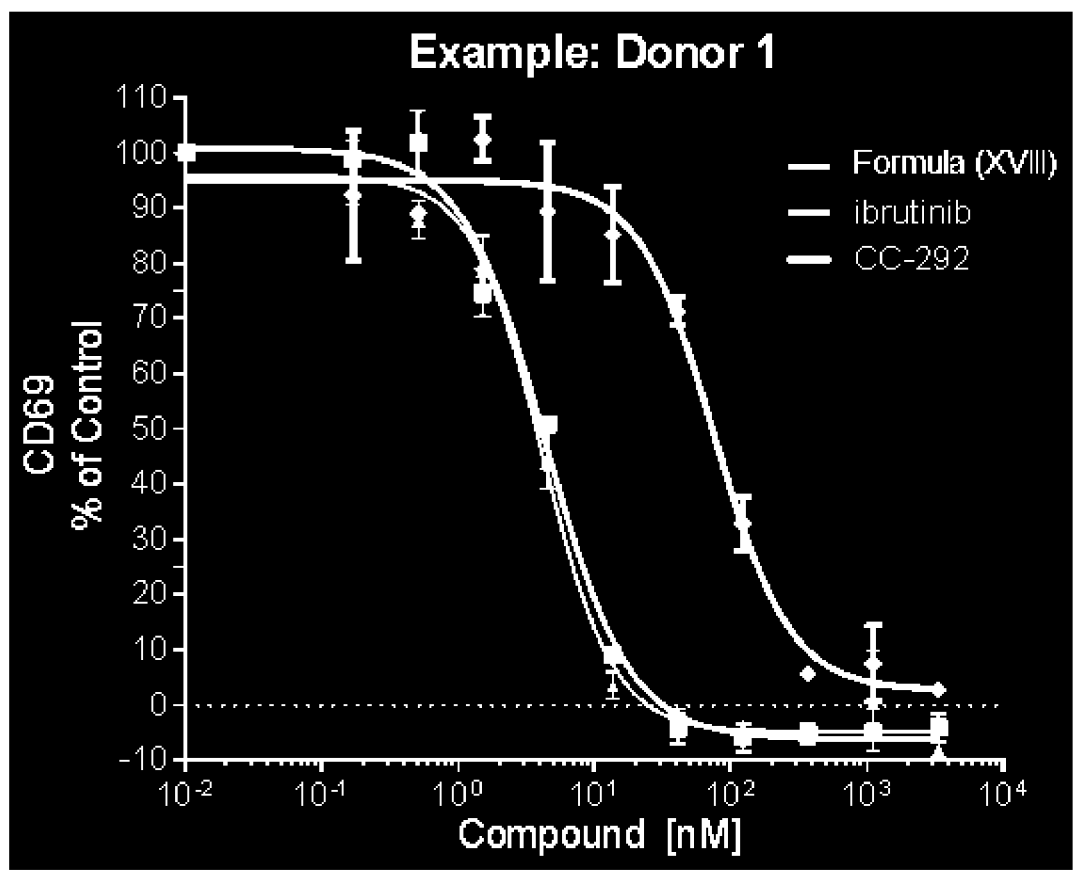

FIG. 149 illustrates in vitro potency in whole blood of Formula (XVIII), ibrutinib and CC-292 in inhibition of signals through the B cell receptor.

Figure 150:
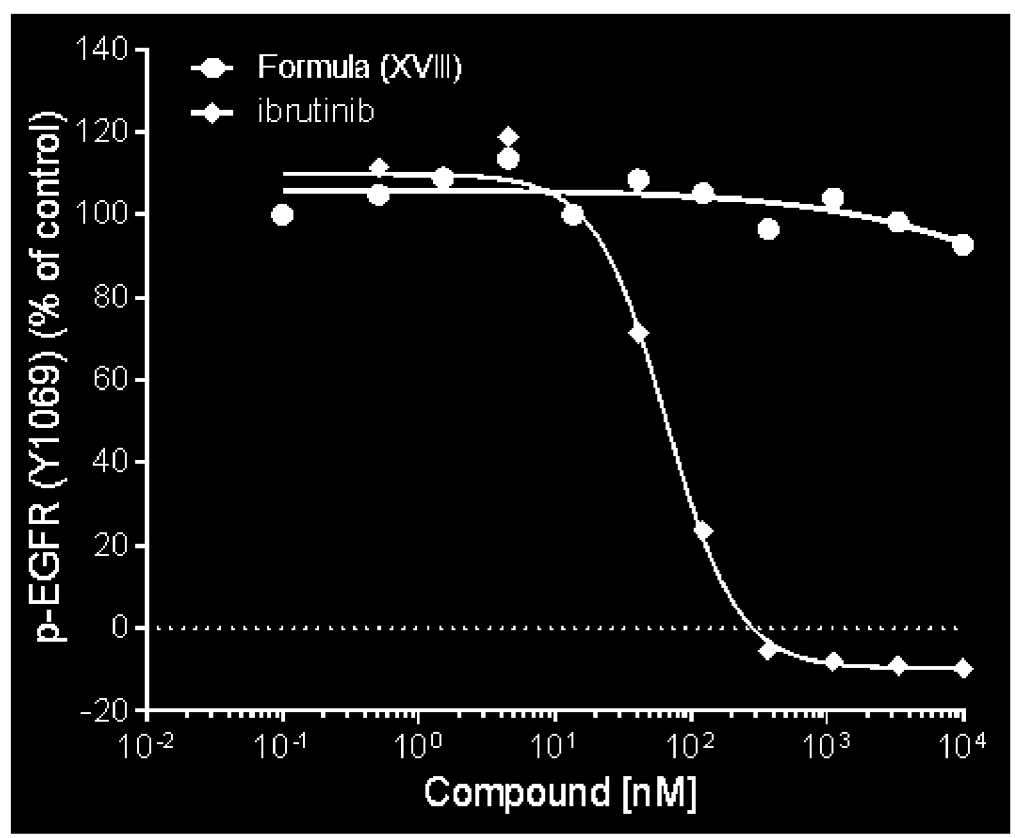

FIG. 150 illustrates EGF receptor phosphorylation in vitro for Formula (XVIII) and ibrutinib.

Figure 151:
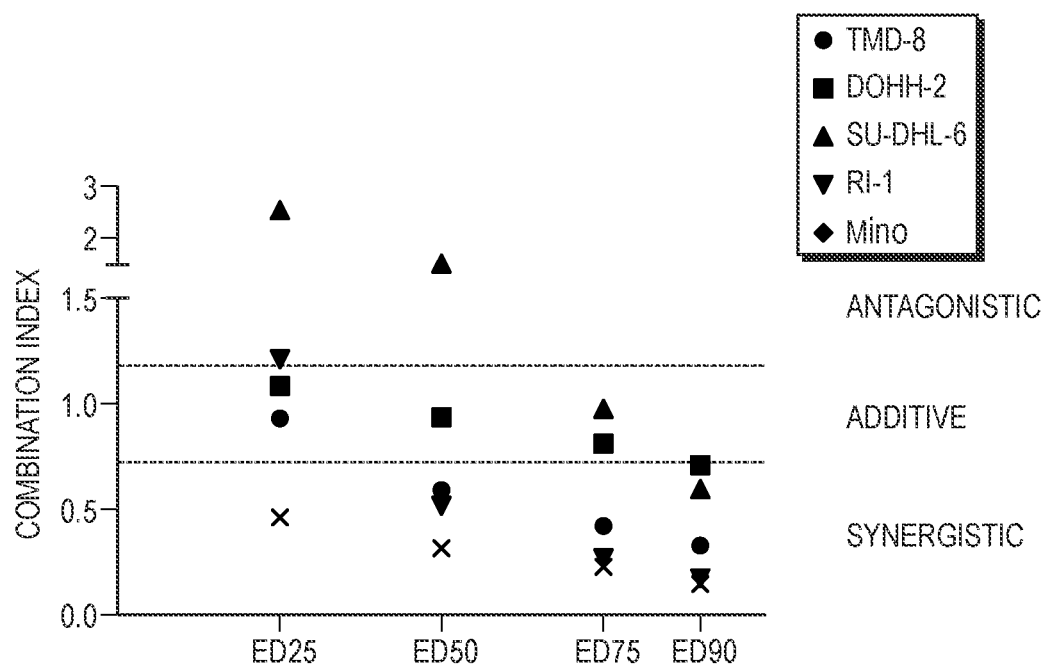

FIG. 151 illustrates the synergy observed in certain cell lines when the BTK inhibitor of Formula (XXVIII-R) (ONO-4059) and the PI3K-δ inhibitor of Formula (XVI) (idelalisib) are combined. The tested cell lines include TMD-8 (DLBCL-ABC), Mino (MCL), RI-1 (NHL), DOHH-2 (follicular lymphoma), and SU-DHL-6 (DLBCL-GCB). The dose-effect curves for these cell lines are given in FIG. 152, FIG. 153, FIG. 154, FIG. 155, and FIG. 156.

Figure 152:
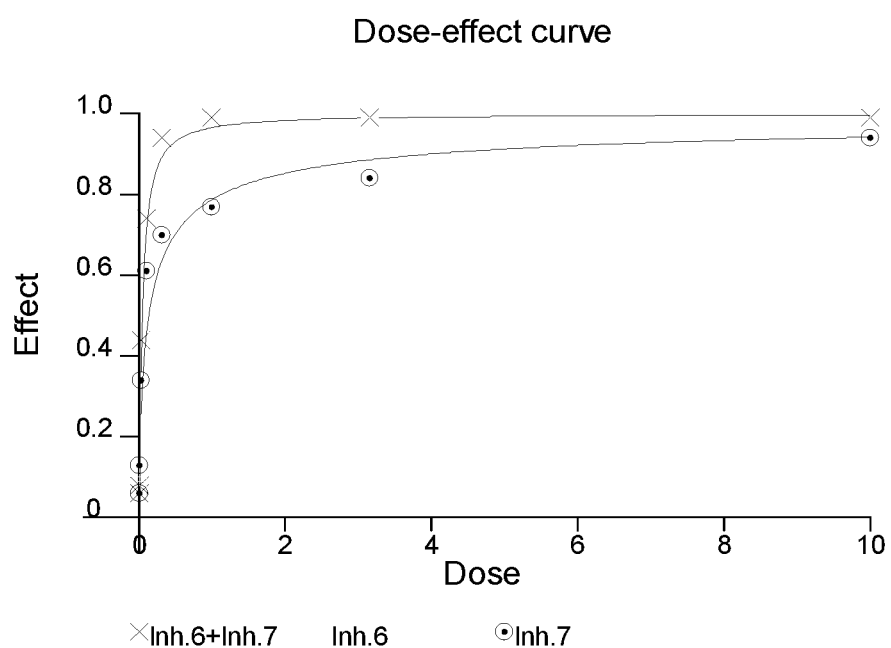

FIG. 152 illustrates the dose-effect curves obtained for the tested TMD-8 cell line (DLBCL-ABC) using combined dosing of the BTK inhibitor of Formula (XXVIII-R) (ONO-4059) ("Inh.6") and the PI3K-δ inhibitor of Formula (XVI) (idelalisib) ("Inh.7"). The y-axis ("Effect") is given in units of Fa (fraction affected) and the x-axis ("Dose") is given in linear units of μM.

Figure 153:
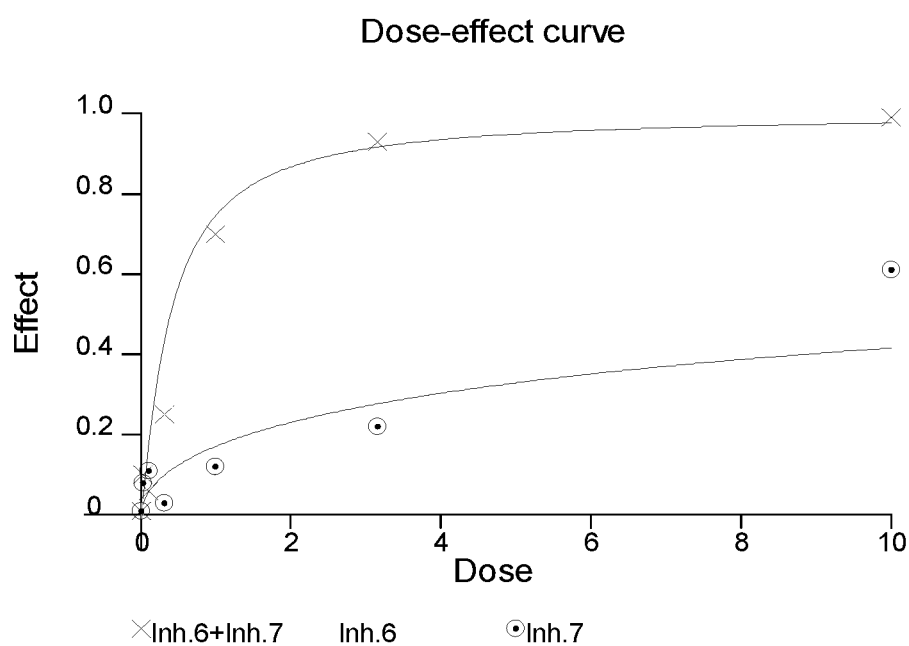

FIG. 153 illustrates the dose-effect curves obtained for the tested Mino cell line (MCL) using combined dosing of the BTK inhibitor of Formula (XXVIII-R) (ONO-4059) ("Inh.6") and the PI3K-δ inhibitor of Formula (XVI) (idelalisib) ("Inh.7"). The y-axis ("Effect") is given in units of Fa (fraction affected) and the x-axis ("Dose") is given in linear units of μM.

Figure 154:
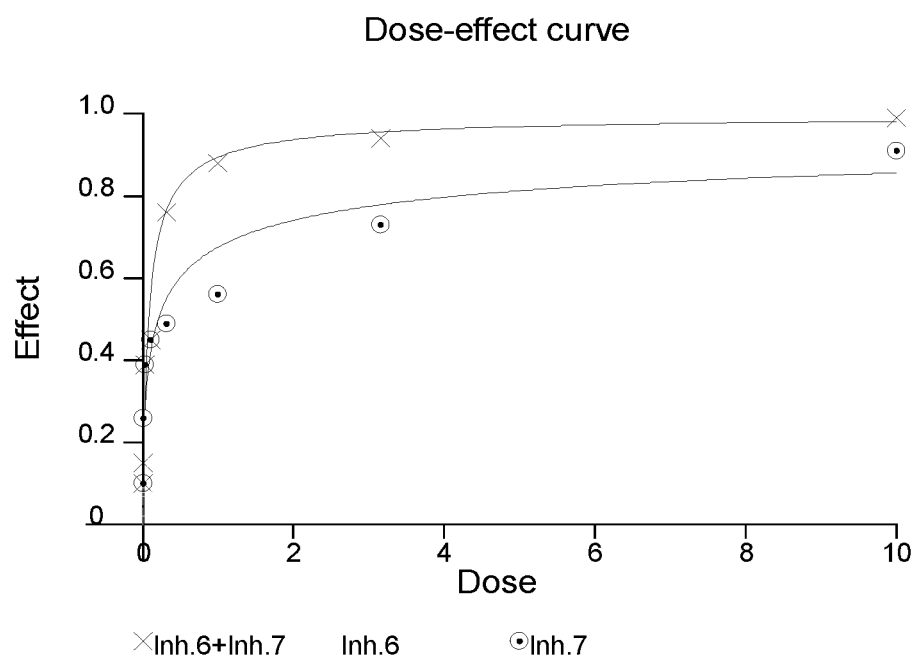

FIG. 154 illustrates the dose-effect curves obtained for the tested RI-1 cell line (NHL) using combined dosing of the BTK inhibitor of Formula (XXVIII-R) (ONO-4059) ("Inh.6") and the PI3K-δ inhibitor of Formula (XVI) (idelalisib) ("Inh.7"). The y-axis ("Effect") is given in units of Fa (fraction affected) and the x-axis ("Dose") is given in linear units of μM.

Figure 155:
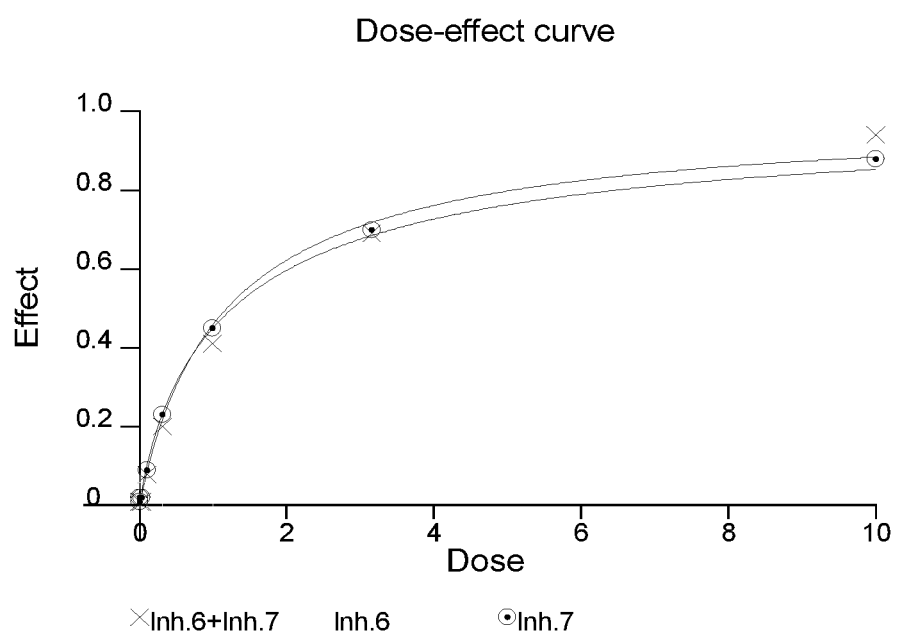

FIG. 155 illustrates the dose-effect curves obtained for the tested DOHH-2 cell line (follicular lymphoma) using combined dosing of the BTK inhibitor of Formula (XXVIII-R) (ONO-4059) ("Inh.6") and the PI3K-δ inhibitor of Formula (XVI) (idelalisib) ("Inh.7"). The y-axis ("Effect") is given in units of Fa (fraction affected) and the x-axis ("Dose") is given in linear units of μM.

Figure 156:
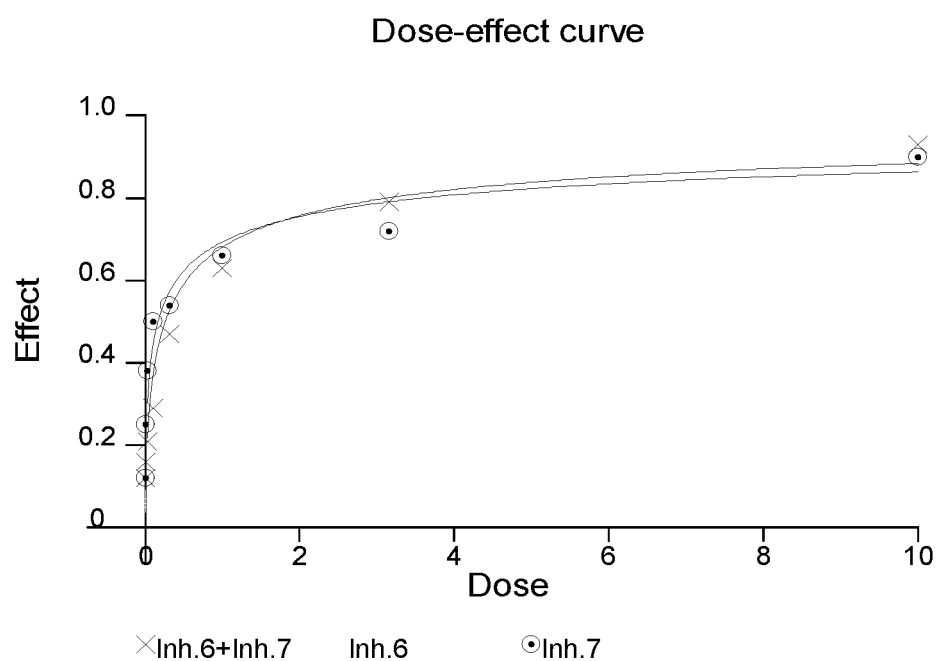

FIG. 156 illustrates the dose-effect curves obtained for the tested SU-DHL-6 cell line (DLBCL-GCB) using combined dosing of the BTK inhibitor of Formula (XXVIII-R) (ONO-4059) ("Inh.6") and the PI3K-δ inhibitor of Formula (XVI) (idelalisib) ("Inh.7"). The y-axis ("Effect") is given in units of Fa (fraction affected) and the x-axis ("Dose") is given in linear units of μM.

Figure 157:
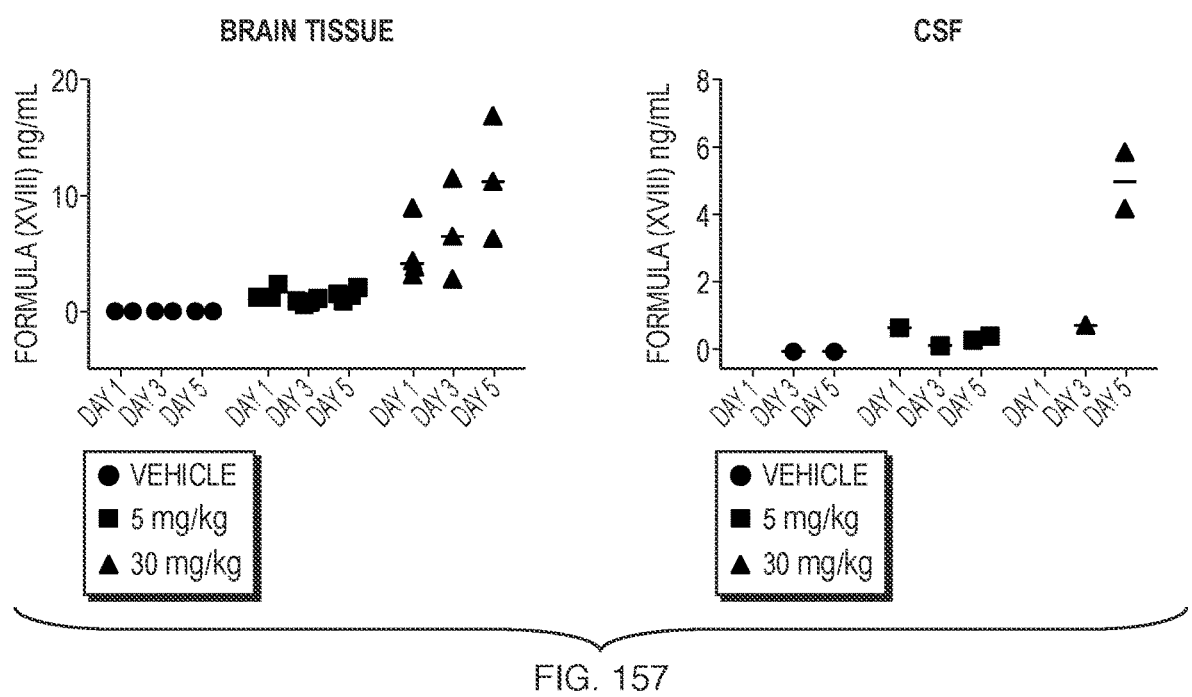

FIG. 157 shows the results of the brain penetration study, demonstrating the surprising result that Formula (XVIII) crosses the blood-brain barrier.

BRIEF DESCRIPTION OF THE SEQUENCE LISTINGS

SEQ ID NO:1 is the heavy chain amino acid sequence of the anti-CD20 monoclonal antibody rituximab.

SEQ ID NO:2 is the light chain amino acid sequence of the anti-CD20 monoclonal antibody rituximab.

SEQ ID NO:3 is the heavy chain amino acid sequence of the anti-CD20 monoclonal antibody obinutuzumab.

SEQ ID NO:4 is the light chain amino acid sequence of the anti-CD20 monoclonal antibody obinutuzumab.

SEQ ID NO:5 is the variable heavy chain amino acid sequence of the anti-CD20 monoclonal antibody ofatumumab.

SEQ ID NO:6 is the variable light chain amino acid sequence of the anti-CD20 monoclonal antibody ofatumumab.

SEQ ID NO:7 is the Fab fragment heavy chain amino acid sequence of the anti-CD20 monoclonal antibody ofatumumab.

SEQ ID NO:8 is the Fab fragment light chain amino acid sequence of the anti-CD20 monoclonal antibody ofatumumab.

SEQ ID NO:9 is the heavy chain amino acid sequence of the anti-CD20 monoclonal antibody veltuzumab.

SEQ ID NO:10 is the light chain amino acid sequence of the anti-CD20 monoclonal antibody veltuzumab.

SEQ ID NO:11 is the heavy chain amino acid sequence of the anti-CD20 monoclonal antibody tositumomab.

SEQ ID NO:12 is the light chain amino acid sequence of the anti-CD20 monoclonal antibody tositumomab.

SEQ ID NO:13 is the heavy chain amino acid sequence of the anti-CD20 monoclonal antibody ibritumomab.

SEQ ID NO:14 is the light chain amino acid sequence of the anti-CD20 monoclonal antibody ibritumomab.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties. Definitions are also provided herein in connection with some embodiments of the invention.

The terms "co-administration" and "administered in combination with" as used herein, encompass administration of two or more active pharmaceutical ingredients (in a preferred embodiment of the present invention, for example, at least one BCL-2 inhibitor and at least one BTK inhibitor) to a subject so that both agents and/or their metabolites are present in the subject at the same time. Co-administration includes simultaneous administration in separate compositions, administration at different times in separate compositions, or administration in a composition in which two or more agents are present. Simultaneous administration in separate compositions and administration in a composition in which both agents are present are preferred. The terms "simultaneous" and "concurrent" are used as synonyms herein.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells, (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In selected embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

"Prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, H., Design of Prodrugs (1985) (Elsevier, Amsterdam). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, either in routine manipulation or in vivo, to yield the active parent compound. Prodrugs include, for example, compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active compound.

As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, heptyl, octyl, nonyl and decyl. The alkyl moiety may be attached to the rest of the molecule by a single bond, such as for example, methyl (Me), ethyl (Et), n-propyl (Pr), 1-methylethyl (iso-propyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., C2-C10 alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e. C2-C10 alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. C3-C10 cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each IV is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each IV is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a C1-C6 alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein "R" is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$)$_2$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each IV is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two IV substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each IV is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., C6-C10 aromatic or C6-C10 aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —SR', —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each IV is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each IV is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo", "halide", or, alternatively, "halogen" is intended to mean fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl", "heteroalkenyl" and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_t R^a$ (where t is 1 or 2), —$S(O)_t OR^a$ (where t is 1 or 2), —$S(O)_t N(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl) heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., C5-C13 heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d] pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_t R^a$ (where t is 1 or 2), —$S(O)_t OR^a$ (where t is 1 or 2), —$S(O)_t N(R^a)_2$ (where t is 1 or 2), or $PO_3(R^a)_2$, where each IV is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$), —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)- and 20% (R)-, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or the Pirkle alcohol, or derivatization of a compounds using a chiral compound such as Mosher's acid followed by chromatography or nuclear magnetic resonance spectroscopy.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The terms "enantiomerically enriched," "enantiomerically pure" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, such as at least 80% by weight. In some embodiments, the enrichment can be significantly greater than 80% by weight, providing a "substantially enantiomerically enriched," "substantially enantiomerically pure" or a "substantially non-racemic" preparation, which refers to preparations of compositions which have at least 85% by weight of one enantiomer relative to other enantiomer, such as at least 90% by weight, such as at least 95% by weight.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions (Wiley Interscience, New York, 1981); E. L. Eliel, Stereochemistry of Carbon Compounds (McGraw-Hill, N Y, 1962); and E. L. Eliel and S. H. Wilen, Stereochemistry of Organic Compounds (Wiley-Interscience, New York, 1994).

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

"Spiroalkyl" means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like. The term "$C_2$-$C_5$-spiroalkyl," as used herein, means $C_2$-spiroalkyl, $C_3$-spiroalkyl, $C_4$-spiroalkyl, and $C_5$-spiroalkyl. The term "$C_2$-spiroalkyl," as used herein, means eth-1,2-ylene, both ends of which replace hydrogen atoms of the same $CH_2$ moiety. The term "$C_3$-spiroalkyl," as used herein, means prop-1,3-ylene, both ends of which replace hydrogen atoms of the same $CH_2$ moiety. The term "$C_4$-spiroalkyl," as used herein, means but-1,4-ylene, both ends of which replace hydrogen atoms of the same $CH_2$ moiety. The term "$C_5$-spiroalkyl," as used herein, means pent-1,5-ylene, both ends of which replace hydrogen atoms of the same $CH_2$ moiety. The term "$C_6$-spiroalkyl," as used herein, means hex-1,6-ylene, both ends of which replace hydrogen atoms of the same $CH_2$ moiety.

"Spiroheteroalkyl" means spiroalkyl having one or two $CH_2$ moieties replaced with independently selected O, C(O), CNOH, CNOCH$_3$, S, S(O), SO$_2$ or NH and one or two CH moieties unreplaced or replaced with N.

"Spiroheteroalkenyl" means spiroalkenyl having one or two $CH_2$ moieties replaced with independently selected O, C(O), CNOH, CNOCH$_3$, S, S(O), SO$_2$ or NH and one or two CH moieties unreplaced or replaced with N and also means spiroalkenyl having one or two $CH_2$ moieties unreplaced or replaced with independently selected O, C(O), CNOH, CNOCH$_3$, S, —S(O), SO$_2$ or NH and one or two CH moieties replaced with N.

"Spirocyclo" means two substituents on the same carbon atom, that, together with the carbon atom to which they are attached, form a cycloalkane, heterocycloalkane, cycloalkene, or heterocycloalkene ring.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

Co-Administration of Compounds

An embodiment of the invention is a combination comprising two or more ingredients selected from a Bruton's tyrosine kinase (BTK) inhibitor, a B-cell lymphoma-2 (BCL-2) inhibitor, a phosphoinositide 3-kinase (PI3K) inhibitor, and a Janus kinase-2 (JAK-2) inhibitor. An embodiment of the invention is a composition, such as a pharmaceutical composition, comprising a combination of a PI3K inhibitor, a BTK inhibitor, a JAK-2 inhibitor, and/or BCL-2 inhibitor. Another embodiment is a kit containing a PI3K inhibitor, a BTK inhibitor, a JAK-2 inhibitor, and/or BCL-2 inhibitor formulated into separate pharmaceutical compositions, which are formulated for co-administration.

Another embodiment of the invention is a method of treating a disease or condition in a subject, in particular a hyperproliferative disorder like leukemia, lymphoma or a solid tumor cancer in a subject, comprising co-administering to the subject in need thereof a therapeutically effective amount of a combination of a PI3K inhibitor, a BTK inhibitor, a JAK-2 inhibitor, and/or BCL-2 inhibitor. The pharmaceutical composition comprising the combination, and the kit, are both for use in treating such disease or condition.

In a preferred embodiment, the solid tumor cancer is selected from the group consisting of breast, lung, colorectal, thyroid, bone sarcoma and stomach cancers.

In an embodiment, the leukemia is selected from the group consisting of acute myelogenous leukemia (AML), chronic myelogenous leukemia (CML), and acute lymphoblastic leukemia (ALL).

In a preferred embodiment, the lymphoma is follicular lymphoma, mantle cell lymphoma, diffuse large B cell lymphoma (DLBCL), B cell chronic lymphocytic leukemia, or Burkitt's lymphoma.

In a preferred embodiment, the PI3K inhibitor is a PI3K-γ inhibitor.

In a preferred embodiment, the PI3K inhibitor is a PI3K-δ inhibitor.

In a preferred embodiment, the PI3K inhibitor is a PI3K-γ,δ inhibitor.

In a preferred embodiment, the PI3K inhibitor is a selective PI3K inhibitor.

In a preferred embodiment, the combination of the PI3K inhibitor, PI3K-γ inhibitor, PI3K-δ inhibitor, or PI3K-γ,δ inhibitor with the BTK inhibitor is administered by oral, intravenous, intramuscular, intraperitoneal, subcutaneous or transdermal means.

In a particularly preferred embodiment, the PI3K inhibitor is a PI3K-δ inhibitor. This PI3K-δ inhibitor is more preferably a compound of Formula VIII, even more preferably the compound of Formula IX.

The BTK inhibitor is preferably a compound of Formula XVII, even more preferably the compound of Formula XVIII.

In one specific embodiment, the PI3K inhibitor is a PI3K-δ inhibitor and the BTK inhibitor is a compound of Formula XVII, even more preferably the compound of Formula XVIII. In a specifically preferred embodiment, the PI3K inhibitor is the compound of Formula IX and the BTK inhibitor is the compound of Formula XVIII. One or both of said inhibitors may also be in the form of a pharmaceutically acceptable salt.

In an embodiment, the PI3K inhibitor, which is preferably a PI3K-γ inhibitor, a PI3K-δ inhibitor, and a PI3K-γ,δ inhibitor, is in the form of a pharmaceutically acceptable salt, derivative, prodrug (such as an ester or phosphate ester), or cocrystal.

In an embodiment, the BTK inhibitor is in the form of a pharmaceutically acceptable salt, derivative, prodrug (such as an ester or phosphate ester), or cocrystal.

In an embodiment, the JAK-2 inhibitor is in the form of a pharmaceutically acceptable salt, derivative, prodrug (such as an ester or phosphate ester), or cocrystal.

The combination may be administered by any route known in the art. In an embodiment, the PI3K inhibitor, which is preferably selected from the group consisting of a PI3K-γ inhibitor, a PI3K-δ inhibitor, and a PI3K-γ,δ inhibitor, is administered to the subject before administration of the BTK inhibitor.

In an embodiment, the PI3K inhibitor, which is preferably selected from the group consisting of a PI3K-γ inhibitor, a PI3K-δ inhibitor, and a PI3K-γ,δ inhibitor, is administered concurrently with the administration of the BTK inhibitor.

In an embodiment, the PI3K inhibitor, which is preferably selected from the group consisting of a PI3K-γ inhibitor, a PI3K-δ inhibitor, and a PI3K-γ,δ inhibitor, is administered to the subject after administration of the BTK inhibitor.

In an embodiment, the JAK-2 inhibitor is administered to the subject before administration of the BTK inhibitor.

In an embodiment, the JAK-2 inhibitor is administered concurrently with the administration of the BTK inhibitor.

In an embodiment, the JAK-2 inhibitor is administered to the subject after administration of the BTK inhibitor.

In an embodiment, the BTK inhibitor, JAK-2 inhibitor, and PI3K inhibitor are administered concurrently.

In an embodiment, the subject is a mammal. In an embodiment, the subject is a human. In an embodiment, the subject is a mammal, such as a canine, feline or equine.

PI3K Inhibitors

Some embodiments (for example combinations, compositions and/or kits) of the invention comprise a PI3K inhibitor. The PI3K inhibitor may be any PI3K inhibitor known in the art. In particular, it is one of the PI3K inhibitors described in more detail in the following paragraphs. Preferably, it is a PI3K inhibitor selected from the group consisting of PI3K-γ inhibitor, PI3K-δ inhibitor, and PI3K-γ,δ inhibitor. In one specific embodiment, it is a PI3K-δ inhibitor. In a preferred embodiment, it is a compound of Formula IX or a pharmaceutically acceptable salt thereof.

In a preferred embodiment, the PI3K inhibitor, which may preferably be selected from the group consisting of a PI3K-γ inhibitor, a PI3K-δ inhibitor, and a PI3K-γ,δ inhibitor, is a compound selected from the structures disclosed in U.S. Pat. Nos. 8,193,182 and 8,569,323, and U.S. Patent Application Publication Nos. 2012/0184568 A1, 2013/0344061 A1, and 2013/0267521 A1, the disclosures of which are incorporated by reference herein. In a preferred embodiment, the PI3K inhibitor, PI3K-γ inhibitor, PI3K-δ inhibitor, or PI3K-γ,δ inhibitor is a compound of Formula (I):

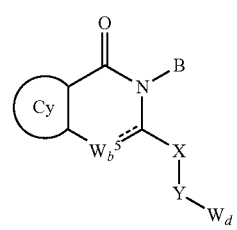

Formula (I)

or a pharmaceutically acceptable salt thereof,
wherein:
Cy is selected from aryl and heteroaryl substituted by 0 or 1 occurrences of $R^3$ and 0, 1, 2, or 3 occurrences of $R^5$;
$W_b^5$ is selected from $CR^8$, $CHR^8$, and N;
$R^8$ is selected from hydrogen, alkyl, alkenyl, alkynyl, cycloalkyl, heteroalkyl, alkoxy, amido, amino, acyl, acyloxy, sulfonamido, halo, cyano, hydroxyl and nitro;
B is selected from hydrogen, alkyl, amino, heteroalkyl, cycloalkyl, heterocyclyl, aryl and heteroaryl, each of which is substituted with 0, 1, 2, 3, or 4 occurrences of $R^2$;
each $R^2$ is independently selected from alkyl, heteroalkyl, alkenyl, alkynyl, cycloalkyl, heterocyclyl, aryl, arylalkyl, heteroaryl, heteroarylalkyl, alkoxy, amido, amino, acyl, acyloxy, alkoxycarbonyl, sulfonamido, halo, cyano, hydroxyl, nitro, phosphate, urea and carbonate;
X is —$(CH(R^9))_z$—;
Y is selected from —$N(R^9)$—$C(=O)$—, —$C(=O)$—$N(R^9)$—, —$C(=O)$—$N(R^9)$—$(CHR^9)$—, —$N(R^9)$—$S(=O)$—, —$S(=O)$—$N(R^9)$—, $S(=O)_2$—$N(R^9)$—, —$N(R^9)$—$C(=O)$—$N(R^9)$ and —$N(R^9)S(=O)_2$—;
z is an integer of 1, 2, 3, or 4;
$R^3$ is selected from alkyl, alkenyl, alkynyl, cycloalkyl, heterocyclyl, fluoroalkyl, heteroalkyl, alkoxy, amido, amino, acyl, acyloxy, sulfinyl, sulfonyl, sulfoxide, sulfone, sulfonamido, halo, cyano, aryl, heteroaryl, hydroxyl and nitro;
each $R^5$ is independently selected from alkyl, alkenyl, alkynyl, cycloalkyl, heteroalkyl, alkoxy, amido, amino, acyl, acyloxy, sulfonamido, halo, cyano, hydroxyl and nitro;
each $R^9$ is independently selected from hydrogen, alkyl, cycloalkyl, heterocyclyl and heteroalkyl; or two adjacent occurrences of $R^9$ together with the atoms to which they are attached form a 4- to 7-membered ring;
$W_d$ is selected from heterocyclyl, aryl, cycloalkyl and heteroaryl, each of which is substituted with one or more $R^{10}$, $R^{11}$, $R^{12}$ or $R^{13}$, and
$R^{10}$, $R^{11}$, $R^{12}$ and $R^{13}$ are each independently selected from hydrogen, alkyl, heteroalkyl, alkenyl, alkynyl, cycloalkyl, heterocyclyl, aryl, arylalkyl, heteroaryl, heteroarylalkyl, alkoxy, heterocyclyloxy, amido, amino, acyl, acyloxy, alkoxycarbonyl, sulfonamido, halo, cyano, hydroxyl, nitro, phosphate, urea, carbonate and NR'R" wherein R' and R" are taken together with nitrogen to form a cyclic moiety.

In an embodiment, the PI3K inhibitor, PI3K-γ inhibitor, PI3K-δ inhibitor, or PI3K-γ,δ inhibitor is a compound of Formula (I-1):

Formula (I-1)

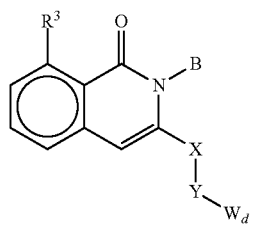

or a pharmaceutically acceptable salt thereof,
wherein:
B is a moiety of Formula (II):

Formula (II)

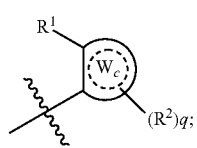

$W_e$ is selected from aryl, heteroaryl, heterocycloalkyl and cycloalkyl;
q is an integer of 0, 1, 2, 3, or 4;
X is selected from a bond and —$(CH(R^9))_z$—;
Y is selected from a bond, —$N(R^9)$—, —O—, —S—, —$S(=O)$—, —$S(=O)_2$, —$C(=O)$—, —$C(=O)(CHR^9)_z$—, —$N(R^9)$—$C(=O)$—, —$N(R^9)$—$C(=O)$NH- and —$N(R^9)C(R^9)_2$—;
z is an integer of 1, 2, 3, or 4;
$W_d$ is:

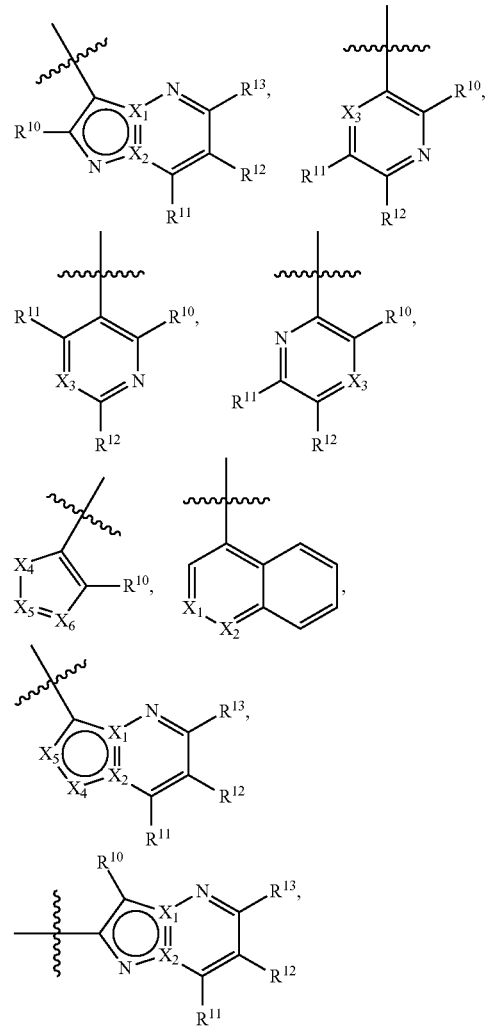

-continued

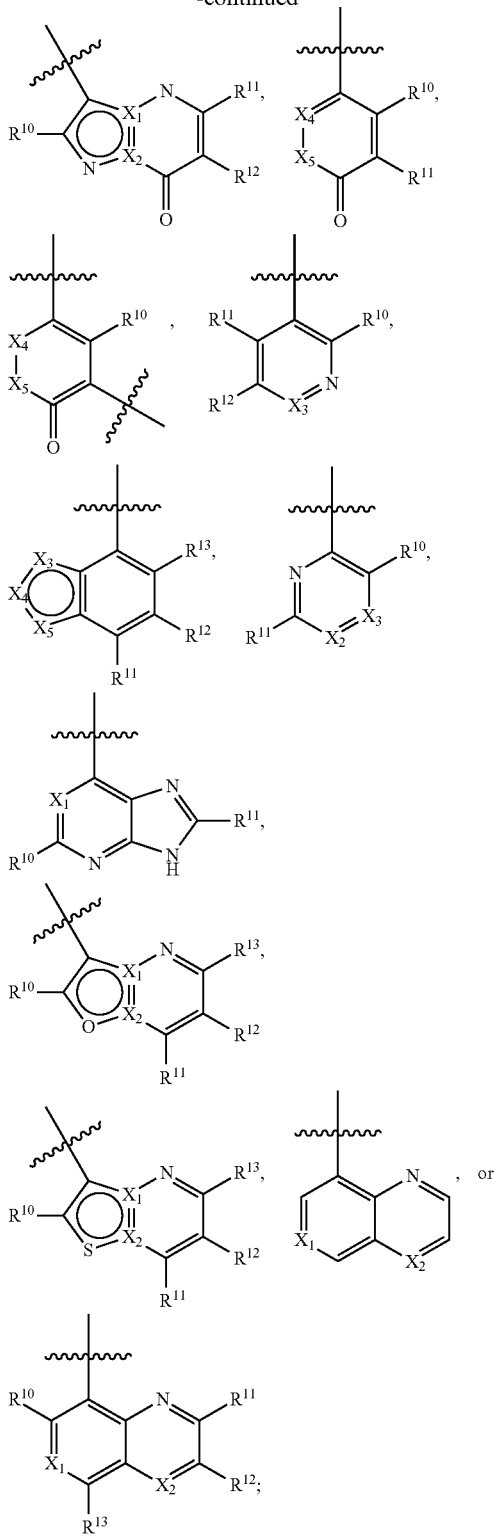

$X_1$, $X_2$ and $X_3$ are each independently selected from C, $CR^{13}$ and N; and $X_4$, $X_5$ and $X_6$ are each independently selected from N, NH, $CR^{13}$, S and O;

$R^1$ is selected from hydrogen, alkyl, alkenyl, alkynyl, alkoxy, amido, alkoxycarbonyl, sulfonamido, halo, cyano and nitro;

$R^2$ is selected from alkyl, alkenyl, alkynyl, cycloalkyl, heterocycloalkyl, aryl, heteroaryl, heteroarylalkyl, alkoxy, amino, halo, cyano, hydroxy and nitro;

$R^3$ is selected from hydrogen, alkyl, alkenyl, alkynyl, cycloalkyl, heterocycloalkyl, alkoxy, amido, amino, alkoxycarbonyl sulfonamido, halo, cyano, hydroxy and nitro;

each instance of $R^9$ is independently selected from hydrogen, alkyl and heterocycloalkyl; and $R^{10}$, $R^{11}$, $R^{12}$ and $R^{13}$ are as defined in relation to formula (I).

In an embodiment, the PI3K inhibitor, PI3K-γ inhibitor, PI3K-δ inhibitor, or PI3K-γ,δ inhibitor is a compound of Formula (III) or Formula (IV):

Formula (III)

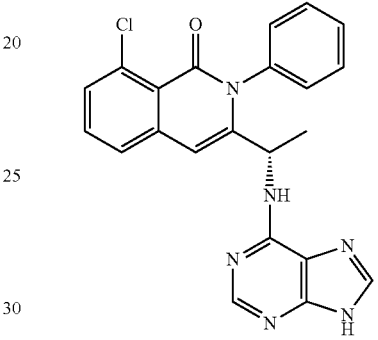

Formula (IV)

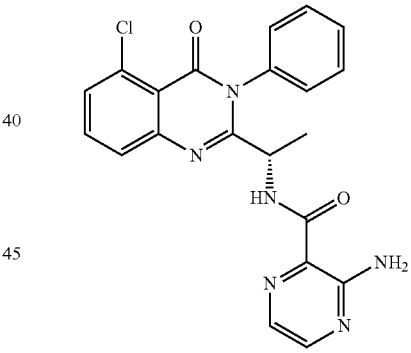

or a pharmaceutically acceptable salt thereof.

In an embodiment, the PI3K inhibitor, PI3K-γ inhibitor, PI3K-δ inhibitor, or PI3K-γ,δ inhibitor is (S)-3-(1-((9H-purin-6-yl)amino)ethyl)-8-chloro-2-phenylisoquinolin-1(2H)-one or a pharmaceutically acceptable salt thereof.

In an embodiment, the PI3K inhibitor, PI3K-γ inhibitor, PI3K-δ inhibitor, or PI3K-γ,δ inhibitor is (S)-3-amino-N-(1-(5-chloro-4-oxo-3-phenyl-3,4-dihydroquinazolin-2-yl)ethyl)pyrazine-2-carboxamide or a pharmaceutically acceptable salt thereof.

In an embodiment, the PI3K inhibitor or PI3K-δ inhibitor is a compound selected from the structures disclosed in U.S. Pat. Nos. 8,193,199 and 8,586,739, the disclosure of which is incorporated by reference herein. In an embodiment, the PI3K inhibitor or PI3K-δ inhibitor is a compound of Formula (V):

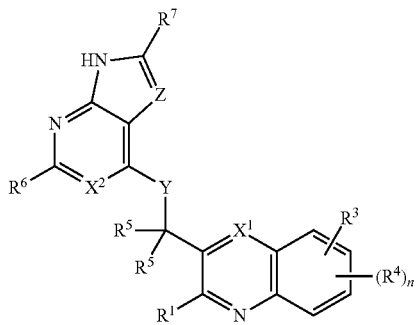

Formula (V)

or any pharmaceutically-acceptable salt thereof, wherein:

$X^1$ is $C(R^9)$ or N;
$X^2$ is $C(R_{10})$ or N;
Y is $N(R^{11})$, O or S;
Z is $CR^8$ or N;
n is 0, 1, 2 or 3;
$R^1$ is a direct-bonded or oxygen-linked saturated, partially saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $C_{1-4}$alkyl, $OC_{1-4}$alkyl, $OC_{1-4}$haloalkyl, $NHC_{1-4}$, $N(C_{1-4}$alkyl$)(C_{1-4}$alkyl$)$ and $C_{1-4}$haloalkyl;
$R^2$ is selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, O$R^a$—OC(=O)$R^a$, —OC(=O)N$R^a$ $R^a$, —OC(=O)N($R^a$)S(=O)$_2R^a$, —O$C_{2-6}$alkyl N$R^aR^a$, —O$C_{2-6}$alkylO$R^a$, —S$R^a$, OS(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$; or $R^2$ is selected from $C_{1-6}$alkyl, phenyl, benzyl, heteroaryl, heterocycle, —(C$_{1-3}$alkyl)heteroaryl, —(C$_{1-3}$alkyl)heterocycle, —O(C$_{1-3}$alkyl)heteroaryl, —O(C$_{1-3}$alkyl)heterocycle, —N$R^a$(C$_{1-3}$alkyl)heteroaryl, —N$R^a$(C$_{1-3}$alkyl)heterocycle, —(C$_{1-3}$alkyl)phenyl, —O(C$_{1-3}$alkyl)phenyl and —N$R^a$(C$_{1-3}$alkyl)phenyl all of which are substituted by 0, 1, 2 or 3 substituents selected from $C_{1-4}$haloalkyl, $OC_{1-4}$alkyl, Br, Cl, F, I and $C_{1-4}$alkyl;
$R^3$ is selected from H, halo, $C_{1-4}$haloalkyl, cyano, nitro, —C(=O)$R^a$, —C(=O)O$R^a$, —C(=O)N$R^aR^a$, —C(=N$R^a$)N$R^aR^a$, O$R^a$—OC(=O)$R^a$, —OC(=O)N$R^aR^a$, —OC(=O)N($R^a$)S(=O)$_2R^2$, —O$C_{2-6}$alkyl N$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aN^aR^a$, —N$R^aC_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$alkyl, Br, Cl, F, I and $C_{1-6}$alkyl;
$R^4$ is, independently, in each instance, selected from halo, nitro, cyano, $C_{1-4}$alkyl, $OC_{1-4}$alkyl, $OC_{1-4}$haloalkyl, $NHC_{1-4}$alkyl, $N(C_{1-4}$alkyl$)(C_{1-4}$alkyl$)$ and $C_{1-4}$haloalkyl;
$R^5$ is, independently, in each instance, selected from H, halo, $C_{1-6}$alkyl, $C_{1-4}$haloalkyl and $C_{1-6}$ alkyl substituted by 1, 2 or 3 substituents selected from halo, cyano, OH, $OC_{1-4}$alkyl, $C_{1-4}$ alkyl, $C_{1-3}$haloalkyl, $OC_{1-4}$alkyl, $NH_2$, $NHC_{1-4}$alkyl, $N(C_{1-4}$alkyl$)(C_{1-4}$alkyl$)$; or both $R^5$ groups together form a $C_{3-6}$spiroalkyl substituted by 0, 1, 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl and $N(C_{1-4}$alkyl$)(C_{1-4}$alkyl$)$;
$R^6$ is selected from H, halo, $C_{1-6}$alkyl, $C_{1-4}$haloalkyl, cyano, nitro, —C(=O)$R^a$, —C(=O)O$R^a$, —C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O)$_2$ N($R^a$)C(=O)O$R^a$ and —S(=O)$_2$N($R^a$)C(=O)N$R^aR^a$;
$R^7$ is selected from H, halo, $C_{1-6}$alkyl, $C_{1-4}$haloalkyl, cyano, nitro, —C(=O)$R^a$, —C(=O)O$R^a$, C(=O)N$R^aR^a$, —C(=N$R^a$)N$R^aR^a$, —S(=O)$R^a$, —S(=O)$_2R^a$, —S(=O)$_2$N$R^aR^a$, —S(=O)$_2$N($R^a$)C(=O)$R^a$, —S(=O) $_2$N($R^a$)C(=O)O$R^a$ and —S(=O)$_2$N($R^a$)C(=O)N$R^aR^a$;
$R^8$ is selected from H, $C_{1-6}$haloalkyl, Br, Cl, F, I, O$R^a$, N$R^aR^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$ alkyl, Br, Cl, F, I and $C_{1-6}$alkyl;
$R^9$ is selected from H, halo, $C_{1-4}$haloalkyl, cyano, nitro, —C(=O)$R^a$, —C(=O)O$R^a$, —C(=O)N$R^aR^aC(=NR^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylO$R^a$, —S$R^a$, —S(=O)$R^a$, —S(=O)$_2R^a$, —S(=O)$_2$N$R^aR^a$, —S(=O)$_2$ N($R^a$)C(=O)$R^a$, —S(=O)$_2$N($R^a$)C(=O) O$R^a$, —S(=O)$_2$N($R^a$)C(=O)N$R^aR^a$, N$R^aR^a$, —N($R^a$)C(=O)$R^a$, —N($R^a$)C(=O)O$R^a$, —N($R^a$)C(O)N$R^aR^aN(R^aC(=NR^a$)N$R^aR^a$, —N($R^a$)S(=O)$_2R^a$, —N($R$) S(=O)$_2$N$R^aR^a$, —N$R^aC_{2-6}$ alkylN$R^aR^a$, —N$R^aC_{1-6}$alkyl, phenyl, benzyl, heteroaryl and heterocycle, wherein the $C_{1-6}$ alkyl, phenyl, benzyl, heteroaryl and heterocycle are additionally substituted by 0, 1, 2 or 3 substituents selected from, $C_{1-4}$haloalkyl, cyano, nitro, —C(=O) $R^a$, —C(=O)O$R^a$, —C(=O)N$R^aR^a$, —C(=N$R^a$)N$R^aR^a$, —O$R^a$, —OC(=O)$R^a$, OC(=O)N$R^aR^a$, —OC(=O)N($R^a$)S(=O)$_2R^a$, —O$C_{2-6}$alkylN$R^aR^a$, —O$C_{2-6}$ alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylO$R^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O) N$R^aR^a$, —OC(=O)N($R^a$) S(=O)$_2R^a$, —O$C_{2-6}$alkyl N$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$) C(=O)$R^a$, —S(=O)$_2$N($R^a$)C(=O)O$R^a$, —S(=O)$_2$N($R^a$) C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)

$NR^aR^a$, $-N(R^a)S(=O)_2R^a$, $-N(R^a)S(=O)_2NR^aR^a$, $-NR^aC_{2-6}alkylNR^aR^a$ and $-NR^aC_{2-6}alkylOR^a$;

$R^{10}$ is selected from H, $C_{1-3}$alkyl, $C_{1-3}$haloalkyl, cyano, nitro, $CO_2R^a$, $C(=O)NR^aR^a$, $-C(=NR^a)NR^aR^a$, $-S(=O)_2N(R^a)C(=O)R^a$, $-S(=O)_2N(R^a)C(=O)OR^a$, $-S(=O)_2N(R^a)C(=O)NR^aR^a$, $-S(=O)R^b$, $S(=O)_2R^b$ and $S(=O)_2NR^aR^a$;

$R^{11}$ is H or $C_{1-4}$alkyl;

$R^a$ is independently, at each instance, H or $R^b$; and $R^b$ is independently, at each instance, phenyl, benzyl or $C_{1-6}$alkyl, the phenyl, benzyl and $C_{1-6}$ alkyl being substituted by 0, 1, 2 or 3 substituents selected from halo, $C_{1-4}$alkyl, $C_{1-3}$ haloalkyl, $-OC_{1-4}$alkyl, $-NH_2$, $-NHC_{1-4}$alkyl, $-N(C_{1-4}$alkyl)$(C_{1-4}$alkyl).

In another embodiment, the PI3K inhibitor or PI3K-δ inhibitor is a compound of Formula (VI):

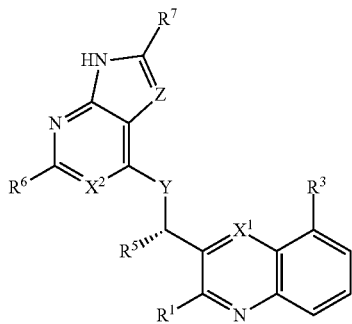

Formula (VI)

or any pharmaceutically-acceptable salt thereof, wherein:

$X^1$ is $C(R^9)$ or N;

$X^2$ is $C(R^{10})$ or N;

Y is $N(R^{11})$, O or S;

Z is $CR^8$ or N;

$R^1$ is a directly-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $OC_{1-4}$alkyl, $OC_{1-4}$haloalkyl, $NHC_{1-4}$alkyl, $N(C_{1-4}$ alkyl)$(C_{1-4}$alkyl) and $C_{1-4}$haloalkyl;

$R^2$ is selected from halo, $C_{1-4}$haloalkyl, cyano, nitro, $-C(=O)R^a$, $-C(=O)OR^a$, $-C(=O)NR^aR^a$, $-C(=NR^a)NR^aR^a$, $-OR^a$, $-OC(=O)R^a$, $-OC(=O)NR^aR^a$, $-OC(=O)N(R^a)S(=O)_2R^a$, $-OC_{2-6}alkylNR^aR^a$, $-OC_{2-6}alkylOR^a$, $-SO)R^a$, $-S(=O)_2R^a$, $-S(=O)_2NR^aR^a$, $-S(=O)_2N(R^a)C(=O)R^a$, $-S(=O)_2 N(R^a)C(=O)OR^a$, $-S(=O)_2N(R^a)C(=O)NR^aR^a$, $-NR^aR^a$, $-N(R^a)C(=O)R^a$, $-N(R^a)C(=O)OR^a$, $-N(R^a)C(=O)NR^aR^a$, $-N(R^a)C(=NR^a)NR^aR^a$, $-N(R^a)S(=O)_2R^a$, $-N(R^a)S(=O)_2NR^aR^a$, $-NR^aC_{2-6}alkylNR^aR^a$ and $-NR^aC_{2-6}alkylOR^a$; or $R^2$ is selected from $C_{1-6}$alkyl, phenyl, benzyl, heteroaryl, heterocycle, $-(C_{1-3}$alkyl)heteroaryl, $-(C_{1-3}$alkyl)heterocycle, $-O(C_{1-3}$alkyl)heteroaryl, $-O(C_{1-3}$alkyl)heterocycle, $-NR^a(C_{1-3}$alkyl)heteroaryl, $-NR^a(C_{1-3}$alkyl)heterocycle, $-(C_{1-3}$alkyl)phenyl, $-O(C_{1-3}$alkyl)phenyl and $-NR^a(C_{1-3}$alkyl)phenyl all of which are substituted by 0, 1, 2 or 3 substituents selected from $C_{1-4}$haloalkyl, $OC_{1-4}$alkyl, Br, Cl, F, I and $C_{1-4}$alkyl;

$R^3$ is selected from H, halo, $C_{1-4}$haloalkyl, cyano, nitro, $-C(=O)R^a$, $-C(=O)OR^a$, $-C(=O)NR^aR^aC(=NR^a)NR^aR^a$, $-OR^a$, $-OC(=O)R^a$, $-OC(=O)NR^aR^a$, $-OC(=O)N(R^a)S(=O)_2R^a$, $-OC_{2-6}alkylNR^aR^a$, $-OC_{2-6}alkylOR^a$, $-SR^a$, $-S(=O)R^a$, $-S(=O)_2R^a$, $-S(=O)_2NR^aR^a$, $-S(=O)_2N(R^a)C(=O)R^a$, $-S(=O)_2 N(R^a)C(=O)OR^a$, $-S(=O)_2N(R^a)C(=O) NR^aR^a$, $NR^aR^a$, $-N(R^a)C(=O)R^a$, $-N(R^a)C(=O)OR^a$, $-N(R^a)C(=O)NR^aR^a$, $-N(R^a)C(=NR^a)NR^aR^a$, $-N(R^a)S(=O)_2R^a$, $-N(R^a)S(=O)_2NR^aR^a$, $-NR^aC_{2-6}alkylOR^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$ alkyl, Br, Cl, F, I and $C_{1-6}$alkyl;

$R^5$ is, independently, in each instance, H, halo, $C_{1-6}$alkyl, $C_{1-4}$haloalkyl, or $C_{1-6}$alkyl substituted by 1, 2 or 3 substituents selected from halo, cyano, OH, $OC_{1-4}$alkyl, $C_{1-4}$alkyl, $-OC_{1-4}$alkyl, $NH_2$, $NHC_{1-4}$alkyl, $N(C_{1-4}$alkyl)$(C_{1-4}$alkyl); or both $R^5$ groups together form a $C_{3-6}$-spiroalkyl substituted by 0, 1, 2 or 3 substituents selected from halo, cyano, OH, $OC_{1-4}$alkyl, $C_{1-4}$alkyl, $OC_{1-4}$alkyl, $NH_2$, $NHC_{1-4}$alkyl, $N(C_{1-4}$alkyl)$(C_{1-4}$alkyl);

$R^6$ is selected from H, halo, $C_{1-4}$alkyl, $C_{1-4}$haloalkyl, cyano, nitro, $-C(=O)R^a$, $-C(=O)OR^a$, $-C(=O)NR^aR^a$, $-C(=NR^a)NR^aR^a$, $-S(=O)R^a$, $-S(=O)_2R^a$, $-S(=O)_2NR^aR^a$, $-S(=O)_2N(R^a)C(=O)R^a$, $-S(=O)_2 N(R^a)C(=O)OR^a$, $-S(=O)_2N(R^a)C(=O) NR^aR^a$;

$R^7$ is selected from H, halo, $C_{1-6}$alkyl, $C_{1-4}$haloalkyl, cyano, nitro, $-C(=O)R^a$, $-C(=O)OR^a$, $-C(=O)NR^aR^a$, $-C(=NR^a)NR^aR^a$, $-S(=O)R^aS(=O)_2R^a$, $-S(=O)_2 NR^aR^a$, $-S(=O)_2N(R^a)C(=O)R^a$, $-S(=O)_2N(R^a)C(=O)OR^a$, $-S(=O)_2N(R^a)C(=O)NR^aR^a$;

$R^8$ is selected from H, $C_{1-6}$haloalkyl, Br, Cl, F, I, $OR^a$, $NR^aR^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$ alkyl, Br, Cl, F, I and $C_{1-6}$alkyl;

$R^9$ is selected from H, halo, $C_{1-4}$haloalkyl, cyano, nitro, $-C(=O)R^a$, $-C(=O)OR^a$, $-C(=O)NR^aR^a$, $-C(=NR^a)NR^aR^a$, $-OR^a$, $-OC(=O)R^a$, $OC(=O)NR^aR^a$, $-OC(=O)N(R^a)S(=O)_2R^a$, $-OC_{2-6}alkylNR^aR^a$, $-OC_{2-6}alkylOR^a$, $-SR^a$, $-S(=O)R^a$, $-S(=O)_2R^a$, $-S(=O)_2NR^aR^a$, $-S(=O)_2N(R^a)C(=O)R^a$, $-S(=O)_2N(R^a)C(=O)OR^a$, $-S(=O)_2N(R^a)C(=O) NR^aR^a$, $-NR^aR^a$, $-N(R^a)C(=O)R^a$, $-N(R^a)C(=O)OR^a$, $-N(R^a)C(=O)NR^aR^a$, $-N(R^a)C(=NR^a)NR^aR^a$, $-N(R^a) S(=O)_2R^a$, $-N(R^a)S(=O)_2NR^aR^a$, $-NR^aC_{2-6}$ alkylNR^aR^a$, $-NR^aC_{2-6}alkylOR^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, $-C(=O)R^a$, $-C(=O)OR^a$, $-C(=O)NR^aR^a$, $-C(=NR^a)NR^aR^a$, $-OR^a$, $-OC(=O)R^a$, $-OC(=O)NR^aR^a$, $-OC(=O)N(R^a)S(=O)_2R^a$, $-OC_{2-6}alkylOR^a$, $-SR^a$, $-S(=O)R^a$, $-S(=O)_2R^a$, $-S(=O)_2NR^aR^a$, $-S(=O)_2 N(R^a)C(=O)R^a$, $-S(=O)_2N(R^a)C(=O)OR^a$, $-S(=O)_2N(R^a)C(=O)NR^aR^a$, $NR^aR^a$, $-N(R^a)C(=O)R^a$, $-N(R^a)C(=O)OR^a$, $-N(R^a)C(=O)NR^aR^a$, $-N(R^a)C(=NR^a)NR^aR^a$, $-N(R^a) S(=O)_2R^a$, $-N(R^a)S(=O)_2NR^aR^a$, $-NR^aC_{2-6}alkylNR^aR^a$, $-NR^aC_{2-6}alkylOR^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a C_{2-6}$alkylN$R^a R^a$ and —N$R^a C_{2-6}$alkylO$R^a$;

$R^{10}$ is H, $C_{1-3}$alkyl, $C_{1-3}$haloalkyl, cyano, nitro, CO$_2 R^a$, C(=O)N$R^a R^a$, —C(=N$R^a$)N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —S(=O)$R^b$, S(=O)$_2 R^b$ or S(=O)$_2$N$R^a R^a$; —$R^{11}$ is H or $C_{1-4}$alkyl;

$R^a$ is independently, at each instance, H or $R^b$; and $R^b$ is independently, at each instance, phenyl, benzyl or $C_{1-6}$alkyl, the phenyl, benzyl and $C_{1-6}$ alkyl being substituted by 0, 1, 2 or 3 substituents selected from halo, $C_{1-4}$alkyl, $C_{1-3}$ haloalkyl, —O$C_{1-4}$alkyl, —NH$_2$, —NH$C_{1-4}$alkyl, —N($C_{1-4}$alkyl)($C_{1-4}$alkyl).

In another embodiment, the PI3K inhibitor or PI3K-δ inhibitor is a compound of Formula (VII):

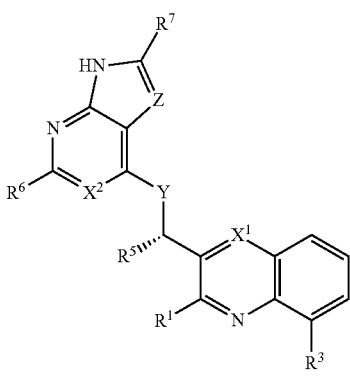

Formula (VII)

or any pharmaceutically-acceptable salt thereof, wherein:
$X^1$ is C($R^9$) or N;
$X^2$ is C($R^{10}$) or N;
Y is N($R^{11}$), O or S;
Z is C$R^8$ or N;
$R^1$ is a direct-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $C_{1-4}$alkyl, O$C_{1-4}$alkyl, O$C_{1-4}$haloalkyl, NH$C_{1-4}$alkyl, N($C_{1-4}$alkyl)($C_{1-4}$alkyl) and $C_{1-4}$haloalkyl;

$R^2$ is selected from halo, $C_{1-4}$haloalkyl, cyano, nitro, —C(=O)$R^a$, —C(=O)O$R^a$, —C(=O)N$R^a R^a$, —C(=N$R^a$)N$R^a R^a$, O$R^a$—OC(=O)$R^a$, —OC(=O)N$R^a R^a$, —OC(=O)N($R^a$)S(=O)$_2 R^a$, —OC$_{2-6}$alkylN$R^a R^a$, —OC$_{2-6}$alkylO$R^a$, —S$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a C_{2-6}$ alkylN$R^a R^a$ and —N$R^a C_{2-6}$alkylO$R^a$; or $R^2$ is selected from $C_{1-6}$alkyl, phenyl, benzyl, heteroaryl, heterocycle, —($C_{1-3}$ alkyl)heteroaryl, —($C_{1-3}$alkyl)heterocycle, —O($C_{1-3}$alkyl)heteroaryl, —O($C_{1-3}$alkyl)heterocycle, —N$R^a$($C_{1-3}$alkyl)heteroaryl, —N$R^a$($C_{1-3}$alkyl)heterocycle, —($C_{1-3}$alkyl)phenyl, —O($C_{1-3}$alkyl)phenyl and —N$R^a$($C_{1-3}$alkyl)phenyl all of which are substituted by 0, 1, 2 or 3 substituents selected from $C_{1-4}$haloalkyl, O$C_{1-4}$alkyl, Br, Cl, F, I and $C_{1-4}$alkyl;

$R^3$ is selected from H, halo, $C_{1-4}$haloalkyl, cyano, nitro, —C(=O)$R^a$, —C(=O)O$R^a$, —C(=O)N$R^a R^a$, —C(=N$R^a$)N$R^a R^a$, O$R^a$—OC(=O)$R^a$, —OC(=O)N$R^a R^a$, —OC(=O)N($R^a$)S(=O)$_2 R^a$, —OC$_{2-6}$alkyl N$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a C_{2-6}$alkylN$R^a R^a$, —N$R^a C_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, O$C_{1-6}$alkyl, Br, Cl, F, I and $C_{1-6}$alkyl;

$R^5$ is, independently, in each instance, H, halo, $C_{1-6}$alkyl, $C_{1-4}$haloalkyl, or $C_{1-6}$alkyl substituted by 1, 2 or 3 substituents selected from halo, cyano, OH, O$C_{1-4}$alkyl, $C_{1-4}$alkyl, $C_{1-3}$haloalkyl, O$C_{1-4}$alkyl, NH$_2$, NH$C_{1-4}$alkyl, N($C_{1-4}$alkyl)($C_{1-4}$alkyl); or both $R^5$ groups together form a $C_{3-6}$-spiroalkyl substituted by 0, 1, 2 or 3 substituents selected from halo, cyano, OH, O$C_{1-4}$alkyl, $C_{1-4}$alkyl, $C_{1-3}$haloalkyl, O$C_{1-4}$alkyl, NH$_2$, NH$C_{1-4}$alkyl, N($C_{1-4}$alkyl)($C_{1-4}$alkyl);

$R^6$ is selected from H, halo, $C_{1-6}$alkyl, cyano, nitro, —C(=O)$R^a$, —C(=O)O$R^a$, —C(=O)N$R^a R^a$, —C(=N$R^a$)N$R^a R^a$, —S(=O)$R^a$S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$;

$R^7$ is selected from H, halo, $C_{1-6}$alkyl, cyano, nitro, —C(=O)$R^a$, —C(=O)O$R^a$, —C(=O)N$R^a R^a$, —C(=N$R^a$)N$R^a R^a$, —S(=O)$R^a$S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$;

$R^8$ is selected from H, $C_{1-6}$haloalkyl, Br, Cl, F, I, O$R^a$, N$R^a R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, O$C_{1-6}$ alkyl, Br, Cl, F, I and $C_{1-6}$alkyl;

$R^9$ is selected from H, halo, $C_{1-4}$haloalkyl, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkyl N$R^a R^a$, —OC$_{2-6}$alkylO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a C_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^8$, —OC(=O)R$^8$, —OC(=O)NR$^2$R$^8$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^8$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$, —NR$^a$C$_{2-6}$alkylOR$^a$; or R$^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

$R^{10}$ is H, $C_{1-3}$alkyl, $C_{1-3}$haloalkyl, cyano, nitro, CO$_2$R$^a$, C(=O)NR$^a$R$^a$, —C(=NR$^a$)NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —S(=O)R$^b$, S(=O)$_2$R$^b$ or S(=O)$_2$NR$^a$R$^a$;

$R^{11}$ is H or $C_{1-4}$alkyl;

$R^a$ is independently, at each instance, H or R$^b$; and $R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —OC$_{1-4}$alkyl, —NH$_2$, —NHC$_{1-4}$ alkyl, —N(C$_{1-4}$alkyl)(C$_{1-4}$alkyl).

In another embodiment, the PI3K inhibitor or PI3K-δ inhibitor is a compound of Formula (VIII):

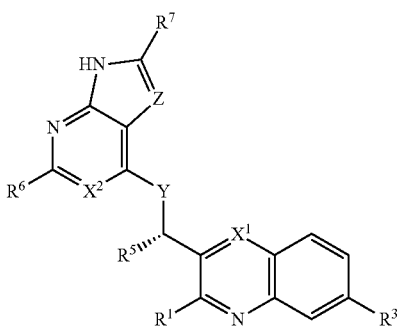

Formula (VIII)

or any pharmaceutically-acceptable salt thereof, wherein:
$X^1$ is C(R$^9$) or N;
$X^2$ is C(R$^{10}$) or N;
Y is N(R$^{11}$), O or S;
Z is CR$^8$ or N;

R$^1$ is a direct-bonded or oxygen-linked saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 R$^2$ substituents, and the ring is additionally substituted by 0, 1, 2 or 3 substituents independently selected from halo, nitro, cyano, $C_{1-4}$alkyl, OC$_{1-4}$alkyl, OC$_{1-4}$haloalkyl, NHC$_{1-4}$alkyl, N(C$_{1-4}$ alkyl)(C$_{1-4}$alkyl) and C$_{1-4}$haloalkyl;

R$^2$ is selected from halo, C$_{1-4}$haloalkyl, cyano, nitro, —C(=O)R$^a$, —C(=O)OR$^a$, —C(=O)NR$^a$R$^a$C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylOR$^a$, —SR$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^2$ is selected from $C_{1-6}$alkyl, phenyl, benzyl, heteroaryl, heterocycle, —(C$_{1-3}$alkyl)heteroaryl, —(C$_{1-3}$alkyl)heterocycle, —O(C$_{1-3}$ alkyl)heteroaryl, —O(C$_{1-3}$alkyl)heterocycle, —NR$^a$(C$_{1-3}$ alkyl)heteroaryl, —NR$^a$(C$_{1-3}$ alkyl)heterocycle, —(C$_{1-3}$alkyl)phenyl, —O(C$_{1-3}$alkyl)phenyl and —NR$^a$(C$_{1-3}$alkyl)phenyl all of which are substituted by 0, 1, 2 or 3 substituents selected from C$_{1-4}$haloalkyl, OC$_{1-4}$alkyl, Br, Cl, F, I and C$_{1-4}$alkyl;

R$^3$ is selected from H, halo, C$_{1-4}$haloalkyl, cyano, nitro, —C(=O)R$^a$, —C(=O)OR$^a$, C(=O)NR$^a$R$^a$C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylOR$^a$, —SR$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$NR$^a$, —NR$^a$, —NR$^a$C$_{2-6}$alkylOR$^a$, C$_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, OC$_{1-6}$alkyl, Br, Cl, F, I and C$_{1-6}$ alkyl;

R$^5$ is, independently, in each instance, H, halo, $C_{1-6}$alkyl, $C_{1-4}$haloalkyl, or $C_{1-6}$alkyl substituted by 1, 2 or 3 substituents selected from halo, cyano, OH, OC$_{1-4}$alkyl, C$_{1-4}$alkyl, C$_{1-3}$haloalkyl, —OC$_{1-4}$alkyl, NH$_2$, NHC$_{1-4}$alkyl, N(C$_{1-4}$alkyl)(C$_{1-4}$alkyl); or both R$^5$ groups together form a $C_{3-6}$-spiroalkyl substituted by 0, 1, 2 or 3 substituents selected from halo, cyano, OH, OC$_{1-4}$alkyl, C$_{1-4}$alkyl, C$_{1-3}$haloalkyl, OC$_{1-4}$alkyl, NH$_2$, NHC$_{1-4}$alkyl, N(C$_{1-4}$alkyl)(C$_{1-4}$alkyl);

R$^6$ is selected from H, halo, $C_{1-6}$alkyl, $C_{1-4}$haloalkyl, cyano, nitro, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$ N(R$^a$)C(=O)OR$^a$, —S(=O)$_2$N(R$^a$)C(=O)NR$^a$R$^a$;

R$^7$ is selected from H, halo, $C_{1-6}$alkyl, $C_{1-4}$haloalkyl, cyano, nitro, —C(=O)R$^a$, —C(=O)OR$^a$, —C(=O)NR$^a$R$^a$, —C(=NR$^a$)NR$^a$R$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$ N(R$^a$)C(=O)OR$^a$, —S(=O)$_2$N(R$^a$)C(=O)NR$^a$R$^a$;

R$^8$ is selected from H, $C_{1-6}$haloalkyl, Br, Cl, F, I, OR$^a$, NR$^a$R$^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$ alkyl, Br, Cl, F, I and $C_{1-6}$alkyl;

$R^9$ is selected from H, halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$) S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O) O$R^a$, —N($R^a$)C(=O)N$R^aR^a$, —N($R^a$)C(=N$R^a$)N$R^aR^a$, —N($R^a$) S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$) S(=O)$_2R^a$, —O$C_{2-6}$alkylO$R^a$, —S$R^a$, —S(=O)$R^a$, —S(=O)$_2R^a$, —S(=O)$_2$N$R^aR^a$, —S(=O)$_2$ N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O) O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$; or $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, C(O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$) S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$ N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, N($R^a$)S(=O)$_2$N$R^aR^a$, —N$R^aC_{2-6}$ alkylN$R^aR^a$ and —N$R^aC_{2-6}$alkylO$R^a$;

$R^{10}$ is H, $C_{1-3}$alkyl, $C_{1-3}$haloalkyl, cyano, nitro, CO$_2R^a$, C(=O)N$R^aR^a$, —C(=N$R^a$)N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —S(=O)$R^b$, —S(=O)$_2R^b$ or S(=O)$_2$N$R^aR^a$;

$R^{11}$ is H or $C_{1-4}$alkyl;

$R^a$ is independently, at each instance, H or $R^b$; and $R^b$ is independently, at each instance, phenyl, benzyl or $C_{1-6}$alkyl, the phenyl, benzyl and $C_{1-6}$ alkyl being substituted by 0, 1, 2 or 3 substituents selected from halo, $C_{1-4}$alkyl, $C_{1-3}$ haloalkyl, —O$C_{1-4}$alkyl, —NH$_2$, —NH$C_{1-4}$alkyl, —N($C_{1-4}$alkyl)($C_{1-4}$alkyl).

Preferred embodiments in relation to compounds of formula (V), formula (VI), formula (VII and formula (III) are as follows.

In a preferred embodiment, $X^1$ is C($R^9$). In a further preferred embodiment, $X^1$ is C($R^9$) and $X^2$ is N. In a further embodiment, $X^1$ is C($R^9$) and $X^2$ is C($R^{10}$).

In another embodiment, in conjunction with any of the above or below embodiments, $R^1$ is phenyl substituted by 0 or 1 $R^2$ substituents, and the phenyl is additionally substituted by 0, 1, 2 or 3 substituents independently selected from halo, nitro, cyano, $C_{1-4}$alkyl, O$C_{1-4}$alkyl, O$C_{1-4}$haloalkyl, NH$C_{1-4}$alkyl, N($C_{1-4}$alkyl)($C_{1-4}$alkyl) and $C_{1-4}$haloalkyl.

In another embodiment, in conjunction with any of the above or below embodiments, $R^1$ is phenyl.

In another embodiment, in conjunction with any of the above or below embodiments, $R^1$ is phenyl substituted by $R^2$, and the phenyl is additionally substituted by 0, 1, 2 or 3 substituents independently selected from halo, nitro, cyano, $C_{1-4}$alkyl, O$C_{1-4}$alkyl, O$C_{1-4}$haloalkyl, NH$C_{1-4}$alkyl, N($C_{1-4}$alkyl)($C_{1-4}$alkyl) and $C_{1-4}$haloalkyl.

In another embodiment, in one specific embodiment, leis selected from 2-methylphenyl, 2-chlorophenyl, 2-trifluoromethylphenyl, 2-fluorophenyl and 2-methoxyphenyl.

In another specific embodiment, $R^1$ is phenoxy.

In another specific embodiment, $R^1$ is a direct-bonded or oxygen-linked saturated, partially-saturated or unsaturated 5-, 6- or 7-membered monocyclic ring containing 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, nitro, cyano, $C_{1-4}$alkyl, O$C_{1-4}$alkyl, O$C_{1-4}$haloalkyl, NH$C_{1-4}$alkyl, N($C_{1-4}$alkyl)($C_{1-4}$ alkyl) and $C_{1-4}$haloalkyl.

In another embodiment, in conjunction with any of the above or below embodiments, $R^1$ is an unsaturated 5- or 6-membered monocyclic ring containing 1, 2, 3 or 4 atoms selected from N, O and S, but containing no more than one O or S, wherein the ring is substituted by 0 or 1 $R^2$ substituents, and the ring is additionally substituted by 0, 1, 2 or 3 substituents independently selected from halo, nitro, cyano, $C_{1-4}$alkyl, O$C_{1-4}$alkyl, O$C_{1-4}$haloalkyl, NH$C_{1-4}$alkyl, N($C_{1-4}$alkyl)($C_{1-4}$alkyl) and $C_{1-4}$haloalkyl.

In another embodiment, in conjunction with any of the above or below embodiments, $R^1$ is an unsaturated 5- or 6-membered monocyclic ring containing 1, 2, 3 or 4 atoms selected from N, O and S, but containing no more than one O or S, wherein the ring is substituted by 0 or 1 $R^2$ substituents, and the ring is additionally substituted by 1, 2 or 3 substituents independently selected from halo, nitro, cyano, $C_{1-4}$alkyl, O$C_{1-4}$alkyl, O$C_{1-4}$haloalkyl, NH$C_{1-4}$alkyl, N($C_{1-4}$alkyl)($C_{1-4}$alkyl) and $C_{1-4}$haloalkyl.

In another embodiment, in conjunction with any of the above or below embodiments, $R^1$ is an unsaturated 5- or 6-membered monocyclic ring containing 1, 2, 3 or 4 atoms selected from N, O and S.

In another embodiment, in conjunction with any of the above or below embodiments, $R^1$ is selected from pyridyl and pyrimidinyl.

In a further specific embodiment, $R^3$ is selected from halo, $C_{1-4}$haloalkyl, cyano, nitro, —C(O)$R^a$, —C(=O)O$R^a$, —C(=O)N$R^aR^a$, —C(N$R^a$)N$R^aR^a$, O$R^a$, —OC(=O)$R^a$, —OC(=O)N$R^aR^a$, —OC(=O)N($R^a$) S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)N$R^aR^a$, —S(=O)$_2$N($R^a$)C(=O)$R^a$, —S(=O)$_2$N($R^a$)C(O)O$R^a$, S(=O)$_2$N($R^a$)C(=O)N$R^aR^a$, —N$R^aR^a$, —N($R^a$)C(=O)O$R^a$, —N($R^a$)C(=O)$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, O$C_{1-6}$alkyl, Br, Cl, F, I and $C_{1-6}$alkyl.

In another specific embodiment, $R^3$ is H.

In another specific embodiment, $R^3$ is selected from F, Cl, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from $C_{1-6}$haloalkyl, $OC_{1-6}$alkyl, Br, Cl, F, I and $C_{1-6}$alkyl.

In further embodiment, $R^5$ is, independently, in each instance, H, halo, $C_{1-6}$alkyl, $C_{1-4}$haloalkyl, or $C_{1-6}$alkyl substituted by 1, 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl, $N(C_{1-4}$alkyl$)(C_{1-4}$alkyl$)$; or both $R^5$ groups together form a $C_{3-6}$spiroalkyl substituted by 0, 1, 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl, $N(C_{1-4}$alkyl$)(C_{1-4}$alkyl$)$.

In another embodiment, in conjunction with any of the above or below embodiments, $R^5$ is H.

In another embodiment, in conjunction with any of the above or below embodiments, one $R^5$ is S-methyl, the other is H.

In another embodiment, in conjunction with any of the above or below embodiments, at least one $R^5$ is halo, $C_{1-6}$alkyl, $C_{1-4}$haloalkyl, or $C_{1-6}$alkyl substituted by 1, 2 or 3 substituents selected from halo, cyano, OH, $OC_{1-4}$alkyl, $C_{1-4}$alkyl, $C_{1-3}$haloalkyl, $OC_{1-4}$alkyl, $NH_2$, $NHC_{1-4}$alkyl, $N(C_{1-4}$alkyl$)(C_{1-4}$alkyl$)$.

In a preferred embodiment, $R^6$ is H.
In a preferred embodiment, $R^6$ is F, Cl, cyano or nitro.
In a preferred embodiment, $R^7$ is H.
In a preferred embodiment, $R^7$ is F, Cl, cyano or nitro.
In a preferred embodiment, $R^8$ is selected from H, $CF_3$, $C_{1-3}$alkyl, Br, Cl and F.
In a preferred embodiment, $R^8$ is selected from H.
In a preferred embodiment, $R^8$ is selected from $CF_3$, $C_{1-3}$alkyl, Br, Cl and F.
In a preferred embodiment, $R^9$ is H.
In a preferred embodiment, $R^9$ is selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$, $C_{1-6}$alkyl, phenyl, benzyl, heteroaryl and heterocycle, wherein the $C_{1-6}$alkyl, phenyl, benzyl, heteroaryl and heterocycle are additionally substituted by 0, 1, 2 or 3 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$, —N$R^aC_{2-6}$alkylO$R^a$.

In another embodiment, in conjunction with any of the above or below embodiments, $R^9$ is a saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2, 3 or 4 substituents selected from halo, $C_{1-4}$haloalkyl, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkylN$R^aR^a$, —O$C_{2-6}$alkylO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any of the above or below embodiments, $R^{10}$ is H.

In another embodiment, in conjunction with any of the above or below embodiments, $R^{10}$ is cyano, nitro, $CO_2R^a$, C(=O)N$R^aR^a$, —C(=N$R^a$)N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, S(=O)$R^b$, S(=O)$_2R^b$ or S(=O)$_2$N$R^aR^a$.

In another embodiment, in conjunction with any of the above or below embodiments, $R^{11}$ is H.

In a preferred embodiment, the PI3K inhibitor is a PI3K-δ inhibitor, which is a compound of Formula (IX):

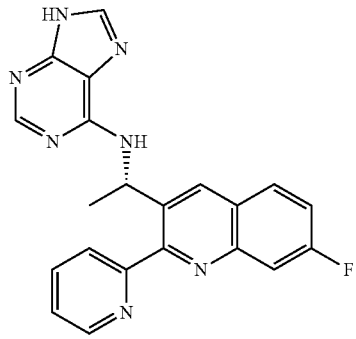

Formula (IX)

which is (S)—N-(1-(7-fluoro-2-(pyridin-2-yl)quinolin-3-yl)ethyl)-9H-purin-6-amine, or a pharmaceutically-acceptable salt thereof.

In a preferred embodiment, the PI3K inhibitor or PI3K-δ inhibitor is a compound of Formula (X'):

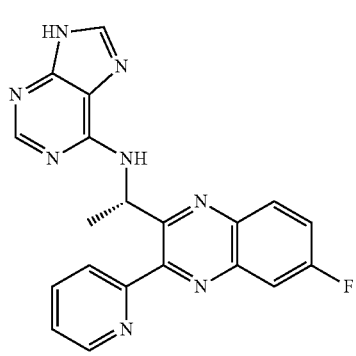

Formula (X)

which is (S)—N-(1-(6-fluoro-3-(pyridin-2-yl)quinoxalin-2-yl)ethyl)-9H-purin-6-amine, or a pharmaceutically-acceptable salt thereof.

In a preferred embodiment, the PI3K inhibitor or PI3K-δ inhibitor is a compound of Formula (XI):

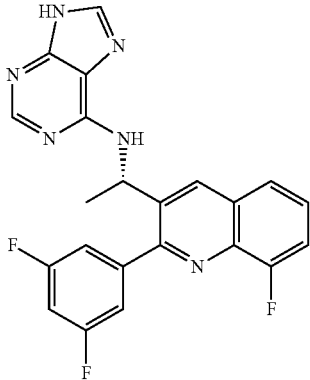

Formula (XI)

which is (S)—N-(1-(2-(3,5-difluorophenyl)-8-fluoroquinolin-3-yl)ethyl)-9H-purin-6-amine, or a pharmaceutically-acceptable salt thereof.

In a preferred embodiment, the PI3K inhibitor or PI3K-δ inhibitor is a compound of Formula (XII):

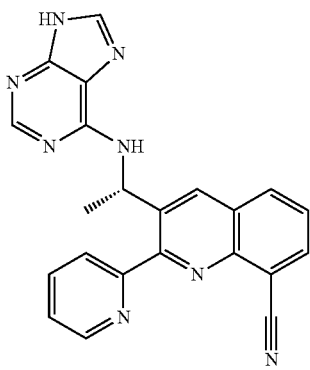

Formula (XII)

which is (S)-3-(1-((9H-purin-6-yl)amino)ethyl)-2-(pyridin-2-yl)quinoline-8-carbonitrile, or a pharmaceutically-acceptable salt thereof In a preferred embodiment, the PI3K inhibitor or PI3K-δ inhibitor is a compound of Formula (XIII):

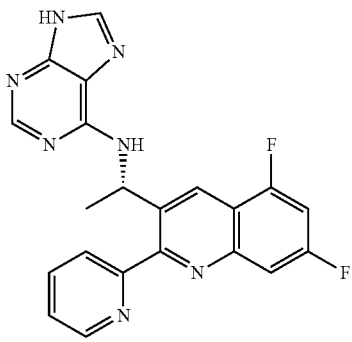

Formula (XIII)

which is (S)—N-(1-(5,7-difluoro-2-(pyridin-2-yl)quinolin-3-yl)ethyl)-9H-purin-6-amine, or a pharmaceutically-acceptable salt thereof.

In an embodiment, the PI3K inhibitor or PI3K-δ inhibitor is a compound selected from the structures disclosed in U.S. Pat. Nos. 7,932,260 and 8,207,153, the disclosure of which is incorporated by reference herein. In an embodiment, the PI3K inhibitor or PI3K-δ inhibitor is a compound of Formula (XIV):

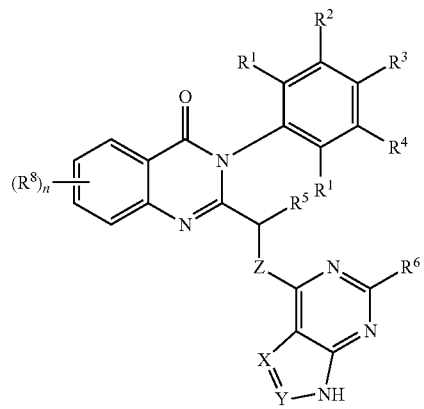

Formula (XIV)

wherein

X and Y, independently, are N or CH;

Z is N—$R^7$ or O;

$R^1$ are the same and are hydrogen, halo, or $C_{1-3}$alkyl;

$R^2$ and $R^3$, independently, are hydrogen, halo, or $C_{1-3}$alkyl;

$R^4$ is selected from hydrogen, halo, O$R^a$, CN, $C_{2-6}$alkynyl, C(=O)$R^a$, C(=O)N$R^aR^b$, $C_{3-6}$heterocycloalkyl, $C_{1-3}$ alkylene$C_{3-6}$heterocycloalkyl, O$C_{1-3}$alkyleneO$R^a$, O$C_{1-3}$alkyleneN$R^aR^b$, O$C_{1-3}$alkylene$C_{3-6}$ cycloalkyl, O$C_{3-6}$ heterocycloalkyl, O$C_{1-3}$alkyleneC≡CH, and O$C_{1-3}$alkyleneC(=O)N$R^aR^b$;

$R^5$ is $C_{1-3}$alkyl, $CH_2CF_3$, phenyl, $CH_2$C≡CH, $C_{1-3}$alkyleneO$R^c$, $C_{1-4}$alkyleneN$R^aR^b$, or $C_{1-4}$ alkylene NHC(=O)O$R^a$, $R^6$ is hydrogen, halo, or N$R^aR^b$;

$R^7$ is hydrogen or $R^5$ and $R^7$ are taken together with the atoms to which they are attached to form a five- or six-membered saturated ring;

$R^8$ is $C_{1-3}$alkyl, halo, $CF_3$, or $CH_2C_{3-6}$heterocycloalkyl;

n is 0, 1, or 2;

$R^a$ is hydrogen, $C_{1-4}$alkyl, or $CH_2C_6H_5$;

$R^b$ is hydrogen or $C_{1-3}$alkyl; and $R^c$ is hydrogen, $C_{1-3}$alkyl, or halo, wherein when the $R^1$ groups are different from hydrogen, $R^2$ and $R^4$ are the same; or a pharmaceutically acceptable salt, or prodrug, or solvate (e.g., hydrate) thereof.

In a preferred embodiment, the PI3K inhibitor or PI3K-δ inhibitor is an enantiomer of Formula (XIV), as shown in Formula (XV):

Formula (XV)

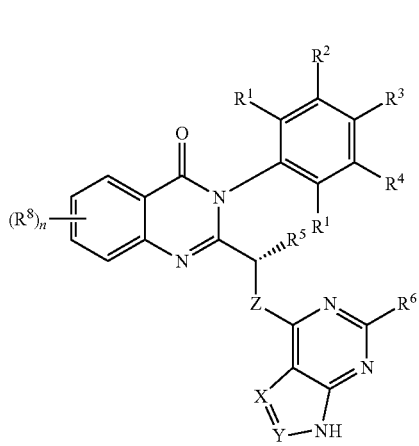

wherein X, Y, Z, le through $R^8$, $R^a$, $R^b$, $R^c$, and n are as defined above for Formula (XIV).

Embodiments in relation to compounds of Formula (XIV) and Formula (XV) are as follows.

In various embodiments exhibiting increased potency relative to other compounds, $R^8$ is $C_{1-3}$alkyl, F, Cl, or $CF_3$. Alternatively, in such embodiments, n is 0 (such that there is no $R^8$ substituent). In some embodiments, n is 1, 2, 3, or 4.

In other embodiments exhibiting such increased potency, X and Y, independently, are N or CH. In further embodiment exhibiting increased potency, X is N and Y is CH. Alternatively, X and Y may also both be CH. In further embodiments exhibiting increased potency, $R^6$ is hydrogen, halo, or $NH_2$.

Unexpectedly, potency against PI3K-δ is conserved when $R^1$ is the same. In structural Formulae (XIV) and (XV), $R^2$ and $R^4$ may differ provided that $R^1$ is H. When $R^1$ is H, free rotation is unexpectedly permitted about the bond connecting the phenyl ring substituent to the quinazoline ring, and the compounds advantageously do not exhibit atropisomerism (i.e., multiple diastereomer formation is avoided). Alternatively, $R^2$ and $R^4$ can be the same such that the compounds advantageously do not exhibit atropisomerism.

As used with respect to Formula (XIV) and Formula (XV), the term "alkyl" is defined as straight chained and branched hydrocarbon groups containing the indicated number of carbon atoms, e.g., methyl, ethyl, and straight chain and branched propyl and butyl groups. The terms "$C_{1-3}$alkylene" and "$C_{1-4}$alkylene" are defined as hydrocarbon groups containing the indicated number of carbon atoms and one less hydrogen than the corresponding alkyl group. The term "$C_{2-6}$alkynyl" is defined as a hydrocarbon group containing the indicated number of carbon atoms and a carbon-carbon triple bond. The term "$C_{3-6}$cycloalkyl" is defined as a cyclic hydrocarbon group containing the indicated number of carbon atoms. The term "$C_{2-6}$heterocycloalkyl" is defined similarly as cycloalkyl except the ring contains one or two heteroatoms selected from the group consisting of O, $NR^a$, and S. The term "halo" is defined as fluoro, bromo, chloro, and iodo.

In preferred embodiments, Z is N—$R^7$, and the bicyclic ring system containing X and Y is:

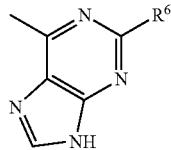 or 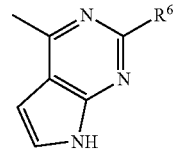

In other preferred embodiments, $R^1$ is hydrogen, fluoro, chloro, methyl, or

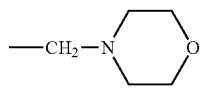

and $R^2$ is hydrogen, methyl, chloro, or fluoro; $R^3$ is hydrogen or fluoro; $R^6$ is $NH_2$, hydrogen, or fluoro; $R^7$ is hydrogen or $R^5$ and $R^7$ are taken together to form

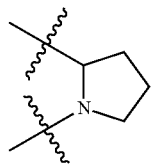 [SMILES: *C1CCCN1*]

$R^8$ is methyl, trifluoromethyl, chloro, or fluoro; $R^4$ is hydrogen, fluoro, chloro, OH, $OCH_3$, $OCH_2C\equiv CH$, $O(CH_2)_2N(CH_3)_2$, $C(=O)CH_3$, $C\equiv CH$, CN, $C(=O)NH_2$, $OCH_2C(=O)NH_2$, $O(CH_2)_2OCH_3$, $O(CH_2)_2N(CH_3)_2$,

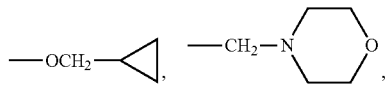

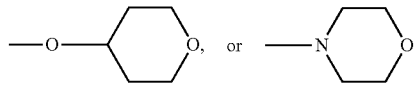

and $R^5$ is methyl, ethyl, propyl, phenyl, $CH_2OH$, $CH_2OCH_2C_6H_5$, $CH_2CF_3$, $CH_2OC(CH_3)_3$, $CH_2C\equiv CH$, $(CH_2)_3N(C_2H_5)_2$, $(CH_2)_3NH_2$, $(CH_2)_4NH_2$, $(CH_2)_3NHC(=O)OCH_2C_6H_5$, or $(CH_2)_4NHC(=O)OCH_2C_6H_5$; RC is hydrogen, methyl, fluoro, or bromo; and n is 0 or 1. Preferably, $R^6$ is hydrogen.

In preferred embodiments exhibiting such increased potency, n is 0 or 1; $R^8$ (if n is 1) is $C_{1-3}$alkyl, F, Cl, or $CF_3$; $R^6$ is hydrogen; X is N and Y is CH or X and Y are both CH; Z is NH; le are the same and are hydrogen, halo, or $C_{1-3}$alkyl; and $R^2$ and $R^3$, independently, are hydrogen, halo, or $C_{1-3}$alkyl. Preferably, R', $R^2$, and $R^3$ are hydrogen.

In a preferred embodiment, the PI3K inhibitor or PI3K-δ inhibitor is idelalisib, also known as GS-1101 or CAL-101, with the chemical name of (S)-2-(1-((9H-purin-6-yl)amino)propyl)-5-fluoro-3-phenylquinazolin-4(3H)-one and the chemical structure shown in Formula (XVI):

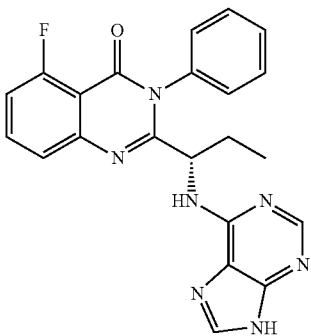

Formula (XVI)

or a pharmaceutically-acceptable salt, solvate, hydrate, cocrystal, or prodrug thereof.

In an embodiment, the PI3K inhibitor or PI3K-δ inhibitor is 4(3H)-quinazolinone, 5-fluoro-3-phenyl-2-[(1S)-1-(9H-purin-6-ylamino)propyl]-5-fluoro-3-phenyl-2-{(1)-1-[(7H-purin-6-yl)amino]propyl}quinazolin-4(3H)-one or or a pharmaceutically-acceptable salt thereof.

In an embodiment, the PI3K-δ inhibitor is GS-9901. Other PI3K inhibitors suitable for use in the described combination with a BTK inhibitor also include, but are not limited to, those described in, for example, U.S. Pat. No. 8,193,182 and U.S. Published Application Nos. 2013/0267521; 2013/0053362; 2013/0029984; 2013/0029982; 2012/0184568; and 2012/0059000, the disclosures of each of which are incorporated by reference in their entireties.

BTK Inhibitors

Some embodiments (for example combinations, compositions and/or kits) of the invention comprise a BTK inhibitor. The BTK inhibitor may be any BTK inhibitor known in the art. In particular, it is one of the BTK inhibitors described in more detail in the following paragraphs. Preferably, it is a compound of Formula XVII or a pharmaceutically acceptable salt thereof. In one specific embodiment, it is a compound of Formula XVIII or a pharmaceutically acceptable salt thereof.

In an embodiment, the BTK inhibitor is a compound of Formula (XVII):

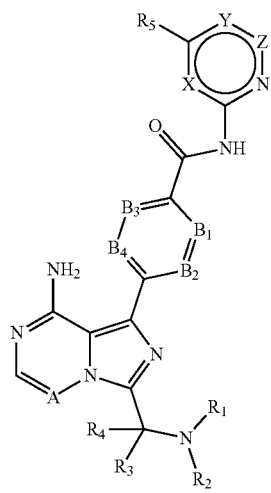

Formula (XVII)

or a pharmaceutically acceptable salt, solvate, hydrate, cocrystal, or prodrug thereof, wherein:

X is CH, N, O or S;
Y is C($R_6$), N, O or S;
Z is CH, N or bond;
A is CH or N;
$B_1$ is N or C($R_7$);
$B_2$ is N or C($R_8$);
$B_3$ is N or C($R_9$);
$B_4$ is N or C($R_{10}$);
$R_1$ is $R_{11}$C(=O), $R_{12}$S(=O), $R_{13}$S(=O)$_2$ or ($C_{1-6}$)alkyl optionally substituted with $R_{14}$;
$R_2$ is H, ($C_{1-3}$)alkyl or ($C_{3-7}$)cycloalkyl;
$R_3$ is H, ($C_{1-6}$)alkyl or ($C_{3-7}$)cycloalkyl); or
$R_2$ and $R_3$ form, together with the N and C atom they are attached to, a ($C_{3-7}$)heterocycloalkyl optionally substituted with one or more fluorine, hydroxyl, ($C_{1-3}$)alkyl, ($C_{1-3}$)alkoxy or oxo;
$R_4$ is H or ($C_{1-3}$)alkyl;
$R_5$ is H, halogen, cyano, ($C_{1-4}$)alkyl, ($C_{1-3}$)alkoxy, ($C_{3-6}$) cycloalkyl, any alkyl group of which is optionally substituted with one or more halogen; or $R_5$ is ($C_{6-10}$)aryl or ($C_{2-6}$)heterocycloalkyl;
$R_6$ is H or ($C_{1-3}$)alkyl; or
$R_5$ and $R_6$ together may form a ($C_{3-7}$)cycloalkenyl or ($C_{2-6}$)heterocycloalkenyl, each optionally substituted with ($C_{1-3}$)alkyl or one or more halogens;
$R_7$ is H, halogen, CF$_3$, ($C_{1-3}$)alkyl or ($C_{1-3}$)alkoxy;
$R_8$ is H, halogen, CF$_3$, ($C_{1-3}$)alkyl or ($C_{1-3}$)alkoxy; or
$R_7$ and $R_8$ together with the carbon atoms they are attached to, form ($C_{6-10}$)aryl or ($C_{1-9}$) heteroaryl;
$R_9$ is H, halogen, ($C_{1-3}$)alkyl or ($C_{1-3}$)alkoxy;
$R_{10}$ is H, halogen, ($C_{1-3}$)alkyl or ($C_{1-3}$)alkoxy;
$R_{11}$ is independently selected from the group consisting of ($C_{1-6}$)alkyl, ($C_{2-6}$)alkenyl and ($C_{2-6}$)alkynyl, where each alkyl, alkenyl or alkynyl is optionally substituted with one or more substituents selected from the group consisting of hydroxyl, ($C_{1-4}$)alkyl, ($C_{3-7}$)cycloalkyl, [($C_{1-4}$)alkyl] amino, di[($C_{1-4}$)alkyl]amino, ($C_{1-3}$)alkoxy, ($C_{3-7}$)cycloalkoxy, ($C_{6-10}$)aryl and ($C_{3-7}$)heterocycloalkyl; or $R_{11}$ is ($C_{1-3}$)alkyl-C(O)—S—($C_{1-3}$)alkyl; or
$R_{11}$ is ($C_{1-5}$)heteroaryl optionally substituted with one or more substituents selected from the group consisting of halogen or cyano;
$R_{12}$ and $R_{13}$ are independently selected from the group consisting of ($C_{2-6}$)alkenyl or ($C_{2-6}$)alkynyl, both optionally substituted with one or more substituents selected from the group consisting of hydroxyl, ($C_{1-4}$)alkyl, ($C_{3-7}$)cycloalkyl, [($C_{1-4}$)alkyl]amino, di[($C_{1-4}$)alkyl] amino, ($C_{1-3}$)alkoxy, ($C_{3-7}$)cycloalkoxy, ($C_{6-10}$)aryl and ($C_{3-7}$)heterocycloalkyl; or a ($C_{1-5}$)heteroaryl optionally substituted with one or more substituents selected from the group consisting of halogen and cyano; and
$R_{14}$ is independently selected from the group consisting of halogen, cyano, ($C_{2-6}$)alkenyl and ($C_{2-6}$)alkynyl, both optionally substituted with one or more substituents selected from the group consisting of hydroxyl, ($C_{1-4}$) alkyl, ($C_{3-7}$)cycloalkyl, ($C_{1-4}$)alkylamino, di[($C_{1-4}$)alkyl] amino, ($C_{1-3}$)alkoxy, ($C_{3-7}$)cycloalkoxy, ($C_{6-10}$)aryl, ($C_{1-5}$)heteroaryl and ($C_{3-7}$)heterocycloalkyl;
with the proviso that:
0 to 2 atoms of X, Y, Z can simultaneously be a heteroatom;
when one atom selected from X, Y is O or S, then Z is a bond and the other atom selected from X, Y can not be O or S;
when Z is C or N then Y is C($R_6$) or N and X is C or N;
0 to 2 atoms of B1, B2, B3 and B4 are N;

with the terms used having the following meanings:

($C_{1-2}$)alkyl means an alkyl group having 1 to 2 carbon atoms, being methyl or ethyl, ($C_{1-3}$)alkyl means a branched or unbranched alkyl group having 1-3 carbon atoms, being methyl, ethyl, propyl or isopropyl;

($C_{1-4}$)alkyl means a branched or unbranched alkyl group having 1-4 carbon atoms, being methyl, ethyl, propyl, isopropyl, butyl, isobutyl, sec-butyl and tert-butyl, ($C_{1-3}$) alkyl groups being preferred;

($C_{1-5}$)alkyl means a branched or unbranched alkyl group having 1-5 carbon atoms, for example methyl, ethyl, propyl, isopropyl, butyl, isobutyl, sec-butyl, tert-butyl, pentyl and isopentyl, ($C_{1-4}$)alkyl groups being preferred. ($C_{1-6}$)Alkyl means a branched or unbranched alkyl group having 1-6 carbon atoms, for example methyl, ethyl, propyl, isopropyl, butyl, tert-butyl, n-pentyl and n-hexyl. ($C_{1-5}$)alkyl groups are preferred, ($C_{1-4}$)alkyl being most preferred;

($C_{1-2}$)alkoxy means an alkoxy group having 1-2 carbon atoms, the alkyl moiety having the same meaning as previously defined;

($C_{1-3}$)alkoxy means an alkoxy group having 1-3 carbon atoms, the alkyl moiety having the same meaning as previously defined. ($C_{1-2}$)alkoxy groups are preferred;

($C_{1-4}$)alkoxy means an alkoxy group having 1-4 carbon atoms, the alkyl moiety having the same meaning as previously defined. ($C_{1-3}$)alkoxy groups are preferred, ($C_{1-2}$)alkoxy groups being most preferred;

($C_{2-4}$)alkenyl means a branched or unbranched alkenyl group having 2-4 carbon atoms, such as ethenyl, 2-propenyl, isobutenyl or 2-butenyl;

($C_{2-6}$)alkenyl means a branched or unbranched alkenyl group having 2-6 carbon atoms, such as ethenyl, 2-butenyl, and n-pentenyl, ($C_{2-4}$)alkenyl groups being most preferred;

($C_{2-4}$)alkynyl means a branched or unbranched alkynyl group having 2-4 carbon atoms, such as ethynyl, 2-propynyl or 2-butynyl;

($C_{2-6}$)alkynyl means a branched or unbranched alkynyl group having 2-6 carbon atoms, such as ethynyl, propynyl, n-butynyl, n-pentynyl, isopentynyl, isohexynyl or n-hexynyl. ($C_{2-4}$)alkynyl groups are preferred; ($C_{3-6}$)cycloalkyl means a cycloalkyl group having 3-6 carbon atoms, being cyclopropyl, cyclobutyl, cyclopentyl or cyclohexyl;

($C_{3-7}$)cycloalkyl means a cycloalkyl group having 3-7 carbon atoms, being cyclopropyl, cyclobutyl, cyclopentyl, cyclohexyl or cycloheptyl;

($C_{2-6}$)heterocycloalkyl means a heterocycloalkyl group having 2-6 carbon atoms, preferably 3-5 carbon atoms, and one or two heteroatoms selected from N, O and/or S, which may be attached via a heteroatom if feasible, or a carbon atom; preferred heteroatoms are N or O; also preferred are piperidine, morpholine, pyrrolidine and piperazine; with the most preferred ($C_{2-6}$)heterocycloalkyl being pyrrolidine; the heterocycloalkyl group may be attached via a heteroatom if feasible;

($C_{3-7}$)heterocycloalkyl means a heterocycloalkyl group having 3-7 carbon atoms, preferably 3-5 carbon atoms, and one or two heteroatoms selected from N, O and/or S. Preferred heteroatoms are N or O; preferred ($C_{3-7}$) heterocycloalkyl groups are azetidinyl, pyrrolidinyl, piperidinyl, homopiperidinyl or morpholinyl; more preferred ($C_{3-7}$)heterocycloalkyl groups are piperidine, morpholine and pyrrolidine; and the heterocycloalkyl group may be attached via a heteroatom if feasible;

($C_{3-7}$)cycloalkoxy means a cycloalkyl group having 3-7 carbon atoms, with the same meaning as previously defined, attached via a ring carbon atom to an exocyclic oxygen atom;

($C_{6-10}$)aryl means an aromatic hydrocarbon group having 6-10 carbon atoms, such as phenyl, naphthyl, tetrahydronaphthyl or indenyl; the preferred ($C_{6-10}$)aryl group is phenyl;

($C_{1-5}$)heteroaryl means a substituted or unsubstituted aromatic group having 1-5 carbon atoms and 1-4 heteroatoms selected from N, O and/or S; the ($C_{1-5}$)heteroaryl may optionally be substituted; preferred ($C_{1-5}$)heteroaryl groups are tetrazolyl, imidazolyl, thiadiazolyl, pyridyl, pyrimidyl, triazinyl, thienyl or furyl, a more preferred ($C_{1-5}$)heteroaryl is pyrimidyl;

($C_{1-9}$)heteroaryl means a substituted or unsubstituted aromatic group having 1-9 carbon atoms and 1-4 heteroatoms selected from N, O and/or S; the ($C_{1-9}$)heteroaryl may optionally be substituted; preferred ($C_{1-9}$)heteroaryl groups are quinoline, isoquinoline and indole;

[($C_{1-4}$)alkyl]amino means an amino group, monosubstituted with an alkyl group containing 1-4 carbon atoms having the same meaning as previously defined; preferred [($C_{1-4}$)alkyl]amino is methylamino;

di[($C_{1-4}$)alkyl]amino means an amino group, disubstituted with alkyl group(s), each containing 1-4 carbon atoms and having the same meaning as previously defined; preferred di[($C_{1-4}$)alkyl]amino group is dimethylamino;

halogen means fluorine, chlorine, bromine or iodine;

($C_{1-3}$)alkyl-C(O)—S—($C_{1-3}$)alkyl means an alkyl-carbonyl-thio-alkyl group, each of the alkyl groups having 1 to 3 carbon atoms with the same meaning as previously defined;

($C_{3-7}$)cycloalkenyl means a cycloalkenyl group having 3-7 carbon atoms, preferably 5-7 carbon atoms; preferred ($C_{3-7}$)cycloalkenyl groups are cyclopentenyl or cyclohexenyl; cyclohexenyl groups are most preferred;

($C_{2-6}$)heterocycloalkenyl means a heterocycloalkenyl group having 2-6 carbon atoms, preferably 3-5 carbon atoms; and 1 heteroatom selected from N, O and/or S; preferred ($C_{2-6}$)heterocycloalkenyl groups are oxycyclohexenyl and azacyclohexenyl group.

In the above definitions with multifunctional groups, the attachment point is at the last group.

When, in the definition of a substituent, it is indicated that "all of the alkyl groups" of said substituent are optionally substituted, this also includes the alkyl moiety of an alkoxy group.

A circle in a ring of Formula (XVII) indicates that the ring is aromatic.

Depending on the ring formed, the nitrogen, if present in X or Y, may carry a hydrogen.

In a preferred embodiment, the BTK inhibitor is a compound of Formula (XVII) or a pharmaceutically acceptable salt thereof, wherein:

X is CH or S;
Y is C($R_6$);
Z is CH or bond;
A is CH;
$B_1$ is N or C($R_7$);
$B_2$ is N or C($R_8$);
$B_3$ is N or CH;
$B_4$ is N or CH;
$R_1$ is $R_{11}$C(=O),
$R_2$ is ($C_{1-3}$)alkyl;
$R_3$ is ($C_{1-3}$)alkyl; or R$_2$ and R$_3$ form, together with the N and C atom they are attached to, a (C$_{3-7}$)heterocycloalkyl ring selected from the group consisting of azetidinyl, pyrrolidinyl, piperidinyl, and morpholinyl, optionally substituted with one or more fluorine, hydroxyl, (C$_{1-3}$)alkyl, or (C$_{1-3}$)alkoxy;

R$_4$ is H;

R$_5$ is H, halogen, cyano, (C$_{1-4}$)alkyl, (C$_{1-3}$)alkoxy, (C$_{3-6}$)cycloalkyl, or an alkyl group which is optionally substituted with one or more halogen;

R$_6$ is H or (C$_{1-3}$)alkyl;

R$_7$ is H, halogen or (C$_{1-3}$)alkoxy;

R$_8$ is H or (C$_{1-3}$)alkyl; or

R$_7$ and R$_8$ form, together with the carbon atom they are attached to a (C$_{6-10}$)aryl or (C$_{1-9}$)heteroaryl;

R$_5$ and R$_6$ together may form a (C$_{3-7}$)cycloalkenyl or (C$_{2-6}$)heterocycloalkenyl, each optionally substituted with (C$_{1-3}$)alkyl or one or more halogen;

R$_{11}$ is independently selected from the group consisting of (C$_{2-6}$)alkenyl and (C$_{2-6}$)alkynyl, where each alkenyl or alkynyl is optionally substituted with one or more substituents selected from the group consisting of hydroxyl, (C$_{1-4}$)alkyl, (C$_{3-7}$)cycloalkyl, [(C$_{1-4}$)alkyl]amino, di[(C$_{1-4}$)alkyl]amino, (C$_{1-3}$)alkoxy, (C$_{3-7}$)cycloalkoxy, (C$_{6-10}$)aryl and (C$_{3-7}$)heterocycloalkyl; with the proviso that 0 to 2 atoms of B$_1$, B$_2$, B$_3$ and B$_4$ are N.

In an embodiment of Formula (XVII), B$_1$ is C(R$_7$); B$_2$ is C(R$_8$); B$_3$ is C(R$_9$); B$_4$ is C(R$_{10}$); R$_7$, R$_9$, and R$_{10}$ are each H; and R$_8$ is hydrogen or methyl.

In an embodiment of Formula (XVII), the ring containing X, Y and Z is selected from the group consisting of pyridyl, pyrimidyl, pyridazyl, triazinyl, thiazolyl, oxazolyl and isoxazolyl.

In an embodiment of Formula (XVII), the ring containing X, Y and Z is selected from the group consisting of pyridyl, pyrimidyl and pyridazyl.

In an embodiment of Formula (XVII), the ring containing X, Y and Z is selected from the group consisting of pyridyl and pyrimidyl.

In an embodiment of Formula (XVII), the ring containing X, Y and Z is pyridyl.

In an embodiment of Formula (XVII), R$_5$ is selected from the group consisting of hydrogen, fluorine, methyl, methoxy and trifluoromethyl.

In an embodiment of Formula (XVII), R$_5$ is hydrogen.

In an embodiment of Formula (XVII), R$_2$ and R$_3$ together form a heterocycloalkyl ring selected from the group consisting of azetidinyl, pyrrolidinyl, piperidinyl, homopiperidinyl and morpholinyl, optionally substituted with one or more of fluoro, hydroxyl, (C$_{1-3}$)alkyl and (C$_{1-3}$)alkoxy.

In an embodiment of Formula (XVII), R$_2$ and R$_3$ together form a heterocycloalkyl ring selected from the group consisting of azetidinyl, pyrrolidinyl and piperidinyl.

In an embodiment of Formula (XVII), R$_2$ and R$_3$ together form a pyrrolidinyl ring.

In an embodiment of Formula (XVII), R$_1$ is independently selected from the group consisting of (C$_{1-6}$)alkyl, (C$_{2-6}$)alkenyl or (C$_{2-6}$)alkynyl, each optionally substituted with one or more substituents selected from the group consisting of hydroxyl, (C$_{1-4}$)alkyl, (C$_{3-7}$)cycloalkyl, [(C$_{1-4}$)alkyl]amino, di[(C$_{1-4}$)alkyl]amino, (C$_{1-3}$)alkoxy, (C$_{3-7}$)cycloalkoxy, (C$_{6-10}$)aryl and (C$_{3-7}$)heterocycloalkyl.

In an embodiment of Formula (XVII), B$_1$, B$_2$, B$_3$ and B$_4$ are CH; X is N; Y and Z are CH; R$_5$ is CH$_3$; A is N; R$_2$, R$_3$ and R$_4$ are H; and R$_1$ is CO—CH$_3$.

In an embodiment of Formula (XVII), B$_1$, B$_2$, B$_3$ and B$_4$ are CH; X and Y are N; Z is CH; R$_5$ is CH$_3$; A is N; R$_2$, R$_3$ and R$_4$ are H; and R$_1$ is CO—CH$_3$.

In an embodiment of Formula (XVII), B$_1$, B$_2$, B$_3$ and B$_4$ are CH; X and Y are N; Z is CH; R$_5$ is CH$_3$; A is CH; R$_2$ and R$_3$ together form a piperidinyl ring; R$_4$ is H; and R$_1$ is CO-ethenyl.

In an embodiment of Formula (XVII), B$_1$, B$_2$, B$_3$ and B$_4$ are CH; X, Y and Z are CH; R$_5$ is H; A is CH; R$_2$ and R$_3$ together form a pyrrolidinyl ring; R$_4$ is H; and R$_1$ is CO-propynyl.

In an embodiment of Formula (XVII), B$_1$, B$_2$, B$_3$ and B$_4$ are CH; X, Y and Z are CH; R$_5$ is CH$_3$; A is CH; R$_2$ and R$_3$ together form a piperidinyl ring; R$_4$ is H; and R$_1$ is CO-propynyl.

In an embodiment of Formula (XVII), B$_1$, B$_2$, B$_3$ and B$_4$ are CH; X and Y are N; Z is CH; R$_5$ is H; A is CH; R$_2$ and R$_3$ together form a morpholinyl ring; R$_4$ is H; and R$_1$ is CO-ethenyl.

In an embodiment of Formula (XVII), B$_1$, B$_2$, B$_3$ and B$_4$ are CH; X and Y are N; Z is CH; R$_5$ is CH$_3$; A is CH; R$_2$ and R$_3$ together form a morpholinyl ring; R$_4$ is H; and R$_1$ is CO-propynyl.

In a preferred embodiment, the BTK inhibitor is a compound of Formula (XVIII):

Formula (XVIII)

or a pharmaceutically acceptable salt, solvate, hydrate, cocrystal, or prodrug thereof. The preparation of this compound is described in International Patent Application Publication No. WO 2013/010868 and U.S. Patent Application Publication No. US 2014/0155385 A1, the disclosure of which is incorporated herein by reference. In brief, Formula (XVIII) and related compounds, such as those according to Formula (XVII), may be prepared as follows.

(S)-4-(8-amino-3-(1-(but-2-ynoyl)pyrrolidin-2-yl)imidazo[1,5-c]pyrazin-1-yl)-N-(pyridin-2-yl)benzamide was made from (S)-4-(8-Amino-3-(pyrrolidin-2-yl)imidazo[1,5-c]pyrazin-1-yl)-N-(pyridin-2-yl)benzamide and 2-butynoic acid as follows. To a solution of (S)-4-(8-Amino-3-(pyrrolidin-2-yl)imidazo[1,5-c]pyrazin-1-yl)-N-(pyridin-2-yl)benzamide (19.7 mg, 0.049 mmol), triethylamine (20 mg, 0.197 mmol, 0.027 mL) 2-butynoic acid (4.12 mg, 0.049 mmol) in dichloromethane (2 mL) was added HATU (18.75 mg, 0.049 mmol). The mixture was stirred for 30 min at room temperature. The mixture was washed with water dried over magnesium sulfate and concentrated in vacuo. The residue was purified by preparative HPLC. Fractions containing product were collected and reduced to dryness to afford the title compound (10.5 mg, 18.0%).

(S)-4-(8-Amino-3-(pyrrolidin-2-yl)imidazo[1,5-c]pyrazin-1-yl)-N-(pyridin-2-yl)benzamide was prepared from the following intermediary compounds.

(a). (3-Chloropyrazin-2-yl)methanamine hydrochloride was prepared as follows. To a solution of 3-chloropyrazine-2-carbonitrile (160 g, ~1.147 mol) in acetic acid (1.5 L) was added Raney Nickel (50% slurry in water, 70 g, 409 mmol). The resulting mixture was stirred under 4 bar hydrogen at room temperature overnight. Raney Nickel was removed by filtration over decalite and the filtrate was concentrated under reduced pressure and co-evaporated with toluene. The remaining brown solid was dissolved in ethyl acetate at 50° C. and cooled on an ice-bath. 2M hydrogen chloride solution in diethyl ether (1.14 L) was added in 30 min. The mixture was allowed to stir at room temperature over weekend. The crystals were collected by filtration, washed with diethyl ether and dried under reduced pressure at 40° C. The product brown solid obtained was dissolved in methanol at 60° C. The mixture was filtered and partially concentrated, cooled to room temperature and diethyl ether (1000 ml) was added. The mixture was allowed to stir at room temperature overnight. The solids formed were collected by filtration, washed with diethyl ether and dried under reduced pressure at 40° C. to give 153.5 g of (3-chloropyrazin-2-yl)methanamine.hydrochloride as a brown solid (74.4%, content 77%).

(b). (S)-benzyl 2-((3-chloropyrazin-2-yl)methylcarbamoyl)pyrrolidine-1-carboxylate was prepared as follows. To a solution of (3-chloropyrazin-2-yl)methanamine HCl (9.57 g, 21.26 mmol, 40% wt) and Z-Pro-OH (5.3 g, 21.26 mmol) in dichloromethane (250 mL) was added triethylamine (11.85 mL, 85 mmol) and the reaction mixture was cooled to 0° C. After 15 min stirring at 0° C., HATU (8.49 g, 22.33 mmol) was added. The mixture was stirred for 1 hour at 0° C. and then overnight at room temperature. The mixture was washed with 0.1 M HCl-solution, 5% NaHCO₃, water and brine, dried over sodium sulfate and concentrated in vacuo. The product was purified using silica gel chromatography (heptane/ethyl acetate=1/4 v/v %) to give 5 g of (S)-benzyl 2-((3-chloropyrazin-2-yl)methylcarbamoyl)pyrrolidine-1-carboxylate (62.7%).

(c). (S)-Benzyl 2-(8-chloroimidazo[1,5-a]pyrazin-3-yl)pyrrolidine-1-carboxylate was prepared as follows. (S)-Benzyl 2-((3-chloropyrazin-2-yl)methylcarbamoyl)pyrrolidine-1-carboxylate (20.94 mmol, 7.85 g) was dissolved in acetonitrile (75 ml), 1,3-dimethyl-2-imidazolidinone (62.8 mmol, 6.9 ml, 7.17 g) was added and the reaction mixture was cooled to 0° C. before POCl3 (84 mmol, 7.81 ml, 12.84 g) was added drop wise while the temperature remained around 5° C. The reaction mixture was refluxed at 60-65° C. overnight. The reaction mixture was poured carefully in ammonium hydroxide 25% in water (250 ml)/crushed ice (500 ml) to give a yellow suspension (pH ~8-9) which was stirred for 15 min until no ice was present in the suspension. Ethyl acetate was added, layers were separated and the aqueous layer was extracted with ethyl acetate (3x). The organic layers were combined and washed with brine, dried over sodium sulfate, filtered and evaporated to give 7.5 g crude product. The crude product was purified using silica gel chromatography (heptane/ethyl acetate=1/4 v/v %) to give 6.6 g of (S)-benzyl 2-(8-chloroimidazo[1,5-a]pyrazin-3-yl)pyrrolidine-1-carboxylate (88%).

(d). (S)-Benzyl 2-(1-bromo-8-chloroimidazo[1,5-a]pyrazin-3-yl)pyrrolidine-1-carboxylate was prepared as follows. N-Bromosuccinimide (24.69 mmol, 4.4 g) was added to a stirred solution of (S)-benzyl 2-(8-chloroimidazo[1,5-a]pyrazin-3-yl)pyrrolidine-1-carboxylate (24.94 mmol, 8.9 g) in DMF (145 mL). The reaction was stirred 3 h at rt. The mixture was poured (slowly) in a stirred mixture of water (145 mL), ethyl acetate (145 mL) and brine (145 mL). The mixture was then transferred into a separating funnel and extracted. The water layer was extracted with 2×145 mL ethyl acetate. The combined organic layers were washed with 3×300 mL water, 300 mL brine, dried over sodium sulfate, filtered and evaporated. The product was purified using silica gel chromatography (ethyl acetate/heptane=3/1 v/v %) to give 8.95 g of (S)-benzyl 2-(1-bromo-8-chloroimidazo[1,5-a]pyrazin-3-yl)pyrrolidine-1-carboxylate (82.3%).

(e). (S)-Benzyl 2-(8-amino-1-bromoimidazo[1,5-c]pyrazin-3-yl)pyrrolidine-1-carboxylate was prepared as follows. (S)-Benzyl 2-(8-amino-1-bromoimidazo[1,5-a]pyrazin-3-yl)pyrrolidine-1-carboxylate (20.54 mmol, 8.95 g) was suspended in 2-propanol (113 ml) in a pressure vessel. 2-propanol (50 ml) was cooled to −78° C. in a pre-weighed flask (with stopper and stirring bar) and ammonia gas (646 mmol, 11 g) was lead through for 15 minutes. The resulting solution was added to the suspension in the pressure vessel. The vessel was closed and stirred at room temperature and a slight increase in pressure was observed. Then the suspension was heated to 110° C. which resulted in an increased pressure to 4.5 bar. The clear solution was stirred at 110° C., 4.5 bar overnight. After 18h the pressure remained 4 bar. The reaction mixture was concentrated in vacuum, the residue was suspended in ethyl acetate and subsequent washed with water. The layers were separated and the aqueous layer was extracted with ethyl acetate. The combined organic layers were washed with water, saturated sodium chloride solution, dried over sodium sulfate and concentrated to give 7.35 g of (S)-benzyl 2-(8-amino-1-bromoimidazo[1,5-a]pyrazin-3-yl)pyrrolidine-1-carboxylate (86%).

(S)-4-(8-Amino-3-(pyrrolidin-2-yl)imidazo[1,5-a]pyrazin-1-yl)-N-(pyridin-2-yl)benzamide was prepared as follows.

(a). (S)-benzyl 2-(8-amino-1-(4-(pyridin-2-ylcarbamoyl)phenyl)imidazo[1,5-a]pyrazin-3-yl)pyrrolidine-1-carboxylate was prepared as follows. (S)-benzyl 2-(8-amino-1-bromoimidazo[1,5-a]pyrazin-3-yl)pyrrolidine-1-carboxylate (0.237 mmol, 98.5 mg) and 4-(pyridin-2-ylaminocarbonyl)benzeneboronic acid (0.260 mmol, 63.0 mg) were suspended in a mixture of 2N aqueous potassium carbonate solution (2.37 mmol, 1.18 mL) and dioxane (2.96 mL). Nitrogen was bubbled through the mixture, followed by the addition of 1,1'-bis(diphenylphosphino)ferrocene palladium (ii) chloride (0.059 mmol, 47.8 mg). The reaction mixture was heated for 20 minutes at 140° C. in the microwave. Water was added to the reaction mixture, followed by an extraction with ethyl acetate (2x). The combined organic layer was washed with brine, dried over magnesium sulfate and evaporated. The product was purified using silicagel and dichloromethane/methanol=9/1 v/v % as eluent to afford 97.1 mg of (S)-benzyl 2-(8-amino-1-(4-(pyridin-2-ylcarbamoyl)phenyl)imidazo[1,5-a]pyrazin-3-yl)pyrrolidine-1-carboxylate (77%).

(b). (S)-4-(8-Amino-3-(pyrrolidin-2-yl)imidazo[1,5-a]pyrazin-1-yl)-N-(pyridin-2-yl)benzamide was prepared as follows. To (S)-benzyl 2-(8-amino-1-(4-(pyridin-2-ylcarbamoyl)phenyl)imidazo[1,5-a]pyrazin-3-yl)pyrrolidine-1-carboxylate (0.146 mmol, 78 mg) was added a 33% hydrobromic acid/acetic acid solution (11.26 mmol, 2 ml) and the mixture was left at room temperature for 1 hour. The mixture was diluted with water and extracted with dichloromethane.

The aqueous phase was neutralized using 2N sodium hydroxide solution, and then extracted with dichloromethane. the organic layer was dried over magnesium sulfate, filtered and evaporated to give 34 mg of (S)-4-(8-Amino-3-(pyrrolidin-2-yl)imidazo[1,5-a]pyrazin-1-yl)-N-(pyridin-2-yl)benzamide (58%).

In a preferred embodiment, the BTK inhibitor is (S)-4-(8-amino-3-(1-(but-2-ynoyl)pyrrolidin-2-yl)imidazo[1,5-c]pyrazin-1-yl)-N-(pyridin-2-yl)benzamide or pharmaceutically acceptable salt, solvate, hydrate, cocrystal, or prodrug thereof.

In a preferred embodiment, the BTK inhibitor is a compound of Formula (XVIII-A):

Formula (XVIII-A)

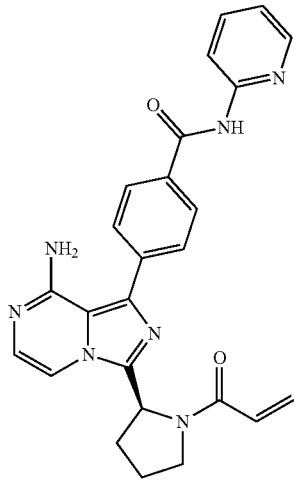

or a pharmaceutically acceptable salt, solvate, hydrate, cocrystal, or prodrug thereof. The preparation of this compound is described in International Patent Application Publication No. WO 2013/010868 and U.S. Patent Application Publication No. US 2014/0155385 A1, the disclosure of which is incorporated herein by reference.

In a preferred embodiment, the BTK inhibitor is a compound of Formula (XVIII-B):

Formula (XVIII-B)

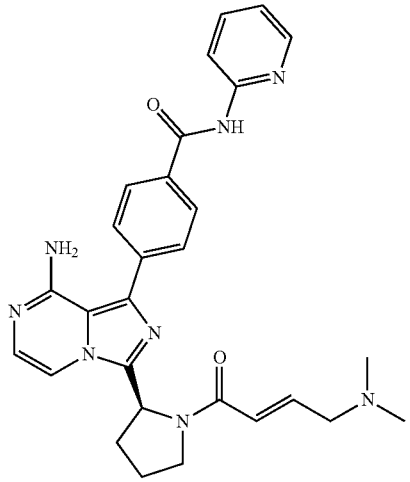

or a pharmaceutically acceptable salt, solvate, hydrate, cocrystal, or prodrug thereof. The preparation of this compound is described in International Patent Application Publication No. WO 2013/010868 and U.S. Patent Application Publication No. US 2014/0155385 A1, the disclosure of which is incorporated herein by reference.

In a preferred embodiment, the BTK inhibitor is a compound of Formula (XVIII-C):

Formula (XVIII-C)

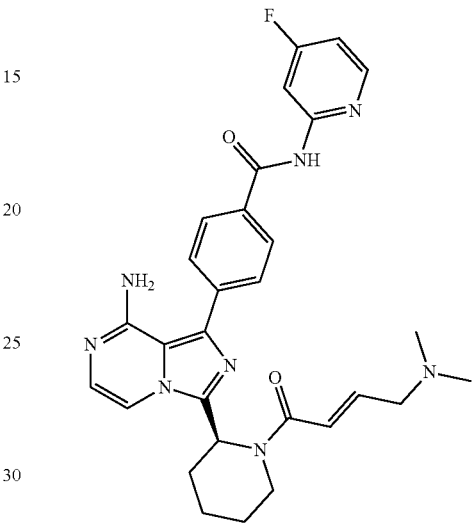

or a pharmaceutically acceptable salt, solvate, hydrate, cocrystal, or prodrug thereof. The preparation of this compound is described in International Patent Application Publication No. WO 2013/010868 and U.S. Patent Application Publication No. US 2014/0155385 A1, the disclosure of which is incorporated herein by reference.

In a preferred embodiment, the BTK inhibitor is a compound of Formula (XVIII-D):

Formula (XVIII-D)

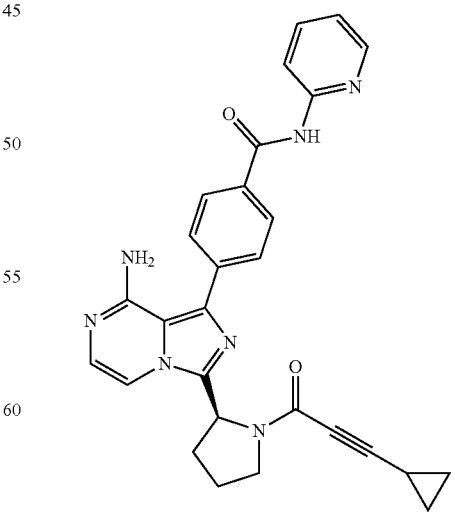

or a pharmaceutically acceptable salt, solvate, hydrate, cocrystal, or prodrug thereof. The preparation of this compound is described in International Patent Application Publication No. WO 2013/010868 and U.S. Patent Application Publication No. US 2014/0155385 A1, the disclosure of which is incorporated herein by reference.

In a preferred embodiment, the BTK inhibitor is a compound of Formula (XVIII-E):

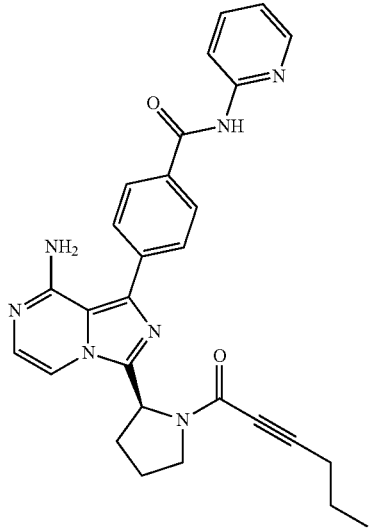

Formula (XVIII-E)

or a pharmaceutically acceptable salt, solvate, hydrate, cocrystal, or prodrug thereof. The preparation of this compound is described in International Patent Application Publication No. WO 2013/010868 and U.S. Patent Application Publication No. US 2014/0155385 A1, the disclosure of which is incorporated herein by reference.

In other embodiments, the BTK inhibitors include, but are not limited to, those compounds described in International Patent Application Publication No. WO 2013/010868 and U.S. Patent Application Publication No. US 2014/0155385 A1, the disclosure of which is specifically incorporated by reference herein.

In an embodiment, the BTK inhibitor is a compound of Formula (XIX):

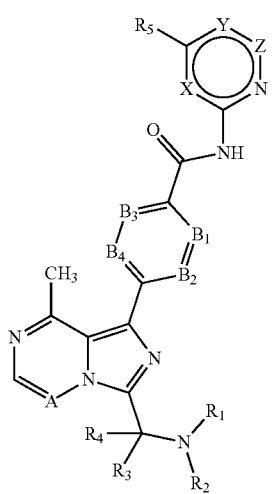

Formula (XIX)

or a pharmaceutically acceptable salt, solvate, hydrate, cocrystal, or prodrug thereof, wherein:
X is CH, N, O or S;
Y is $C(R_6)$, N, O or S;
Z is CH, N or bond;
A is CH or N;
$B_1$ is N or $C(R_7)$;
$B_2$ is N or $C(R_8)$;
$B_3$ is N or $C(R_9)$;
$B_4$ is N or $C(R_{10})$;
$R_1$ is $R_{11}C(O)$, $R_{12}S(O)$, $R_{13}SO_2$ or $(C_{1-6})$alkyl optionally substituted with $R_{14}$;
$R_2$ is H, $(C_{1-3})$alkyl or $(C_{3-7})$cycloalkyl;
$R_3$ is H, $(C_{1-6})$alkyl or $(C_{3-7})$cycloalkyl); or
$R_2$ and $R_3$ form, together with the N and C atom they are attached to, a $(C_{3-7})$heterocycloalkyl optionally substituted with one or more fluorine, hydroxyl, $(C_{1-3})$alkyl, $(C_{1-3})$alkoxy or oxo;
$R_4$ is H or $(C_{1-3})$alkyl;
$R_5$ is H, halogen, cyano, $(C_{1-3})$alkoxy, $(C_{3-6})$cycloalkyl; all alkyl groups of $R_5$ are optionally substituted with one or more halogen; or RS is $(C_{6-10})$aryl or $(C_{2-6})$heterocycloalkyl;
$R_6$ is H or $(C_{1-3})$alkyl; or $R_5$ and $R_6$ together may form a $(C_{3-7})$cycloalkenyl, or $(C_{2-6})$heterocycloalkenyl; each optionally substituted with $(C_{1-3})$alkyl, or one or more halogen;
$R_7$ is H, halogen, $CF_3$, $(C_{1-3})$alkyl or $(C_{1-3})$alkoxy;
$R_8$ is H, halogen, $CF_3$, $(C_{1-3})$alkyl or $(C_{1-3})$alkoxy; or
$R_7$ and $R_8$ together with the carbon atoms they are attached to, form $(C_{6-10})$aryl or $(C_{1-5})$heteroaryl;
$R_9$ is H, halogen, $(C_{1-3})$alkyl or $(C_{1-3})$alkoxy;
$R_{10}$ is H, halogen, $(C_{1-3})$alkyl or $(C_{1-3})$alkoxy;
$R_{11}$ is independently selected from a group consisting of $(C_{1-6})$alkyl, $(C_{2-6})$alkenyl and $(C_{2-6})$alkynyl each alkyl, alkenyl or alkynyl optionally substituted with one or more groups selected from hydroxyl, $(C_{1-4})$alkyl, $(C_{3-7})$cycloalkyl, $[(C_{1-4})$alkyl]amino, di$[(C_{1-4})$alkyl]amino, $(C_{1-3})$alkoxy, $(C_{3-7})$cycloalkoxy, $(C_{6-10})$aryl or $(C_{3-7})$heterocycloalkyl, or
$R_{11}$ is $(C_{1-3})$alkyl-$C(O)$—S—$(C_{1-3})$alkyl; or
$R_{11}$ is $(C_{1-5})$heteroaryl optionally substituted with one or more groups selected from halogen or cyano.
$R_{12}$ and $R_{13}$ are independently selected from a group consisting of $(C_{2-6})$alkenyl or $(C_{2-6})$alkynyl both optionally substituted with one or more groups selected from hydroxyl, $(C_{1-4})$alkyl, $(C_3-7)$cycloalkyl, $[(C_{1-4})$alkyl]amino, di$[(C_{1-4})$alkyl]amino, $(C_{1-3})$alkoxy, $(C_{3-7})$cycloalkoxy, $(C_{6-10})$aryl, or $(C_{3-7})$heterocycloalkyl; or
$(C_{1-5})$heteroaryl optionally substituted with one or more groups selected from halogen or cyano;
$R_{14}$ is independently selected from a group consisting of halogen, cyano or $(C_{2-6})$alkenyl or $(C_{2-6})$alkynyl both optionally substituted with one or more groups selected from hydroxyl, $(C_{1-4})$alkyl, $(C_{3-7})$cycloalkyl, $[(C_{1-4})$alkyl]amino, di$[(C_{1-4})$alkyl]amino, $(C_{1-3})$alkoxy, $(C_{3-7})$cycloalkoxy, $(C_{6-10})$aryl, $(C_{1-5})$heteroaryl or $(C_{3-7})$heterocycloalkyl;
with the proviso that
0 to 2 atoms of X, Y, Z can simultaneously be a heteroatom;
when one atom selected from X, Y is O or S, then Z is a bond and the other atom selected from X, Y can not be O or S;
when Z is C or N then Y is $C(R_6)$ or N and X is C or N;
0 to 2 atoms of $B_1$, $B_2$, $B_3$ and $B_4$ are N;

with the terms used having the following meanings:

($C_{1-3}$)alkyl means a branched or unbranched alkyl group having 1-3 carbon atoms, being methyl, ethyl, propyl or isopropyl;

($C_{1-4}$)alkyl means a branched or unbranched alkyl group having 1-4 carbon atoms, being methyl, ethyl, propyl, isopropyl, butyl, isobutyl, sec-butyl and tert-butyl, ($C_{1-3}$) alkyl groups being preferred;

($C_{1-6}$)alkyl means a branched or unbranched alkyl group having 1-6 carbon atoms, for example methyl, ethyl, propyl, isopropyl, butyl, tert-butyl, n-pentyl and n-hexyl. ($C_{1-5}$)alkyl groups are preferred, ($C_{1-4}$)alkyl being most preferred;

($C_{1-2}$)alkoxy means an alkoxy group having 1-2 carbon atoms, the alkyl moiety having the same meaning as previously defined;

($C_{1-3}$)alkoxy means an alkoxy group having 1-3 carbon atoms, the alkyl moiety having the same meaning as previously defined, with ($C_1$-2)alkoxy groups preferred;

($C_{2-3}$)alkenyl means an alkenyl group having 2-3 carbon atoms, such as ethenyl or 2-propenyl;

($C_{2-4}$)alkenyl means a branched or unbranched alkenyl group having 2-4 carbon atoms, such as ethenyl, 2-propenyl, isobutenyl or 2-butenyl;

($C_{2-6}$)alkenyl means a branched or unbranched alkenyl group having 2-6 carbon atoms, such as ethenyl, 2-butenyl, and n-pentenyl, with ($C_{2-4}$)alkenyl groups preferred, and ($C_{2-3}$)alkenyl groups even more preferred;

($C_{2-4}$)alkynyl means a branched or unbranched alkynyl group having 2-4 carbon atoms, such as ethynyl, 2-propynyl or 2-butynyl;

($C_{2-3}$)alkynyl means an alkynyl group having 2-3 carbon atoms, such as ethynyl or 2-propynyl;

($C_{2-6}$)alkynyl means a branched or unbranched alkynyl group having 2-6 carbon atoms, such as ethynyl, propynyl, n-butynyl, n-pentynyl, isopentynyl, isohexynyl or n-hexynyl, with ($C_{2-4}$)alkynyl groups preferred, and ($C_{2-3}$)alkynyl groups more preferred;

($C_{3-6}$)cycloalkyl means a cycloalkyl group having 3-6 carbon atoms, being cyclopropyl, cyclobutyl, cyclopentyl or cyclohexyl;

($C_{3-7}$)cycloalkyl means a cycloalkyl group having 3-7 carbon atoms, being cyclopropyl, cyclobutyl, cyclopentyl, cyclohexyl or cycloheptyl;

($C_{2-6}$)heterocycloalkyl means a heterocycloalkyl group having 2-6 carbon atoms, preferably 3-5 carbon atoms, and one or two heteroatoms selected from N, O and/or S, which may be attached via a heteroatom if feasible, or a carbon atom; preferred heteroatoms are N or O; preferred groups are piperidine, morpholine, pyrrolidine and piperazine; a most preferred ($C_{2-6}$)heterocycloalkyl is pyrrolidine; and the heterocycloalkyl group may be attached via a heteroatom if feasible;

($C_{3-7}$)heterocycloalkyl means a heterocycloalkyl group having 3-7 carbon atoms, preferably 3-5 carbon atoms, and one or two heteroatoms selected from N, O and/or S; preferred heteroatoms are N or O; preferred ($C_{3-7}$) heterocycloalkyl groups are azetidinyl, pyrrolidinyl, piperidinyl, homopiperidinyl or morpholinyl; more preferred ($C_{3-7}$)heterocycloalkyl groups are piperidine, morpholine and pyrrolidine; even more preferred are piperidine and pyrrolidine; and the heterocycloalkyl group may be attached via a heteroatom if feasible;

($C_{3-7}$)cycloalkoxy means a cycloalkyl group having 3-7 carbon atoms, with the same meaning as previously defined, attached via a ring carbon atom to an exocyclic oxygen atom;

($C_{6-10}$)aryl means an aromatic hydrocarbon group having 6-10 carbon atoms, such as phenyl, naphthyl, tetrahydronaphthyl or indenyl; the preferred ($C_{6-10}$)aryl group is phenyl;

($C_{1-5}$)heteroaryl means a substituted or unsubstituted aromatic group having 1-5 carbon atoms and 1-4 heteroatoms selected from N, O and/or S, wherein the ($C_{1-5}$)heteroaryl may optionally be substituted; preferred ($C_{1-5}$)heteroaryl groups are tetrazolyl, imidazolyl, thiadiazolyl, pyridyl, pyrimidyl, triazinyl, thienyl or furyl, and the more preferred ($C_{1-5}$)heteroaryl is pyrimidyl;

[($C_{1-4}$)alkyl]amino means an amino group, monosubstituted with an alkyl group containing 1-4 carbon atoms having the same meaning as previously defined; the preferred [($C_{1-4}$)alkyl]amino group is methylamino;

di[($C_{1-4}$)alkyl]amino means an amino group, disubstituted with alkyl group(s), each containing 1-4 carbon atoms and having the same meaning as previously defined; the preferred di[($C_{1-4}$)alkyl]amino group is dimethylamino;

halogen means fluorine, chlorine, bromine or iodine;

($C_{1-3}$)alkyl-C(O)—S—($C_{1-3}$)alkyl means an alkyl-carbonyl-thio-alkyl group, each of the alkyl groups having 1 to 3 carbon atoms with the same meaning as previously defined;

($C_{3-7}$)cycloalkenyl means a cycloalkenyl group having 3-7 carbon atoms, preferably 5-7 carbon atoms; preferred ($C_{3-7}$)cycloalkenyl groups are cyclopentenyl or cyclohexenyl; and cyclohexenyl groups are most preferred;

($C_{2-6}$)heterocycloalkenyl means a heterocycloalkenyl group having 2-6 carbon atoms, preferably 3-5 carbon atoms; and 1 heteroatom selected from N, O and/or S; the preferred ($C_{2-6}$)heterocycloalkenyl groups are oxycyclohexenyl and azacyclohexenyl groups.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

A circle in a ring of Formula (XIX) indicates that the ring is aromatic.

Depending on the ring formed, the nitrogen, if present in X or Y, may carry a hydrogen.

In a preferred embodiment, the invention relates to a compound according to Formula (XIX) wherein $B_1$ is $C(R_7)$; $B_2$ is $C(R_8)$; $B_3$ is $C(R_9)$ and $B_4$ is $C(R_{10})$.

In other embodiments, the BTK inhibitors include, but are not limited to, those compounds described in International Patent Application Publication No. WO 2013/010869 and U.S. Patent Application Publication No. US 2014/0155406 A1, the disclosure of which is specifically incorporated by reference herein.

In an embodiment, the BTK inhibitor is a compound of Formula (XX):

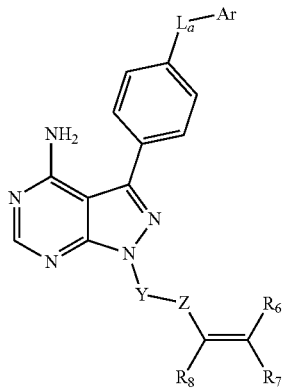

Formula (XX)

or a pharmaceutically acceptable salt thereof,
wherein:

$L_a$ is $CH_2$, O, NH or S;

Ar is a substituted or unsubstituted aryl, or a substituted or unsubstituted heteroaryl;

Y is an optionally substituted group selected from the group consisting of alkyl, heteroalkyl, cycloalkyl, heterocycloalkyl, aryl and heteroaryl;

Z is C(=O), OC(=O), NRC(=O), C(=S), S(=O)$_x$, OS(=O)$_x$ or NRS(=O)$_x$, where x is 1 or 2;

$R^7$ and $R^8$ are each independently H; or $R^7$ and $R^8$ taken together form a bond;

$R^6$ is H; and

R is H or $C_1$-$C_6$alkyl.

In a preferred embodiment, the BTK inhibitor is ibrutinib or a pharmaceutically-acceptable salt thereof.

In a preferred embodiment, the BTK inhibitor is a compound of Formula (XXI):

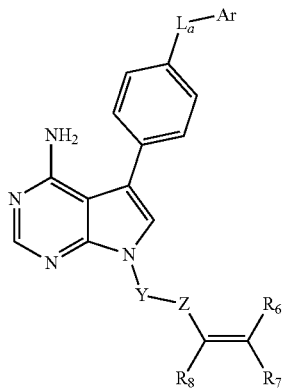

Formula (XXI)

or a pharmaceutically acceptable salt thereof,
wherein $L_a$, Ar, Y, Z, $R^6$, $R^7$ and $R^8$ are as defined in relation to formula (XX).

In a preferred embodiment, the BTK inhibitor is a compound of Formula (XXII):

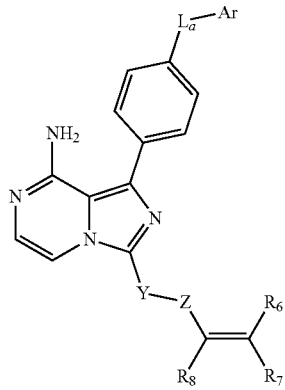

Formula (XXII)

or a pharmaceutically acceptable salt thereof,
wherein $L_a$, Ar, Y, Z, $R^6$, $R^7$ and $R^8$ are as defined in relation to formula (XX).

In a preferred embodiment, the BTK inhibitor is a compound of Formula (XXIII):

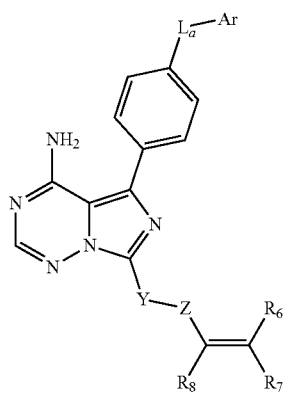

Formula (XXIII)

or a pharmaceutically acceptable salt thereof,
wherein $L_a$, Ar, Y, Z, $R^6$, $R^7$ and $R^8$ are as defined in relation to formula (XX).

In a preferred embodiment, the BTK inhibitor is a compound of Formula (XXIV):

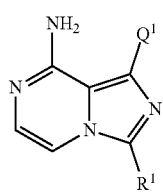

Formula (XXIV)

or a pharmaceutically acceptable salt thereof,
wherein:

$Q^1$ is aryl$^1$, heteroaryl$^1$, cycloalkyl, heterocyclyl, cycloalkenyl, or heterocycloalkenyl, any of which is optionally substituted by one to five independent $G^1$ substituents;

$R^1$ is alkyl, cycloalkyl, bicycloalkyl, aryl, heteroaryl, aralkyl, heteroaralkyl, heterocyclyl, or heterobicycloalkyl, any of which is optionally substituted by one or more independent $G^{11}$ substituents;

$G^1$ and $G^{41}$ are each independently halo, oxo, —CF$_3$, —OCF$_3$, —OR$^2$, —NR$^2$R$^3$(R$^{3a}$)$_{j1}$, —C(O)R$^2$, —CO$_2$R$^2$, —CONR$^2$R$^3$, —NO$_2$, —CN, —S(O)$_{j1}$R$^2$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —(C=S)OR$^2$, —(C=O)SR$^2$, —NR$^2$(C=NR$^3$)NR$^{2a}$R$^{3a}$, —NR$^2$(C=NR$^3$)OR$^{2a}$, —NR$^2$(C=NR$^3$)SR$^{3a}$, —O(C=O)OR$^2$, —O(C=O)NR$^2$R$^3$, —O(C=O)SR$^2$, —S(C=O)OR$^2$, —S(C=O)NR$^2$R$^3$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$ alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{222}$, —NR$^{222}$R$^{333}$(R$^{333}$a)$_{j1a}$, —C(O)R$^{222}$, —CO$_2$R$^{222}$, —CONR$^{222}$R$^{333}$, —NO$_2$, —CN, —S(O)$_{j1a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, O(C=O)SR$^{222}$, —S(C=O)OR$^{222}$, or —S(C=O)NR$^{222}$R$^{333}$ substituents; or —(X$^1$)$_n$—(Y$^1$)$_n$—R$^4$; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{222}$, —NR$^{222}$R$^{333}$(R$^{333a}$)$_{j2a}$, —C(O)R$^{222}$, —CO$_2$R$^{222}$, —CONR$^{222}$R$^{333}$, —NO$_2$, —CN, —S(O)$_{j2a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j2a}$R$^{333}$, (C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{222}$, —NR$^{222}$R$^{333}$(R$^{333a}$)$_{j3a}$, —C(O)R$^{222}$, —CO$_2$R$^{222}$, —CONR$^{222}$R$^{333}$, —NO$_2$, —CN, —S(O)$_{j3a}$R$^{222}$, —SO$_2$NR$^{222}$R$^{333}$, —NR$^{222}$(C=O)R$^{333}$, NR$^{222}$(C=O)OR$^{333}$, NR$^{222}$(C=O)NR$^{222}$R$^{333}$, NR$^{222}$S(O)$_{j3a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents;

$G^{11}$ is halo, oxo, —CF$_3$, —OCF$_3$, —OR$^{21}$, —NR$^{21}$R$^{31}$(R$^{3a1}$)$_{j4}$, —C(O)R$^{21}$, —CO$_2$R$^{21}$, —CONR$^{21}$R$^{31}$, —NO$_2$, —CN, —S(O)$_{j4}$R$^{21}$, —SO$_2$NR$^{21}$R$^{31}$, NR$^{21}$(C=O)R$^{31}$, NR$^{21}$(C=O)OR$^{31}$, NR$^{21}$(C=O)NR$^{21}$R$^{31}$, NR$^{21}$S(O)$_{j4}$R$^{31}$, —(C=S)OR$^{21}$, —(C=O)SR$^{21}$, —NR$^{21}$(C=NR$^{31}$)NR$^{2a1}$R$^{3a1}$, —NR$^{21}$(C=NR$^{31}$)OR$^{2a1}$, —NR$^{21}$(C=NR$^{31}$)SR$^{3a1}$, —O(C=O)OR$^{21}$, —O(C=O)NR$^{21}$R$^{31}$, —O(C=O)SR$^{21}$, —S(C=O)OR$^{21}$, —S(C=O)NR$^{21}$R$^{31}$, —P(O)OR$^{21}$OR$^{31}$, C$_{2-10}$alkenyl, C$_{2-10}$alkynyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —NR$^{2221}$R$^{3331}$(R$^{333a1}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j4a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O)OR$^{2221}$OR$^{3331}$, or —S(C=O)NR$^{2221}$R$^{3331}$ substituents; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{2221}$, —NR$^{2221}$R$^{3331}$(R$^{333a1}$)$_{j5a}$, —C(O)R$^{2221}$, —CO$_2$R$^{2221}$, —CONR$^{2221}$R$^{3331}$, —NO$_2$, —CN, —S(O)$_{j5a}$R$^{2221}$, —SO$_2$NR$^{2221}$R$^{3331}$, NR$^{2221}$(C=O)R$^{3331}$, NR$^{2221}$(C=O)OR$^{3331}$, —NR$^{2221}$(C=O)NR$^{2221}$R$^{3331}$, NR$^{2221}$S(O)$_{j5a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O)OR$^{2221}$R$^{3331}$, or —S(C=O)NR$^{2221}$R$^{3331}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{333a1}$)$_{j6a}$, —C(O)R$^{2221}$, —CO$_2$R$^{2221}$, —CONR$^{2221}$R$^{3331}$, —CN, —S(O)$_{j6a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j6a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, NR$^{2221}$(C=NR$^{3331}$)SR$^{333a1}$, O(C=O)OR$^{2221}$, —O(C=O)NR$^{2221}$R$^{3331}$, —O(C=O)SR$^{2221}$, —S(C=O)OR$^{2221}$, —P(O)OR$^{2221}$OR$^{3331}$, or —S(C=O)NR$^{2221}$R$^{3331}$ substituents; or GH is taken together with the carbon to which it is attached to form a double bond which is substituted with R$^5$ and G$^{111}$;

R$^2$, R$^{2a}$, R$^3$, R$^{3a}$, R$^{222}$, R$^{222a}$, R$^{333}$, R$^{333a}$, R$^{21}$, R$^{2a1}$, R$^{31}$, R$^{3a1}$, R$^{2221}$, R$^{222a1}$, R$^{3331}$, and R$^{333a1}$ are each independently equal to C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl cycloC$_{3-8}$alkylC$_{2-10}$alkenyl, cycloC$_{3-8}$alkenyl C$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted by one or more G$^{111}$ substituents; or aryl-C$_{0-10}$alkyl, aryl-C$_{2-10}$alkenyl, or aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted by one or more G$^{111}$ substituents; or in the case of —NR$^2$R$^3$(R$^{3a}$)$_{j1}$ or —NR$^{222}$R$^{333}$(R$^{333}$a)$_{j1a}$ or —NR$^{222}$R$^{333}$(R$^{333}$a)$_{j2a}$ or —NR$^{222}$R$^{333}$ NR$^{2221}$R$^{3331}$(R$^{333a1}$)$_{j3a}$ or —NR$^{2221}$R$^{3331}$(R$^{333a1}$)$_{j4a}$ or —NR$^{2221}$R$^{3331}$(R$^{333a1}$)$_{j5a}$ or —NR$^{2221}$R$^{3331}$(R$^{333a1}$)$_{j6a}$, R$^2$ and R$^3$ or R$^{222}$ and R$^{333}$ or R$^{2221}$ and R$^{3331}$ taken together with the nitrogen atom to which they are attached form a 3-10 membered saturated ring, unsaturated ring, heterocyclic saturated ring, or heterocyclic unsaturated ring, wherein said ring is optionally substituted by one or more Gill substituents;

$X^1$ and $Y^1$ are each independently —O—, —NR$^7$—, —S(O)$_{j7}$—, —CR$^5$R$^6$—, —N(C(O)OR$^7$)—, —N(C(O)R$^7$)—, —N(SO$_2$R$^7$)—, —CH$_2$O—, —CH$_2$S—, —CH$_2$N(R$^7$)—, —CH(NR$^7$)—, —CH$_2$N(C(O)R$^7$)—, —CH$_2$N(C(O)OR$^7$)—, —CH$_2$N(SO$_2$R$^7$)—, —CH(NHR$^7$)—, —CH(NHC(O)R$^7$)—, —CH(NHSO$_2$R$^7$)—, —CH(NHC(O)OR$^7$)—, —CH(OC(O)R$^7$)—, —CH(OC(O)NHR$^7$)—, —CH=CH—, —C.ident.C—, —C(=NOR$^7$)—, —C(O)—, —CH(OR$^7$)—, —C(O)N(R$^7$)—, —N(R$^7$)C(O)—, —N(R$^7$)S(O)—, —N(R$^7$)S(O)$_2$—, —OC(O)N(R$^7$)—, —N(R$^7$)C(O)N(R$^7$)—, —NR$^7$C(O)O—, —S(O)N(R$^7$)—, —S(O)$_2$N(R$^7$)—, —N(C(O)R$^7$)S(O)—, —N(C(O)R$^7$)S(O)$_2$-, —N(R$^7$)S(O)N(R$^7$)—, —N(R$^7$)S(O)$_2$N(R$^7$)—, —C(O)N(R$^7$)C(O)—, —S(O)N(R$^7$)C(O)—, —S(O)$_2$N(R$^7$)C(O)—, —OS(O)N(R$^7$)—, —OS(O)$_2$N(R$^7$)—, —N(R$^7$)S(O)O—, —N(R$^7$)S(O)$_2$O—, —N(R$^7$)S(O)C(O)—, —N(R$^7$)S(O)$_2$C(O)—, —SON(C(O)R$^7$)—, —SO$_2$N(C(O)R$^7$)—, —N(R$^7$)SON(R$^7$)—, —N(R$^7$)SO$_2$N(R$^7$)—, —C(O)O—, —N(R$^7$)P(OR$^8$)O—, —N(R$^7$)P(OR$^8$)—, —N(R$^7$)P(O)(OR$^8$)O—, —N(R$^7$)P(O)(OR$^8$)—, —N(C(O)R$^7$)P(OR$^8$)O—, —N(C(O)R$^7$)P(OR$^8$)—, —N(C(O)R$^7$)P(O)(OR$^8$)O—, —N(C(O)R$^7$)P(OR$^8$)—, —CH(R$^7$)S(O)—, —CH(R$^7$)S(O)$_2$-, —CH(R$^7$)N(C(O)OR$^7$)—, —CH(R$^7$)N(C(O)R$^7$)—, —CH(R$^7$)N(SO$_2$R$^7$)—, —CH(R$^7$)O—, —CH(R$^7$)S—, —CH(R$^7$)N(R$^7$)—, —CH(R$^7$)N(C(O)R$^7$)—, —CH(R$^7$)N(C(O)OR$^7$)—, —CH(R$^7$)N(SO$_2$R$^7$)—, —CH(R$^7$)C(=NOR$^7$)—, —CH(R$^7$)C(O)—, —CH(R$^7$)CH(OR$^7$)—, —CH(R$^7$)C(O)N(R$^7$)—, —CH(R$^7$)N(R$^7$)C(O)—, —CH(R$^7$)N(R$^7$)S(O)—, —CH(R$^7$)N(R$^7$)S(O)$_2$-, —CH(R$^7$)OC(O)N(R$^7$)—, —CH(R$^7$)N(R$^7$)C(O)N(R$^7$)—, —CH(R$^7$)NR$^7$C(O)O—, —CH(R$^7$)S(O)N(R$^7$)—, —CH(R$^7$)S(O)$_2$N(R$^7$)—, —CH(R$^7$)N(C(O)R$^7$)S(O)—, —CH(R$^7$)N(C(O)R$^7$)S(O)—, —CH(R$^7$)N(R$^7$)S(O)N(R$^7$)—, —CH(R$^7$)N(R$^7$)S(O)$_2$N(R$^7$)—, —CH(R$^7$)C(O)N(R$^7$)C(O)—, —CH(R$^7$)S(O)N(R$^7$)C(O)—, —CH(R$^7$)S(O)$_2$N(R$^7$)C(O)—, —CH(R$^7$)OS(O)N(R$^7$)—, —CH(R$^7$)OS(O)$_2$N(R$^7$)—, —CH(R$^7$)N(R$^7$)S(O)O—, —CH(R$^7$)N(R$^7$)S(O)$_2$O—, —CH(R$^7$)N(R$^7$)S(O)C(O)—, —CH(R$^7$)N(R$^7$)S(O)$_2$C(O)—, —CH(R$^7$)SON(C(O)R$^7$)—, —CH(R$^7$)SO$_2$N(C(O)R$^7$)—, —CH(R$^7$)N(R$^7$)SON(R$^7$)—, —CH(R$^7$)N(R$^7$)SO$_2$N(R$^7$)—, —CH(R$^7$)C(O)O—, —CH(R$^7$)N(R$^7$)P(OR$^8$)O—, —CH(R$^7$)N(R$^7$)P(OR$^8$)—, —CH(R$^7$)N(R$^7$)P(O)(OR$^8$)O—, —CH(R$^7$)N(R$^7$)P(O)(OR$^8$)—, —CH(R$^7$)N(C(O)R$^7$)P(OR$^8$)O—, —CH(R$^7$)N(C(O)R$^7$)P(OR$^8$)—, —CH(R$^7$)N(C(O)R$^7$)P(O)(OR$^8$)O—, or —CH(R$^7$)N(C(O)R$^7$)P(OR$^8$)—;

or $X^1$ and $Y^1$ are each independently represented by one of the following structural formulas:

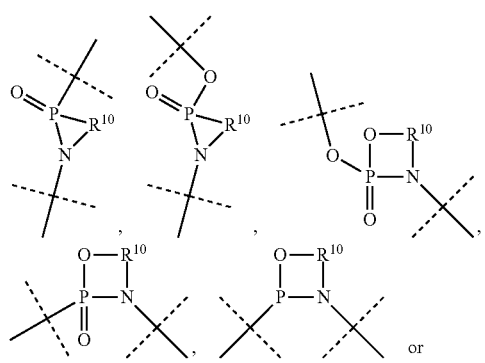

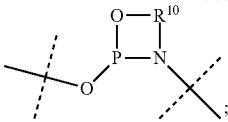

$R^{10}$, taken together with the phosphinamide or phosphonamide, is a 5-, 6-, or 7-membered aryl, heteroaryl or heterocyclyl ring system;

$R^5$, $R^6$, and $G^{111}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, —NR$^{77}$(C=O)R$^{87}$, NR$^{77}$(C=O)OR$^{87}$, NR$^{77}$(C=O)NR$^{78}$R$^{87}$, NR$^{77}$S(O)$_{j5a}$R$^{87}$, —(C=S)OR$^{77}$, —(C=O)SR$^{77}$, —NR$^{77}$(C=NR$^{87}$)NR$^{78}$R$^{88}$, —NR$^{77}$(C=NR$^{87}$)OR$^{78}$, —NR$^{77}$(C=NR$^{87}$)SR$^{78}$, —O(C=O)OR$^{77}$, —O(C=O)NR$^{77}$R$^{87}$, —O(C=O)SR$^{77}$, —S(C=O)OR$^{77}$, —P(O)OR$^{77}$OR$^{87}$, or —S(C=O)NR$^{77}$R$^{87}$ substituents; or aryl-$C_{0-10}$alkyl, aryl-$C_{2-10}$alkenyl, or aryl-$C_{2-10}$alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, —NR$^{77}$(C=O)R$^{87}$, NR$^{77}$(C=O)OR$^{87}$, NR$^{77}$(C=O)NR$^{78}$R$^{87}$, NR$^{77}$S(O)$_{j5a}$R$^{87}$, —(C=S)OR$^{77}$, —(C=O)SR$^{77}$, —NR$^{77}$(C=NR$^{87}$)NR$^{78}$R$^{88}$, —NR$^{77}$(C=NR$^{87}$)OR$^{78}$, —NR$^{77}$(C=NR$^{87}$)$_5$R$^{78}$, —O(C=O)OR$^{77}$, —O(C=O)NR$^{77}$R$^{87}$, —O(C=O)SR$^{77}$, —S(C=O)OR$^{77}$, —P(O)OR$^{77}$R$^{87}$, or —S(C=O)NR$^{77}$R$^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, NR$^{77}$(C=O)R$^{87}$, NR$^{77}$(C=O)OR$^{87}$, NR$^{77}$(C=O)NR$^{78}$R$^{87}$, NR$^{77}$S(O)$_{j5a}$R$^{87}$, —(C=S)OR$^{77}$, —(C=O)SR$^{77}$, —NR$^{77}$(C=NR$^{87}$)NR$^{78}$R$^{88}$, —NR$^{77}$(C=NR$^{87}$)OR$^{78}$, —NR$^{77}$(C=NR$^{87}$)SR$^{78}$, —O(C=O)OR$^{77}$, —O(C=O)NR$^{77}$R$^{87}$, —O(C=O)SR$^{77}$, —S(C=O)OR$^{77}$, —P(O)OR$^{77}$OR$^{87}$, or —S(C=O)NR$^{77}$R$^{87}$ substituents; or $R^5$ with $R^6$ taken together with the respective carbon atom to which they are attached, form a 3-10 membered saturated or unsaturated ring, wherein said ring is optionally substituted with R$^{69}$; or $R^5$ with $R^6$ taken together with the respective carbon atom to which they are attached, form a 3-10 membered saturated or unsaturated heterocyclic ring, wherein said ring is optionally substituted with R$^{69}$;

$R^7$ and $R^8$ are each independently H, acyl, alkyl, alkenyl, aryl, heteroaryl, heterocyclyl or cycloalkyl, any of which is optionally substituted by one or more $G^{111}$ substituents;

$R^4$ is H, alkyl, alkenyl, alkynyl, aryl, heteroaryl, cycloalkyl, heterocyclyl, cycloalkenyl, or heterocycloalkenyl, any of which is optionally substituted by one or more $G^{41}$ substituents;

$R^{69}$ is equal to halo, —$OR^a$, —SH, —$NR^{78}R^{88}$, —$CO_2R^{78}$, —$CONR^{78}R^{88}$, —$NO_2$, —CN, —$S(O)_8R^{78}$, —$SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^a$, —$SO_2NR^{778}R^{888}$, or —$NR^{778}R^{888}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$, or —$NR^{778}R^{888}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$, or —$NR^{778}R^{888}$ substituents; or mono($C_{1-6}$alkyl)amino$C_{1-6}$alkyl, di($C_{1-6}$ alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$ $SO_2NR^{778}R^{888}$, or —$NR^{778}R^{888}$ substituents; or in the case of —$NR^{78}R^{88}$, $R^{78}$ and $R^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{778}R^{888}$, or —$NR^{778}R^{888}$ substituents;

$R^{77}$, $R^{78}$, $R^{87}$, $R^{88}$, $R^{778}$, and $R^{888}$ are each independently $C_{0-10}$alkyl, $C_{2-10}$alkenyl, $C_{2-10}$alkynyl, $C_{1-10}$alkoxy $C_{1-10}$alkyl, $C_{1-10}$alkoxy$C_{2-10}$alkenyl, $C_{1-10}$alkoxy $C_{2-10}$alkynyl, $C_{1-10}$alkylthio$C_{1-10}$alkyl, $C_{1-10}$alkylthio $C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo $C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2N(C_{0-4}$alkyl)($C_{0-4}$alkyl), or —N($C_{0-4}$alkyl)($C_{0-4}$alkyl) substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —CON ($C_{0-4}$alkyl)($C_{0-10}$alkyl), —$SO_2N(C_{0-4}$alkyl)($C_{0-4}$alkyl), or —N($C_{0-4}$alkyl)($C_{0-4}$alkyl) substituents; or hetaryl-$C_{0-10}$ alkyl, hetaryl-$C_{2-10}$alkenyl, or hetaryl-$C_{2-10}$alkynyl, any of which is optionally substituted with one or more independent halo, cyano, nitro, —O($C_{0-4}$alkyl), $C_{1-10}$alkyl $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON($C_{0-4}$alkyl)($C_{0-4}$alkyl), —$SO_2N(C_{0-4}$alkyl)($C_{0-4}$ alkyl), or —N($C_{0-4}$alkyl)($C_{0-4}$alkyl) substituents; or mono ($C_{1-6}$alkyl)amino$C_{1-6}$alkyl, di($C_{1-6}$alkyl)amino$C_{1-6}$ alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —O(Co-4alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$ alkynyl, —COOH, $C_{1-4}$alkoxycarbonyl, —CON($C_{0-4}$ alkyl)($C_{0-4}$alkyl), —$SO_2N$(Co-4alkyl)(Co-4alkyl), or —N($C_{0-4}$alkyl)($C_{0-4}$alkyl) substituents; and n, m, j1, j1a, j2a, j3a, j4, j4a, j5a, j6a, j7, and j8 are each independently equal to 0, 1, or 2.

In an embodiment, the BTK inhibitor is a compound selected from the structures disclosed in U.S. Pat. Nos. 8,450,335 and 8,609,679, and U.S. Patent Application Publication Nos. 2010/0029610 A1, 2012/0077832 A1, 2013/0065879 A1, 2013/0072469 A1, and 2013/0165462 A1, the disclosures of which are incorporated by reference herein. In an embodiment, the BTK inhibitor is a compound of Formula (XXV) or Formula (XXVI):

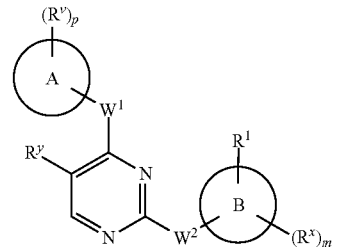

Formula (XXV)

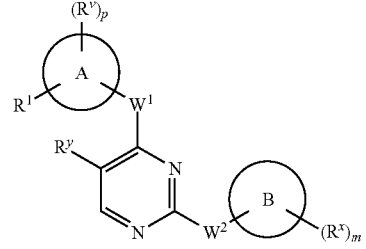

Formula (XXVI)

or a pharmaceutically acceptable salt thereof, wherein:

Ring A is an optionally substituted group selected from phenyl, an optionally substituted 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, an optionally substituted 4-7 membered saturated or partially unsaturated heterocyclic ring having 1-3 heteroatoms independently selected from nitrogen, oxygen, or sulfur, an optionally substituted 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is an optionally substituted group selected from phenyl, an optionally substituted 3-7 membered saturated or partially unsaturated carbocyclic ring, an 8-10 membered bicyclic saturated, partially unsaturated or aryl ring, an optionally substituted 5-6 membered monocyclic heteroaryl ring having 1-4 heteroatoms independently selected from nitrogen, oxygen, or sulfur, an optionally substituted 4-7 membered saturated or partially unsaturated heterocyclic ring having 1-3 heteroatoms independently selected from nitrogen, oxygen, or sulfur, an optionally substituted 7-10 membered bicyclic saturated or partially unsaturated heterocyclic ring having 1-5 heteroatoms independently selected from nitrogen, oxygen, or sulfur, or an optionally substituted 8-10 membered bicyclic heteroaryl ring having 1-5 heteroatoms independently selected from nitrogen, oxygen, or sulfur;

$R^1$ is a warhead group;

$R^y$ is hydrogen, halogen, —CN, —$CF_3$, $C_{1-4}$ aliphatic, $C_{1-4}$ haloaliphatic, —OR, —C(O)R, or C(O)N(R)$_2$;

each R group is independently hydrogen or an optionally substituted group selected from $C_{1-6}$ aliphatic, phenyl, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$W^1$ and $W^2$ are each independently a covalent bond or a bivalent $C_{1-3}$ alkylene chain wherein one methylene unit of $W^1$ or $W^2$ is optionally replaced by —$NR^2$—, —N($R^2$)C(O)—, C(O)N($R^2$)—, —N($R^2$)$SO_2$—, —$SO_2$N($R^2$)—, —O—, —C(O)—, —OC(O)—, —C(O)O—, —S—, —SO— or —$SO_2$—;

$R^2$ is hydrogen, optionally substituted $C_{1-6}$ aliphatic, or —C(O)R, or:

$R^2$ and a substituent on Ring A are taken together with their intervening atoms to form a 4-6 membered saturated, partially unsaturated, or aromatic fused ring, or:

$R^2$ and $R^y$ are taken together with their intervening atoms to form a 4-7 membered partially unsaturated or aromatic fused ring;

m and p are independently 0-4; and $R^x$ and $R^v$ are independently selected from —R, halogen, —OR, —O($CH_2$)$_q$OR, CN, —$NO_2$, —$SO_2$R, —$SO_2$N(R)$_2$, —SOR, —C(O)R, —$CO_2$R, —C(O)N(R)$_2$, —NRC(O)R, —NRC(O)N$R_2$, —NR$SO_2$R, or —N(R)$_2$, wherein q is 1-4; or:

$R^x$ and $R^1$ when concurrently present on Ring B are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or $C_{1-6}$ aliphatic; or $R^v$ and $R^1$ when concurrently present on Ring A are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or $C_{1-6}$ aliphatic.

In an embodiment, the BTK inhibitor is a compound of Formula (XXV) or Formula (XXVI), wherein:

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, an optionally substituted 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, an optionally substituted 4-7 membered saturated or partially unsaturated heterocyclic ring having 1-3 heteroatoms independently selected from nitrogen, oxygen, or sulfur, an optionally substituted 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^1$ is -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(=S)—, —C(=NR)—, —N=N—, or —C(=$N_2$)—;

Y is hydrogen, $C_{1-6}$ aliphatic optionally substituted with oxo, halogen, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 groups independently selected from -Q-Z, oxo, $NO_2$, halogen, CN, or $C_{1-6}$ aliphatic, wherein:

Q is a covalent bond or a bivalent $C_{1-6}$ saturated or unsaturated, straight or branched, hydrocarbon chain, wherein one or two methylene units of Q are optionally and independently replaced by —NR—, —S—, —O—, —C(O)—, —SO—, or —$SO_2$—; and Z is hydrogen or $C_{1-6}$ aliphatic optionally substituted with oxo, halogen, or CN;

Ry is hydrogen, halogen, —CN, —$CF_3$, $C_{1-4}$ aliphatic, $C_{1-4}$ haloaliphatic, —OR, —C(O)R, or —C(O)N(R)$_2$;

each R group is independently hydrogen or an optionally substituted group selected from $C_{1-6}$ aliphatic, phenyl, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$W^1$ and $W^2$ are each independently a covalent bond or a bivalent $C_{1-3}$ alkylene chain wherein one methylene unit of $W^1$ or $W^2$ is optionally replaced by —$NR^2$—, —N($R^2$)C(O)—, —C(O)N($R^2$)—, —N($R^2$)$SO_2$—, —$SO_2$N($R^2$)—, —O—, —C(O)—, —OC(O)—, —C(O)O—, —S—, —SO— or —$SO_2$—;

$R^2$ is hydrogen, optionally substituted $C_{1-6}$ aliphatic, or —C(O)R, or:

$R^2$ and a substituent on Ring A are taken together with their intervening atoms to form a 4-6 membered partially unsaturated or aromatic fused ring; or $R^2$ and $R^y$ are taken together with their intervening atoms to form a 4-6 membered saturated, partially unsaturated, or aromatic fused ring;

m and p are independently 0-4; and $R^x$ and $R^v$ are independently selected from —R, halogen, —OR, —O(CH$_2$)$_q$OR, CN, —NO$_2$, —SO$_2$R, —SO$_2$N(R)$_2$, —SOR, —C(O)R, —CO$_2$R, —C(O)N(R)$_2$, —NRC(O)R, —NRC(O)NR$_2$, —NRSO$_2$R, or —N(R)$_2$, or:

$R^x$ and $R^1$ when concurrently present on Ring B are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or C$_{1-6}$ aliphatic; or $R^v$ and $R^1$ when concurrently present on Ring A are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or C$_{1-6}$ aliphatic.

As defined generally above, Ring A is an optionally substituted group selected from phenyl, a 3-7 membered saturated or partially unsaturated carbocyclic ring, an optionally substituted 8-10 membered bicyclic saturated, partially unsaturated or aryl ring, a 5-6 membered monocyclic heteroaryl ring having 1-4 heteroatoms independently selected from nitrogen, oxygen, or sulfur, an optionally substituted 4-7 membered saturated or partially unsaturated heterocyclic ring having 1-3 heteroatoms independently selected from nitrogen, oxygen, or sulfur, an optionally substituted 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, Ring A is an optionally substituted phenyl group. In some embodiments, Ring A is an optionally substituted naphthyl ring or a bicyclic 8-10 membered heteroaryl ring having 1-4 heteroatoms independently selected from nitrogen, oxygen, or sulfur. In certain other embodiments, Ring A is an optionally substituted 3-7 membered carbocyclic ring. In yet other embodiments, Ring A is an optionally substituted 4-7 membered heterocyclic ring having 1-3 heteroatoms independently selected from nitrogen, oxygen, or sulfur.

In some embodiments, Ring A is substituted as defined herein. In some embodiments, Ring A is substituted with one, two, or three groups independently selected from halogen, R°, or —(CH$_2$)$_{0-4}$OR°, or —O(CH$_2$)$_{0-4}$R°, wherein each R° is as defined herein. Exemplary substituents on Ring A include Br, I, Cl, methyl, —CF$_3$, —OCH$_2$phenyl, —OCH$_2$(fluorophenyl), or OCH$_2$pyridyl.

In a preferred embodiment, the BTK inhibitor is a compound of Formula (XXVII), also known as CC-292 (Celgene):

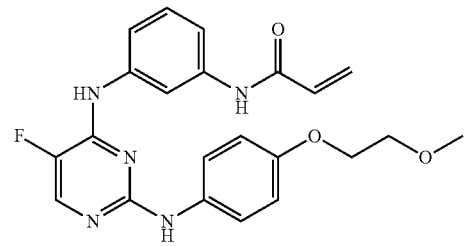

Formula (XXVII)

or a pharmaceutically acceptable salt thereof, or a besylate salt thereof. The preparation of this compound is described in U.S. Patent Application Publication No. 2010/0029610 A1 at Example 20. The preparation of the besylate salt of this compound is described in U.S. Patent Application Publication No. 2012/0077832 A1.

In a preferred embodiment, the BTK inhibitor is N-(3-((5-fluoro-2-((4-(2-methoxyethoxy)phenyl)amino)pyrimidin-4-yl)amino)phenyl)acrylamide or a pharmaceutically acceptable salt thereof, or a hydrochloride salt thereof. The preparation of this compound is described in U.S. Patent Application Publication No. 2012/0077832 A1.

In a preferred embodiment, the BTK inhibitor is (N-(3-(5-fluoro-2-(4-(2-methoxyethoxy)phenylamino)pyrimidin-4-ylamino)phenyl)acrylamide), or a pharmaceutically acceptable salt thereof, or a besylate salt thereof. The preparation of this compound is described in U.S. Patent Application Publication No. 2010/0029610 A1 at Example 20. The preparation of its besylate salt is described in U.S. Patent Application Publication No. 2012/0077832 A1.

In a preferred embodiment, the BTK inhibitor is a compound of Formula (XXVIII):

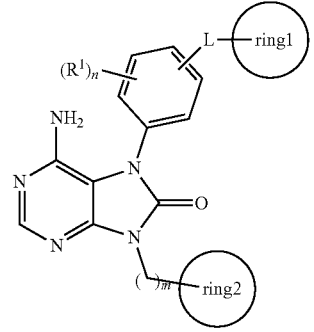

Formula (XXVIII)

or a pharmaceutically acceptable salt, hydrate, solvate, cocrystal, or prodrug thereof, wherein L represents (1) —O—, (2) —S—, (3) —SO—, (4) —SO$_2$—(5) —NH—, (6) —C(O)—, (7) —CH$_2$O—, (8) —O—CH$_2$—, (9) —CH$_2$—, or (10) —CH(OH)—;

$R^1$ represents (1) a halogen atom, (2) a C$_{1-4}$ alkyl group, (3) a C$_{1-4}$ alkoxy group, (4) a C$_{1-4}$ haloalkyl group, or (5) a C$_{1-4}$ haloalkoxy group;

ring1 represents a 4- to 7-membered cyclic group, which may be substituted by from one to five substituents each independently selected from the group consisting of (1) halogen atoms, (2) C$_{1-4}$ alkyl groups, (3) C$_{1-4}$ alkoxy groups, (4) nitrile, (5) C$_{1-4}$ haloalkyl groups, and (6) C$_{1-4}$ haloalkoxy groups, wherein when two or more substituents are present on ring1, these substituents may form a 4- to 7-membered cyclic group together with the atoms in ring1 to which these substituents are bound;

ring2 represents a 4- to 7-membered saturated heterocycle, which may be substituted by from one to three —K—$R^2$; K represents (1) a bond, (2) a $C_{1-4}$ alkylene, (3) —C(O)—, (4) —C(O)—$CH_2$—, (5) —$CH_2$—C(O)—, (6) —C(O)O—, or (7) —$SO_2$— (wherein the bond on the left is bound to the ring2);

$R^2$ represents (1) a $C_{1-4}$ alkyl, (2) a $C_{2-4}$ alkenyl, or (3) a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;

$R^3$ and $R^4$ each independently represent (1) a hydrogen atom, or (2) a $C_{1-4}$ alkyl group which may be substituted by $OR^9$ or $CONR^{10}R^{11}$; $R_3$ and $R^4$ may, together with the nitrogen atom to which they are bound, form a 4- to 7-membered nitrogenous saturated heterocycle, which may be substituted by an oxo group or a hydroxyl group;

$R^5$ and $R^6$ each independently represent (1) a hydrogen atom, (2) a $C_{1-4}$ alkyl group, or (3) a phenyl group;

$R^7$ represents (1) a hydrogen atom or (2) a $C_{1-4}$ alkyl group;

$R^8$ represents (1) a hydrogen atom, (2) a $C_{1-4}$ alkyl group, (3) a phenyl group, or (4) a benzotriazolyl group; $R^9$ represents (1) a hydrogen atom or (2) a $C_{1-4}$ alkyl group;

$R^{10}$ and $R^{11}$ each independently represent (1) a hydrogen atom or (2) a $C_{1-4}$ alkyl group;

n represents an integer from 0 to 4;

m represents an integer from 0 to 2; and when n is two or more, the $R^1$'s may be the same as each other or may differ from one another).

In a preferred embodiment, the BTK inhibitor is a compound of Formula (XXVIII-A):

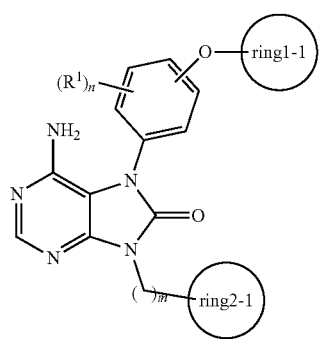

Formula (XXVIII-A)

or a pharmaceutically acceptable salt, hydrate, solvate, cocrystal, or prodrug thereof, wherein $R^1$ represents (1) a halogen atom, (2) a $C_{1-4}$ alkyl group, (3) a $C_{1-4}$ alkoxy group, (4) a $C_{1-4}$ haloalkyl group, or (5) a $C_{1-4}$ haloalkoxy group;

ring1 represents a benzene, cyclohexane, or pyridine ring, each of which may be substituted by from one to five substituents each independently selected from the group consisting of (1) halogen atoms, (2) $C_{1-4}$ alkyl groups, (3) $C_{1-4}$ alkoxy groups, (4) nitrile, (5) $CF_3$;

ring2 represents a 4- to 7-membered nitrogenous saturated heterocycle, which may be substituted by from one to three —K—$R^2$; wherein K represents (1) a bond, (2) a $C_{1-4}$ alkylene, (3) —C(O)—, (4) —C(O)—$CH_2$—, (5) —$CH_2$—C(O)—, (6) —C(O)O—, or (7) —$SO_2$— (wherein the bond on the left is bound to the ring2);

$R^2$ represents (1) a $C_{1-4}$ alkyl, (2) a $C_{2-4}$ alkenyl, or (3) a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;

$R^3$ and $R^4$ each independently represent (1) a hydrogen atom, or (2) a $C_{1-4}$ alkyl group which may be substituted by $OR^9$ or $CONR^{10}R^{11}$; $R_3$ and $R^4$ may, together with the nitrogen atom to which they are bound, form a 4- to 7-membered nitrogenous saturated heterocycle, which may be substituted by an oxo group or a hydroxyl group;

$R^5$ and $R^6$ each independently represent (1) a hydrogen atom, (2) a $C_{1-4}$ alkyl group, or (3) a phenyl group;

$R^7$ represents (1) a hydrogen atom or (2) a $C_{1-4}$ alkyl group;

$R^8$ represents (1) a hydrogen atom, (2) a $C_{1-4}$ alkyl group, (3) a phenyl group, or (4) a benzotriazolyl group; $R^9$ represents (1) a hydrogen atom or (2) a $C_{1-4}$ alkyl group;

$R^{10}$ and $R^{11}$ each independently represent (1) a hydrogen atom or (2) a $C_{1-4}$ alkyl group;

n represents an integer from 0 to 4;

m represents an integer from 0 to 2; and when n is two or more, the $R^1$'s may be the same as each other or may differ from one another).

In a preferred embodiment, the BTK inhibitor is a compound of Formula (XXVIII-B):

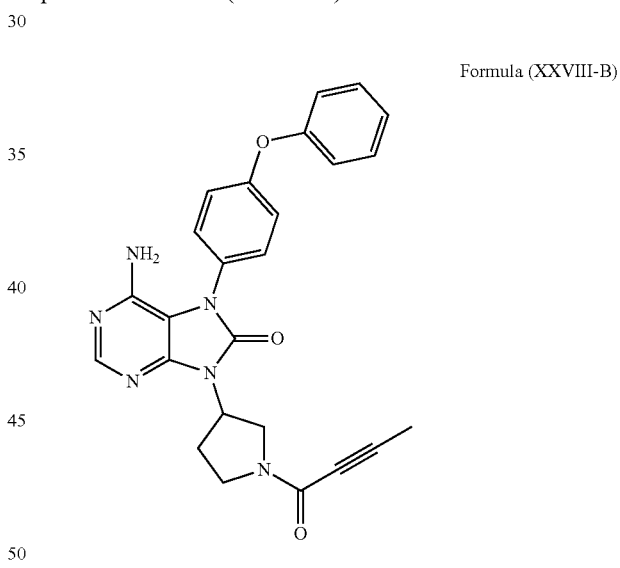

Formula (XXVIII-B)

or a pharmaceutically acceptable salt, solvate, hydrate, cocrystal, or prodrug thereof, or a hydrochloride salt thereof. The preparation of this compound is described in International patent Application Publication No. WO 2013/081016 A1. In an embodiment, the BTK inhibitor is 6-amino-9-(1-(but-2-ynoyl)pyrrolidin-3-yl)-7-(4-phenoxyphenyl)-7,9-dihydro-8H-purin-8-one or a pharmaceutically acceptable salt, solvate, hydrate, cocrystal, or prodrug thereof, or a hydrochloride salt thereof. In an embodiment, the BTK inhibitor is 6-amino-9-[(3S)-1-(2-butynoyl)-3-pyrrolidinyl]-7-(4-phenoxyphenyl)-7,9-dihydro-8H-purin-8-one or a pharmaceutically acceptable salt, solvate, hydrate, cocrystal, or prodrug thereof, or a hydrochloride salt thereof.

The R-enantiomer of Formula (XXVIII-B) is also known as ONO-4059, and is given by Formula (XXVIII-R):

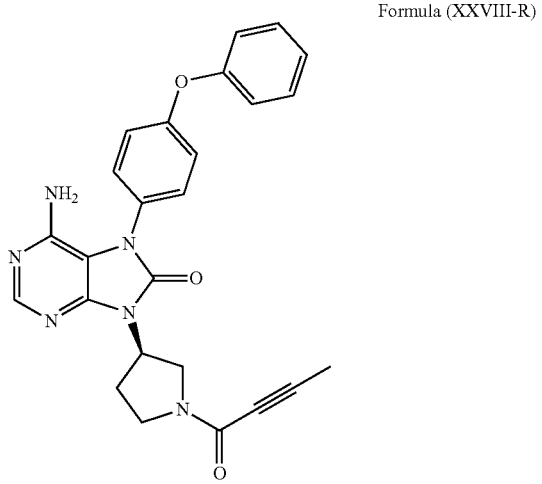 [SMILES: CC#CC(=O)N1CC[C@@H](n2c(=O)n(-c3ccc(Oc4ccccc4)cc3)c3c(N)ncnc32)C1]

Formula (XXVIII-R)

or a pharmaceutically acceptable salt, solvate, hydrate, cocrystal, or prodrug thereof, or a hydrochloride salt thereof.

In a preferred embodiment, the BTK inhibitor is 6-amino-9-[(3R)-1-(2-butynoyl)-3-pyrrolidinyl]-7-(4-phenoxyphenyl)-7,9-dihydro-8H-purin-8-one or a pharmaceutically acceptable salt, solvate, hydrate, cocrystal, or prodrug thereof, or a hydrochloride salt thereof.

The preparation of Formula (XXVIII-R) is described in International Patent Application Publication No. WO 2013/081016 A1. In brief, the BTK inhibitor of Formula (XXVIII-R) can be prepared by the following procedure.

Step 1: A solution of dibenzylamine (10.2 g) in dichloromethane (30 mL) is dripped into a solution of 4,6-dichloro-5-nitropyrimidine (10 g) in dichloromethane (70 mL) on an ice bath. Then triethylamine (14.4 mL) is added, and the mixture is stirred for 1 hour. Water is added to the reaction mixture, the organic layer is washed with a saturated aqueous sodium chloride solution and dried over anhydrous sodium sulfate, and the solvent is concentrated under reduced pressure to obtain N,N-dibenzyl-6-chloro-5-nitropyrimidine-4-amine (19.2 g).

Step 2: The compound prepared in Step 1 (19 g) and tert-butyl (3R)-3-aminopyrrolidine-1-carboxylate (10.5 g) are dissolved in dioxane (58 mL). Triethylamine (8.1 mL) is added, and the mixture is stirred for 5 hours at 50° C. The reaction mixture is returned to room temperature, the solvent is distilled off, water is added, and extraction is performed with ethyl acetate. The organic layer is washed with saturated aqueous sodium chloride solution, then dried over anhydrous sodium sulfate, and the solvent is distilled off. The residue is purified by silica gel column chromatography to obtain tert-butyl (3R)-3-{[6-(dibenzylamino)-5-nitropyrimidin-4-yl]amino}pyrrolid-ine-1-carboxylate (27.0 g).

Step 3: An ethyl acetate (360 mL) solution of the compound prepared in Step 2 (17.5 g) is dripped into a mixture of zinc (23.3 g) and a 3.0 M aqueous ammonium chloride solution (11.4 g) on an ice bath, and the temperature is immediately raised to room temperature. After stirring for 2 hours, the reaction mixture is filtered through CELITE and the solvent is distilled off. The residue is purified by silica gel column chromatography to obtain tert-butyl (3R)-3-{[5-amino-6-(dibenzylamino)pyrimidin-4-yl]amino}pyrrolidine-1-carboxylate (12.4 g).

Step 4: The compound prepared in Step 3 (8.4 g) and 1,1'-carbonyl diimidazole (5.9 g) are dissolved in tetrahydrofuran (120 mL) and the solution is stirred for 15 hours at 60° C. The solvent is distilled off from the reaction mixture, water is added, and extraction with ethyl acetate is performed. The organic layer is washed with saturated aqueous sodium chloride solution, dried over anhydrous sodium sulfate, and the solvent is distilled off. The residue is purified by silica gel column chromatography to obtain tert-butyl (3R)-3-[6-(dibenzylamino)-8-oxo-7,8-dihydro-9H-purin-9-yl]pyrrolidin-1-carboxylate (7.8 g).

Step 5: The compound prepared in Step 4 (7.8 g) is dissolved in methanol (240 mL) and ethyl acetate (50 mL), 20% Pearlman's catalyst (Pd(OH)$_2$/C) (8.0 g, 100 wt %) is added, hydrogen gas replacement is carried out, and stirring is performed for 7.5 hours at 60° C. The reaction mixture is filtered through CELITE and the solvent is distilled off to obtain tert-butyl (3R)-3-(6-amino-8-oxo-7,8-dihydro-9H-purin-9-yl)pyrrolidine-1-carboxylate (5.0 g).

Step 6: At room temperature p-phenoxy phenyl boronic acid (2.1 g), copper(II) acetate (1.48 g), molecular sieve 4A (2.5 g), and pyridine (0.82 mL) are added to a dichloromethane suspension (200 mL) of the compound prepared in Step 5 (2.5 g), followed by stirring for 21 hours. The reaction mixture is filtered through CELITE and the residue is purified by silica gel column chromatography to obtain tert-butyl (3R)-3-[6-amino-8-oxo-7-(4-phenoxyphenyl)-7,8-dihydro-9H-purin-9-yl]pyrrolidine-1-carboxylate (1.3 g).

Step 7: At room temperature 4 N HCl/dioxane (13 mL) is added to a methanol (13 mL) suspension of the compound prepared in Step 6 (1.3 g 2.76 mmol, 1.0 equivalent), and the mixture is stirred for 1 hour. The solvent is then distilled off to obtain (3R)-6-amino-9-pyrrolidin-3-yl-7-(4-phenoxyphenyl)-7,9-dihydro-8H-purin-8-one dihydrochloride (1.5 g).

Step 8: After 2-butynoic acid (34 mg), 1-ethyl-3-(3-dimethylaminopropyl) carbodiimide hydrochloride (EDC) (78 mg), 1-hydroxybenzotriazole (HOBt) (62 mg), and triethylamine (114 mL) are added to a solution of the compound prepared in Step 7 (100 mg) in dimethyl formamide (3 mL), the mixture is stirred at room temperature for 3 hours. Water is added to the reaction mixture and extraction with ethyl acetate is performed. The organic layer is washed with saturated sodium carbonate solution and saturated aqueous sodium chloride solution, then dried over anhydrous sodium sulfate, and the solvent is distilled off. The residue is purified by thin layer chromatography (dichloromethane:methanol:28% ammonia water=90:10:1) to obtain 6-amino-9-[(3R)-1-(2-butynoyl)-3-pyrrolidinyl]-7-(4-phenoxyphenyl)-7,9-dihydro-8H-purin-8-one (Formula (XXVIII-R)) (75 mg).

The hydrochloride salt of the compound of Formula (XXVIII-R) can be prepared as follows: 6-amino-9-[(3R)-1-(2-butynoyl)-3-pyrrolidinyl]-7-(4-phenoxyphenyl)-7,9-dihydro-8H-purin-8-one (3.0 g) (which may be prepared as described above) is placed in a 300 mL 3-neck pear-shaped flask, ethyl acetate (30 mL) and 1-propanol (4.5 mL) are added, and the external temperature is set at 70° C. (internal temperature 61° C.). After it is confirmed that the compound prepared in Step 8 has dissolved completely, 10% HO/methanol (3.5 mL) is added, and after precipitation of crystals is confirmed, the crystals are ripened by the following sequence: external temperature 70° C. for 30 min, external temperature 60° C. for 30 min, external temperature 50° C. for 60 min, external temperature 40° C. for 30 min, room temperature for 30 min, and an ice bath for 30 min. The resulting crystals are filtered, washed with ethyl acetate (6 mL), and dried under vacuum at 50° C. to obtain white crystals of 6-amino-9-[(3R)-1-(2-butynoyl)-3-pyrrolidinyl]-7-(4-phenoxyphenyl)-7,9-dihydro-8H-purin-8-one hydrochloride (2.76 g).

In an embodiment, the BTK inhibitor is a compound selected from the structures disclosed in U.S. Patent Application Publication No. US 2014/0330015 A1, the disclosure of which is incorporated by reference herein.

In a preferred embodiment, the BTK inhibitor is a compound of Formula (B):

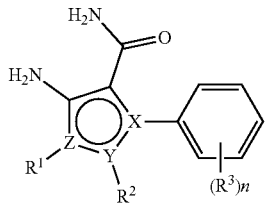

Formula (B)

or a pharmaceutically acceptable salt, solvate, hydrate, cocrystal, or prodrug thereof, or a hydrochloride salt thereof, wherein:

X—Y—Z is N—C—C and $R^2$ is present, or C—N—N and $R^2$ is absent;

$R^1$ is a 3-8 membered, N-containing ring, wherein the N is unsubstituted or substituted with $R^4$;

$R^2$ is H or lower alkyl, particularly methyl, ethyl, propyl or butyl; or $R^1$ and $R^2$ together with the atoms to which they are attached, form a 4-8 membered ring, preferably a 5-6 membered ring, selected from cycloalkyl, saturated or unsaturated heterocycle, aryl, and heteroaryl rings unsubstituted or substituted with at least one substituent L-$R^4$;

$R^3$ is in each instance, independently halogen, alkyl, S-alkyl, CN, or $OR^5$;

n is 1, 2, 3, or 4, preferably 1 or 2;

L is a bond, NH, heteroalkyl, or heterocyclyl;

$R^4$ is COR', $CO_2R'$, or $SO_2R'$, wherein R' is substituted or unsubstituted alkyl, substituted or unsubstituted alkenyl, substituted or unsubstituted alkynyl;

$R^5$ is H or unsubstituted or substituted heteroalkyl, alkyl, cycloalkyl, saturated or unsaturated heterocyclyl, aryl, or heteroaryl.

In some embodiments, the BTK inhibitor is one of the following particular embodiments of Formula B:

X—Y—Z is C—N—N and $R^2$ is absent; and $R^1$ is 3-8 membered, N-containing ring, N-substituted with $R^4$;

X—Y—Z is N—C—C and $R^2$ is present, $R^1$ is 3-8 membered, N-containing ring, N-substituted with $R^4$; and $R^2$ is H or lower alkyl;

X—Y—Z is N—C—C and $R^2$ is present; and $R^1$ and $R^2$ together with the atoms to which they are attached, form a 4-8 membered ring selected from cycloalkyl, saturated or unsaturated heterocycle, aryl, and heteroaryl rings unsubstituted or substituted with at least one substituent L-$R^4$, wherein preferred rings of $R^1$ and $R^2$ are 5-6-membered, particularly dihydropyrrole, tetrahydropyridine, tetrahydroazepine, phenyl, or pyridine;

X—Y—Z is N—C—C and $R^2$ is present; and $R^1$ and $R^2$ together with the atoms to which they are attached, form a 5-6 membered ring, preferably (a) phenyl substituted with a single -L-$R^4$, or (b) dihydropyrrole or tetrahydropyridine, N-substituted with a single -L-$R^4$ wherein L is bond;

$R^1$ is piperidine or azaspiro[3.3]heptane, preferably N-substituted with $R^4$;

$R^4$ is COR' or $SO_2R'$, particularly wherein R' is substituted or unsubstituted alkenyl, particularly substituted or unsubstituted ethenyl; or $R^5$ is unsubstituted or substituted alkyl or aryl, particularly substituted or unsubstituted phenyl or methyl, such as cyclopropyl-substituted methyl with or tetrabutyl-substituted phenyl.

In some embodiments, the BTK inhibitor is one of the following particular embodiments of Formula B:

$R^1$ is piperidine or azaspiro[3.3]heptane, N-substituted with $R^4$, wherein $R^4$ is H, COR' or $SO_2R'$, and R' is substituted or unsubstituted alkenyl, particularly substituted or unsubstituted ethenyl;

$R^3$ is —$OR^5$, $R^5$ is phenyl, and n is 1;

$R^1$ and $R^2$, together with the atoms to which they are attached, form a 5-6 membered ring, preferably (a) phenyl substituted with a single -L-$R^4$, or (b) dihydropyrrole or tetrahydropyridine, N-substituted with a single -L-$R^4$ wherein L is bond; $R^3$ is —$OR^5$; n is 1; $R^4$ is COR', and R' is ethenyl; and $R^5$ is phenyl; and X—Y—Z is C—N—N and $R^2$ is absent; $R^1$ is piperidine, N-substituted with $R^4$; $R^3$ is —$OR^5$; n is 1; $R^4$ is COR', and R' is unsubstituted or substituted alkenyl, particularly ethenyl; and $R^5$ is substituted or unsubstituted aryl, particularly phenyl.

In a preferred embodiment, the BTK inhibitor is a compound of Formula ($B_1$), Formula (B1-2), or Formula (B1-3):

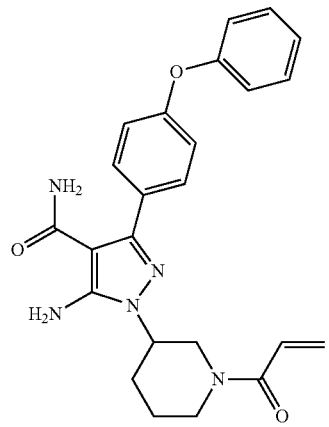

Formula (B1-1)

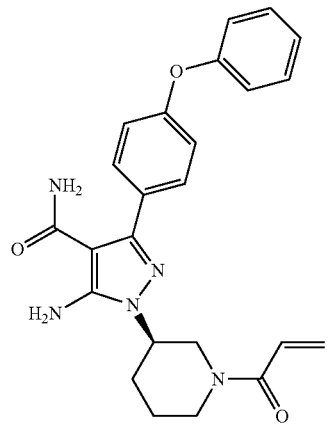

Formula (B1-2)

Formula (B1-3)

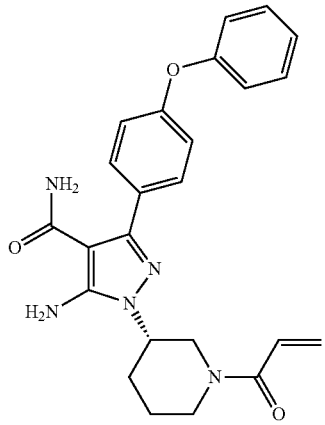

or a pharmaceutically acceptable salt, solvate, hydrate, cocrystal, or prodrug thereof, or a hydrochloride salt thereof. Formula (B₁-2) is also known as BGB-3111. The preparation of these compounds is described in International Patent Application Publication No. WO 2014/173289 A1 and U.S. Patent Application Publication No. US 2015/0005277 A1.

In brief, the BTK inhibitor of Formula (B₁) can be prepared by the following procedure.

Step 1. Preparation of 2-(hydroxy(4-phenoxyphenyl)methylene)malononitrile

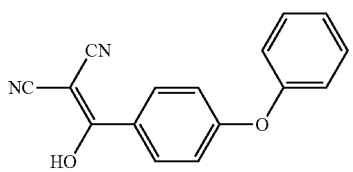 [SMILES: COC(=C(C#N)C#N)c1ccc(Oc2ccccc2)cc1]

A solution of 4-phenoxybenzoic acid (300 g, 1.4 mol) in SOCl₂ (1.2 L) is stirred at 80° C. under N₂ for 3 hours. The mixture is concentrated in vacuum to give the intermediate (315 g) which is used for next step without further purification.

To a solution of propanedinitrile (89.5 g, 1355 mmol) and DIEA (350 g, 2710 mmol) in THF (800 mL) is dropwise a solution of the intermediate (315 g) in toluene (800 mL) at 0-5° C. over 2 hours. The resultant mixture is allowed to warm to RT and stirred for 16 hours. The reaction is quenched with water (2.0 L) and extracted with of EA (2.0 L×3). The combined organic layers are washed with 1000 mL of 3 N HCl aqueous solution, brine (2.0 L×3), dried over Na₂SO₄ and concentrated to give the crude product (330 g, 93%).

Step 2. Preparation of 2-(Methoxy(4-phenoxyphenyl)methylene)malononitrile

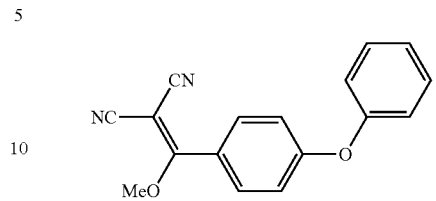

A solution of 2-(hydroxy(4-phenoxyphenyl)methylene)malononitrile (50 g, 190.8 mmol) in CH(OMe₃) (500 mL) is heated to 75° C. for 16 hours. Then the mixture is concentrated to a residue and washed with MeOH (50 mL) to give 25 g (47.5%) of 2-(methoxy(4-phenoxyphenyl)methylene)malononitrile as a yellow solid.

Step 3. Preparation of 5-amino-3-(4-phenoxyphenyl)-1H-pyrazole-4-carbonitrile

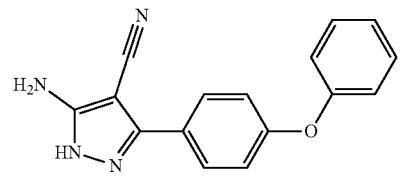 [SMILES: N#Cc1c(-c2ccc(Oc3ccccc3)cc2)n[nH]c1N]

To a solution of 2-(methoxy(4-phenoxyphenyl)methylene)malononitrile (80 g, 290 mmol) in ethanol (200 mL) is added hydrazine hydrate (20 mL). The mixture is stirred at RT for 16 hours then is concentrated to give the crude product and washed with MeOH (30 mL) to afford 55 g (68.8%) of 5-amino-3-(4-phenoxyphenyl)-1H-pyrazole-4-carbonitrile as a off-white solid.

Step 4. Preparation of tert-butyl 3-(tosyloxy)piperidine-1-carboxylate

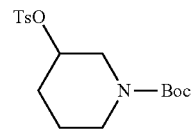 [SMILES: Cc1ccc(S(=O)(=O)OC2CCCN(C(=O)OC(C)(C)C)C2)cc1]

To a solution of tert-butyl 3-hydroxypiperidine-1-carboxylate (1.05 g, 5.0 mmol) in pyridine (8 mL) is added TsCl (1.425 g, 7.5 mmol). The mixture is stirred at RT under N₂ for two days. The mixture is concentrated and partitioned between 100 mL of EA and 100 mL of HCl (1 N) aqueous solution. The organic layer is separated from aqueous layer, washed with saturated NaHCO₃ aqueous solution (100 mL×2), brine (100 mL×3) and dried over Na₂SO₄. The organic layer is concentrated to afford 1.1 g (60%) of tert-butyl 3-(tosyloxy)piperidine-1-carboxylate as a colorless oil.

Step 5. Preparation of tert-butyl 3-(5-amino-4-cyano-3-(4-phenoxyphenyl)-1H-pyrazol-1-yl)piperidine-1-carboxylate

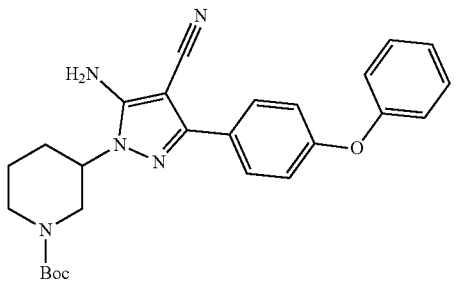 [SMILES: CC(C)(C)OC(=O)N1CCCC(n2nc(-c3ccc(Oc4ccccc4)cc3)c(C#N)c2N)C1]

To a solution of tert-butyl 3-(tosyloxy)piperidine-1-carboxylate (355 mg, 1.0 mmol) and 5-amino-3-(4-phenoxyphenyl)-1H-pyrazole-4-carbonitrile (276 mg, 1.0 mmol) in 5 mL of DMF is added $Cs_2CO_3$ (650 mg, 2.0 mmol). The mixture is stirred at RT for 16 hours, 75° C. for 3 hours and 60° C. for 16 hours. The mixture is concentrated washed with brine (100 mL×3) and dried over $Na_2SO_4$. The material is concentrated and purified by chromatography column on silica gel (eluted with petroleum ether/ethyl actate=3/1) to afford 60 mg (13%) of tert-butyl 3-(5-amino-4-cyano-3-(4-phenoxyphenyl)-1H-pyrazol-1-yl)piperidine-1-carboxylate as a yellow oil.

Step 6. Preparation of tert-butyl 3-(5-amino-4-carbamoyl-3-(4-phenoxyphenyl)-1H-pyrazol-1-yl)piperidine-1-carboxylate

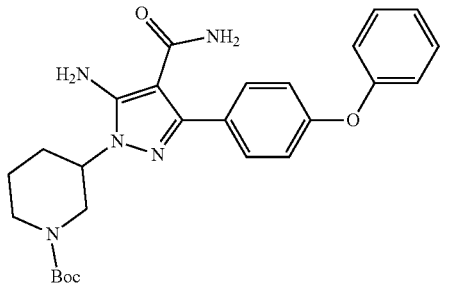 [SMILES: CC(C)(C)OC(=O)N1CCCC(n2nc(-c3ccc(Oc4ccccc4)cc3)c(C(N)=O)c2N)C1]

To a solution of tert-butyl 3-(5-amino-4-cyano-3-(4-phenoxyphenyl)-1H-pyrazol-1-yl)piperidine-1-carboxylate (100 mg, 0.22 mmol) in DMSO (2 mL) and ethanol (2 mL) was added the solution of NaOH (200 mg, 5 mmol) in water (1 mL) and $H_2O_2$ (1 mL). The mixture is stirred at 60° C. for 15 min and concentrated to remove EtOH, after which 10 mL of water and 50 mL of ethyl acetate are added. The organic layer is separated from aqueous layer, washed with brine (30 mL×3) and dried over $Na_2SO_4$. After concentration, 50 mg of residue is used directly in the next step, wherein 50 mg of residue is purified by pre-TLC (eluted with petroleum ether/ethyl actate=1/1) to afford 12 mg (30%) of tert-butyl 3-(5-amino-4-carbamoyl-3-(4-phenoxyphenyl)-1H-pyrazol-1-yl)piperidine-1-carboxylate as a white solid.

Step 7. Preparation of 5-amino-3-(4-phenoxyphenyl)-1-(piperidin-3-yl)-1H-pyrazole-4-carboxamide

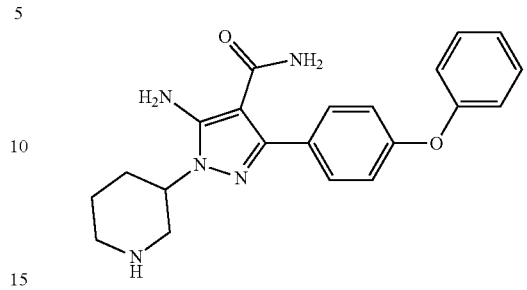

To a solution of tert-butyl 3-(5-amino-4-carbamoyl-3-(4-phenoxyphenyl)-1H-pyrazol-1-yl)piperidine-1-carboxylate (50 mg, 0.11 mmol) in ethyl acetate (1 mL) is added concentrated HCl (0.75 mL). The mixture is stirred at RT for 1 hour. Then saturated $NaHCO_3$ is added until pH >7, followed by ethyl acetate (50 mL). Organic layer is separated from aqueous layer, washed with brine (50 mL×3) and dried over $Na_2SO_4$. Concentrated and purified by Pre-TLC (eluted with dichloromethane/MeOH/$NH_3$—$H_2O$=5/1/0.01) to afford 10 mg (25%) of 5-amino-3-(4-phenoxyphenyl)-1-(piperidin-3-yl)-1H-pyrazole-4-carboxamide as a white solid.

Step 8. Preparation of 1-(1-acryloylpiperidin-3-yl)-5-amino-3-(4-phenoxyphenyl)-1H-pyrazole-4-carboxamide

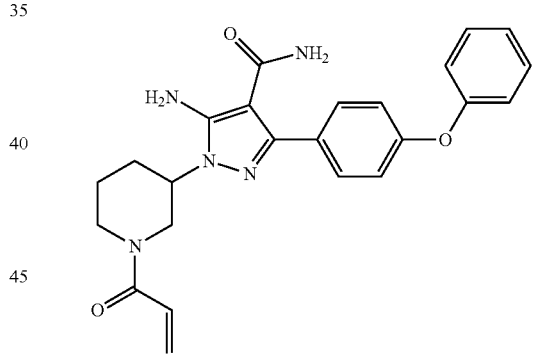

To a solution of 5-amino-3-(4-phenoxyphenyl)-1-(piperidin-3-yl)-1H-pyrazole-4-carboxamide (63 mg, 0.17 mmol) in dichloromethane (4 mL) is added pyridine (27 mg, 0.34 mmol). Then a solution of acryloyl chloride (12 mg, 0.17 mmol) in dichloromethane (1 mL) was added dropwise. After stirring at RT for 4 hours, the mixture is partitioned between 100 mL of dichloromethane and 100 mL of brine. Organic layer is separated from aqueous layer, washed with brine (100 mL×2) and dried over $Na_2SO_4$. Concentrated and purified by Pre-TLC (eluted with dichloromethane/MeOH=10/1) to afford 4 mg (5.5%) of 1-(1-acryloylpiperidin-3-yl)-5-amino-3-(4-phenoxyphenyl)-1H-pyrazole-4-carboxamide as a white solid.

The enantiomers of Formula ($B_1$) provided by the procedure above may be prepared from 5-amino-3-(phenoxyphenyl)-1H-pyrazole-4-carbonitrile and (S)-tert-butyl 3-hydroxypiperidine-1-carboxylate using a similar procedure (step 4 to 8) for Formula ($B_1$-2), or from (R)-tert-butyl 3-hydroxypiperidine-1-carboxylate using a similar procedure (step 4 to 8) for Formula (B$_1$-3). Under appropriate conditions recognized by one of ordinary skill in the art, a racemic mixture of Formula (B$_1$) may be separated by chiral HPLC, the crystallization of chiral salts, or other means described above to yield Formula (B$_1$-2) and Formula (B$_1$-3) of high enantiomeric purity.

In an embodiment, the BTK inhibitor is a compound selected from the structures disclosed in U.S. Patent Application Publication No. US 2015/0005277A1, the disclosure of which is incorporated by reference herein.

BTK inhibitors suitable for use in the described combination with a PI3K inhibitor, a PI3K-γ inhibitor, and/or a PI3K-δ inhibitor also include, but are not limited to, those described in, for example, International Patent Application Publication Nos. WO 2013/010868; WO 2012/158843; WO 2012/135944; WO 2012/135937; U.S. Patent Application Publication No. 2011/0177011; and U.S. Pat. Nos. 8,501,751; 8,476,284; 8,008,309; 7,960,396; 7,825,118; 7,732,454; 7,514,444; 7,459,554; 7,405,295; and 7,393,848, the disclosures of these U.S. Patents and Patent Application Publications are incorporated herein by reference.

JAK-2 Inhibitors

Some embodiments (for example combinations, compositions and/or kits) of the invention comprise a JAK inhibitor, for example a JAK-2 inhibitor. In some embodiments, the compositions and methods described include a JAK inhibitor, for example a JAK-2 inhibitor. In some embodiments, the compounds provided herein are selective for JAK-2, in that the compounds bind or interact with JAK-2 at substantially lower concentrations than they bind or interact with other JAK receptors, including the JAK-3 receptor. In some embodiments, the compounds bind to the JAK-3 receptor at a binding constant at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration.

In a preferred embodiment, the JAK-2 inhibitor is a compound of Formula (XXIX):

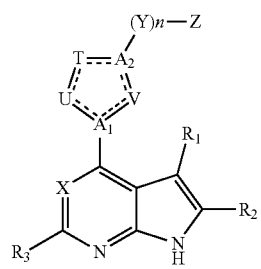

Formula (XXIX)

including a pharmaceutically acceptable salt, solvate, hydrate, cocrystal, or prodrug thereof, wherein:

$A^1$ and $A^2$ are independently selected from C and N;

T, U, and V are independently selected from O, S, N, $CR^5$, and $NR^6$;

wherein the 5-membered ring formed by $A^1$, $A^2$, U, T, and V is aromatic;

X is N or $CR^4$;

Y is $C_{1-8}$ alkylene, $C_{2-8}$ alkenylene, $C_{2-8}$ alkynylene, $(CR^{11}R^{12})_p$—$(C_{3-10}$ cycloalkylene$)$-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene$)$-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, $(CR^{11}R^{12})_pS(CR^{11}R^{12})_q$, $(CR^{11}R_{12})_pC(O)(CR^{11}R^{12})_q$, $(CR^{11}R^{12})_pC(O)NR^c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_pOC(O)NR^c(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from $-D^1-D^2-D^3-D^4$;

Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, =C—$R^i$, =N—$R^i$, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, —$C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}alkyl)R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, —$OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl)$R^b$, and $S(O)_2NR^cR^d$;

wherein when Z is H, n is 1;

or the —$(Y)_n$—Z moiety is taken together with i) $A^2$ to which the moiety is attached, ii) $R^5$ or $R^6$ of either T or V, and iii) the C or N atom to which the $R^5$ or $R^6$ of either T or V is attached to form a 4- to 20-membered aryl, cycloalkyl, heteroaryl, or heterocycloalkyl ring fused to the 5-membered ring formed by $A^1$, $A^2$, U, T, and V, wherein said 4- to 20-membered aryl, cycloalkyl, heteroaryl, or heterocycloalkyl ring is optionally substituted by 1, 2, 3, 4, or 5 substituents independently selected from —$(W)_m$-Q;

W is $C_{1-8}$ alkylenyl, $C_{2-8}$ alkenylenyl, $C_{2-8}$ alkynylenyl, O, S, C(O), C(O)$NR^{c'}$, C(O)O, OC(O), OC(O)$NR^{c'}$, $NR^{c'}$, $NR^{c'}$-C(O)$NR^{d'}$, S(O), S(O)$NR^{c'}$, $S(O)_2$, or $S(O)_2NR^{c'}$;

Q is H, halo, CN, $NO_2$, $C_{1-8}$ alkyl, $C_{2-8}$ alkenyl, $C_{2-8}$ alkynyl, $C_{1-8}$ haloalkyl, halosulfanyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^i$, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{b'}$, —$NR^{c'}C(O)NR^{c'}R^{d'}$, $NR^{c'}C(O)OR^{a'}$, $S(O)R^{b'}$, $S(O)NR^{c'}R^{d'}$, $S(O)_2R^{b'}$, $NR^{c'}S(O)_2R^{b'}$, and $S(O)_2NR^{c'}R^{d'}$;

$Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, CN, $NO_2$, $OR^{a''}$, $SR^{a''}$, $C(O)R^{b''}$, $C(O)NR^{c''}R^{d''}$, $C(O)OR^{a''}$, —$OC(O)R^{b''}OC(O)NR^{c''}R^{d''}$, $NR^{c''}R^{d''}$, $NR^{c''}C(O)R^{b''}$, $NR^{c''}C(O)OR^{a''}$, $NR^{c''}S(O)R^{b''}$, —$NR^{c''}S(O)_2R^{b''}$, $S(O)R^{b''}$, $S(O)NR^{c''}R^{d''}$, $S(O)_2R^{b''}$ and $S(O)_2NR^{c''}R^{d''}$;

$R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, halosulfanyl, aryl, cycloalkyl, heteroaryl, heterocycloalkyl, CN, $NO_2$, $OR^7$, $SR^7$, $C(O)R^8$, $C(O)NR^9R^{10}$, $C(O)OR^7 OC(O)R^8$, $OC(O)NR^9R^{10}$, $NR^9R^{10}$, $NR^9C(O)R^8$, —$NR^cC(O)OR^7$, $S(O)R^8$, $S(O)NR^9R^{10}$, $S(O)_2R^8$, $NR^9S(O)_2R^8$, and $S(O)_2NR^9R^{10}$;

$R^5$ is selected from H, halo, $C_{1-4}$ alkyl, $C_{2-4}$ alkenyl, $C_{2-4}$ alkynyl, $C_{1-4}$ haloalkyl, halosulfanyl, CN, $NO_2$, $OR^7$, $SR^7$, $C(O)R^8$, $C(O)NR^9R^{10}$, $C(O)OR^7$, $OC(O)R^8$, $OC(O)NR^9R^{10}$, $NR^9R^{10}$, —$NR^9C(O)R^8$, $NR^9C(O)OR^7$, $S(O)R^8$, $S(O)NR^9R^{10}$, $S(O)_2R^8$, $NR^9S(O)_2R^8$ and $S(O)_2NR^9R^{10}$;

$R^6$ is selected from H, $C_{1-4}$ alkyl, $C_{2-4}$ alkenyl, $C_{2-4}$ alkynyl, $C_{1-4}$ haloalkyl, $OR^7$, $C(O)R^8$, —$C(O)NR^9R^{10}$, $C(O)OR^7$, $S(O)R^8$, $S(O)NR^9R^{10}$, $S(O)_2R^8$ and $S(O)_2NR^9R^{10}$;

$R^7$ is selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl;

$R^8$ is selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl;

$R^9$ and $R^{10}$ are independently selected from H, $C_{1-10}$ alkyl, $C_{1-6}$ haloalkyl, $C_{2-6}$ alkenyl, $C_{2-6}$ alkynyl, $C_{1-6}$ alkylcarbonyl, aryl carbonyl, $C_{1-6}$ alkyl sulfonyl, aryl sulfonyl, aryl, heteroaryl, cycloalkyl, heterocycloalkyl, arylalkyl, heteroarylalkyl, cycloalkylalkyl and heterocycloalkylalkyl;

or $R^9$ and $R^{10}$ together with the N atom to which they are attached form a 4-, 5-, 6- or 7-membered heterocycloalkyl group;

$R^{11}$ and $R^{12}$ are independently selected from H and -$E^1$-$E^2$-$E^3$-$E^4$;

$D^1$ and $E^1$ are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$D^2$ and $E^2$ are independently absent or independently selected from $C_{1-6}$ alkylene, $C_{2-6}$ alkenylene, $C_{2-6}$ alkynylene, $(C_{1-6}$ alkylene$)_r$-O-$(C_{1-6}$ alkylene$)_s$, $(C_{1-6}$ alkylene$)_r$-S-$(C_{1-6}$ alkylene$)_s$, $(C_{1-6}$ alkylene$)_s$, —$NR_e$—$(C_{1-6}$ alkylene$)_s$, $(C_{1-6}$ alkylene$)_r$-CO-$(C_{1-6}$ alkylene$)_s$, $(C_{1-6}$ alkylene$)_r$-COO-$(C_{1-6}$ alkylene$)_s$, $(C_{1-6}$ alkylene$)_r$-CONR$^e$-$(C_{1-6}$ alkylene$)_s$, $(C_{1-6}$ alkylene$)_r$-SO-$(C_{1-6}$ alkylene$)_s$, $(C_{1-6}$ alkylene$)_r$-SO$_2$-$(C_{1-6}$ alkylene$)_s$, $(C_{1-6}$ alkylene$)_r$-SONR$^e$-$(C_{1-6}$ alkylene$)_s$, and $(C_{1-6}$ alkylene$)_r$-NR$^e$CONR$^f$-$(C_{1-6}$ alkylene$)_s$, wherein each of the $C_{1-6}$ alkylene, $C_{2-6}$ alkenylene, and $C_{2-6}$ alkynylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$D^3$ and $E^3$ are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, $N_3$, SCN, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, amino, $C_{1-6}$ alkylamino, and $C_{2-8}$ dialkylamino;

$D^4$ and $E^4$ are independently selected from H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}alkyl)R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $s(O)NR^cR^d$, $S(O)_2R^b$, $NR^cS(O)_2R^b$, $C(=NOH)R^b$, $C(=NO(C_{1-6}alkyl))R^b$, and $S(O)_2NR^cR^d$;

$R^a$ is selected from H, $Cy^1$, —$(C_{1-6}$ alkyl$)$-$Cy^1$, $C_{1-6}$ alkyl, $C_{1-6}$ haloalkyl, $C_{2-6}$ alkenyl and $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_1$-6 alkyl, $C_{1-6}$ haloalkyl, halosulfanyl, aryl, arylalkyl, heteroaryl, heteroarylalkyl, cycloalkyl and heterocycloalkyl;

$R^b$ is selected from H, $Cy^1$, —$(C_{1-6}$ alkyl$)$-$Cy^1$, $C_{1-6}$ alkyl, $C_{1-6}$ haloalkyl, $C_{2-6}$ alkenyl and $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_1$-6 alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R^{a'}$ and $R^{a''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, halosulfanyl, aryl, arylalkyl, heteroaryl, heteroarylalkyl, cycloalkyl and heterocycloalkyl;

$R^{b'}$ and $R^{b''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, halosulfanyl, aryl, arylalkyl, heteroaryl, heteroarylalkyl, cycloalkyl and heterocycloalkyl;

$R_c$ and $R^d$ are independently selected from H, $Cy^1$, —$(C_{1-6}$ alkyl$)$-$Cy^1$, $C_{1-10}$ alkyl, $C_{1-6}$ haloalkyl, $C_{2-6}$ alkenyl, $C_{2-6}$ alkynyl, wherein said $C_{1-10}$ alkyl, $C_{1-6}$ haloalkyl, $C_{2-6}$ alkenyl, or $C_{2-6}$ alkynyl, is optionally substituted with 1, 2, or 3 substituents independently selected from Cy¹, —(C$_{1-6}$ alkyl)-Cy¹, OH, CN, amino, halo, C$_{1-6}$ alkyl, C$_{1-6}$ haloalkyl, C$_{1-6}$ haloalkyl, and halosulfanyl;

or R$^c$ and R$^d$ together with the N atom to which they are attached form a 4-, 5-, 6- or 7-membered heterocycloalkyl group optionally substituted with 1, 2, or 3 substituents independently selected from Cy¹, —(C$_{1-6}$ alkyl)-Cy¹, OH, CN, amino, halo, C$_{1-6}$ alkyl, C$_{1-6}$ haloalkyl, C$_{1-6}$ haloalkyl, and halosulfanyl;

R$^{c'}$ and R$^{d'}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

or R$^{c'}$ and R$^{d'}$ together with the N atom to which they are attached form a 4-, 5-, 6- or 7-membered heterocycloalkyl group optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^{c''}$ and R$^{d''}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, C$_{1-6}$ alkyl, C$_{1-6}$ haloalkyl, halosulfanyl, C$_{1-6}$ haloalkyl, aryl, arylalkyl, heteroaryl, heteroarylalkyl, cycloalkyl and heterocycloalkyl;

or R$^{c''}$ and R$^{d''}$ together with the N atom to which they are attached form a 4-, 5-, 6- or 7-membered heterocycloalkyl group optionally substituted with 1, 2, or 3 substituents independently selected from OH, CN, amino, halo, C$_{1-6}$ alkyl, C$_{1-6}$ haloalkyl, C$_{1-6}$ haloalkyl, halosulfanyl, aryl, arylalkyl, heteroaryl, heteroarylalkyl, cycloalkyl and heterocycloalkyl;

R$^i$ is H, CN, NO$_2$, or C$_{1-6}$ alkyl;
R$^e$ and R$^f$ are independently selected from H and C$_{1-6}$ alkyl;
R$^i$ is H, CN, or NO$_2$;
m is 0 or 1;
n is 0 or 1;
p is 0, 1, 2, 3, 4, 5, or 6;
q is 0, 1, 2, 3, 4, 5 or 6;
r is 0 or 1; and
s is 0 or 1.

In some embodiments, when X is N, n is 1, and the moiety formed by A¹, A², U, T, V, and —(Y)$_n$—Z has the formula:

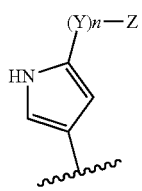

then Y is other than (CR$^{11}$R$^{12}$)$_p$C(O)NR$^c$(CR$^{11}$R$^{12}$)$_q$.

In some embodiments, when X is N, the 5-membered ring formed by A¹, A², U, T, and V is other than pyrrolyl.

In some embodiments, when X is CH, n is 1, and the moiety formed by A¹, A², U, T, V, and —(Y)$_n$—Z has the formula:

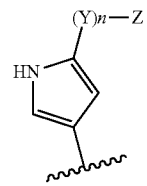

then —(Y)$_n$—Z is other than COOH.

In some embodiments, when X is CH or C-halo, R', R², and R³ are each H, n is 1, and the moiety formed by A¹, A², U, T, V, and —(Y)$_n$—Z has the formula:

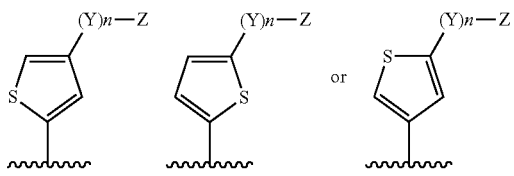

then Y is other than (CR$^{11}$R$^{12}$)$_p$C(O)NR$^c$(CR$^{11}$R$^{12}$)$_q$ or (CR$^{11}$R$^{12}$)$_p$C(O)(CR$^{11}$R$^{12}$)$_q$.

In some embodiments, when X is CH or C-halo, R¹, R², and R³ are each H, n is 0, and the moiety formed by A¹, A², U, T, V, and —(Y)$_n$—Z has the formula:

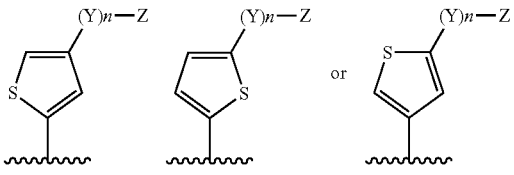

then Z is other than CN, halo, or C$_{1-4}$ alkyl.

In some embodiments, when X is CH or C-halo, R¹, R², and R³ are each H, n is 1, and the moiety formed by A¹, A², U, T, V, and —(Y)$_n$—Z has the formula:

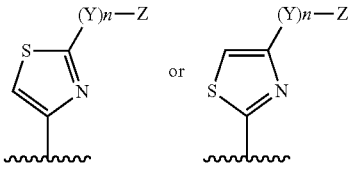

then Y is other than (CR$^{11}$R$^{12}$)$_p$C(O)NR$^c$(CR$^{11}$R$^{12}$)$_q$ or (CR$^{11}$R$^{12}$)$_p$C(O)(CR$^{11}$R$^{12}$)$_q$.

In some embodiments, when X is CH or C-halo, R¹, R², and R³ are each H, n is 1, and the moiety formed by A¹, A², U, T, V, and —(Y)$_n$—Z has the formula:

$(Y)n$—Z structure (furan with Y)n—Z substituent and methyl group then Y is other than $(CR^{11}R^{12})_p NR^c (CR^{11}R^{12})_q$.

In some embodiments, when X is CH or C-halo and $R^1$, $R^2$, and $R^3$ are each H, then the moiety formed by $A^1$, $A^2$, U, T, V, and —$(Y)_n$—Z has a formula other than:

[benzofuran, benzothiophene-2-yl, or benzothiophene-3-yl structures]

In some embodiments:

Z is H, halo, CN, $NO_2$, $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$ $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$;

Q is H, halo, CN, $NO_2$, $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl, wherein said $C_{1-8}$ alkyl, $C_{2-8}$ alkenyl, $C_{2-8}$ alkynyl, $C_{1-8}$ haloalkyl, aryl, cycloalkyl, heteroaryl, or heterocycloalkyl is optionally substituted with 1, 2, 3 or 4 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^2$, CN, $NO_2$, $OR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{b'}$, $NR^{c'}C(O)NR^{c'}R^{d'}$, —$NR^{c'}C(O)OR^{a'}$, $S(O)R^{b'}$, $S(O)NR^{c'}R^{d'}$, $S(O)_2R^{b'}$, $NR^{c'}S(O)_2R^{b'}$, and $S(O)_2NR^{c'}R^{d'}$;

$Cy^1$ and $Cy^1$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{b''}$, $NR^{c''}C(O)OR^{a''}$, $NR^{c''}S(O)R^{b''}$, $NR^{c''}S(O)_2R^{b''}$, $S(O)R^{b''}$, $S(O)NR^{c''}R^{d''}$, $S(O)_2R^{b''}$, and $S(O)_2NR^{c''}R^{d''}$;

$R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^7$, $SR^7$, $C(O)R^8$, $C(O)NR^9R^{10}$, $C(O)OR^7OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, and $S(O)_2NR^9R^{10}$;

$R^5$ is H, halo, $C_{1-4}$ alkyl, $C_{2-4}$ alkenyl, $C_{2-4}$ alkynyl, $C_{1-4}$ haloalkyl, CN, $NO_2$, $OR^7$, $SR^7$, $C(O)R^8$, $C(O)NR^9R^{10}$, $C(O)OR^7$, $OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, or $S(O)_2NR^9R^{10}$;

$R^6$ is H, $C_{1-4}$ alkyl, $C_{2-4}$ alkenyl, $C_{2-4}$ alkynyl, $C_{1-4}$ haloalkyl, $OR^7$, $C(O)R^8$, $C(O)NR^9R^{10}$, $C(O)OR^7$, $S(O)R^8$, $S(O)NR^9R^{10}$, $S(O)_2R^8$, or $S(O)_2NR^9R^{10}$;

$R^7$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^8$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl;

$R^9$ and $R^{10}$ are independently selected from H, $C_{1-10}$ alkyl, $C_{1-6}$ haloalkyl, $C_{2-6}$ alkenyl, $C_{2-6}$ alkynyl, $C_{1-6}$ alkylcarbonyl, aryl carbonyl, $C_{1-6}$ alkyl sulfonyl, aryl sulfonyl, aryl, heteroaryl, cycloalkyl, heterocycloalkyl, arylalkyl, heteroarylalkyl, cycloalkylalkyl and heterocycloalkylalkyl;

or $R^9$ and $R^{10}$ together with the N atom to which they are attached form a 4-, 5-, 6- or 7-membered heterocycloalkyl group;

$R^{11}$ and $R^{12}$ are independently selected from H, halo, OH, CN, $C_{1-4}$ alkyl, $C_{1-4}$ haloalkyl, $C_{2-4}$ alkenyl, $C_{2-4}$ alkynyl, $C_{1-4}$ hydroxyalkyl, $C_{1-4}$ cyanoalkyl, aryl, heteroaryl, cycloalkyl, and heterocycloalkyl;

$R^a$, $R^{a'}$, and $R^{a''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, aryl, arylalkyl, heteroaryl, heteroarylalkyl, cycloalkyl and heterocycloalkyl;

$R^b$, $R^{b'}$ and $R^{b''}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{c'}$ and $R^{d'}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c'}$ and $R^{d'}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{c''}$ and $R^{d''}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl; and or $R^{c''}$ and $R^{d''}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl.

In some embodiments, X is N.
In some embodiments, X is $CR^4$.
In some embodiments, $A^1$ is C.
In some embodiments, $A^1$ is N.
In some embodiments, $A^2$ is C.
In some embodiments, $A^2$ is N.
In some embodiments, at least one of $A^1$, $A^2$, U, T, and V is N.
In some embodiments, the 5-membered ring formed by $A^1$, $A^2$, U, T, and V is pyrrolyl, pyrazolyl, imidazolyl, oxazolyl, thiazolyl, or oxadiazolyl.
In some embodiments, the 5-membered ring formed by $A^1$, $A^2$, U, T, and V is selected from:

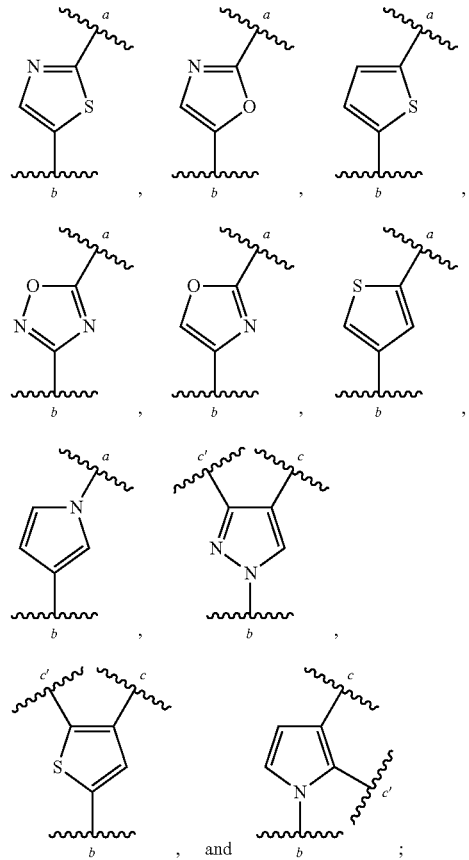

wherein:
a designates the site of attachment of moiety $-(Y)_n-Z$;
b designates the site of attachment to the core moiety:

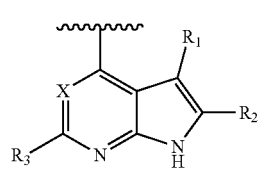

and
c and c' designate the two sites of attachment of the fused 4- to 20-membered aryl, cycloalkyl, heteroaryl, or heterocycloalkyl ring.

In some embodiments, the 5-membered ring formed by $A^1$, $A^2$, U, T, and V is selected from:

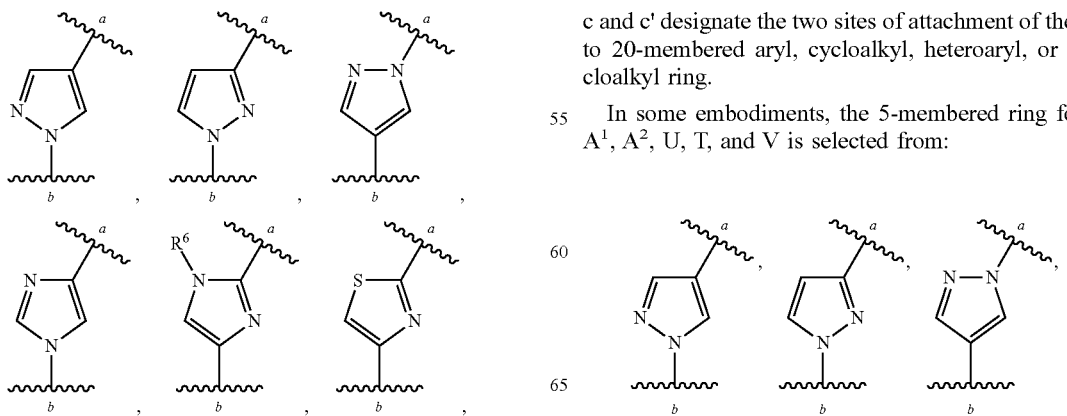

-continued

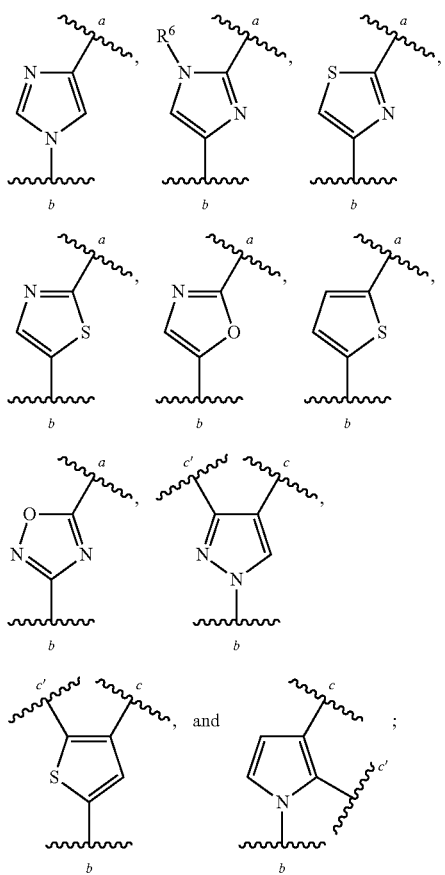

wherein:

a designates the site of attachment of moiety —(Y)$_n$—Z;

b designates the site of attachment to the core moiety.

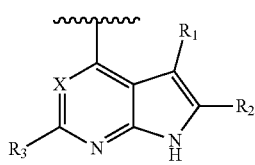

and c and c' designate the two sites of attachment of the fused 4- to 20-membered aryl, cycloalkyl, heteroaryl, or heterocycloalkyl ring.

In some embodiments, the 5-membered ring formed by $A^1$, $A^2$, U, T, and V is selected from:

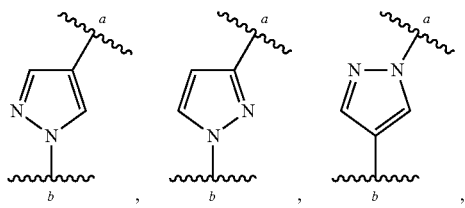

-continued

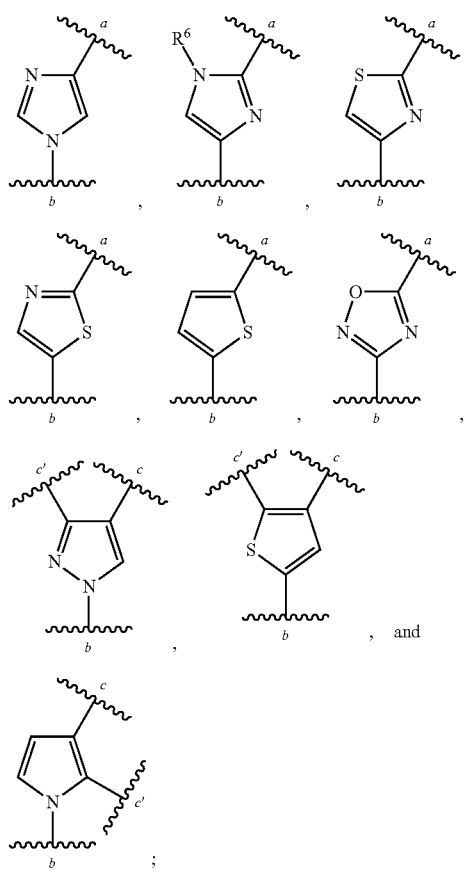

wherein:

a designates the site of attachment of moiety —(Y)$_n$—Z;

b designates the site of attachment to the core moiety:

and c and c' designate the two sites of attachment of the fused 4- to 20-membered aryl, cycloalkyl, heteroaryl, or heterocycloalkyl ring.

In some embodiments, the 5-membered ring formed by $A^1$, $A^2$, U, T, and V is selected from:

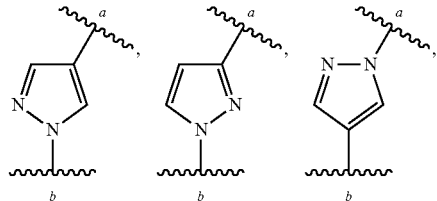

-continued

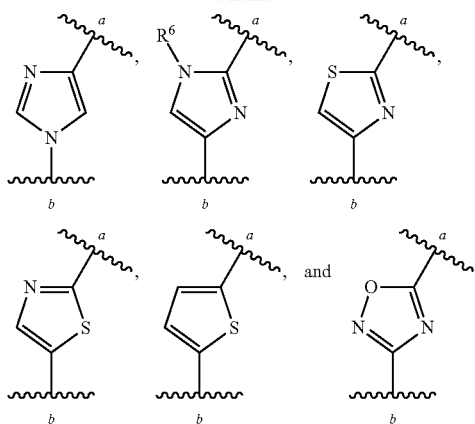

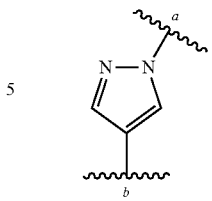

wherein:
a designates the site of attachment of moiety —(Y)$_n$—Z;
b designates the site of attachment to the core moiety:

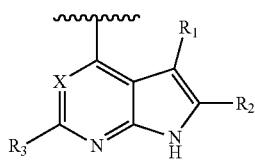

In some embodiments, the 5-membered ring formed by A$^1$, A$^2$, U, T, and V is selected from:

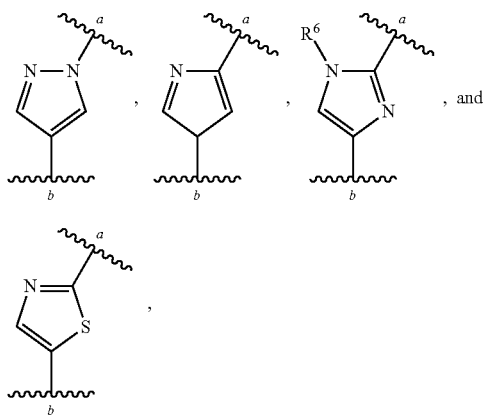

wherein:
a designates the site of attachment of moiety —(Y)$_n$—Z;
b designates the site of attachment to the core moiety:

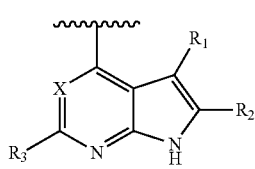

In some embodiments, the 5-membered ring formed by A$^1$, A$^2$, U, T, and V is selected from:

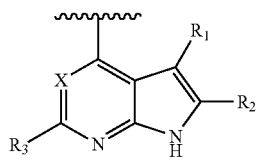

In some embodiments, n is 0.
In some embodiments, n is 1.
In some embodiments, n is 1 and Y is C$_{1-8}$ alkylene, C$_{2-8}$ alkenylene, (CR$^{11}$R$^{12}$)$_p$C(O)(CR$^{11}$R$^{12}$)$_q$, (CR$^{11}$R$^{12}$)$_p$C(O)NR$^c$(CR$^{11}$R$^{12}$)$_q$, (CR$^{11}$R$^{12}$)$_p$C(O)O(CR$^{11}$R$^{12}$)$_q$, (CR$^{11}$R$^{12}$)$_p$OC(O)(CR$^{11}$R$^{12}$)$_q$, wherein said C$_{1-8}$ alkylene or C$_{2-8}$ alkenylene, is optionally substituted with 1, 2, or 3 halo, OH, CN, amino, C$_{1-4}$ alkylamino, or C$_{2-8}$ dialkylamino.

In some embodiments, n is 1 and Y is C$_{1-8}$ alkylene, (CR$^{11}$R$^{12}$)$_p$C(O)(CR$^{11}$R$^{12}$)$_q$, (CR$^{11}$R$^{12}$)$_p$C(O)NR$^c$(CR$^{11}$R$^{12}$)$_q$, (CR$^{11}$R$^{12}$)$_p$C(O)O(CR$^{11}$R$^{12}$)$_q$, wherein said C$_{1-8}$ alkylene is optionally substituted with 1, 2, or 3 halo, OH, CN, amino, C$_{1-4}$ alkylamino, or C$_{2-8}$ dialkylamino.

In some embodiments, n is 1 and Y is C$_{1-8}$ alkylene optionally substituted with 1, 2, or 3 halo, OH, CN, amino, C$_{1-4}$ alkylamino, or C$_{2-8}$ dialkylamino.

In some embodiments, n is 1 and Y is ethylene optionally substituted with 1, 2, or 3 halo, OH, CN, amino, C$_{1-4}$ alkylamino, or C$_{2-8}$ dialkylamino.

In some embodiments, n is 1 and Y is (CR$^{11}$R$^{12}$)$_p$C(O)(CR$^{11}$R$^{12}$)$_q$, (CR$^{11}$R$^{12}$)$_p$C(O)NR$^c$(CR$^{11}$R$^{12}$)$_q$, or (CR$^{11}$R$^{12}$)$_p$C(O)O(CR$^{11}$R$^{12}$)$_q$.

In some embodiments, Y is C$_{1-8}$ alkylene, C$_{2-8}$ alkenylene, C$_{2-8}$ alkynylene, (CR$^{11}$R$^{12}$)$_p$—(C$_{3-10}$cycloalkylene)-(CR$^{11}$R$^{12}$)$_q$, (CR$^{11}$R$^{12}$)$_p$-(arylene)-(CR$^{11}$R$^{12}$)$_q$, (CR$^{11}$R$^{12}$)$_p$—(C$_{1-10}$ heterocycloalkylene)-(CR$^{11}$R$^{12}$)$_q$, (CR$^{11}$R$^{12}$)$_p$-(heteroarylene)-(CR$^{11}$R$^{12}$)$_q$, (CR$^{11}$R$^{12}$)$_p$O(CR$^{11}$R$^{12}$)$_q$, or (CR$^{11}$R$^{12}$)$_p$S(CR$^{11}$R$^{12}$)$_q$, wherein said C$_{1-8}$ alkylene, C$_{2-8}$ alkenylene, C$_{2-8}$ alkynylene, cycloalkylene, arylene, heterocycloalkylene, or heteroarylene, is optionally substituted with 1, 2, or 3 substituents independently selected from -131-D2-D3-D4.

In some embodiments, Y is C$_{1-8}$ alkylene, C$_{2-8}$ alkenylene, C$_{2-8}$ alkynylene, (CR$^{11}$R$^{12}$)$_p$—(C$_{3-10}$cycloalkylene)-(CR$^{11}$R$^{12}$)$_q$, (CR$^{11}$R$^{12}$)$_p$-(arylene)-(CR$^{11}$R$^{12}$)$_q$, (CR$^{11}$R$^{12}$)$_p$—(C$_{1-10}$ heterocycloalkylene)-(CR$^{11}$R$^{12}$)$_q$, (CR$^{11}$R$^{12}$)$_p$-(heteroarylene)-(CR$^{11}$R$^{12}$)$_q$, (CR$^{11}$R$^{12}$)$_p$O(CR$^{11}$R$^{12}$)$_q$, (CR$^{11}$R$^{12}$)$_p$S(CR$^{11}$R$^{12}$)$_q$, wherein said C$_{1-8}$ alkylene, C$_{2-8}$ alkenylene, C$_{2-8}$ alkynylene, cycloalkylene, arylene, heterocycloalkylene, or heteroarylene, is optionally substituted with 1, 2, or 3 substituents independently selected from D$^4$.

In some embodiments, Y is C$_{1-8}$ alkylene, C$_{2-8}$ alkenylene, C$_{2-8}$ alkynylene, or (CR$^{11}$R$^{12}$)$_p$—(C$_{3-10}$ cycloalkylene)-$(CR^{11}R^{12})_q$, wherein said $C_{1-8}$ alkylene, $C_{2-8}$ alkenylene, $C_{2-8}$ alkynylene, or cycloalkylene, is optionally substituted with 1, 2, or 3 substituents independently selected from -$D^1$-$D^2$-$D^3$-$D^4$.

In some embodiments, Y is $C_{1-8}$ alkylene, $C_{2-8}$ alkenylene, $C_{2-8}$ alkynylene, or $(CR^{11}R^{12})_p$—$(C_{3-10}$ cycloalkylene)-$(CR^{11}R^{12})_q$, wherein said $C_{1-8}$ alkylene, $C_{2-8}$ alkenylene, $C_{2-8}$ alkynylene, or cycloalkylene, is optionally substituted with 1, 2, or 3 substituents independently selected from $D^4$.

In some embodiments, Y is $C_{1-8}$ alkylene, $C_{2-8}$ alkenylene, or $C_{2-8}$ alkynylene, each optionally substituted with 1, 2, or 3 substituents independently selected from -$D^1$-$D^2$-$D^3$-$D^4$.

In some embodiments, Y is $C_{1-8}$ alkylene optionally substituted with 1, 2, or 3 substituents independently selected from -$D^1$-$D^2$-$D^3$-$D^4$.

In some embodiments, Y is $C_{1-8}$ alkylene optionally substituted with 1, 2, or 3 substituents independently selected from $D^4$.

In some embodiments, Y is $C_{1-8}$ alkylene, $C_{2-8}$ alkenylene, $C_{2-8}$ alkynylene, $(CR^{11}R^{12})_pO$—$(CR^{11}R^{12})_q$, $(CR^{11}R^{12})_pS(CR^{11}R^{12})_q$, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_pOC(O)NR^c(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene is optionally substituted with 1, 2, or 3 substituents independently selected from halo, OH, CN, amino, $C_{1-4}$ alkylamino, and $C_{2-8}$ dialkylamino.

In some embodiments, Y is $C_{1-8}$ alkylene, $C_{2-8}$ alkenylene, $C_{2-8}$ alkynylene, $(CR^{11}R^{12})_p$—$(C_{3-10}$cycloalkylene)-$(CR^{11}R^{12})_q$, $(CR^{11}R^{12})_p$-(arylene)-$(CR^{11}R^{12})_q$, $(CR^{11}R^{12})_p$—$(C_{1-10}$ heterocycloalkylene)-$(CR^{11}R^{12})_q$, $(CR^{11}R^{12})_p$-(heteroarylene)-$(CR^{11}R^{12})_q$, $(CR^{11}R^{12})_pO(CR^{11}R^{12})_q$, $(CR^{11}R^{12})_p$—$(CR^{11}R^{12})_q$, $(CR^{11}R^{12})_pC(O)(CR^{11}R^{12})_q$, $(CR^{11}R^{12})_pC(O)NR^c(CR^{11}R^{12})_q$, $(CR^{11}R^{12})_pC(O)O(CR^{11}R^{12})_q$, $(CR^{11}R^{12})_pOC(O)(CR^{11}R^{12})_q$, $(CR^{11}R^{12})_pOC(O)NR^c(CR^{11}R^{12})_q$, $(CR^{11}R^{12})_pNR^c(CR^{11}R^{12})_q$, $(CR^{11}R^{12})_pNR^cC(O)NR^d(CR^{11}R^{12})_q$, $(CR^{11}R^{12})_pS(O)(CR^{11}R^{12})_q$, $(CR^{11}R^{12})_pS(O)NR^c(CR^{11}R^{12})_q$, $(CR^{11}R^{12})_pS(O)_2(CR^{11}R^{12})_q$, or $(CR^{11}R^{12})_pS(O)_2NR^c(CR^{11}R^{12})_q$, wherein said $C_{1-8}$ alkylene, $C_{2-8}$ alkenylene, $C_{2-8}$ alkynylene, cycloalkylene, arylene, heterocycloalkylene, or heteroarylene, is optionally substituted with 1, 2, or 3 substituents independently selected from halo, OH, CN, amino, $C_{1-4}$ alkylamino, and $C_{2-8}$ dialkylamino.

In some embodiments, p is 0.
In some embodiments, p is 1.
In some embodiments, p is 2.
In some embodiments, q is 0.
In some embodiments, q is 1.
In some embodiments, q is 2.
In some embodiments, one of p and q is 0 and the other of p and q is 1, 2, or 3.

In some embodiments, Z is H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$))R^b$, and $S(O)_2NR^cR^d$, wherein said $C_{1-8}$alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl$))R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl, cycloalkyl, heteroaryl, or heterocycloalkyl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl or heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is aryl or heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $s(O)NR^cR^d$, $S(O)_2R^b$, $NR^cS(O)_2R^b$, and $S(O)_2NR^cR^d$.

In some embodiments, Z is phenyl or 5- or 6-membered heteroaryl, each optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, and $S(O)_2NR^cR^d$.

In some embodiments, Z is phenyl optionally substituted with 1, 2, 3, 4, 5, or 6 substituents selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is phenyl optionally substituted with 1, 2, 3, 4, 5, or 6 substituents selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is cycloalkyl or heterocycloalkyl, each optionally substituted with 1, 2, 3, 4, 5, or 6 substituents selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is cycloalkyl or heterocycloalkyl, each optionally substituted with 1, 2, 3, 4, 5, or 6 substituents selected from halo, C$_{1-4}$ alkyl, C$_{2-4}$ alkenyl, C$_{2-4}$ alkynyl, C$_{1-4}$ haloalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^1$)NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is cyclopropyl, cyclobutyl, cyclopentyl, cyclohexyl, or cycloheptyl, each optionally substituted with 1, 2, 3, 4, 5, or 6 substituents selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is C$_{1-8}$ alkyl, C$_{2-8}$ alkenyl, or C$_{2-8}$ alkynyl, each optionally substituted with 1, 2, 3, 4, 5, or 6 substituents selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$) NR$^c$R$^d$, NR$_c$C(=NR$^i$)NR$^c$R$^d$, S(O)R$^b$, s(O)NR$^c$R$^d$, S(O)$_2$R$^b$, NR$^c$S(O)$_2$R$^b$, and S(O)$_2$NR$^c$R$^d$.

In some embodiments, Z is C$_{1-8}$ alkyl, C$_{2-8}$ alkenyl, or C$_{2-8}$ alkynyl, each optionally substituted with 1, 2, 3, 4, 5, or 6 substituents selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^i$)NR$^c$R$^d$, NR$^c$C(=NR$^i$)NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is aryl, cycloalkyl, heteroaryl, or heterocycloalkyl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is aryl, cycloalkyl, heteroaryl, or heterocycloalkyl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is aryl or heteroaryl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is aryl or heteroaryl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$ R$^b$, NR$^c$S(O)$_2$R$^b$, and S(O)$_2$NR$^c$R$^d$.

In some embodiments, Z is phenyl or 5- or 6-membered heteroaryl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is phenyl or 5- or 6-membered heteroaryl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is phenyl optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is phenyl optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is cycloalkyl or heterocycloalkyl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is cycloalkyl or heterocycloalkyl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is C$_{1-8}$ alkyl, C$_{2-8}$ alkenyl, or C$_{2-8}$ alkynyl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is C$_{1-8}$ alkyl, C$_{2-8}$ alkenyl, or C$_{2-8}$ alkynyl, each optionally substituted with 1, 2, 3, 4, 5, or 6 substituents independently selected from halo, C$_{1-4}$ alkyl, C$_{2-4}$ alkenyl, C$_{2-4}$ alkynyl, C$_{1-4}$ haloalkyl, C$_{1-4}$, hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is C$_{1-8}$ alkyl, C$_{2-8}$ alkenyl, C$_{2-8}$ alkynyl, aryl, cycloalkyl, heteroaryl, or heterocycloalkyl, each optionally substituted with 1, 2, 3, 4, 5, or 6 substituents independently selected from halo, C$_{1-4}$ alkyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, C(O)NR$^c$R$^d$, C(O)OR$^a$, NR$^c$R$^d$, NR$^c$C(O)R$^b$, and S(O)$_2$R$^b$.

In some embodiments, Z is C$_{1-8}$ alkyl, C$_{2-8}$ alkenyl, C$_{2-8}$ alkynyl, aryl, cycloalkyl, heteroaryl, or heterocycloalkyl, each optionally substituted with 1, 2, 3, 4, 5, or 6 substituents independently selected from halo, C$_{1-4}$ alkyl, C$_{1-4}$ haloalkyl, C$_{1-4}$ hydroxyalkyl, C$_{1-4}$ cyanoalkyl, Cy$^1$, CN, NO$_2$, OR$^a$, C(O)NR$^c$R$^d$, C(O)OR$^a$, NR$^c$R$^d$, NR$^c$C(O)R$^b$, and S(O)$_2$R$^b$.

In some embodiments, Z is C$_{1-8}$ alkyl, C$_{2-8}$ alkenyl, C$_{2-8}$ alkynyl, aryl, cycloalkyl, heteroaryl, or heterocycloalkyl, each optionally substituted with 1, 2, or 3 substituents independently selected from halo, C$_{1-4}$ alkyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, C(O)NR$^c$R$^d$, C(O)OR$^a$, NR$^c$R$^d$, NR$^c$C(O)R$^b$, and S(O)$_2$R$^b$.

In some embodiments, Z is C$_{1-8}$ alkyl, C$_{2-8}$ alkenyl, C$_{2-8}$ alkynyl, aryl, cycloalkyl, heteroaryl, or heterocycloalkyl, each optionally substituted with 1, 2, or 3 substituents independently selected from halo, C$_{1-4}$ alkyl, C$_{1-4}$ haloalkyl, C$_{1-4}$ hydroxyalkyl, C$_{1-4}$ cyanoalkyl, Cy$^1$, CN, NO$_2$, OR$^a$, C(O)NR$^c$R$^d$, C(O)OR$^a$, NR$^c$R$^d$, NR$^c$C(O)R$^b$, and S(O)$_2$R$^b$.

In some embodiments, Z is substituted with at least one substituent comprising at least one CN group.

In some embodiments, Z is C$_{1-8}$ alkyl, C$_{2-8}$ alkenyl, C$_{2-8}$ alkynyl, aryl, cycloalkyl, heteroaryl, or heterocycloalkyl, each substituted with at least one CN or C$_{1-4}$ cyanoalkyl and optionally substituted with 1, 2, 3, or 5 further substituents selected from halo, C$_{1-4}$ alkyl, C$_{2-8}$ alkenyl, C$_{2-4}$ alkynyl, C$_{1-4}$ haloalkyl, halosulfanyl, C$_{1-4}$ hydroxyalkyl, C$_{1-4}$ cyanoalkyl, Cy$^1$, CN, NO$_2$, OR$^a$, SR$^a$ C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, Z is C$_{1-8}$ alkyl, C$_{2-8}$ alkenyl, C$_{2-8}$ alkynyl, aryl, cycloalkyl, heteroaryl, or heterocycloalkyl, each substituted with at least one CN or C$_{1-4}$ cyanoalkyl and optionally substituted with 1, 2, 3, or 5 further substituents selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, wherein the —(Y)$_n$—Z moiety is taken together with i) A$^2$ to which said moiety is attached, ii) R$^5$ or R$^6$ of either T or V, and iii) the C or N atom to which said R$^5$ or R$^6$ of either T or V is attached to form a 4- to 20-membered aryl, cycloalkyl, heteroaryl, or heterocycloalkyl ring fused to the 5-membered ring formed by A$^1$, A$^2$, U, T, and V, wherein said 4- to 20-membered aryl, cycloalkyl, heteroaryl, or heterocycloalkyl ring is optionally substituted by 1, 2, 3, 4, or 5 substituents independently selected from —(W)$_m$-Q.

In some embodiments, wherein the —(Y)$_n$—Z moiety is taken together with i) A$^2$ to which said moiety is attached, ii) R$^5$ or R$^6$ of either T or V, and iii) the C or N atom to which said R$^5$ or R$^6$ of either T or V is attached to form a 4- to 8-membered aryl, cycloalkyl, heteroaryl, or heterocycloalkyl ring fused to the 5-membered ring formed by A$^1$, A$^2$, U, T, and V, wherein said 4- to 8-membered aryl, cycloalkyl, heteroaryl, or heterocycloalkyl ring is optionally substituted by 1, 2, 3, 4, or 5 substituents independently selected from —(W)$_m$-Q.

In some embodiments, the —(Y)$_n$—Z moiety is taken together with i) A$^2$ to which said moiety is attached, ii) R$^5$ or R$^6$ of either T or V, and iii) the C or N atom to which said R$^5$ or R$^6$ of either T or V is attached to form a 6-membered aryl, cycloalkyl, heteroaryl, or heterocycloalkyl ring fused to the 5-membered ring formed by A$^1$, A$^2$, U, T, and V, wherein said 6-membered aryl, cycloalkyl, heteroaryl, or heterocycloalkyl ring is optionally substituted by 1, 2, or 3 substituents independently selected from halo, CN, NO$_2$, C$_{1-8}$ alkyl, C$_{2-8}$ alkenyl, C$_{2-8}$ alkynyl, C$_1$-8 haloalkyl, aryl, cycloalkyl, heteroaryl, or heterocycloalkyl wherein said C$_{1-8}$ alkyl, C$_{2-8}$ alkenyl, C$_{2-8}$ alkynyl, C$_{1-8}$ haloalkyl, aryl, cycloalkyl, heteroaryl, or heterocycloalkyl is optionally substituted by 1, 2 or 3 CN.

In some embodiments, Cy$^1$ and Cy$^2$ are independently selected from aryl, heteroaryl, cycloalkyl, and heterocycloalkyl, each optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ cyanoalkyl, CN, NO$_2$, OR$^{a''}$, SR$^{a''}$, C(O)R$^{b''}$, C(O)NR$^{c''}$R$^{d''}$, C(O)OR$^{a''}$, —OC(O)R$^{b''}$, OC(O)NR$^{c''}$ NR$^{c''}$C(O)R$^{b''}$, NR$^{c''}$C(O)OR$^{a''}$, S(O)R$^{b''}$, S(O)NR$^{c''}$R$^{d''}$, —S(O)$_2$R$^{b''}$, and S(O)$_2$NR$^{c''}$R$^{d''}$.

In some embodiments, Cy$^1$ and Cy$^2$ are independently selected from aryl, heteroaryl, cycloalkyl, and heterocycloalkyl, each optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$, NR$^{c''}$C(O)R$^{b''}$, NR$^{c''}$C(O)OR$^{a''}$S(O)R$^{b''}$, S(O)NR$^{c''}$R$^{d''}$, S(O)$_2$R$^{b''}$ and S(O)$_2$NR$^{c''}$R$^{d''}$.

In some embodiments, Cy$^1$ and Cy$^2$ are independently selected from cycloalkyl and heterocycloalkyl, each optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$OC(O)NR$^{c''}$, NR$^{c''}$C(O)R$^{b''}$, NR$^{c''}$C(O)OR$^{a''}$, S(O)R$^{b''}$, S(O)NR$^{c''}$R$^{d''}$, S(O)$_2$R$^{b''}$, and S(O)$_2$NR$^{c''}$R$^{d''}$.

In some embodiments, Cy$^1$ and Cy$^2$ are independently selected from cycloalkyl optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{b''}$, NR$^{c''}$C(O)OR$^{a''}$S(O)R$^{b''}$, S(O)NR$^{c''}$R$^{d''}$, S(O)$_2$R$^{b''}$, and S(O)$_2$NR$^{c''}$R$^{d''}$.

In some embodiments, $R^1$, $R^2$, $R^3$, and $R^4$ are independently selected from H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^7$, $C(O)R^8$, $C(O)NR^9R^{10}$, $C(O)OR^7OC(O)R^8$, $OC(O)NR^9R^{10}$, $NR^9R^{10}$, $NR^9C(O)R^8$, $NR^cC(O)OR^7$, $S(O)R^8$, $S(O)NR^9R^{10}$, $S(O)_2R^8$, $NR^9S(O)_2R^8$, and $S(O)_2NR^9R^{10}$.

In some embodiments, $R^1$, $R^2$, $R^3$, and $R^4$ are independently selected from H, halo, and $C_{1-4}$ alkyl.

In some embodiments, $R^1$, $R^2$, $R^3$, and $R^4$ are each H.

In some embodiments, $R^1$ is H, halo, or $C_{1-4}$ alkyl.

In some embodiments, $R^5$ is H, halo, $C_{1-4}$ alkyl, $C_{2-4}$ alkenyl, $C_{2-4}$ alkynyl, $C_{1-4}$ haloalkyl, CN, $NO_2$, $OR^7$, $SR^7$, $C(O)R^8$, $C(O)NR^9R^{10}$, $C(O)OR^7$, $OC(O)R^8$, $OC(O)NR^9R^{10}$, $NR^9R^{10}$, $NR^9C(O)R^8$, $NR^9C(O)OR^7$, $S(O)R^8$, $S(O)NR^9R^{10}$, $S(O)_2R^8$, $NR^9S(O)_2R^8$, or $S(O)_2NR^9R^{10}$.

In some embodiments, $R^5$ is H, halo, $C_{1-4}$ alkyl, $C_{1-4}$ haloalkyl, halosulfanyl, CN, or $NR^9R^{10}$.

In some embodiments, $R^5$ is H, halo, $C_{1-4}$ alkyl, $C_{1-4}$ haloalkyl, CN, or $NR^9R^{10}$.

In some embodiments, $R^5$ is H.

In some embodiments, $R^6$ is H or $C_{1-4}$ alkyl.

In some embodiments, $R^6$ is H.

In some embodiments, $R^{11}$ and $R^{12}$ are independently selected from H, halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$ $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl)$R^b$, and $S(O)_2NR^cR^d$, wherein said $C_{1-8}$ alkyl, $C_{2-8}$ alkenyl, or $C_{2-8}$ alkynyl, is optionally substituted with 1, 2, 3, 4, 5, or 6 substituents independently selected from halo, $C_{1-4}$ alkyl, $C_{2-4}$ alkenyl, $C_{2-4}$ alkynyl, $C_{1-4}$ haloalkyl, halosulfanyl, $C_{1-4}$ hydroxyalkyl, $C_{1-4}$ cyanoalkyl, $Cy^1$, CN, $NO_2$, $OR^a$, $SR^a$ $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $S(O)R^b$, $S(O)NR^cR^d$, $S(O)_2R^b$, $NR^cS(O)_2R^b$, $C(=NOH)R^b$, $C(=NO(C_{1-6}$ alkyl))$R^b$, and $S(O)_2NR^cR^d$.

In some embodiments, $R^{11}$ and $R^{12}$ are independently selected from H, halo, OH, CN, $(C_{1-4})$alkyl, $(C_{1-4})$haloalkyl, halosulfanyl, SCN, $(C_{2-4})$alkenyl, $(C_{2-4})$alkynyl, $(C_{1-4})$hydroxyalkyl, $(C_{1-4})$cyanoalkyl, aryl, heteroaryl, cycloalkyl, and heterocycloalkyl.

In some embodiments, $R^{11}$ and $R^{12}$ are independently selected from H, halo, OH, CN, $(C_{1-4})$alkyl, $(C_{1-4})$haloalkyl, $(C_{2-4})$alkenyl, $(C_{2-4})$alkynyl, $(C_{1-4})$hydroxyalkyl, $(C_{1-4})$cyanoalkyl, aryl, heteroaryl, cycloalkyl, and heterocycloalkyl.

In an embodiment, the JAK-2 inhibitor is ruxolitinib (available from Incyte Corp. and Novartis AG). In an embodiment, the JAK-2 inhibitor is ruxolitinib phosphate (available from Incyte Corp. and Novartis AG). In an embodiment, the JAK-2 inhibitor is (R)-3-(4-(7H-pyrrolo[2,3-d]pyrimidin-4-yl)-1H-pyrazol-1-yl)-3-cyclopentylpropanenitrile. In an embodiment, the JAK-2 inhibitor is the phosphate salt of (R)-3-(4-(7H-pyrrolo[2,3-d]pyrimidin-4-yl)-1H-pyrazol-1-yl)-3-cyclopentylpropanenitrile. In an embodiment, the JAK-2 inhibitor is (3R)-3-cyclopentyl-3-[4-(7H-pyrrolo[2,3-d]pyrimidin-4-yl)-1H-pyrazol-1-yl]propanenitrile. In an embodiment, the JAK-2 inhibitor has the chemical structure shown in Formula (XXX):

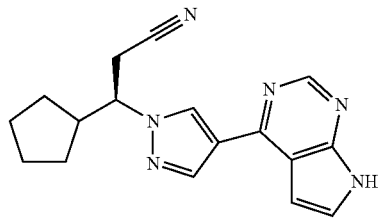

Formula (XXX)

or a pharmaceutically acceptable salt, solvate, hydrate, cocrystal, or prodrug thereof. The preparation of this compound is described in U.S. Pat. Nos. 8,604,043, 7,834,022, 8,486,902, 8,530,485, 7,598,257, 8,541,425, and 8,410,265 and U.S. Patent Application Publication Nos. 2010/0298355 A1, 2008/0312258 A1, 2011/0082159 A1, 2011/0086810 A1, 2013/0345157 A1, 2014/0018374 A1, 2014/0005210 A1, 2011/0223210 A1, 2011/0224157 A1, 2007/0135461 A1, 2010/0022522 A1, 2013/0253193 A1, 2013/0253191 A1, 2013/0253190 A1, 2010/0190981 A1, 2013/0338134 A1, 2008/0312259 A1, 2014/0094477 A1, and 2014/0094476 A1, the disclosures of which are incorporated by reference herein. In an embodiment, the JAK-2 inhibitor is a compound selected from the structures disclosed in U.S. Pat. Nos. 8,604,043, 7,834,022, 8,486,902, 8,530,485, 7,598,257, 8,541,425, and 8,410,265 and U.S. Patent Application Publication Nos. 2010/0298355 A1, 2008/0312258 A1, 2011/0082159 A1, 2011/0086810 A1, 2013/0345157 A1, 2014/0018374 A1, 2014/0005210 A1, 2011/0223210 A1, 2011/0224157 A1, 2007/0135461 A1, 2010/0022522 A1, 2013/0253193 A1, 2013/0253191 A1, 2013/0253190 A1, 2010/0190981 A1, 2013/0338134 A1, 2008/0312259 A1, 2014/0094477 A1, and 2014/0094476 A1, the disclosures of which are incorporated by reference herein.

Ruxolitinib may be prepared according to the procedures given in the references above, or by the procedure of Example 67 of U.S. Pat. No. 7,598,257, the disclosure of which is specifically incorporated by reference herein. Briefly, the preparation is as follows:

Step 1. (2E)- and (2Z)-3-Cyclopentylacrylonitrile. To a solution of 1.0 M potassium tert-butoxide in THF (235 mL) at 0° C. was added dropwise a solution of diethyl cyanomethylphosphonate (39.9 mL, 0.246 mol) in TBF (300 mL). The cold bath was removed and the reaction was warmed to room temperature followed by recooling to 0° C., at which time a solution of cyclopentanecarbaldehyde (22.0 g, 0.224 mol) in THF (60 mL) was added dropwise. The bath was removed and the reaction warmed to ambient temperature and stirred for 64 hours. The mixture was partitioned between diethyl ether and water, the aqueous was extracted with three portions of ether, followed by two portions of ethyl acetate. The combined extracts were washed with brine, then dried over sodium sulfate, filtered and concentrated in vacuo to afford a mixture containing 24.4 g of olefin isomers which was used without further purification (89%). $^1$H NMR (400 MHz, CDCl3): δ 6.69 (dd, 1H, trans olefin), 6.37 (t, 1H, cis olefin), 5.29 (dd, 1H, trans olefin), 5.20 (d, 1H, cis olefin), 3.07-2.95 (m, 1H, cis product), 2.64-2.52 (m, 1H, trans product), 1.98-1.26 (m, 16H).

Step 2. (3R)- and (3 S)-3-Cyclopentyl-3-[4-(7-[2-(trimethylsilyl)ethoxy]methyl-7H-pyrrolo[2,3-c/]-pyrimidin-4-yl)-1H-pyrazol-1-yl]propanenitrile. To a solution of 4-(1H-pyrazol-4-yl)-7-[2-(trimethylsilyl)ethoxy]methyl-7H-pyrrolo[2,3-d]-pyrimidine (15.0 g, 0.0476 mol) in ACN (300 mL) was added 3-cyclopentylacrylonitrile (15 g, 0.12 mol)

(as a mixture of cis and trans isomers), followed by DBU (15 mL, 0.10 mol). The resulting mixture was stirred at room temperature overnight. The ACN was evaporated. The mixture was diluted with ethyl acetate, and the solution was washed with 1.0 N HCl. The aqueous layer was back-extracted with three portions of ethyl acetate. The combined organic extracts were washed with brine, dried over sodium sulfate, filtered and concentrated. The crude product was purified by silica gel chromatography (gradient of ethyl acetate/hexanes) to yield a viscous clear syrup, which was dissolved in ethanol and evaporated several times to remove ethyl acetate, to afford 19.4 g of racemic adduct (93%). The enantiomers were separated by preparative-HPLC, (OD-H column, 15% ethanol/hexanes) and used separately in the next step to generate their corresponding final product. The final products (see Step 3) stemming from each of the separated enantiomers were found to be active JAK inhibitors; however, the final product stemming from the second peak to elute from the preparative-HPLC was more active than its enantiomer. The products may be isolated by preparative HPLC or other means known to those of skill in the art for use in Step 3 below. $^1$H NMR (300 MHz, CDCl3): δ 8.85 (s, 1H), 8.32 (s, 2H), 7.39 (d, 1H), 6.80 (d, 1H), 5.68 (s, 2H), 4.26 (dt, 1H), 3.54 (t, 2H), 3.14 (dd, 1H), 2.95 (dd, 1H), 2.67-2.50 (m, 1H), 2.03-1.88 (m, 1H), 1.80-1.15 (m, 7H), 0.92 (t, 2H), −0.06 (s, 9H); MS(ES): 437 (M+1).

Step 3. To a solution of 3-cyclopentyl-3-[4-(7-[2-(trimethylsilyl)ethoxy]methyl-7H-pyrrolo[2,3-d]-pyrimidin-4-yl)-1H-pyrazol-1-yl]propanenitrile (6.5 g, 0.015 mol, R or S enantiomer as isolated above) in DCM (40 mL) was added TFA (16 mL) and this was stirred for 6 hours. The solvent and TFA were removed in vacuo. The residue was dissolved in DCM and concentrated using a rotary evaporator two further times to remove as much as possible of the TFA. Following this, the residue was stirred with ethylenediamine (4 mL, 0.06 mol) in methanol (30 mL) overnight. The solvent was removed in vacuo, water was added and the product was extracted into three portions of ethyl acetate. The combined extracts were washed with brine, dried over sodium sulfate, decanted and concentrated to afford the crude product which was purified by flash column chromatography (eluting with a gradient of methanol/DCM). The resulting mixture was further purified by preparative-HPLC/MS ($C_{1-8}$ eluting with a gradient of ACN/H2O containing 0.15% NH$_4$OH) to afford product (2.68 g, 58%). $^1$H NMR (400 MHz, D6-dmso): δ 12.11 (br s, 1H), 8.80 (s, 1H), 8.67 (s, 1H), 8.37 (s, 1H), 7.60 (d, 1H), 6.98 (d, 1H), 4.53 (dt, 1H), 3.27 (dd, 1H), 3.19 (dd, 1H), 2.48-2.36 (m, 1H), 1.86-1.76 (m, 1H), 1.68-1.13 (m, 7H); MS(ES): 307 (M+1).

Ruxolitinib prepared according to the steps above, or any other procedure, may be used as its free base for the compositions and methods described herein. Ruxolitinib may also be used in a salt form. For example, a crystalline phosphoric acid salt of (R)-3-(4-(7H-pyrrolo[2,3-d]pyrimidin-4-yl)-1H-pyrazol-1-yl)-3-cyclopentylpropanenitrile may be prepared from the free base as follows according to the procedure given in Example 2 of U.S. Pat. No. 8,722,693, the disclosure of which is specifically incorporated herein by reference. To a test tube was added (R)-3-(4-(7H-pyrrolo[2,3-c]pyrimidin-4-yl)-1H-pyrazol-1-yl)-3-cyclopentylpropanenitrile (153.5 mg) and phosphoric acid (56.6 mg) followed by isopropyl alcohol (IPA) (5.75 mL). The resulting mixture was heated to clear, cooled to room temperature, and then stirred for another 2 hours. The precipitate was collected by filtration and the cake was washed with 0.6 mL of cold IPA. The cake was dried under vacuum to constant weight to provide the final salt product (171.7 mg). The phosphoric acid salt is a 1:1 salt by $^1$H NMR and crystallinity is confirmed by X-ray powder diffraction (XRPD). Differential scanning calorimetry (DSC) of the produce yields a sharp melting peak at about 198.7° C.

In an embodiment, the JAK-2 inhibitor is a compound of Formula (XXXI):

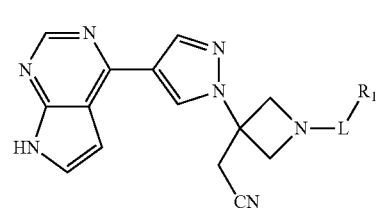

Formula (XXXI)

or a pharmaceutically acceptable salt, solvate, hydrate, cocrystal, or prodrug thereof, wherein: L is $SO_2$ or CO;
$R^1$ is $C_{1-6}$ alkyl, $C_{3-7}$ cycloalkyl, phenyl, 5- or 6-membered heteroaryl, indolyl, $NR^2R^3$, or $OR^4$, wherein said alkyl, cycloalkyl, phenyl, or heteroaryl is optionally substituted with 1, 2, or 3 substituents independently selected from F, CN, and $C_{1-4}$ alkyl;
$R^2$ and $R^3$ are independently selected from H, $C_{1-4}$ alkyl, and phenyl; and
$R^4$ is $C_{1-6}$ alkyl, phenyl, or benzyl.
In some embodiments, when L is $SO_2$, then $R^1$ is other than $OR^4$.
In some embodiments, when L is $SO_2$, then $R^1$ is $C_{1-6}$ alkyl, $C_{3-7}$ cycloalkyl, phenyl, 5- or 6-membered heteroaryl, or $NR^2R^3$, wherein said alkyl, cycloalkyl, phenyl, or heteroaryl is optionally substituted with 1, 2, or 3 substituents independently selected from F and $C_{1-4}$ alkyl.
In some embodiments, when L is CO, then $R^1$ is $C_{3-7}$ cycloalkyl, phenyl, 5- or 6-membered heteroaryl, indolyl, $NR^2R^3$, or $OR^4$, wherein said cycloalkyl, phenyl, or heteroaryl is optionally substituted with 1, 2, or 3 substituents independently selected from CN and $C_{1-4}$ alkyl.
In some embodiments, L is $SO_2$.
In some embodiments, L is CO.
In some embodiments, $R^1$ is methyl, ethyl, n-propyl, isopropyl, n-butyl, t-butyl, 2-methylprop-1-yl, 1-methylprop-1-yl, each optionally substituted with 1, 2, or 3 F.
In some embodiments, $R^1$ is $C_{1-4}$ alkyl.
In some embodiments, $R^1$ is ethyl.
In some embodiments, $R^1$ is $C_{3-7}$ cycloalkyl optionally substituted by $C_{1-4}$ alkyl.
In some embodiments, $R^1$ is phenyl optionally substituted with F, methyl, or CN.
In some embodiments, $R^1$ is 5-membered heteroaryl selected from thienyl, pyrazolyl, pyrrolyl, 1,2,4-oxadiazolyl, and isoxazolyl, each optionally substituted with $C_{1-4}$ alkyl.
In some embodiments, $R^1$ is pyridinyl.
In some embodiments, $R^1$ is $NR^2R^3$ or $OR^4$.
In some embodiments, L is $SO_2$ and $R^1$ is $C_{1-6}$ alkyl.

In an embodiment, the JAK-2 inhibitor is baricitinib (available from Incyte Corp. and Eli Lilly & Co.). In an embodiment, the JAK-2 inhibitor is 2-(3-(4-(7H-pyrrolo[2,3-d]pyrimidin-4-yl)-1H-pyrazol-1-yl)-1-(ethylsulfonyl)azetidin-3-yl)acetonitrile. In an embodiment, the JAK-2 inhibitor has the chemical structure shown in Formula (XXXII):

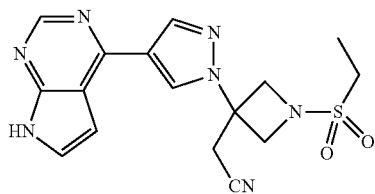

Formula (XXXII)

or a pharmaceutically acceptable salt, solvate, hydrate, cocrystal, or prodrug thereof. The preparation of this compound is described in U.S. Pat. Nos. 8,158,616 and 8,420,629, U.S. Patent Application Publication Nos. 2009/0233903 A1; 2013/0225556 A1; and, 2012/0077798 A1, and International Patent Application Publication No. WO 2014/0028756, the disclosures of these U.S. Patents and Patent Application Publications are incorporated by reference herein. In an embodiment, the JAK-2 inhibitor is a compound described in U.S. Pat. Nos. 8,158,616 and 8,420,629, U.S. Patent Application Publication Nos. 2009/0233903 A1; 2013/0225556 A1; and, 2012/0077798 A1, and International Patent Application Publication No. WO 2014/0028756, the disclosures of these U.S. Patents and Patent Application Publications are incorporated by reference herein.

In an embodiment, the JAK-2 inhibitor is a compound of Formula (XXXIII):

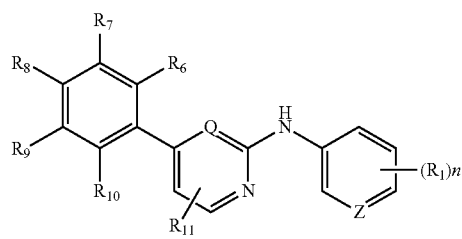

Formula (XXXIII)

or a pharmaceutically acceptable salt, solvate, hydrate, cocrystal, or prodrug thereof, wherein:

Q and Z are independently selected from N and CR'; n is 1, 2 or 3;

$R^1$ is independently selected from hydrogen, halogen, $R^2$, $OR^2$, OH, $R^4$, $OR^4$, CN, $CF_3$, $(CH_2)_nN(R^2)_2$, $NO_2$, $R^2R^4$, $SO_2R^4$, $NR^2SO_2R^3$, $COR^4$, $NR^2COR^3$, $CO_2H$, $CO_2R^2$, $NR^2COR^4$, $R^2CN$, $R^2CN$, $R^2OH$, $R^2OR^3$ and $OR^5R^4$; or two $R^1$ substituents together with the carbons which they are attached to form an unsaturated 5 or 6 membered heterocyclyl;

$R^2$ is substituted or unsubstituted $C_{1-4}$alkyl or substituted or unsubstituted $C_{1-4}$ alkylene where up to 2 carbon atoms can be optionally replaced with CO, $NR^Y$, $CONR^Y$, S, $SO_2$ or O;

$R^3$ is $R^2$, $C_{2-4}$ alkenyl or substituted or unsubstituted aryl;

$R^4$ is $NH_2$, $NHR^2$, $N(R^1)_2$, substituted or unsubstituted morpholino, substituted or unsubstituted thiomorpholino, substituted or unsubstituted thiomorpholino-1-oxide, substituted or unsubstituted thiomorpholino-1,1-dioxide, substituted or unsubstituted piperazinyl, substituted or unsubstituted piperidinyl, substituted or unsubstituted pyridinyl, substituted or unsubstituted pyrrolidinyl, substituted or unsubstituted pyrrolyl, substituted or unsubstituted oxazolyl, substituted or unsubstituted imidazolyl, substituted or unsubstituted tetrahydrofuranyl and substituted or unsubstituted tetrahydropyranyl;

$R^5$ is substituted or unsubstituted $C_{1-4}$alkylene;

$R^6$-$R^{10}$ are independently selected from H, $R^XCN$, halogen, substituted or unsubstituted $C_M$alkyl, $OR^1$, $CO_2R^1$, N(R')$_2$, $NO_2$, $CON(R')_{2J}$ $SO_2N(R^Y)_2$, $N(SO_2R^\wedge_2$, substituted or unsubstituted piperazinyl, $N(R^Y)SO_2R^2$ and $CF_3$, $R^x$ is absent or substituted or unsubstituted $C_{1-6}$alkylene wherein up to 2 carbon atoms can be optionally replaced with CO, $NSO_2R^1$, $NR^Y$, $CONR^Y$, S, $SO_2$ or O; $R^y$ is H or substituted or unsubstituted $C_{1-4}$ alkyl; and $R^{11}$ is selected from H, halogen, substituted or unsubstituted $C_{1-4}$ alkyl, $OR^2$, $CO_2R^2$, CN, $CON(R^1)_2$ and $CF_3$, or an enantiomer thereof.

In a preferred embodiment, the JAK-2 inhibitor is momelotinib (Gilead Sciences). Momelotinib is also known as CYT-387. In a preferred embodiment, the JAK-2 inhibitor is N-(cyanomethyl)-4-(2-((4-morpholinophenyl)amino)pyrimidin-4-yl)benzamide. In a preferred embodiment, the JAK-2 inhibitor is a compound of Formula (XXXIV):

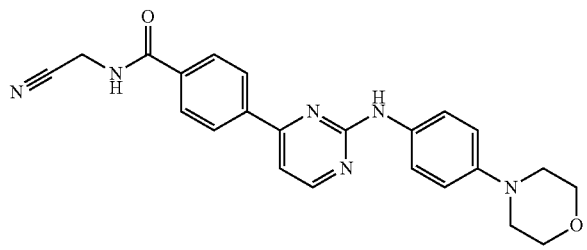

Formula (XXXIV)

or a pharmaceutically acceptable salt, solvate, hydrate, cocrystal, or prodrug thereof. The preparation of this compound is described in U.S. Pat. No. 8,486,941 and U.S. Patent Application Publication Nos. 2010/0197671 A1; 2014/0005180 A1; 2014/0011803 A1; and, 2014/0073643 A1, the disclosures of which are incorporated by reference herein. In an embodiment, the JAK-2 inhibitor is a compound described in U.S. Pat. No. 8,486,941 and U.S. Patent Application Publication Nos. 2010/0197671 A1; 2014/0005180 A1; 2014/0011803 A1; and, 2014/0073643 A1, the disclosures of which are incorporated by reference herein.

In an embodiment, the JAK-2 inhibitor is a compound of Formula (XXXV):

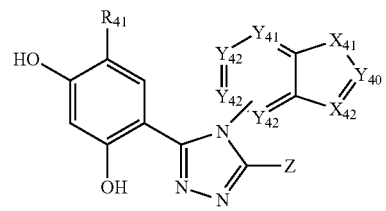

Formula (XXXV)

or a tautomer thereof, or a clathrate thereof, or a pharmaceutically acceptable salt, solvate, hydrate, cocrystal, or prodrug thereof, wherein:

$X_{41}$ is O, S, or $NR_{42}$;

$X_{42}$ is $CR_{44}$ or N;

$Y_{40}$ is N or $CR_{43}$;

$Y_{41}$ is N or $CR_{45}$;

$Y_{42}$, for each occurrence, is independently N, C or $CR_{46}$;

Z is OH SH, or $NHR_7$;

$R_{41}$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy or cycloalkoxy, a haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC_{(8)}OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, $SS(O)_pNR_{10}R_{11}$, —$OP(O)(OR_7)_2$, or —$SP(O)(OR_7)_2$;

$R_{42}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, —$C(O)R_7$, —$(CH_2)_mC(O)OR_7$, —$C(O)OR_7$, —$OC(O)R_7$, —$C(O)NR_{10}R_{11}$, —$S(O)_pR_7$, —$S(O)_pOR_7$, or $S(O)_pNR_{10}R_{11}$;

$R_{43}$ and $R_{44}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, —$S(O)_pNR_{10}R_{11}$, or $R_{43}$ and $R_{44}$ taken together with the carbon atoms to which they are attached form an optionally substituted cycloalkenyl, an optionally substituted aryl, an optionally substituted heterocyclyl, or an optionally substituted heteroaryl;

$R_{45}$ is —H, —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCR_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_1$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(N_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, or $NR_7C(N_8)NR_{10}R_{11}$;

$R_{46}$, for each occurrence, is independently, selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$;

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{26}$, for each occurrence is, is independently, a lower alkyl;
p, for each occurrence, is, independently, 1 or 2; and
m, for each occurrence, is independently, 1, 2, 3, or 4.

In an embodiment, the JAK-2 inhibitor is a compound of Formula (XXXVI):

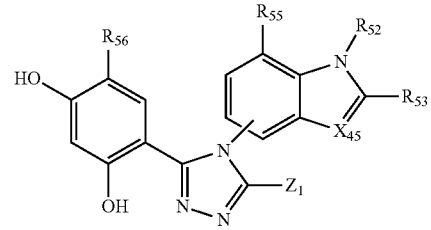

Formula (XXXVI)

or a tautomer thereof, or a clathrate thereof, or a pharmaceutically acceptable salt, solvate, hydrate, cocrystal, or prodrug thereof, wherein:

$X_{45}$ is $CR_{54}$ or N;
$Z_1$ is —OH or —SH;
$R_{56}$ is selected from the group consisting of —H, methyl, ethyl, isopropyl, and cyclopropyl;
$R_{52}$ is selected from the group consisting of —H, methyl, ethyl, n-propyl, isopropyl, n-butyl, n-pentyl, n-hexyl, —$(CH_2)_2OCH_3$, —$CH_2C(O)OH$, and —$C(O)N(CH_3)_2$;
$R_{53}$ and $R_{54}$ are each, independently, —H, methyl, ethyl, or isopropyl; or $R_{53}$ and $R_{54}$ taken together with the carbon atoms to which they are attached form a phenyl, cyclohexenyl, or cyclooctenyl ring; and $R_{55}$ is selected from the group consisting of —H, —OH, —OCH$_3$, and —OCH$_2$CH$_3$.

In a preferred embodiment, the JAK-2 inhibitor is ganetespib. In an embodiment, the JAK-2 inhibitor is 5-(2,4-dihydroxy-5-isopropylphenyl)-4-(1-methyl-1H-indol-5-yl)-2,4-dihydro-3H-1,2,4-triazol-3-one. In a preferred embodiment, the JAK-2 inhibitor has the chemical structure shown in Formula (XXXVII):

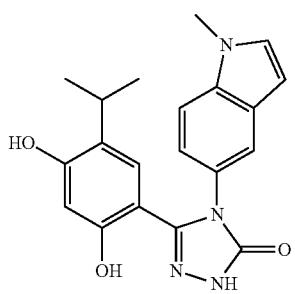

Formula (XXXVII)

or a pharmaceutically acceptable salt, solvate, hydrate, cocrystal, or prodrug thereof. The preparation of this compound is described in U.S. Pat. Nos. 7,825,148 and 8,628,752, U.S. Patent Application Publication Nos. 2006/0167070 A1; 2014/0024030 A1; 2014/0051665 A1; 2014/0045908 A1; 2012/0128665 A1; 2013/0109045 A1, and 2014/0079636 A1, and, International Patent Application Publication No. WO 2013/170182; WO 2013/028505; WO 2013/067162; WO 2013/173436; WO 2013/006864; WO 2012/162584; WO 2013/170159; WO 2013/067165; WO 2013/074594; WO 2012/162372; WO 2012/162293; and WO 2012/155063. In an embodiment, the JAK-2 inhibitor is a compound described in U.S. Pat. Nos. 7,825,148 and 8,628,752, U.S. Patent Application Publication Nos. 2006/0167070 A1; 2014/0024030 A1; 2014/0051665 A1; 2014/0045908 A1; 2012/0128665 A1; 2013/0109045 A1, and 2014/0079636 A1, and, International Patent Application Publication No. WO 2013/170182; WO 2013/028505; WO 2013/067162; WO 2013/173436; WO 2013/006864; WO 2012/162584; WO 2013/170159; WO 2013/067165; WO 2013/074594; WO 2012/162372; WO 2012/162293; and WO 2012/155063.

In a preferred embodiment, the JAK-2 inhibitor is a compound of Formula (XXXVIII):

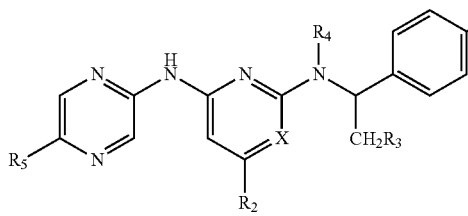

Formula (XXXVIII)

or a pharmaceutically acceptable salt, solvate, hydrate, cocrystal, or prodrug thereof, wherein the compound is defined by the following (I) or (II).

(I): X represents CH or N; 1e represents a halogen; $R^2$ represents: (1) H, (2) a halogen, (3) cyano, (4) a group represented by the following general formula [2]:

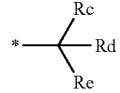

[2]

(wherein * indicates the binding position; and $R^C$, $R^D$ and $R^E$ are the same or different and each represents (a) H, or (b) alkyl optionally substituted by hydroxy or alkoxy, or alternatively two of $R^C$, $R^D$ and $R^E$ are taken together with the adjacent C to represent a N-containing saturated heterocyclic group and the other one is H, the saturated heterocyclic group optionally substituted by alkylsulfonyl), (5) a group represented by the following general formula [3]:

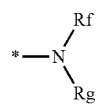

[3]

(wherein * has the same meaning as described above; and $R^F$ and $R^G$ are the same or different and each represents (a) H, (b) alkyl optionally substituted by one or two groups selected from the group consisting of hydroxy, amino, dialkylamino, a saturated cyclic amino group, alkylcarbonylamino, alkylsulfonylamino, aryl, heteroaryl optionally substituted by alkyl, tetrahydrofuranyl, and carbamoyl, (c) alkylcarbonyl, (d) alkylsulfonyl, (e) carbamoyl, or (f) heteroaryl optionally substituted by alkyl, or alternatively $R^F$ and $R^G$ are taken together with the adjacent N to represent a saturated cyclic amino group, which may optionally be substituted by one or two groups selected from the group consisting of (a) halogen, (b) cyano, (c) hydroxy, (d) alkyl optionally substituted by one or two groups selected from the group consisting of hydroxy, alkoxy, amino, alkoxycarbonylamino, alkylsulfonylamino, and alkylcarbonylamino, (e) cycloalkyl, (f) haloalkyl, (g) alkoxy, (h) oxo, (i) a group represented by the following general formula [4]:

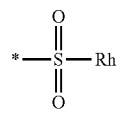

[4]

(wherein * has the same meaning as described above; and $R^H$ represents alkyl or aryl), (j) a group represented by the following general formula [5]:

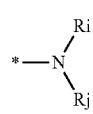

[5]

(wherein * has the same meaning as described above; and $R^I$ and $R^J$ are the same or different and each represents H, alkyl, carbamoyl, alkylcarbonyl, or alkylsulfonyl), (k) a group represented by the following general formula [6]:

(wherein * has the same meaning as described above; and $R^K$ represents alkyl, hydroxy, amino, alkylamino, dialkylamino, cycloalkylamino, (cycloalkyl)alkylamino, (hydroxyalkyl)amino, (alkoxyalkyl)amino, alkoxy, alkylsulfonylamino, or a saturated cyclic amino group), and (1) a saturated cyclic amino group optionally substituted by hydroxy; and the saturated cyclic amino group, which is formed by combining $R^F$, $R^G$ and the adjacent N, may form a spiro-linkage with a group represented by the following general formula [7A] or [7B]:

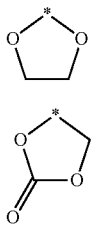

(wherein has the same meaning as described above)),
(6) a group represented by the following general formula [8]:

(wherein * has the same meaning as described above; and $R^L$ represents (a) alkyl, (b) hydroxy, (c) alkoxy, (d) saturated cyclic amino group optionally substituted by alkyl or alkylsulfonyl, or (e) an amino optionally substituted by one or two groups selected from the group consisting of alkyl, cycloalkyl, (cycloalkyl)alkyl, aralkyl; haloalkyl, dialkylaminoalkyl, alkoxyalkyl, and hydroxyalkyl),
(7) a group represented by the following general formula [9]:

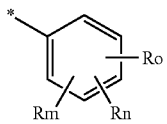

(wherein * has the same meaning as described above; and $R^M$, $R^N$ and $R^O$ are the same or different and each represents H, halogen, cyano, alkoxy, carbamoyl, sulfamoyl, monoalkylaminosulfonyl, or alkylsulfonyl, or alternatively two of $R^M$, $R^N$ and $R^O$ are taken together to represent methylenedioxy),
(8) —$OR^P$ (le represents an alkyl optionally substituted by a group selected from the group consisting of hydroxy, dialkylamino, alkoxy, tetrahydrofuranyl, and cycloalkyl, or an optionally O-containing saturated cyclic group optionally substituted by hydroxy), or
(9) a heteroaryl optionally substituted by one or two groups selected from the group consisting of cyano, halogen, hydroxy, alkoxy, alkylcarbonyl, carbamoyl, alkyl, cycloalkyl, (cycloalkyl)alkyl, aralkyl, hydroxycarbonyl and alkoxyalkyl;
$R^3$ represents H or hydroxy;
$R^2$ represents H or alkyl; and
$R^5$ represents H or alkyl;
(II): X represents —$CR^4$;
$R^4$ represents a group represented by the following general formula [10]:

(wherein * has the same meaning as described above; and $R^B$ represents (a) amino optionally substituted by one or two groups selected from the group consisting of alkyl, cycloalkyl, (cycloalkyl)alkyl, and alkoxyalkyl, (b) alkoxy, (c) hydroxy, or (d) a saturated cyclic amino group);
$R^1$ represents a halogen;
$R^2$ represents H;
$R^3$ represents E or hydroxy;
$R^4$ represents H or alkyl; and
$R^5$ represents H or alkyl.
In a preferred embodiment, the JAK-2 inhibitor is NS-018. In an embodiment, the JAK-2 inhibitor is (S)—$N^2$-(1-(4-fluorophenyl)ethyl)-6-(1-methyl-1H-pyrazol-4-yl)-$N^4$-(pyrazin-2-yl)pyrimidine-2,4-diamine. In an embodiment, the JAK-2 inhibitor has the chemical structure shown in Formula (XXXIX):

Formula (XXXIX)

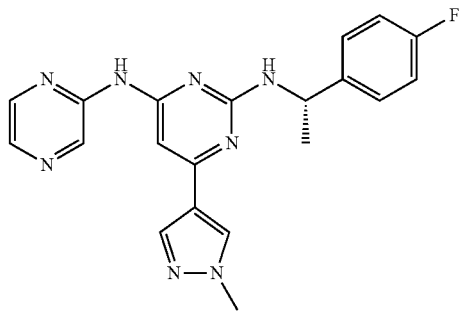

or a pharmaceutically acceptable salt, solvate, hydrate, cocrystal, or prodrug thereof. The preparation of this compound is described in U.S. Pat. Nos. 8,673,891 and 8,586,591, U.S. Patent Application Publication Nos. 2011/0288065 A1 and 2013/0131082 A1, and International Patent Application Publication No. WO 2012/020787 and WO 2012/020786, the disclosures of these U.S. Patents and Patent Application Publications are incorporated by reference herein. In an embodiment, the JAK-2 inhibitor is a compound described in U.S. Pat. Nos. 8,673,891 and 8,586,591, U.S. Patent Application Publication Nos. 2011/0288065 A1 and 2013/

0131082 A1, and International Patent Application Publication No. WO 2012/020787 and WO 2012/020786, the disclosures of these U.S. Patents and Patent Application Publications are incorporated by reference herein.

In a preferred embodiment, the JAK-2 inhibitor is a compound of Formula (XL):

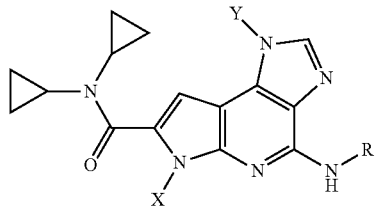

Formula (XL)

or a stereoisomer, tautomer, or pharmaceutically acceptable salt, solvate, hydrate, cocrystal, or prodrug thereof, wherein:
Y is $C_{1-4}$ alkyl;
X is $C_{1-4}$ alkyl;
R is

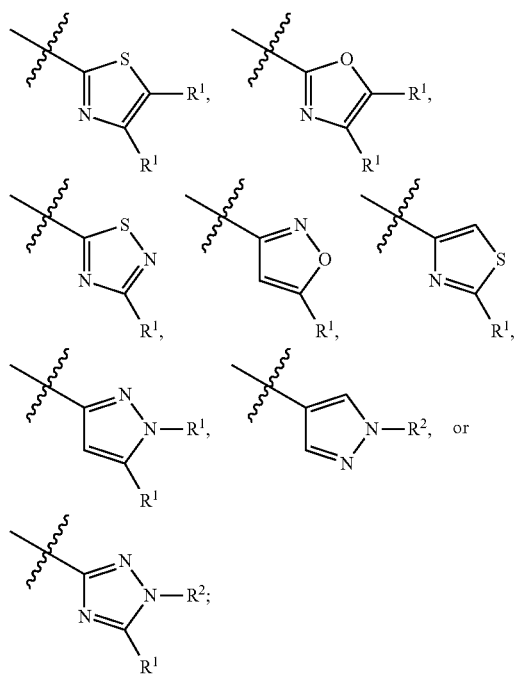

any of which are optionally fused with a 5 or 6 membered carbocycle or heterocycle having one heteroatom selected from $NR^3$ or S, said fused carbocycle or heterocycle being optionally substituted with 0-3 $R^1$.

$R^1$ is H, halo, CN, $C_{1-6}$ alkyl substituted with 0-3 $R^c$, $CF_3$, $CONR^aR^a$, $NR^aR^a$, $COOR^b$, $SO_2$—$(C_{1-4})$alkyl, $C(O)R^d$, cycloalkyl substituted with 0-3 $R^e$, furanyl, tetrahydropyranyl, or pyridinyl;

$R^2$ is absent, H, $C_{1-6}$ alkyl substituted with 0-3 $R^e$, C(O)O—$(C_{1-4})$alkyl, $SO_2$—$(C_{1-4})$alkyl, cycloalkyl substituted with 0-3 $R^e$, or tetrahydropyranyl;

$R^3$ is absent, H, or C(O)O—$(C_{1-4})$alkyl;

$R^a$ is H, $C_{1-6}$ alkyl substituted with 0-3 $R^e$, $C_{3-6}$ cycloalkyl substituted with 0-3 $R^e$, tetrahydropyranyl, or dioxotetrahydrothiophenyl;

$R^b$ is H or $C_{1-6}$ alkyl;

$R^c$ is H, halo, CN, OH, O—$(C_{1-4})$alkyl, O—$(C_{1-4})$alkyl-O—$(C_{1-4})$alkyl, $NH_2$, $N(C_{1-4}$ alkyl$)_2$, $C(O)N(C_{1-4}$alkyl$)_2$, $SO_2$—$(C_{1-4})$alkyl, or morpholinyl or piperazinyl, either of which are optionally substituted with 0-1 $C_{1-4}$ alkyl;

$R^d$ is $C_{1-6}$ alkyl, or azeridinyl, azetidinyl, pyrrolidinyl, piperidinyl, morpholinyl, piperazinyl, dioxidothiomorpholinyl or tetrahydropyranyl, any of which are substituted with 0-2 $R^e$; and $R^e$ is H, halo, CN, $C_{1-4}$ alkyl, OH, O—$(C_{1-4})$alkyl, $SO_2$—$(C_{1-4})$alkyl, NHC(O)—$(C_{1-4})$alkyl, morpholinyl, OC(O)—$(C_{1-4})$alkyl, $C(O)N(C_{1-4}$alkyl$)_2$, or O—$(C_{1-4})$alkyl-O—$(C_{1-4})$alkyl.

In another embodiment are compounds of Formula (XL), wherein:
R is:

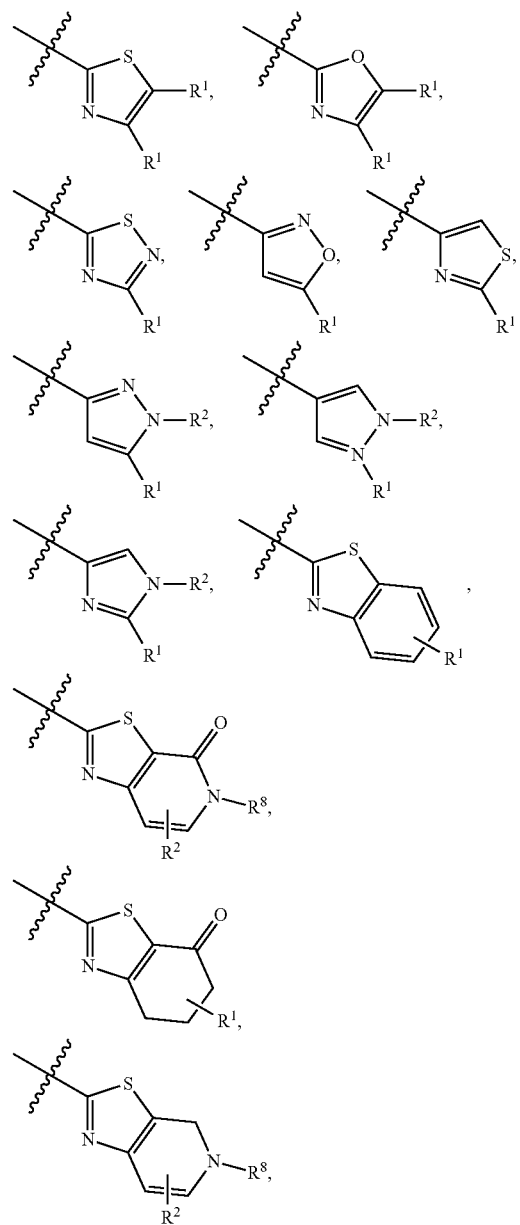

-continued

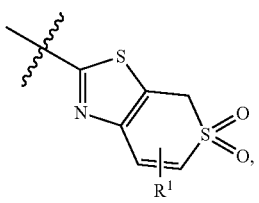

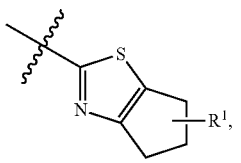 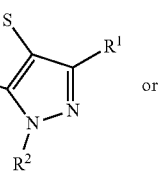

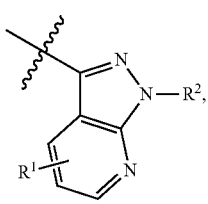

any of which are optionally substituted with 0-3 $R^1$.

In another embodiment are compounds of Formula (XL), wherein:
Y is methyl; and
X is ethyl.

In another embodiment are compounds of Formula (XL), wherein:
R is:

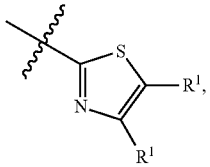 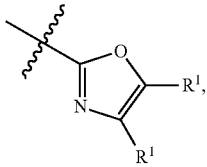

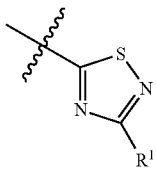 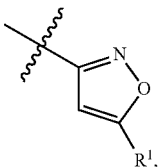

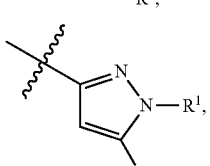 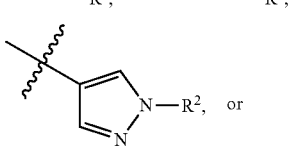

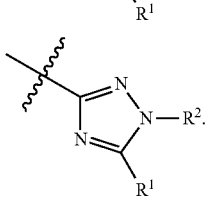

In another embodiment are compounds of Formula (XL), wherein:
R is:

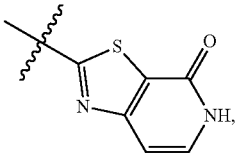

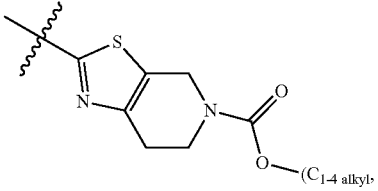

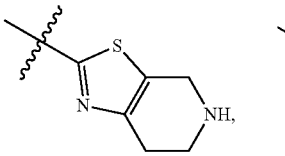

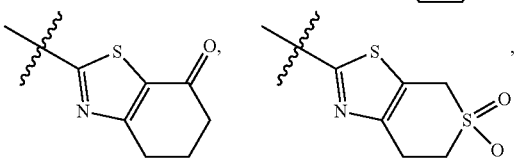

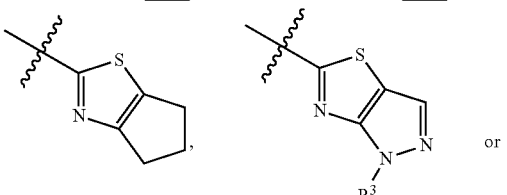

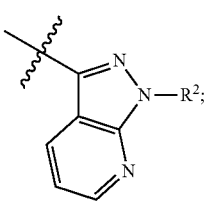

any of which are optionally substituted with 0-2 $R^1$

In another embodiment are compounds of Formula (XL), wherein
R is:

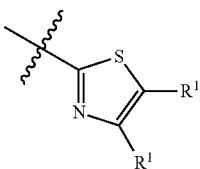

$R^1$ is H, halo, CN, $C_{1-6}$ alkyl substituted with 0-3 $R^e$, $CF_3$, $CONR^aR^a$, $COOR^b$, $SO_2$—$(C_{1-4})$alkyl, $C(O)R^d$, cycloalkyl substituted with 0-3 $R^e$, or pyridinyl;
$R^a$ is H, $C_{1-6}$ alkyl substituted with 0-3 $R^e$, $C_{3-6}$ cycloalkyl substituted with 0-3 $R^e$, tetrahydropyranyl or dioxotetrahydrothiophenyl;
$R^b$ is H or $C_{1-6}$ alkyl;
$R^e$ is H, halo, OH, O—$(C_{1-4})$alkyl, $SO_2$—$(C_{1-4})$alkyl or morpholinyl;

$R^d$ is $C_{1-6}$ alkyl, or azetidinyl, pyrrolidinyl, morpholinyl, piperazinyl or dioxidothiomorpholinyl, any of which are substituted with 0-2 $R^e$;

$R^e$ is H, halo, CN, OH, O—$(C_{1-4})$alkyl, $SO_2$—$(C_{1-4})$alkyl, NHC(O)—$(C_{1-4})$alkyl or morpholinyl.

In another embodiment are compounds of Formula (XL), wherein:

R is:

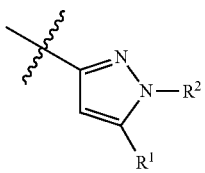

$R^1$ is H, halo, $C_{1-6}$ alkyl substituted with 0-3 $R^e$, $CF_3$, $CONR^aR^a$, $COOR^b$, $C(O)R^d$, cycloalkyl substituted with 0-3 $R^e$ or furanyl;

$R^2$ is H, $C_{1-6}$ alkyl substituted with 0-3 $R^e$, $SO_2$—$(C_{1-4})$ alkyl, cycloalkyl substituted with 0-3 $R^e$, or tetrahydropyranyl;

$R^a$ is H, or $C_{1-6}$ alkyl substituted with 0-3 $R^e$;

$R^b$ is H or $C_{1-6}$ alkyl;

$R^c$ is H, halo, CN, OH, O—$(C_{1-4})$alkyl, O—$(C_{1-4})$alkyl-O—$(C_{1-4})$alkyl, $NH_2$, $N(C_{1-4}$ alkyl$)_2$, $C(O)N(C_{1-4}$alkyl$)_2$, $SO_2$—$(C_{1-4})$alkyl, or morpholinyl or piperazinyl, either of which are optionally substituted with 0-1 $C_{1-4}$ alkyl;

$R^d$ is $C_{1-6}$ alkyl, or morpholinyl, piperazinyl or dioxidothiomorpholinyl, any of which are substituted with 0-2 $R^e$; and $R^e$ is H, $C_{1-4}$ alkyl, CN, OH, NHC(O)—$(C_{1-4})$alkyl or morpholinyl.

In another embodiment are compounds of Formula (XL), wherein:

R is:

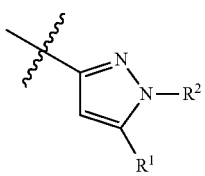

$R^1$ is $C_{1-6}$ alkyl substituted with 0-3 $R^e$; and
$R^2$ is $C_{1-6}$ alkyl.

In an embodiment, the JAK-2 inhibitor is BMS-911543. In an embodiment, the JAK-2 inhibitor is N,N-dicyclopropyl-4-((1,5-dimethyl-1H-pyrazol-3-yl)amino)-6-ethyl-1-methyl-1,6-dihydroimidazo[4,5-d]pyrrolo[2,3-b]pyridine-7-carboxamide. In an embodiment, the JAK-2 inhibitor has the chemical structure shown in Formula (XLI):

Formula (XLI)

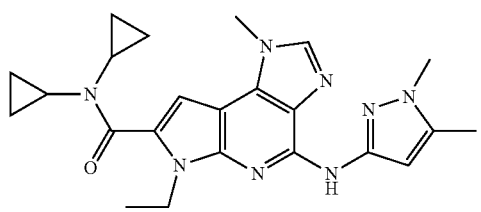

or a pharmaceutically acceptable salt, solvate, hydrate, cocrystal, or prodrug thereof. The preparation of this compound is described in U.S. Pat. Nos. 8,673,933 and 8,202,881 and U.S. Patent Application Publication Nos. 2013/0225551 A1 and 2011/0059943 A1, the disclosures of which are incorporated by reference herein. In an embodiment, the JAK-2 inhibitor is a compound described in U.S. Pat. Nos. 8,673,933 and 8,202,881 and U.S. Patent Application Publication Nos. 2013/0225551 A1 and 2011/0059943 A1, the disclosures of which are incorporated by reference herein.

In an embodiment, the JAK-2 inhibitor is gandotinib. In an embodiment, the JAK-2 inhibitor is 3-(4-chloro-2-fluorobenzyl)-2-methyl-N-(5-methyl-1H-pyrazol-3-yl)-8-(morpholinomethyl)imidazo[1,2-b]pyridazin-6-amine. In an embodiment, the JAK-2 inhibitor has the chemical structure shown in Formula (XLII):

Formula (XLII)

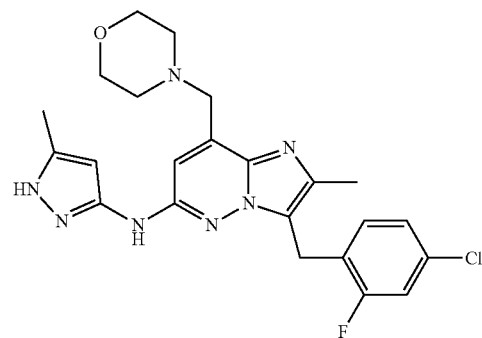

or a pharmaceutically acceptable salt, solvate, hydrate, cocrystal, or prodrug thereof. The preparation of this compound is described in U.S. Pat. No. 7,897,600 and U.S. Patent Application Publication Nos. 2010/0152181 A1 and 2010/0286139 A1, the disclosures of which are incorporated by reference herein. In an embodiment, the JAK-2 inhibitor is a compound described in U.S. Pat. No. 7,897,600 and U.S. Patent Application Publication Nos. 2010/0152181 A1 and 2010/0286139 A1, the disclosures of which are incorporated by reference herein.

In an embodiment, the JAK-2 inhibitor is a compound of Formula (XLIII):

Formula (XLIII)

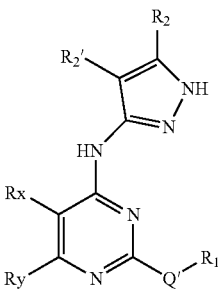

or a pharmaceutically acceptable derivative or prodrug thereof, wherein:

$R^x$ and $R^y$ are independently selected from the group consisting of -T-$R^3$ and -L-Z—$R^3$;

Q' is selected from the group consisting of —$CR^{6''}$=$CR^{6''}$— and wherein said —$CR^{6''}$=$CR^{6''}$— may be a cis or trans double bond or a mixture thereof, $R^1$ is -T-(Ring D);

Ring D is a 5-7 membered monocyclic ring or 8-10 membered bicyclic ring selected from the group consisting of aryl, heteroaryl, heterocyclyl, and carbocyclyl, said heteroaryl or heterocyclyl ring having 1-4 ring heteroatoms selected from the group consisting of nitrogen, oxygen, and sulfur, wherein each substitutable ring carbon of Ring D is independently substituted by oxo, -T-$R^5$ or —V—Z—$R^5$, and each substitutable ring nitrogen of Ring D is independently substituted by —$R^4$;

T is a valence bond or —(C($R^{6'}$)$_2$)-A-;

A is a valence bond or a $C_1$-$C_3$ alkylidene chain wherein a methylene unit of said $C_{1-3}$ alkylidene chain is optionally replaced by —O—, —S—, —N($R^4$)—, —CO—, —CONH—, —NHCO—, —SO$_2$—, —SO$_2$NH—, —NHSO$_2$—, —CO$_2$—, —OC(O)—, —OC(O)NH—, or —NHCO$_2$—;

Z is a $C_{1-4}$ alkylidene chain;

L is selected from the group consisting of —O—, —S—, —SO—, —SO$_2$—, —N($R^6$)SO$_2$—SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$—, —C($R^6$)$_2$SO—, —C($R^6$)$_2$SO$_2$—, C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, and —C($R^6$)$_2$N($R^6$)CON($R^6$)—;

$R^2$ and $R^{2'}$ are independently selected from the group consisting of —R and -T-W—$R^6$, or $R^2$ and $R^{2'}$ taken together with their intervening atoms form a fused, 5-8 membered, unsaturated or partially unsaturated ring having 0-3 ring heteroatoms selected from the group consisting of nitrogen, oxygen, and sulfur, wherein each substitutable ring carbon of said fused ring formed by $R^2$ and $R^{2'}$ is independently substituted by halo, oxo, —CN, —NO$_2$, $R^7$, or —V—$R^6$, and each substitutable ring nitrogen of said ring formed by $R^2$ and $R^{2'}$ is independently substituted by —$R^4$;

$R^3$ is selected from the group consisting of —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, SO$_2$N($R^7$)$_2$, —OC(=O)R, —N($R^7$)COR, —N($R^7$)CO$_2$(C$_{1-6}$ aliphatic), —N($R^4$)N($R^4$)$_2$, C=NN($R^4$)$_2$, —C=N—OR, —N($R^7$)CON($R^7$)$_2$, —N($R^7$)SO$_2$N($R^7$)$_2$, —N($R^4$)SO$_2$R, and OC(=O)N(R)$_2$;

each R is independently hydrogen or an optionally substituted group selected from the group consisting of $C_{1-6}$ aliphatic, $C_6$-10 aryl, a heteroaryl ring having 5-10 ring atoms, and a heterocyclyl ring having 5-10 ring atoms;

each $R^4$ is independently selected from the group consisting of —$R^7$, —COR$^7$, —CO$_2$ (optionally substituted $C_{1-6}$ aliphatic), —CON($R^7$)$_2$, and —SO$_2$R$^7$;

each $R^5$ is independently selected from the group consisting of —R, halo, —OR, —C(=O)R, CO$_2$R, —COCOR, —NO$_2$, —CN, —S(O)R, —SO$_2$R, —SR, —N($R^4$)$_2$, —CON($R^4$)$_2$, SO$_2$N($R^4$)$_2$, —OC(=O)R, —N($R^4$)COR, —N($R^4$)CO$_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, and —OC(=O)N($R^4$)$_2$;

V is selected from the group consisting of —O—, —S—, —SO—, —SO$_2$—, —N($R^6$)SO$_2$—, SO$_2$N($R^6$)—, —N($R^6$)—, —CO—, —N($R^6$)CO—, —N($R^6$)C(O)O—, —N($R^6$)CON($R^6$)—, —N($R^6$)SO$_2$N($R^6$)—, —N($R^6$)N ($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, and —C($R^6$)$_2$N($R^6$)CON($R^6$)—;

W is selected from the group consisting of —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —CO—, CO$_2$ C($R^6$)OC(O)—, —C($R^6$)OC(O)N($R^6$)—, —C($R^6$)$_2$N($R^6$)CO—, —C($R^6$)$_2$N($R^6$)C(O)O—, C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, —C($R^6$)$_2$N($R^6$)CON($R^6$)—, and —CON($R^6$)—;

each $R^6$ is independently selected from the group consisting of hydrogen and an optionally substituted $C_{1-4}$ aliphatic group, or two $R^6$ groups on the same nitrogen atom may be taken together with the nitrogen atom to form a 3-6 membered heterocyclyl or heteroaryl ring;

each $R^{6'}$ is independently selected from the group consisting of hydrogen and a $C_{1-4}$ aliphatic group, or two $R^{6'}$ on the same carbon atom are taken together to form a 3-8 membered carbocyclic ring;

each $R^{6''}$ is independently selected from the group consisting of hydrogen, a $C_{1-4}$ aliphatic group, halogen, optionally substituted aryl, and optionally substituted heteroaryl, or two $R^6$ on adjacent carbon atoms are taken together to form a 5-7 membered carbocyclic ring; and each $R^7$ is independently selected from the group consisting of hydrogen and an optionally substituted $C_{1-6}$ aliphatic group, or two $R^7$ on the same nitrogen are taken together with the nitrogen to form a 5-8 membered heterocyclyl or heteroaryl ring.

In an embodiment, the JAK-2 inhibitor is ENMD-2076. In an embodiment, the JAK-2 inhibitor is (E)-N-(5-methyl-1H-pyrazol-3-yl)-6-(4-methylpiperazin-1-yl)-2-styrylpyrimidin-4-amine. In an embodiment, the JAK-2 inhibitor has the chemical structure shown in Formula (XLIV):

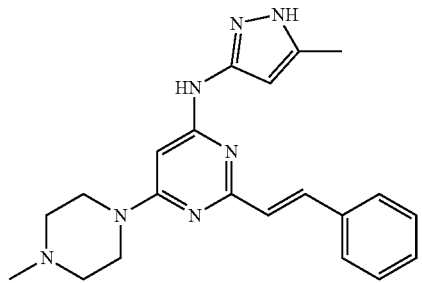

Formula (XLIV)

or a pharmaceutically acceptable salt, solvate, hydrate, cocrystal, or prodrug thereof. The preparation of this compound is described in U.S. Pat. Nos. 8,153,630; 7,563,787; and, 8,114,870 and U.S. Patent Application Publication Nos. 2008/0200485 A1; 2007/0142368 A1; 2009/0264422 A1; 2011/0318393 A1; and, 2009/0029992 A1, the disclosures of which are incorporated by reference herein. In an embodiment, the JAK-2 inhibitor is a compound described in U.S. Pat. Nos. 8,153,630; 7,563,787; and, 8,114,870 and U.S. Patent Application Publication Nos. 2008/0200485 A1; 2007/0142368 A1; 2009/0264422 A1; 2011/0318393 A1; and, 2009/0029992 A1, the disclosures of which are incorporated by reference herein.

In an embodiment, the JAK-2 inhibitor is a compound of Formula (XLV):

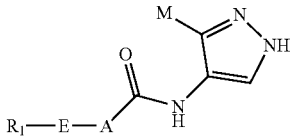

Formula (XLV)

or a salt, solvate, tautomer or N-oxide thereof,
wherein M is selected from a group D1 and a group D2:

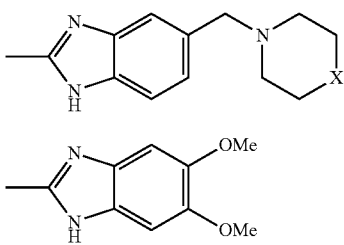

and wherein:
(A) when M is a group D1:
X is selected from O, NH and NCH$_3$;
A is selected from a bond and a group NR$_2$ where R$_2$ is hydrogen or methyl;
E is selected from a bond, CH$_2$, CH(CN) and C(CH$_3$)$_2$;
R$_1$ is selected from:
(i) a cycloalkyl group of 3 to 5 ring members optionally substituted by hydroxy, fluorine, amino, methylamino, methyl or ethyl;
(ii) a saturated heterocyclic group of 4 to 6 ring members containing 1 or 2 heteroatom ring members selected from O, N, S and SO$_2$, the heterocyclic group being optionally substituted by (C$_{1-4}$)alkyl, amino or hydroxy; but excluding unsubstituted 4-morpholinyl, unsubstituted tetrahydropyran-4-yl, unsubstituted 2-pyrrolidinyl, and unsubstituted and 1-substituted piperidine-4-yl;
(iii) a 2,5-substituted phenyl group of the formula:

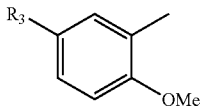

wherein (a) when X is NH or N—CH$_3$, R$_3$ is selected from chlorine and cyano;
and (b) when X is O, R$_3$ is CN;
(iv) a group CR$_6$R$_7$R$_8$ wherein R$_6$ and R$_7$ are each selected from hydrogen and methyl, and R$_8$ is selected from hydrogen, methyl, (C$_{1-4}$)alkylsulphonylmethyl, hydroxymethyl and cyano;
(v) a pyridazin-4-yl group optionally substituted by one or two substituents selected from methyl, ethyl, methoxy and ethoxy;
(vi) a substituted imidazothiazole group wherein the substituents are selected from methyl, ethyl, amino, fluorine, chlorine, amino and methylamino; and
(vii) an optionally substituted 1,3-dihydro-isoindol-2-yl or optionally substituted 2,3-dihydro-indol-1-yl group wherein the optional substituents in each case are selected from halogen, cyano, amino, C$_{1-4}$ mono- and dialkylamino, CONH$_2$ or CONH—(C$_{1-4}$)alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino;
(viii) 3-pyridyl optionally substituted by one or two substituents selected from hydroxy, halogen, cyano, amino, C$_{1-4}$ mono- and dialkylamino, CONH$_2$ or CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino, but excluding the compounds 2-oxo-1,2-dihydro-pyridine-3-carboxylic acid [3-(5-morpholin-4-ylmethyl-1H-benzoimidazol-2-yl)-1H-pyrazol-4-yl]-amide and 2,6-dimethoxy-N-[3-(5-morpholin-4-ylmethyl-1H-benzoimidazol-2-yl)-1H-pyrazol-4-yl]-nicotinamide;
(ix) thiomorpholine or an S-oxide or S,S-dioxide thereof optionally substituted by one or two substituents selected from halogen, cyano, amino, C$_{1-4}$ mono- and dialkylamino, CONH$_2$ or CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino; and
when E-A is NR$_2$, R$_1$ is additionally selected from:
(x) 2-fluorophenyl, 3-fluorophenyl, 4-fluorophenyl, 2,4-difluorophenyl, 3,4-difluorophenyl, 2,5-difluorophenyl, 3,5-difluorophenyl, 2,4,6-trifluorophenyl, 2-methoxyphenyl, 5-chloro-2-methoxyphenyl, cyclohexyl, unsubstituted 4-tetrahydropyranyl and tert-butyl;
(xi) a group NR$_{10}$R$_{11}$ where R$_{10}$ and R$_{11}$ are each C$_{1-4}$ alkyl or R$_{10}$ and R$_{11}$ are linked so that NR$_{10}$R$_{11}$ forms a saturated heterocyclic group of 4 to 6 ring members optionally containing a second heteroatom ring member selected from O, N, S and SO$_2$, the heterocyclic group being optionally substituted by C$_{1-4}$ alkyl, amino or hydroxy;
(xii) pyridone optionally substituted by one or two substituents selected from hydroxy, halogen, cyano, amino, C$_{1-4}$ mono- and dialkylamino, CONH$_2$, CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino;
when E-A is C(CH$_3$)$_2$NR$_2$ or CH$_2$—NR$_2$, R$_1$ is additionally selected from:
(xiii) unsubstituted 2-furyl and 2,6-difluorophenyl; and
when E-A is C(CH$_3$)$_2$NR$_2$, R$_1$ is additionally selected from:
(xiv) unsubstituted phenyl; and
when E is CH$_2$, R$_1$ is additionally selected from:
(xv) unsubstituted tetrahydropyran-4-yl; and
(B) when M is a group D2:
A is selected from a bond and a group NR$_2$ where R$_2$ is hydrogen or methyl;
E is selected from a bond, CH$_2$, CH(CN) and C(CH$_3$)$_2$;
R$_1$ is selected from:
(xvi) a 2-substituted 3-furyl group of the formula:

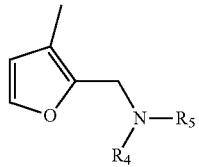

wherein R$_4$ and R$_5$ are the same or different and are selected from hydrogen and C$_{1-4}$ alkyl, or R$_4$ and R$_5$ are linked so that NR$_4$R$_5$ forms a 5- or 6-membered saturated heterocyclic group optionally containing a second heteroatom or group selected from O, NH, NMe, S or SO$_2$, the 5- or 6-membered saturated ring being optionally substituted by hydroxy, fluorine, amino, methylamino, methyl or ethyl; (xvii) a 5-substituted 2-furyl group of the formula:

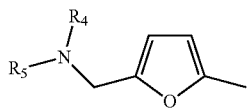

wherein R$_4$ and R$_5$ are the same or different and are selected from hydrogen and C$_{1-4}$ alkyl, or R$_4$ and R$_5$ are linked so that NR$_4$R$_5$ forms a 5- or 6-membered saturated heterocyclic group optionally containing a second heteroatom or group selected from 0, NH, NMe, S or SO$_2$, the 5- or 6-membered saturated heterocyclic group being optionally substituted by hydroxy, fluorine, amino, methylamino, methyl or ethyl; with the proviso that the compound is not 5-piperidin-1-ylmethyl-furan-2-carboxylic acid [3-(5,6-dimethoxy-1H-benzoimidazol-2-yl)-1H-pyrazol-4-yl]-amide;
(xviii) a group of the formula:

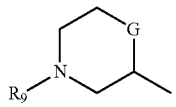

wherein R$_9$ is hydrogen, methyl, ethyl or isopropyl; G is CH, O, S, SO, SO$_2$ or NH and the group is optionally substituted by one, two or three substituents selected from C$_{1-4}$ hydrocarbyl, hydroxy, C$_{1-4}$ hydrocarbyloxy, fluorine, amino, mono- and di-C$_{1-4}$ alkylamino and wherein the C$_{1-4}$ hydrocarbyl and C$_{1-4}$ hydrocarbyloxy groups are each optionally substituted by hydroxy, fluorine, amino, mono- or di-C$_{1-4}$ alkylamino; and
(xix) a 3,5-disubstituted phenyl group of the formula:

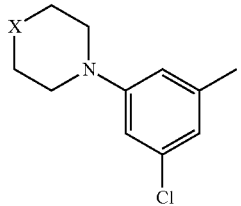

wherein X is selected from O, NH and NCH$_3$; and
(C) when M is a group D1:
and X is O; A is a group NR$_2$ where R$_2$ is hydrogen; E is a bond; and R$_1$ is 2,6-difluorophenyl; then the compound of the Formula (XLV) is an acid addition salt selected from salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecyl sulphuric, ethane-1,2-di sulphonic, ethanesulphonic, fumaric, galactaric, gentisic, glucoheptonic, D-gluconic, glucuronic (e.g. D-glucuronic), glutamic (e.g. L-glutamic), a-oxoglutaric, glycolic, hippuric, hydrochloric, isethionic, isobutyric, lactic (e.g. (+)-L-lactic and (±)-DL-lactic), lactobionic, laurylsulphonic, maleic, malic, (-)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

In an embodiment, the JAK-2 inhibitor is AT-9283. In an embodiment, the JAK-2 inhibitor is 1-cyclopropyl-3-(3-(5-(morpholinomethyl)-1H-benzo[d]imidazol-2-yl)-1H-pyrazol-4-yl)urea. In an embodiment, the JAK-2 inhibitor has the chemical structure shown in Formula (XLVI):

Formula (XLVI)

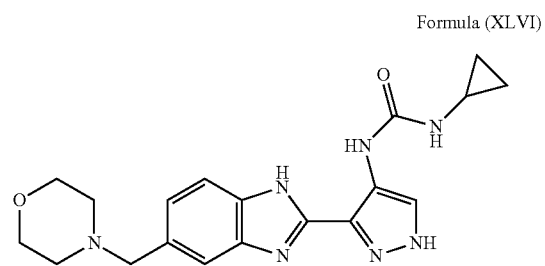 [SMILES: O=C(Nc1c[nH]nc1-c1nc2cc(CN3CCOCC3)ccc2[nH]1)NC1CC1]

or a pharmaceutically acceptable salt, solvate, hydrate, cocrystal, or prodrug thereof. The preparation of this compound is described in U.S. Pat. Nos. 8,399,442 and 7,977,477 and U.S. Patent Application Publication Nos. 2010/0004232 A1; 2014/0010892 A1; 2011/0224203 A1; and, 2007/0135477, the disclosures of which are incorporated by reference herein. In an embodiment, the JAK-2 inhibitor is a compound described in U.S. Pat. Nos. 8,399,442 and 7,977,477 and U.S. Patent Application Publication Nos. 2010/0004232 A1; 2014/0010892 A1; 2011/0224203 A1; and, 2007/0135477, the disclosures of which are incorporated by reference herein.

In an embodiment, the JAK-2 inhibitor is a compound of Formula (XLVII):

Formula (XLVII)

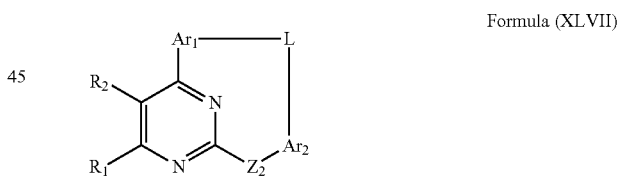

wherein:
R$^1$ and R$^2$ are each independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, aryl alkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^3$, —COOR$^3$, —CONHR$^3$, —NHCOR$^3$, —NHCOOR$^3$, —NHCONHR$^3$, alkoxycarbonyl, alkylaminocarbonyl, sulfonyl, alkyl sulfonyl, alkylsulfinyl, aryl sulfonyl, arylsulfinyl, aminosulfonyl, —SR$^3$, R⁴S(O)R⁶—, R⁴S(O)₂R⁶—, R⁴C(O)N(R⁵)R⁶—, R⁴SO₂N(R⁵)R⁶—, R⁴N(R⁵)C(O)R⁶—, R⁴N(R⁵)SO₂R⁶—, R⁴N(R⁵)C(O)N(R⁵)R⁶— and acyl, each of which may be optionally substituted;

each R³, R⁴, and R⁵ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each R⁶ is independently selected from the group consisting of a bond, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

Z² is independently selected from the group consisting of a bond, O, S, —N(R⁷)—, —N(R⁷)C₁₋₂alkyl-, and —C₁₋₂alkylN(R⁷)—;

each R⁷ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

Ar¹ and Ar² are each independently selected from the group consisting of aryl and heteroaryl, each of which may be optionally substituted;

L is a group of formula:

—X¹—Y—X²— wherein X¹ is attached to AO and X² is attached to Ar², and wherein X¹, X² and Y are selected such that the group L has between 5 and 15 atoms in the normal chain, X¹ and X² are each independently a heteroalkyl group containing at least one oxygen atom in the normal chain, Y is a group of formula —CRᵃ=CRᵇ— or an optionally substituted cycloalkyl group, wherein Rᵃ and Rᵇ are each independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted, or Rᵃ and Rᵇ may be joined such that when taken together with the carbon atoms to which they are attached they form a cycloalkenyl or cycloheteroalkenyl group;

or a pharmaceutically acceptable salt, solvate, hydrate, cocrystal, or prodrug thereof, or an N-oxide thereof.

In some embodiments Z² is selected from the group consisting of a bond, —N(R⁷)—, and —S—. In one specific embodiment Z² is —N(R⁷)—. In an even more specific embodiment Z² is N(H)—.

Ar¹ and Ar² are each independently selected from the group consisting of aryl and heteroaryl and may be monocyclic, bicyclic or polycyclic moieties. In some embodiments each of Ar¹ and Ar² is a monocyclic or bicyclic moiety. In some embodiments each of Ar¹ and Ar² are a monocyclic moiety.

In some embodiments AO is selected from the group consisting of:

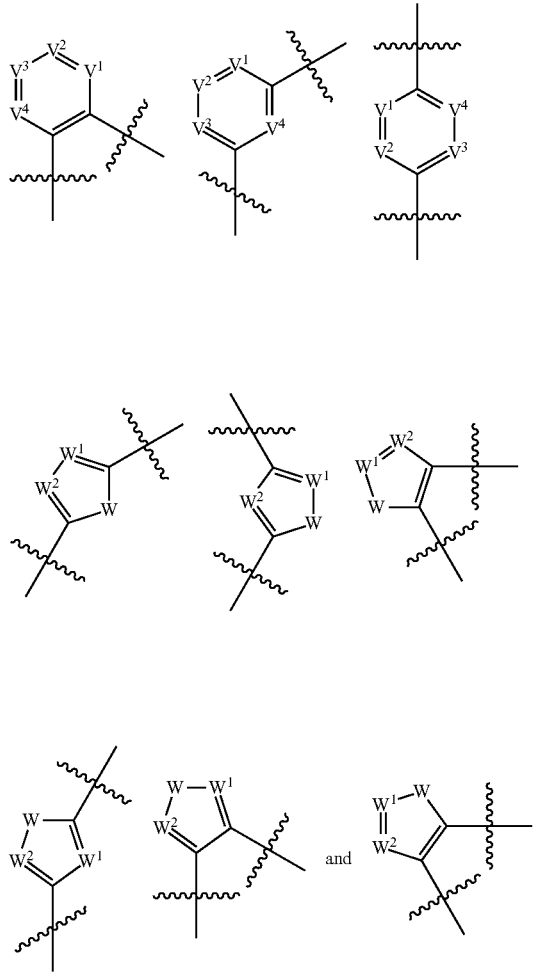

wherein V¹, V², V³ and V⁴ are each independently selected from the group consisting of N, and C(R¹⁰);
W is selected from the group consisting of O, S and NR¹⁰;
W¹ and W² are each independently selected from the group consisting of N and CR¹⁰;
wherein each R¹⁰ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, aryl alkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —CORˢ, —COORˢ, CONHR³, —NHCOR³, —NHCOOR³, —NHCONHR³, alkoxycarbonyl, alkylaminocarbonyl, sulfonyl, alkyl sulfonyl, alkylsulfinyl, aryl sulfonyl, arylsulfinyl, aminosulfonyl, —SR³, R⁴S(O)R⁶—, R⁴S(O)₂R⁶—, R⁴C(O)N(R⁵)R⁶—, R⁴SO₂N(R⁵)R⁶—, R⁴N(R⁵)C(O)R⁶—, R⁴N(R⁵)SO₂R⁶—, R⁴N(R⁵)C(O)N(R⁵)R⁶— and acyl, each of which may be optionally substituted,
wherein R³, R⁴, R⁵ and R⁶ are as defined above.

In some embodiments AO is selected from the group consisting of:

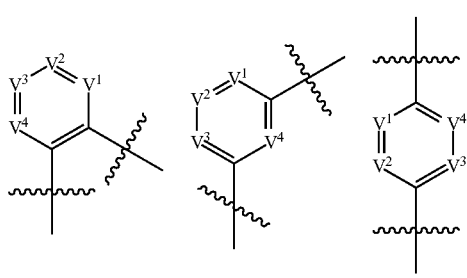

wherein $V^1$, $V^2$, $V^3$, $V^4$, W, W', $W^2$, $R^3$, $R^4$, $R^5$ and $R^6$ are as defined above.

In some embodiments AO is selected from the group consisting of:

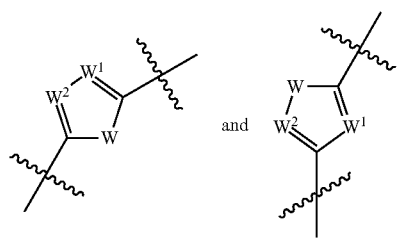

wherein each $R^{10}$ is independently as defined above, k is an integer selected from the group consisting of 0, 1, 2, 3, and 4; and n is an integer selected from the group consisting of 0, 1, and 2.

In yet an even further embodiment AO is selected from the group consisting of:

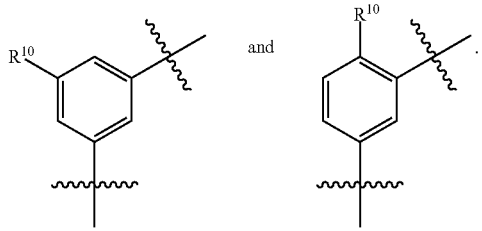

wherein $R^{10}$ is as defined above.

In some embodiments AO is selected from the group consisting of:

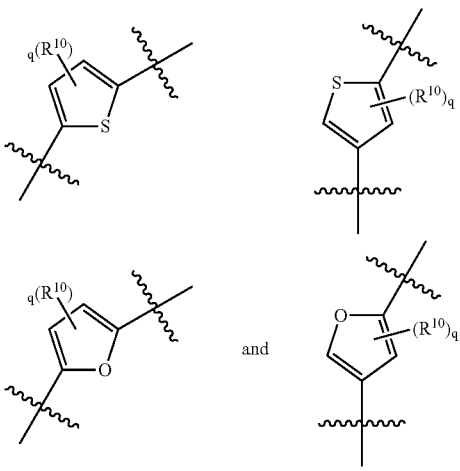

wherein each $R^{10}$ is independently as defined above, and q is an integer selected from the group consisting of 0, 1 and 2.

In some embodiments AO is selected from the group consisting of:

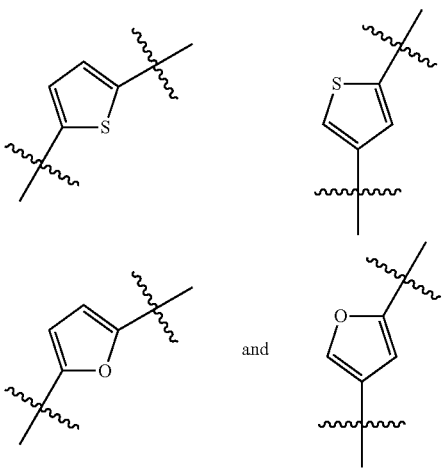

In some embodiments AO is selected from the group consisting of:

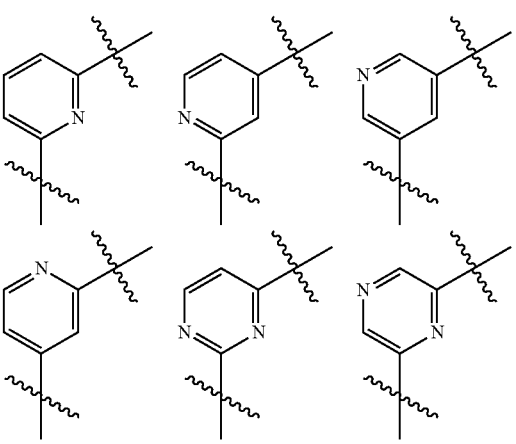

—NHCOOR$^3$, NHCONHR$^3$, alkoxycarbonyl, alkylaminocarbonyl, sulfonyl, alkyl sulfonyl, alkylsulfinyl, aryl sulfonyl, arylsulfinyl, aminosulfonyl, —SR$^3$, R$^4$S(O)R$^6$—, R$^4$S(O)$_2$R$^6$—, R$^4$C(O)N(R$^5$)R$^6$—, R$^4$SO$_2$N(R$^5$)R$^6$—, R$^4$N(R$^5$)C(O)R$^6$—, R$^4$N(R$^5$)SO$_2$R$^6$—, R$^4$N(R$^5$)C(O)N(R$^5$)R$^6$— and acyl, each of which may be optionally substituted.

In some embodiments Ar$^2$ is selected from the group consisting of:

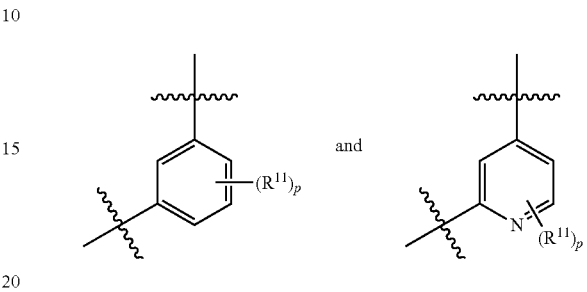

wherein each R$^{11}$ is independently as defined above o is an integer selected from the group consisting of 0, 1, 2, 3, and 4; and p is an integer selected from the group consisting of 0, 1, 2, and 3.

In some embodiments Ar$^2$ is selected from the group consisting of:

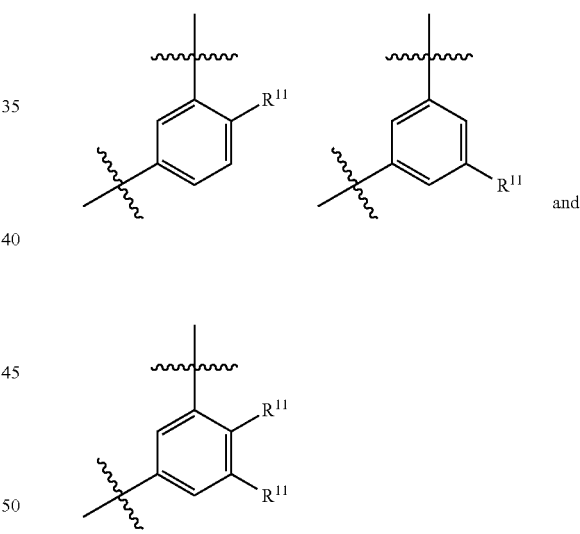

wherein each R$^{11}$ is as defined above.

In an even further embodiment Ar$^2$ is selected from the group consisting of:

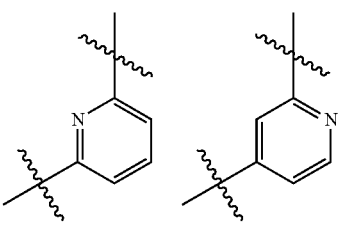

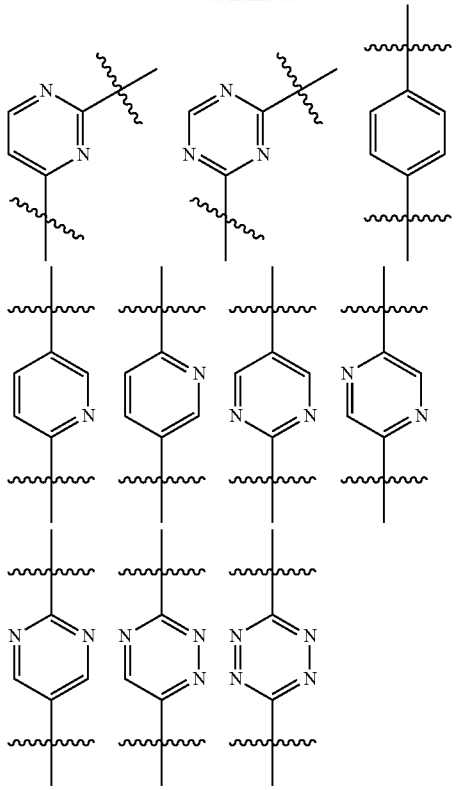

In some embodiments Ar$^e$ is selected from the group consisting of:

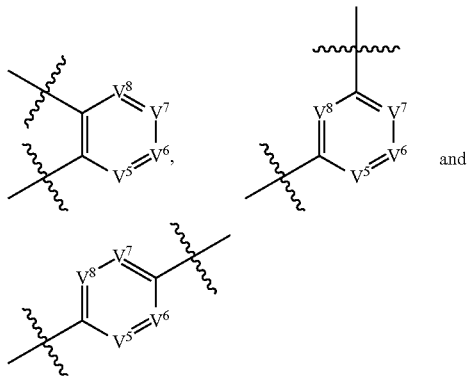

wherein V$^5$, V$^6$, V$^7$ and V$^8$ are independently selected from the group consisting of N, and C(R$^{11}$);

wherein each R$^{11}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, phenoxy, benzyloxy, heteroaryloxy, amino, alkylamino, aminoalkyl, acylamino, arylamino, sulfonylamino, sulfinylamino, —COOH, —COR$^S$, —COOR$^S$, —CONHR$^3$, —NHCOR$^3$, -continued

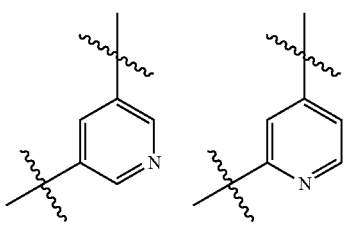

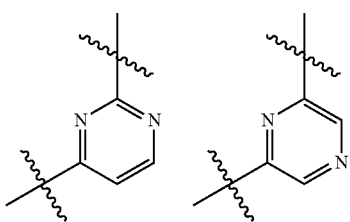

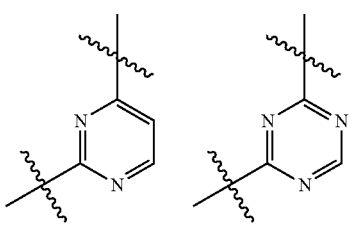

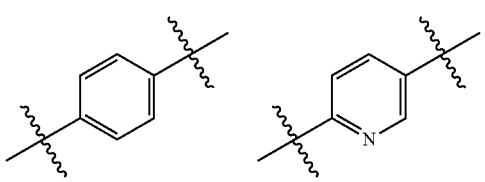

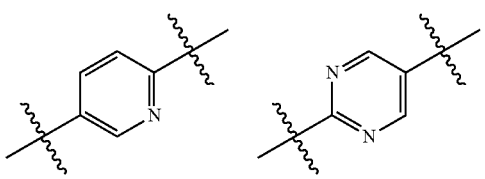

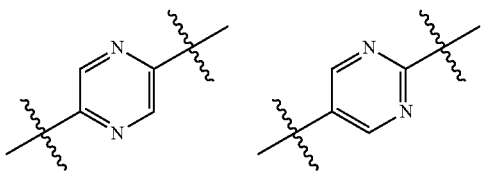

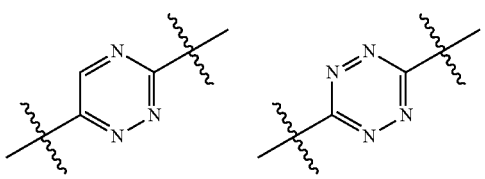

In an embodiment, the JAK-2 inhibitor is a compound of Formula (XLVIII):

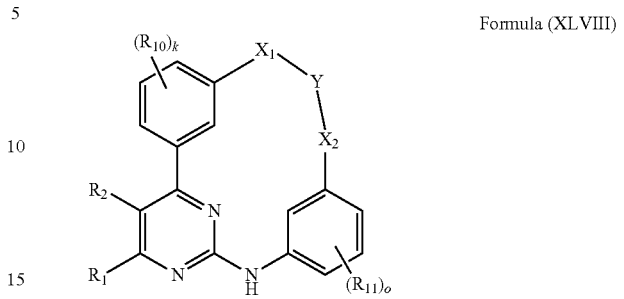

Formula (XLVIII)

or a pharmaceutically acceptable salt, solvate, hydrate, cocrystal, or prodrug thereof wherein $R^1$, $R^2$, $R^{10}$, $R^{11}$, $X^1$, $X^2$, Y, k and o are as defined above.

In an embodiment, the JAK-2 inhibitor is a compound of Formula (XLIX):

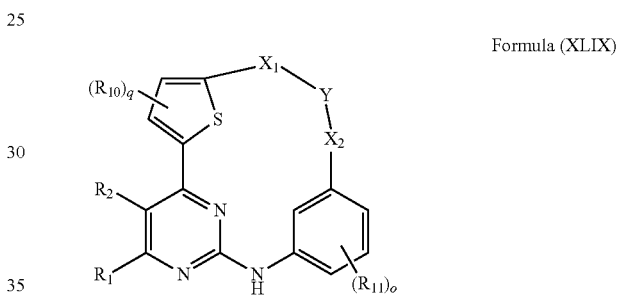

Formula (XLIX)

or a pharmaceutically acceptable salt, solvate, hydrate, cocrystal, or prodrug thereof.

wherein $R^1$, $R^2$, $R^{10}$, $R^{11}$, $X^1$, $X^2$, Y, q and o are as defined above.

In an embodiment, the JAK-2 inhibitor is a compound of Formula (L):

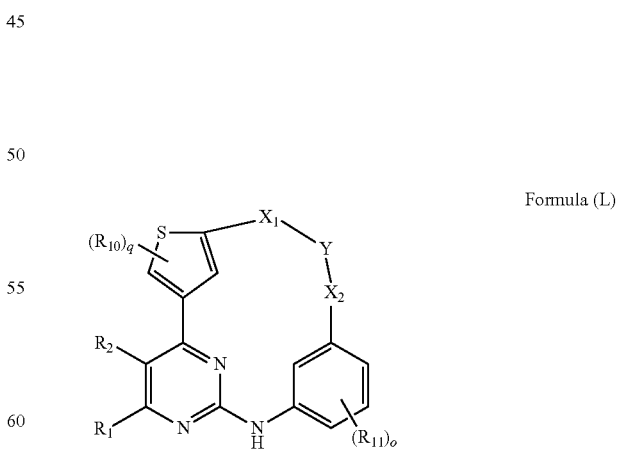

Formula (L)

or a pharmaceutically acceptable salt, solvate, hydrate, cocrystal, or prodrug thereof.

wherein $R^1$, $R^2$, $R^{10}$, $R^{11}$, $X^1$, $X^2$, Y, q and o are as defined above.

In an embodiment, the JAK-2 inhibitor is a compound of Formula (LI):

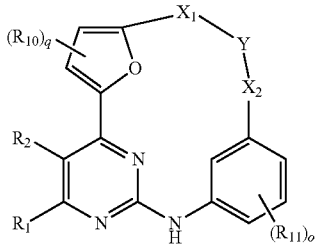

Formula (LI)

or a pharmaceutically acceptable salt, solvate, hydrate, cocrystal, or prodrug thereof.
wherein $R^1$, $R^2$, $R^{10}$, $R^{11}$, $X^1$, $X^2$, Y, q and o are as defined above.

In an embodiment, the JAK-2 inhibitor is a compound of Formula (LII):

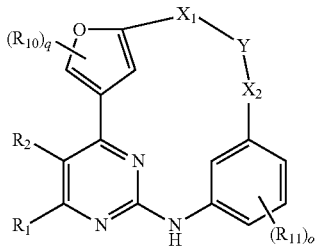

Formula (LII)

or a pharmaceutically acceptable salt, solvate, hydrate, cocrystal, or prodrug thereof.
wherein $R^1$, $R^2$, $R^{10}$, $R^{11}$, $X^1$, $X^2$, Y, q and o are as defined above.

In an embodiment, the JAK-2 inhibitor is a compound of Formula (LIII):

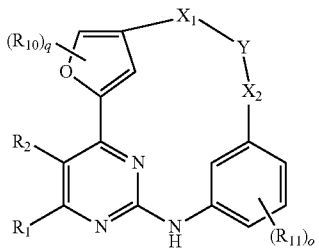

Formula (LIII)

or a pharmaceutically acceptable salt, solvate, hydrate, cocrystal, or prodrug thereof.
wherein $R^1$, $R^2$, $R^{10}$, $R^{11}$, $X^1$, $X^2$, Y, q and o are as defined above.

In embodiments where the JAK-2 inhibitor has a compound of Formulas (XLVII)-(LIII), $X^1$, $X^2$ and Y are chosen such that there are between 5 and 1:5 atoms in the normal chain. In one embodiment, $X^1$, $X^2$ and Y are chosen such that there are between 6 and 15 atoms in the normal chain. In one specific embodiment, $X^1$, $X^2$ and Y are chosen such that there are 7 atoms in the normal chain. In another specific embodiment, $X^1$, $X^2$ and Y are chosen such that there are 8 atoms in the normal chain.

In embodiments where the JAK-2 inhibitor has a compound of Formulas (XLVII)-(LIII), $X^1$ and $X^2$ are each independently a heteroalkyl group containing at least one oxygen atom in the normal chain. In some embodiments is selected from the group consisting of: (a) —O($C_{1-5}$)alkyl-, (b) —($C_{1-5}$)alkylO—, and (c) —($C_{1-5}$)alkylO($C_{1-5}$)alkyl. In some embodiments $X^1$ is selected from the group consisting of: (a) —OCH$_2$— (b) —CH$_2$O—, (c) —OCH$_2$CH$_2$—, (d) —CH$_2$CH$_2$O—, (e) —CH$_2$OCH$_2$—, and (f) —CH$_2$CH$_2$OCH$_2$—. In one specific embodiment $X^1$ is —OCH$_2$—. In another specific embodiment $X^1$ is CH$_2$O. In another specific embodiment $X^1$ is OCH$_2$CH$_2$. In another specific embodiment $X^1$ is CH$_2$CH$_2$O In another specific embodiment $X^1$ is —CH$_2$OCH$_2$—. In another specific embodiment $X^1$ is —CH$_2$CH$_2$OCH$_2$—. In some embodiments $X^2$ is selected from the group consisting of: (a) —O($C_{1-5}$)alkyl-, (b) —($C_{1-5}$)alkylO—, and (c) —($C_{1-5}$)alkylO($C_{1-5}$)alkyl. In some embodiments $X^2$ is selected from the group consisting of: (a) —OCH$_2$—, (b) —CH$_2$O—, (c) —OCH$_2$CH$_2$—, (d) —CH$_2$CH$_2$O—, (e) —CH$_2$OCH$_2$—, and (f) —CH$_2$CH$_2$OCH$_2$—. In one specific embodiment. $X^2$ is OCH$_2$. In another specific embodiment $X^1$ is —CH$_2$O—. In another specific embodiment $X^2$ is —OCH$_2$CH$_2$—. In another specific embodiment $X^2$ is —CH$_2$CH$_2$O—. In another specific embodiment $X^2$ is —CH$_2$OCH$_2$—. In another specific embodiment $X^2$ is —CH$_2$CH$_2$OCH$_2$—.

In an embodiment, the JAK-2 inhibitor is pacritinib. In an embodiment, the JAK-2 inhibitor is (E)-4$^4$-(2-(pyrrolidin-1-yl)ethoxy)-6,11-dioxa-3-aza-2(4,2)-pyrimidina-1,4(1,3)-dibenzenacyclododecaphan-8-ene. In an embodiment, the JAK-2 inhibitor is the chemical structure shown in Formula (LIV):

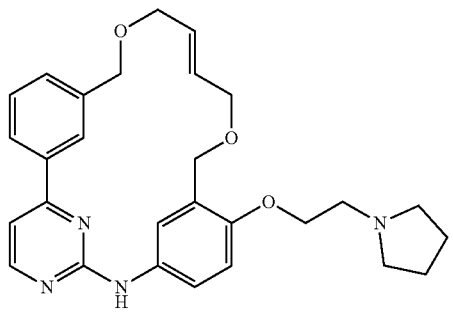

Formula (LIV)

or a pharmaceutically acceptable salt, solvate, hydrate, cocrystal, or prodrug thereof. The preparation of this compound is described in U.S. Pat. Nos. 8,143,255; 8,153,632; and, 8,415,338 and U.S. Patent Application Publication Nos. 2009/0258886 A1; 2012/0142680 A1; 2012/0196855 A1; and 2013/0172338 A1, the disclosures of which are incorporated by reference herein. The preparation and properties of this JAK-2 inhibitor are known to those of ordinary skill in the art, and for example are described in: Hart et al., SB1518, a novel macrocyclic pyrimidine-based JAK2 inhibitor for the treatment of myeloid and lymphoid malignancies, Leukemia 2011, 25, 1751-1759; Hart et al., Pacritinib (SB1518), a JAK2/FLT3 inhibitor for the treatment of acute myeloid leukemia, *Blood Cancer J.*, 2011, 1(11), e44; William et al. Discovery of the macrocycle 11-(2-pyrrolidin-1-yl-ethoxy)-14,19-dioxa-5,7,26-triaza-tetracyclo[19.3.1.1 (2,6).1(8,12)]heptacosa-1(25),2(26),3,5,8,10,12(27),16,21, 23-decaene (SB1518), a potent Janus kinase 2/fms-like tyrosine kinase-3 (JAK2/FLT3) inhibitor for the treatment of myelofibrosis and lymphoma. *J. Med. Chem.* 2011, 54, 4638-4658; Poulsen et al. Structure-based design of oxygen-linked macrocyclic kinase inhibitors: discovery of SB1518 and SB1578, potent inhibitors of Janus kinase 2 (JAK2) and Fms-like tyrosine kinase-3 (FLT3). *J. Comput. Aided Mol. Des.* 2012, 26, 437-450.

In an embodiment, the JAK-2 inhibitor is selected from the structures disclosed in U.S. Pat. Nos. 8,143,255; 8,153,632; and 8,415,338 and U.S. Patent Application Publication Nos. 2009/0258886 A1; 2012/0142680 A1; 2012/0196855 A1; and 2013/0172338 A1, the disclosures of which are incorporated by reference herein.

In an embodiment, the JAK-2 inhibitor is (E)-4$^4$-(2-(pyrrolidin-1-yl)ethoxy)-6,11-dioxa-3-aza-2(4,2)-pyrimidina-1(2,5)-furana-4(1,3)-benzenacyclododecaphan-8-ene. In an embodiment, the JAK-2 inhibitor is (9E)-15-(2-(pyrrolidin-1-yl)ethoxy)-7,12,25-trioxa-19,21,24-triaza-tetracyclo[18.3.1.1(2,5). 1(14,18)]hexacosa-1(24),2,4,9,14(26),15,17,20,22-nonaene. In an embodiment, the JAK-2 inhibitor is the chemical structure shown in Formula (LIV-A):

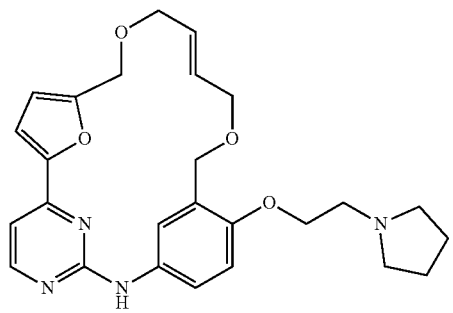

Formula (LIV-A)

or a pharmaceutically acceptable salt, solvate, hydrate, cocrystal, or prodrug thereof. The preparation and properties of this JAK-2 inhibitor are known to those of ordinary skill in the art, and for example are described in: Madan et al., SB1578, a novel inhibitor of JAK2, FLT3, and c-Fms for the treatment of rheumatoid arthritis, *J. Immunol.* 2012, 189, 4123-4134 and William et al., Discovery of the macrocycle (9E)-15-(2-(pyrrolidin-1-yl)ethoxy)-7,12,25-trioxa-19,21, 24-triaza-tetracyclo[18.3.1.1(2,5).1(14,18)]hexacosa-1(24), 2,4,9,14(26),15,17,20,22-nonaene (SB1578), a potent inhibitor of j anus kinase 2/fms-like tyrosine kinase-3 (JAK2/FLT3) for the treatment of rheumatoid arthritis. *J. Med. Chem.* 2012, 55, 2623-2640.

In an embodiment, the JAK-2 inhibitor is a compound selected from the structures disclosed in U.S. Pat. No. 8,349,851 and U.S. Patent Application Publication Nos. 2010/0317659 A1, 2013/0245014, 2013/0296363 A1, the disclosures of which are incorporated by reference herein. In an embodiment, the JAK-2 inhibitor is a compound of Formula (LV):

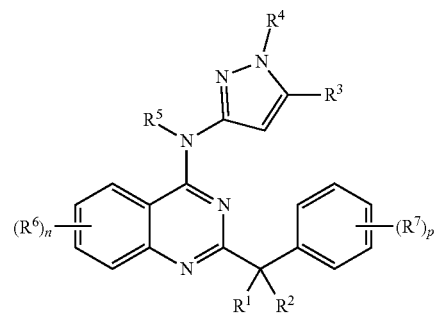

Formula (LV)

or a pharmaceutically acceptable salt, solvate, hydrate, cocrystal, or prodrug thereof, wherein
$R^1$ and $R^2$ are selected from (i), (ii), (iii), (iv), and (v) as follows:
(i) $R^1$ and $R^2$ together form =O, =S, =NR$^9$ or =CR$^{10}$R$^{11}$;
(ii) $R^1$ and $R^2$ are both —OR$^8$, or $R^1$ and $R^2$, together with the carbon atom to which they are attached, form dioxacycloalkyl;
(iii) $R^1$ is hydrogen or halo; and $R^2$ is halo; and
(iv) $R^1$ is alkyl, alkenyl, alkynyl, cycloalkyl or aryl, wherein the alkyl, alkenyl, alkynyl, cycloalkyl and aryl is optionally substituted with one or more substitutents selected from halo, cyano, alkyl, —R$^x$OR$^w$, —R$^x$S(O)$_q$R$^v$, —R$^x$NR$^y$R$^z$ and —C(O)OR$^w$; and $R^2$ is halo or —OR$^8$; and
(v) $R^1$ is halo, deutero, —OR$^{12}$, —NR$^{13}$R$^{14}$, or —S(O)$_q$R$^{15}$; and $R^2$ is hydrogen, deutero, alkyl, alkenyl, alkynyl, cycloalkyl or aryl, wherein the alkyl, alkenyl, alkynyl, cycloalkyl and aryl, is optionally substituted with one or more substitutents selected from halo, cyano, alkyl, —R$^x$OR$^w$, —R$^x$S(O)$_q$R$^v$ and —R$^x$NR$^y$R$^z$;
$R^3$ is hydrogen, halo, alkyl, cyano, haloalkyl, cycloalkyl, cycloalkylalkyl, hydroxy or alkoxy;
$R^4$ and $R^5$ are each independently hydrogen or alkyl;
each $R^6$ is independently selected from halo, alkyl, alkenyl, alkynyl, haloalkyl, cycloalkyl, R$^x$OR$^{18}$, —R$^x$NR$^{19}$R$^{20}$, and —R$^x$S(O)$_q$R$^y$;
each $R^7$ is independently halo, alkyl, haloalkyl or —R$^x$OR$^w$;
$R^8$ is alkyl, alkenyl or alkynyl;
$R^9$ is hydrogen, alkyl, haloalkyl, hydroxy, alkoxy or amino;
$R^{10}$ is hydrogen or alkyl;
$R^{11}$ is hydrogen, alkyl, haloalkyl or —C(O)OR$^8$;
$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)R$^O$, —C(O)OR$^w$ and —C(O)NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;
$R^{13}$ and $R^{14}$ are selected as follows:
(i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)R$^v$, —C(O)OR$^w$, —C(O)NR$^y$R$^z$ and —S(O)$_q$R$^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio; or (ii) R[13] and R[14], together with the nitrogen atom to which they are attached, form heterocyclyl or heteroaryl wherein the heterocyclyl or heteroaryl is optionally substituted with one or more substituents independently selected from halo, alkyl, hydroxy, alkoxy, amino and alkylthio and wherein the heterocyclyl is also optionally substituted with oxo;

R[15] is alkyl, alkenyl, alkynyl, cycloalkyl, cycloalkylalkyl, heterocyclyl, heterocyclylalkyl, aryl, aralkyl, heteroaryl, heteroaralkyl, —C(O)NR[y]R[z] or —NR[y]R[z], wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;

R[18] is hydrogen, alkyl, haloalkyl, hydroxy($C_{2-6}$)alkyl, alkenyl, alkynyl, cycloalkyl, cycloalkylalkyl, heterocyclyl, heterocyclylalkyl, aryl, aralkyl, heteroaryl or heteroarylalkyl; wherein R[18] is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, alkoxysulfonyl, hydroxycarbonyl, cycloalkyl, heterocyclyl, aryl, heteroaryl, haloaryl and amino;

R[19] and R[20] are selected as follows:
(i) R[10] and R[20] are each independently hydrogen or alkyl; or
(ii) R[19] and R[20], together with the nitrogen atom to which they are attached, form a heterocyclyl or heteroaryl which is optionally substituted with 1 to 2 groups each independently selected from halo, alkyl, haloalkyl, hydroxyl and alkoxy;

each R[x] is independently alkylene or a direct bond;
R[v] is hydrogen, alkyl, alkenyl or alkynyl;
R[v] is independently hydrogen, alkyl, alkenyl, alkynyl or haloalkyl;
R[y] and R[z] are selected as follows:
(i) R[y] and R[z] are each independently hydrogen, alkyl, alkenyl, alkynyl, cycloalkyl or haloalkyl;
(ii) R[y] and R[z], together with the nitrogen atom to which they are attached, form a heterocyclyl or heteroaryl which is optionally substituted with 1 to 2 groups each independently selected from halo, alkyl, haloalkyl, hydroxyl and alkoxy;
n is 0-4;
p is 0-5; and
each q is independently 0, 1 or 2.

In an embodiment, the JAK-2 inhibitor is AC-410 (available from Ambit Biosciences). In an embodiment, the JAK-2 inhibitor is (S)-(4-fluorophenyl)(4-((5-methyl-1H-pyrazol-3-yl)amino)quinazolin-2-yl)methanol. In an embodiment, the JAK-2 inhibitor has the chemical structure of Formula (LVI):

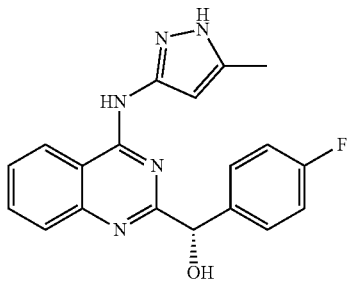

Formula (LVI)

or a pharmaceutically acceptable salt, solvate, hydrate, cocrystal, or prodrug thereof. The preparation of racemic (4-fluorophenyl)(4-((5-methyl-1H-pyrazol-3-yl)amino)quinazolin-2-yl)methanol hydrochloride is described in Examples 3 and 12 of U.S. Pat. No. 8,349,851, the disclosure of which is incorporated by reference herein. Other preparation methods known to one of skill in the art also may be used. The preparation of Formula (LVI) is also described in the following paragraphs.

The preparation of (4-fluorophenyl)(4-(5-methyl-1H-pyrazol-3-ylamino)quinazolin-2-yl)methanone is accomplished by the following two steps (A and B). Step A: To a solution of ethyl 4-chloroquinazoline-2-carboxylate (0.6 g, 2.53 mmol) in THF (6 mL) at −40° C., was added dropwise a 1 M solution of 4-fluorophenylmagnesium bromide in THF (3 mL, 3.0 mmol, 1.2 eq). The mixture was stirred at −40 C for 4 h. The reaction was quenched by adding 0.5 N HCl solution (5 mL) and the mixture was extracted with EtOAc (2×10 mL). The combined organic layers were washed with brine and dried over $MgSO_4$. The crude product was purified on a silica gel column using a mixture of EtOAc-hexanes as eluent. (4-chloroquinazoline-2-yl)(4-fluorophenyl)methanone was obtained as a light yellow solid (440 mg, 60%). $^1$H NMR (300 MHz, DMSO-d6) δ 7.45-740 (m, 2H), 8.07-8.03 (m, 1H), 8.17-8.13 (m, 2H), 8.23 (m, 2H), 8.42 (d, 1H); LC-MS (ESI) m/z 287 (M+H)$^+$. Step B: To a solution of (4-chloroquinazolin-2-yl)(4-fluorophenyl)methanone (84 mg, 0.30 mmol) in DMF (3 mL) were added DIEA (0.103 mL, 0.6 mmol) and 5-methyl-1H-pyrazol-3-amine (88 mg, 0.9 mmol at rt. The reaction mixture was heated at 40° C. overnight. The reaction was quenched by adding water and the yellow precipitate was collected by filtration and washed with water. The crude product was purified by silica gel chromatography eluting with DCM/MeOH to give (4-fluorophenyl)(4-(5-methyl-1H-pyrazol-3-ylamino)quinazolin-2-yl)methanone (30 mg, 29%). $^1$H NMR (300 MHz, DMSO-d6) δ 2.19 (s, 3H), 6.54 (s, 1H), 7.40 (m, 2H), 7.68 (t, 1H), 7.9-7.7 (m, 2H), 8.08 (m, 2H), 8.74 (d, 1H), 10.66 (s, 1H), 12.20 (s, 1H); LC-MS (ESI) m/z 348 (M+H)$^+$.

To a solution of 4-fluorophenyl)(4-(5-methyl-1H-pyrazol-3-ylamino)quinazolin-2-yl)methanone (60 mg, 0.172 mmol) in 1:1 MeOH/THF (10 mL) at 0° C., was added $NaBH_4$ (64 mg, 1.69 mmol). The reaction mixture was stirred at 0° C. for 1.5 h. The reaction mixture was quenched by adding a few drops of acetone and concentrated to dryness. The crude solid was purified on HPLC to afford (4-fluorophenyl)(4-(5-methyl-1H-pyrazol-3-ylamino)quinazolin-2-yl)methanol (18 mg, 30%); $^1$H NMR (300 MHz, DMSO-d6) δ 2.25 (s, 3H), 5.67 (s, 1H), 5.83 (bs, 1H), 6.40 (bs, 1H), 7.13 (m, 2H), 7.55-7.53 (m, 3H), 7.79 (s, 2H), 8.57 (bs, 1H), 10.43 (s, 1H), 12.12 (bs, 1H); LC-MS (ESI) m/z 350 (M+H)$^−$.

To a suspension of (4-fluorophenyl)(4-(5-methyl-1H-pyrazol-3-ylamino)quinazolin-2-yl)methanol (2.3 g) in 30% MeOH/DCM (60 mL) at 0° C. was added dropwise 4M HCl/1,4-dioxane (10 mL). After all solid material had dissolved, the mixture was concentrated under reduced pressure, and to the residue was added 30% $CH_3CN/H_2O$ (80 mL) and the mixture was sonicated until all solid material had dissolved. The mixture was frozen and lyophilized overnight to afford (4-fluorophenyl)(4-(5-methyl-1H-pyrazol-3-ylamino)quinazolin-2-yl)methanol hydrochloride (100%). $^1$H NMR (300 MHz, DMSO-d6) δ 2.25 (s, 3H), 6.02 (s, 1H), 6.20 (s, 1H), 7.27 (t, 2H), 7.60 (qt, 2H), 7.80 (t, 1H), 8.08 (t, 1H), 8.23 (d, 1H), 8.83 (d, 1H), 12.16 (s, 1H), 14.51 (b, 1H); LC-MS (ESI) m/z 350 (M+H)$^+$. Formula LVI, (S)-(4-fluorophenyl)(4-((5-methyl-1H-pyrazol-3-yl)amino)

quinazolin-2-yl)methanol, may be obtained from this preparation by chiral liquid chromatographic separation of the enantiomers, or by other well known techniques for resolution of enantiomers, such as those described in: Eliel et al., *Stereochemistry of Organic Compounds*, Wiley-Interscience, New York, 1994.

In another embodiment, the JAK-2 inhibitor is (R)-(4-fluorophenyl)(4-((5-methyl-1H-pyrazol-3-yl)amino)quinazolin-2-yl)methanol, which is also known in the art to be active as a JAK-2 inhibitor. In an embodiment, the JAK-2 inhibitor is racemic (4-fluorophenyl)(4-(5-methyl-1H-pyrazol-3-yl)amino)quinazolin-2-yl)methanol, which is also known in the art to be active as a JAK-2 inhibitor.

In some preferred embodiments, JAK-2 inhibitors having Formulas (LV) or (LVI) can be prepared, isolated, or obtained by any method known to one of skill in the art, including, but not limited to, synthesis from a suitable optically pure precursor, asymmetric synthesis from an achiral starting material, or resolution of a racemic or enantiomeric mixture, for example, chiral chromatography, recrystallization, resolution, diastereomeric salt formation, or derivatization into diastereomeric adducts followed by separation.

In one embodiment, provided herein is a method for preparation of the compound of Formula (LVI), which comprises resolving racemic (4-fluorophenyl)(4-(5-methyl-1H-pyrazol-3-ylamino)quinazolin-2-yl)methanol with chiral chromatography. In some embodiments, the two individual enantiomers are separated using a chiral column, wherein the stationary phase is silica gel coated with a chiral selector such as tris-(3,5-dimethylphenyl)carbamoyl cellulose.

In another embodiment, provided herein is a method for preparation of the compound of Formula (LVI), comprising the step of reducing the achiral ketone (4-fluorophenyl)(4-(5-methyl-1H-pyrazol-3-ylamino)quinazolin-2-yl)methanone, prepared as described above or by other methods known to one of skill in the art, with hydrogen in the present of a chiral catalyst. The achiral ketone (4-fluorophenyl)(4-(5-methyl-1H-pyrazol-3-ylamino)quinazolin-2-yl)methanone may be reduced to predominantly a single enantiomeric product with a chiral reducing system of "type A" or "type B," wherein type A and type B differ from each other solely by having chiral auxiliaries of opposite chiralities. in some embodiments, the chiral catalyst is [(S)—P-Phos RuCl$_2$ (S)-DAIPEN].

In some embodiments, the reduction of the achiral ketone (4-fluorophenyl)(4-(5-methyl-1H-pyrazol-3-ylamino)quinazolin-2-yl)methanone in presence of a chiral catalyst is carried out in isopropyl alcohol as a solvent. In some embodiments, the reduction of achiral ketone (4-fluorophenyl)(4-(5-methyl-1H-pyrazol-3-ylamino)quinazolin-2-yl) methanone in the presence of a chiral catalyst is carried out in isopropyl alcohol and water mixture as a solvent. In some embodiments, isopropyl alcohol and water are used in a ratio of 1:1, 8:1 or 9:1. In one embodiment, DMSO is used as a cosolvent in the reaction. In one embodiment, DMSO is used in 10, 20 or 30% based on the total amount of isopropyl alcohol and water mixture. In some embodiments, isopropyl alcohol, DMSO and water are used in a ratio of 1:1:1, 4:4:0.5, 8:1:1, 47:47:6, 41:58:1, 44:50:6, or 18:79:3. In some embodiments, isopropyl alcohol, DMSO and water are used in a ratio of 41:58:1. In some embodiments, isopropyl alcohol, and DMSO are used in a ratio of 1:1. In some embodiments, the reduction is carried out in presence of a base, such as potassium hydroxide, potassium tert-butoxide and others. In some embodiments, the base is used in 2-15 mol %, in one embodiment, 2 mol %, 5 mol %, 10 mol %, 12.5 mol % or 15 mol %. In some embodiments, the reduction is carried out at a temperature of 40-80° C., in one embodiment, 40° C., 50° C., 60° C., 70° C. or 80° C. In some embodiments, the reduction is carried out at a temperature of 70° C. In some embodiments, the reduction is carried out at a pressure of 4 bar to 30 bar, in one embodiment, 4, 5, 10, 15, 20, 25 or 30 bar. In some embodiments, the reduction is carried out at a pressure of 4 bar. In some embodiments, the catalyst loading in the reaction is 100/1, 250/1, 500/1, 1000/1, 2000/1, 3000/1, 4000/1, 5000/1, 7000/1, 10,0000/1 or 20,000/1. In some embodiments, the catalyst loading in the reaction is 2000/1 or 4000/1.

In another embodiment, provided herein is a method for preparation of the compound of Formula (LVI), which comprises the step of reducing the achiral ketone (4-fluorophenyl)(4-(5-methyl-1H-pyrazol-3-ylamino)quinazolin-2-yl)methanone with a ketoreductase (e.g., alcohol dehydrogenase). See Moore et al., *Acc. Chem. Res.* 2007, 40, 1412-1419; Daussmann et al., *Engineering in Life Sciences* 2006, 6, 125-129; Schlummer et al., *Specialty Chemicals Magazine* 2008, 28, 48-49; Osswald et al., *Chimica Oggi* 2007, 25(Suppl.), 16-18; and Kambourakis et al., *PharmaChem* 2006, 5(9), 2-5.

In yet another embodiment, provided herein is a method for preparation of the compound of Formula (LVI), comprising the step of reducing the achiral ketone (4-fluorophenyl)(4-(5-methyl-1H-pyrazol-3-ylamino)quinazolin-2-yl) methanone with a reducing reagent (e.g., borane or borohydride reagents) in the presence of a chiral catalyst. In some embodiments, the reducing agent is borane or a borohydride reagent. In some embodiments, the chiral catalyst is a chiral oxazaborolidine. See, Cory et al., *Tetrahedron Letters* 1996, 37, 5675; and Cho, *Chem. Soc. Rev.* 2009, 38, 443.

In another embodiment, provided herein is a method for preparation of the compound of Formula (LVI) comprising the step of reducing the achiral ketone (4-fluorophenyl)(4-(5-methyl-1H-pyrazol-3-ylamino)quinazolin-2-yl)methanone via asymmetric hydrosilylation, as described in U.S. Patent Application Publication No. 2008/0269490, the disclosure of which is specifically incorporated herein by reference in its entirety.

In still another embodiment, provided herein is a method for preparation of the compound of Formula (LVI), comprising the step of reducing the achiral ketone (4-fluorophenyl)(4-(5-methyl-1H-pyrazol-3-ylamino)quinazolin-2-yl) methanone via transfer hydrogenation catalyzed by an iridium complex, as described in Malacea et al., *Coordination Chemistry Reviews* 2010, 254, 729-752.

The starting materials used in the synthesis of the compound of Formula LVI provided herein are either commercially available or can be prepared by a method known to one of skill in the art. For example, the achiral ketone (4-fluorophenyl)(4-(5-methyl-1H-pyrazol-3-ylamino)quinazolin-2-yl)methanone can be prepared according to the methods described in U.S. Pat. No. 8,349,851, issued Jan. 8, 2013, and U.S. Pat. No. 8,703,943, issued Apr. 22, 2014, the disclosures of which are incorporated herein by reference in their entireties.

In some embodiments, the compositions and methods described include one or more JAK-2 inhibitors described in PCT Application Publication No. 2012/030914, published Mar. 8, 2012, contents of which are incorporated herein in their entireties. In some embodiments, the the JAK-2 inhibitors have the structure of Formula (LV-A):

Formula (LV-A)

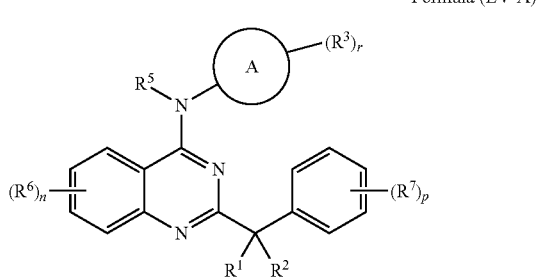

or a pharmaceutically acceptable salt, solvate or hydrate thereof, wherein

A is azolyl other than pyrazolyl;

$R^1$ and $R^2$ are selected from (i), (ii), (iii), (iv) and (v) as follows:

(i) $R^1$ and $R^2$ together form =O, =S, =$NR^9$ or =$CR^{10}R^n$;

(ii) $R^1$ and $R^2$ are both —$OR^8$, or $R^1$ and $R^2$, together with the carbon atom to which they are attached, form cycloalkyl or heterocyclyl wherein the cycloalkyl is substituted with one to four substituents selected from halo, deutero, alkyl, haloalkyl, —OR, —N(R)$_2$, and —S(O)$_q$R and wherein the heterocyclyl contains one to two heteroatoms wherein each heteroatom is independently selected from O, $NR^{24}$, S, S(O) and S(O)$_2$;

(iii) $R^1$ is hydrogen or halo; and $R^2$ is halo;

(iv) $R^1$ is alkyl, alkenyl, alkynyl, cycloalkyl or aryl, wherein the alkyl, alkenyl, alkynyl, cycloalkyl and aryl are each optionally substituted with one to four substituents selected from halo, deutero, alkyl, cycloalkyl, heterocyclyl, aryl, heteroaryl, cyano, =O, =N—$OR^{21}$, —$R^xOR^{21}$, —$R^XNR^{22})_2$, —$R^xS(O)_qR_{23}$, —$C(O)R^{21}$, —$C(O)OR^{21}$ and —$C(O)N(R^{22})_2$; and (v) $R^1$ is halo, deutero, —$OR^{12}$, —$NR^{13}R^{14}$, or —S(O)$_qR^{15}$; and $R^2$ is hydrogen, deutero, alkyl, alkenyl, alkynyl, cycloalkyl or aryl, wherein the alkyl, alkenyl, alkynyl, cycloalkyl and aryl are each optionally substituted with one to four substituents selected from halo, cyano, alkyl, —$R^xOR^w$, —$R^xS(O)_qR^v$ and —$R^xNR^yR^z$;

$R^3$ is hydrogen, deutero, halo, alkyl, cyano, haloalkyl, deuteroalkyl, cycloalkyl, cycloalkylalkyl, hydroxy or alkoxy;

$R^5$ is hydrogen or alkyl; each $R^6$ is independently selected from halo, alkyl, alkenyl, alkynyl, haloalkyl, cycloalkyl, —$R^xOR^{18}$, —$R^XNR^{19}R^{20}$, and —$R^xS(O)_qR^v$;

each $R^7$ is independently halo, alkyl, haloalkyl or —$R^xOR_w$;

R is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —$C(O)OR^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —$C(O)R^O$, —$C(O)OR^w$ and —$C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:

(i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —$C(O)R^O$, —$C(O)OR^w$, —$C(O)NR^yR^z$ and —$S(O)_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or (ii) $R^{13}$ and $R^{14}$, together with the nitrogen atom to which they are attached, form heterocyclyl or heteroaryl wherein the heterocyclyl or heteroaryl are substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is optionally substituted with oxo; $R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —$C(O)NR^yR^z$ or —$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;

$R^{19}$ and $R^{20}$ are selected as follows:

(i) $R^{10}$ and $R^{20}$ are each independently hydrogen or alkyl; or (ii) $R^{19}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;

$R^{21}$ is hydrogen, alkyl, alkenyl, alkynyl, haloalkyl or cycloalkyl;

each $R^{22}$ is independently hydrogen, alkyl, alkenyl, alkynyl, haloalkyl or cycloalkyl; or both $R^{22}$, together with the nitrogen atom to which they are attached, form a heterocyclyl optionally substituted with oxo;

$R^{23}$ is alkyl, alkenyl, alkynyl or haloalkyl;

$R^{24}$ is hydrogen or alkyl;

each $R^x$ is independently alkylene or a direct bond;

$R^v$ is hydrogen, alkyl, alkenyl or alkynyl;

$R^w$ is independently hydrogen, alkyl, alkenyl, alkynyl or haloalkyl;

$R^y$ and $R^z$ are selected as follows:

(i) $R^y$ and $R^z$ are each independently hydrogen, alkyl, alkenyl, alkynyl, cycloalkyl or haloalkyl; or (ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-4;

p is 0-5;

each q is independently 0, 1 or 2; and r is 1-3.

In some embodiments, the JAK-2 inhibitor of Formula (LV-A) has the structure of Formula (LV-B):

Formula (LV-B)

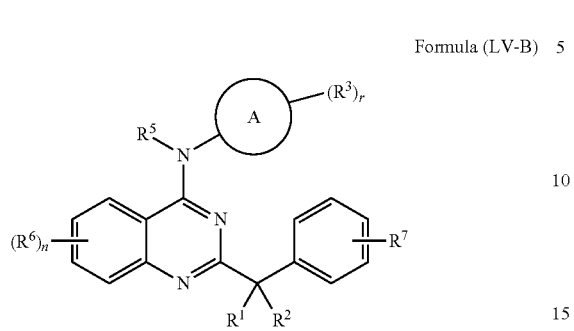

or a pharmaceutically acceptable salt, solvate or hydrate thereof, wherein
A is imidazolyl, oxazolyl, thiazolyl, thiadiazolyl, or triazolyl;
$R^3$ is hydrogen, alkyl, haloalkyl or cycloalkyl;
each $R^6$ is independently selected from halo, alkyl, alkenyl, alkynyl, haloalkyl, cycloalkyl, $-R^xOR^{18}$, $-R^xNR^{19}R^{20}$, and $-R^xS(O)_qR^v$;
$R^7$ is halo;
$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, oxo, haloalkyl, alkoxy, aryloxy, alkoxyalkyl, alkoxycarbonyl, alkoxysulfonyl, carboxyl, cycloalkyl, heterocyclyl, aryl, heteroaryl, haloaryl and amino;
$R^{10}$ and $R^{20}$ are selected as follows:
(i) $R^{10}$ and $R^{20}$ are each independently hydrogen or alkyl; or
(ii) $R^{10}$ and $R^{20}$, together with the nitrogen atom to which they are attached, form a heterocyclyl or heteroaryl which are each optionally substituted with 1 to 2 groups each independently selected from halo, oxo, alkyl, haloalkyl, hydroxyl and alkoxy;
each $R^x$ is independently alkylene or a direct bond;
$R^v$ is hydrogen, alkyl, alkenyl or alkynyl;
$R^y$ and $R^z$ are selected as follows:
(i) $R^y$ and $R^z$ are each independently hydrogen, alkyl, alkenyl, alkynyl, cycloalkyl or haloalkyl; or
(ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;
n is 0-3;
each q is independently 0, 1 or 2; and
r is 1-3.

In some preferred embodiments of the JAK-2 inhibitor of Formula (LV-A) or (LV-B), $R^3$ is hydrogen or alkyl.

In some preferred embodiments of the JAK-2 inhibitor of Formula (LV-A) or (LV-B), A is imidazolyl, oxazolyl, thiazolyl, thiadiazolyl, or triazolyl.

In some preferred embodiments of the JAK-2 inhibitor of Formula (LV-A) or (LV-B), $R^7$ is fluro.

In some preferred embodiments, JAK-2 inhibitor of Formula (LV-A) has the structure of Formula (LV-C):

Formula (LV-C)

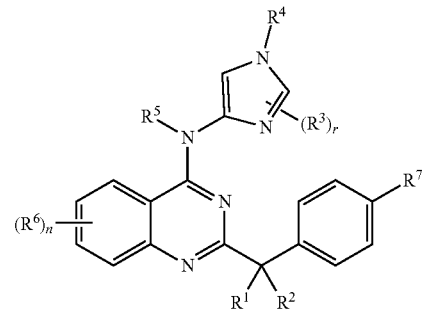

or a pharmaceutically acceptable salt, solvate or hydrate thereof, where
$R^1$ and $R^2$ are selected as follows:
(i) $R^1$ and $R^2$ together form $=O$;
(ii) $R^1$ and $R^2$, together with the carbon atom to which they are attached, form dioxacycloalkyl or cycloalkyl wherein the cycloalkyl is substituted with one to four substituents selected from halo, deutero, alkyl, cycloalkyl, heterocyclyl, aryl, heteroaryl, cyano, $=O$, and hydroxy;
(iii) $R^1$ is hydrogen or halo; and $R^2$ is halo;
(iv) $R^1$ is alkyl, and $R^2$ is hydrogen, alkyl, halo, hydroxy or alkoxy; or
(v) $R^1$ is halo, hydroxy or alkoxy; and $R^2$ is hydrogen or alkyl;
$R^3$ is hydrogen, alkyl or cycloalkyl,
$R^4$ is hydrogen or alkyl;
$R^5$ is hydrogen or alkyl;
$R^7$ is halo; and
n is 0-3.

In some preferred embodiments of the JAK-2 inhibitor of Formula (LV-C), n is 0.

In some preferred embodiments, JAK-2 inhibitor of Formula (LV-A) has the structure of Formula (LV-D):

Formula (LV-D)

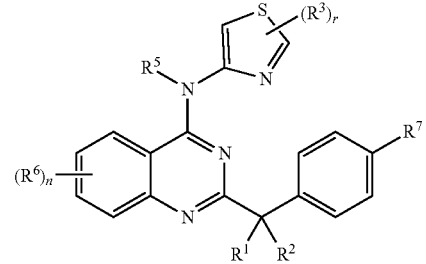

or a pharmaceutically acceptable salt, solvate or hydrate thereof, where
$R^1$ and $R^2$ are selected as follows:
(i) $R^1$ and $R^2$ together form $=O$;
(ii) $R^1$ and $R^2$, together with the carbon atom to which they are attached, form dioxacycloalkyl or cycloalkyl wherein the cycloalkyl is substituted with one to four substituents selected from halo, deutero, alkyl, cycloalkyl, heterocyclyl, aryl, heteroaryl, cyano, =0, and hydroxy;
(iii) $R^1$ is hydrogen or halo; and $R^2$ is halo;
(iv) $R^1$ is alkyl, and $R^2$ is hydrogen, alkyl, halo, hydroxy or alkoxy; or (v) $R^1$ is halo, hydroxy or alkoxy; and $R^2$ is hydrogen or alkyl; $R^3$ is hydrogen, alkyl or cycloalkyl,
$R^5$ is hydrogen or alkyl;
$R^7$ is halo; and
n is 0-3.

In some preferred embodiments of the JAK-2 inhibitor of Formula (LV-D), n is 0.

In some preferred embodiments, JAK-2 inhibitor of Formula (LV-D) is selected from the group consisting of:
(4-fluorophenyl)(4-((1-methyl-1H-imidazol-4-yl)amino) quinazolin-2-yl)methanol; (4-((1H-imidazol-4-yl)amino) quinazolin-2-yl)(4-fluorophenyl)methanol;
(4-fluorophenyl)(4-(thiazol-4-ylamino)quinazolin-2-yl) methanol;
(4-fluorophenyl)(4-((5-methylthiazol-2-yl)amino)quinazolin-2-yl)methanol; and 2-(difluoro(4-fluorophenyl) methyl)-N-(1-methyl-1H-imidazol-4-yl)quinazolin-4-amine,
or a pharmaceutically acceptable salt, solvate or hydrate thereof.

In an embodiment, the JAK-2 inhibitor is a compound of Formula (LVII):

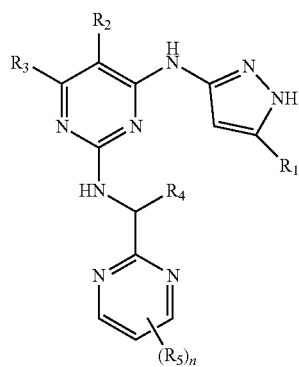

Formula (LVII)

including a pharmaceutically acceptable salt, solvate, hydrate, cocrystal, or prodrug thereof, wherein:
$R^1$ is selected from hydrogen, hydroxy, amino, mercapto, $C_{1-6}$alkyl, $C_{2-6}$alkenyl, $C_{2-6}$alkynyl, $C_{1-6}$alkoxy, $C_{1-6}$alkanoyloxy, N—($C_{1-6}$alkyl)amino, N,N—($C_{1-6}$alkyl)$_2$ amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;
$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, ($C_{1-6}$alkyl)$_2$N—S(O)$_2$—NH—, ($C_{1-6}$alkyl)NH—S(O)$_2$—NH—, NH$_2$—S(O)$_2$—NH—, ($C_{1-6}$alkyl)$_2$N—S(O)$_2$—N($C_{1-6}$alkyl)-, ($C_{1-6}$alkyl)NH—S(O)$_2$—N($C_{1-6}$alkyl)-, NH$_2$—S(O)$_2$—N($C_{1-6}$alkyl)-, N—($C_{1-6}$alkyl)-N—($C_{1-6}$alkylsulphonyl)amino, $C_{1-6}$ alkylsulphonylamino, carbocyclyl-$R^{19}$— or heterocyclyl-$R^{21}$; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;
$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl) carbamoyl, N,N—($C_{1-6}$alkyl)$_2$carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from $R^{11}$;
$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl) sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;
n=0, 1, 2 or 3; wherein the values of $R^5$ may be the same or different;
$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O), wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^8$, $R^{10}$ and $R^{11}$ independently of each other may be optionally substituted on carbon by one or more $R^{14}$; and wherein if said heterocyclyl contains an —NH— moiety that nitrogen may be optionally substituted by a group selected from $R^{15}$;
$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;
$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkyl S(O), wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from R";
$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from a direct bond, —O—, —N($R^{22}$)—, —C(O)—, N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $C_{1-6}$ alkyl and s is 0-2;

$R^{18}$ is selected from $C_{1-6}$ alkyl, $C_{1-6}$ alkanoyl, $C_{1-6}$ alkylsulphonyl, $C_{1-6}$ alkoxycarbonyl, carbamoyl, N—($C_{1-6}$ alkyl)carbamoyl, N,N—($C_{1-6}$ alkyl)carbamoyl, benzyl, benzyloxycarbonyl, benzoyl and phenylsulphonyl;

or a pharmaceutically acceptable salt, solvate, hydrate, cocrystal, or prodrug thereof.

In another aspect, the invention provides compounds of Formula (LVII), wherein: $R^1$ is selected from hydrogen, hydroxy, amino, mercapto, $C_{1-6}$alkyl, $C_{2-6}$alkenyl, $C_{2-6}$alkynyl, $C_{1-6}$alkoxy, $C_{1-6}$alkanoyloxy, N—($C_{1-6}$alkyl)amino, N,N—($C_{1-6}$alkyl)$_2$amino, $C_{1-6}$alkanoylamino, $C_{1-6}$ alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{19}$- or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from R";

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;

n=0, 1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkyl S(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from R";

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from —O—, —N($R^{22}$)—, —C(O)—, —N($R^{23}$)C(O)—, —C(O)N($R^{24}$)—, —SO$_2$N($R^{25}$)- or —N($R^{26}$)SO$_2$—; wherein $R^{22}$, $R^{23}$, $R^{24}$, $R^{25}$ and $R^{26}$ are independently selected from hydrogen or $C_{1-6}$alkyl and s is 0-2;

$R^{18}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt, solvate, hydrate, cocrystal, or prodrug thereof.

In another aspect, the invention provides compounds of Formula (LVII), wherein: leis selected from hydrogen, hydroxy, amino, mercapto, $C_{1-6}$alkyl, $C_{2-6}$alkenyl, $C_{2-6}$alkynyl, $C_{1-6}$alkoxy, $C_{1-6}$alkanoyloxy, N—($C_{1-6}$alkyl)amino, N,N—($C_{1-6}$alkyl)$_2$amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, N—($C_{1-6}$alkyl)-N—($C_{1-6}$alkylsulphonyl)amino, $C_{1-6}$alkylsulphonylamino, carbocyclyl-$R^{19}$- or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from R";

n=0, 1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O), wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from ($C_{1-6}$)alkyl, ($C_{1-6}$)alkanoyl, ($C_{1-6}$)alkylsulphonyl, ($C_{1-6}$)alkoxycarbonyl, carbamoyl, N—(($C_{1-6}$)alkyl)carbamoyl, N,N—(($C_{1-6}$)alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, ($C_{1-6}$)alkyl, ($C_{2-6}$)alkenyl, ($C_{2-6}$)alkynyl, ($C_{1-6}$)alkoxy, ($C_{1-6}$)alkanoyl, ($C_{1-6}$)alkanoyloxy, N—(($C_{1-6}$)alkyl)amino, N,N—(($C_{1-6}$)alkyl)$_2$amino, ($C_{1-6}$)alkanoylamino, N—(($C_{1-6}$)alkyl)carbamoyl, N,N—(($C_{1-6}$)alkyl)$_2$carbamoyl, ($C_{1-6}$)alkylS(O)$_a$ wherein a is 0 to 2, ($C_{1-6}$)alkoxycarbonyl, N—(($C_{1-6}$)alkyl)sulphamoyl, N,N—(($C_{1-6}$)alkyl)$_2$sulphamoyl, ($C_{1-6}$)alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from R";

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from a direct bond, —O—, —N($R^{22}$)—, —C(O)—, N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or ($C_{1-6}$)alkyl and s is 0-2;

$R^{18}$ is selected from ($C_{1-6}$)alkyl, ($C_{1-6}$)alkanoyl, ($C_{1-6}$)alkylsulphonyl, ($C_{1-6}$)alkoxycarbonyl, carbamoyl, N—(($C_{1-6}$)alkyl)carbamoyl, N,N—(($C_{1-6}$)alkyl)carbamoyl, benzyl, benzyloxycarbonyl, benzoyl and phenylsulphonyl;

or a pharmaceutically acceptable salt, solvate, hydrate, cocrystal, or prodrug thereof.

Particular values of the variable groups contained in Formula (LVII) are as follows. Such values may be used, where appropriate, with any of the definitions, claims or embodiments defined hereinbefore or hereinafter.

$R^1$ is selected from ($C_{1-6}$)alkyl, ($C_{1-6}$)alkoxy, 3-5-membered carbocyclyl, and N,N—(($C_{1-6}$)alkyl)$_2$amino, wherein $R^1$ may be optionally substituted on carbon by one or more $R^6$; and wherein $R^6$ is halo, $R^1$ is ($C_{1-6}$)alkoxy or 3-5-membered carbocyclyl.

$R^1$ is selected from ($C_{1-6}$)alkyl, ($C_{1-6}$)alkoxy or 3-5-membered carbocyclyl.

$R^1$ is ($C_{1-6}$)alkyl or ($C_{1-6}$)alkoxy.

$R^1$ is 3-5 membered carbocyclyl.

$R^1$ is N,N(($C_{1-6}$)alkyl)$_2$amino.

$R^1$ is ($C_{1-6}$)alkyl.

$R^1$ is ($C_{1-4}$)alkyl.

$R^1$ is ($C_{1-6}$)alkoxy.

$R^1$ is selected from methyl, methoxy, trifluoroethoxy, isopropoxy, cyclopropyl, and N,N-dimethylamino;

$R^1$ is isopropoxy or cyclopropyl.

$R^1$ is methyl, methoxy, isopropoxy or cyclopropyl.

$R^1$ is selected from methyl, methoxy, isopropoxy, N,N-dimethylamino, and cyclopropyl.

$R^1$ is isopropoxy.

$R^1$ is methyl.

$R^1$ is ethyl.

$R^1$ is selected from methyl, ethyl, propyl, and butyl.

$R^1$ is selected from ($C_{1-4}$)alkyl, ($C_{1-4}$)alkoxy, and cyclopropyl.

$R^1$ is methoxy.

$R^1$ is cyclopropyl. $R^1$ is N,N-dimethylamino.

$R^2$ is selected from hydrogen, halo, nitro, and $(C_{1-6})$alkyl, wherein $R^2$ may be optionally substituted on carbon by one or more $R^8$; and wherein $R^8$ is halo.

$R^2$ is selected from hydrogen, chloro, fluoro, bromo, nitro, and trifluoromethyl.

$R^2$ is halo.

$R^2$ is $(C_{1-6})$alkyl, wherein $R^2$ may be optionally substituted on carbon by one or more $R^8$; and wherein $R^8$ is halo.

$R^2$ and $R^3$ are independently selected from hydrogen, halo, nitro, cyano, hydroxy, amino, carboxy, carbamoyl, mercapto, sulphamoyl, $(C_{1-6})$alkyl, $(C_{2-6})$alkenyl, $(C_{2-6})$alkynyl, $(C_{1-6})$alkoxy, $(C_{1-6})$alkanoyl, $(C_{1-6})$alkanoyloxy, N—$((C_{1-6})$alkyl)amino, N,N—$((C_{1-6})$alkyl)$_2$amino, $(C_{1-6})$alkanoylamino, N—$((C_{1-6})$alkyl)carbamoyl, N,N—$((C_{1-6})$alkyl)$_2$carbamoyl, $(C_{1-6})$alkylS(O)$_a$ wherein a is 0 to 2, $(C_{1-6})$alkoxycarbonyl, N—$((C_{1-6})$alkyl)sulphamoyl, N,N—$((C_{1-6})$alkyl)$_2$sulphamoyl, $(C_{1-6})$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$.

$R^2$ and $R^3$ are independently selected from hydrogen, halo, nitro, cyano, hydroxy, amino, carboxy, carbamoyl, mercapto, sulphamoyl, $(C_{1-6})$alkyl, $(C_{2-6})$alkenyl, $(C_{2-6})$alkynyl, $(C_{1-6})$alkoxy, $(C_{1-6})$alkanoyl, $(C_{1-6})$alkanoyloxy, N—$((C_{1-6})$alkyl)amino, N,N—$((C_{1-6})$alkyl)$_2$amino, $(C_{1-6})$alkanoylamino, N—$((C_{1-6})$alkyl)carbamoyl, N,N—$((C_{1-6})$alkyl)$_2$carbamoyl, $(C_{1-6})$alkylS(O)$_a$ wherein a is 0 to 2, $(C_{1-6})$alkoxycarbonyl, N—$( )C_{1-6})$alkyl)sulphamoyl, N,N—$((C_{1-6})$alkyl)$_2$sulphamoyl, N—$((C_{1-6})$alkyl)-N—$((C_{1-6})$alkylsulphonyl)amino, $(C_{1-6})$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$.

$R^2$ and $R^3$ are independently selected from hydrogen, halo, N—$((C_{1-6})$alkyl)-N—$((C_{1-6})$alkylsulphonyl)amino, or heterocyclyl-$R^{21}$—; wherein $R^{21}$ is a direct bond.

$R^2$ and $R^3$ are independently selected from hydrogen and halo.

$R^2$ and $R^3$ are independently selected from hydrogen and chloro.

$R^2$ and $R^3$ are independently selected from hydrogen, fluoro, chloro, bromo, N-methyl-N-mesylamino and morpholino.

$R^2$ is halo and $R^3$ is hydrogen.

$R^2$ is chloro and $R^3$ is hydrogen.

$R^2$ is chloro or fluoro and $R^3$ is hydrogen. $R^3$ is selected from hydrogen, halo, cyano, N—$((C_{1-6})$alkyl)-N—$((C_{1-6})$alkylsulphonyl)amino, $(C_{1-6})$alkyl, $((C_{1-6})$alkyl)$_2$N—S(O)$_2$—N$((C_{1-6})$alkyl)-, and heterocyclyl-$R^{21}$—, wherein $R^3$ may be optionally substituted on carbon by one or more $R^8$; wherein $R^8$ is halo; and wherein $R^{21}$ is a bond.

$R^3$ is hydrogen.

$R^3$ is halo.

$R^3$ is selected from N—$((C_{1-6})$alkyl)-N—$((C_{1-6})$alkylsulphonyl)amino and $((C_{1-6})$alkyl)$_2$N—S(O)$_2$—N$((C_{1-6})$alkyl)-.

$R^3$ is selected from heterocyclyl-$R^{21}$—, wherein $R^3$ may be optionally substituted on carbon by one or more $R^5$; wherein $R^5$ is halo; and wherein $R^{21}$ is a bond.

$R^3$ is selected from hydrogen, chloro, cyano, trifluoromethyl, $(CH_3)_2$N—S(O)$_2$—N(CH$_3$)—, N-methyl-N-mesylamino, and morpholino.

$R^3$ is $(CH_3)_2$N—S(O)$_2$—N(CH$_3$)—.

$R^3$ is N-methyl-N-mesylamino, $R^3$ is morpholino.

$R^4$ is $(C_{1-6})$alkyl.

$R^4$ is methyl.

$R^5$ is halo.

$R^5$ is fluoro.

n=1.

$R^{19}$ and $R^{21}$ are independently selected from —O—, —N($R^{22}$)—, —C(O)—, —N($1^{23}$)C(O)—, —C(O)N($R^{24}$)—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $(C_{1-6})$alkyl and s is 0-2.

Therefore in a further aspect of the invention there is provided a compound of Formula (LVII) (as depicted herein above) wherein:

$R^1$ is selected from $(C_{1-6})$alkyl, $(C_{1-6})$alkoxy or 3-5-membered carbocyclyl;

$R^1$ and $R^3$ are independently selected from hydrogen, halo, N—$((C_{1-6})$alkyl)-N—$((C_{1-6})$alkylsulphonyl)amino, or heterocyclyl-$R^{21}$—;

$R^4$ is $(C_{1-6})$alkyl;

$R^5$ is halo;

n=1;

$R^{21}$ is a direct bond;

or a pharmaceutically acceptable salt, solvate, hydrate, cocrystal, or prodrug thereof.

Therefore in a further aspect of the invention there is provided a compound of Formula (LVII) (as depicted herein above) wherein:

$R^1$ is $(C_{1-6})$alkoxy;

$R^2$ and $R^3$ are independently selected from hydrogen and halo;

$R^4$ is $(C_{1-6})$alkyl;

$R^5$ is halo;

n=1;

or a pharmaceutically acceptable salt, solvate, hydrate, cocrystal, or prodrug thereof.

Therefore in a further aspect of the invention there is provided a compound of Formula (LVII) (as depicted herein above) wherein:

$R^1$ is methyl, methoxy, isopropoxy or cyclopropyl;

$R^2$ and $R^3$ are independently selected from hydrogen, fluoro, chloro, bromo, N-methyl-N-mesylamino and morpholino;

$R^4$ is methyl;

$R^5$ is fluoro; and n=1;

or a pharmaceutically acceptable salt, solvate, hydrate, cocrystal, or prodrug thereof.

Therefore in a further aspect of the invention there is provided a compound of Formula (LVII) (as depicted herein above) wherein:

$R^1$ is selected from $(C_{1-6})$alkyl, $(C_{1-6})$alkoxy, 3-5-membered carbocyclyl, and N,N—$((C_{1-6})$alkyl)$_2$amino, wherein $R^1$ may be optionally substituted on carbon by one or more $R^6$;

$R^2$ is selected from hydrogen, halo, nitro, and $(C_{1-6})$alkyl, wherein $R^2$ may be optionally substituted on carbon by one or more $R^8$;

$R^3$ is selected from hydrogen, halo, cyano, N—$((C_{1-6})$alkyl)-N—$((C_{1-6})$alkylsulphonyl)amino, $(C_{1-6})$alkyl, $((C_{1-6})$alkyl)$_2$N—S(O)$_2$—N$((C_{1-6})$alkyl)-, and heterocyclyl-$R^{21}$—, wherein $R^3$ may be optionally substituted on carbon by one or more $R^8$;

$R^4$ is $(C_{1-6})$alkyl;

$R^5$ is halo;

$R^6$ is halo;

$R^8$ is halo;

$R^{21}$ is a bond; and n=1;

or a pharmaceutically acceptable salt, solvate, hydrate, cocrystal, or prodrug thereof.

Therefore in a further aspect of the invention there is provided a compound of Formula (LVII) (as depicted herein above) wherein:

$R^1$ is selected from methyl, methoxy, trifluoroethoxy, isopropoxy, cyclopropyl, and N,N-dimethylamino;

$R^2$ is selected from hydrogen, chloro, fluoro, bromo, nitro, and trifluoromethyl;

$R^3$ is selected from hydrogen, chloro, cyano, trifluoromethyl, $(CH_3)_2N—S(O)_2—N(CH_3)—$, N-methyl-N-mesylamino, and morpholino;

$R^4$ is methyl;

$R^5$ is fluoro; and n is 1;

or a pharmaceutically acceptable salt, solvate, hydrate, cocrystal, or prodrug thereof.

Therefore in a further aspect of the invention there is provided a compound of Formula (LVII) (as depicted herein above) wherein:

$R^1$ is selected from $(C_{1-6})$alkoxy, wherein $R^1$ may be optionally substituted on carbon by one or more $R^6$;

$R^2$ is selected from hydrogen and halo;

$R^3$ is selected from hydrogen, halo, and heterocyclyl-$R^{21}$—;

$R^4$ is $(C_{1-6})$alkyl;

$R^5$ is halo;

$R^6$ is halo;

$R^{21}$ is a bond;

n is 1;

or a pharmaceutically acceptable salt, solvate, hydrate, cocrystal, or prodrug thereof.

Therefore in a further aspect of the invention there is provided a compound of Formula (LVII) (as depicted herein above) wherein:

$R^1$ is selected from $(C_{1-4})$alkyl, $(C_{1-4})$alkoxy, and cyclopropyl;

$R^2$ is selected from hydrogen, halo, nitro, and $(C_{1-6})$alkyl, wherein $R^2$ may be optionally substituted on carbon by one or more $R^8$;

$R^3$ is selected from hydrogen, halo, cyano, N—$((C_{1-6})$alkyl)-N—$((C_{1-6})$alkylsulphonyl)amino, $(C_{1-6})$alkyl, $((C_{1-6})$alkyl$)_2$N—S(O)$_2$—N$((C_{1-6})$alkyl)-, and heterocyclyl-$R^{21}$—, wherein $R^3$ may be optionally substituted on carbon by one or more $R^8$;

$R^4$ is $(C_{1-6})$alkyl;

$R^5$ is halo;

$R^6$ is halo;

$R^8$ is halo;

$R^{21}$ is a bond; and n=1;

or a pharmaceutically acceptable salt, solvate, hydrate, cocrystal, or prodrug thereof.

In a preferred embodiment, the JAK-2 inhibitor is AZD-1480. In a preferred embodiment, the JAK-2 inhibitor is (5)-5-chloro-N²-(1-(5-fluoropyrimidin-2-yl)ethyl)-N⁴-(5-methyl-1H-pyrazol-3-yl)pyrimidine-2,4-diamine. In a preferred embodiment, the JAK-2 inhibitor has the chemical structure shown in Formula (LVIII):

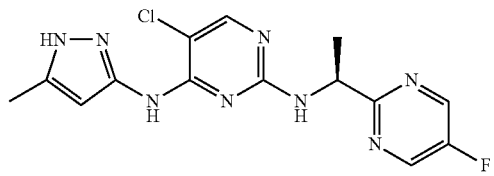

Formula (LVIII)

or a pharmaceutically acceptable salt, solvate, hydrate, cocrystal, or prodrug thereof. The preparation of this compound is described in U.S. Pat. No. 8,088,784 and U.S. Patent Application Publication Nos. 2008/0287475 A1; 2010/0160325 A1; and, 2012/0071480 A1, the disclosures of which are incorporated by reference herein. In an embodiment, the JAK-2 inhibitor is selected from the compounds described in U.S. Pat. No. 8,088,784 and U.S. Patent Application Publication Nos. 2008/0287475 A1; 2010/0160325 A1; and, 2012/0071480 A1, the disclosures of which are incorporated by reference herein.

In an embodiment, the JAK-2 inhibitor is a compound of Formula (LIX):

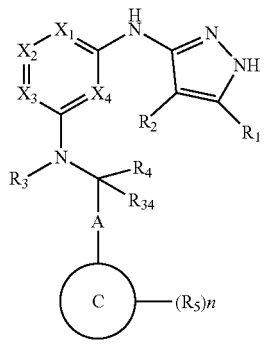

Formula (LIX)

or a pharmaceutically acceptable salt, solvate, hydrate, cocrystal, or prodrug thereof, wherein:

$R^1$ and $R^2$ are independently selected from hydrogen, halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—$(C_{1-6}$alkyl)amino, N,N—$(C_{1-6}$ alkyl)$_2$-amino, $C_{1-6}$ alkanoylamino, N—$(C_{1-6}$alkyl)carbamoyl, N,N—$(C_{1-6}$alkyl)$_2$-carbamoyl, $C_{1-6}$ alkylS(O), wherein a is 0 to 2, $C_{1-6}$ alkoxycarbonyl, N—$(C_{1-6}$ alkyl)sulphamoyl, N,N—$(C_{1-6}$ alkyl)$_2$sulphamoyl, $C_{1-6}$ alkylsulphonylamino, carbocyclyl or heterocyclyl; wherein $R^1$ and $R^2$ independently of each other may be optionally substituted on carbon by one or more $R^6$; and wherein if said heterocyclyl contains an —NH— moiety that nitrogen may be optionally substituted by a group selected from $R^7$;

one of $X^1$, $X^2$, $X^3$ and $X^4$ is =N—, the other three are independently selected from =CR⁸—, =CR⁹— and =CR¹⁰—;

$R^3$ is hydrogen or optionally substituted $C_{1-6}$ alkyl; wherein said optional substituents are selected from one or more $R^{11}$;

$R^4$ and $R^{34}$ are independently selected from hydrogen, halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$ amino, $C_{1-6}$ alkanoylamino, N—($C_{1-6}$alkyl)carbamoyl, N,N—($C_{1-6}$alkyl)$_2$carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkylsulphonylamino, carbocyclyl or heterocyclyl; wherein $R^4$ and $R^{11}$ may be independently optionally substituted on carbon by one or more $R^{12}$; and wherein if said heterocyclyl contains an —NH— moiety that nitrogen may be optionally substituted by a group selected from $R^{13}$;

A is a direct bond or $C_{1-2}$alkylene; wherein said $C_{1-2}$alkylene may be optionally substituted by one or more $R^{14}$;

Ring C is carbocyclyl or heterocyclyl; wherein if said heterocyclyl contains an —NH— moiety that nitrogen may be optionally substituted by a group selected from $R^{15}$;

$R^5$ is selected from halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$alkyl)$_2$carbamoyl, $C_{1-6}$ alkylS(O)$_a$ wherein a is 0 to 2, $C_{1-6}$ alkoxycarbonyl, N—($C_{1-6}$alkyl)sulphamoyl, N,N—($C_{1-6}$alkyl)$_2$sulphamoyl, $C_{1-6}$ alkylsulphonylamino, carbocyclyl-$R^{37}$— or heterocyclyl-$R^{38}$—; wherein $R^5$ may be optionally substituted on carbon by one or more $R^{16}$; and wherein if said heterocyclyl contains an —NH— moiety that nitrogen may be optionally substituted by a group selected from $R^{17}$;

n is 0, 1, 2 or 3; wherein the values of $R^5$ may be the same or different;

$R^8$, $R^9$ and $R^{10}$ are independently selected from hydrogen, halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$ amino, $C_{1-6}$ alkanoylamino, N—($C_{1-6}$ alkyl)carbamoyl, N,N—($C_{1-6}$ alkyl)$_2$carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkyl sulphonylamino, carbocyclyl-$R^{25}$- or heterocyclyl-$R^{26}$—; wherein $R^8$, $R^9$ and $R^{10}$ independently of each other may be optionally substituted on carbon by one or more $R^{18}$; and wherein if said heterocyclyl contains an —NH— moiety that nitrogen may be optionally substituted by a group selected from $R^{19}$;

$R^6$, $R^{11}$, $R^{12}$, $R^{14}$, $R^{16}$ and $R^{18}$ are independently selected from halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkyl sulphonylamino, carbocyclyl-$R^{27}$- or heterocyclyl-$R^{28}$—; wherein $R^6$, $R^{11}$, $R^{12}$, $R^{14}$, $R^{16}$ and $R^{18}$ independently of each other may be optionally substituted on carbon by one or more $R^{20}$; and wherein if said heterocyclyl contains an NH— moiety that nitrogen may be optionally substituted by a group selected from $R^{21}$;

$R^7$, $R^{13}$, $R^{15}$, $R^{17}$, $R^{19}$ and $R^{21}$ are independently selected from $C_{1-6}$ alkyl, $C_{1-6}$ alkanoyl, $C_{1-6}$ alkylsulphonyl, $C_{1-6}$ alkoxycarbonyl, carbamoyl, N—($C_{1-6}$alkyl)carbamoyl, N,N—($C_{1-6}$ alkyl)carbamoyl, benzyl, benzyloxycarbonyl, benzoyl and phenylsulphonyl; wherein $R^7$, $R^{13}$, $R^{15}$, $R^{17}$, $R^{19}$ and $R^{21}$ independently of each other may be optionally substituted on carbon by on or more $R^{22}$;

$R^{20}$ and $R^{22}$ are independently selected from halo, nitro, cyano, hydroxy, trifluoromethoxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$alkyl)carbamoyl, N,N—($C_{1-6}$ alkyl)$_2$carbamoyl, $C_{1-6}$ alkylS(O)$_a$ wherein a is 0 to 2, $C_{1-6}$ alkoxycarbonyl, N—($C_{1-6}$ alkyl)sulphamoyl, N,N—($C_{1-6}$ alkyl)$_2$sulphamoyl, $C_{1-6}$ alkyl sulphonylamino, $C_{1-6}$ alkylsulphonyl-N—($C_{1-6}$ alkyl)amino, carbocyclyl-$R^{35}$— or heterocyclyl-$R^{36}$—; wherein $R^{20}$ and $R^{22}$ independently of each other may be optionally substituted on carbon by one or more $R^{23}$; and wherein if said heterocyclyl contains an —NH— moiety that nitrogen may be optionally substituted by a group selected from $R^{24}$;

$R^{25}$, $R^{26}$, $R^{27}$, $R^{28}$, $R^{35}$, $R^{36}$, $R^{37}$ and $R^{38}$ are independently selected from a direct bond, —O—, N($R^{29}$)—, —C(O)—, —N($R^{30}$)C(O)—, —C(O)N($R^{31}$)—, —S(O)$_s$—, —NH=CH—, —SO$_2$N($R^{32}$)— or —N($R^{33}$)SO$_2$—; wherein $R^{29}$, $R^{30}$, $R^{31}$, $R^{32}$ and $R^{33}$ are independently selected from hydrogen or $C_{1-6}$ alkyl and s is 0-2;

$R^{23}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl or phenyl; and $R^{24}$ is selected from $C_{1-6}$ alkyl, $C_{1-6}$ alkanoyl, $C_{1-6}$ alkylsulphonyl, $C_{1-6}$ alkoxycarbonyl, carbamoyl, N—($C_{1-6}$ alkyl) carbamoyl, N,N—($C_{1-6}$ alkyl)carbamoyl, benzyl, benzyloxycarbonyl, benzoyl and phenylsulphonyl;

or a pharmaceutically acceptable salt, solvate, hydrate, cocrystal, or prodrug thereof.

In a preferred embodiment, the JAK-2 inhibitor is (S)-5-fluoro-2-((1-(4-fluorophenyl)ethyl)amino)-6-((5-methyl-1H-pyrazol-3-yl)amino)nicotinonitrile. In a preferred embodiment, the JAK-2 inhibitor has the chemical structure shown in Formula (LX):

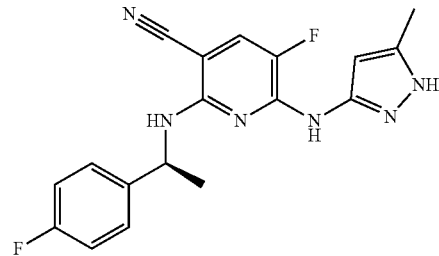

Formula (LX)

or a pharmaceutically acceptable salt, solvate, hydrate, cocrystal, or prodrug thereof. The preparation of this compound is described in U.S. Pat. No. 8,324,252 and U.S. Patent Application Publication Nos. 2008/0139561 A1 and 2013/

0090358 A1, the disclosures of which are incorporated by reference herein. In an embodiment, the JAK-2 inhibitor is selected from the compounds described in U.S. Pat. No. 8,324,252 and U.S. Patent Application Publication Nos. 2008/0139561 A1 and 2013/0090358 A1, the disclosures of which are incorporated by reference herein.

In an embodiment, the JAK-2 inhibitor is a compound of Formula (LXII):

Formula (LXII)

or a pharmaceutically acceptable salt, solvate, hydrate, cocrystal, or prodrug thereof, wherein:

D is CH or N;
E is CH or N;
X is $CH_2$, $NR_4$, O or S;
U is CH or N;
V is CH or N;
Y is CH or N;
Z is CH or N;
$R_1$ is $NR_5R_6$, $CR_5R_6R_7$, $SR_5$ or $OR_5$;
$R_2$ is (C=O)OH, (C=O)$NH_2$, (C=O)$NHR_4$ or heterocyclyl;
$R_3$ is
  (a) hydrogen;
  (b) $C_{1-6}$ alkyl, which is optionally substituted with halo, hydroxyl, amino, phenyl, heterocyclyl, $C_{1-6}$ alkyl or $R_{10}$;
  (c) $C_{2-6}$ alkenyl, which is optionally substituted with halo, hydroxyl, amino, phenyl, heterocyclyl, $C_{1-6}$ alkyl or $R_4$;
  (d) $C_{3-10}$ cycloalkyl, which is optionally substituted with $C_{1-6}$ alkyl, $OR_4$, $NR_8R_4$, phenyl (which is optionally substituted with $C_{1-6}$ alkyl, $OR_4$ or $NR_8R_4$), halo, $R_{10}$ or heterocyclyl;
  (e) —(CO)$R_8$;
  (f) —(CO)—$NR_8R_9$;
  (g) $C_{4-10}$ heterocyclyl, which is optionally substituted on either the carbon or the heteroatom with $C_{1-6}$ alkyl, halo, $R_{10}$, $OR_4$, $NR_8R_4$, phenyl (which is optionally substituted with $C_{1-6}$ alkyl, $OR_4$ or $NR_8R_4$), —(CO)$R_8$ or —(CO)—$NR_8R_9$;
  (h) $OR_4$;
  (i) $NR_8R_4$;
  (j) halo;
  (k) Aryl, which is optionally substituted with one or more groups selected from $C_{1-6}$ alkyl (which is optionally substituted with one to three halo), halo or $R_{10}$;
  (l) Heteroaryl, which is optionally substituted with one or more groups selected from $C_{1-6}$ alkyl (which is optionally substituted with one to three halo), halo or $R_{10}$;
  (m) O-aryl, which is optionally substituted with one or more groups selected from $C_{1-6}$ alkyl, halo or $R_{10}$;
  (n) O—$C_{1-6}$ alkyl, which is optionally substituted with $C_{1-6}$ alky, halo or $R_{10}$; or
  (o) L-A-$R_{10}$;
$R_4$ is
  (a) hydrogen;
  (b) $C_{1-6}$ alkyl, which is optionally substituted with halo, hydroxyl, amino, aryl or heterocyclyl;
  (c) $C_{3-10}$ cycloalkyl, which is optionally substituted with $C_{1-6}$ alkyl, $OR_{11}$, $NR_8R_{11}$, phenyl (which is optionally substituted with $C_{1-6}$ alkyl, $OR_{11}$ or $NR_8R_{11}$), heterocyclyl, aryl or heteroaryl;
  (d) —(CO)$R_8$;
  (e) —(CO)—$NR_8R_9$;
  (f) $C_{4-10}$ heterocyclyl, which is optionally substituted on either the carbon or the heteroatom with $C_{1-6}$ alkyl, $OR_{11}$, $NR_8R_{11}$, phenyl (which is optionally substituted with $C_{1-6}$ alkyl, $OR_{11}$ or $NR_8R_{11}$), heterocyclyl, —(CO)$R_8$ or —(CO)—$NR_8R_9$;
  (g) $OR_{11}$;
  (h) $NR_8R_{11}$;
  (i) Aryl, which is optionally substituted with one to five halo or $R_{10}$;
  (j) Heteroaryl (wherein the heteroaryl has 5 or 6 members in which 1, 2, 3, or 4 of the atoms is a heteroatom selected from N, S and O), which is optionally substituted with one to five halo or $R_{10}$;
$R_5$ is
  (a) hydrogen;
  (b) $C_{1-8}$ alkyl, which is optionally substituted with halo, hydroxyl, amino, aryl, cycloalkyl or heterocyclyl;
  (c) $C_{3-10}$ cycloalkyl, which is optionally substituted with $C_{1-6}$ alkyl, ($C_{1-6}$ alkyl)aryl, ($C_{1-6}$ alkyl)$OR_9$, $OR_4$, $NR_8R_4$, phenyl (which is optionally substituted with $C_{1-6}$ alkyl, $OR_4$, —$NR_8R_4$, heterocyclyl, —(CO)$R_8$ or —(CO)—$NR_8R_9$);
  (d) —(CO)$R_8$;
  (e) —(CO)—$NR_8R_9$;
  (f) $C_{1-6}$ alkyl(C=O)$NR_8CR_9$(C=O)$NR_8R_9$;
  (g) $C_{4-10}$ heterocyclyl which is optionally substituted on either the carbon or the heteroatom with one to three substituents selected from $C_{1-6}$ alkyl, halo, $OR_4$, $NR_8R_4$, (CO)$R_8$, ($C_0$)—$NR_8R_9$ or phenyl (which is optionally substituted with $C_{1-6}$ alkyl, $OR_4$, —$NR_8R_4$, heterocyclyl, —(CO)$R_8$ or —(CO)—$NR_8R_9$);
$R_6$ is
  (a) hydrogen;
  (b) $C_{1-8}$ alkyl, which is optionally substituted with halo, hydroxyl, amino, aryl, cycloalkyl or heterocyclyl;
  (c) $C_{3-10}$ cycloalkyl, which is optionally substituted with $C_{1-6}$ alkyl, ($C_{1-6}$ alkyl)aryl, ($C_{1-6}$ alkyl)$OR_9$, $OR_4$, $NR_8R_4$, phenyl (which is optionally substituted with $C_{1-6}$ alkyl, $OR_4$, —$NR_8R_4$, heterocyclyl, —(CO)$R_8$ or —(CO)—$NR_8R_9$;
  (d) —(CO)$R_8$;
  (e) —(CO)—$NR_8R_9$;
  (f) $C_{1-6}$ alkyl(C=O)$NR_8CR_9$(C=O)$NR_8R_9$;
  (g) $C_{4-10}$ heterocyclyl which is optionally substituted on either the carbon or the heteroatom with one to three substituents selected from $C_{1-6}$ alkyl, halo, $OR_4$, $NR_8R_4$, (CO)$R_8$, (CO)—$NR_8R_9$ or phenyl (which is optionally substituted with $C_{1-6}$ alkyl, $OR_4$, —$NR_8R_4$, heterocyclyl, —(CO)$R_8$ or —(CO)—$NR_8R_9$);
$R_7$ is
  (a) hydrogen;
  (b) $C_{1-6}$ alkyl, which is optionally substituted with halo, hydroxyl, amino, phenyl or heterocyclyl;
  (c) $C_{3-10}$ cycloalkyl, which is optionally substituted with $C_{1-6}$ alkyl, $OR_4$, $NR_8R_4$, phenyl (which is optionally substituted with $C_{1-6}$ alkyl, $OR_4$, $NR_8R_4$, heterocyclyl, —(CO)$R_8$ or —(CO)—$NR_8R_9$);
  (d) $C_{4-10}$ heterocyclyl which is optionally substituted on either the carbon or the heteroatom with $C_{1-6}$ alkyl, OR$_4$, NR$_8$R$_4$, phenyl (which is optionally substituted with C$_{1-6}$ alkyl, OR$_4$, NR$_8$R$_4$, heterocyclyl, —(CO)R$_8$ or —(CO)—NR$_8$R$_9$);

Or R$_5$ and R$_6$, together with the atoms between them, can form a three to ten membered heterocyclic or heteroaryl ring which is optionally substituted with C$_{1-6}$ alkyl, (C$_{1-6}$ alkyl)aryl, (C$_{1-6}$ alkenyl)aryl, (C$_{1-6}$ alkyl)OR$_9$, OR$_4$, NR$_8$R$_4$, phenyl (which is optionally substituted with C$_{1-6}$ alkyl, OR$_4$, NR$_8$R$_4$, heterocyclyl, —(CO)R$_8$ or —(CO)—NR$_8$R$_9$), —(CO)R$_8$; —(CO)—NR$_8$R$_9$, or heterocyclyl;

R$_8$ is hydrogen or C$_{1-6}$ alkyl, —(CO)R$_{11}$, —(CO)N(R$_{11}$)$_2$;

R$_9$ is hydrogen or C$_{1-6}$ alkyl;

R$_{10}$ is:
(a) hydrogen;
(b) CO$_2$R$_{11}$;
(c) C(O)R$_{11}$;
(d) NHR$_{11}$;
(e) NR$_{11}$R$_{12}$;
(f) NHS(O)$_2$R$_{11}$;
(g) NHC(O)R$_{11}$;
(h) NHC(O)OR$_{11}$;
(i) NH—C=(NH)NH$_2$;
(j) NHC(O)NH$_2$;
(k) NHC(O)NHR$_{11}$;
(l) NHC(O)NR$_{11}$R$_{12}$;
(m) NC3-6cycloalkyl;
(n) C(O)NHR$_{11}$;
(o) C(O)NR$_{11}$R$_{12}$;
(p) SO$_2$NHR$_{11}$;
(q) SO$_2$NHC(O)R$_{12}$; or
(r) SO$_2$R$_{11}$;

R$_{11}$ is selected from the group consisting of:
(a) hydrogen,
(b) C3-6cycloalkyl, which is optionally substituted with aryl, heteroaryl or one to five halo;
(c) C$_{1-6}$ alkyl, which is optionally substituted with aryl, heteroaryl, or one to five halo;
(d) Aryl, which is optionally substituted with one to five halo;
(e) Heteroaryl (wherein the heteroaryl has 5 or 6 members in which 1, 2, 3, or 4 of the atoms is a heteroatom selected from N, S and O), which is optionally substituted with one to five halo;

R$_{12}$ is selected from the group consisting of:
(a) hydrogen,
(b) C1-6alkyl, which is optionally substituted with aryl, heteroaryl or one to five halo;
(c) C3-6cycloalkyl, which is optionally substituted with aryl, heteroaryl or one to five halo;
(d) Aryl, which is optionally substituted with one to five halo;
(e) Heteroaryl (wherein the heteroaryl has 5 or 6 members in which 1, 2, 3, or 4 of the atoms is a heteroatom selected from N, S and O), which is optionally substituted with one to five halo;

A is absent or is selected from the group consisting of: aryl or heteroaryl (wherein the heteroaryl is a monocyclic ring of 5 or 6 atoms or a bicyclic ring of 9 or 10 atoms in which 1, 2, 3, or 4 of the atoms is a heteroatom selected from N, S and O), wherein said aryl or heteroaryl is optionally substituted with one or more substituents selected from halo, (C$_{1-3}$)alkyl, —C(O)OH, CF$_3$, —SO$_2$(C$_{1-3}$)alkyl, SO$_2$N(C$_{1-3}$)alkyl, SO$_2$NHC(O)—(C$_{1-3}$)alkyl or N(CH$_3$)$_2$;

L is absent or is selected from the group consisting of: —(CH$_2$)$_k$—W—, —Z—(CH$_2$)$_k$—, —C≡C—, —C$_{1-6}$alkyl-, —C$_{3-6}$cycloalkyl- and —C$_{2-5}$alkene-, wherein the alkene is optionally substituted with one or more groups selected from C$_{1-6}$alkyl or C$_{1-6}$cycloalkyl;

W is selected from the group consisting of: O, NH, NC$_{1-6}$ alkyl and S(O)m, with the proviso that when W is O, S(O)m, NH or NC$_{1-6}$alkyl and simultaneously A is absent then R$_{10}$ is CO$_2$R$_{11}$, COR$_{11}$, CONHR$_{11}$ or CONR$_{11}$R$_{12}$;

k=0, 1, 2, 3, 4, or 5;

m=0, 1, or 2;

n=0, 1, 2, or 3;

or a pharmaceutically acceptable salt, solvate, hydrate, cocrystal, or prodrug thereof, or stereoisomer thereof.

In a preferred embodiment, the JAK-2 inhibitor is ((R)-7-(2-aminopyrimidin-5-yl)-1-((1-cyclopropyl-2,2,2-trifluoroethyl)amino)-5H-pyrido[4,3-b]indole-4-carboxamide, which is also named 7-(2-aminopyrimidin-5-yl)-1-{[(1R)-1-cyclopropyl-2,2,2-trifluoroethyl]amino}-5H-pyrido[4,3-b]indole-4-carboxamide. In a preferred embodiment, the JAK-2 inhibitor has the chemical structure shown in Formula (LXII):

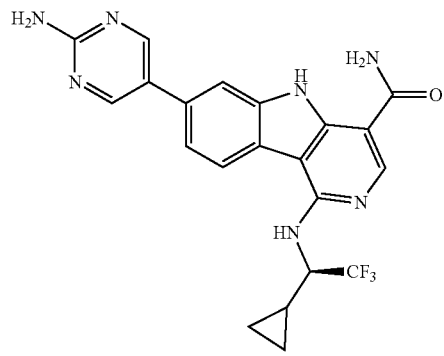

Formula (LXII)

or a pharmaceutically acceptable salt, solvate, hydrate, cocrystal, or prodrug thereof. The preparation of this compound is known to those of ordinary skill in the art, and is described in J. Lim, et al., Discovery of 1-amino-5H-pyrido[4,3-b] indol-4-carboxamide inhibitors of Janus kinase-2 (JAK2) for the treatment of myeloproliferative disorders, *J. Med. Chem.* 2011, 54, 7334-7349.

In selected embodiments, the JAK-2 inhibitor is a compound selected from the JAK-2 inhibitors disclosed in U.S. Patent No. U.S. Pat. No. 8,518,964 or U.S. Patent Application Publication Nos. 2010/0048551 A1, the disclosures of which are incorporated by reference herein.

BCL-2 Inhibitors

Some embodiments (for example combinations, compositions and/or kits) of the invention comprise a BCL-2 inhibitor. The BCL-2 inhibitor may be any BCL-2 inhibitor known in the art. In particular, it is one of the BCL-2 inhibitors described in more detail in the following paragraphs. Preferably, it is a compound of Formula (LXVI) or a pharmaceutically acceptable salt thereof.

In an embodiment, the BCL-2 inhibitor is a compound of Formula (LXIII):

Formula (LXIII)

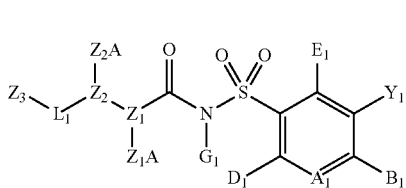

or a pharmaceutically acceptable salt thereof, wherein:
$A^1$ is N or $C(A^2)$;
$A^2$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)$OR^1$, $NR^1C(O)OR^1$, NHC(O)$NH_2$, NHC(O)$NHR^1$, NHC(O)$N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, —$NR^1SO_2N(R^1)_2$, C(O)NHNOH, C(O)NHNO$R^1$, C(O)NHSO$_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH$_3$), $CF_3$, C(O)OH, C(O)NH$_2$ or C(O)$OR^{14}$;
$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)$OR^1$, $NR^1C(O)OR^1$, NHC(O)$NH_2$, NHC(O)$NHR^1$, NHC(O)$N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, —$NR^1SO_2N(R^1)_2$, C(O)NHNOH, C(O)NHNO$R^1$, C(O)NHSO$_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH$_3$), $CF_3$, C(O)OH, C(O)NH$_2$ or C(O)$OR^{14}$;
$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)$OR^1$, $NR^1C(O)OR^1$, NHC(O)$NH_2$, NHC(O)$NHR^1$, NHC(O)$N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, —$NR^1SO_2N(R^1)_2$, C(O)NHNOH, C(O)NHNO$R^1$, C(O)NHSO$_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH$_3$), $CF_3$, C(O)OH, C(O)NH$_2$ or C(O)$OR^{14}$;
$E^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)$OR^1$, $NR^1C(O)OR^1$, NHC(O)$NH_2$, NHC(O)$NHR^1$, NHC(O)$N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, —$NR^1SO_2N(R^1)_2$, C(O)NHNOH, C(O)NHNO$R^1$, C(O)NHSO$_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH$_3$), $CF_3$, C(O)OH, C(O)NH$_2$ or C(O)$OR^{14}$; and
$Y^1$ is H, CN, $NO_2$, C(O)OH, F, Cl, Br, I, $CF_3$, $OCF_3$, $CF_2CF_3$, $OCF_2CF_3$, $OR^{17}$, $C(O)R^{17}$, $C(O)OR^{17}$, $SR^{17}$, $SO_2R^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$; or $E^1$ and $Y^1$, together with the atoms to which they are attached, are benzene, naphthylene, heteroarene, cycloalkane, cycloalkene, heterocycloalkane or heterocycloalkene; and
$A^2$, $B^1$, and $D^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)$OR^1$, $NR^1C(O)OR^1$, NHC(O)$NH_2$, NHC(O)$NHR^1$, NHC(O)$N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, C(O)NHNO$R^1$, C(O)NHSO$_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH$_3$), $CF_3$, C(O)OH, C(O)NH$_2$ or C(O)$OR^{14}$; or
$Y^1$ and $B^1$, together with the atoms to which they are attached, are benzene, naphthylene, heteroarene, cycloalkane, cycloalkene, heterocycloalkane or heterocycloalkene; and
$A^2$, $D^1$, and $E^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)$OR^1$, $NR^1C(O)OR^1$, NHC(O)$NH_2$, NHC(O)$NHR^1$, NHC(O)$N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, C(O)NHNO$R^1$, C(O)NHSO$_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH$_3$), $CF_3$, C(O)OH, C(O)NH$_2$ or C(O)$OR^{14}$; or
$A^2$ and $B^1$, together with the atoms to which they are attached, are benzene, naphthylene, heteroarene cycloalkane, cycloalkene, heterocycloalkane or heterocycloalkene; and
$D^1$, $E^1$, and $Y^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)$OR^1$, $NR^1C(O)OR^1$, NHC(O)$NH_2$, NHC(O)$NHR^1$, NHC(O)$N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, C(O)NHNO$R^1$, C(O)NHSO$_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH$_3$), $CF_3$, C(O)OH, C(O)NH$_2$ or C(O)$OR^{14}$; or
$A^2$ and $D^1$, together with the atoms to which they are attached, are benzene, naphthalene, heteroarene, cycloalkane, cycloalkene, heterocycloalkane or heterocycloalkene; and
$B^1$, $E^1$, and $Y^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, $NR^1C(O)R^1$, NHC(O)$OR^1$, $NR^1C(O)OR^1$, NHC(O)$NH_2$, NHC(O)$NHR^1$, NHC(O)$N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, C(O)NHNO$R^1$, C(O)NHSO$_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, CH(NOCH$_3$), $CF_3$, C(O)OH, C(O)NH$_2$ or C(O)$OR^{14}$;
$G^1$ is H, or C(O)OR;
R is alkyl;
$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with $R^{2A}$; $R^{2A}$ is benzene, heteroarene, cycloalkane, cycloalkene, heterocycloalkane or heterocycloalkene;

$R^3$ is heteroaryl, which is unfused or fused with $R^{3A}$; $R^{3A}$ is benzene, heteroarene, cycloalkane, cycloalkene, heterocycloalkane or heterocycloalkene;

$R^4$ is cycloalkyl, cycloalkenyl, heterocycloalkyl or heterocycloalkenyl, each of which is unfused or fused with $R^{4A}$; $R^{4A}$ is benzene, heteroarene, cycloalkane, cycloalkene, heterocycloalkane or heterocycloalkene;

$R^5$ is alkyl, alkenyl or alkynyl, each of which is unsubstituted or substituted with one or two or three of independently selected $R^6$, $NC(R^{6A})(R^{6B})$, $R^7$, OW, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^7$, OH, (O), C(O)OH, $N_3$, CN, $NH_2$, $CF_3$, $CF_2CF_3$, F, Cl, Br or I;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^6$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl, which is unfused or fused with $R^{8A}$; $R^{8A}$ is benzene, heteroarene, cycloalkane, cycloalkene, heterocycloalkane or heterocycloalkene;

$R^9$ is heteroaryl, which is unfused or fused with $R^{9A}$; $R^{9A}$ is benzene, heteroarene, cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with $R^{10A}$; $R^{10A}$ is benzene, heteroarene, cycloalkane, cycloalkene, heterocycloalkane or heterocycloalkene;

$R^{11}$ is alkyl, alkenyl or alkynyl, each of which is unsubstituted or substituted with one or two or three of independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{12}$ is $R^{13}$, $R^{14}$, $R^{15}$ or $R^{16}$, $R^{13}$ is phenyl, which is unfused or fused with $R^{13A}$; $R^{13A}$ is benzene, heteroarene, cycloalkane, cycloalkene, heterocycloalkane or heterocycloalkene;

$R^{14}$ is heteroaryl, which is unfused or fused with $R^{14A}$; $R^{14A}$ is benzene, heteroarene, cycloalkane, cycloalkene, heterocycloalkane or heterocycloalkene;

$R^{15}$ is cycloalkane, cycloalkene, heterocycloalkane or heterocycloalkene, each of which is unfused or fused with $R^{15A}$; $R^{15A}$ is benzene, heteroarene, cycloalkane, cycloalkene, heterocycloalkane or heterocycloalkene;

$R^{16}$ is alkyl, alkenyl or alkynyl;

$R^{17}$ is $R^{18}$, $R^{19}$, $R^{20}$ or $R^{21}$;

$R^{18}$ is phenyl, which is unfused or fused with $R^{18A}$; $R^{18A}$ is benzene, heteroarene, cycloalkane, cycloalkene, heterocycloalkane or heterocycloalkene;

$R^{19}$ is heteroaryl, which is unfused or fused with $R^{19A}$; $R^{19A}$ is benzene, heteroarene, cycloalkane, cycloalkene, heterocycloalkane or heterocycloalkene;

$R^{20}$ is cycloalkyl, cycloalkenyl, heterocycloalkyl or heterocycloalkenyl each of which is unfused or fused with $R^{20A}$; $R^{20A}$ is benzene, heteroarene, cycloalkane, cycloalkene, heterocycloalkane or heterocycloalkene;

$R^{21}$ is alkyl, alkenyl or alkynyl, each of which is unsubstituted or substituted with one or two or three of independently selected $R^{22}$, $OR^{22}$, $SR^{22}$, $S(O)R^{22}$, $SO_2R^{22}$, $C(O)R^{22}$, $CO(O)R^{22}$, $OC(O)R^{22}$, $OC(O)OR^{22}$, $NH_2$, $NHR^{22}$, $N(R^{22})_2$, $NHC(O)R^{22}$, $NR^{22}C(O)R^{22}$, $NHS(O)_2R^{22}$, $NR^{22}S(O)_2R^{22}$, $NHC(O)OR^{22}$, $NR^{22}C(O)OR^{22}$, $NHC(O)NH_2$, $NHC(O)NHR^{22}$, $NHC(O)N(R^{22})_2$, $NR^{22}C(O)NHR^{22}$, $NR^{22}C(O)N(R^{22})_2$, $C(O)NH_2$, $C(O)NHR^{22}$, $C(O)N(R^{22})_2$, $C(O)NHOH$, $C(O)NHOR^{22}$, $C(O)NHSO_2R^{22}$, $C(O)NR^{22}SO_2R^{22}$, $SO_2NH_2$, $SO_2NHR^{22}$, $SO_2N(R^{22})_2$, $C(O)H$, $C(O)OH$, $C(N)NH_2$, $C(N)NHR^{22}$, $C(N)N(R^{22})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{22}$ is $R^{23}$, $R^{24}$ or $R^{25}$;

$R^{23}$ is phenyl, which is unfused or fused with $R^{23A}$; $R^{23A}$ is benzene, heteroarene, cycloalkane, cycloalkene, heterocycloalkane or heterocycloalkene;

$R^{24}$ is heteroarene, which is unfused or fused with $R^{24A}$; $R^{24A}$ is benzene, heteroarene, cycloalkane, cycloalkene, heterocycloalkane or heterocycloalkene;

$R^{25}$ is cycloalkyl, cycloalkenyl, heterocycloalkyl or heterocycloalkenyl, each of which is unfused or fused with $R^{25A}$; $R^{25A}$ is benzene, heteroarene, cycloalkane, cycloalkene, heterocycloalkane or heterocycloalkene;

$Z^1$ is $R^{26}$ or $R^{27}$;

$Z^2$ is $R^{28}$, $R^{29}$ or $R^{30}$;

$Z^{1A}$ and $Z^{2A}$ are both absent or are taken together to form $CH_2$, $CH_2CH_2$ or $Z^{12A}$;

$Z^{12A}$ is $C_2$-$C_6$-alkylene having one or two $CH_2$ moieties replaced by NH, $N(CH_3)$, S, S(O) or $SO_2$;

$L^1$ is a $R^{37}$, $OR^{37}$, $SR^{37}$, $S(O)R^{37}$, $SO_2R^{37}$, $C(O)R^{37}$, $CO(O)R^{37}$, $OC(O)R^{37}$, $OC(O)OR^{37}$, $NHR^{37}$, C(O)NH, $C(O)NR^{37}$, $C(O)NHOR^{37}$, $C(O)NHSO_2R^{37}$, $SO_2NH$, $SO_2NHR^{37}$, C(N)NH, $C(N)NHR^{37}$;

$R^{26}$ is phenylene, which is unfused or fused with $R^{26A}$; $R^{26A}$ is benzene, heteroarene, cycloalkane, cycloalkene, heterocycloalkane or heterocycloalkene;

$R^{27}$ is heteroarylene, which is unfused or fused with $R^{27A}$; $R^{27A}$ is benzene, heteroarene, cycloalkane, cycloalkene, heterocycloalkane or heterocycloalkene;

$R^{28}$ is phenylene, which is unfused or fused with $R^{28A}$; $R^{28A}$ is benzene, heteroarene, cycloalkane, cycloalkene, heterocycloalkane or heterocycloalkene;

$R^{29}$ is heteroarylene, which is unfused or fused with $R^{29A}$; $R^{29A}$ is benzene, heteroarene, cycloalkane, cycloalkene, heterocycloalkane or heterocycloalkene;

$R^{30}$ is cycloalkylene, cycloalkenylene, heterocycloalkylene or heterocycloalkenylene, each of which is unfused or fused with $R^{30A}$; $R^{30A}$ is benzene, heteroarene, cycloalkane, cycloalkene, heterocycloalkane or heterocycloalkene;

$R^{37}$ is a bond or $R^{37A}$;

$R^{37A}$ is alkylene, alkenylene, or alkynylene, each of which is unsubstituted or substituted with one or two or three independently selected $R^{37B}$, $OR^{37B}$, $SR^{37B}$, $S(O)R^{37B}$, $SO_2R^{37B}$, $C(O)R^{37B}$, $CO(O)R^{37B}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^{37B}$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)NHSO_2R^{37B}$, $C(O)NR^{37B}SO_2R^{37B}$, $SO_2NH_2$, $SO_2NHR^{37B}$, $SO_2N(R^{37B})_2$, $C(O)H$, $C(O)OH$, $C(N)NH_2$, $C(N)NHR^{37B}$, $C(N)N(R^{37B})_2$, CNOH, $CNOCH_3$, OH, (O), CN, $N_3$, $NO_2$, $CF_3$, $CF_2CF_3$, $OCF_3$, $—OCF_2CF_3$, F, Cl, Br and I substituents;

$R^{37B}$ is alkyl, alkenyl, alkynyl, or $R^{37C}$;

$R^{37C}$ is phenyl, heteroaryl, cycloalkyl, cycloalkenyl, heterocycloalkyl, or heterocycloalkenyl;

$Z^3$ is $R^{38}$, $R^{39}$ or $R^{40}$;

$R^{38}$ is phenyl, which is unfused or fused with $R^{38A}$; $R^{38A}$ is benzene, heteroarene, cycloalkane, cycloalkene, heterocycloalkane or heterocycloalkene;

$R^{39}$ is heteroaryl, which is unfused or fused with $R^{39A}$; $R^{39A}$ is benzene, heteroarene, cycloalkane, cycloalkene, heterocycloalkane or heterocycloalkene;

$R^{40}$ is cycloalkyl, cycloalkenyl, heterocycloalkyl or heterocycloalkenyl, each of which is unfused or fused with $R^{40A}$; $R^{40A}$ is benzene, heteroarene, cycloalkane, cycloalkene, heterocycloalkane or heterocycloalkene;

wherein the moieties represented by $R^{26}$ and $R^{27}$ are substituted (i.e., if $Z^{1A}$ and $Z^{2A}$ are absent) or further substituted (i.e., if $Z^{1A}$ and $Z^{2A}$ are present) with $R^{41}$, $OR^{41}$, $SR^{41}$, $S(O)R^{41}$, $SO_2R^{41}$, $C(O)R^{41}$, $CO(O)R^{41}$, $OC(O)R^{41}$, $OC(O)OR^{41}$, $NHR^{41}$, $N(R^{41})_2$, $NHC(O)R^{41}$, $NR^{41}C(O)R^{41}$ $NHS(O)_2 R^{41}$, $NR^{41}S(O)_2R^{41}$, $NHC(O)OR^{41}$, $NR^{41}C(O)OR^{41}$, $NHC(O)NHR^{41}$, $NHC(O)N(R^{41})_2$, $NR^{41}C(O)NHR^{41}$, $NR^{41}C(O)N(R^{41})_2$, $C(O)NHR^{41}$, $C(O)N(R^{41})_2$, $C(O)NHOR^{41}$, $C(O)NHSO_2R^{41}$, $C(O)NR^{41}SO_2R^{41}$, $SO_2NHR^{41}$, $SO_2N(R^{41})_2$, $C(N)NHR^{41}$, or $C(N)N(R^{41})_2$;

$R^{41}$ is heteroaryl, which is fused with $R^{43A}$; $R^{43A}$ is benzene, heteroarene, cycloalkane, cycloalkene, heterocycloalkane or heterocycloalkene; which is unfused or fused with benzene, heteroarene or $R^{43B}$; $R^{43B}$ is cycloalkane, cycloalkene, heterocycloalkane or heterocycloalkene; wherein the cyclic moieties represented by $E^1$ and $Y^1$ together, $Y^1$ and $B^1$ together, $A^2$ and $B^1$ together $A^2$ and $D^1$ together $R^{1A}$, $R^2$, $R^{2A}$, $R^3$, $R^{3A}$, $R^4$, $R^{4A}$, $R^6$, $R^{6C}$, $R^8$, $R^{8A}$, $R^9$, $R^{9A}$, $R^{10}$, $R^{10A}$, $R^{13}$, $R^{13A}$, $R^{14}$, $R^{14A}$, $R^{15}$, $R^{15A}$, $R^{18}$, $R^{18A}$, $R^{19}$, $R^{19A}$, $R^{20}$, $R^{20A}$, $R^{23}$, $R^{23A}$, $R^{24}$, $R^{24A}$, $R^{25}$, $R^{25A}$, $R^{26}$, $R^{26A}$, $R^{27}$, $R^{27A}$, $R^{28}$, $R^{28A}$, $R^{29}$, $R^{29A}$, $R^{30}$, $R^{30A}$, $R^{37B}$, $R^{38}$, $R^{38A}$, $R^{39}$, $R^{39A}$, $R^{40}$, and $R^{40A}$ are independently unsubstituted, further unsubstituted, substituted or further substituted with one or two or three or four or five of independently selected $R^{57A}$, $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{57A}$ is spiroalkyl, or spiroheteroalkyl;

$R^{57}$ is $R^{58}$, $R^{59}$, $R^{60}$ or $R^{61}$;

$R^{58}$ is phenyl, which is unfused or fused with $R^{58A}$; $R^{58A}$ is benzene, heteroarene, cycloalkane, cycloalkene, heterocycloalkane or heterocycloalkene;

$R^{59}$ is heteroaryl, which is unfused or fused with $R^{59A}$; $R^{59A}$ is benzene, heteroarene, cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with $R^{60A}$, $R^{60A}$ is benzene, heteroarene, cycloalkane, cycloalkene, heterocycloalkane or heterocycloalkene;

$R^{61}$ is alkyl, alkenyl or alkynyl, each of which is unsubstituted or substituted with one or two or three of independently selected. $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(V^2)_2$, $C(O)NH$, $C(O)NHR^{62}$, $C(O)N(R^{62})_2$, $C(O)NHOH$, $C(O)NHOR^{62}$, $C(O)NHSO_2R^{62}$, $C(O)NHSO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$ CNOH, $CNOCH_3$, OH, (O), CN, $N_3$, $NO_2$, $CF_3$, $CF_2CF_1$, $OCF_3$ $OCF_2CF_3$, F, Cl, Br or I;

$R^{62}$ is $R^{63}$, $R^{64}$, $R^{65}$ or $R^{66}$;

$R^{63}$ is phenyl, which is unfused or fused with $R^{63A}$; $R^{63A}$ is benzene, heteroarene, cycloalkane, cycloalkene, heterocycloalkane or heterocycloalkene;

$R^{64}$ is heteroaryl, which is unfused or fused with $R^{64A}$; $R^{64A}$ is benzene, heteroarene, cycloalkane, cycloalkene, heterocycloalkane or heterocycloalkene;

$R^{65}$ is cycloalkyl, cycloalkenyl, heterocycloalkyl, or heterocycloalkenyl, each of which is unfused or fused with $R^{65A}$; $R^{65A}$ is benzene, heteroarene, cycloalkane, cycloalkene, heterocycloalkane or heterocycloalkene;

$R^{66}$ is alkyl, alkenyl or alkynyl, each of which is unsubstituted or substituted with one or two or three of independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67}$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the cyclic moieties represented by $R^{57A}$, $R^{58}$, $R^{59}$, $R^{60}$, $R^{63}$, $R^{64}$, $R^{65}$, and $R^{67}$ are unsubstituted or substituted with one or two or three or four of independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NH_0R^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, CNOH, $CNOCH_3$, OH, (O), CN, $N_3$ $NO_2$, $CF_3$, $CF_2CF_3$, $OCF_3$ $OCF_2CF_3$, F, Cl, Br or I;

$R^{68}$ is $R^{69}$, $R^{70}$, $R^{71}$ or $R^{72}$;

$R^{69}$ is phenyl, which is unfused or fused with $R^{69A}$; $R^{69A}$ is benzene, heteroarene, cycloalkane, cycloalkene, heterocycloalkane or heterocycloalkene;

$R^{70}$ is heteroaryl, which is unfused or fused with $R^{70A}$; $R^{70A}$ is benzene, heteroarene, cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with $R^{71A}$; $R^{71A}$ is benzene, heteroarene, cycloalkane, cycloalkene, heterocycloalkane or heterocycloalkene;

$R^{72}$ is alkyl, alkenyl or alkynyl, each of which is unsubstituted or substituted with one or two or three of independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{73}$ is alkyl, alkenyl, alkenyl, phenyl, heteroaryl, cycloalkyl, cycloalkenyl, heterocycloalkyl or heterocycloalkenyl; and wherein the moieties represented by $R^{69}$, $R^{70}$, and $R^{71}$ are unsubstituted or substituted with one or two or three or four of independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, $(O)$, $CN$ $N_3$, $NO_2$, $CF_3$, $CF_2CF_3$, $OCF_3$, $OCF_2CF_3$, F, Cl, Br or I.

Another embodiment pertains to compounds of Formula (LXIII) wherein $A^1$ is N or $C(A^2)$; $A^2$ is H, and $G^1$ is H.

Another embodiment pertains to compounds of Formula (LXIII) wherein $A^1$ is N or $C(A^2)$; $A^2$ is H; $G^1$ is H, and $B^I$ is $NHR^1$.

Another embodiment pertains to compounds of Formula (LXIII) wherein $A^1$ is N or $C(A^2)$; $A^2$ is H; $G^1$ is H, $B^1$ is $NHR^1$; and $D^1$ is H.

Another embodiment pertains to compounds of Formula (LXIII) wherein $A^1$ is N or $C(A^2)$; $A^2$ is H; $G^1$ is H, $B^1$ is $NHR^1$; $D^1$ is H; and $E^1$ is H, Another embodiment pertains to compounds of Formula (LXIII) wherein $A^1$ is N or $C(A^2)$; $A^2$ is H; $G^1$ is H, $B^1$ is $NHR^1$; $D^1$ is H; $B^1$ is H; and $Y^1$ is $NO_2$.

In an embodiment, the BCL-2 inhibitor is a compound of Formula (LXIV):

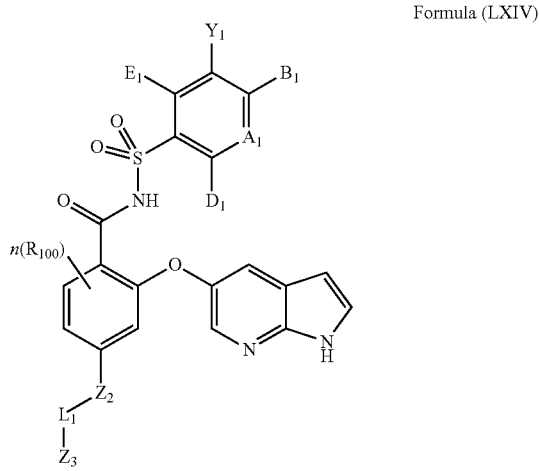

Formula (LXIV)

or a pharmaceutically acceptable salt thereof, wherein
$R^{100}$ is as described for substituents on $R^{26}$;
n is 0, 1, 2, or 3;
$A^1$, $B^1$, $D^1$, $E^1$, $Y^1$, $Z^2$, $L^1$ and $Z^3$ are as defined in relation to Formula (LXIII).

In an embodiment, the BCL-2 inhibitor is a compound of Formula (LXV):

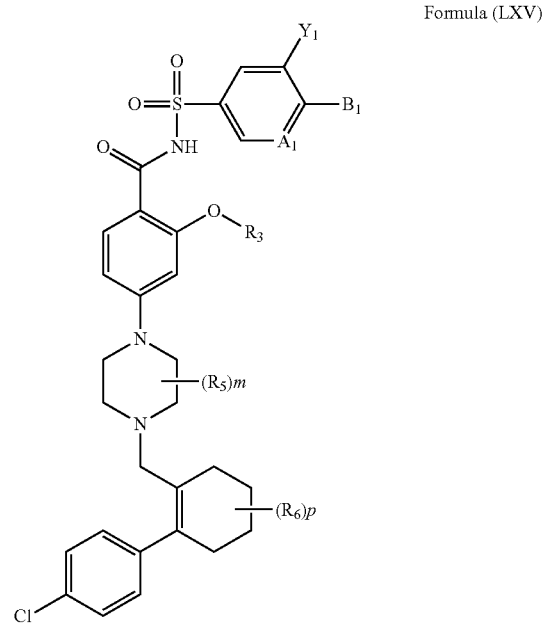

Formula (LXV)

including pharmaceutically acceptable salt forms or prodrugs thereof, wherein:
$A^1$ is N or CH;
$B^1$ is $OR^1$ or $NHR^1$;
$Y^1$ is CN, $NO_2$, $CF_3$, F or $C_1$;
$R^1$ is $(CH_2)_nR^2$;
$R^2$ is cycloalkyl or heterocyclyl; wherein the heterocyclyl and cycloalkyl are optionally substituted with one or more independently selected $R^4$, $OR^4$, OH, CN, or F;
$R^3$ is heteroaryl; wherein the heteroaryl is optionally substituted with one or more independently selected $NH_2$, $C_1$, or F;
$R^4$ is alkyl, cycloalkyl, heterocyclyl, or spiroheterocyclyl; wherein the alkyl is optionally substituted with one or more F;
$R^5$ is hydrogen or deuterium;
each $R^6$ is independently selected from $CH_3$, spirocyclopropyl and OH;
m is 0, 1, 2, 3, 4, 5, or 6;
n is 0 or 1; and
p is 0, 1, or 2.

Methods for making selective BCL-2 inhibitors, such as those encompassed by Formula (LXV) and which can be used in the methods of the present invention are described in U.S. Pat. Nos. 8,546,399; 8,586,754; 8,563,735; and, 8,557,983 and U.S. Patent Application Publication Nos. 2010/0305122 A1; 2010/0298321 A1; 2010/0152183 A1; 2010/0298323 A1; and, 2010/0160322 A1, the disclosures of which are incorporated by reference herein.

In a preferred embodiment, the BCL-2 inhibitor is venetoclax (available from AbbVie, Inc.). In a preferred embodiment, the BCL-2 inhibitor is ABT-199. In a preferred embodiment, the BCL-2 inhibitor is 24(1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N—((3-nitro-4-((((tetrahydro-2H-pyran-4-yl)methyl)amino)phenyl)sulfonyl)benzamide. In a preferred embodiment, the BCL-2 inhibitor has the chemical structure shown in Formula (LXVI):

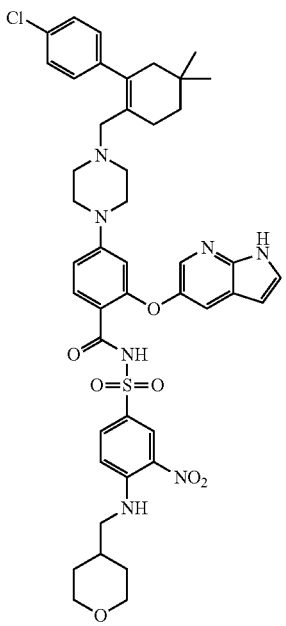

Formula (LXVI)

or a pharmaceutically acceptable salt thereof. An alternative chemical name for Formula (LXVI) is 4-(4-{[2-(4-chlorophenyl)-4,4-dimethylcyclohex-1-en-1-yl]methyl}piperazin-1-yl)-N—({3-nitro-4-[(tetrahydro-2H-pyran-4-ylmethyl)amino]phenyl}sulfonyl)-2-(1H-pyrrolo[2,3-b]pyridin-5-yloxy)benzamide. The efficacy of venetoclax in cancer is known to one of ordinary skill in the art, and for example, is described in: Souers, et al., *Nat Med.* 2013, 19, 202-208.

The preparation of venetoclax is described in U.S. Pat. Nos. 8,722,657, 8,580,794, 8,546,399, 8,557,983, and 8,338,466, and U.S. Patent Application Publication Nos. 2012/0129853, 2012/0157470, 2012/0277210, 2012/0108590, 2011/0124628, 2013/0267514, 2010/0305122, 2012/0190688, 2013/0267534, 2014/0094471, 2014/0113910, 2010/0298323, 2014/0088106, 2010/0184766, and 2013/0184278, the disclosures of which are incorporated by reference herein. For example, venetoclax (Formula (LXVI)) suitable for use with the present inventions may be prepared by the following procedure.

Compound A, 3-nitro-4-((tetrahydro-2H-pyran-4-yl) methylamino) benzenesulfonamide, may be prepared as follows. A mixture of 4-fluoro-3-nitrobenzenesulfonamide (2.18 g), 1-(tetrahydropyran-4-yl)methylamine (1.14 g), and triethylamine (1 g) in tetrahydrofuran (30 mL) were stirred overnight, neutralized with concentrated HCl and concentrated. The residue was suspended in ethyl acetate and the precipitates were collected, washed with water and dried to provide Compound A.

Compound B, methyl 4,4-dimethyl-2-(trifluoromethylsulfonyloxy)cyclohex-1-enecarboxylate, may be prepared as follows. To a suspension of hexane washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoroacetic anhydride (40 mL) was added. The reaction mixture was warmed to room temperature and stirred for 24 hours. The organic layer was washed with brine, dried ($Na_2SO_4$), filtered, and concentrated to give the product (Compound B).

Compound C, methyl 2-(4-chlorophenyl)-4,4-dimethylcyclohex-1-enecarboxylate, may be prepared as follows. Compound B (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether (4×200 mL) was added and the mixture was filtered. The combined ether solution was concentrated to give the product (Compound C).

Compound D, (2-(4-chlorophenyl)-4,4-dimethylcyclohex-1-enyl)methanol, may be prepared as follows. To a mixture of $LiBH_4$ (13 g), Compound C (53.8 g) and ether (400 mL), was added methanol (25 mL) slowly by syringe. The mixture was stirred at room temperature for 24 hours. The reaction was quenched with 1N HCl with ice cooling. The mixture was diluted with water and extracted with ether (3×100 mL). The extracts were dried ($Na_2SO_4$), filtered, and concentrated. The crude product was chromatographed on silica gel with 0-30% ethyl acetatelhexanes to provide the product (Compound D).

Compound E, t-butyl 4-((2-(4-chlorophenyl)-4,4-dimethylcyclohex-1-enyl)methy l)piperazine-1-carboxylate, may be prepared as follows. Mesyl chloride (7.5 mL) was added via syringe to Compound D (29.3 g) and triethylamine (30 mL) in $CH_2Cl_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, ($Na_2SO_4$), filtered, and concentrated. The crude product was chromatographed on silica gel with 10-20% ethyl acetatelhexanes to provide the product (Compound E).

Compound F, 1-(2-(4-chlorophenyl)-4,4-dimethylcyclohex-1-enyl)methyl)piperazine, may be prepared as follows. Compound E (200 mg) and triethylsilane (1 mL) were stirred in dichloromethane (15 mL) and trifluoroacetic acid (15 mL) for 1 hour. The mixture was concentrated, taken up in ethyl acetate, washed twice with $NaH_2PO_4$, and brine, and dried ($Na_2SO_4$), filtered and concentrated to provide the product (Compound F).

Compound G, 5-bromo-1-(triisopropylsilyl-1H-pyrrolo[2,3-b]pyridine, may be prepared as follows. To a mixture of 5-bromo-1H-pyrrolo[2,3-b]pyridine (15.4 g) in tetrahydrofuran (250 mL) was added 1 M lithium hexamethyldisilazide in tetrahydrofuran (86 mL), and after 10 minutes, TIPS-$C_1$ (triisopropylchlorosilane) (18.2 mL) was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes to provide the product (Compound G).

Compound H, 1-(triisopropylsilyl)-1H-pyrrolo[2,3-b] pyridin-5-ol, may be prepared as follows. To a mixture of Compound G (24.3 g) in tetrahydrofuran (500 mL) at −78° C. was added 2.5M BuLi (30.3 mL). After 2 minutes, trimethylborate (11.5 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 mL) at 0° C., and 1M NaOH (69 mL) was added, followed by 30% $H_2O_2$ (8.43 mL), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried (Na$_2$SO$_4$), filtered, and concentrated. The crude product was chromatographed on silica gel with 5-25% ethyl acetate/hexanes.

Compound I, methyl 2-(1H-pyrrolo[2,3-b]pyridin-5-yloxy)-4-fluorobenzoate, may be prepared as follows. A mixture of Compound H (8.5 g), methyl 2,4-difluorobenzoate (7.05 g), and K$_3$PO$_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes to provide the product (Compound I).

Compound J, methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate, may be prepared as follows. A mixture of Compound I (1.55 g), Compound F (2.42 g), and HK$_2$PO$_4$ (1.42 g) in dimethylsulfoxide (20 mL) at 135° C. was stirred for 24 hours. The reaction was cooled, diluted with ether (400 mL), and washed with 3×1M NaOH, and brine, and concentrated. The crude product was chromatographed on silica gel with 10-50% ethyl acetate/hexanes to provide the product (Compound J).

Compound K, 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic acid, may be prepared as follows. Compound J (200 mg) in dioxane (10 mL) and 1M NaOH (6 mL) at 50° C. was stirred for 24 hours. The reaction was cooled, added to NaH$_2$PO$_4$ solution, and extracted three times with ethyl acetate. The combined extracts were washed with brine, and concentrated to give the pure product.

Compound L, the free base of venetoclax (4-(4-{[2-(4-chlorophenyl)-4,4-dimethylcyclohex-1-en-1-yl]methyl}piperazin-1-yl)-N-(3-nitro-4-[(tetrahydro-2H-pyran-4-ylmethyl)amino]phenyl}sulfonyl)-2-(1H-pyrrolo[2,3-b]pyridin-5-yloxy)benzamide), may be prepared as follows. Compound K (3.39 g), Compound A (1.87 g), (dimethylamino)propyl]-carbodiimide hydrochloride (2.39 g), and 4-dimethylaminopyridine (1.09 g) were stirred in CH$_2$Cl$_2$ (40 mL) for 24 hours. The reaction was cooled and chromatographed on silica gel with 25-100% ethyl acetate/hexanes, then 10% methanol/ethyl acetate with 1% acetic acid, to give the product (1.62 g, 32%) as a solid. $^1$H NMR (300 MHz, dimethylsulfoxide-d6) 11.65 (br s, 1H), 8.55 (br s, 1H), 8.04 (d, 1H), 7.89 (dd, 1H), 7.51 (m, 3H), 7.33 (d, 2H), 7.08 (m, 1H), 7.04 (d, 2H), 6.68 (dd, 1H), 6.39 (d, 1H), 6.19 (d, 1H), 3.84 (m, 1H), 3.30 (m, 4H), 3.07 (m, 4H), 2.73 (m, 2H), 2.18 (m, 6H), 1.95 (m, 2H), 1.61 (dd, 2H), 1.38 (m, 2H), 1.24 (m, 4H), 0.92 (s, 6H).

With respect to venetoclax, the term "free base" is used for convenience herein to refer to venetoclax parent compound as distinct from any salt thereof, while recognizing that the parent compound, strictly speaking, is zwitterionic at neutral conditions and thus does not always behave as a true base. Crystalline forms and salts of venetoclax are described in U.S. Pat. No. 8,722,657. In a preferred embodiment, the BCL-2 inhibitor includes venetoclax in the anhydrate crystalline form of "Compound 1 Free Base Anhydrate PXRD Pattern A," as described in U.S. Pat. No. 8,722,657, which is incorporated by reference herein. The following route may be used to prepare this anhydrate crystalline form. Venetoclax free base Compound 1 free base solid was suspended in ethyl acetate at ambient temperatures to reach its solubility. After equilibrating, the solids were isolated at ambient temperature to provide an ethyl acetate solvate having a powder X-ray diffraction (PXRD) pattern characterized by reflections at 5.8, 7.1, 9.5, 9.9, 10.6, 11.6, 13.1, 13.8, 14.8, 16.0, 17.9, 20.2, 21.2, 23.2, 24.4, and 26.4° 2θ. The free base ethyl acetate solvate may be dried at ambient conditions to provide the anhydrate crystalline form of venetoclax, where drying at ambient conditions involves leaving the solid material at room temperature and exposed to air overnight. The anhydrate crystalline form of venetoclax is characterized by a PXRD pattern with reflections at 6.3, 7.1, 9.0, 9.5, 12.5, 14.5, 14.7, 15.9, 16.9, and 18.9° 2θ.

In an embodiment, the BCL-2 inhibitor is a compound of Formula (LXVII):

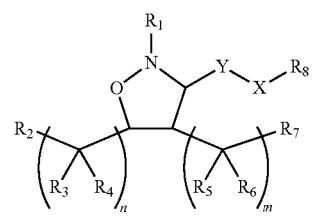

Formula (LXVII)

or pharmaceutically acceptable salts, solvates, or hydrates thereof,
wherein
Y is —C(R$_9$)$_2$—, —C(O)—, —C(S)—, or —C(=NR$_{10}$)—;
X is —N(R$_{11}$)—, an optionally substituted phenyl group, or a bond;
X$^1$ represents independently for each occurrence O, N(R$_{10}$), or S;
m is 0, 1, 2, 3, 4, 5, or 6;
n represents independently for each occurrence 0, 1, 2, 3, 4, 5, or 6;
R$_1$ is alkyl, aralkyl, heteroaralkyl, has the formula 1a:

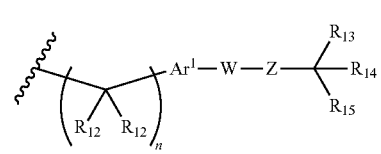

1a wherein
R$_{12}$ represents independently for each occurrence H, alkyl, aryl, heteroaryl, or aralkyl; wherein any two instances of R$_{12}$ may be connected by a covalent bond;
Ar$^1$ is a monocyclic or bicyclic aryl with 6-14 ring atoms; or a monocyclic or bicyclic heteroaryl with 5-14 ring atoms, of which one, two or three ring atoms are independently S, O or N;
W is a bond; or bivalent alkyl, alkenyl, or alkynyl chain;
Z is a bond, —(C(R$_{12}$)$_2$)$_n$—, or —X'(C(R$_{12}$)$_2$)$_n$—;
R$_{13}$ and R$_{14}$ are independently H, alkyl, aryl, cycloalkyl, heterocycloalkyl, aralkyl, heteroaryl, heteroaralkyl, or -A$^1$-A$^2$-A$^3$; or R$_{13}$ and R$_{14}$ taken together form a monocyclic or polycyclic ring; or R$_{13}$ and R$_{14}$ taken together with R$_{15}$ form a cycloalkenyl ring, aromatic ring, or heteroaromatic ring;
R$_{15}$ is halide, hydroxyl, alkoxyl, aryl, aryloxy, acyloxy, —N(R$_{10}$)$_2$, acylamino, aralkyl, nitro, acylthio, carboxamide, carboxyl, nitrile, —COR$_{10}$, —CO$_2$R$_{10}$, —N(R$_{10}$)CO$_2$R$_{10}$, —OC(O)N(R$_{10}$)$_2$, —N(R$_{10}$)SO$_2$R$_{19}$, —N(R$_{10}$)C(X')N(R$_{19}$)$_2$, —N(R$_{10}$)(C(R$_9$)$_2$)$_n$-A$^1$-A$^2$-A$^3$, (C(R$_9$)$_2$)$_n$-halogen, or —CH$_2$O-heterocyclyl; or R$_{15}$ taken together with Rn and R$_{14}$ form a cycloalkenyl ring, aromatic ring, or heteroaromatic ring; or R$_1$ or R$_{15}$ are each represented independently by formula 1b:

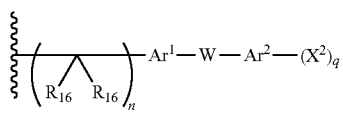

$R_{16}$ represents independently for each occurrence H, alkyl, cycloalkyl, heterocycloalkyl, aryl, aralkyl, halide, hydroxyl, alkoxyl, aryloxy, acyloxy, amino, alkylamino, arylamino, acylamino, aralkylamino, nitro, acylthio, carboxamide, carboxyl, nitrile, —$COR_{10}$, —$CO_2R_{10}$, —$N(R_{10})CO_2R_{10}$, —$OC(O)N(R_{10})_2$, —$N(R_{10})SO_2R_{10}$, or —$N(R_{10})C(X')N(R_{10})_2$; wherein any two instances of $R_{16}$ may be connected by a covalent bond to form a ring;

$Ar^2$ represents independently for each occurrence a monocyclic or bicyclic aryl with 6-14 ring atoms; or a monocyclic or bicyclic heteroaryl with 5-14 ring atoms, of which one, two or three ring atoms are independently S, O or N;

$X^1$ represents independently for each occurrence a bond, O, S, S(O), S(O)$_2$, S(O)$_3$, amino, alkylamino diradical, alkoxyl diradical, alkyl diradical, alkenyl diradical, alkynyl diradical, amido, carbonyl, —$N(R_{10})CO_2$—, —$OC(O)N(R_{10})$—, or —$N(R_{10})C(X')N(R_{10})$—;

$X^2$ represents independently for each occurrence H, halide, hydroxyl, alkoxyl, aryloxy, acyloxy, amino, alkylamino, arylamino, acylamino, aralkylamino, nitro, acylthio, carboxamide, carboxyl, nitrile, —$COR_{10}$, —$CO_2R_{10}$, —$N(R_{10})CO_2R_{10}$, —$OC(O)N(R_{10})_2$, —$N(R_{10})SO_2R_{10}$, —$N(R_{10})C(X')N(R_{10})_2$, or —$CH_2O$-heterocyclyl; and q represents independently for each occurrence 1, 2, 3, 4, or 5;

$R_2$ and $R_7$ are independently H, hydroxyl, alkyl, alkoxyl, amino, alkylamino, or acylamino; or $R_2$ and $R_7$ taken together form a —OC(O)O— linkage, —$N(R_{10})C(O)N(R_{10})$— linkage, or an optionally substituted covalent linkage comprising 1 to 6 carbon atoms and 0, 1, or 2 nitrogen, oxygen, or sulfur atoms to form a 5-8 membered ring; or $R_7$ is a bond to $R_8$;

$R_3$ and $R_6$ each represent independently for each occurrence H, hydroxyl, or alkyl;

$R_4$ and $R_5$ each represent independently for each occurrence independently H or alkyl;

$R_8$ is H, a branched or unbranched alkyl or alkenyl, cycloalkyl, heterocycloalkyl, bicycloalkyl, a bond to $R_7$, heterocycloalkyl substituted with an aralkyl group, or has the formula 1c:

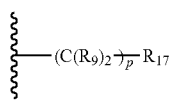

wherein
p is 0, 1, 2, 3, 4, 5, or 6; and
$R_{17}$ is aryl, cycloalkyl, cycloalkenyl, heterocyclyl, alkoxyl, heteroaryl, —$OR_{18}$, —$SR_{18}$, —$N(R_{18})_2$, —$N(R_{10})CO_2$-alkyl, —$CO_2R_{10}$, —$C(O)N(R_{10})$aryl, or a polycyclic ring containing 8-14 carbon atoms; wherein $R_{18}$ is independently for each occurrence H, alkyl, aryl, aralkyl, acyl, -$A^1$-$A^2$-$A^3$, or —$CR_9$=$CR_9(C(R_9)_2)_nCR_9$=$C(R_9)_2$; or two $R_{18}$ taken together form a ring;
$R^9$ represents independently for each occurrence H or alkyl;
$R_{10}$ and $R_{11}$ represent independently for each occurrence H, alkyl, aryl, cycloalkyl, aralkyl, heteroaryl, or heteroaralkyl;
$R_{19}$ represents independently for each occurrence H, alkyl, aryl, cycloalkyl, aralkyl, heteroaryl, heteroaralkyl, or -$A^1$-$A^2$-$A^3$;
$A^1$ and $A^3$ each represent independently for each occurrence alkyl, cycloalkyl, heterocycloalkyl, aryl, heteroaryl, aralkyl, or heteroaralkyl;
$A^2$ represents independently for each occurrence O, N($R_{10}$), S, or a bond; and
the stereochemical configuration at any stereocenter of a compound represented by 1 is R, S, or a mixture of these configurations.

In some embodiments, the present invention provides Formula (LXVII) or Formula (LXVIII), wherein $R_8$ or $R_{8a}$ is:

In some embodiments, the present invention provides Formula (LXVII), wherein Y is —C(O)—, X is —N($R_{11}$)—, $R_2$ and $R_7$ are hydroxyl, $R_6$ is methyl, ethyl, or propyl, and $R_3$, $R_4$, and $R_5$ are H.

In some embodiments, the present invention provides Formula (LXVII), wherein the compound has Formula (LXVIII):

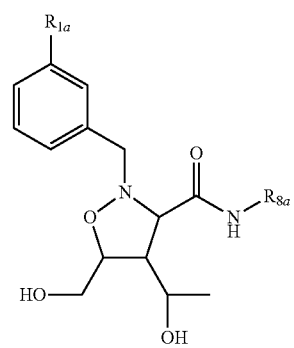

Formula (LXVIII)

wherein
$R_{1a}$ has formula 1e:

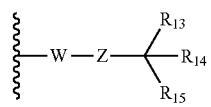

1e wherein
W is a bond; or bivalent alkyl, alkenyl, or alkynyl chain;
Z is a bond, —$(C(R_{12})_2)_n$—, or ~$O(C(R_{12})_2)_n$—;
$R_{13}$ and $R_{14}$ are independently H, alkyl, aryl, cycloalkyl, heterocycloalkyl, aralkyl, heteroaryl, heteroaralkyl, or -$A^1$-$A^2$-$A^3$; or $R_{13}$ and $R_{14}$ taken together form a monocyclic or polycyclic ring; or $R_{13}$ and $R_{14}$ taken together with $R_{15}$ form a cycloalkenyl ring, aromatic ring, or heteroaromatic ring;
$R_{15}$ is halide, hydroxyl, alkoxyl, aryl, aryloxy, acyloxy, —$N(R_{10})_2$, acylamino, aralkyl, nitro, acylthio, carboxamide, carboxyl, nitrile, —$COR_{10}$, —$CO_2R_{10}$, —$N(R_{10})CO_2R_{10}$, —$OC(O)N(R_{10})_2$, —$N(R_{10})SO_2R_{19}$, —$N(R_{10})C(O)N(R_{19})_2$, —$N(R_{10})(C(R_9)_2)_n$-$A^1$-$A^2$-$A^3$, $(C(R_9)_2)_n$-halogen, or —$CH_2O$-heterocyclyl; or $R_{15}$ taken together with $R_{13}$ and $R_{14}$ form a cycloalkenyl ring, aromatic ring, or heteroaromatic ring; or has the formula if:

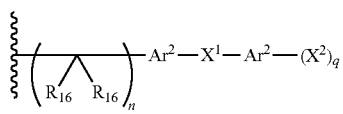

$R_{16}$ represents independently for each occurrence H, alkyl, cycloalkyl, heterocycloalkyl, aryl, aralkyl, halide, hydroxyl, alkoxyl, aryloxy, acyloxy, amino, alkylamino, arylamino, acylamino, aralkylamino, nitro, acylthio, carboxamide, carboxyl, nitrile, —$COR_{10}$, —$CO_2R_{10}$, —$N(R_{10})CO_2R_{10}$, —$OC(O)N(R_{10})_2$, —$N(R_{10})SO_2R_{10}$, or —$N(R_{10})C(O)N(R_{10})_2$; wherein any two instances of $R_{16}$ may be connected by a covalent bond to form a ring;

$Ar^2$ represents independently for each occurrence a monocyclic or bicyclic aryl with 6-14 ring atoms; or a monocyclic or bicyclic heteroaryl with 5-14 ring atoms, of which one, two or three ring atoms are independently S, O or N;

$X^1$ is a bond, O, S, S(O), S(O)$_2$, S(O)$_3$, amino, alkylamino diradical, alkoxyl diradical, alkyl diradical, alkenyl diradical, alkynyl diradical, amido, carbonyl, —$N(R_{10})CO_2R_{10}$, —$OC(O)N(R_{10})_2$, or —$N(R_{10})C(O)N(R_{10})_2$;

$X^2$ represents independently for each occurrence H, halide, hydroxyl, alkoxyl, aryloxy, acyloxy, amino, alkylamino, arylamino, acylamino, aralkylamino, nitro, acylthio, carboxamide, carboxyl, nitrile, —$COR_{10}$, —$CO_2R_{10}$, —$N(R_{10})CO_2R_{10}$, —$C(O)N(R_{10})_2$, —$N(R_{10})SO_2R_{10}$, —$N(R_{10})C(O)N(R_{10})_2$, or —$CH_2O$— heterocyclyl; and q is 1, 2, 3, 4, or 5; and $R_{8a}$ is H, a branched or unbranched alkyl or alkenyl, cycloalkyl, heterocycloalkyl, bicycloalkyl, a bond to $R_7$, heterocycloalkyl substituted with an aralkyl group, or has the formula 1g:

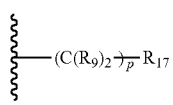

wherein p is 0, 1, 2, 3, 4, 5, or 6; and $R_{17}$ is aryl, cycloalkyl, cycloalkenyl, heterocyclyl, alkoxyl, heteroaryl, —$OR_{18}$, —$SR_{18}$, —$N(R_{18})_2$, —$N(R_{10})CO_2$-alkyl, —$CO_2R_{10}$, —$C(O)N(R_{10})$aryl, or a polycyclic ring containing 8-14 carbon atoms; wherein $R_{18}$ is independently for each occurrence H, alkyl, aryl, aralkyl, acyl, -$A^1$-$A^2$-$A^3$, or —$CR_9$=$CR_9(C(R_9)_2)_nCR_9$=$C(R_9)_2$; or two $R_{18}$ taken together form a ring.

In some embodiments, the present invention provides Formula (LXVII) or Formula (LXVIII), wherein $R_{13}$ and $R_{14}$ are independently H, alkyl, or aryl; or $R_{13}$ and $R_{14}$ taken together form a monocyclic or polycyclic ring; or $R_{13}$ and $R_{14}$ taken together with $R_{15}$ form a cycloalkenyl ring or heteroaromatic ring;

$R_{15}$ is halide, hydroxyl, alkoxyl, aryl, aryloxy, acyloxy, —$N(R_{10})_2$, acylamino, aralkyl, —$N(R_{10})SO_2R_{19}$, or —$N(R_{10})C(O)N(R_{19})_2$; or $R_{15}$ taken together with $R_{13}$ and $R_{14}$ form a cycloalkenyl ring or heteroaromatic ring; or has the formula 1f:

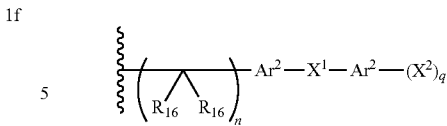

wherein $R_{16}$ is H;

$Ar^2$ represents independently for each occurrence a monocyclic aryl with 6-14 ring atoms; or a monocyclic heteroaryl with 5-14 ring atoms, of which one, two or three ring atoms are independently S, O or N;

$X^1$ is a bond;

$X^2$ represents independently for each occurrence H, halide, hydroxyl, or alkoxyl; and q is 1 or 2.

In some embodiments, the present invention provides Formula (LXVII), wherein $R_8$ is bicycloalkyl, heterocycloalkyl substituted with an aralkyl group, or has the formula 1g:

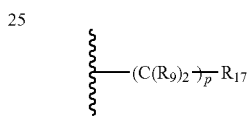

wherein p is 0, 1, 2, 3, 4, 5, or 6; and $R_{17}$ is aryl, cycloalkyl, cycloalkenyl, heterocyclyl, alkoxyl, heteroaryl, —$OR_{18}$, —$SR_{18}$, —$N(R_{18})_2$, or a polycyclic ring containing 8-14 carbon atoms; wherein $R_{18}$ is independently for each occurrence H, alkyl, aryl, aralkyl, acyl, or -$A^1$-$A^2$-$A^3$.

In some embodiments, the present invention provides Formula (LXVII) or Formula (LXVIII), wherein W is an alkynyl chain and Z is a bond.

In some embodiments, the present invention provides Formula (LXVII) or Formula (LXVIII), wherein $R_{13}$ and $R_{14}$ are H and $R_{15}$ is acylamino.

In some embodiments, the present invention provides Formula (LXVII) or Formula (LXVIII), wherein $R_{13}$ and $R_{14}$ taken together form a cyclohexyl ring and $R_{15}$ is an amino group.

In some embodiments, the present invention provides Formula (LXVII) or Formula (LXVIII), wherein $R_8$ and/or $R_{8a}$ is a bicycloalkyl.

In some embodiments, the present invention provides Formula (LXVII) or Formula (LXVIII), wherein $R_8$ and/or $R_8$a has formula 1g and $R_{17}$ is N(CH$_3$)Ph.

In some embodiments, the present invention provides Formula (LXVIII), wherein $R_{1a}$ is:

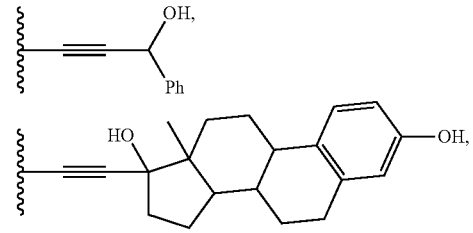

-continued

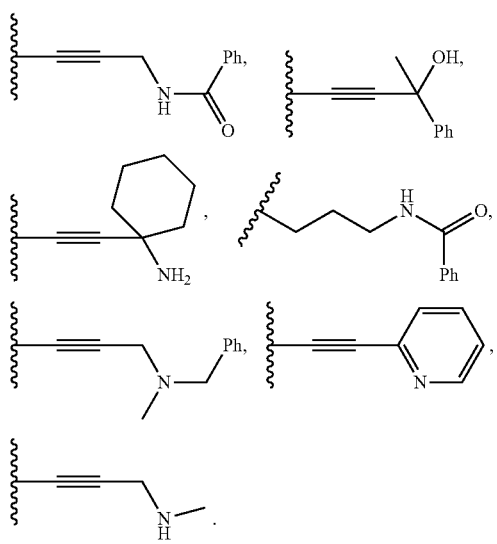

In some embodiments, the present invention provides Formula (LXVII) or Formula (LXVIII), wherein $R_8$ or $R_{8a}$ is:

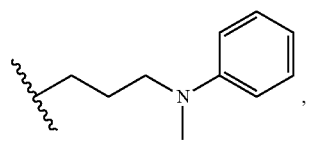 [SMILES: *CCCN(C)c1ccccc1]

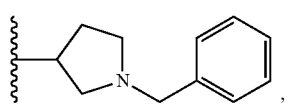

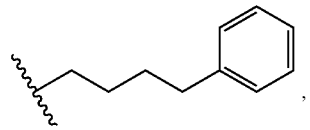

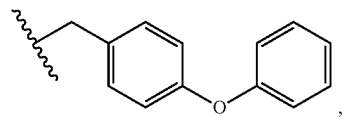

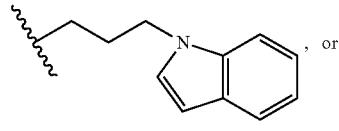

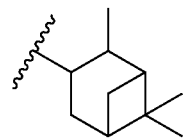

In some embodiments, the present invention provides Formula (LXVII) or Formula (LXVIII), wherein $R_8$ or $R_{8a}$ is

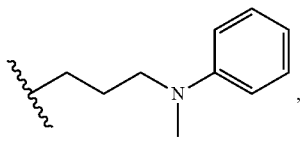 [SMILES: *CCCN(C)c1ccccc1]

and $R_1$ has formula 1a and —W—Z—$CR_{13}R_{14}R_{15}$ of formula 1a is or $R_{1a}$ is:

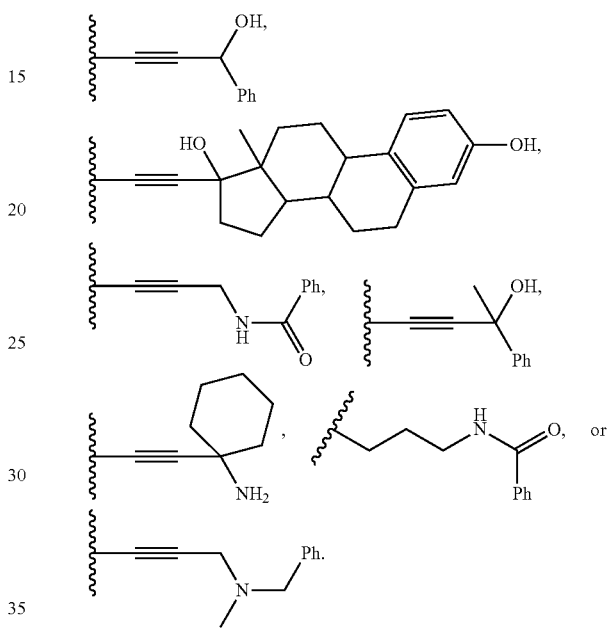

In some embodiments, the present invention provides Formula (LXVII) or Formula (LXVIII), wherein $R_1$ has formula 1a and —W—Z—$CR_{13}R_{14}R_{15}$ of formula 1a is or $R_{1a}$ is

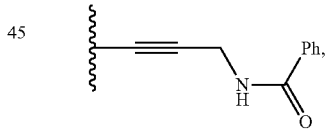

$R_8$ or $R_{8a}$ is:

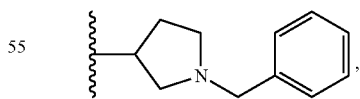

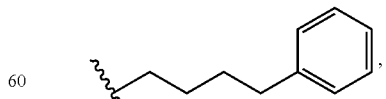

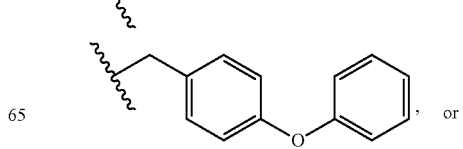

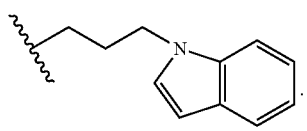

In some embodiments, the present invention provides Formula (LXVII) or Formula (LXVIII), wherein $R_8$ or $R_{8a}$ is

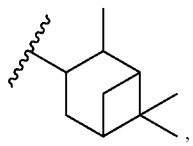

and $R_1$ has formula 1a and —W—Z—$CR_{13}R_{14}R_{15}$ of formula 1a is or $R_{1a}$ is:

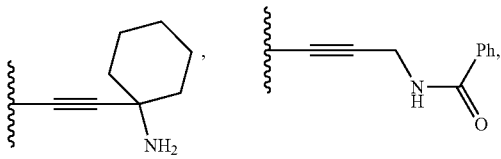

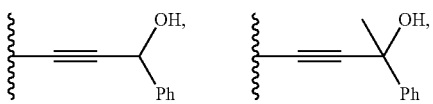

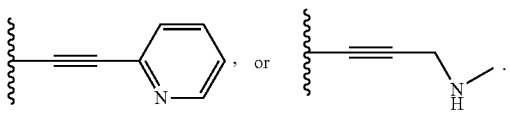

In some embodiments, the present invention provides Formula (LXVII) or Formula (LXVIII), wherein $R_1$ has formula 1a and —W—Z—$CR_{13}R_{14}R_{15}$ of formula 1a is or $R_{1a}$ is

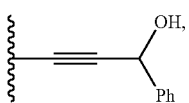

and $R_8$ or $R_{8a}$ is

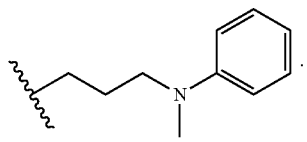 [SMILES: *CCCN(C)c1ccccc1]

In some embodiments, the present invention provides Formula (LXVII) or Formula (LXVIII), wherein $R_1$ has formula 1a and —W—Z—$CR_{13}R_{14}R_{15}$ of formula 1a is or $R_{1a}$ is

and $R_8$ or $R_{8a}$ is

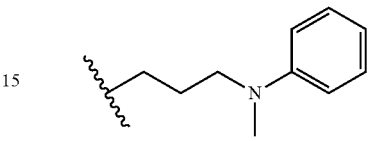

In some embodiments, the present invention provides Formula (LXVII) or Formula (LXVIII), wherein $R_1$ has formula 1a and —W—Z—$CR_{13}R_{14}R_{15}$ of formula 1a is or $R_{1a}$ is

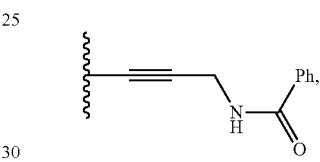

and $R_8$ or $R_{8a}$ is

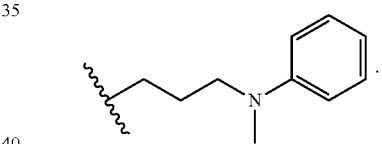

In some embodiments, the present invention provides Formula (LXVII) or Formula (LXVIII), wherein $R_1$ has formula 1a and —W—Z—$CR_{13}R_{14}R_{15}$ of formula 1a is or $R_{1a}$ is

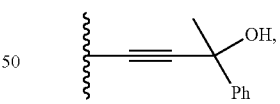

and $R_8$ or $R_{8a}$ is

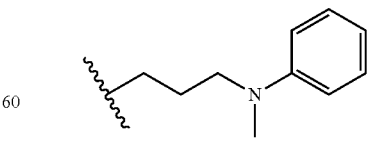

In some embodiments, the present invention provides Formula (LXVII) or Formula (LXVIII), wherein $R_1$ has formula 1a and —W—Z—$CR_{13}R_{14}R_{15}$ of formula 1a is or $R_{1a}$ is

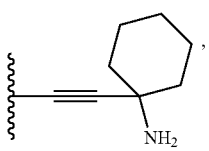 [SMILES: *C#CC1(N)CCCCC1]

and R$_8$ or R$_{8a}$ is

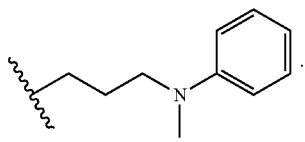 [SMILES: *CCCN(C)c1ccccc1]

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

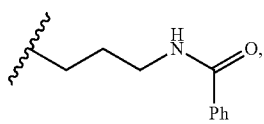 [SMILES: *CCCNC(=O)c1ccccc1]

and R$_8$ or R$_{8a}$ is

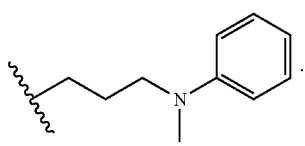 [SMILES: *CCCN(C)c1ccccc1]

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

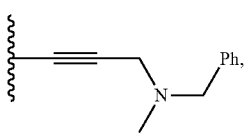

and R$_8$ or R$_{8a}$ is

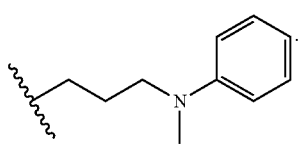 [SMILES: *CCCN(C)c1ccccc1]

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

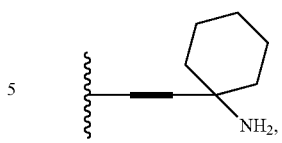

and R$_8$ or R$_{8a}$ is

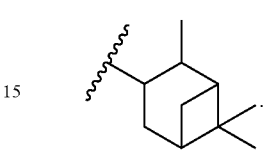

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

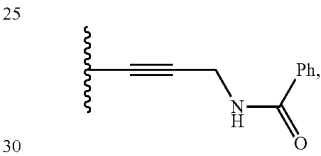

and R$_8$ or R$_{8a}$ is

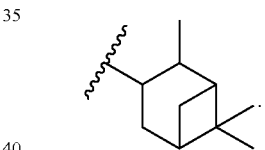

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

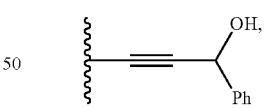

and R$_8$ or R$_{8a}$ is

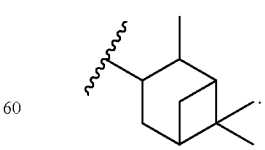

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

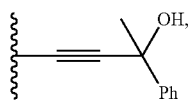 [SMILES: *C#CC(C)(O)c1ccccc1]

and R$_8$ or R$_{8a}$ is

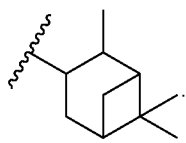 [SMILES: *C1CC2CC(C1C)C2(C)C]

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

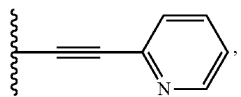

and R$_8$ or R$_{8a}$ is

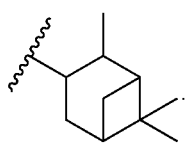 [SMILES: *C1CC2CC(C1C)C2(C)C]

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

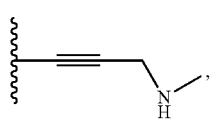

and R$_8$ or R$_{8a}$ is

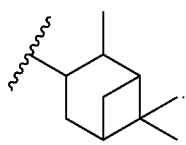 [SMILES: *C1CC2CC(C1C)C2(C)C]

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

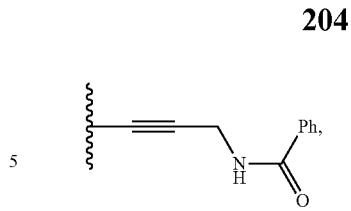

and R$_8$ or R$_{8a}$ is

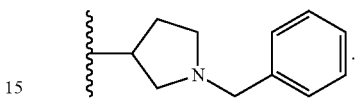

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

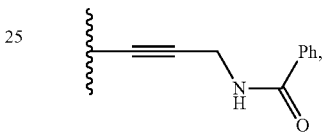

and R$_8$ or R$_{8a}$ is

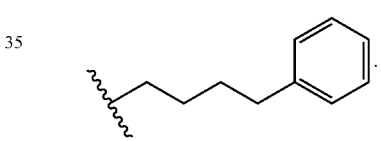

In some embodiments, the present invention provides Formula (LXVII) or Formula (LXVIII), wherein R$_1$ has formula 1a and —W—Z—CR$_{13}$R$_{14}$R$_{15}$ of formula 1a is or RI, is

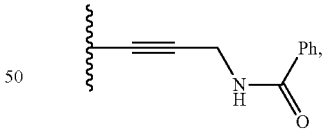

and R$_8$ or R$_{8a}$ is

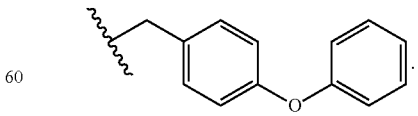

In some embodiments, the present invention provides Formula (LXVII) or Formula (LXVIII), wherein R$_1$ has formula 1a and —W—Z—CR$_{13}$R$_{14}$R$_{15}$ of formula 1a is or R$_{1a}$ is

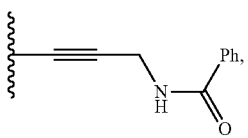 [SMILES: *C#CCNC(=O)c1ccccc1]

and $R_8$ or $R_{8a}$ is

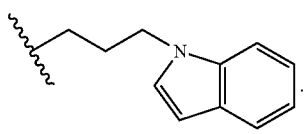 [SMILES: *CCCn1ccc2ccccc21]

In general, the compounds captured by Formula (LXVII) or Formula (LXVIII) may be prepared by the methods illustrated in U.S. Pat. No. 7,851,637 and U.S. Patent Application Publication No. 2006/0025460 A1, which describe general reaction schemes or modifications thereof, using readily available starting materials, reagents, conventional synthesis procedures or known variants thereof. The disclosures are incorporated by reference herein.

In an embodiment, the BCL-2 inhibitor is a compound of Formula (LXVIV):

Formula (LXVIV)

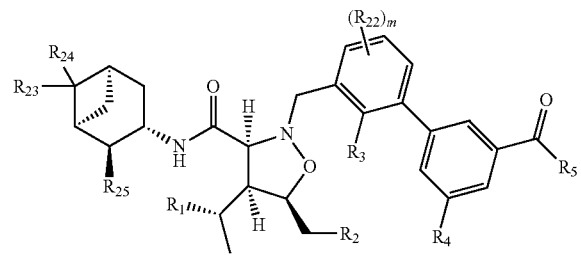

or a pharmaceutically acceptable salt thereof.
wherein independently for each occurrence
m is 0, 1, 2, or 3;
n, o, and p are independently for each occurrence 1, 2, 3, 4, or 5;
$R_1$ is —OH, —OC(O)$R_6$, —OC(O)N($R_6$)($R_7$), or —N($R_6$)($R_7$);
$R_2$ is —OH, —N($R_8$)($R_9$), —N(R)C(O)N($R_8$)($R_9$), or —N(R)C(O)$R_{10}$; or has the formula 1b;

1b

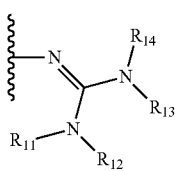

$R_3$ is alkyl, halide, alkoxy, (cycloalkyl)alkoxy, aralkyloxy, or —O(CH$_2$)$_2$—N($R_{15}$)($R_{16}$);
$R_4$ is alkyl, alkoxy, hydroxyalkyl, alkoxyalkyl, halide, nitro, amino, acyl, amido, acylamino, aminoalkyl, acylaminoalkyl, acylaminoalkylamino, sulfonylaminoalkylamino, carboxylate, or N=C(N(R)$_2$)$_2$;
$R_5$ is —OH or —N($R_{17}$)($R_{18}$);
$R_6$ and $R_7$ are independently for each occurrence H, alkyl, aralkyl, heteroaralkyl, or —[C($R_{15}$)($R_{16}$)]$_n$—$R_{19}$;
$R_8$ and $R_9$ are independently for each occurrence H, alkyl, aralkyl, or heteroaralkyl;
$R_{10}$ is alkyl, haloalkyl, or —[C($R_{15}$)($R_{16}$)]$_o$—COOR;
R, $R_{11}$, $R_{12}$, $R_{13}$, $R_{14}$, $R_{15}$, and $R_{16}$ are independently for each occurrence H or alkyl;
$R_{17}$ and $R_{18}$ are independently for each occurrence H, alkyl, aralkyl, heteroaralkyl, alkoxy, or [C($R_{19}$)($R_{20}$)]$_p$—$R_{21}$;
$R_{19}$ and $R_{20}$ are independently for each occurrence H, hydroxy, alkyl, alkoxy, amino, aminoalkyl, acylamino, sulfonylamino, aryl, aralkyl, cycloalkyl, heterocyclyl, heterocyclylalkyl, heteroaryl, or heteroaralkyl;
$R_{21}$ is independently for each occurrence H, alkyl, aryl, heteroaryl, heterocyclyl, heterocyclylalkyl, alkoxy, alkyl sulfonyl, aryl sulfonyl, alkyl sulfonamido, aryl sulfonamido, amino, amido, or carboxyl;
$R_{22}$ independently for each occurrence is halide or alkyl;
$R_{23}$ is selected from the group consisting of alkyl, hydroxyalkyl, alkoxyalkyl, acyloxyalkyl, and haloalkyl;
$R_{24}$ is selected from the group consisting of alkyl, hydroxyalkyl, alkoxyalkyl, acyloxyalkyl, and haloalkyl; and
$R_{25}$ is selected from the group consisting of alkyl, hydroxyalkyl, alkoxyalkyl, acyloxyalkyl, and haloalkyl.

In some embodiments, the present invention provides Formula (LXVIV) and any of the attendant definitions, wherein $R_1$ is selected from the group consisting of —OH, —OC(O)Me, —OC(O)(CH$_2$)$_2$Ph, —OC(O)CH$_2$CHMe$_2$, —OC(O)NHMe, —OC(O)NMe$_2$, —OC(O)NHCH$_2$(4-(OH)-Ph), —OC(O)NHPh, —OC(O)NHCH$_2$Ph, —OC(O)NH(CH$_2$)$_4$Ph, —OC(O)NH(CH$_2$)$_2$Ph, —OC(O)NH(CH$_2$)$_2$Me, —OC(O)NH(CH$_2$)$_2$NMe$_2$, —OC(O)NH(CH$_2$)$_2$NHC(O)Me, —OC(O)NH(CH$_2$)$_2$CHMe$_2$, —NHMe, —NH(CH$_2$)$_2$ Ph, —NHC(O)Me, and —NH(CH$_2$)$_2$NMe$_2$.

In some embodiments, the present invention provides Formula (LXVIV) and any of the attendant definitions, wherein $R_1$ is —OH.

In some embodiments, the present invention provides Formula (LXVIV) and any of the attendant definitions, wherein $R_2$ is —OH, —OC(O)Me, —OCH$_2$CO$_2$H, —OCH$_2$CO$_2$Et, —N$_3$, —N=C(NMe$_2$)$_2$, —NH$_2$, —NMe$_2$, —NHC(O)Me, —NHC(O)CF$_3$, —NHC(O)Ph, NHC(O)NHPh, —NHC(O)CH$_2$CH$_2$CO$_2$H, —NHC(O)CH$_2$CH$_2$CO$_2$Me, —NHCH$_2$Ph, NHCH$_2$(4-pyridyl), —NHCH$_2$(2-pyridyl), —NHCH$_2$(4-(CO$_2$H)Ph), —NHCH$_2$(3-(CO$_2$H)Ph), NHEt, —NHCHMe$_2$, —NHCH$_2$CHMe$_2$, —N(CH$_2$CHMe$_2$)$_2$, —NHCH$_2$(cyclopropyl), or NHC(O)CH$_2$CH$_2$NMe$_2$.

In some embodiments, the present invention provides Formula (LXVIV) and any of the attendant definitions, wherein $R_2$ is —OH or —NH$_2$.

In some embodiments, the present invention provides Formula (LXVIV) and any of the attendant definitions, wherein $R_2$ is —NH$_2$.

In some embodiments, the present invention provides Formula (LXVIV) and any of the attendant definitions, wherein $R_2$ is —OH.

In some embodiments, the present invention provides Formula (LXVIV) and any of the attendant definitions, wherein $R_3$ is —OMe, —OEt, —OCH$_2$(cyclopropyl), F, —O(CH$_2$)$_2$NMe$_2$, —O(CH$_2$)$_2$(4-morpholino), —OCH$_2$(4-(MeO)Ph), or —OCH$_2$(2-pyridyl).

In some embodiments, the present invention provides Formula (LXVIV) and any of the attendant definitions, wherein $R_3$ is —OMe.

In some embodiments, the present invention provides Formula (LXVIV) and any of the attendant definitions, wherein $R_4$ is -NMe$_2$, —NEt$_2$, —NHEt, —NHCH$_2$CHMe$_2$, N(Me)CH$_2$CHMe$_2$, —N(Me)CH$_2$CH$_2$NHC(O)Me, —N(Me)CH$_2$CH$_2$NHS(O)$_2$Me, N(Me)CH$_2$CH$_2$NHS(O)$_2$CF$_3$, —NHCH$_2$CH$_2$NMe$_2$, —NHCH$_2$CH$_2$NMeCH$_2$CH$_2$C$_1$, NHCH$_2$CH$_2$OH, —N(Me)CH$_2$CH$_2$OH, —N(CH$_2$CH$_2$OH)$_2$, —N(Me)CH$_2$CO$_2$H, N(Me)CH$_2$C(O)NH$_2$, —N(Me)CH$_2$C(O)NHMe, —N(Me)CH$_2$C(O)NMe$_2$, —NHC(O)Me, NHC(O)CHMe$_2$, 1-pyrrolidinyl, 1-piperidinyl, 4-morpholino, (R)-2-(hydroxymethyl)-1-pyrrolidinyl, (S)-2-(hydroxymethyl)-1-pyrrolidinyl, (R)-2-(C(O)NMe$_2$)-1-pyrrolidinyl, (S)-2-(C(O)NMe$_2$)-1-pyrrolidinyl, —NH$_2$, —NO$_2$, Br, Cl, F, —C(O)Me, —C(O)NMe$_2$, —C(O)NH$_2$, —CO$_2$H, —CHO, —CH$_2$OH, —CH(Me)OH, —CH$_2$NH$_2$, —CH$_2$NHMe, —CH$_2$NMe$_2$, CH$_2$NHC(O)Me, —CF$_3$, or tert-butyl.

In some embodiments, the present invention provides Formula (LXVIV) and any of the attendant definitions, wherein $R_4$ is amino.

In some embodiments, the present invention provides Formula (LXVIV) and any of the attendant definitions, wherein $R_4$ is -NMe$_2$, —N(Me)CH$_2$CH$_2$OH, —N(Me)CH$_2$C(O)NMe$_2$, N(Me)CH$_2$C(O)NHMe, (R)-2-(hydroxymethyl)-1-pyrrolidinyl, or (R)-2-(C(O)NMe$_2$)-1-pyrrolidinyl.

In some embodiments, the present invention provides Formula (LXVIV) and any of the attendant definitions, wherein $R_4$ is -NMe$_2$.

In some embodiments, the present invention provides Formula (LXVIV) and any of the attendant definitions, wherein $R_{22}$ is selected from the group consisting of F, Cl, and tert-butyl; and m is 0 or 1.

In some embodiments, the present invention provides Formula (LXVIV) and any of the attendant definitions, wherein $R_{22}$ is F; and m is 0 or 1.

In some embodiments, the present invention provides Formula (LXVIV) and any of the attendant definitions, wherein $R_{22}$ is selected from the group consisting of F, Cl, and tert-butyl; and m is 1.

In some embodiments, the present invention provides Formula (LXVIV) and any of the attendant definitions, wherein $R_{22}$ is F; and m is 1.

In some embodiments, the present invention provides Formula (LXVIV) and any of the attendant definitions, wherein $R_{23}$ is selected from the group consisting of methyl, hydroxymethyl, alkoxymethyl, acyloxymethyl, and halomethyl.

In some embodiments, the present invention provides Formula (LXVIV) and any of the attendant definitions, wherein $R_{24}$ is selected from the group consisting of methyl, hydroxymethyl, alkoxymethyl, acyloxymethyl, and halomethyl.

In some embodiments, the present invention provides Formula (LXVIV) and any of the attendant definitions, wherein $R_{23}$ is methyl.

In some embodiments, the present invention provides Formula (LXVIV) and any of the attendant definitions, wherein $R_{24}$ is methyl.

In some embodiments, the present invention provides Formula (LXVIV) and any of the attendant definitions, wherein $R_{23}$ is methyl; and $R_{24}$ is methyl.

In some embodiments, the present invention provides Formula (LXVIV) and any of the attendant definitions, wherein $R_{25}$ is selected from the group consisting of methyl, hydroxymethyl, alkoxymethyl, acyloxymethyl, and halomethyl.

In some embodiments, the present invention provides Formula (LXVIV) and any of the attendant definitions, wherein $R_{25}$ is methyl.

In some embodiments, the present invention provides Formula (LXVIV) and any of the attendant definitions, wherein $R_{23}$ is methyl; $R_{24}$ is methyl; and $R_{25}$ is methyl.

In some embodiments, the present invention provides Formula (LXVIV) and any of the attendant definitions, wherein $R_1$ is —OH; and $R_2$ is —OH or —NH$_2$.

In some embodiments, the present invention provides Formula (LXVIV) and any of the attendant definitions, wherein $R_1$ is —OH; $R_2$ is —OH or —NH$_2$; and $R_3$ is —OMe.

In some embodiments, the present invention provides Formula (LXVIV) and any of the attendant definitions, wherein $R_1$ is —OH; $R_2$ is —OH or —NH$_2$; $R_3$ is —OMe; and $R_4$ is amino.

In some embodiments, the present invention provides Formula (LXVIV) and any of the attendant definitions, wherein $R_1$ is —OH; $R_2$ is —OH or —NH$_2$; $R_3$ is —OMe; and $R_4$ is NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl.

In some embodiments, the present invention provides Formula (LXVIV) and any of the attendant definitions, wherein $R_1$ is —OH; $R_2$ is —OH or —NH$_2$; $R_3$ is —OMe; and $R_4$ is NMe$_2$.

In some embodiments, the present invention provides Formula (LXVIV) and any of the attendant definitions, wherein $R_1$ is —OH; $R_2$ is —OH or —NH$_2$; $R_{23}$ is methyl; $R_{24}$ is methyl; and $R_{25}$ is methyl.

In some embodiments, the present invention provides Formula (LXVIV) and any of the attendant definitions, wherein $R_1$ is —OH; $R_2$ is —OH or —NH$_2$; $R_3$ is —OMe; $R_{23}$ is methyl; $R_{24}$ is methyl; and $R_{25}$ is methyl.

In some embodiments, the present invention provides Formula (LXVIV) and any of the attendant definitions, wherein $R_1$ is —OH; $R_2$ is —OH or —NH$_2$; $R_3$ is —OMe; $R_4$ is amino; $R_{23}$ is methyl; $R_{24}$ is methyl; and $R_{25}$ is methyl.

In some embodiments, the present invention provides Formula (LXVIV) and any of the attendant definitions, wherein $R_1$ is —OH; $R_2$ is —OH or —NH$_2$; $R_3$ is —OMe; $R_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl; $R_{23}$ is methyl; $R_{24}$ is methyl; and $R_{25}$ is methyl.

In some embodiments, the present invention provides Formula (LXVIV) and any of the attendant definitions, wherein $R_1$ is —OH; $R_2$ is —OH or —NH$_2$; $R_3$ is —OMe; $R_4$ is —NMe$_2$; $R_{23}$ is methyl; $R_{24}$ is methyl; and $R_{25}$ is methyl.

In general, the compounds captured by Formula (LXVIV) may be prepared by the methods illustrated in U.S. Pat. Nos. 7,928,244; 8,178,690; and, 8,609,706 and U.S. Patent Application Publication Nos. 2008/0114167 A1; 2011/0213145 A1; and, 2013/0131063 A1, which describe general reaction schemes or modifications thereof, using readily available starting materials, reagents, conventional synthesis procedures or known variants thereof. The disclosures are incorporated by reference herein.

In an embodiment, the BCL-2 inhibitor is a compound of Formula (LXX):

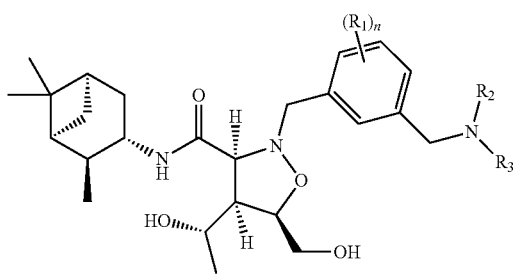

Formula (LXX)

or a pharmaceutically acceptable salt thereof.
wherein independently for each occurrence;
n is 0, 1, 2, 3, or 4;
$R^1$ independently for each occurrence is H, alkyl, alkenyl, alkynyl, aryl, aralkyl, heterocyclyl, heterocyclylalkyl, heteroaryl, heteroaralkyl, halide, hydroxyl, alkoxyl, aryloxy, acyloxy, amino, alkylamino, arylamino, acylamino, aralkylamino, nitro, acylthio, carboxamide, carboxyl, nitrile, —$COR^5$, —$CO_2R^5$, —$N(R^5)CO_2R^6$, —$OC(O)N(R^5)(R^6)$, —$N(R^5)SO_2R^6$, or —$N(R^5)C(O)N(R^5)(R^6)$;
$R^2$ and $R^3$ independently for each occurrence are H, alkyl, alkenyl, alkynyl, aryl, aralkyl, heterocyclyl, heterocyclylalkyl, heteroaryl, heteroaralkyl, or —$[C(R^5)(R^6)]_p$—$R^4$;
where p is an integer from 0 to 5, or has the formula 1a:

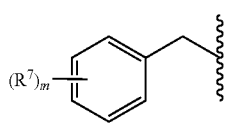

1a wherein
m is 0, 1, 2, 3, 4, or 5;
$R^7$ for each occurrence independently is H, alkyl, aryl, alkenyl, halide, hydroxyl, alkoxyl, alkenyloxy, aryloxy, acyloxy, amino, alkylamino, arylamino, acylamino, aralkylamino, nitro, acylthio, carboxamide, carboxyl, nitrile, $OSO_3R^5$, —$SO_2R^5$, —$S(O)R^5$, —$SR^5$, —$PO_2OR^5$, $OPO_2OR^5$, —$COR^5$, $CO_2R^5$, —$OCH_2CO_2R^5$, or —$OCH_2(O)N(R^5)(R^6)$; or two occurrences of $R^7$ taken together may form a monocyclic ring between 5-8 ring atoms, of which, one, two, or three atoms are independently S, O, or N;
$R^4$ is halide, hydroxyl, alkoxyl, aryloxy, acyloxy, amino, alkylamino, arylamino, acylamino, aralkylamino, nitro, acylthio, carboxamide, carboxyl, nitrile, —$OSO_3R^5$, —$SO_2R^5$, —$S(O)R^5$, $PO_2OR^5$, —$OPO_2OR^5$, —$COR^5$, —$CO_2R^5$, —$N(R^5)CO_2R^6$, —$OC(O)N(R^5)(R^6)$, —$N(R^5)SO_2R^6$, or —$N(R^5)C(O)N(R^5)(R^6)$; and
each of $R^5$ and $R^6$ independently for each occurrence is H, alkyl, alkenyl, alkynyl, aryl, aralkyl, cycloalkyl, heterocyclyl, heterocyclylalkyl, heteroaryl, or heteroaralkyl; or $R^5$ and $R^6$ taken together form a monocyclic ring with 4-8 ring atoms, of which one, two, or three ring atoms are independently S, O, or N.

The compounds of Formula (LXX) may be prepared by the methods illustrated in U.S. Pat. Nos. 7,842,815 and 8,461,191 and U.S. Patent Application Publication Nos. 2008/0306127, 2007/0161690, and 2011/0160259, the disclosures of which are incorporated by reference herein. U.S. Pat. Nos. 7,842,815 and 8,461,191 and U.S. Patent Application Publication Nos. 2008/0306127, 2007/0161690, and 2011/0160259 describe general reaction schemes or modifications thereof, using readily available starting materials, reagents, conventional synthesis procedures or known variants thereof, which may be used to prepare the compounds of Formula (LXX).

In an embodiment, the BCL-2 inhibitor is a compound of Formula (LXXI):

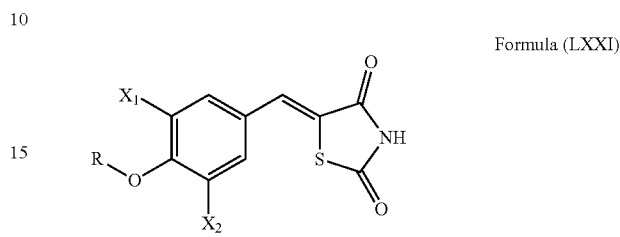

Formula (LXXI)

or a pharmaceutically acceptable salt thereof.

wherein R is selected from aryl, heteroaryl, cycloalkyl, heterocycloalkyl, alkylaryl, and combinations thereof and wherein R may be substituted at one or more substitutable positions with a hydroxyl, or alkyl substituent;

wherein $X_1$ is selected from the group consisting of H, alkyl, alkoxy, halo, nitro, haloalkylaryl, haloaryl, alkylaryl, and combinations thereof; and, wherein $X_2$ is selected from the group consisting of H, alkyl, alkoxy, halo, and combinations thereof.

In some embodiments of Formula (LXXI), R is selected from the group consisting of:

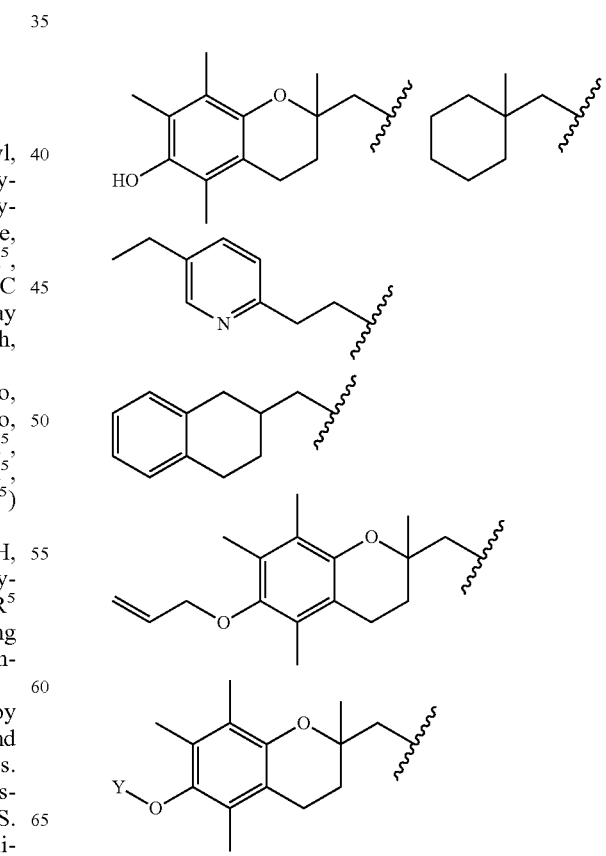

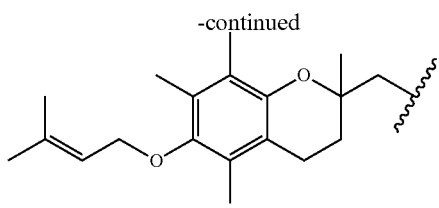

wherein Y is selected from the group consisting of straight-chain alkenyl, branched alkenyl, and combinations thereof.

In some embodiments of Formula (LXXI), $X_1$ is selected from H, Br, $CH_3$, $OCH_3$, $OCH_2CH_3$, $NO_2$, and Cl and $X_2$ is selected from H, $CH_3$, $OCH_3$, and Br.

In some embodiments of Formula (LXXI), $X_1$ is selected from the group consisting of H, methyl, methoxy, ethoxy, fluoro, chloro, bromo, nitro, trifluoromethylphenyl, fluorophenyl, and ethylphenyl; and $X_2$ is selected from the group consisting of H, methyl, methoxy, and bromo.

In some embodiments of Formula (LXXI), Y is selected from:

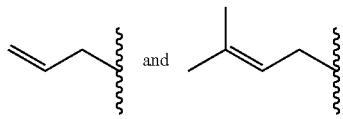

In an embodiment, the BCL-2 inhibitor is a compound of Formula (LXXI) prepared for oral (i.e. a tablet, capsule, suspension or liquid), injection, intravenous, intramuscular, subcutaneous, intraperitoneal, or parenteral administration or the like as described in U.S. Pat. Nos. 7,714,005 and 8,309,582 and U.S. Patent Application Publication Nos. 2006/0252801 A1 and 2010/0168184 A1, the disclosures of which are incorporated by reference herein.

In an embodiment, the BCL-2 inhibitor is a compound of Formula (LXXII):

Formula (LXXII)

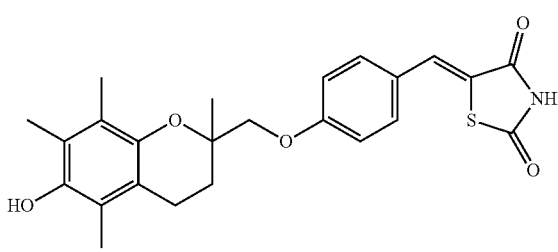

or a pharmaceutically acceptable salt thereof.

The preparation of the compound in Formula (LXXII) was achieved by a trifluoroacetic acid treatment of carbonic acid tert-butyl ester 2-{4-[2,4-dioxothiazolidin-(5Z)-ylidenemethyl]phenoxymethyl}-2,5,7,8-tetramethylchroman-6-yl ester, which is a result of modification of troglitazone by known methods. For example, see Colin C., Salamone S., Grillier-Vuissoz I., Boisbrun M., Kuntz S., Lecomte J., Chapleur Y., Flament S. (2010) New troglitazone derivatives devoid of PPARc agonist activity display an increased antiproliferative effect in both hormonedependent and hormone-independent breast cancer cell lines, Breast Cancer Res. Treat 124:101-110; Boschi D., Tron G. C., Lazzarato L. et al. (2006)NO-donor phenols: a new class of products endowed with antioxidant and vasodilator properties. J. Med. Chem. 49:2886-2897; and, Huang J. W., Shiau C. W., Yang J. et al. (2006) Development of smallmolecule cyclin D1-ablative agents. J. Med. Chem. 49:4684-4689.

In an embodiment, the BCL-2 inhibitor is a compound of Formula (LXXIII):

Formula (LXXIII)

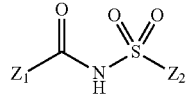

or a pharmaceutically acceptable salt thereof.

In one embodiment, $Z_1$ is selected from the group consisting of hydrocarbyl, substituted hydrocarbyl, heteroaryl, heterocyclo, aryl, substituted aryl, and,

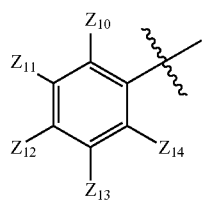

wherein $Z_{10}$, $Z_{11}$, $Z_{12}$, $Z_{13}$, and $Z_{14}$ are independently hydrogen, hydroxyl, protected hydroxyl, halo, hydrocarbyl, substituted hydrocarbyl, heterocyclo, heteroaryl, alkoxy, alkenoxy, alkynoxy, aryloxy, arylalkoxy (heterocyclo) alkoxy, trihaloalkoxy, amino, amido, nitro or cyano, or two of $Z_{10}$, $Z_{11}$, $Z_{12}$, $Z_{13}$, and $Z_{14}$, together with the carbon atoms to which they are attached, form a fused carbocyclic (e.g., napthyl) or heterocyclic ring.

In one embodiment, $Z_{10}$, $Z_{11}$, $Z_{12}$, $Z_{13}$, and $Z_{14}$ are independently hydrogen, hydrocarbyl, substituted hydrocarbyl, amino, alkoxy, nitro, or trihalomethoxy.

In one embodiment, $Z_1$ is substituted or unsubstituted furyl, thienyl, pyridyl, oxazolyl, isoxazolyl, imidazolyl, pyridyl, pyrimidyl, purinyl, triazolyl, or thiazolyl.

In one embodiment, $Z_1$ is substituted or unsubstituted morpholino, pyran, tetrahydropyran, piperazinyl, piperidinyl, tetrahydropyridinyl, pyrrolidinyl, pyrrolinyl, 1,4-diazepanyl, or azepinyl.

In one embodiment, $Z_1$ is —$(CH_2)_x$—$Z_{102}$ wherein $Z_{102}$ is hydrogen, hydrocarbyl, substituted hydrocarbyl, hydroxyl, protected hydroxyl, heteroaryl, heterocyclo, amino, amido, alkoxy, aryloxy, cyano, nitro, thiol, or an acetal, ketal, ester, ether, or thioether, and x is 1, 2, or 3.

In one embodiment, $Z_1$ is

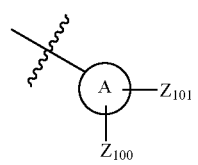

wherein A is phenyl or a five- or six-membered aromatic carbocyclic or heterocyclic ring wherein from one to three carbon atoms may be replaced by a heteroatom selected from N, O, or S, and wherein A is substituted with $Z_{100}$ and $Z_{101}$ through ring carbon atoms or ring heteroatoms, and $Z_{100}$ and $Z_{101}$ are independently hydrogen, hydrocarbyl, substituted hydrocarbyl, heteroaryl, heterocyclo, alkoxy, alkenoxy, alkynoxy, aryloxy, heterocyclo(alkoxy), or halo.

In one embodiment, $Z_2$ is substituted or unsubstituted alkyl, alkenyl, alkynyl, aryl, alkaryl, or aralkyl.

In one embodiment, $Z_2$ is selected from the group consisting of hydrocarbyl, substituted hydrocarbyl, heteroaryl, or heterocyclo, and,

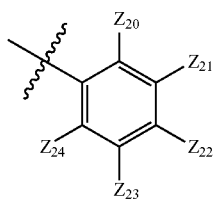

wherein $Z_{20}$, $Z_{21}$, $Z_{22}$, $Z_{23}$, and $Z_{24}$ are independently hydrogen, halo, hydrocarbyl, substituted hydrocarbyl, alkoxy, alkenoxy, alkynoxy, aryloxy, nitro, cyano, amino, or amido, or two of $Z_{20}$, $Z_{21}$, $Z_{22}$, $Z_{23}$, and $Z_{24}$, together with the carbon atoms to which they are attached, form a fused carbocyclic or heterocyclic ring.

In one embodiment, $Z_{20}$, $Z_{21}$, $Z_{22}$, $Z_{23}$, and $Z_{24}$ are independently alkyl, substituted alkyl, amino, alkoxy, alkenoxy, alkynoxy, or aryloxy.

In one embodiment, $Z_2$ is phenyl, substituted phenyl, napthyl, or substituted napthyl.

In one embodiment, $Z_2$ is —$(CH_2)_x$—$Z_{200}$ wherein $Z_{200}$ is hydrogen, hydrocarbyl, substituted hydrocarbyl, hydroxyl, protected hydroxyl, heteroaryl, heterocyclo, amino, amido, alkoxy, aryloxy, cyano, nitro, thiol, or an acetal, ketal, ester, ether, or thioether, and x is 1, 2, or 3.

In one embodiment, $Z_2$ is —$(CH_2)_x$—$Z_{200}$ wherein x is 1, 2, or 3 and $Z_{200}$ is $N(Z_{201})(Z_{202})$, wherein $Z_{201}$ and $Z_{202}$ are independently hydrogen, alkyl, substituted alkyl, aryl, substituted aryl, or $Z_{201}$ and $Z_{202}$, together with the nitrogen atom to which they are attached, for a substituted or unsubstituted alicyclic, bicyclic, aryl, heteroaryl, or heterocyclic moiety.

In one embodiment, wherein $Z_2$ is substituted or unsubstituted furyl, thienyl, pyrrolyl, oxazolyl, imidazolyl, pyridyl, pyrimidyl, purinyl, triazolyl, or thiazolyl.

In one embodiment, $Z_2$ is substituted or unsubstituted morpholino, pyran, tetrahydropyran, piperazinyl, piperidinyl, tetrahydropyridinyl, pyrrolidinyl, pyrrolinyl, 1,4-diazepanyl, or azepinyl.

The preparation of this compound is described in U.S. Patent Application Publication No. 2013/0203709 A1, the disclosure of which is incorporated by reference herein.

In an embodiment, the BCL-2 inhibitor is a compound of Formula (LXXIV):

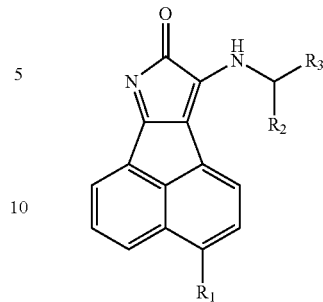

Formula (LXXIV)

wherein $R^1$ is selected from H, thiomorpholinyl or $XR^4$;
$R^2$ is selected from $(CH_2)_nZ$ or $(CH_2)_n$Ph-(o,m,p)Z; Z is selected from $NO_2$, Ph, $CF_3$, $OCH_3$, $SCH_3$, $NH_2$, $NHCH_3$, $N(CH_3)_2$, unsubstituted linear or branched $C_{1-8}$ alkyl and linear or branched $C_{1-8}$ alkyl that is substituted with halogen, amino, hydroxyl, ester or carboxyl;
$R^3$ is selected from $(CH_2)_nW$, W is selected from H, CN, $NO_2$, $NH_2$, COOH, CHO, OH or $SO_3H$;
$R^4$ is selected from $(CH_2)_xY$, thenoyl, tetrahydropyrane, tetrahydrothiopyran and $(CH_2)_n$Ph-(o,m,p)Y; Y is selected from a straight or branched $C_{1-8}$ alkyl, wherein the straight or branched $C_{1-8}$ alkyl can be unsubstituted linear or substituted by halogen, amino, hydroxyl, ester or carboxyl;
X is selected from O, S, amino, carbonyl, ester, amide or sulfamide; and,
n is 0 to 4.

In one embodiment, Z is selected from a straight or branched $C_{1-4}$ alkyl, wherein the straight or branched $C_{1-4}$ alkyl can be unsubstituted or substituted.

In one embodiment, $R^2$ is selected from $(CH_2)_n$Ph-(o,m,p)Z, wherein Z is selected from a straight or branched $C_{1-3}$ alkyl that can be unsubstituted or substituted.

In one embodiment, W is selected from H, $NH_2$ or OH.
In one embodiment, X is selected from 0 or S.
In one embodiment, $R^4$ is selected from Ph—$(CH_2)_n$Y, wherein Y is selected from Ph, $CF_3$, $OCH_3$, $SCH_3$, $NH_2$, Br, isopropyl, isobutyl or secbutyl.

In some embodiments, the compound of Formula (LXXIV) is selected from:
9-(butylamino)-8H-acenaphtho[1,2-b]pyrrol-8-one;
9-(hexylamino)-8H-acenaphtho[1,2-b]pyrrol-8-one;
9-(3-phenylpropylamino)-8H-acenaphtho[1,2-b]pyrrol-8-one;
3-ethoxy-9-(3-phenylpropylamino)-8H-acenaphtho[1,2-b]pyrrol-8-one;
3-benzoyl-9-(butylamino)-8H-acenaphtho[1,2-b]pyrrol-8-one;
9-(butyl(methyl)amino)-8H-acenaphtho[1,2-b]pyrrol-8-one;
3-(4-bromophenylthio)-9-(butylamino)-8H-acenaphtho[1,2-b]pyrrol-8-one;
3-(4-bromophenylthio)-9-(3-phenylpropylamino)-8H-acenaphtho[1,2-b]pyrrol-8-one;
9-(butylamino)-3-thiomorpholino-8H-acenaphtho[1,2-b]pyrrol-8-one;
9-(3-phenylpropylamino)-3-thiomorpholino-8H-acenaphtho[1,2-b]pyrrol-8-one;
9-(butylamino)-3-(4-isopropylphenoxy)-8H-acenaphtho[1,2-b]pyrrol-8-one;
3-(4-isopropylphenoxy)-9-(3-phenylpropylamino)-8H-acenaphtho[1,2-b]pyrrol-8-one;
or a pharmaceutically acceptable salt thereof.

In an embodiment, the BCL-2 inhibitor is a compound of Formula (LXXV):

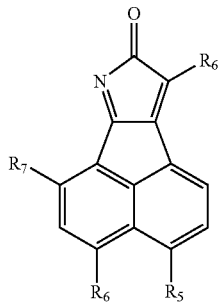

Formula (LXXV)

wherein $R^5$, $R^6$ and $R^7$ are each independently selected from $XR^9$ or H;
$R^8$ is selected from CN, COOH, $COOR^{10}$ or $CONHR^{10}$;
X is selected from O, carbonyl, ester, amide or sulfamide;
where $R^9$ is selected from $(CH_2)_nY$ or $(CH_2)_n$Ph-(o,m,p)Y;
Y is selected from unsubstituted linear or branched $C_{2-8}$ alkyl and linear or branched $C_{1-8}$ alkyl that is substituted with halogen, amino, hydroxyl, ester or carboxyl;
where $R^{10}$ is selected from unsubstituted linear or branched $C_{1-6}$ alkyl that is substituted with halogen, amino, hydroxyl, ester, carboxyl or $(CH_2)_n$Ph-(o,m,p)Z; Z is selected from $CH_3$, $C_2H_5$, $NO_2$, Ph, F, Cl, Br, $CF_3$, $OCH_3$, $SCH_3$, $NH_2$, $N(CH_3)_2$;
X is S;
where $R^9$ is selected from $(CH_2)_n$Ph-(o,m,p)Y; Y is selected from linear or branched $C_{2-8}$ alkyl and linear or branched $C_{1-8}$ alkyl that is substituted with halogen, amino, hydroxyl, ester or carboxyl;
where $R^{10}$ is selected from unsubstituted linear or branched $C_{1-6}$ alkyl and linear or branched $C_{1-6}$ alkyl that is substituted with halogen, amino, hydroxyl, ester, carboxyl or $(CH_2)_n$Ph-(o,m,p)Z; Z is selected from $CH_3$, $C_2H_5$, $NO_2$, Ph, F, Cl, Br, $CF_3$, $OCH_3$, $SCH_3$, $NH_2$, $N(CH_3)_2$;
n is 0 to 4.
In one embodiment, $R^5$ and $R^6$ are each independently selected from $XR^9$ or H.
In one embodiment, $R^8$ is CN.
In one embodiment, $R^9$ is selected from $(CH_2)_n$Ph-(o,m,p)Y.
In one embodiment, X is selected from O or S; Y is selected from linear or branched $C_3$-5 alkyl.
In one embodiment, Y is selected from isopropyl, isobutyl or secbutyl.
In some embodiments, the compound of Formula (LXXV) is selected from:
3-(4-sec-butylphenoxy)-8-oxo-8H-acenaphtho[1,2-b]pyrrole-9-carbonitrile;
4-(4-sec-butylphenoxy)-8-oxo-8H-acenaphtho[1,2-b]pyrrole-9-carbonitrile;
3-(4-isobutylphenoxy)-8-oxo-8H-acenaphtho[1,2-b]pyrrole-9-carbonitrile;
4-(4-isobutylphenoxy)-8-oxo-8H-acenaphtho[1,2-b]pyrrole-9-carbonitrile;
3-(4-isopropylphenoxy)-8-oxo-8H-acenaphtho[1,2-b]pyrrole-9-carbonitrile;
3-(4-isobutylphenylthio)-8-oxo-8H-acenaphtho[1,2-b]pyrrole-9-carbonitrile;
4-(4-isobutylphenylthio)-8-oxo-8H-acenaphtho[1,2-b]pyrrole-9-carbonitrile;
3-(4-isopropylphenylthio)-8-oxo-8H-acenaphtho[1,2-b]pyrrole-9-carbonitrile;
3-(4-sec-butylphenylthio)-8-oxo-8H-acenaphtho[1,2-b]pyrrole-9-carbonitrile;
or a pharmaceutically acceptable salt thereof.

The preparation of the compounds of Formula (LXXIV) and Formula (LXXV) is described in U.S. Pat. No. 8,614,333 and U.S. Patent Application Publication No. 2013/0123492 A1, the disclosure of which is incorporated by reference herein.

In an embodiment, the BCL-2 inhibitor is (R)-1,1',6,6',7,7'-hexahydroxy-5,5'-diisopropyl-3,3'-dimethyl-[2,2'-binaphthalene]-8,8'-dicarbaldehyde with the chemical structure shown in Formula (LXXVI):

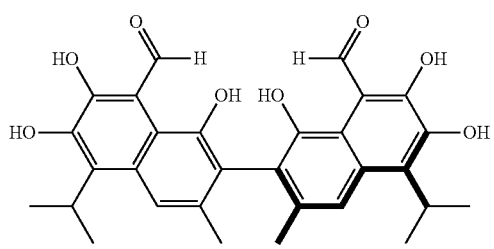

Formula (LXXVI)

or pharmaceutically acceptable salts, enantiomers, metabolites, derivatives, and Schiff's bases thereof. Alternative names for the compound of Formula (LXXVI) include: (−)-gossypol and AT-101. The preparation of this compound is described in at least one of U.S. Pat. Nos. 7,696,372; 7,342,046; 7,432,300; and 7,557,251 and U.S. Patent Application Publication Nos. 2003/0008924 A1; 2007/0293585 A1; 2009/0082445 A1; 2005/0234135 A1; 2009/0088590 A1; and 2008/0021110 A1, the disclosures of which are incorporated by reference herein.

Other suitable gossypol compounds comtemplated for use as BCL-2 inhibitors include, but are not limited to (±)-gossypol; (−)-gossypol; (+)-gossypol; (±)-gossypolone; (−)-gossypolone; (+)-gossypolone; (±)-gossypol acetic acid; (−)-gossypol acetic acid; (+)-gossypol acetic acid; (±)-ethyl gossypol; (−)-ethyl gossypol; (+)-ethyl gossypol; (±)-hemigossypolone; (−)-hemigossypolone; (+)-hemigossypolone; Schiff's base of (±)-gossypol; Schiff's base of (−)-gossypol; Schiff's base of (+)-gossypol; Schiff's base of (±)-gossypolone; Schiffs base of (−)-gossypolone; Schiff's base of (+)-gossypolone; Schiff's base of (±)-gossypol acetic acid; Schiffs base of (−)-gossypol acetic acid; Schiffs base of (+)-gossypol acetic acid; Schiff's base of (±)-ethyl gossypol; Schiffs base of (−)-ethyl gossypol; Schiffs base of (+)-ethyl gossypol; Schiff's base of (±)-hemigossypolone; Schiff's base of (−)-hemigossypolone; and the Schiffs base of (+)-hemigossypolone, and the like.

In an embodiment, the BCL-2 inhibitor is a compound of Formula (LXXVII):

Formula (LXXVII)

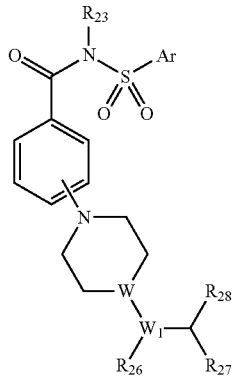

or its geometric isomers, enantiomers, diastereomers, racemates, pharmaceutically acceptable salts, prodrugs and solvates thereof, wherein
W is N or CH;
Ar is aryl, substituted aryl, heteroaryl, substituted heteroaryl;
$R_{23}$ is selected from hydrogen, acyl, aliphatic and substituted aliphatic; W is N or CH;
$W_1$ is absent, N or CH;
$R_{26}$ is hydrogen, alkyl, aryl, alkylcarbonyl, or arylcarbonyl;
$R_{27}$ is aryl, substituted aryl, heteroaryl, or substituted heteroaryl; and
$R_{28}$ is hydrogen, oxo, aryl, substituted aryl, heteroaryl, or substituted heteroaryl.

In an embodiment, the BCL-2 inhibitor is a compound of Formula (LXXVIII):

unsubstituted alkylamino, substituted or unsubstituted dialkylamino, $CF_3$, CN, $NO_2$, $N_3$, sulfonyl, acyl, aliphatic, and substituted aliphatic;
$R_{22}$ is hydrogen, acyl, aliphatic or substituted aliphatic;
n is 1-5;
$B_1$ is absent, $N(R_8)$, CO, $C_1$-$C_6$ alkyl, $C_2$-$C_6$ alkenyl, $C_2$-$C_6$ alkynyl, cycloalkyl, heterocyclic or aryl;
$B_2$ is absent, O, S, SO, $SO_2$, $N(R_8)$ or CO;
$B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl;
$B_4$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl;
$B_5$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl;
$B_6$ is absent, $C_1$-$C_6$ alkyl, $C_2$-$C_6$ alkenyl, $C_2$-$C_6$ alkynyl, cycloalkyl, substituted cycloalkyl, heterocyclic, substituted heterocyclic, aryl, substituted aryl, heteroaryl or substituted heteroaryl;
$R_8$ is independently hydrogen, acyl, aliphatic or substituted aliphatic;
Ar is aryl, substituted aryl, heteroaryl, substituted heteroaryl;
$R_{23}$ is selected from hydrogen, acyl, aliphatic and substituted aliphatic; W is N or CH;
$W_1$ is absent, N or CH; Z is S;
$R_{26}$ is hydrogen, alkyl, aryl, alkylcarbonyl, or arylcarbonyl;
$R_{27}$ is aryl, substituted aryl, heteroaryl, or substituted heteroaryl; and
$R_{28}$ is hydrogen, oxo, aryl, substituted aryl, heteroaryl, or substituted heteroaryl.

In an embodiment, the BCL-2 inhibitor is a compound of Formula (LXXIV):

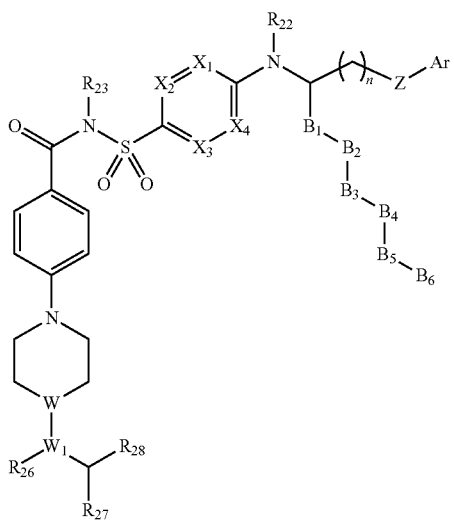

Formula (LXXVIII)

or its geometric isomers, enantiomers, diastereomers, racemates, pharmaceutically acceptable salts, prodrugs and solvates thereof;
wherein $X_1$-$X_4$ are independently N or $CR_{25}$, where $R_{25}$ is independently selected from hydrogen, hydroxy, amino, halogen, substituted or unsubstituted alkoxy, substituted or or its geometric isomers, enantiomers, diastereomers, racemates, pharmaceutically acceptable salts, prodrugs and solvates thereof;
wherein $X_1$-$X_9$ are independently N or $CR_{25}$, where $R_{25}$ is independently selected from hydrogen, hydroxy, amino, halogen, substituted or unsubstituted alkoxy, substituted or unsubstituted alkylamino, substituted or unsubstituted dialkylamino, $CF_3$, CN, $NO_2$, $N_3$, sulfonyl, acyl, aliphatic, and substituted aliphatic;

$R_{20}$ and $R_{21}$ are each independently selected from hydrogen, acyl, aliphatic and substituted aliphatic; alternatively, $R_{20}$ and $R_{21}$ can be taken together with the atom they are attached to form a heterocyclic or substituted heterocyclic;

$R_{22}$ and $R_{23}$ are each independently selected from hydrogen, acyl, aliphatic and substituted aliphatic;

$R_{26}$ is hydrogen, alkyl, aryl, alkylcarbonyl, or arylcarbonyl;

$R_{27}$ is aryl, substituted aryl, heteroaryl, or substituted heteroaryl;

$R_{28}$ is hydrogen, oxo, aryl, substituted aryl, heteroaryl, or substituted heteroaryl;

W is N or CH; Wi is absent, N or CH; and, Z is S.

The preparation of the compounds of Formula (LXXVII) to Formula (LXXIV) is described in International Patent Application Publication No. WO 2009/036035 A1.

In an embodiment, the BCL-2 inhibitor is (R)-4-(4-((4'-chloro-[1,1'-biphenyl]-2-yl)methyl)piperazin-1-yl)-N—((4-((4-(dimethylamino)-1-(phenylthio)butan-2-yl)amino)-3-nitrophenyl)sulfonyl)benzamide with the chemical structure shown in Formula (LXXV):

$R^1$ and $R^2$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl, or alternatively $R^1$ and $R^2$, taken together with the atoms to which they are bonded, form an aryl, substituted aryl, cycloalkyl, substituted cycloalkyl, cycloheteroalkyl, substituted cycloheteroalkyl, heteroaryl or substituted heteroaryl ring;

D and E are independently O, C(═O), C(═S), C(═$NR^3$) or $S(O)_2$;

$R^3$ is hydrogen, alkyl or substituted alkyl;

$R^4$ is hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —N═$NR^9$, —C(O)$NR^9R^{10}$ or —S(O)$_2NR^9R^{10}$;

$R^5$ is hydrogen, amino, substituted amino, alkyl, substituted alkyl, acyl, substituted acyl, aryl, substituted aryl, arylalkyl, substituted arylalkyl, aryloxy, substituted aryloxy, heteroaryl, substituted heteroaryl, heteroarylalkyl, substituted heteroarylalkyl, heteroalkyl, substituted heteroalkyl, —C(O)$NR^{11}R^{12}$ or —S(O)$_2NR^{11}R^{12}$;

Formula (LXXV)

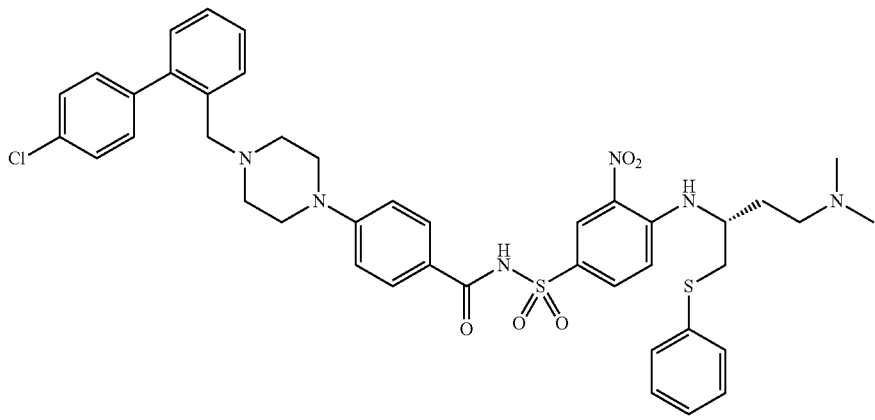

or its geometric isomers, enantiomers, diastereomers, racemates, pharmaceutically acceptable salts, prodrugs and solvates thereof. An alternative name for the compound of Formula (LXXV) includes ABT-737. The preparation of this compound is described in U.S. Pat. Nos. 7,973,161; 8,354,404; and 8,686,136; U.S. Patent Application Publication Nos. 2007/0072860 A1 (e.g., Example 2); 2011/0144112 A1; 2011/0256129 A1; and 2013/0190488 A1, the disclosures of which are incorporated by reference herein.

In an embodiment, the BCL-2 inhibitor is a compound of Formula (LXXVI):

Formula (LXXVI)

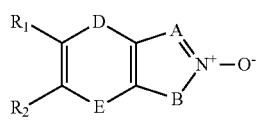

or a salt, solvate, or physiologically functional derivative thereof;

wherein A is N or C($R^4$); B is N($R^5$), C($R^6R^7$), C($R^8$), C(═$NR^{15}$), O, S, or C(═O);

$R^6$, $R^7$ and $R^{15}$ are independently hydrogen, alkyl, substituted alkyl, acyl, substituted acyl, aryl, substituted aryl, arylalkyl, substituted arylalkyl, heteroaryl, substituted heteroaryl, heteroarylalkyl, substituted heteroarylalkyl, heteroalkyl, substituted heteroalkyl, —C(O)$NR^{13}R^{14}$ or —S(O)$_2NR^{13}R^{14}$;

$R^8$ is alkyldiyl, substituted alkyldiyl, heteroalkyldiyl or substituted heteroalkyldiyl; and $R^9$, $R^{10}$, $R^{11}$, $R^{12}$, $R^{13}$ and $R^{14}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^9$ and $R^{10}$, taken together with the atoms to which they are bonded, form a cycloheteroalkyl or substituted cycloheteroalkyl ring.

In one embodiment of Formula (LXXVI), D and E are C(═O).

In one embodiment of Formula (LXXVI), A is N and B is N($R^5$).

In one embodiment of Formula (LXXVI), D and E are C(═O), A is N and B is N($R^5$).

In one embodiment of Formula (LXXVI), $R^5$ is amino, substituted amino, alkyl, or substituted alkyl.

In one embodiment of Formula (LXXVI), $R^1$ and $R^2$, taken together with the atoms to which they are bonded, form an aryl, substituted aryl, cycloalkyl, substituted cycloalkyl, heteroaryl or substituted heteroaryl ring.

In one embodiment of Formula (LXXVI), $R^1$ and $R^2$, taken together with the atoms to which they are bonded, form a thienyl, substituted thienyl, furanyl, substituted furanyl, pyridinyl, substituted pyridinyl, pyrimidinyl, substituted pyrimidinyl, oxazolyl, substituted oxazolyl, phenyl or substituted phenyl ring.

In one embodiment of Formula (LXXVI), $R^1$ and $R^2$, taken together with the atoms to which they are bonded, form a phenyl or substituted phenyl ring.

In one embodiment of Formula (LXXVI), A is $CR^4$ and B is $NR^5$.

In one embodiment of Formula (LXXVI), D and E are C(=O), A is $CR^4$ and B is $NR^5$.

In specific embodiments of Formula (LXXVI), a compound may have the following structure:

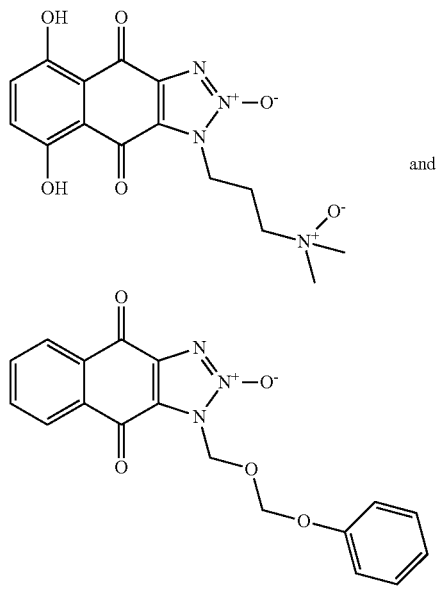

and

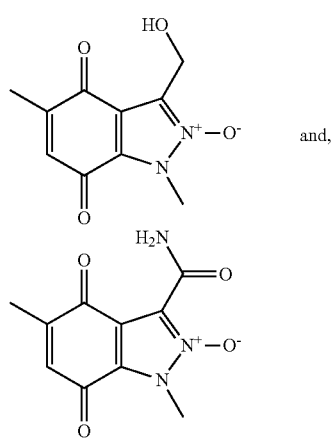

or a salt, solvate, or physiologically functional derivative thereof.

In specific embodiments of Formula (LXXVI), a compound may have the following structure:

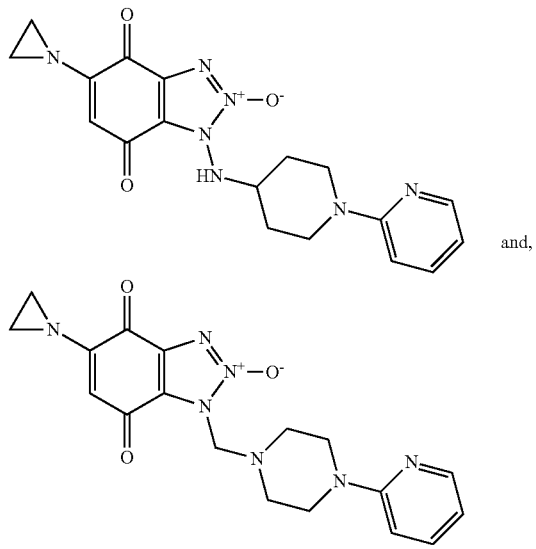

and,

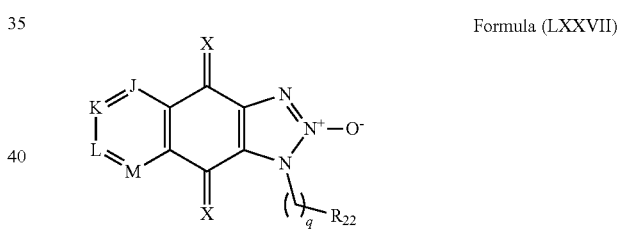

or a salt, solvate, or physiologically functional derivative thereof.

In an embodiment, the BCL-2 inhibitor is a compound of Formula (LXXVII):

Formula (LXXVII)

or a salt, solvate, or physiologically functional derivative thereof;

wherein: q is 0, 1, 2, 3, 4 or 5;

X and Y are independently O, S, or $NR^{21}$;

J, K, L and M are independently $CR^{25}$ or N.

$R^{21}$ is hydrogen, alkyl or substituted alkyl;

$R^{22}$ is halo, hydrogen, alkyl, substituted alkyl, cycloheteroalkyl, substituted cycloheteroalkyl, —OC(O)$R^{23}$, —NR$^{23}$R$^{24}$, —N(R$^{23}$)C(O)R$^{24}$, heteroalkyl, substituted heteroalkyl, aryl, substituted aryl, —C(O)NR$^{23}$R$^{24}$, S(O)$_2$ NR$^{23}$R$^{24}$, heteroaryloxy or substituted heteroaryloxy;

$R^{23}$ and $R^{24}$ are independently hydrogen, alkyl, substituted alkyl, cycloheteroalkyl, substituted cycloheteroalkyl, heteroalkyl, substituted heteroalkyl, aryl, substituted aryl, arylalkyl, substituted arylalkyl, heteroaryl, substituted heteroaryl, heteroarylalkyl, or substituted heteroarylalkyl, or alternatively, $R^{23}$ and $R^{24}$, taken together with the atoms to which they are bonded, form a cycloheteroalkyl or substituted cycloheteroalkyl ring;

$R^{25}$ is halo, cyano, nitro, OR$^{26}$, S(O)$_t$R$^{26}$, CO$_2$R$^{26}$, CONR$^{26}$R$^{27}$ or NR$^{26}$R$^{27}$, alkyl, substituted alkyl, heteroalkyl or substituted heteroalkyl, wherein t is 0, 1, or 2; and Each $R^{26}$ and $R^{27}$ are independently hydrogen, alkyl, substituted alkyl, cycloheteroalkyl, substituted cycloheteroalkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{26}$ and $R^{27}$, taken together with the atoms to which they are bonded, form a cycloheteroalkyl or substituted cycloheteroalkyl ring.

In one embodiment of Formula (LXXVII), q is 0, X and Y are 0, and $R^{22}$ is amino, substituted amino, heteroaryloxy, or substituted heteroaryloxy.

In one embodiment of Formula (LXXVII), q is 1, X and Y are (0) and $R^{22}$ is hydrogen, amino, substituted amino, heteroalkyl, substituted heteroalkyl, aryl, substituted aryl, cycloheteroalkyl or substituted cycloheteroalkyl.

In one embodiment of Formula (LXXVII) wherein q is 1, $R^{22}$ is phenyl or substituted phenyl.

In one embodiment of Formula (LXXVII) wherein q is 1, $R^{22}$ is

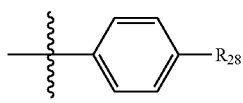

wherein $R^{28}$ is cycloheteroalkyl, substituted cycloheteroalkyl, heteroaryl, substituted heteroaryl, phenyl or substituted phenyl.

In one embodiment of Formula (LXXVII) wherein q is 1, $R^{22}$ is amino or substituted amino.

In one embodiment of Formula (LXXVII), q is 2 and $R^{22}$ is amino, substituted amino, alkyl, substituted alkyl, aryl, substituted aryl, cycloheteroalkyl substituted cycloheteroalkyl OC(O)$R^{23}$ or —C(O)N$R^{23}R^{24}$.

In one embodiment of Formula (LXXVII) wherein q is 2, $R^{22}$ is phenyl or substituted phenyl. In specific examples, the substituted phenyl comprises one or more substituents selected from the group consisting of phenyl, substituted phenyl, heteroaryl, substituted heteroaryl, cycloalkyl, substituted cycloalkyl, cycloheteroalkyl, and substituted cycloheteroalkyl.

In one embodiment of Formula (LXXVII) wherein q is 2, $R^{22}$ is C(O)N$R^{23}R^{24}$ and $R^{23}$ and $R^{24}$, taken together with the atoms to which they are bonded, form a cycloheteroalkyl or substituted cycloheteroalkyl ring. In specific examples, the substituted cycloheteroalkyl comprises one or more substituents selected from the group consisting of phenyl, substituted phenyl, heteroaryl, substituted heteroaryl, cycloalkyl, substituted cycloalkyl, cycloheteroalkyl, and substituted cycloheteroalkyl.

In one embodiment of Formula (LXXVII), q is 3 and $R^{22}$ is —OC(O)$R^{23}$, —N$R^{23}R^{24}$, aryl, substituted aryl, heteroaryl, substituted heteroaryl, cycloheteroalkyl or substituted cycloheteroalkyl.

In one embodiment of Formula (LXXVII) wherein q is 3, $R^{22}$ is substituted cycloheteroalkyl which comprises substituents selected from the group consisting of aryl, substituted aryl, alkyl, substituted alkyl, arylalkyl, substituted arylalkyl, cycloalkyldiyl, substituted cycloalkydiyl, cycloheteroalkyldiyl, substituted cycloheteroalkydiyl, and hydroxyl.

In specific embodiments of Formula (LXXVII), a compound may have the following structure:

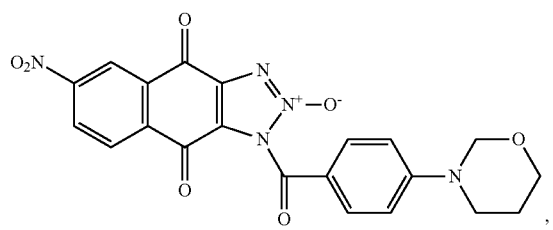
,
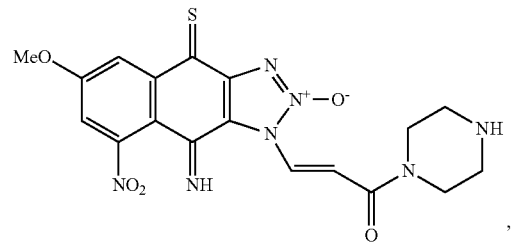
,
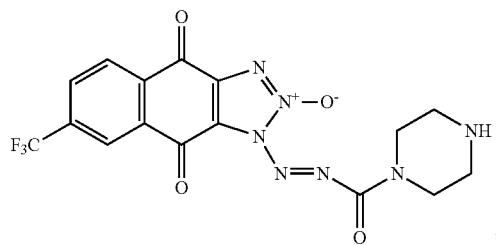
,
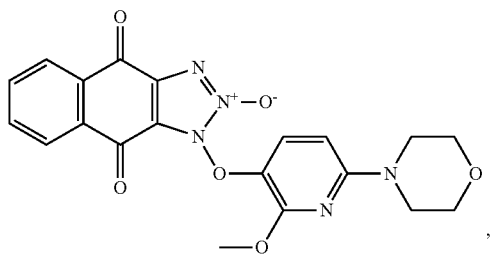
,
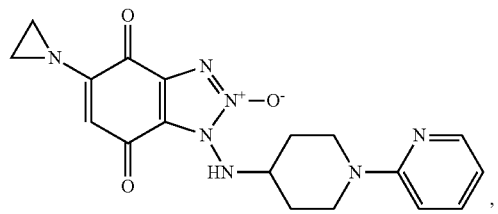
,
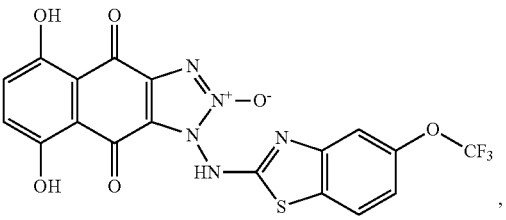
,

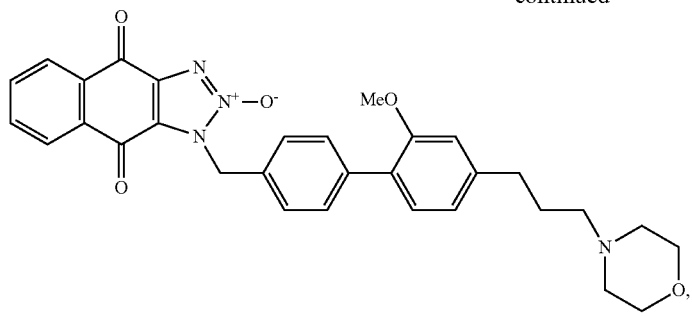
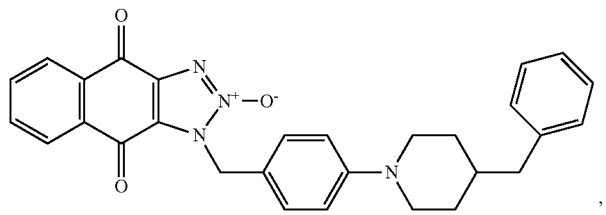
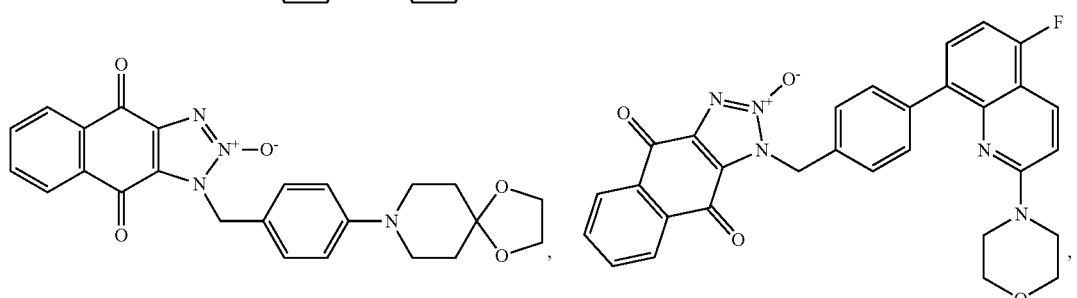
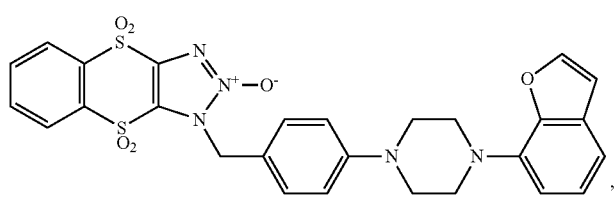
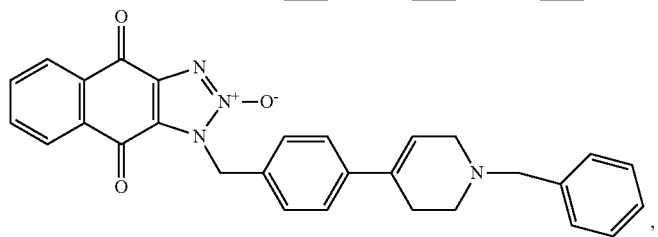
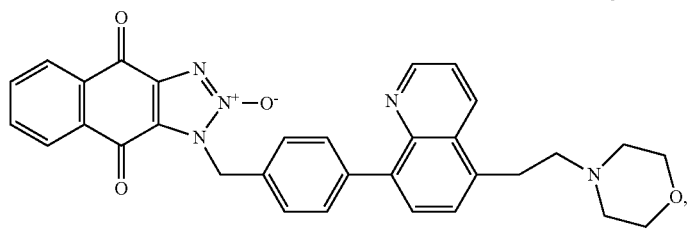
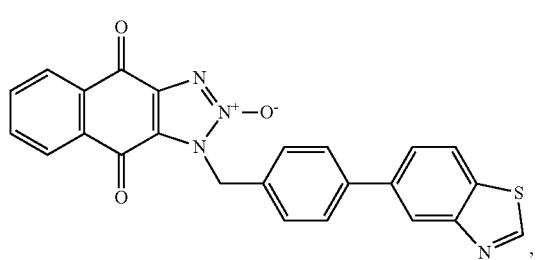

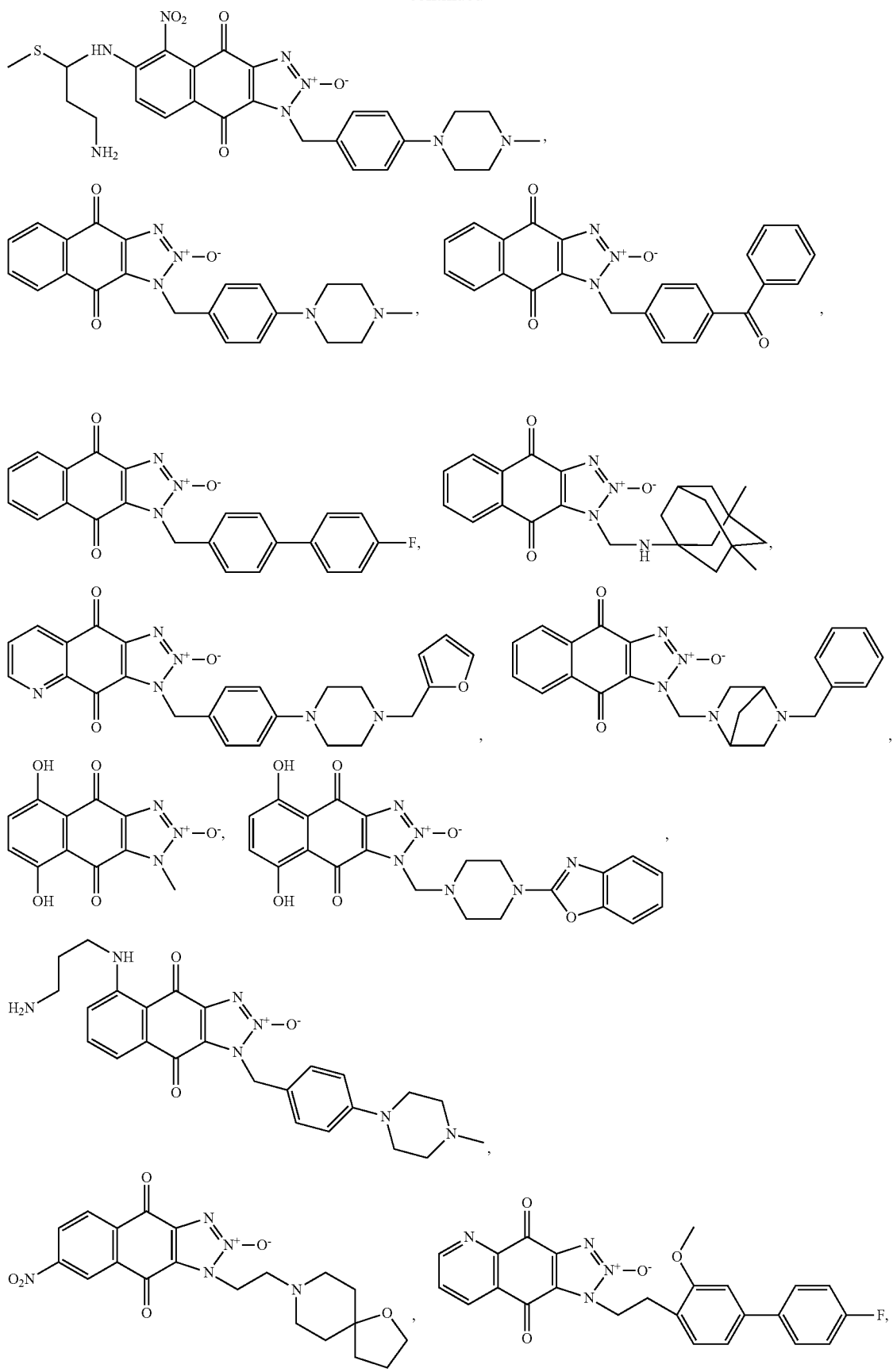

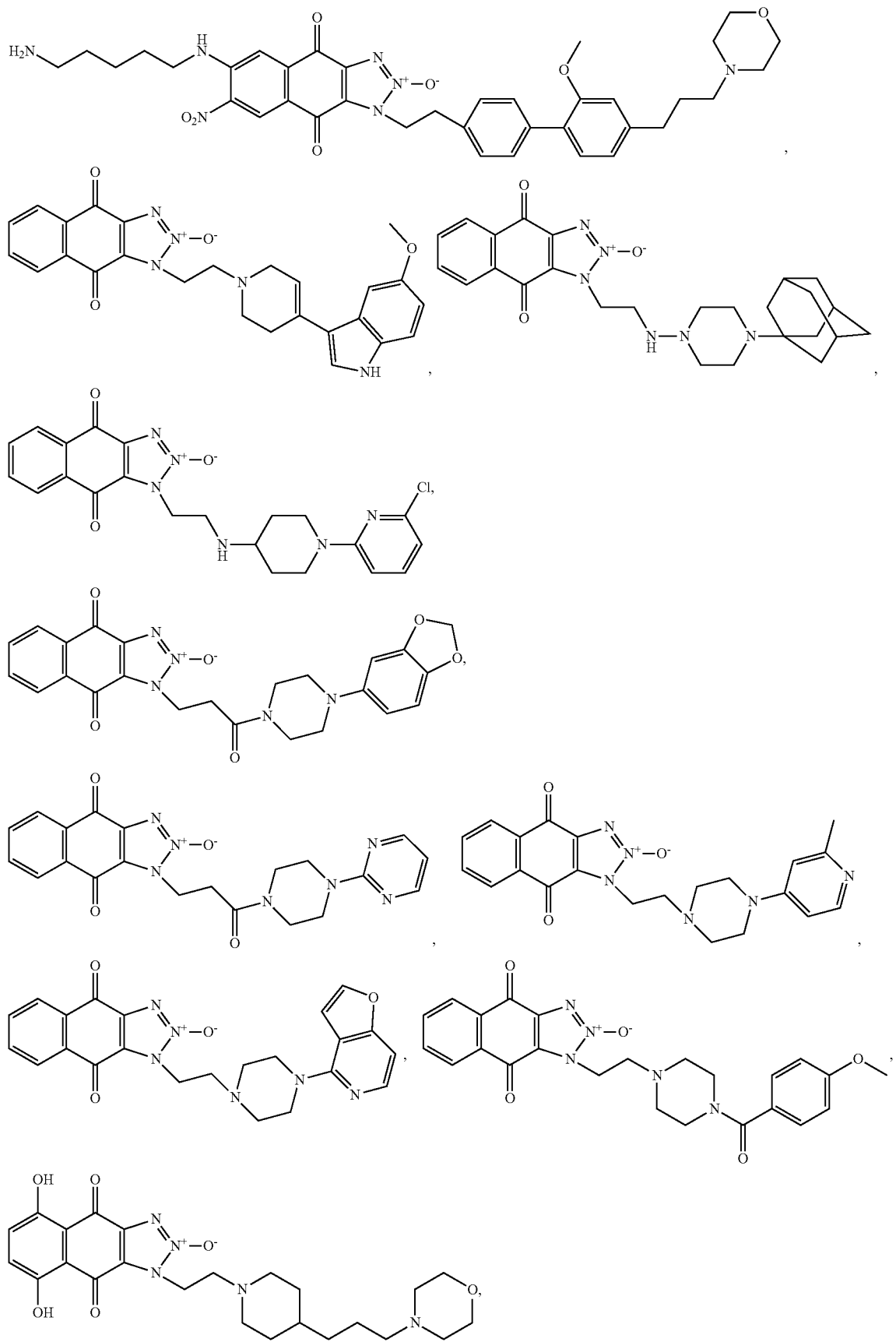

-continued
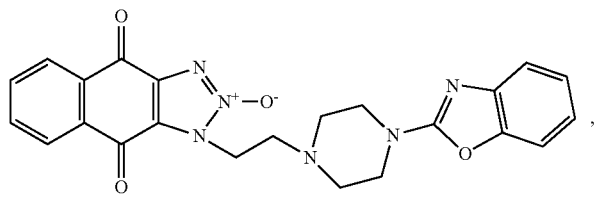
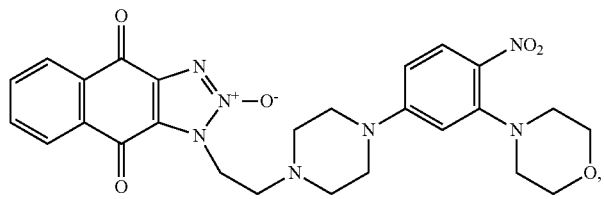
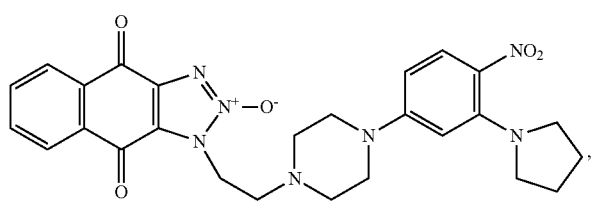
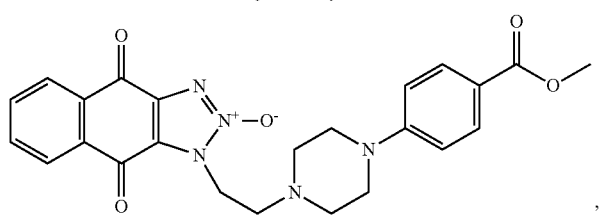
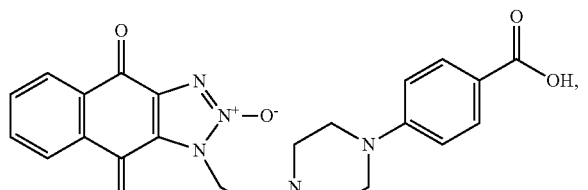
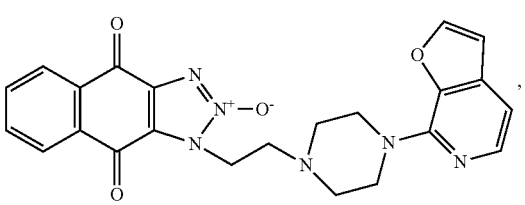
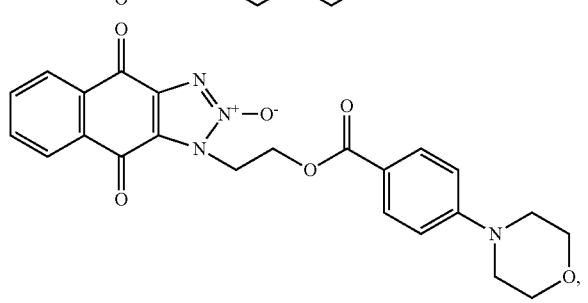
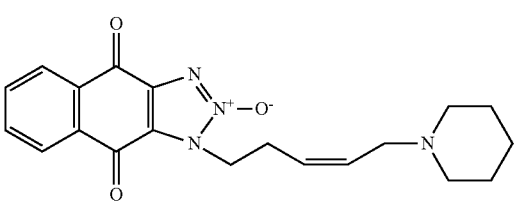
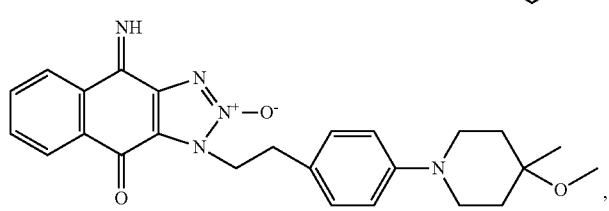
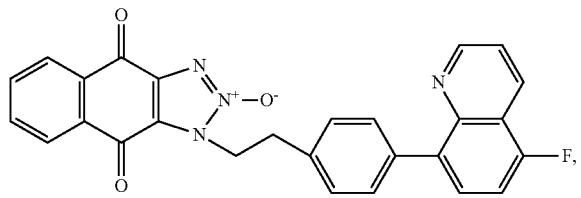

-continued
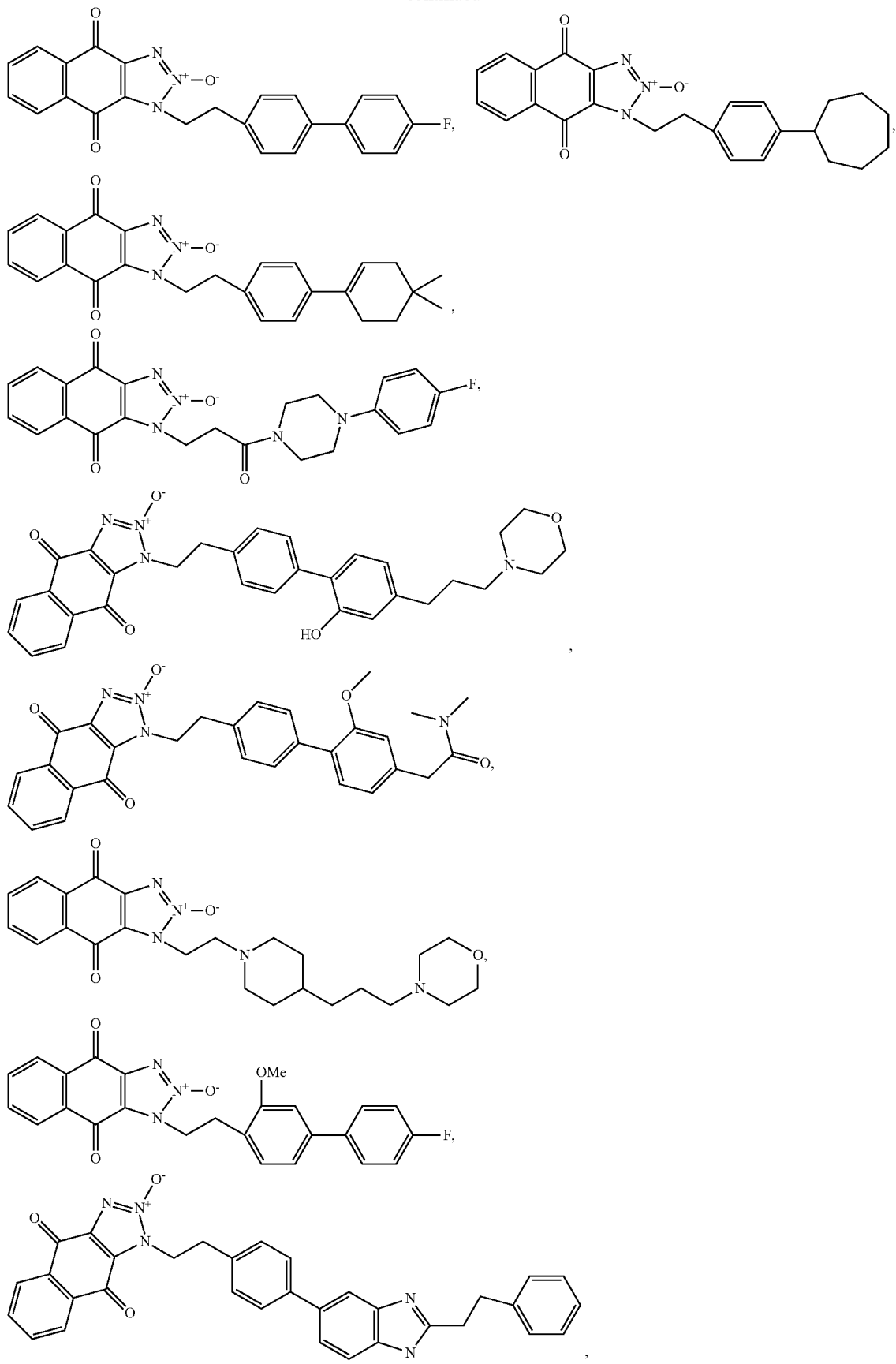

-continued
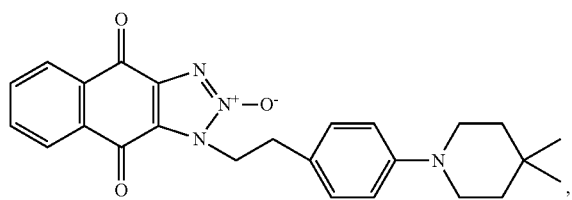
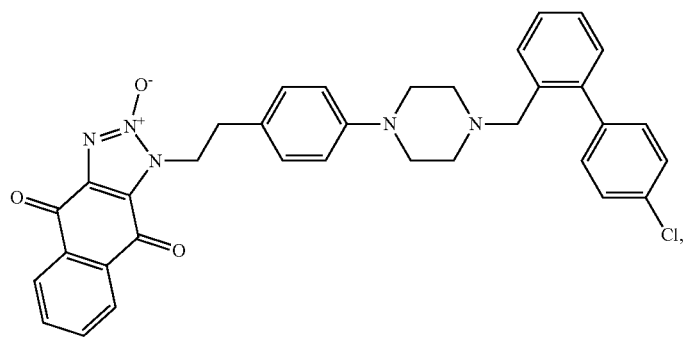
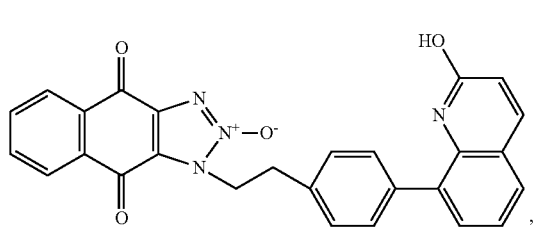
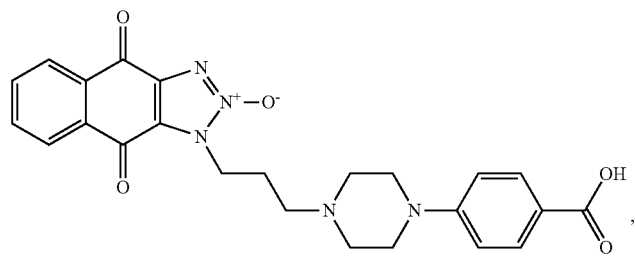
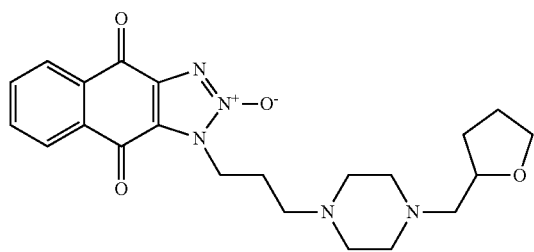
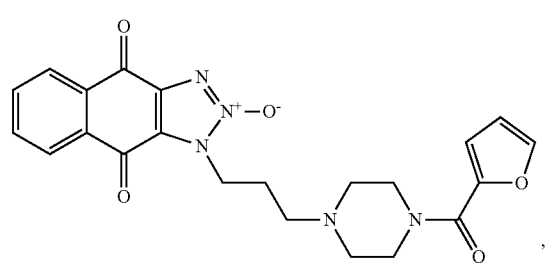
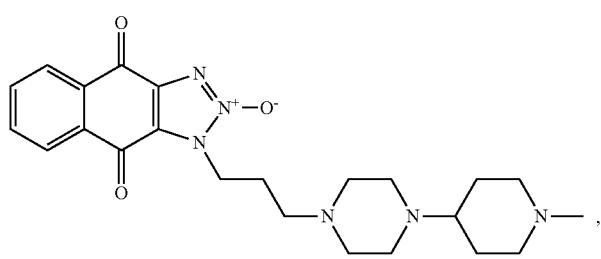
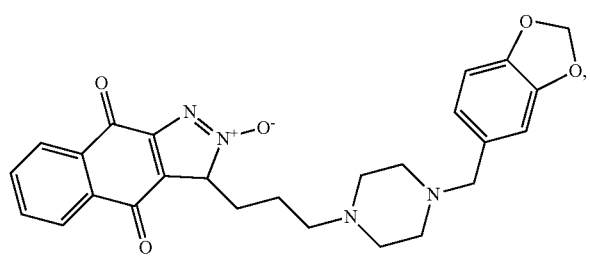

-continued
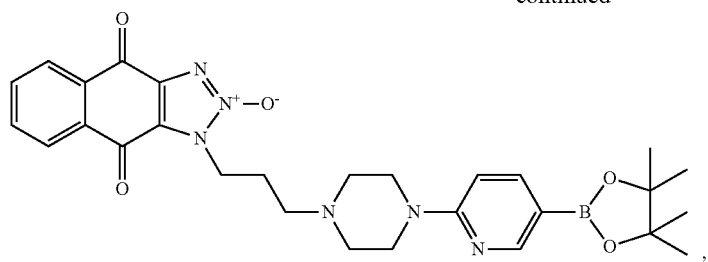,
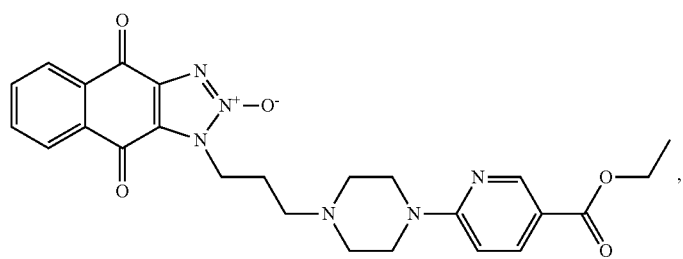,
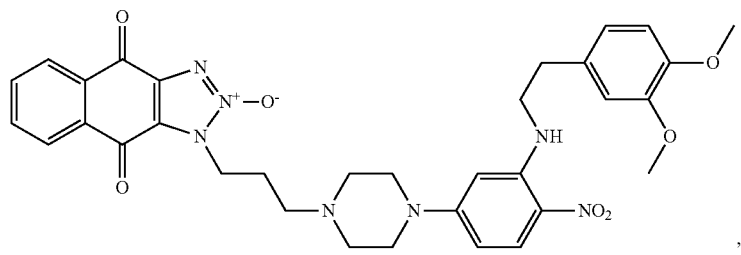,
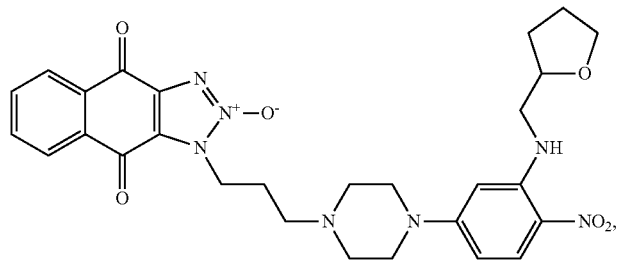,
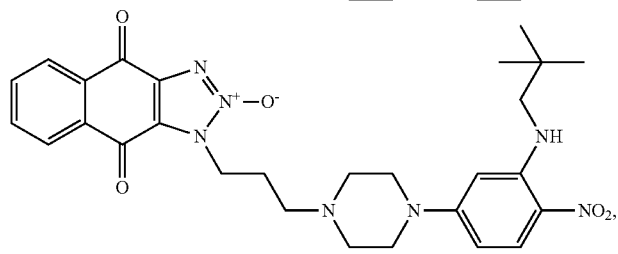,
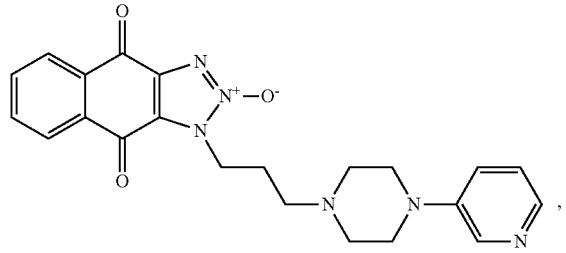,

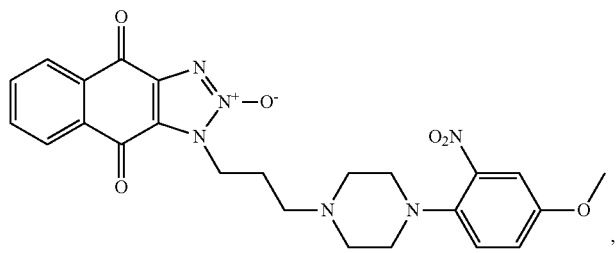
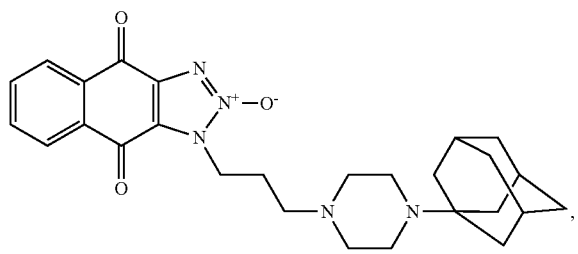
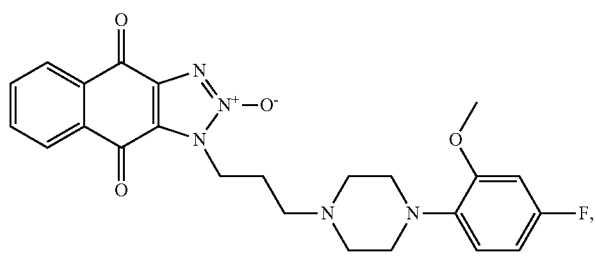
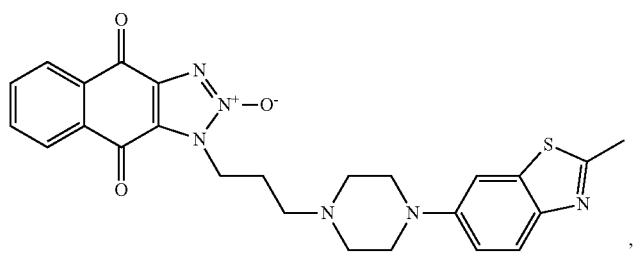
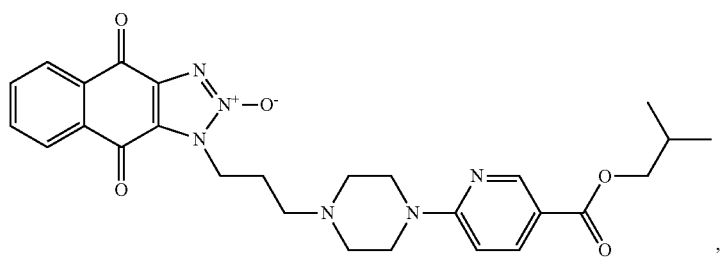
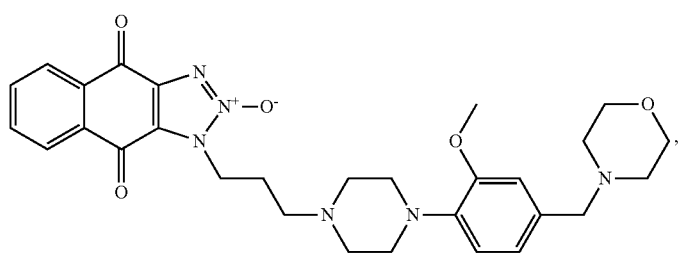

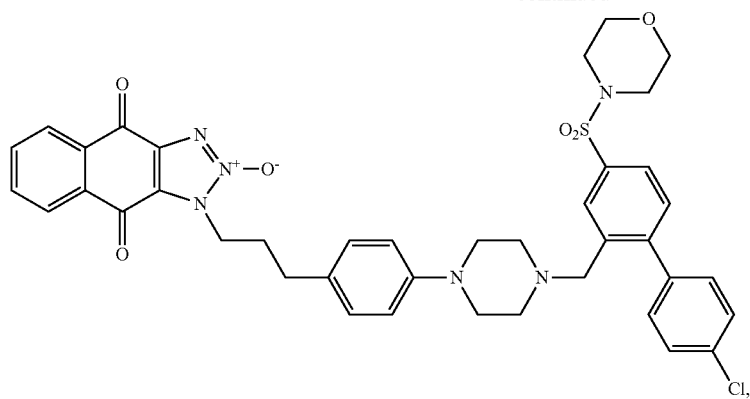
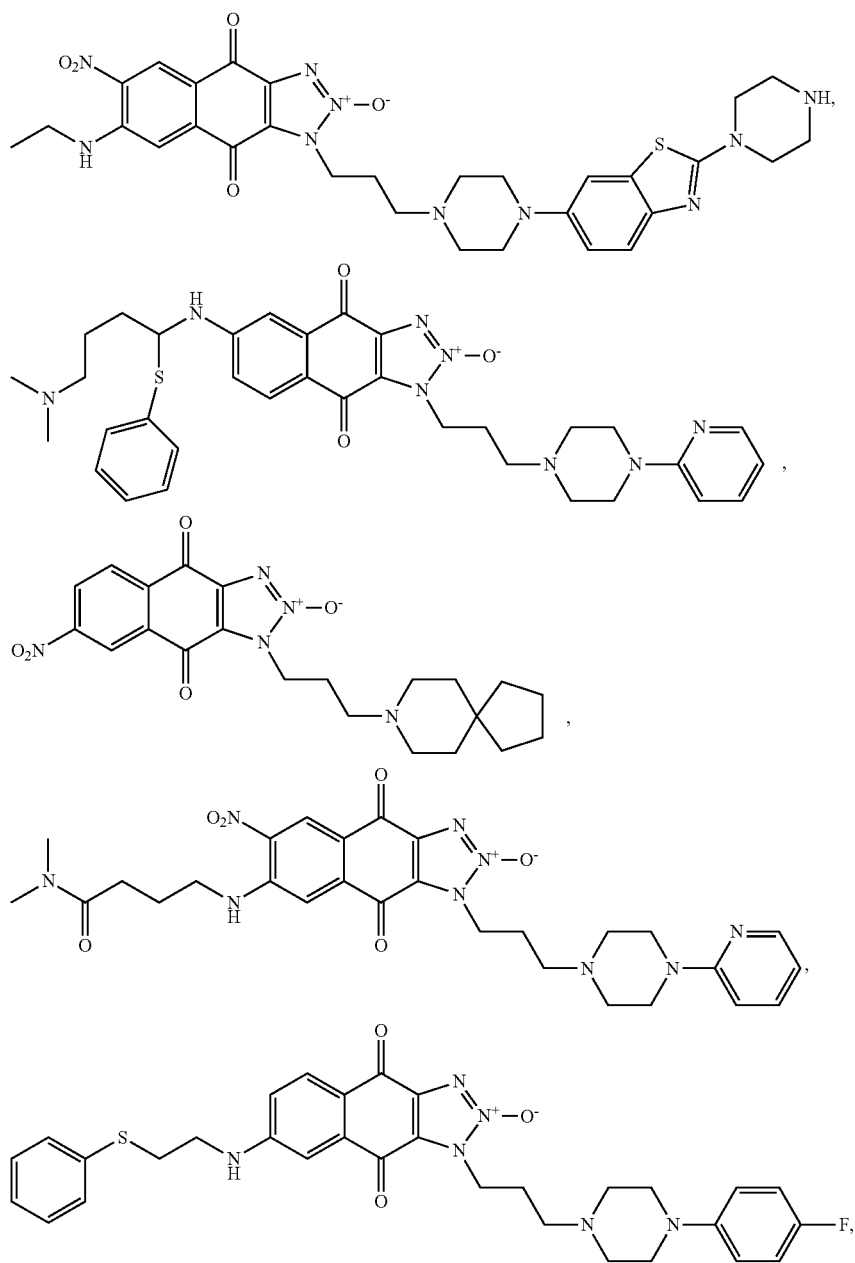

-continued
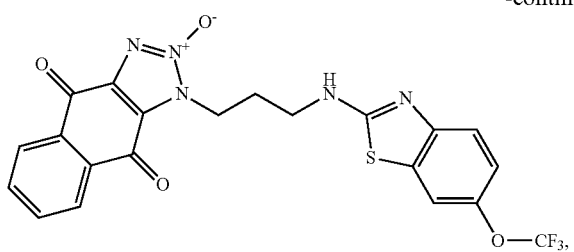
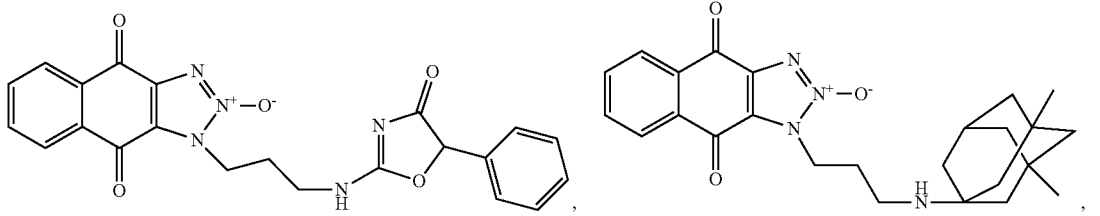
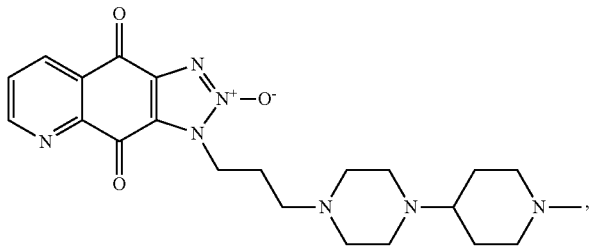
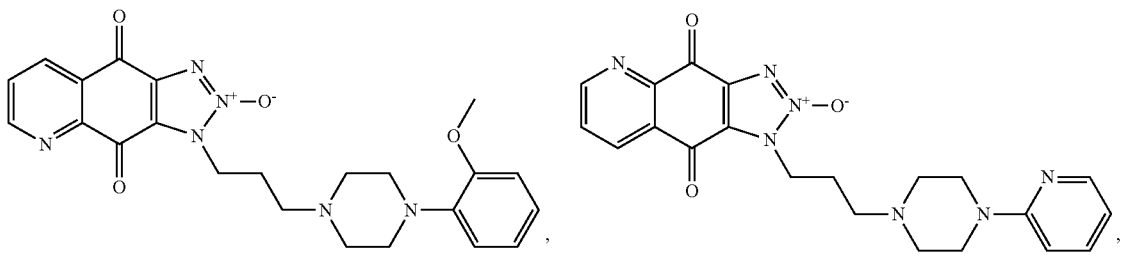
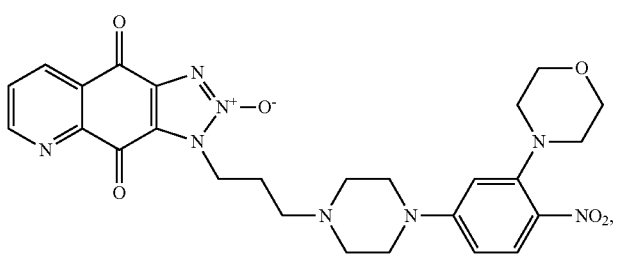
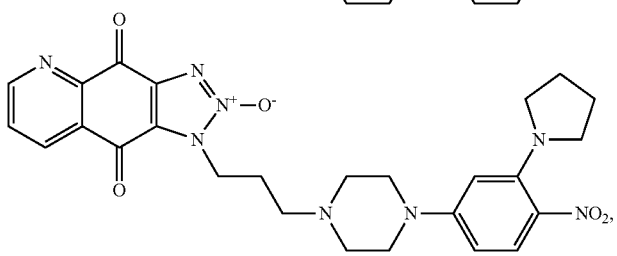
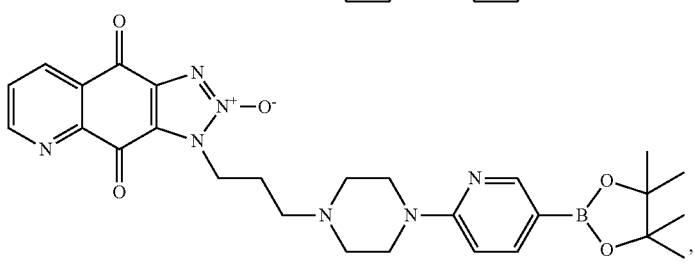

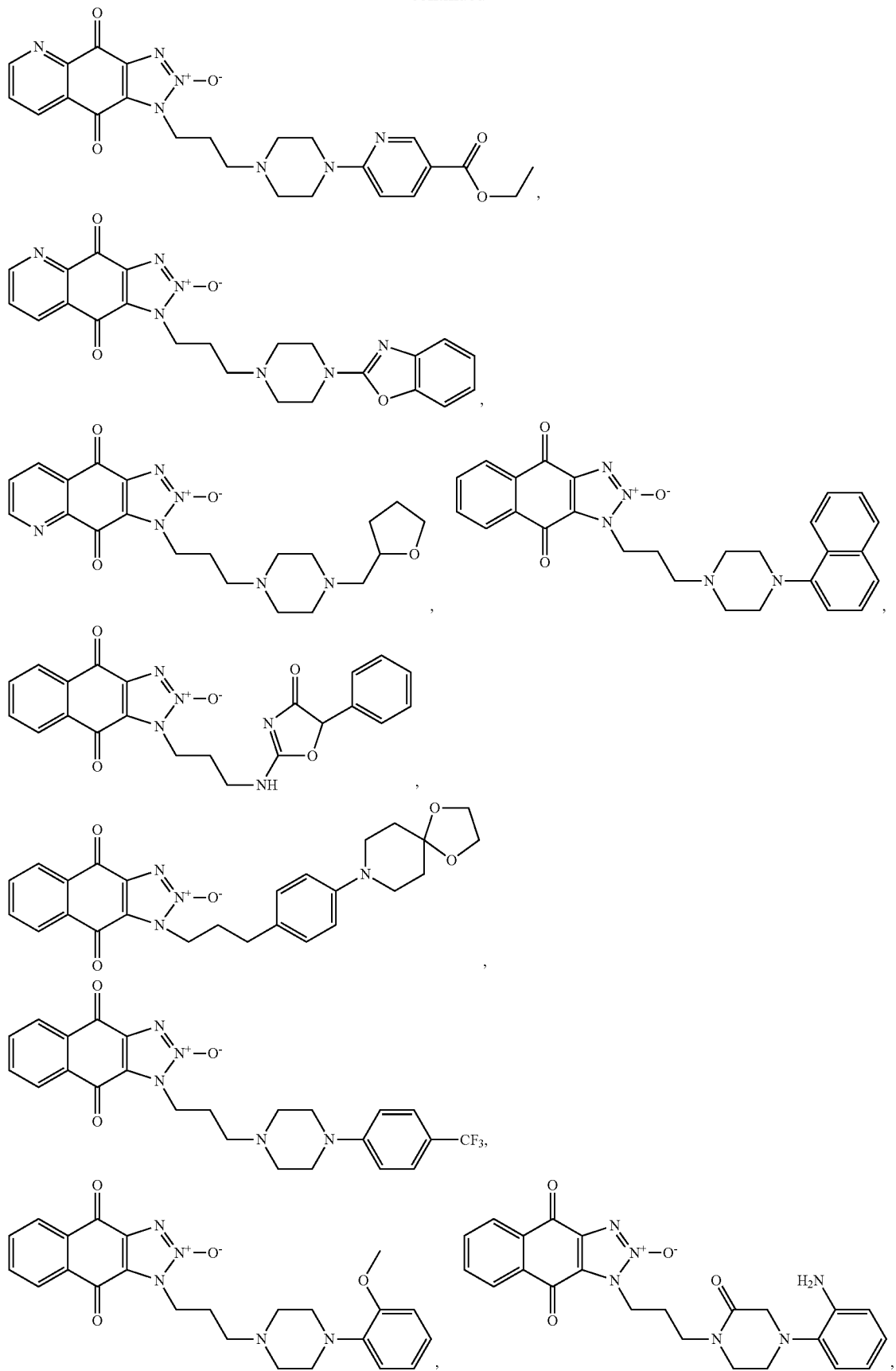

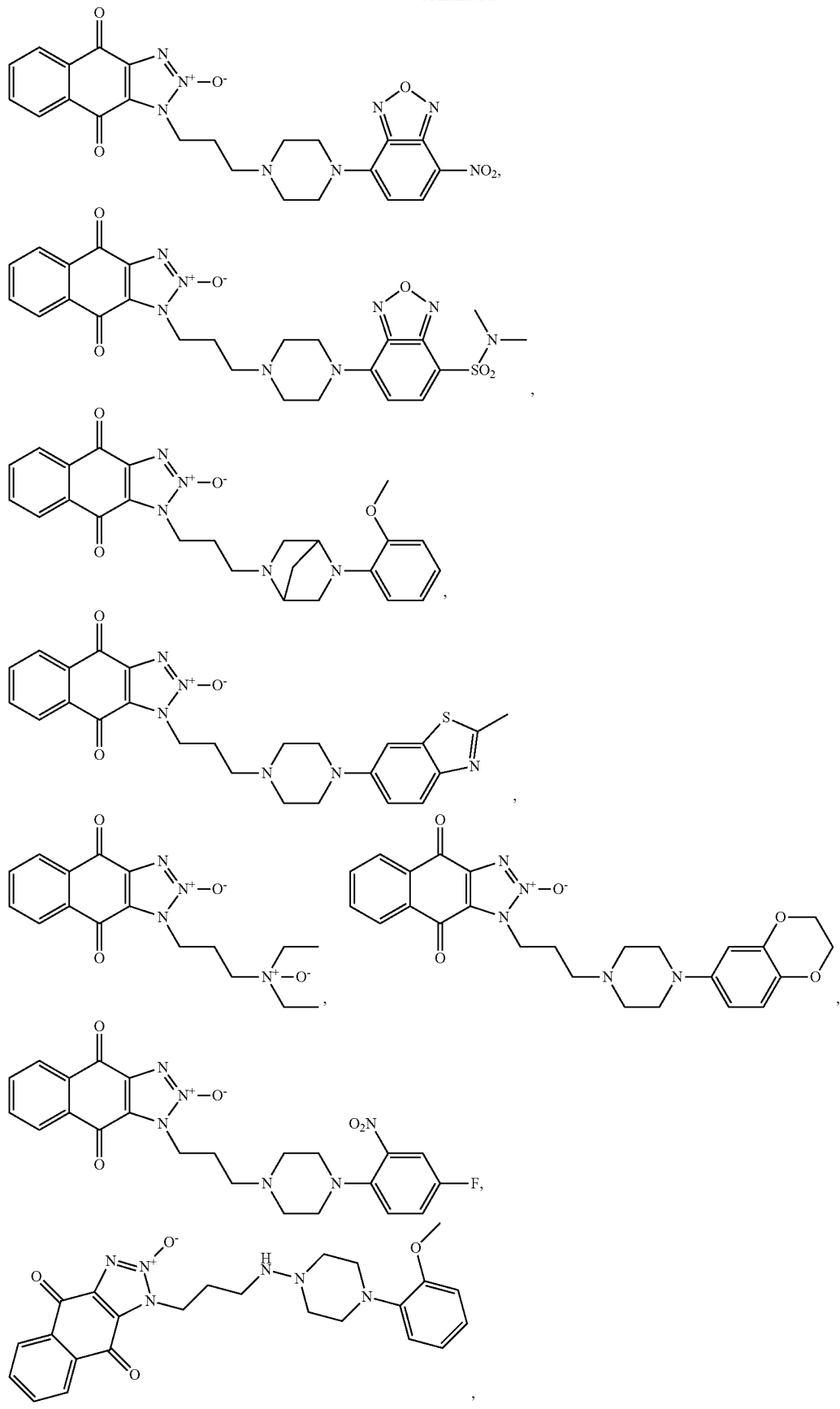

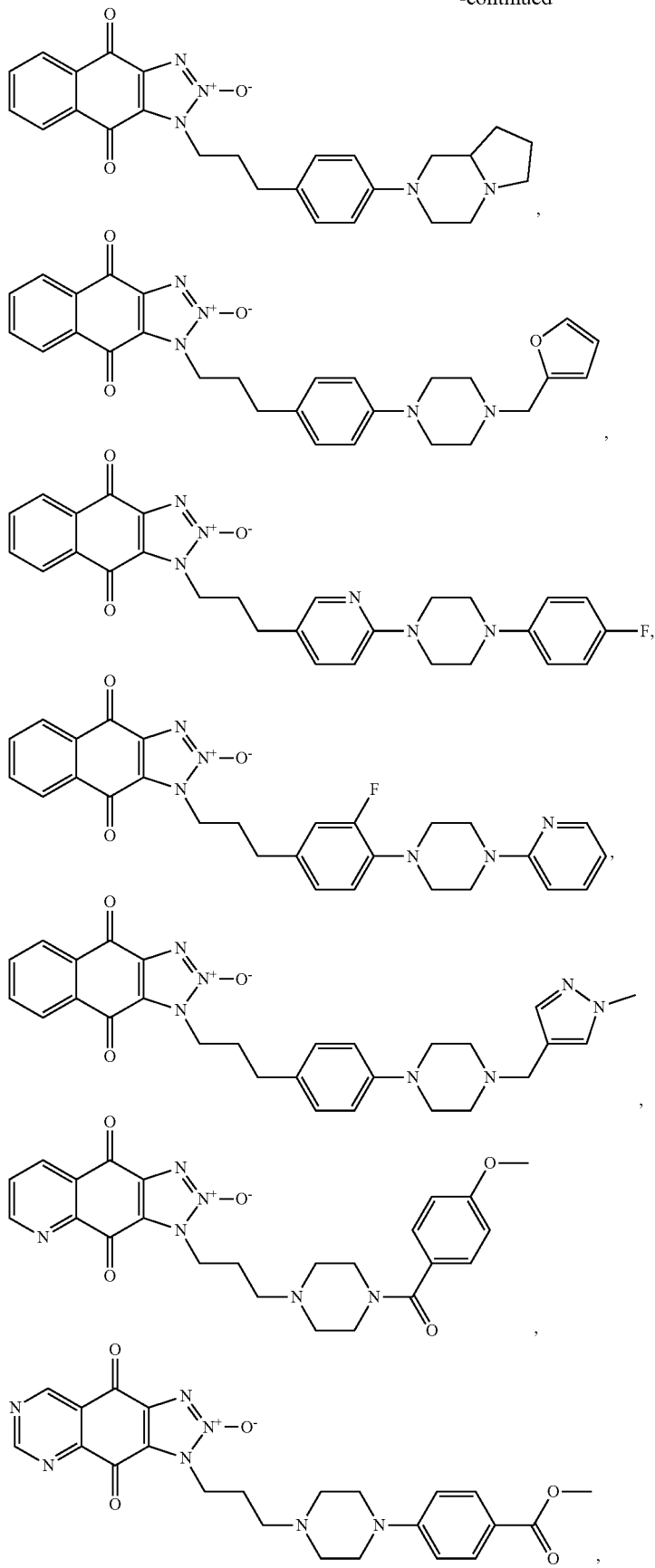

251        252
-continued
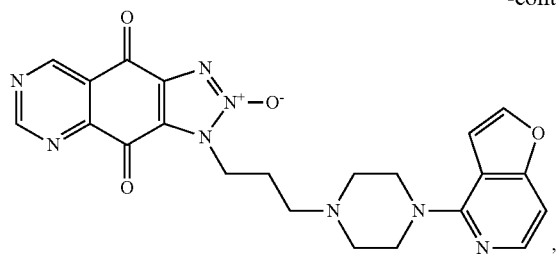 , 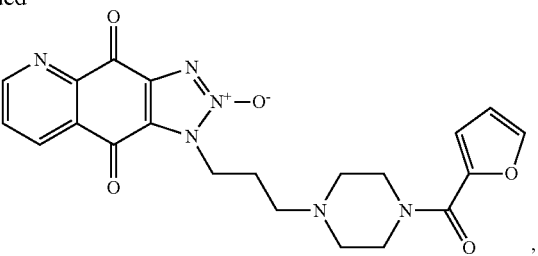 ,
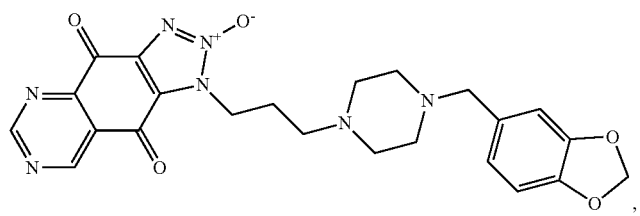 ,
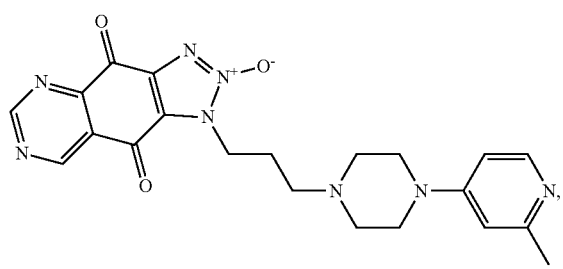 ,
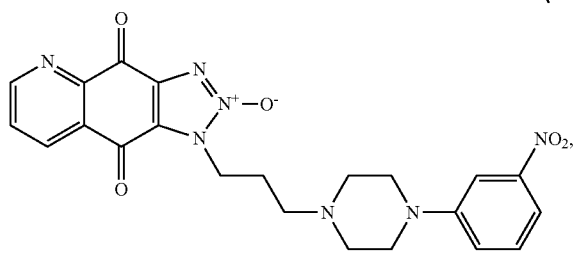 ,
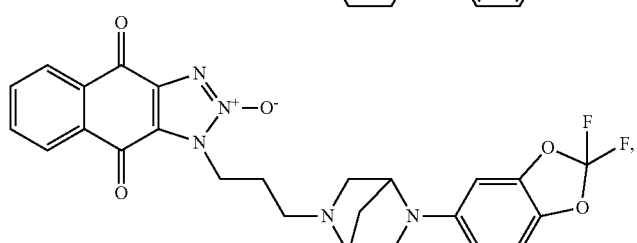 ,
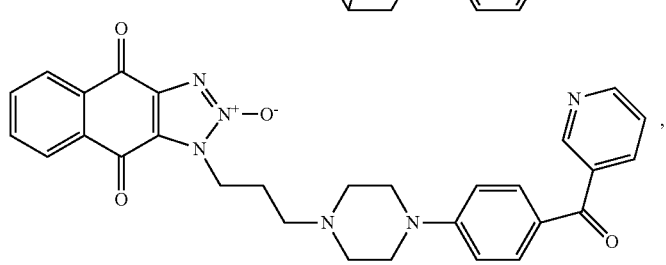 ,
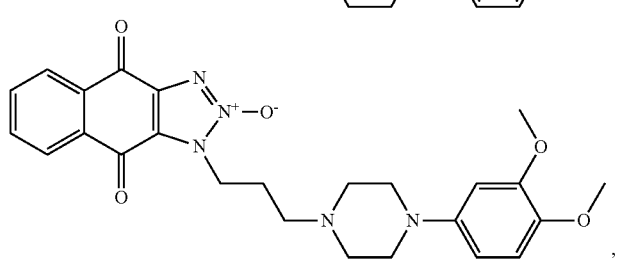 , 253
-continued
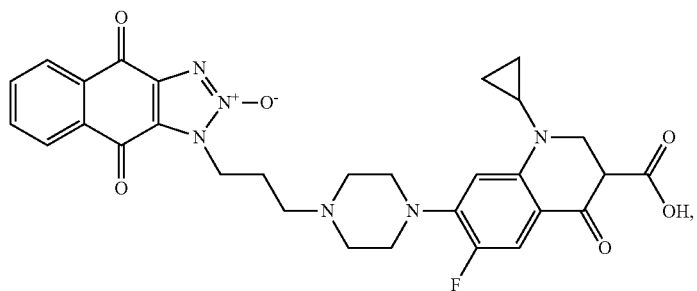
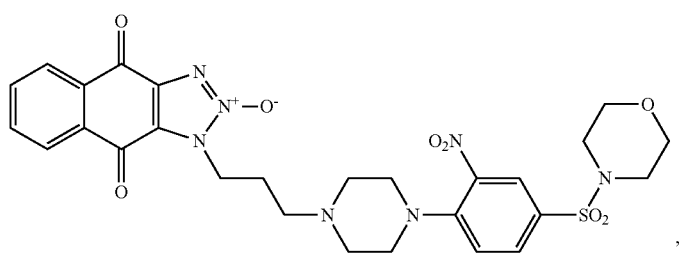
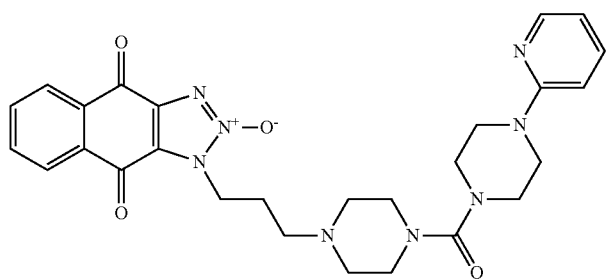
254
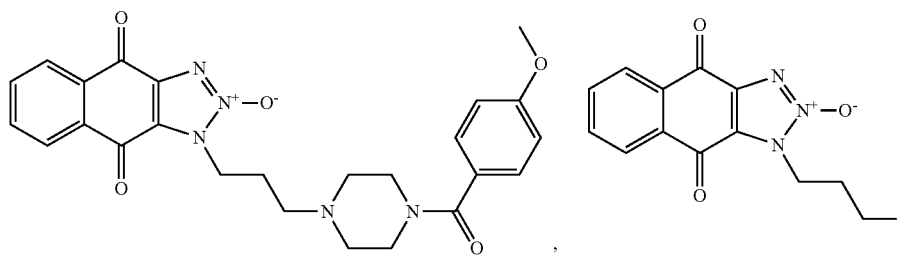
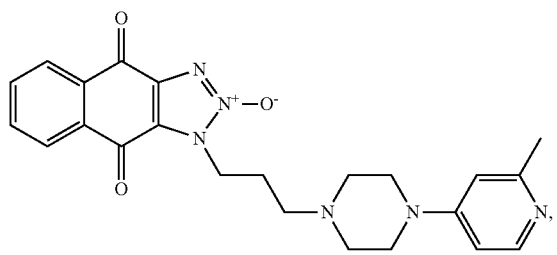
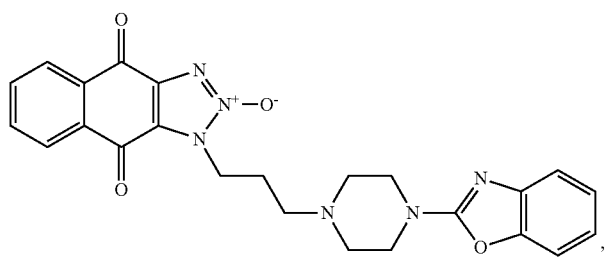

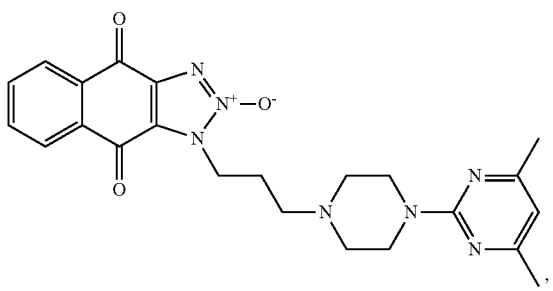
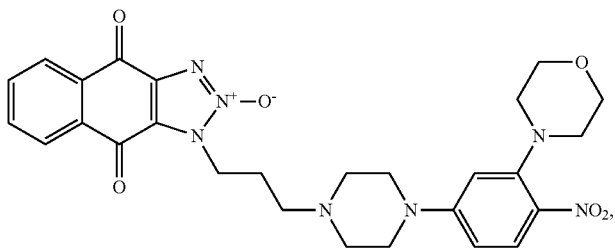
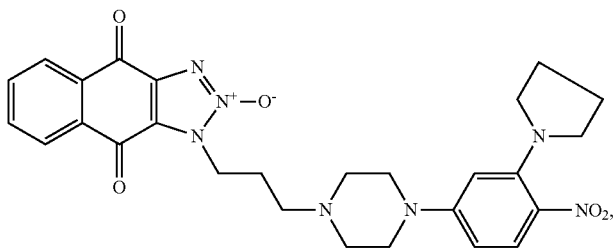
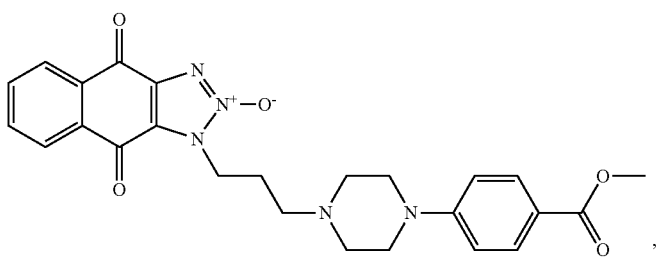
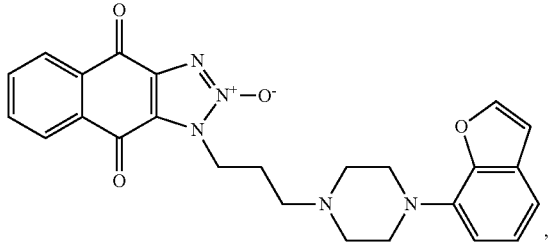
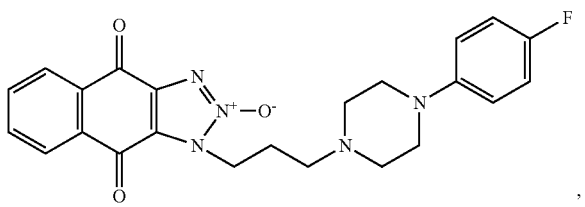
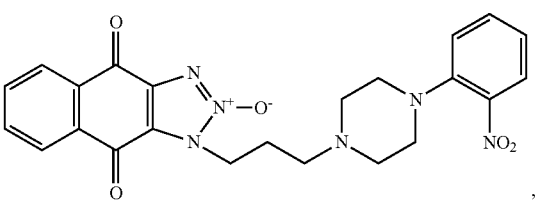
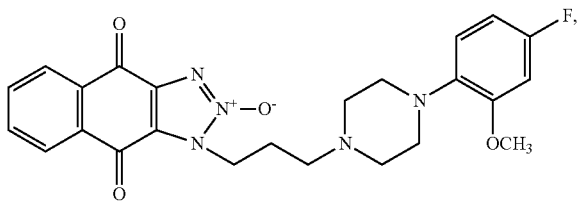

-continued
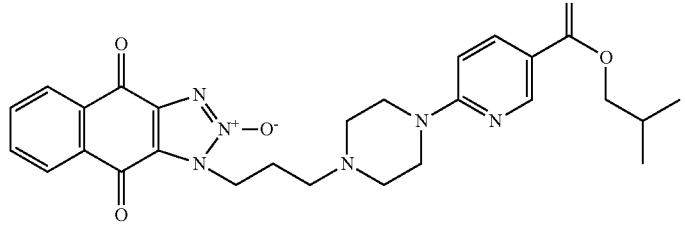
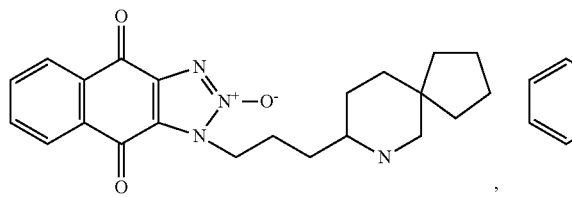
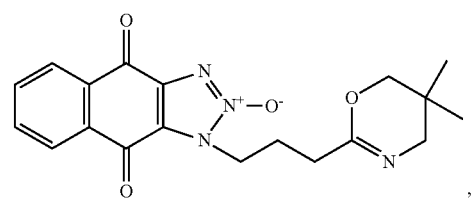
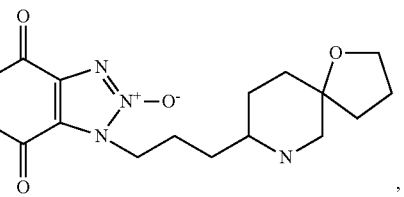
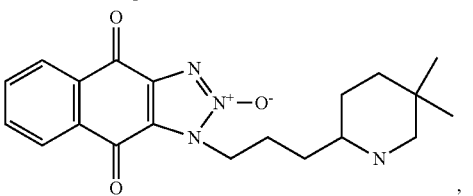
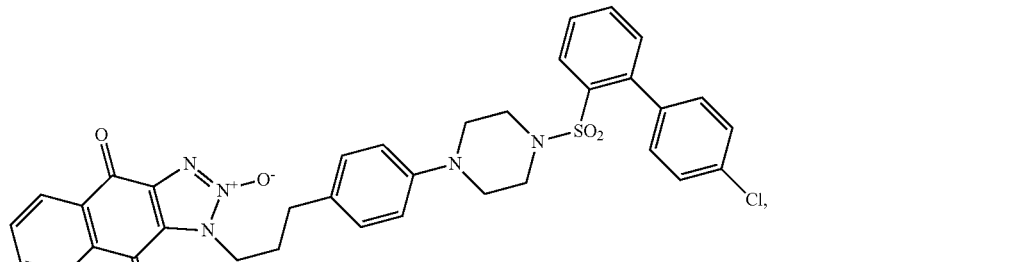
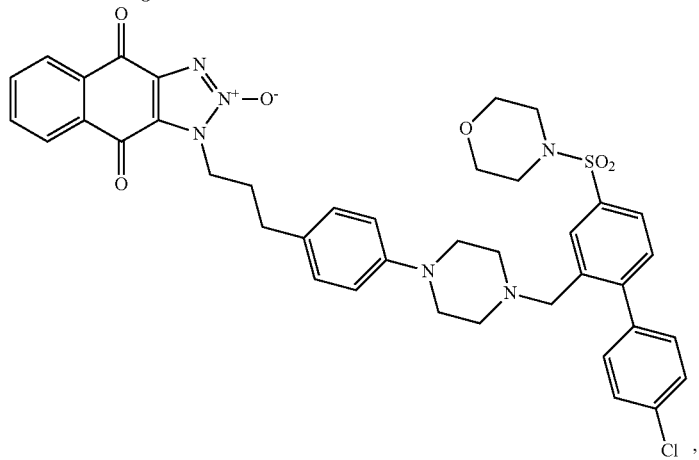

-continued
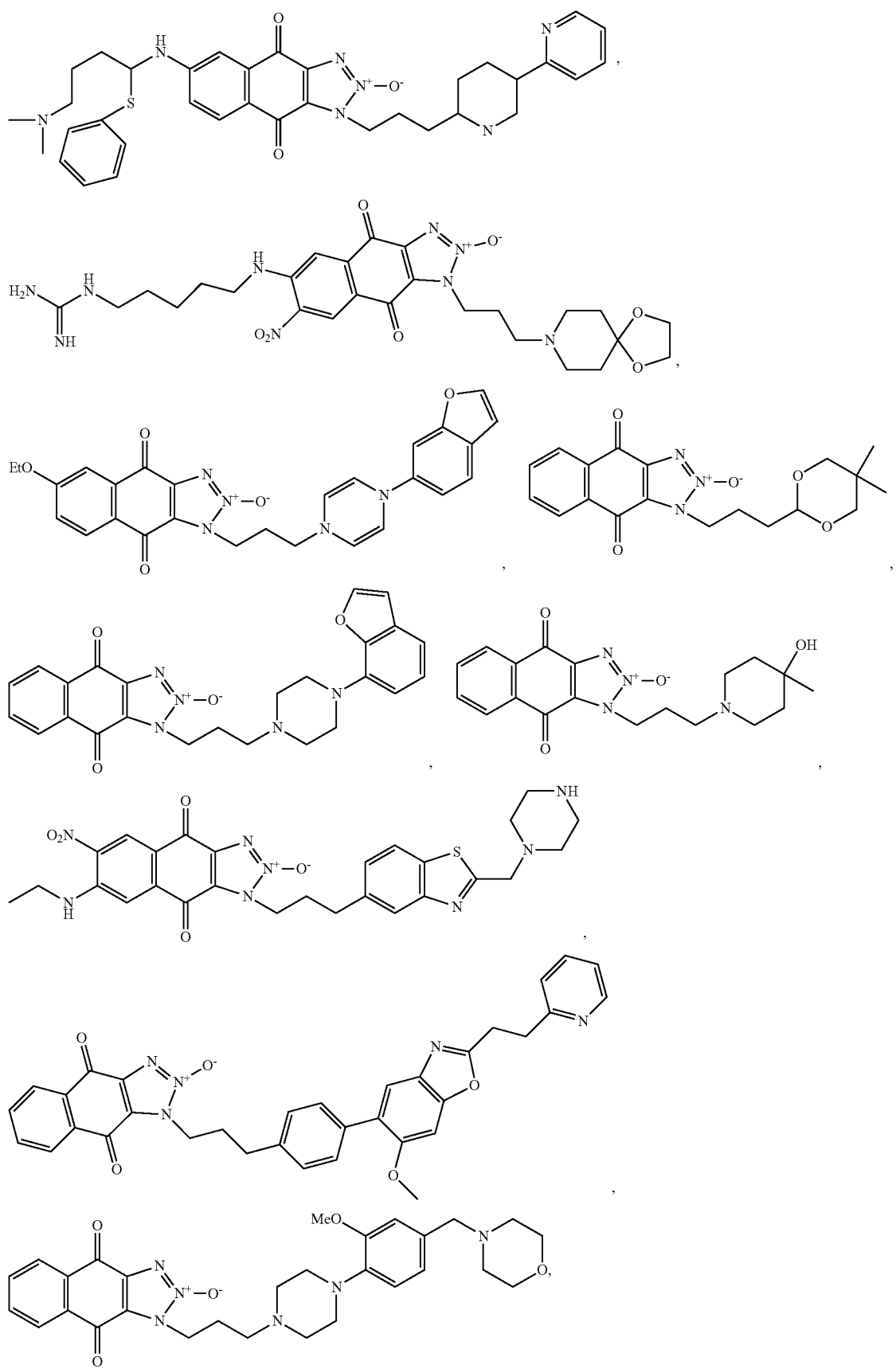

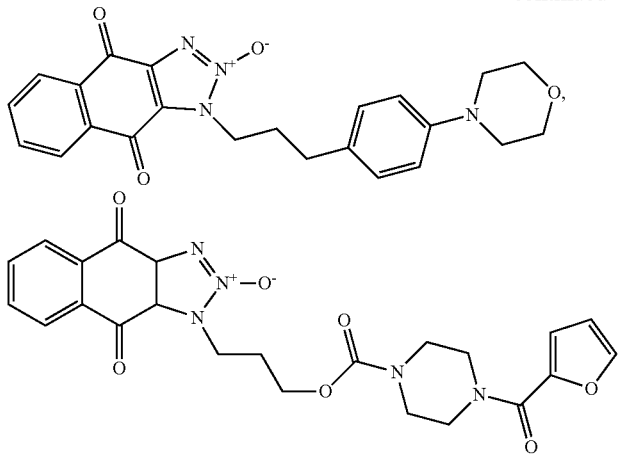

The preparation of the compounds of Formula (LXXVI) and Formula (LXXVII) is described in U.S. Pat. No. 8,618,110 and U.S. Patent Application Publication No. 2010/0267671 A1, the disclosures of which is incorporated by reference herein.

In an embodiment, the BCL-2 inhibitor is a compound of Formula (LXXVIII):

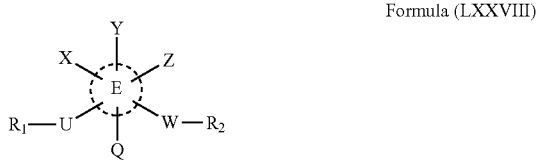

Formula (LXXVIII)

or a pharmaceutically acceptable salt or prodrug thereof, wherein:
E is phenyl or a heteroaromatic group;
X, Y, and Z are independently H, OH, carboxylic acid, amide, sulfonic acid, sulfonamide, sulfinic acid, sulfinamide, aldehyde, phosphoric acid, phosphonamide, alkyl, alkoxy, or aryl, or one of X and Y or Y and Z form a heterocyclic ring, and at least one of X, Y, and Z is OH, carboxylic acid, amide, sulfonic acid, sulfonamide, sulfinic acid, sulfinamide, aldehyde, phosphoric acid, or phosphonamide;
U and W are independently CO, SO, $SO_2$, $(CH_2)_n$, S, NH, NHCO, P, PO, or $PO_2$;
n is 0 or 1;
Q is H, alkyl, alkenyl, alkynyl, or halogen; or
Q forms a ring with U and/or W;
$R_1$ and $R_2$ are independently hydrogen, alkyl, alkenyl, alkynyl, cycloalkyl, aryl, heteroaryl, partially saturated heterocycle, heterocycle; $NR_3R_4$, $OR_3$, $SR_3$, or $CR_3R_4R_5$, anyone of which may be optionally substituted; and
$R_3$-$R_5$ are independently alkyl, alkenyl, alkynyl, cycloalkyl, aryl, aralkyl, heteroaryl, heteroaralkyl, heterocycle or form a ring, anyone of which may be optionally substituted.
In one embodiment, at least one of X, Y, and Z is OH.
Useful alkyl groups include straight-chained or branched $C_{1-8}$ alkyl groups, especially methyl, ethyl, propyl, isopropyl, t-butyl, sec-butyl, 3-pentyl, adamantyl, norbornyl, and 3-hexyl groups.
Useful alkenyl groups include straight-chained or branched $C_{2-18}$ alkyl groups, especially ethenyl, propenyl, isopropenyl, butenyl, isobutenyl, and hexenyl.
Useful alkynyl groups are $C_{2-18}$ alkynyl groups, especially ethynyl, propynyl, butynyl, and 2-butynyl groups
Useful cycloalkyl groups are $C_{3-8}$ cycloalkyl. Typical cycloalkyl groups include cyclopropyl, cyclobutyl, cyclopentyl, cyclohexyl and cycloheptyl.
Useful aryl groups include $C_6$-14 aryl, especially phenyl, naphthyl, phenanthrenyl, anthracenyl, indenyl, azulenyl, biphenyl, biphenylenyl, and fluorenyl groups.
Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, P-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.
Optional substituents include one or more alkyl; halo; haloalkyl; cycloalkyl; aryl optionally substituted with one or more lower alkyl, lower alkoxy, methylenedioxy, halo, haloalkyl, aminosulfonyl, aryl, or heteroaryl groups; aryloxy optionally substituted with one or more lower alkyl, lower alkoxy, methylenedioxy, halo, haloalkyl, aminosulfonyl, aryl, or heteroaryl groups; aralkyl; heteroaryl optionally substituted with one or more lower alkyl, lower alkoxy, methylenedioxy, halo, haloalkyl, aminosulfonyl, aryl, or heteroaryl groups; heteroaryloxy optionally substituted with one or more lower alkyl, lower alkoxy, methylenedioxy, halo, haloalkyl, aminosulfonyl, aryl, or heteroaryl groups; alkoxy; alkylthio; arylthio; amido; amino; aminosulfonyl; sulfonamide; arylsulfonyl optionally substituted with one or more lower alkyl, lower alkoxy, methylenedioxy, halo, haloalkyl, aminosulfonyl, aryl, or heteroaryl groups; acyloxy; arylacyloxy optionally substituted with one or more lower alkyl, lower alkoxy, methylenedioxy, halo, haloalkyl, aminosulfonyl, aryl, or heteroaryl groups; diphenylphosphinyloxy optionally substituted with one or more lower alkyl, lower alkoxy, methylenedioxy, halo, haloalkyl, aminosulfonyl, aryl, or heteroaryl groups; heterocyclo optionally substituted with one or more lower alkyl, lower alkoxy, methylenedioxy, halo, haloalkyl, aminosulfonyl, aryl, heteroaryl, amino acid substituted sulfonyl, or amino acid derivative substituted sulfonyl groups and lower alkyl and aralkyl esters thereof; heterocycloalkoxy optionally substituted with one or more lower alkyl, lower alkoxy, methylenedioxy, halo, haloalkyl, aminosulfonyl, aryl, or heteroaryl groups; partially unsaturated heterocycloalkyl optionally substituted with one or more lower alkyl, lower alkoxy, methylenedioxy, halo, haloalkyl, aminosulfonyl, aryl, or heteroaryl groups; or partially unsaturated heterocycloalkyloxy optionally substituted with one or more lower alkyl, lower alkoxy, methylenedioxy, halo, haloalkyl, aminosulfonyl, aryl, or heteroaryl groups.

Useful amino acid residues include those derived from D and L alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, and histidine. Amino acid derivatives include the amide derivatives.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful alkylaryl and alkylheteroaryl groups include any of the above-mentioned $C_1$-18 alkyl groups substituted by any of the above-mentioned $C_6$-14 aryl groups or heteroaryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above. Also included are the sulfoxides and sulfones of such alkylthio groups.

Useful amido groups include carbonylamido (i.e., carbonyl bonded to an amino group) as well as any optionally substituted $C_{1-6}$ acyl (alkanoyl) attached to an amino nitrogen, e.g., acetamido, haloacetamido such as trifluoroacetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g., formyloxy, acetoxy, propionoyloxy, butanoyloxy, pentanoyloxy, hexanoyloxy and the like.

Useful arylacyloxy groups include any of the aryl groups mentioned above substituted on any of the acyloxy groups mentioned above, e.g., 2,6-dichlorobenzoyloxy, 2,6-difluorobenzoyloxy and 2,6-di-(trifluoromethyl)-benzoyloxy groups.

Useful amino groups include —$NH_2$, —$NHR_{11}$, and —$NR_{11}R_{12}$, wherein $R_{11}$ and $R_{12}$ are alkyl, aminoalkyl, optionally substituted aryl, optionally substituted arylalkyl, or cycloalkyl groups as defined above or where $R_{11}$ and $R_{12}$ form a $C_5$-$C_6$ heterocyclic ring such as piperidinyl, pyrrolidinyl, pyrazinyl, or morpholino optionally substituted by a heteroaryl or an acyl group on the nitrogen.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl, tetramoyl, or tetrahydroisoquinolinyl groups.

Certain of the compounds of Formula (LXXVIII) may exist as stereoisomers including optical isomers. The invention provides all stereoisomers and both the racemic mixtures of such stereoisomers as well as the individual enantiomers that may be separated according to methods that are well known to those of skill in the art.

In a preferred embodiment, the BCL-2 inhibitor is TW-37, which has the chemical name N-(4-((2-(tert-butyl)phenyl)sulfonyl)phenyl)-2,3,4-trihydroxy-5-(2-isopropylbenzyl) benzamide, with the chemical structure shown in Formula (LXXVIV):

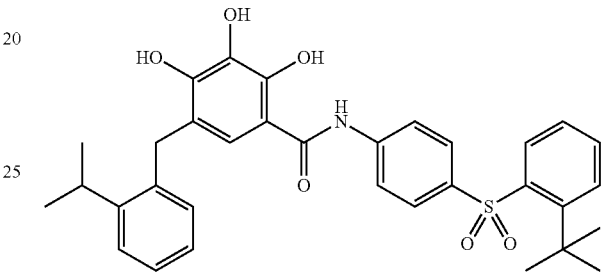

Formula (LXXVIV)

or a pharmaceutically acceptable salt thereof. The preparation of this compound is described in U.S. Pat. No. 8,557,812 and U.S. Patent Application Publication No. 2006/0084647 A1, the disclosures of which are incorporated by reference herein.

In an embodiment, the BCL-2 inhibitor is a compound of Formula (LXXX):

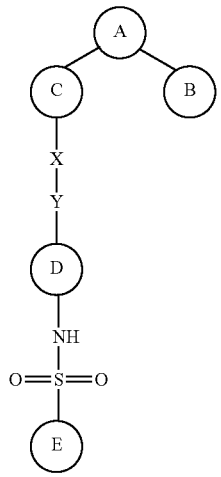

Formula (LXXX)

or a pharmaceutically acceptable salt, hydrate, or solvate thereof;

wherein A is null, optionally substituted phenyl, or an optionally substituted five or six-membered aromatic ring in which 1 to 4 carbon atoms individually are replaced by nitrogen, oxygen, or sulfur;

B, C, D, and E individually are optionally substituted phenyl or an optionally substituted five or six-membered aromatic ring in which 1 to 4 carbon atoms individually are replaced by nitrogen, oxygen, or sulfur;

X and Y, independently, are null, O, S, CO, SO$_2$, SO, PO$_3$H, NR', BR', PR', POR', alkylene, cycloalkylene, alkenylene, cycloalkenylene, alkynylene, or arylene; or X and Y can be taken together to form a 5-7 membered ring, or X and Y can be Z—(CH$_2$)$_{1-3}$-E, wherein Z and Z', independently, are O, S, NR', CO, SO, SO$_2$, PO$_3$H, PR', or POR'; and R' is H, alkyl, cycloalkyl, alkenyl, cycloalkenyl, alkynyl, aryl, heteroaryl, or heterocycloalkyl.

Examples of rings A, B, C, D, and E include, but are not limited to:

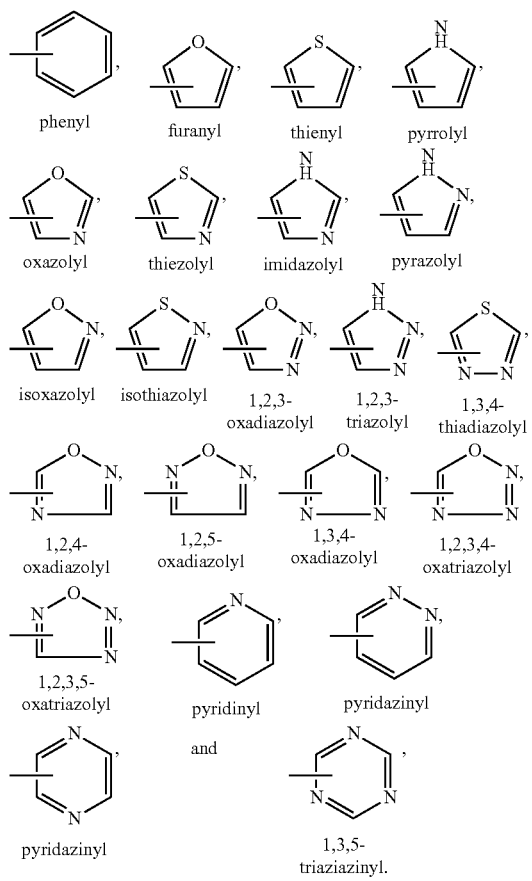

Specific non-limiting examples of ring B include:

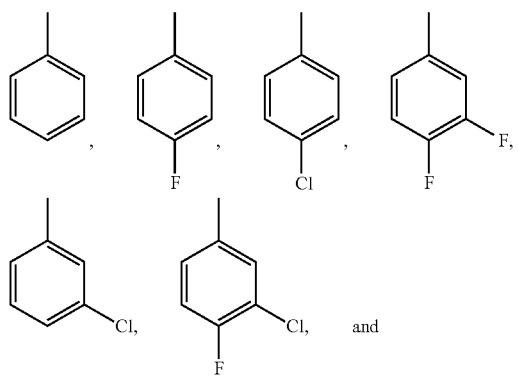

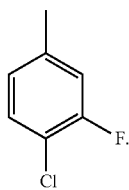

Ring A of the compound of structural Formula (LXXX) also is phenyl or a five- or six-membered aromatic ring in which one to four, and preferably one to three, of the carbon atoms, independently, are replaced by nitrogen, oxygen, or sulfur. In some preferred embodiments, ring A is selected form the group consisting of:

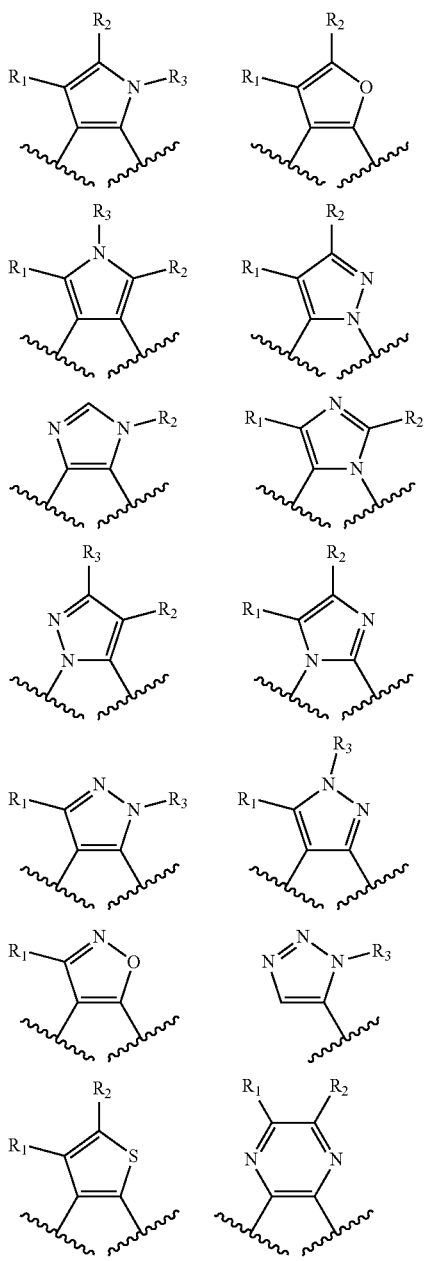

-continued

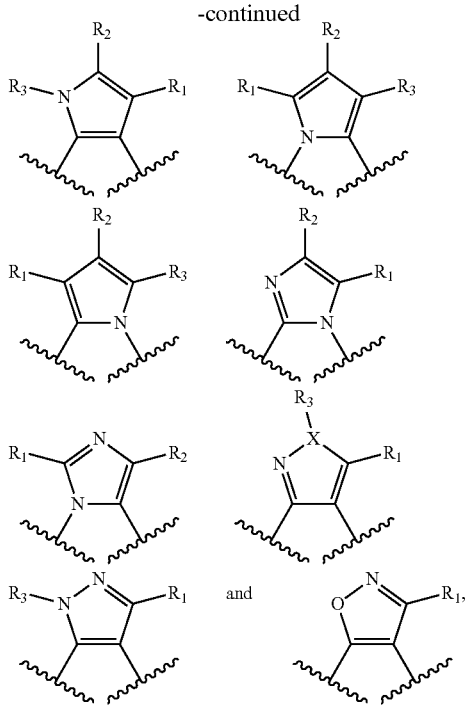

wherein $R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', —NR'R", COR', $CO_2R'$, OCOR', CONR'R", CONR'$SO_2$R", NR'COR", NR'CONR"R'", NR'C=SNR"R'", NR'$SO_2$R", $SO_2$R', and $SO_2$NR'R";

$R_3$ is selected from a group consisting of H, alkyl, cycloalkyl, alkenyl, cycloalkenyl, alkynyl, aryl, heteroaryl, heterocycloalkyl, OR', NR'R", $CO_2R'$, COR', CONR'R", CONR'$SO_2$R", $C_{1-3}$alkyleneCH(OH)$CH_2$OH, $SO_2$R', and $SO_2$NR'R";

R', R", and R'", independently, are H, alkyl, cycloalkyl, alkenyl, cycloalkenyl, alkynyl, aryl, $C_{1-3}$alkyleneheterocycloalkyl, or heterocycloalkyl;

R' and R", or R" and R'", can be taken together with the atom to which they are bound to form a 3 to 7 membered ring.

In some preferred embodiments, the A ring is

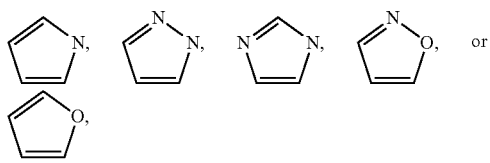

In other preferred embodiments, a non-aromatic nitrogen atom of the A ring is substituted with $C_{1-6}$alkyl, e.g., methyl, ethyl, n-propyl, isopropyl, or n-butyl; cycloalkyl, e.g., cyclopropyl; $(CH_2)_{1-3}N(CH_3)_2$, or —$(CH_2)_{1-3}$CH(OH)$CH_2$OH.

In another preferred embodiment, a non-aromatic nitrogen atom of the A ring and an adjacent carbon of the A ring are taken together to form a five or six membered ring.

In some preferred embodiments, the C ring is phenyl, optionally substituted with one or two substituents selected from halo and $C_{1-3}$alkyl. Specific embodiments include a phenyl ring substituted with one or two fluoro, bromo, chloro, or methyl.

In other preferred embodiments, the moiety —X—Y— is selected from the group consisting of —C=C—, —$CH_2CH_2$—, —NH$CH_2CH_2$NH—, —O$CH_2CH_2$—O—,

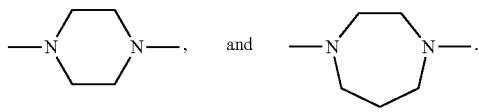

In yet another preferred embodiment, the D ring is phenyl, either unsubstituted or substituted. Specific embodiments include a phenyl ring having the structure:

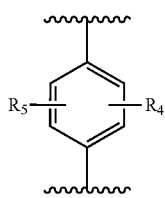

wherein $R_4$ and $R_5$, independently, are selected from a group consisting of H, CN, $NO_2$, halo, alkyl, cycloalkyl, alkenyl, cycloalkenyl, alkynyl, aryl, heteroaryl, heterocycloalkyl, OR', SR', —NR'R", $CO_2R'$, OCOR', CONR'R", CONR'$SO_2$R", NR'COR", NR'CONR"R'", NR'C=SNR"R'", —NR'$SO_2$R", $SO_2$R', and $SO_2$NR'R". All other rings and R groups are defined as above.

One preferred $R_4$ or $R_5$ group is halo, e.g., fluoro.

In still another preferred embodiment, the E ring is phenyl, preferably containing one to five, and more preferably one or two, substituents. Specific embodiments include a phenyl ring having the structure:

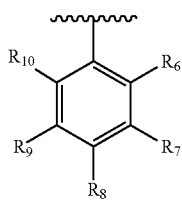

wherein $R_6$, $R_7$, $R_8$, $R_9$ and $R_{10}$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", CONR'$SO_2$R", NR'COR", NR'CONR"R'", —NR'C=SNR"R'", NR'$SO_2$R", $SO_2$R', and $SO_2$NR'R". All other rings and R groups are defined as above.

Additionally, salts, hydrates, and solvates of the compound of Formula (LXXX) also are included in the present invention. The present invention further includes all possible stereoisomers and geometric isomers of the compound of Formula (LXXX). The present invention includes both racemic compounds and optically active isomers. When a compound of Formula (LXXX) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compound of Formula (LXXX) are possible, the present invention is intended to include all tautomeric forms of the compounds.

In a preferred embodiment, the BCL-2 inhibitor is BM-1197, which has the chemical name (R)—S-(5-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-((4-(4-hydroxypiperidin-1-yl)-1-(phenylthio)butan-2-yl)amino)phenyl) trifluoro-14-oxidanecarbothioate, with the chemical structure shown in Formula (LXXXI):

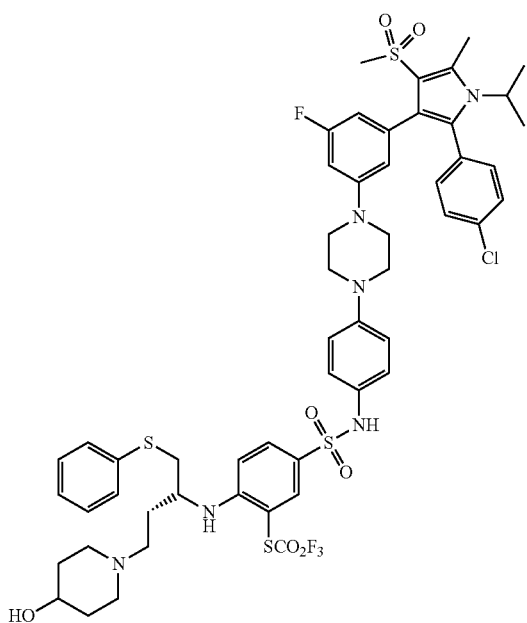

Formula (LXXXI)

or a pharmaceutically acceptable salt thereof. The preparation of this compound is described in U.S. Pat. No. 8,691,184 and U.S. Patent Application Publication No. 2012/0189539 A1, the disclosures of which are incorporated by reference herein.

In an embodiment, the BCL-2 inhibitor is a compound of Formula (LXXXII):

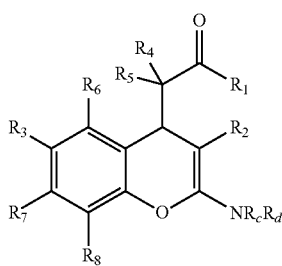

Formula (LXXXII)

wherein $R_1$ is $(C_1-C_6)$alkoxy or $NR_aR_b$;
$R_2$ is cyano, $(C_1-C_6)$alkoxycarbonyl or $C(O)NR_eR_f$;
Each of $R_3$, $R_6$, $R_7$ and $R_8$ is independently hydrogen, halo, cyano, $(C_1-C_6)$alkyl, cycloalkyl, aryl, heteroaryl, aryl$(C_1-C_6)$alkyl or $(C_1-C_6)$alkoxycarbonyl;

$R_c$ and $R_d$ are independently hydrogen, $(C_1-C_6)$alkyl, $(C_1-C_6)$alkanoyl or arylcarbonyl; or $R_c$ and $R_d$ taken together with the nitrogen to which they are attached form a pyrrolidino, piperidino, piperazino, or morpholino ring;
$R_e$ and $R_f$ are independently hydrogen or $(C_1-C_6)$alkyl; or $R_e$ and $R_f$ taken together with the nitrogen to which they are attached form a pyrrolidino, piperidino, piperazino, or morpholino ring;
$R_4$ and $R_5$ are each hydrogen; or $R_4$ is $(C_1-C_6)$alkyl and $R_5$ is cyano;
$R_a$ and $R_b$ are independently hydrogen or $(C_1-C_6)$alkyl; or $R_a$ and $R_b$ taken together with the nitrogen to which they are attached form a pyrrolidino, piperidino, piperazino, or morpholino ring;
wherein any aryl or heteroaryl of $R_3$, $R_6$, $R_7$ or $R_8$ is optionally substituted with one or more (e.g. 1, 2, 3, or 4) groups independently selected from halo, hydroxy, cyano, $CF_3$, $OCF_3$, $OCHF_2$, $(C_1-C_6)$alkyl, $(C_1-C_6)$alkoxy, $(C_1-C_6)$alkanoyl, aryl oxy, $NR_gR_h$, benzyloxy, $(C_1-C_6)$alkoxycarbonyl, and $(C_1-C_6)$alkanoyloxy; and
each $R_g$ and $R_h$ is independently hydrogen or $(C_1-C_6)$alkyl; or $R_g$ and $R_h$ taken together with the nitrogen to which they are attached form a pyrrolidino, piperidino, piperazino, or morpholino ring;
or a salt thereof.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; and aryl can be phenyl, indenyl, or naphthyl.

A specific value for $R_1$ is $(C_1-C_6)$alkoxy.
A specific value for $R_1$ is $NR_aR_b$.
A specific value for $R_1$ is ethoxy or isopropoxy.
A specific value for $R_1$ is ethoxy.
A specific value for $R_1$ is piperidino.
A specific value for $R_1$ is morpholino.
A specific value for $R_1$ is piperazino.
A specific value for $R_1$ is diethylamino.
A specific value for $R_2$ is cyano.
A specific value for $R_2$ is $(C_1-C_6)$alkoxycarbonyl.
A specific value for $R_2$ is ethoxycarbonyl, isopropoxycarbonyl, or cyano.
A specific value for $R_2$ is ethoxycarbonyl.
A specific value for $R_3$ is hydrogen.
A specific value for $R_3$ is halo.
A specific value for $R_3$ is bromo.
A specific value for $R_3$ is $(C_1-C_6)$alkyl.
A specific value for $R_3$ is aryl, which is optionally substituted with one or more (e.g. 1, 2, 3, or 4) groups independently selected from halo, hydroxy, cyano, $CF_3$, $OCF_3$, $OCHF_2$, $(C_1-C_6)$alkyl, $(C_1-C_6)$alkoxy, $(C_1-C_6)$alkanoyl, aryloxy, $NR_gR_h$, benzyloxy, $(C_1-C_6)$alkoxycarbonyl, and $(C_1-C_6)$alkanoyloxy.
A specific value for $R_3$ is aryl, which is optionally substituted with one or more (e.g. 1, 2, 3, or 4) groups independently selected from halo, hydroxy, $(C_1-C_6)$alkyl, $(C_1-C_6)$alkoxy, $(C_1-C_6)$alkoxycarbonyl, and $(C_1-C_6)$alkanoyloxy.
A specific value for $R_3$ is phenyl, which is optionally substituted with one or more (e.g. 1, 2, 3, or 4) $(C_1-C_6)$alkyl groups.

A specific value for $R_3$ is hydrogen, bromo, propyl, phenyl, 4-tert-butylphenyl, 3-methoxy,5-hydroxyphenyl, 3,5-dihydroxyphenyl, or 3,5-dimethoxyphenyl.

A specific value for $R_3$ is hydrogen, bromo, propyl, phenyl, or 4-tert-butylphenyl. A specific value for $R_4$ and $R_5$ are each hydrogen.

A specific value for $R_4$ is $(C_1\text{-}C_6)$alkyl and for $R_5$ is cyano.

In an embodiment, the BCL-2 inhibitor is a compound of Formula (LXXXIII):

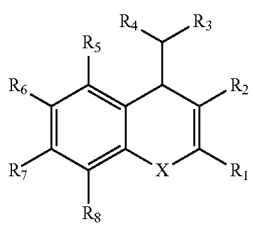

Formula (LXXXIII)

wherein:
X is selected from the group consisting of $CH_2$; $CHOCH_3$; NH; $NCH_3$; O; and S;
$R_1$ is selected from the group consisting of OH; $NH_2$; CHO; $COCH_3$; COOH; $N(C_{1-3}$ alkyl$)_2$; $NH(C_{1-3}$ alkyl); $OCOCH_3$; $OCOCH_2CH_3$; $NHCOCH_3$; $NHNHCOCH_3$; $NHNHCONH_2$; $N(C_{1-3}$alkyl$)_2$; $NH(C_{1-3}$ alkyl); and five- and six-member heterocyclic rings, preferably a heterocyclic ring selected from the group consisting piperidinyl, piperazinyl, morpholino, pyrimidyl, pyrrolyl, pyrrolidino and imidazyl;
$R_2$ is selected from the group consisting of $C_{1-3}$ alkyl; $C_{1-3}$alkoxy; OH; $NH_2$; CHO; $COCH_3$; $OCOCH_3$; $OCOCH_2CH_3$; COOH; $COOCH_3$; $COOCH_2CH_3$; $COOCH_2CH_3$;
$R_3$ is selected from the group consisting of $C_{1-3}$ alkyl; $C_{1-3}$ alkoxy; CN; $CH_2CN$; $CH_2NO_2$; CHO; $COCH_3$; COOH; $OCOCH_3$; $OCOCH_2CH_3$; $NHCOCH_3$; $NHNHCOCH_3$; $NHNHCONH_2$; $CH=CH_2$; $CH_2CH=CH_2$; $CH_2CHO$; and five- and six-member heterocyclic rings, preferably a heterocyclic ring selected from the group consisting piperidinyl, piperazinyl, morpholino, pyrimidyl, pyrrolyl, pyrrolidino and imidazyl;
$R_4$ is selected from the group consisting of $C_{1-3}$ alkyl; $C_{1-3}$ alkoxy; CN; $CH_2CN$; $CH_2NO_2$; CHO; $COCH_3$; $COCH_3$; COOH; $COOCH_3$; $COOCH_2CH_3$; $COOCH_2CH_3$; $OCOCH_3$; $OCOCH_2CH_3$;
$R_5$ is selected from the group consisting of hydrogen $CH_3$; $OCH_3$; OH: $NH_2$; Br; Cl; and F; and
$R_6$, $R_7$ and $R_8$ are selected from the group consisting of hydrogen, $CH_3$; $CH_2CH_3$; $CF_3$; $NH_2$; OH; $OCH_3$; CN; $NO_2$; $C_1$; Br; F; COOH; and $COOCH_3$; provided, at least one member of the group $R_6$, $R_7$ or $R_8$ must be $C_1$, Br or F when the remaining members of said group are hydrogen;
or a pharmaceutically acceptable salt thereof when the compound includes at least one $NH_2$ or COOH substituent.

Preferred for Formula (LXXXIII) are the following:
$R_1$: $NH_2$; $N(C_{1-3}$ alkyl$)_2$; and $NH(C_{1-3}$)alkyl; piperidinyl; piperazinyl; morpholino; pyrimidyl; pyrrolyl; pyrrolidino; and imidazyl;

$R_2$: $COCH_3$; $OCOCH_3$; $OCOCH_2CH_3$; COOH; $COOCH_3$; $COOCH_2CH_3$; and $COOCH_2CH_2CH_3$;

$R_3$: CN; $CH_2CN$; $CH_2NO_2$; $CH=CH_2$; $CH_2CH=CH_2$; and $CH_2CHO$;

$R_4$: $COCH_3$; $OCOCH_3$; $OCOCH_2CH_3$; COOH; $COOCH_3$; $COOCH_2CH_3$; and $COOCH_2CH_2CH_3$;

$R_5$: hydrogen, Br; Cl; and F;

$R_6$, $R_7$ and $R_8$: $NH_2$; OH; $OCH_3$; CN; $NO_2$; $C_1$; Br and F. When $R_6$, $R_7$ or $R_8$ are Br, Cl or $OCH_3$, the preferred positions of the substitution are $R_6$ and $R_8$.

In a preferred embodiment, the BCL-2 inhibitor is HA 14-1, which has the chemical name ethyl 2-amino-6-bromo-4-(1-cyano-2-ethoxy-2-oxoethyl)-4H-chromene-3-carboxylate, with the chemical structure shown in Formula (LXXXIV):

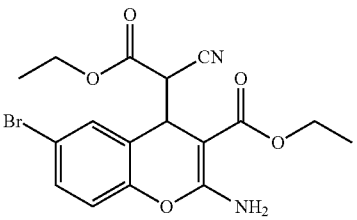

Formula (LXXXIV)

or a pharmaceutically acceptable salt thereof. The preparation of this compound is described in U.S. Pat. Nos. 8,394,794 and 6,492,389 and U.S. Patent Application Publication No. 2010/0197686 A1, the disclosures of which are incorporated by reference herein.

In a preferred embodiment, the BCL-2 inhibitor is a compound having the chemical name ethyl 2-amino-6-bromo-4-(2-ethoxy-2-oxoethyl)-4H-chromene-3-carboxylate, with the chemical structure shown in Formula (LXXXV):

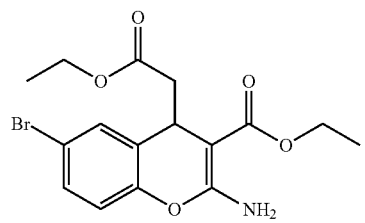

Formula (LXXXV)

or a pharmaceutically acceptable salt thereof. The preparation of this compound is described in U.S. Pat. No. 8,394,794 and U.S. Patent Application Publication No. 2010/0197686 A1, the disclosures of which are incorporated by reference herein.

In an embodiment, the BCL-2 inhibitor is a compound of Formula (LXXXVI):

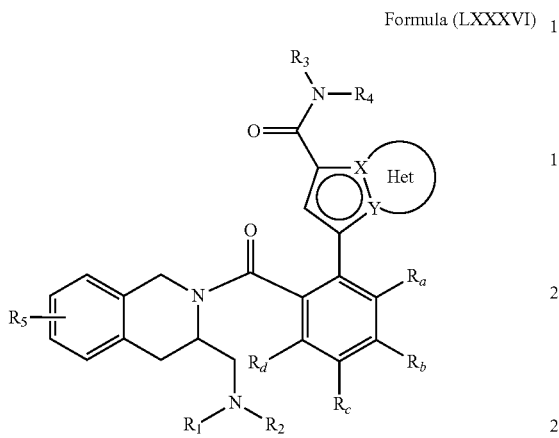

Formula (LXXXVI)

or a pharmaceutically acceptable salt thereof;
wherein,
X and Y represent a carbon atom or a nitrogen atom, wherein X and Y cannot simultaneously represent the same atom;
Het represents a 5, 6, or 7 membered ring, aromatic or not, and may contain, in addition to the nitrogen represented by X or Y, 1 to 3 heteroatoms selected from oxygen, sulfur and nitrogen, wherein the nitrogen may be substituted by a group R represented by a hydrogen atom, a linear or branched alkyl group ($C_1$-$C_6$),
$R_1$ and $R_2$ represent independently from each other hydrogen or ($C_1$-$C_6$) alkyl, or $R_1$ and $R_2$ together with the nitrogen atom which carries them, a heterocycloalkyl consisting of 4 to 7 members and may contain, in addition to the nitrogen atom, another heteroatom selected from oxygen, sulfur and NR, wherein R has the same definition as above;
$R_3$ represents a linear or branched ($C_1$-$C_6$) alkyl, aryl or heteroaryl;
$R_4$ represents an aryl, cycloalkyl or ($C_1$-$C_6$) alkyl;
$R_5$ represents a hydrogen or halogen atom;
$R_a$, $R_b$, $R_c$ and $R_d$ are independently of each other a hydrogen atom, a halogen atom, a linear or branched ($C_1$-$C_6$) alkyl group, a linear or branched ($C_1$-$C_6$) alkoxy group, a hydroxy group, a linear or branched ($C_1$-$C_6$) polyhaloalkyl group, or trifluoromethoxy group, or the substituents of one of the pairs ($R_a$, $R_b$), ($R_b$, $R_c$) or ($R_c$, $R_d$) form together with the carbon atoms which carry them, a ring composed of 5 to 7 members, which may contain from one to three heteroatoms selected from oxygen, sulfur and nitrogen, wherein the nitrogen may be substituted by an R group representing a hydrogen atom, a linear or branched ($C_1$-$C_6$) alkyl, wherein one or more carbon atoms of the ring may be deuterated;
wherein "aryl" means a phenyl, naphthyl, indenyl or biphenyl; "heteroaryl" means any mono or bi-cyclic group consisting of 5 to 10 members having at least one aromatic moiety and containing from 1 to 3 heteroatoms selected from oxygen, sulfur or nitrogen; "heterocycloalkyl" refers to any non-aromatic group-containing mono or bicyclic 4-10 membered ring which may contain 1 to 3 heteroatoms selected from oxygen, nitrogen or sulfur;
wherein alkyl, heteroaryl, aryl and heterocycloalkyl as defined may be substituted by 1 to 3 groups selected from linear or branched ($C_1$-$C_6$) alkyl groups, spiro ($C_3$-$C_6$), alkoxy, hydroxy, nitro, cyan, —COOR', NR'R", ($C_1$-$C_6$) polyhaloalkyl, trifluoromethoxy, or halogen, provided that R' and R" represent, independently of each other, a hydrogen atom or a linear or branched ($C_1$-$C_6$) alkyl, their enantiomers and diastereoisomers, and their acid addition or base to a pharmaceutically acceptable salt thereof.

The preparation of compounds of the form of Formula (LXXXVI) are described in International Patent Application Publication No. WO 2013/110890 A1.

In a preferred embodiment, the BCL-2 inhibitor is BXI-61 (NSC-354961), which has the chemical name (E)-3-((9-amino-7-ethoxyacridin-3-yl)diazenyl)pyridine-2,6-diamine, with the chemical structure shown in Formula (LXXXVII):

Formula (LXXXVII)

or a pharmaceutically acceptable salt thereof.

In a preferred embodiment, the BCL-2 inhibitor is BXI-72 (NSC-334072), which has the chemical name 2'-(4-ethoxyphenyl)-5-(4-methylpiperazin-1-yl)-1H,1'H-2,5'-bibenzo[d]imidazole, with the chemical structure shown in Formula (LXXXVIII):

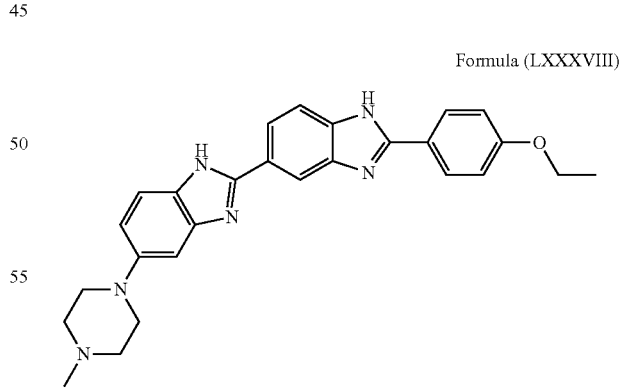

Formula (LXXXVIII)

or a pharmaceutically acceptable salt thereof.

Pharmaceutical Compositions

In a preferred embodiment, the invention provides a composition comprising (1) a BCL-2 inhibitor or a pharmaceutically acceptable salt, solvate, hydrate, cocrystal, or prodrug thereof; and (2) a BTK inhibitor having the structure:

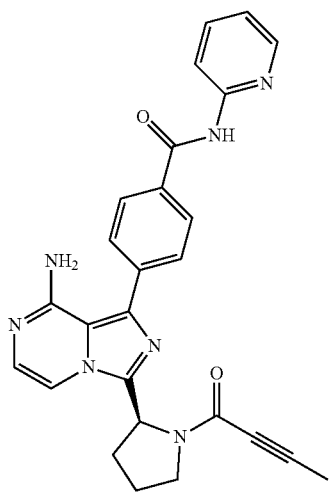 [SMILES: CC#CC(=O)N1CCC[C@H]1c1nc(-c2ccc(C(=O)Nc3ccccn3)cc2)c2c(N)nccn12]

or a pharmaceutically-acceptable salt, cocrystal, hydrate, solvate, or prodrug thereof. This composition is typically a pharmaceutical composition. Also provided is a kit comprising this same BCL-2 inhibitor or a pharmaceutically acceptable salt, solvate, hydrate, cocrystal, or prodrug thereof and this same BTK inhibitor or a pharmaceutically-acceptable salt, cocrystal, hydrate, solvate, or prodrug thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor having the structure:

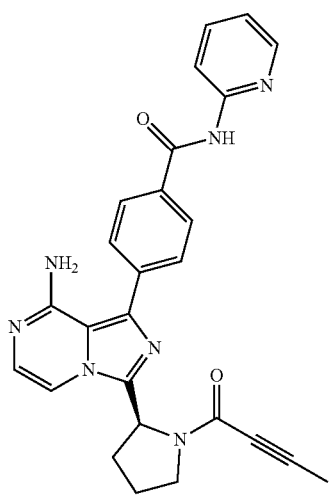 [SMILES: CC#CC(=O)N1CCC[C@H]1c1nc(-c2ccc(C(=O)Nc3ccccn3)cc2)c2c(N)nccn12]

or a pharmaceutically-acceptable salt, cocrystal, hydrate, solvate, or prodrug thereof; and (3) a PI3K inhibitor or a pharmaceutically acceptable salt, solvate, hydrate, cocrystal, or prodrug thereof. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof and this same PI3K inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor having the structure:

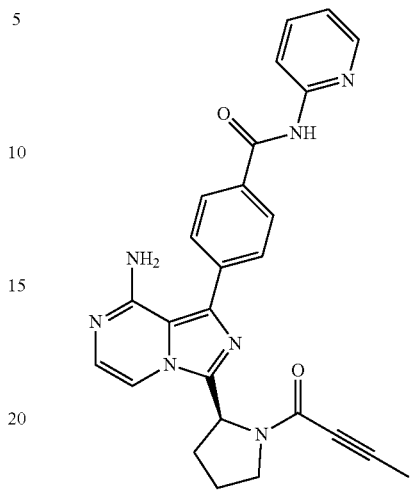

or a pharmaceutically-acceptable salt, cocrystal, hydrate, solvate, or prodrug thereof; and (3) a PI3K-δ inhibitor or a pharmaceutically acceptable salt, solvate, hydrate, cocrystal, or prodrug thereof. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof and this same PI3K-δ inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof (2) a BTK inhibitor having the structure:

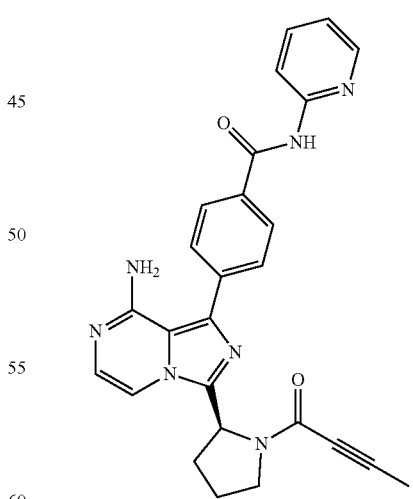

or a pharmaceutically-acceptable salt, cocrystal, hydrate, solvate, or prodrug thereof and (3) an anti-coagulant or antiplatelet active pharmaceutical ingredient. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof and this same anti-coagulant or antiplatelet active pharmaceutical ingredient.

The invention provides a combination comprising two or more ingredients selected from a BTK inhibitor, a BCL-2 inhibitor, a PI3K inhibitor, and a JAK-2 inhibitor.

The invention provides a composition comprising two or more ingredients selected from a BTK inhibitor, a BCL-2 inhibitor, a PI3K inhibitor, and a JAK-2 inhibitor.

The invention provides a kit comprising two or more compositions and optionally a package insert or label providing directions for administering the compositions simultaneously, separately or sequentially wherein each composition comprises at least one of a BTK inhibitor, a BCL-2 inhibitor, a PI3K inhibitor or a JAK-2 inhibitor or a pharmaceutically acceptable salt, solvate, hydrate, cocrystal, or prodrug thereof and wherein the two or more compositions together comprise two or more ingredients selected from a BTK inhibitor, a BCL-2 inhibitor, a PI3K inhibitor and a JAK-2 inhibitor or a pharmaceutically acceptable salt, solvate, hydrate, cocrystal, or prodrug thereof.

Preferred compounds that are BTK inhibitors, BCL-2 inhibitors, PI3K inhibitors, and JAK-2 inhibitors for use in embodiments of the invention are described in detail herein. Some of these preferred compounds include Formula (XVIII), Formula (IX), Formula (LXVI) (venetoclax), Formula (XXX) (ruxolitinib), and Formula (LIV) (pacritinib).

In one embodiment, there is provided a combination, a composition and/or a kit as described herein comprising a BTK inhibitor and a BCL-2 inhibitor wherein the BTK inhibitor is a compound of formula (XVIII) or a pharmaceutically acceptable salt, solvate, hydrate, cocrystal, or prodrug thereof and the BCL-2 inhibitor is a compound of formula (LXVI) or a pharmaceutically acceptable salt, solvate, hydrate, cocrystal, or prodrug thereof. In an embodiment, the combination, composition and/or kit are for use in the treatment of cancer as described herein, for example for the treatment of leukemia, lymphoma and/or a solid tumor cancer.

In one embodiment, there is provided a combination, a composition and/or a kit as described herein comprising a BTK inhibitor, a BCL-2 inhibitor and a PI3K inhibitor wherein the BTK inhibitor is a compound of formula (XVIII) or a pharmaceutically acceptable salt, solvate, hydrate, cocrystal, or prodrug thereof, the BCL-2 inhibitor is a compound of formula (LXVI) or a pharmaceutically acceptable salt, solvate, hydrate, cocrystal, or prodrug thereof and the PI3K inhibitor is a compound of formula (IX) or a pharmaceutically acceptable salt, solvate, hydrate, cocrystal, or prodrug thereof. In an embodiment, the combination, composition and/or kit are for use in the treatment of cancer as described herein, for example for the treatment of leukemia, lymphoma and/or a solid tumor cancer.

In one embodiment, there is provided a combination, a composition and/or a kit as described herein comprising a BTK inhibitor, a BCL-2 inhibitor and a JAK-2 inhibitor wherein the BTK inhibitor is a compound of formula (XVIII) or a pharmaceutically acceptable salt, solvate, hydrate, cocrystal, or prodrug thereof, the BCL-2 inhibitor is a compound of formula (LXVI) or a pharmaceutically acceptable salt, solvate, hydrate, cocrystal, or prodrug thereof and the JAK-2 inhibitor is a compound of formula (XXX) or a pharmaceutically acceptable salt, solvate, hydrate, cocrystal, or prodrug thereof. In an embodiment, the combination, composition and/or kit are for use in the treatment of cancer as described herein, for example for the treatment of leukemia, lymphoma and/or a solid tumor cancer.

In one embodiment, there is provided a combination, a composition and/or a kit as described herein comprising a BTK inhibitor, a BCL-2 inhibitor and a JAK-2 inhibitor wherein the BTK inhibitor is a compound of formula (XVIII) or a pharmaceutically acceptable salt, solvate, hydrate, cocrystal, or prodrug thereof, the BCL-2 inhibitor is a compound of formula (LXVI) or a pharmaceutically acceptable salt, solvate, hydrate, cocrystal, or prodrug thereof and the JAK-2 inhibitor is a compound of formula (LIV) or a pharmaceutically acceptable salt, solvate, hydrate, cocrystal, or prodrug thereof. In an embodiment, the combination, composition and/or kit are for use in the treatment of cancer as described herein, for example for the treatment of leukemia, lymphoma and/or a solid tumor cancer.

In one embodiment, there is provided a combination, a composition and/or a kit as described herein comprising a BTK inhibitor and a PI3K inhibitor wherein the BTK inhibitor is a compound of formula (XVIII) or a pharmaceutically acceptable salt, solvate, hydrate, cocrystal, or prodrug thereof and the PI3K inhibitor is a compound of formula (IX) or a pharmaceutically acceptable salt, solvate, hydrate, cocrystal, or prodrug thereof. In an embodiment, the combination, composition and/or kit are for use in the treatment of cancer as described herein, for example for the treatment of leukemia, lymphoma and/or a solid tumor cancer.

In one embodiment, there is provided a combination, a composition and/or a kit as described herein comprising a BTK inhibitor and a JAK-2 inhibitor wherein the BTK inhibitor is a compound of formula (XVIII) or a pharmaceutically acceptable salt, solvate, hydrate, cocrystal, or prodrug thereof and the JAK-2 inhibitor is a compound of formula (XXX) or a pharmaceutically acceptable salt, solvate, hydrate, cocrystal, or prodrug thereof. In an embodiment, the combination, composition and/or kit are for use in the treatment of cancer as described herein, for example for the treatment of leukemia, lymphoma and/or a solid tumor cancer.

In one embodiment, there is provided a combination, a composition and/or a kit as described herein comprising a BTK inhibitor and a JAK-2 inhibitor wherein the BTK inhibitor is a compound of formula (XVIII) or a pharmaceutically acceptable salt, solvate, hydrate, cocrystal, or prodrug thereof and the JAK-2 inhibitor is a compound of formula (LIV) or a pharmaceutically acceptable salt, solvate, hydrate, cocrystal, or prodrug thereof. In an embodiment, the combination, composition and/or kit are for use in the treatment of cancer as described herein, for example for the treatment of leukemia, lymphoma and/or a solid tumor cancer.

The combinations, compositions and/or kits disclosed herein may be used in the treatment of cancer for example for the treatment of leukemia, lymphoma and/or a solid tumor cancer. The combinations, compositions and/or kits disclosed herein may be used, for example as a research tool, in discovery and/or development of pharmaceutical products for the treatment of any of several types of cancers such as leukemia, lymphoma and solid tumor cancers. In a preferred embodiment, the solid tumor cancer is selected from the group consisting of breast, lung, colorectal, thyroid, bone sarcoma and stomach cancers. In an embodiment, the leukemia is selected from the group consisting of acute myelogenous leukemia (AML), chronic myelogenous leukemia (CML), and acute lymphoblastic leukemia (ALL). In a preferred embodiment, the lymphoma is follicular lymphoma, mantle cell lymphoma, diffuse large B cell lymphoma (DLBCL), B cell chronic lymphocytic leukemia, or Burkitt's lymphoma.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor having the structure:

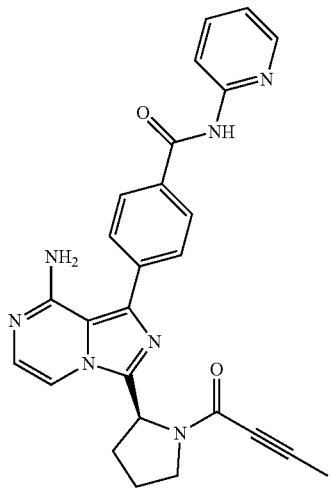 [SMILES: CC#CC(=O)N1CCC[C@H]1c1nc(-c2ccc(C(=O)Nc3ccccn3)cc2)c2c(N)nccn12]

or a pharmaceutically-acceptable salt, cocrystal, hydrate, solvate, or prodrug thereof; and (3) a PI3K-δ inhibitor or a pharmaceutically acceptable salt, solvate, hydrate, cocrystal, or prodrug thereof and (4) an anti-coagulant or antiplatelet active pharmaceutical ingredient. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof, this same PI3K-δ inhibitor or a pharmaceutically acceptable salt, solvate, hydrate, cocrystal, or prodrug thereof and this same anti-coagulant or antiplatelet active pharmaceutical ingredient.

In a preferred embodiment, the invention provides a composition comprising (1) a BCL-2 inhibitor or a pharmaceutically acceptable salt, solvate, hydrate, cocrystal, or prodrug thereof and (2) a BTK inhibitor selected from the group consisting of ibrutinib:

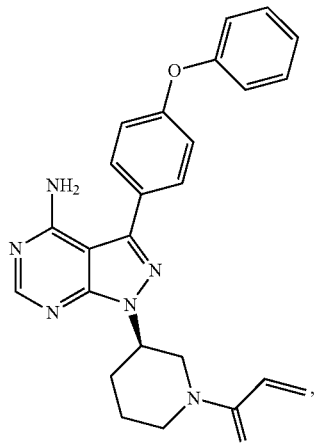

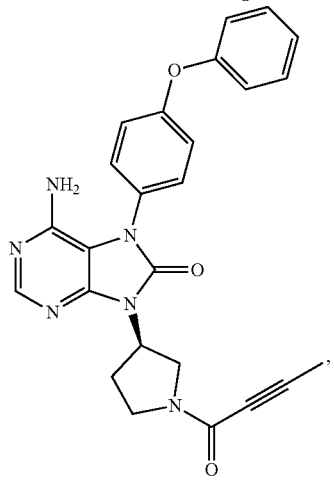

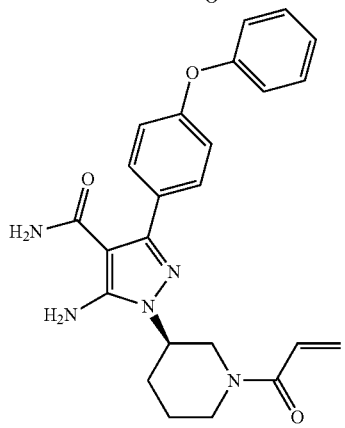

and pharmaceutically-acceptable salts, cocrystals, hydrates, solvates, or prodrugs thereof. This composition is typically a pharmaceutical composition. Also provided is a kit comprising this same BCL-2 inhibitor or a pharmaceutically acceptable salt, solvate, hydrate, cocrystal, or prodrug thereof and this same BTK inhibitor or a pharmaceutically-acceptable salt, cocrystal, hydrate, solvate, or prodrug thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor selected from the group consisting of ibrutinib:

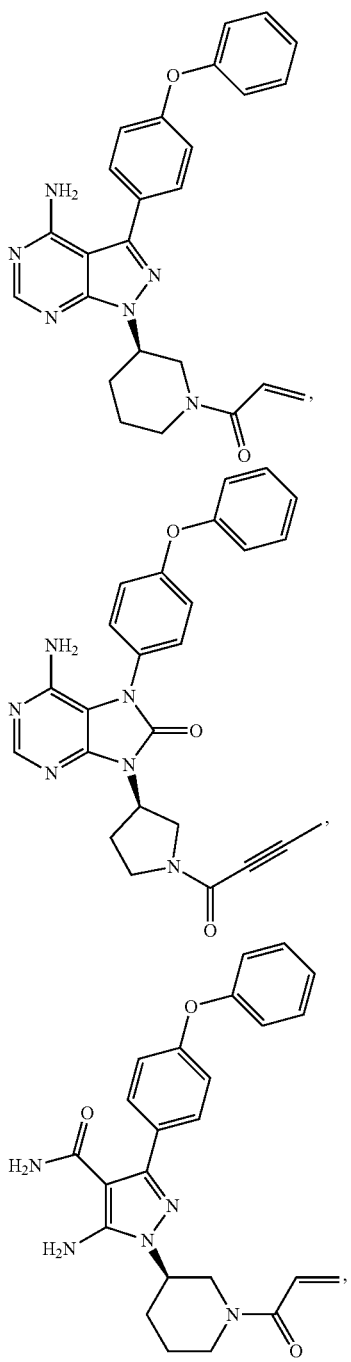

and pharmaceutically-acceptable salts, cocrystals, hydrates, solvates, or prodrugs thereof; and (3) a PI3K inhibitor or a pharmaceutically acceptable salt, solvate, hydrate, cocrystal, or prodrug thereof. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof and this same PI3K inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof (2) a BTK inhibitor selected from the group consisting of ibrutinib:

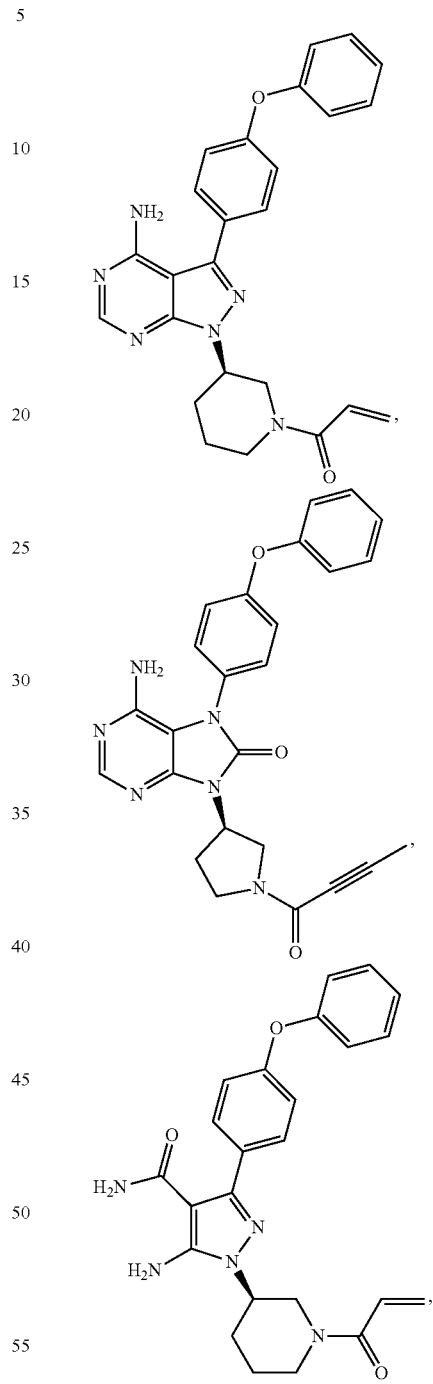

and pharmaceutically-acceptable salts, cocrystals, hydrates, solvates, or prodrugs thereof and (3) a PI3K-δ inhibitor or a pharmaceutically acceptable salt, solvate, hydrate, cocrystal, or prodrug thereof. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof and this same PI3K-δ inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof (2) a BTK inhibitor selected from the group consisting of ibrutinib:

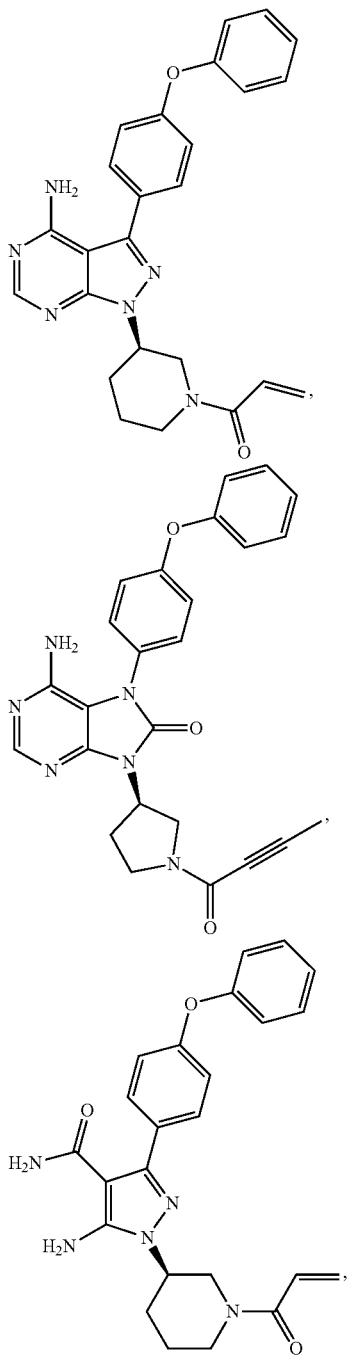

and pharmaceutically-acceptable salts, cocrystals, hydrates, solvates, or prodrugs thereof and (3) an anti-coagulant or antiplatelet active pharmaceutical ingredient. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof and this same anti-coagulant or antiplatelet active pharmaceutical ingredient.

In a preferred embodiment, the invention provides a composition comprising (1) a BCL-2 inhibitor or a pharmaceutically acceptable salt, solvate, hydrate, cocrystal, or prodrug thereof (2) a BTK inhibitor selected from the group consisting of ibrutinib:

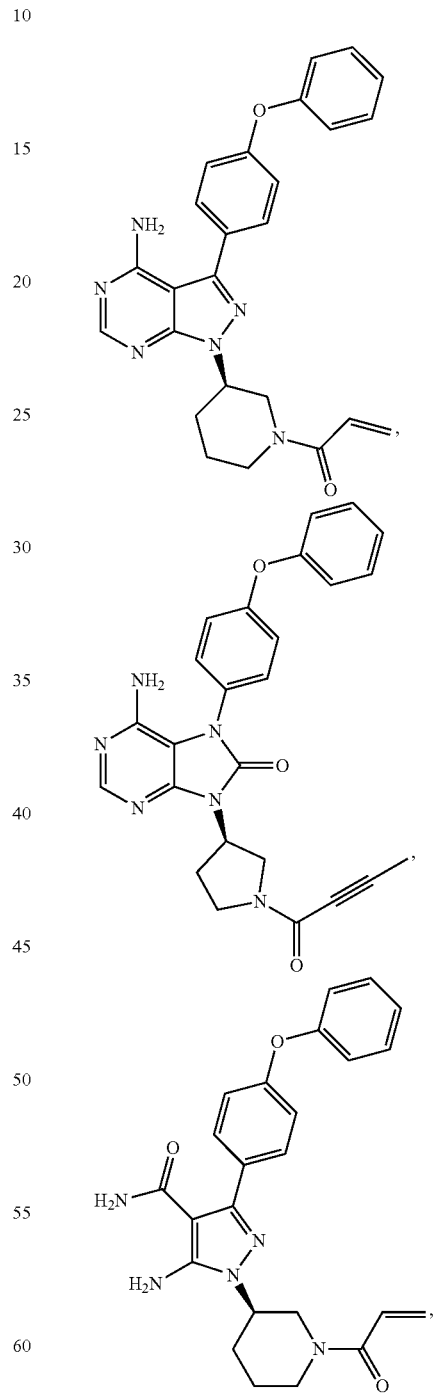

and pharmaceutically-acceptable salts, cocrystals, hydrates, solvates, or prodrugs thereof; and (3) a PI3K-δ inhibitor or a pharmaceutically acceptable salt, solvate, hydrate, cocrystal, or prodrug thereof; and (4) an anti-coagulant or antiplatelet active pharmaceutical ingredient. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof, this same PI3K-δ inhibitor or a pharmaceutically acceptable salt, solvate, hydrate, cocrystal, or prodrug thereof and this same anti-coagulant or antiplatelet active pharmaceutical ingredient.

In a preferred embodiment, the invention provides a composition comprising (1) a BCL-2 inhibitor having the structure:

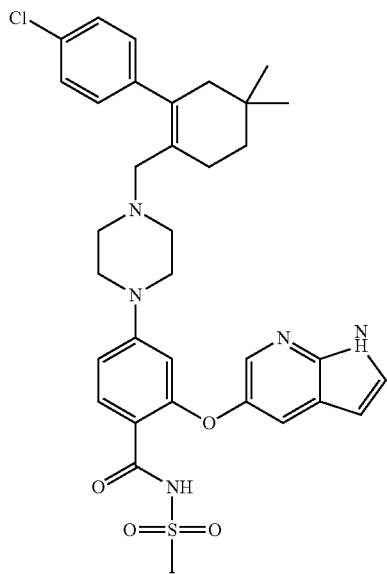

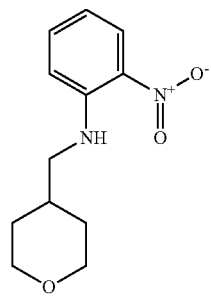

or a pharmaceutically-acceptable salt, cocrystal, hydrate, solvate, or prodrug thereof. This composition is typically a pharmaceutical composition. Also provided is a kit comprising this same BCL-2 inhibitor or a pharmaceutically acceptable salt, solvate, hydrate, cocrystal, or prodrug thereof.

In a preferred embodiment, the invention provides a composition comprising (1) a BCL-2 inhibitor having the structure:

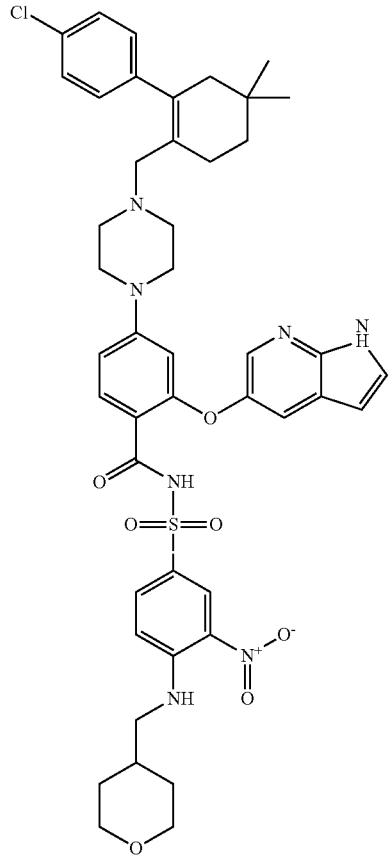 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

or a pharmaceutically-acceptable salt, cocrystal, hydrate, solvate, or prodrug thereof; and (2) a PI3K inhibitor or a pharmaceutically acceptable salt, solvate, hydrate, cocrystal, or prodrug thereof. This composition is typically a pharmaceutical composition. Also provided is a kit comprising this same BCL-2 inhibitor or a pharmaceutically acceptable salt, solvate, hydrate, cocrystal, or prodrug thereof and this same PI3K inhibitor or a pharmaceutically acceptable salt, solvate, hydrate, cocrystal, or prodrug thereof.

In a preferred embodiment, the invention provides a composition comprising (1) a BCL-2 inhibitor having the structure:

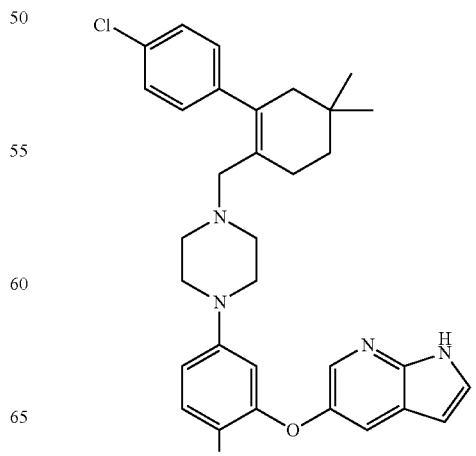

-continued

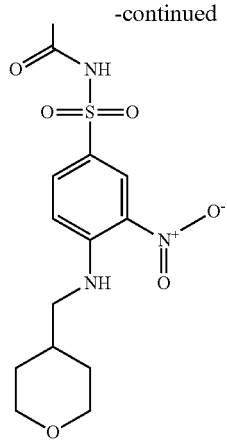

or a pharmaceutically-acceptable salt, cocrystal, hydrate, solvate, or prodrug thereof (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof and this same PI3K-δ inhibitor or a pharmaceutically acceptable salt, solvate, hydrate, cocrystal, or prodrug thereof.

In a preferred embodiment, the invention provides a composition comprising (1) a BCL-2 inhibitor having the structure:

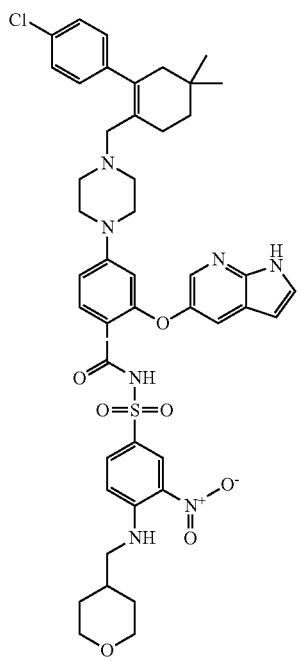 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

or a pharmaceutically-acceptable salt, cocrystal, hydrate, solvate, or prodrug thereof; (2) a BTK inhibitor or a pharmaceutically acceptable salt, solvate, hydrate, cocrystal, or prodrug thereof; and (3) an anti-coagulant or antiplatelet active pharmaceutical ingredient. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof and this same anti-coagulant or antiplatelet active pharmaceutical ingredient.

In a preferred embodiment, the invention provides a composition comprising (1) a BCL-2 inhibitor having the structure:

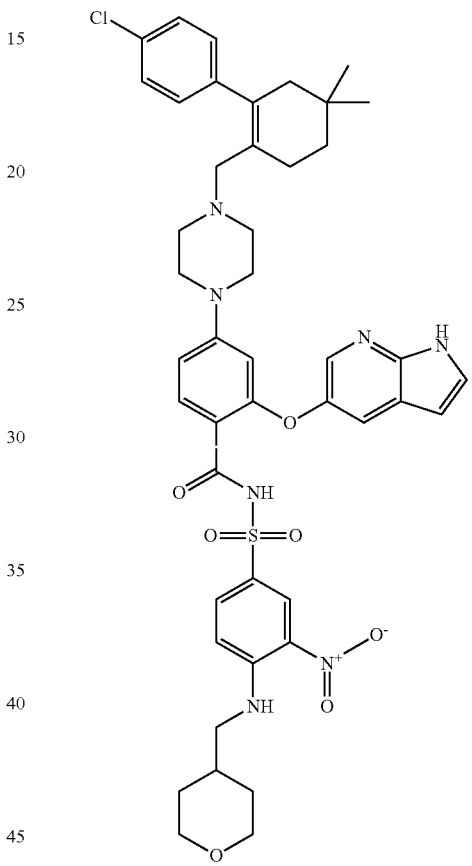

or a pharmaceutically-acceptable salt, cocrystal, hydrate, solvate, or prodrug thereof; (2) a BTK inhibitor or a pharmaceutically acceptable salt, solvate, hydrate, cocrystal, or prodrug thereof; and (3) a PI3K inhibitor or a pharmaceutically acceptable salt, solvate, hydrate, cocrystal, or prodrug thereof; and (4) an anti-coagulant or antiplatelet active pharmaceutical ingredient. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof, this same PI3K inhibitor or a pharmaceutically acceptable salt, solvate, hydrate, cocrystal, or prodrug thereof and this same anti-coagulant or antiplatelet active pharmaceutical ingredient.

In a preferred embodiment, the invention provides a composition comprising (1) a BCL-2 inhibitor having the structure:

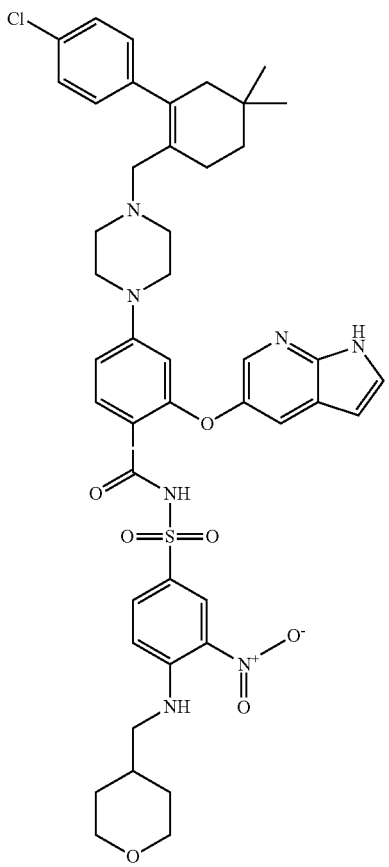 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

or a pharmaceutically-acceptable salt, cocrystal, hydrate, solvate, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof; and (4) an anti-coagulant or antiplatelet active pharmaceutical ingredient. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof, this same PI3K-δ inhibitor or a pharmaceutically acceptable salt, solvate, hydrate, cocrystal, or prodrug thereof and this same anti-coagulant or antiplatelet active pharmaceutical ingredient.

In a preferred embodiment, the invention provides a composition comprising (1) a BCL-2 inhibitor, which preferably is venetoclax, or a pharmaceutically-acceptable salt, cocrystal, hydrate, solvate, or prodrug thereof. This composition is typically a pharmaceutical composition. Also provided is a kit comprising (1) a BCL-2 inhibitor, which is preferably venetoclax, or a pharmaceutically acceptable salt, solvate, hydrate, cocrystal, or prodrug thereof.

In a preferred embodiment, the invention provides a composition comprising (1) a BCL-2 inhibitor, which preferrably is venetoclax, or a pharmaceutically-acceptable salt, cocrystal, hydrate, solvate, or prodrug thereof; and (3) a PI3K inhibitor or a pharmaceutically acceptable salt, solvate, hydrate, cocrystal, or prodrug thereof. This composition is typically a pharmaceutical composition. Also provided is a kit comprising (1) a BCL-2 inhibitor, which preferably is venetoclax, or a pharmaceutically-acceptable salt, cocrystal, hydrate, solvate, or prodrug thereof; and (3) a PI3K inhibitor or a pharmaceutically acceptable salt, solvate, hydrate, cocrystal, or prodrug thereof.

In a preferred embodiment, the invention provides a composition comprising (1) a BCL-2 inhibitor, which preferrably is venetoclax, or a pharmaceutically-acceptable salt, cocrystal, hydrate, solvate, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof. This composition is typically a pharmaceutical composition. Also provided is a kit comprising (1) a BCL-2 inhibitor, which preferably is venetoclax, or a pharmaceutically-acceptable salt, cocrystal, hydrate, solvate, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof.

In a preferred embodiment, the invention provides a composition comprising (1) a BCL-2 inhibitor, which preferably is venetoclax, or a pharmaceutically-acceptable salt, cocrystal, hydrate, solvate, or prodrug thereof; (2) a BTK inhibitor or a pharmaceutically acceptable salt, solvate, hydrate, cocrystal, or prodrug thereof; and (3) an anti-coagulant or antiplatelet active pharmaceutical ingredient. This composition is typically a pharmaceutical composition. Also provided is a kit comprising (1) a BCL-2 inhibitor, which preferably is venetoclax, or a pharmaceutically-acceptable salt, cocrystal, hydrate, solvate, or prodrug thereof; (2) a BTK inhibitor or a pharmaceutically acceptable salt, solvate, hydrate, cocrystal, or prodrug thereof; and (3) an anti-coagulant or antiplatelet active pharmaceutical ingredient.

In a preferred embodiment, the invention provides a composition comprising (1) a BCL-2 inhibitor, which preferably is venetoclax, or a pharmaceutically-acceptable salt, cocrystal, hydrate, solvate, or prodrug thereof; (2) a BTK inhibitor having the structure of Formula (XVIII) or a pharmaceutically-acceptable salt, cocrystal, hydrate, solvate, or prodrug thereof; and (3) a PI3K inhibitor or a pharmaceutically acceptable salt, solvate, hydrate, cocrystal, or prodrug thereof; and (4) an anti-coagulant or antiplatelet active pharmaceutical ingredient. This composition is typically a pharmaceutical composition. Also provided is a kit comprising (1) a BCL-2 inhibitor, which preferably is venetoclax, or a pharmaceutically-acceptable salt, cocrystal, hydrate, solvate, or prodrug thereof; (2) a BTK inhibitor having the structure of: or a pharmaceutically-acceptable salt, cocrystal, hydrate, solvate, or prodrug thereof; and (3) a PI3K inhibitor or a pharmaceutically acceptable salt, solvate, hydrate, cocrystal, or prodrug thereof; and (4) an anti-coagulant or antiplatelet active pharmaceutical ingredients.

In a preferred embodiment, the invention provides a composition comprising (1) a BCL-2 inhibitor, which preferably is venetoclax, or a pharmaceutically-acceptable salt, cocrystal, hydrate, solvate, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof; and (4) an anti-coagulant or antiplatelet active pharmaceutical ingredient. This composition is typically a pharmaceutical composition. Also provided is a kit comprising (1) a BCL-2 inhibitor, which preferably is venetoclax, or a pharmaceutically-acceptable salt, cocrystal, hydrate, solvate, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof; and (4) an anti-coagulant or antiplatelet active pharmaceutical ingredient.

In a preferred embodiment, the invention provides a composition comprising (1) a BCL-2 inhibitor or a pharmaceutically acceptable salt, solvate, hydrate, cocrystal, or prodrug thereof (2) a BTK inhibitor or a pharmaceutically acceptable salt, solvate, hydrate, cocrystal, or prodrug thereof and (3) a PI3K-δ inhibitor selected from the group consisting of:

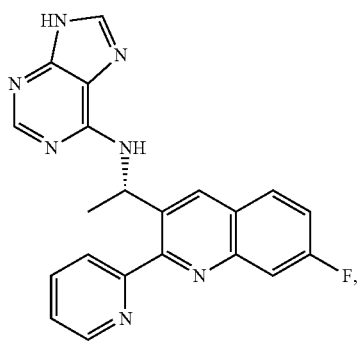

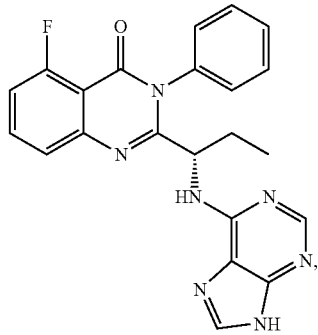 [SMILES: CC[C@H](Nc1ncnc2[nH]cnc12)c1nc2cccc(F)c2c(=O)n1-c1ccccc1]

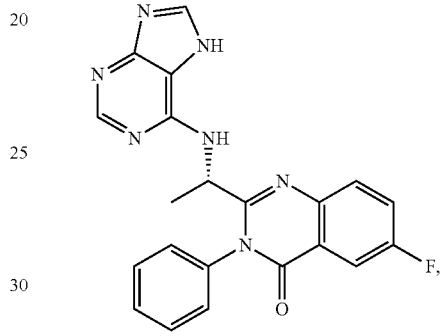

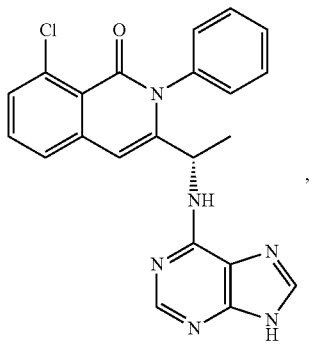

and pharmaceutically acceptable salts, solvates, hydrates, cocrystals, or prodrugs thereof. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof and this same PI3K-δ inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a PI3K inhibitor selected from the group consisting of:

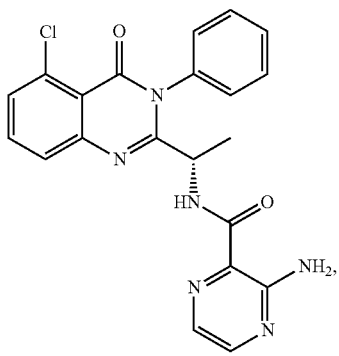

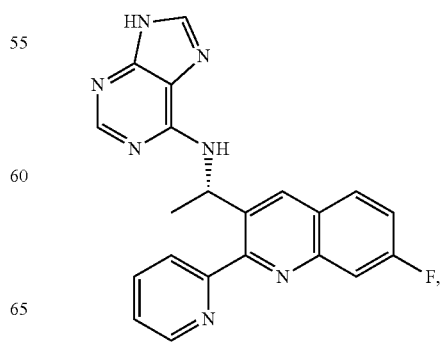

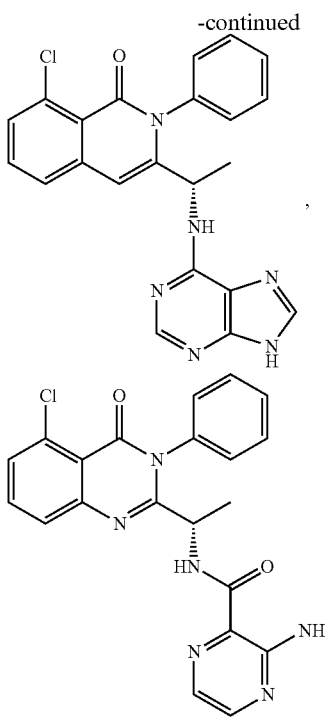

idelalisib:

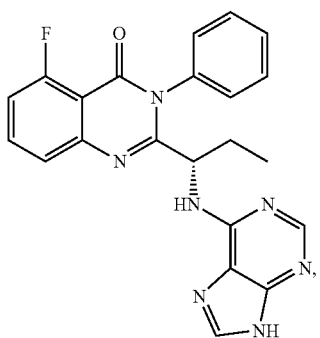

acalisib:

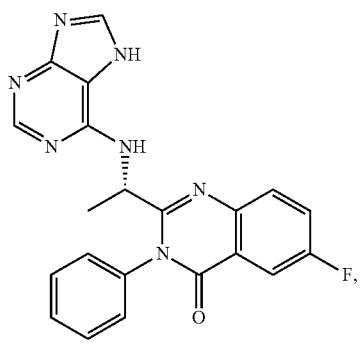 [SMILES: C[C@H](Nc1ncnc2nc[nH]c12)c1nc2ccc(F)cc2c(=O)n1-c1ccccc1]

and pharmaceutically acceptable salts, solvates, hydrates, cocrystals, or prodrugs thereof; and (4) an anti-coagulant or antiplatelet active pharmaceutical ingredient. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof, this same PI3K-δ inhibitor or a pharmaceutically acceptable salt, solvate, hydrate, cocrystal, or prodrug thereof and this same anti-coagulant or antiplatelet active pharmaceutical ingredient.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-δ inhibitor selected from the group consisting of:

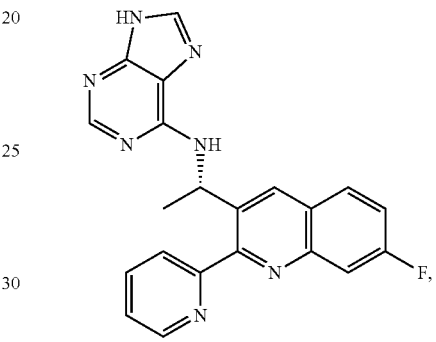

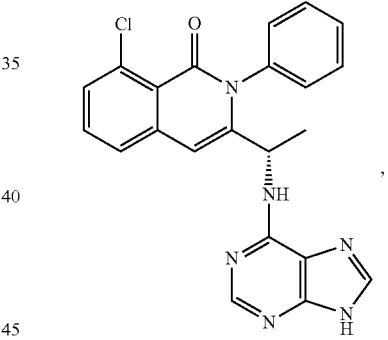

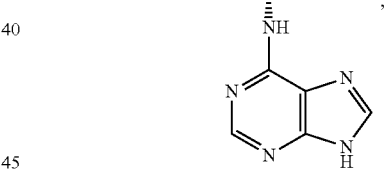

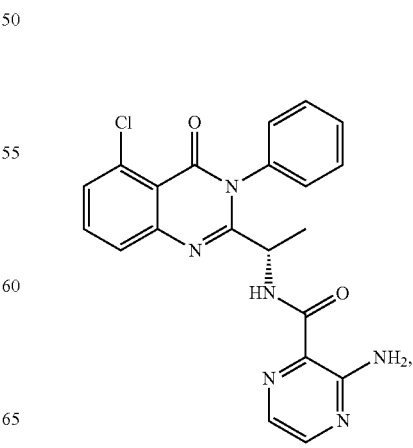

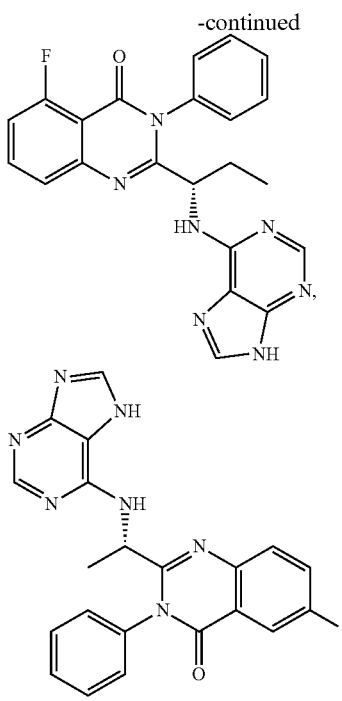

and pharmaceutically acceptable salts, solvates, hydrates, cocrystals, or prodrugs thereof; and (4) an anti-coagulant or antiplatelet active pharmaceutical ingredient. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof, this same PI3K-δ inhibitor or a pharmaceutically acceptable salt, solvate, hydrate, cocrystal, or prodrug thereof and this same anti-coagulant or antiplatelet active pharmaceutical ingredient.

In an embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof; and (4) an anti-coagulant or antiplatelet active pharmaceutical ingredient, wherein the anti-coagulant or the anti-platelet active pharmaceutical ingredient is a compound selected from the group consisting of acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, and combinations thereof. This composition is typically a pharmaceutical composition. Also provided is a kit comprising this same BCL-2 inhibitor or a pharmaceutically acceptable salt, solvate, hydrate, cocrystal, or prodrug thereof, this same BTK inhibitor or a pharmaceutically-acceptable salt, cocrystal, hydrate, solvate, or prodrug thereof, this same PI3K-δ inhibitor or a pharmaceutically acceptable salt, solvate, hydrate, cocrystal, or prodrug thereof and this same anti-coagulant or antiplatelet active pharmaceutical ingredient.

In a preferred embodiment, the invention provides a composition comprising (1) a BCL-2 inhibitor or a pharmaceutically acceptable salt, solvate, hydrate, cocrystal, or prodrug thereof; and (2) a BTK inhibitor or a pharmaceutically acceptable salt, solvate, hydrate, cocrystal, or prodrug thereof; and (4) a JAK-2 inhibitor or a pharmaceutically acceptable salt, solvate, hydrate, cocrystal, or prodrug thereof. This composition is typically a pharmaceutical composition. Also provided is a kit comprising (1) a BCL-2 inhibitor or a pharmaceutically acceptable salt, solvate, hydrate, cocrystal, or prodrug thereof; and (2) a BTK inhibitor or a pharmaceutically acceptable salt, solvate, hydrate, cocrystal, or prodrug thereof; and (4) a JAK-2 inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof (3) a PI3K inhibitor or a pharmaceutically acceptable salt, solvate, hydrate, cocrystal, or prodrug thereof; and (4) a JAK-2 inhibitor or a pharmaceutically acceptable salt, solvate, hydrate, cocrystal, or prodrug thereof. This composition is typically a pharmaceutical composition. Also provided is a kit comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) a PI3K inhibitor or a pharmaceutically acceptable salt, solvate, hydrate, cocrystal, or prodrug thereof; and (4) a JAK-2 inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof (2) a BTK inhibitor or a pharmaceutically acceptable salt, solvate, hydrate, cocrystal, or prodrug thereof; (3) a PI3K-δ inhibitor or a pharmaceutically acceptable salt, solvate, hydrate, cocrystal, or prodrug thereof; and (4) a JAK-2 inhibitor or a pharmaceutically acceptable salt, solvate, hydrate, cocrystal, or prodrug thereof. This composition is typically a pharmaceutical composition. Also provided is a kit comprising (1) a BCL-2 inhibitor or a pharmaceutically acceptable salt, solvate, hydrate, cocrystal, or prodrug thereof (2) a BTK inhibitor or a pharmaceutically acceptable salt, solvate, hydrate, cocrystal, or prodrug thereof; (3) a PI3K-δ inhibitor or a pharmaceutically acceptable salt, solvate, hydrate, cocrystal, or prodrug thereof; and (4) a JAK-2 inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) an anti-coagulant or antiplatelet active pharmaceutical ingredient; and (4) a JAK-2 inhibitor or a pharmaceutically acceptable salt, solvate, hydrate, cocrystal, or prodrug thereof. This composition is typically a pharmaceutical composition. Also provided is a kit comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) an anti-coagulant or antiplatelet active pharmaceutical ingredient; and (4) a JAK-2 inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K inhibitor or a pharmaceutically acceptable salt, solvate, hydrate, cocrystal, or prodrug thereof; (4) an anti-coagulant or antiplatelet active pharmaceutical ingredient; and (5) a JAK-2 inhibitor or a pharmaceutically acceptable salt, solvate, hydrate, cocrystal, or prodrug thereof. This composition is typically a pharmaceutical composition. Also provided is a kit comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K inhibitor or a pharmaceutically acceptable salt, solvate, hydrate, cocrystal, or prodrug thereof; (4) an anti-coagulant or antiplatelet active pharmaceutical ingredient; and (5) a JAK-2 inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof; and (4) an anti-coagulant or antiplatelet active pharmaceutical ingredient; and (5) a JAK-2 inhibitor or a pharmaceutically acceptable salt, solvate, hydrate, cocrystal, or prodrug thereof. This composition is typically a pharmaceutical composition. Also provided is a kit comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; and (3) a PI3K-δ inhibitor or a pharmaceutically acceptable salt, solvate, hydrate, cocrystal, or prodrug thereof; and (4) an anti-coagulant or antiplatelet active pharmaceutical ingredient; and (5) a JAK-2 inhibitor or a pharmaceutically acceptable salt, solvate, hydrate, cocrystal, or prodrug thereof.

In a preferred embodiment, the invention provides a composition comprising (1) a BCL-2 inhibitor or a pharmaceutically acceptable salt, solvate, hydrate, cocrystal, or prodrug thereof; and (2) a BTK inhibitor or a pharmaceutically acceptable salt, solvate, hydrate, cocrystal, or prodrug thereof; and (4) a JAK-2 inhibitor, which is selected from the group consisting of ruxolitinib:

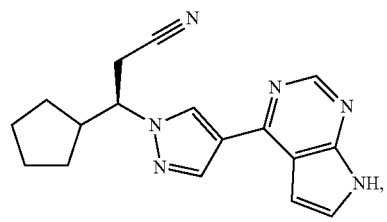 [SMILES: N#CC[C@H](C1CCCC1)n1cc(-c2ncnc3[nH]ccc23)cn1]

pacritinib:

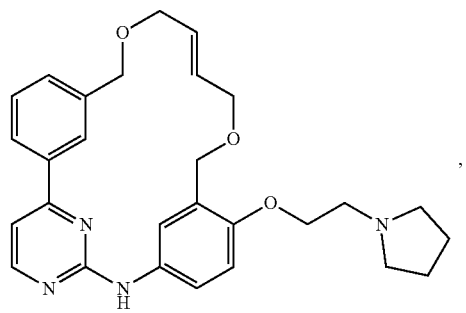 [SMILES: C1=C/COCc2cc(ccc2OCCN2CCCC2)Nc2nccc(n2)-c2cccc(c2)COC/1]

and pharmaceutically-acceptable salts, cocrystals, hydrates, solvates, or prodrugs thereof. This composition is typically a pharmaceutical composition. Also provided is a kit comprising (1) this same BCL-2 inhibitor or a pharmaceutically acceptable salt, solvate, hydrate, cocrystal, or prodrug thereof; (2) this same BTK inhibitor or a pharmaceutically acceptable salt, solvate, hydrate, cocrystal, or prodrug thereof; and (4) this same JAK-2 inhibitor and pharmaceutically-acceptable salts, cocrystals, hydrates, solvates, or prodrugs thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof (3) a PI3K inhibitor or a pharmaceutically acceptable salt, solvate, hydrate, cocrystal, or prodrug thereof; and (4) a JAK-2 inhibitor, which is selected from the group consisting of ruxolitinib:

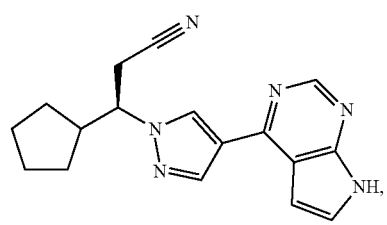 [SMILES: N#CC[C@H](C1CCCC1)n1cc(-c2ncnc3[nH]ccc23)cn1]

pacritinib:

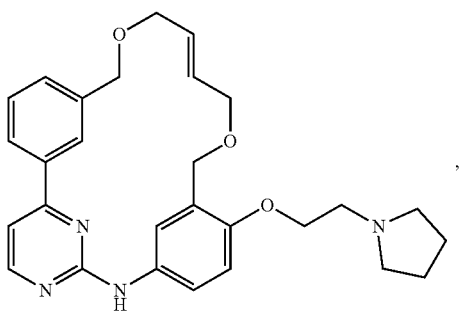 [SMILES: C1=C/COCc2cc(ccc2OCCN2CCCC2)Nc2nccc(n2)-c2cccc(c2)COC/1]

and pharmaceutically-acceptable salts, cocrystals, hydrates, solvates, or prodrugs thereof. This composition is typically a pharmaceutical composition. Also provided is a kit comprising (1) this same BCL-2 inhibitor or a pharmaceutically acceptable salt, solvate, hydrate, cocrystal, or prodrug thereof (2) this same BTK inhibitor or a pharmaceutically acceptable salt, solvate, hydrate, cocrystal, or prodrug thereof (3) this same PI3K inhibitor or a pharmaceutically acceptable salt, solvate, hydrate, cocrystal, or prodrug thereof; and (4) this same JAK-2 inhibitor and pharmaceutically-acceptable salts, cocrystals, hydrates, solvates, or prodrugs thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) a PI3K-δ inhibitor or a pharmaceutically acceptable salt, solvate, hydrate, cocrystal, or prodrug thereof; and (4) a JAK-2 inhibitor, which is selected from the group consisting of ruxolitinib:

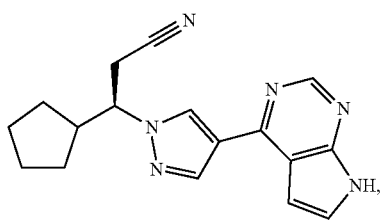 [SMILES: N#CC[C@H](C1CCCC1)n1cc(-c2ncnc3[nH]ccc23)cn1]

pacritinib:

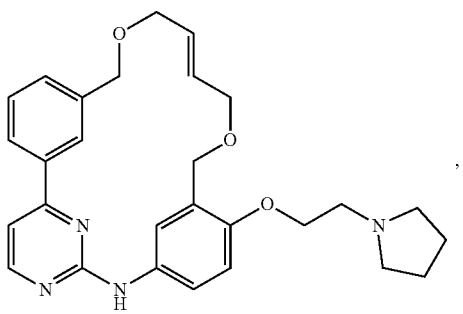 [SMILES: C1=C/COCc2cc(ccc2OCCN2CCCC2)Nc2nccc(n2)-c2cccc(c2)COC/1]

and pharmaceutically-acceptable salts, cocrystals, hydrates, solvates, or prodrugs thereof. This composition is typically a pharmaceutical composition. Also provided is a kit comprising (1) this same BCL-2 inhibitor or a pharmaceutically acceptable salt, solvate, hydrate, cocrystal, or prodrug thereof; (2) this same BTK inhibitor or a pharmaceutically acceptable salt, solvate, hydrate, cocrystal, or prodrug thereof; (3) this same PI3K-δ inhibitor or a pharmaceutically acceptable salt, solvate, hydrate, cocrystal, or prodrug thereof; and (4) this same JAK-2 inhibitor and pharmaceutically-acceptable salts, cocrystals, hydrates, solvates, or prodrugs thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof; (3) an anti-coagulant or antiplatelet active pharmaceutical ingredient; and (4) a JAK-2 inhibitor, which is selected from the group consisting of ruxolitinib:

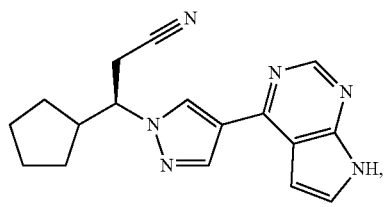 [SMILES: N#CC[C@H](C1CCCC1)n1cc(-c2ncnc3[nH]ccc23)cn1]

pacritinib:

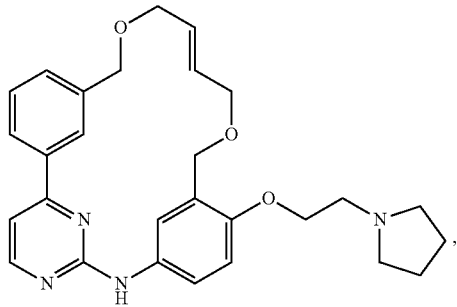 [SMILES: C1=C/COCc2cc(ccc2OCCN2CCCC2)Nc2nccc(n2)-c2cccc(c2)COC/1]

and pharmaceutically-acceptable salts, cocrystals, hydrates, solvates, or prodrugs thereof. This composition is typically a pharmaceutical composition. Also provided is a kit comprising (1) this same BCL-2 inhibitor or a pharmaceutically acceptable salt, solvate, hydrate, cocrystal, or prodrug thereof (2) this same BTK inhibitor or a pharmaceutically acceptable salt, solvate, hydrate, cocrystal, or prodrug thereof; (3) this same anti-coagulant or antiplatelet active pharmaceutical ingredient; and (4) this same JAK-2 inhibitor and pharmaceutically-acceptable salts, cocrystals, hydrates, solvates, or prodrugs thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a PI3K inhibitor or a pharmaceutically acceptable salt, solvate, hydrate, cocrystal, or prodrug thereof; (4) an anti-coagulant or antiplatelet active pharmaceutical ingredient; and (5) a JAK-2 inhibitor, which is selected from the group consisting of ruxolitinib:

301

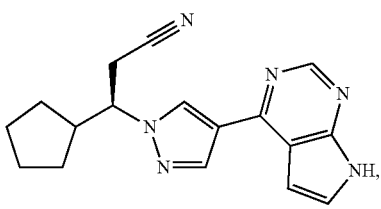 [SMILES: N#CC[C@H](C1CCCC1)n1cc(-c2ncnc3[nH]ccc23)cn1]

pacritinib:

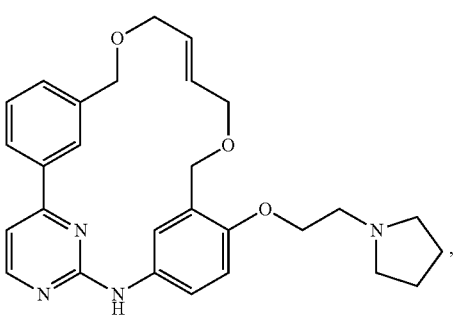 [SMILES: C1=C/COCc2cc(ccc2OCCN2CCCC2)Nc2nccc(n2)-c2cccc(c2)COC/1]

and pharmaceutically-acceptable salts, cocrystals, hydrates, solvates, or prodrugs thereof. This composition is typically a pharmaceutical composition. Also provided is a kit comprising (1) this same BCL-2 inhibitor or a pharmaceutically acceptable salt, solvate, hydrate, cocrystal, or prodrug thereof (2) this same BTK inhibitor or a pharmaceutically acceptable salt, solvate, hydrate, cocrystal, or prodrug thereof (3) this same PI3K inhibitor or a pharmaceutically acceptable salt, solvate, hydrate, cocrystal, or prodrug thereof; (4) this same anti-coagulant or antiplatelet active pharmaceutical ingredient; and (5) this same JAK-2 inhibitor and pharmaceutically-acceptable salts, cocrystals, hydrates, solvates, or prodrugs thereof.

In a preferred embodiment, the invention provides a composition comprising (1) a BCL-2 inhibitor or a pharmaceutically acceptable salt, solvate, hydrate, cocrystal, or prodrug thereof; (2) a BTK inhibitor or a pharmaceutically acceptable salt, solvate, hydrate, cocrystal, or prodrug thereof and (3) a PI3K-δ inhibitor or a pharmaceutically acceptable salt, solvate, hydrate, cocrystal, or prodrug thereof and (4) an anti-coagulant or antiplatelet active pharmaceutical ingredient; and (5) a JAK-2 inhibitor, which is selected from the group consisting of ruxolitinib:

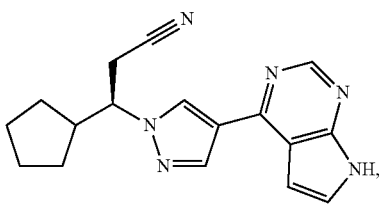 [SMILES: N#CC[C@H](C1CCCC1)n1cc(-c2ncnc3[nH]ccc23)cn1]

302 pacritinib:

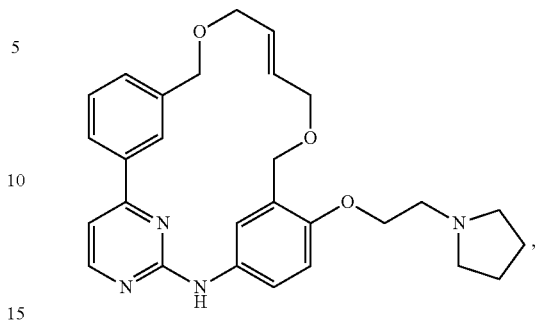

and pharmaceutically-acceptable salts, cocrystals, hydrates, solvates, or prodrugs thereof. This composition is typically a pharmaceutical composition. Also provided is a kit comprising (1) this same BCL-2 inhibitor or a pharmaceutically acceptable salt, solvate, hydrate, cocrystal, or prodrug thereof; (2) this same BTK inhibitor or a pharmaceutically acceptable salt, solvate, hydrate, cocrystal, or prodrug thereof (3) this same PI3K-δ inhibitor or a pharmaceutically acceptable salt, solvate, hydrate, cocrystal, or prodrug thereof; (4) this same anti-coagulant or antiplatelet active pharmaceutical ingredient; and (5) this same JAK-2 inhibitor and pharmaceutically-acceptable salts, cocrystals, hydrates, solvates, or prodrugs thereof.

In selected embodiments, the invention provides pharmaceutical compositions for treating solid tumor cancers, lymphomas, and leukemias.

The invention also provides embodiments where combinations, compositions and kits are useful in the discovery and/or development of pharmaceutical products for the treatment of solid tumor cancers, lymphomas, and leukemias.

The pharmaceutical compositions are typically formulated to provide a therapeutically effective amount of a combination of a PI3K inhibitor, including a PI3K-γ or PI3K-δ inhibitor, a JAK-2 inhibitor, a BTK inhibitor and/or a BCL-2 inhibitor as the active ingredients, or a pharmaceutically acceptable salt, ester, prodrug, solvate, hydrate or derivative thereof. Where desired, the pharmaceutical compositions contain a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The pharmaceutical compositions are administered as a combination of a PI3K inhibitor, including a PI3K-γ or PI3K-δ inhibitor, a JAK-2 inhibitor, a BTK inhibitor and/or a BCL-2 inhibitor. Where desired, other agent(s) may be mixed into a preparation or both components may be formulated into separate preparations for use in combination separately or at the same time.

In selected embodiments, the concentration of each of the PI3K, JAK-2, BTK and BCL-2 inhibitors provided in the pharmaceutical compositions of the invention is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v.

In selected embodiments, the concentration of each of the PI3K, JAK-2, BTK and BCL-2 inhibitors provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v.

In selected embodiments, the concentration of each of the PI3K, JAK-2 BTK and BCL-2 inhibitors of the invention is independently in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v.

In selected embodiments, the concentration of each of the PI3K, JAK-2, BTK and BCL-2 inhibitors of the invention is independently in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v.

In selected embodiments, the amount of each of the PI3K, JAK-2, BTK and BCL-2 inhibitors of the invention is independently equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g.

In selected embodiments, the amount of each of the PI3K, JAK-2, BTK and BCL-2 inhibitors of the invention is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5, 4 g, 4.5 g, 5 g, 5.5 g, 6 g, 6.5 g, 7 g, 7.5 g, 8 g, 8.5 g, 9 g, 9.5 g or 10 g.

Each of the PI3K, JAK-2, BTK and BCL-2 inhibitors according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting exemplary pharmaceutical compositions and methods for preparing the same.

Pharmaceutical Compositions for Oral Administration

In selected embodiments, the invention provides a pharmaceutical composition for oral administration containing the combination of two or more active ingredients selected from PI3K, JAK-2, BTK and BCL-2 inhibitor, and a pharmaceutical excipient suitable for oral administration.

In selected embodiments, the invention provides a solid pharmaceutical composition for oral administration containing: (i) an effective amount of a PI3K, JAK-2, BTK and/or BCL-2 inhibitor in combination and (ii) a pharmaceutical excipient suitable for oral administration. In selected embodiments, the composition further contains (iii) an effective amount of a fourth compound.

In selected embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the PI3K, JAK-2, BTK and BCL-2 inhibitors as active ingredients can be combined with one or more of the PI3K, JAK-2, BTK and BCL-2 inhibitors in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an hydrophilic-lipophilic balance (HLB) value of at least 10, while suitable lipophilic surfactants may generally have an HLB value of or less than about 10. The HLB value is an empirical parameter used to characterize the relative hydrophilicity and hydrophobicity of non-ionic amphiphilic compounds. Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, E-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, 6-valerolactone and isomers thereof, 0-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In selected embodiments, the invention provides a pharmaceutical composition for injection containing the combination of two or more active ingredient selected from PI3K, JAK-2, BTK and BCL-2 inhibitors and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating the combination of two or more of the PI3K, JAK-2, BTK and BCL-2 inhibitors in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In some embodiments, the invention provides a pharmaceutical composition for transdermal delivery containing the combination of two or more active ingredients selected from PI3K, JAK-2, BTK and BCL-2 inhibitors and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of the combination of the PI3K, JAK-2, BTK and BCL-2 inhibitors in controlled amounts, either with or without another agent.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al. eds., *Handbook of Clinical Drug Data*, Tenth Edition, McGraw-Hill, 2002; and Pratt and Taylor, eds., *Principles of Drug Action*, Third Edition, Churchill Livingston, N.Y., 1990, each of which is incorporated by reference herein in its entirety.

Administration of the combination of two of more active ingredients selected from PI3K, BCL-2, JAK-2, and BTK inhibitors or pharmaceutical composition of these compounds can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The combination of compounds can also be administered intraadiposally or intrathecally.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g. PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. The combination of the PI3K, BCL-2, JAK-2, and/or BTK inhibitors may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. The combination of the PI3K, BCL-2, JAK-2, and/or BTK inhibitors may additionally be administered intravascularly from a balloon used during angioplasty. Extravascular administration of the combination of the PI3K, BCL-2, JAK-2, and/or BTK inhibitors via the pericard or via advential application of formulations of the invention may also be performed to decrease restenosis.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include each of the PI3K, BCL-2, JAK-2, and/or BTK inhibitors, either alone or in combination in suitable packaging, and written material (for example in the form of a package insert or label) that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In selected embodiments, the PI3K, BCL-2, JAK-2, and/or BTK inhibitors and the agent are provided as separate compositions in separate containers within the kit. In selected embodiments, the PI3K, BCL-2, JAK-2, and/or BTK inhibitors and the agent are provided as a single composition within a container in the kit. Suitable packaging and additional articles for use (e.g., measuring cup for liquid preparations, foil wrapping to minimize exposure to air, and the like) are known in the art and may be included in the kit.

Kits described herein can be provided, marketed and/or promoted to health providers, including physicians, nurses, pharmacists, formulary officials, and the like. Kits may also, in selected embodiments, be marketed directly to the consumer.

Dosages and Dosing Regimens

The amounts of the combination of the PI3K, BCL-2, JAK-2, and/or BTK inhibitors administered will be dependent on the mammal being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day.

In selected embodiments, the combination of the PI3K, BCL-2, JAK-2, and/or BTK inhibitors is administered in a single dose. Typically, such administration will be by injection—e.g., intravenous injection, in order to introduce the agents quickly. However, other routes may be used as appropriate. A single dose of the combination of the PI3K and BTK inhibitors may also be used for treatment of an acute condition.

In selected embodiments, the combination of the PI3K, BCL-2, JAK-2, and/or BTK inhibitors is administered in multiple doses. Dosing may be about once, twice, three times, four times, five times, six times, or more than six times per day. Dosing may be about once a month, once every two weeks, once a week, or once every other day. In other embodiments, the combination of the PI3K, BCL-2, JAK-2, and/or BTK inhibitors is administered about once per day to about 6 times per day. In another embodiment the administration of the combination of the PI3K, BCL-2, JAK-2, and/or BTK inhibitors continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In selected embodiments, the combination of the PI3K, BCL-2, JAK-2, and/or BTK inhibitors is administered for more than 1, 2, 3, 4, 5, 6, 7, 14, or 28 days. In some embodiments, the combination of the PI3K, BCL-2, JAK-2, and/or BTK inhibitors is administered for less than 28, 14, 7, 6, 5, 4, 3, 2, or 1 day. In selected embodiments, the combination of the PI3K, BCL-2, JAK-2, and/or BTK inhibitors is administered chronically on an ongoing basis—e.g., for the treatment of chronic effects.

An effective amount of the combination of the PI3K, BCL-2, JAK-2, and/or BTK inhibitors may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

Methods of Treating Cancers, Including Solid Tumor Cancers, and Other Diseases

In selected embodiments, the invention provides a method of treating a hyperproliferative disorder in a mammal that comprises administering to said mammal a therapeutically effective amount of a BCL-2 inhibitor and a BTK inhibitor, or a pharmaceutically acceptable salt or ester, prodrug, solvate or hydrate of the BTK inhibitor or BCL-2 inhibitor. In selected embodiments, the invention provides a method of treating a hyperproliferative disorder in a mammal that comprises administering to said mammal a therapeutically effective amount of a BCL-2 inhibitor, a BTK inhibitor, and a PI3K inhibitor (or a PI3K-γ inhibitor, PI3K-δ inhibitor, or PI3K-γ,δ inhibitor) or a pharmaceutically acceptable salt or ester, prodrug, solvate or hydrate of any of the PI3K inhibitor, BCL-2 inhibitor, and BTK inhibitor. In selected embodiments, the invention provides a method of treating a hyperproliferative disorder in a mammal that comprises administering to said mammal a therapeutically effective amount of a BCL-2 inhibitor, a BTK inhibitor, a JAK-2 inhibitor, and a PI3K inhibitor (or a PI3K-γ inhibitor, PI3K-δ inhibitor, or PI3K-γ,δ inhibitor) or a pharmaceutically acceptable salt or ester, prodrug, solvate or hydrate of any of the PI3K inhibitor, BCL-2 inhibitor, JAK-2 inhibitor, and/or BTK inhibitor.

In selected embodiments, the invention provides a method of treating, with a combination of a PI3K inhibitor, including a PI3K-γ or PI3K-δ inhibitor, a JAK-2 inhibitor, a BTK inhibitor, and/or a BCL-2 inhibitor, a hyperproliferative disorder in a mammal selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancers such as cervical carcinoma (human papillomavirus), B-cell lymphoproliferative disease and nasopharyngeal carcinoma (Epstein-Barr virus), Kaposi's Sarcoma and primary effusion lymphomas (Kaposi's sarcoma herpesvirus), hepatocellular carcinoma (hepatitis B and hepatitis C viruses), and T-cell leukemias (Human T-cell leukemia virus-1), glioblastoma, esophogeal tumors, hematological neoplasms, non-small-cell lung cancer, chronic myelocytic leukemia, diffuse large B-cell lymphoma (including activated B-cell (ABC) and germinal center B-cell (GCB) subtypes), esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

In selected embodiments, the invention provides a method of treating an inflammatory, immune, or autoimmune disorder in a mammal with a combination of a PI3K inhibitor, including a PI3K-γ or PI3K-δ inhibitor, a JAK-2 inhibitor, a BTK inhibitor, and/or a BCL-2 inhibitor. In selected embodiments, the invention also provides a method of treating a disease with a combination of a PI3K inhibitor, including a PI3K-γ or PI3K-δ inhibitor, a JAK-2 inhibitor, a BTK inhibitor, and/or a BCL-2 inhibitor, wherein the disease is selected from the group consisting of tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcets disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spondylitis, Crohn's Disease, lupus, and lupus nephritis.

In selected embodiments, the invention provides a method of treating, with a composition including a PI3K inhibitor, including a PI3K-γ or PI3K-δ inhibitor, a JAK-2 inhibitor, a BTK inhibitor, and/or a BCL-2 inhibitor, disorders such as hyperproliferative disorder, including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., lymphoma and Kaposi's sarcoma) or viral-induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)). In some embodiments, the invention provides a method of treating a hyperproliferative disorder selected from the group consisting of myeloproliferative proliferative neoplasm, chronic myelogenous leukemia, chronic neutrophilic leukemia, polycythemia vera, primary myelofibrosis, essential thrombocythemia, chronic eosinophilic leukemia, mastocytosis, and myelodysplastic syndrome. In some embodiments, the invention provides a method of treating a glioma, wherein the glioma is selected from the group consisting of fibrillary astrocytoma, anaplastic astrocytoma, pilocytic astrocytoma, astrocytoma, pleomorphic xanthoastrocytoma, subependymal giant cell astrocytoma, glioblastoma multiforme, oligodendroglioma, ependymoma, subependymoma, choroid plexus tumor, choroid plexus papilloma, choroid plexus carcinoma, oligoastrocytoma, gliomatosis cerebri, and gliosarcoma. In some embodiments, the invention provides a method of treating a cancer, wherein the cancer is selected from primary central nervous system lymphoma, reticulum cell sarcoma, diffuse histiocytic lymphoma, and microglioma.

In selected embodiments, the invention provides a method of treating a solid tumor cancer with a composition including a combination of a PI3K inhibitor, including a PI3K-γ or PI3K-δ inhibitor, a JAK-2 inhibitor, a BTK inhibitor, and/or a BCL-2 inhibitor, wherein the dose is effective to inhibit signaling between the solid tumor cells and at least one microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts. In selected embodiments, the invention provides a method of treating pancreatic cancer, breast cancer, ovarian cancer, melanoma, lung cancer, head and neck cancer, and colorectal cancer using a combination of a BTK inhibitor, a PI3K inhibitor, a JAK-2 inhibitor, and/or a BCL-2 inhibitor, wherein the dose is effective to inhibit signaling between the solid tumor cells and at least one microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts. In an embodiment, the invention provides a method for treating pancreatic cancer, breast cancer, ovarian cancer, melanoma, lung cancer, head and neck cancer, and colorectal cancer using a combination of a BTK inhibitor and gemcitabine, or a pharmaceutically-acceptable salt, cocrystal, hydrate, solvate, or prodrug thereof. In an embodiment, the invention provides a method for treating pancreatic cancer, breast cancer, ovarian cancer, melanoma, lung cancer, head and neck cancer, and colorectal cancer using a combination of a BTK inhibitor and gemcitabine, or a pharmaceutically-acceptable salt, cocrystal, hydrate, solvate, or prodrug thereof, wherein the BTK inhibitor is a compound of Formula (XVIII). Efficacy of the compounds and combinations of compounds described herein in treating, preventing and/or managing the indicated diseases or disorders can be tested using various models known in the art. For example, models for determining efficacy of treatments for pancreatic cancer are described in Herreros-Villanueva, et al. *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for melanoma are described, e.g., in Damsky, et al., *Pigment Cell & Melanoma Res.* 2010, 23, 853-859. Models for determining efficacy of treatments for lung cancer are described e.g. in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32. Models for determining efficacy of treatments for colorectal cancer, including the CT26 model, are described below in the examples.

Efficacy of the compounds and combinations of compounds described herein in treating, preventing and/or managing other indicated diseases or disorders described here can also be tested using various models known in the art. Efficacy in treating, preventing and/or managing asthma can be assessed using the ova induced asthma model described, for example, in Lee, et al., *J. Allergy Clin. Immunol.* 2006, 118, 403-9. Efficacy in treating, preventing and/or managing arthritis (e.g., rheumatoid or psoriatic arthritis) can be assessed using the autoimmune animal models described in, for example, Williams, et al., *Chem. Biol.* 2010, 17, 123-34, WO 2009/088986, WO 2009/088880, and WO 2011/008302. Efficacy in treating, preventing and/or managing psoriasis can be assessed using transgenic or knockout mouse model with targeted mutations in epidermis, vasculature or immune cells, mouse model resulting from spontaneous mutations, and immuno-deficient mouse model with xenotransplantation of human skin or immune cells, all of which are described, for example, in Boehncke, et al., *Clinics in Dermatology,* 2007, 25, 596-605. Efficacy in treating, preventing and/or managing fibrosis or fibrotic conditions can be assessed using the unilateral ureteral obstruction model of renal fibrosis, which is described, for example, in Chevalier, et al., *Kidney International* 2009, 75, 1145-1152; the bleomycin induced model of pulmonary fibrosis described in, for example, Moore et al., *Am. J. Physiol. Lung. Cell. Mol. Physiol.* 2008, 294, L152-L160; a variety of liver/biliary fibrosis models described in, for example, Chuang, et al., *Clin. Liver Dis.* 2008, 12, 333-347 and Omenetti, et al., *Laboratory Investigation*, 2007, 87, 499-514 (biliary duct-ligated model); or any of a number of myelofibrosis mouse models such as described in Varicchio, et al., *Expert Rev. Hematol.* 2009, 2, 315-334. Efficacy in treating, preventing and/or managing scleroderma can be assessed using a mouse model induced by repeated local injections of bleomycin described, for example, in Yamamoto et al., *J. Invest. Dermatol.* 1999, 112, 456-462. Efficacy in treating, preventing and/or managing dermatomyositis can be assessed using a myositis mouse model induced by immunization with rabbit myosin as described, for example, in Phyanagi, et al., *Arthritis & Rheumatism*, 2009, 60(10), 3118-3127. Efficacy in treating, preventing and/or managing lupus can be assessed using various animal models described, for example, in Ghoreishi, et al., *Lupus*, 2009, 19, 1029-1035; Ohl et al., *J. Biomed. & Biotechnol., Article ID* 432595 (2011); Xia, et al., *Rheumatology*, 2011, 50, 2187-2196; Pau, et al., *PLoS ONE*, 2012, 7(5), e36761; Mustafa, et al., *Toxicology*, 2011, 90, 156-168; Ichikawa, et al., *Arthritis & Rheumatism*, 2012, 62(2), 493-503; Rankin, et al., *J. Immunology*, 2012, 188, 1656-1667. Efficacy in treating, preventing and/or managing Sjögren's syndrome can be assessed using various mouse models described, for example, in Chiorini, et al., *J. Autoimmunity*, 2009, 33, 190-196.

Methods of Treating Patients Sensitive to Bleeding Events

In selected embodiments, the invention provides a method of treating a cancer in a human sensitive to bleeding events, comprising the step of administering a therapeutically effective dose of a BTK inhibitor, or a pharmaceutically-acceptable salt, cocrystal, hydrate, solvate, or prodrug thereof, and a BCL-2 inhibitor, or a pharmaceutically-acceptable salt, cocrystal, hydrate, solvate, or prodrug thereof. In a preferred embodiment, the invention provides a method of treating a cancer in a human sensitive to bleeding events, comprising the step of administering a therapeutically effective dose of a BTK inhibitor, wherein the BTK inhibitor is Formula (XVIII), or a pharmaceutically-acceptable salt, cocrystal, hydrate, solvate, or prodrug thereof. In some embodiments, the invention provides a method of treating a hyperproliferative disorder, such as a cancer or an inflammatory, immune, or autoimmune disease, in a human intolerant to ibrutinib.

In an embodiment, the invention provides a method of treating a cancer in a human sensitive to bleeding events, comprising the step of administering a therapeutically effective dose of a BTK inhibitor, wherein the BTK inhibitor is Formula (XVIII), or a pharmaceutically-acceptable salt, cocrystal, hydrate, solvate, or prodrug thereof, and a BCL-2 inhibitor, or a pharmaceutically-acceptable salt, cocrystal, hydrate, solvate, or prodrug thereof, further comprising the step of administering a therapeutically effective dose of an anticoagulent or antiplatelet active pharmaceutical ingredient.

In selected embodiments, the invention provides a method of treating a cancer in a human sensitive to bleeding events, comprising the step of administering a therapeutically effective dose of a BTK inhibitor, wherein the BTK inhibitor is Formula (XVIII), and wherein the cancer is selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

In selected embodiments, the invention provides a method of treating a cancer in a human sensitive to platelet-mediated thrombosis comprising the step of administering a therapeutically effective dose of a BTK inhibitor, wherein the BTK inhibitor is Formula (XVIII), or a pharmaceutically-acceptable salt, cocrystal, hydrate, solvate, or prodrug thereof, and a BCL-2 inhibitor, or a pharmaceutically-acceptable salt, cocrystal, hydrate, solvate, or prodrug thereof.

In selected embodiments, the BTK inhibitor and the anticoagulent or the antiplatelet active pharmaceutical ingredient are administered sequentially. In selected embodiments, the BTK inhibitor and the anticoagulent or the antiplatelet active pharmaceutical ingredient are administered concomittently. In selected embodiments, the BTK inhibitor is administered before the anticoagulent or the antiplatelet active pharmaceutical ingredient. In selected embodiments, the BTK inhibitor is administered after the anticoagulent or the antiplatelet active pharmaceutical ingredient. In selected embodiments, a BCL-2 inhibitor is co-administered with the BTK inhibitor and the anticoagulent or the antiplatelet active pharmaceutical ingredient at the same time or at different times.

Selected anti-platelet and anticoagulant active pharmaceutical ingredients for use in the methods of the present invention include, but are not limited to, cyclooxygenase inhibitors (e.g., aspirin), adenosine diphosphate (ADP) receptor inhibitors (e.g., clopidogrel and ticlopidine), phosphodiesterase inhibitors (e.g., cilostazol), glycoprotein IIb/IIIa inhibitors (e.g., abciximab, eptifibatide, and tirofiban), adenosine reuptake inhibitors (e.g., dipyridamole), and acetylsalicylic acid (aspirin). In other embodiments, examples of anti-platelet active pharmaceutical ingredients for use in the methods of the present invention include anagrelide, aspirin/extended-release dipyridamole, cilostazol, clopidogrel, dipyridamole, prasugrel, ticagrelor, ticlopidine, vorapaxar, tirofiban HCl, eptifibatide, abciximab, argatroban, bivalirudin, dalteparin, desirudin, enoxaparin, fondaparinux, heparin, lepirudin, apixaban, dabigatran etexilate mesylate, rivaroxaban, and warfarin.

In an embodiment, the invention provides a method of treating a cancer, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-c]pyrazin-1-yl)-N-(pyridin-2-yl)benzamide or a pharmaceutically acceptable salt, solvate, hydrate, cocrystal, or prodrug thereof, and a BCL-2 inhibitor, or a pharmaceutically acceptable salt, solvate, hydrate, cocrystal, or prodrug thereof, further comprising the step of administering a therapeutically effective dose of an anticoagulant or antiplatelet active pharmaceutical ingredient, wherein the anticoagulant or antiplatelet active pharmaceutical ingredient is selected from the group consisting of acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, and combinations thereof.

In selected embodiments, the invention provides a method of treating a cancer in a human sensitive to platelet-mediated thrombosis, comprising the step of administering a therapeutically effective dose of a BTK inhibitor, or a pharmaceutically-acceptable salt, cocrystal, hydrate, solvate, or prodrug thereof. In a preferred embodiment, the invention provides a method of treating a cancer in a human sensitive to platelet-mediated thrombosis, comprising the step of administering a therapeutically effective dose of a BTK inhibitor, wherein the BTK inhibitor is Formula (XVIII), or a pharmaceutically-acceptable salt, cocrystal, hydrate, solvate, or prodrug thereof. In a preferred embodiment, the invention provides a method of treating a cancer in a human sensitive to platelet-mediated thrombosis, comprising the step of administering a therapeutically effective dose of a BTK inhibitor, wherein the BTK inhibitor is Formula (XVIII), or a pharmaceutically-acceptable salt, cocrystal, hydrate, solvate, or prodrug thereof, further comprising the step of administering a therapeutically effective dose of an anticoagulent or antiplatelet agent.

In selected embodiments, the invention provides a method of treating a cancer in a human with a history of thrombosis, comprising the step of administering a therapeutically effective dose of a BTK inhibitor, wherein the BTK inhibitor is Formula (XVIII), or a pharmaceutically-acceptable salt, cocrystal, hydrate, solvate, or prodrug thereof, further comprising the step of administering a therapeutically effective dose of an anticoagulent or antiplatelet agent, wherein the anticoagulent or antiplatelet agent is selected from the group consisting of clopidogrel, prasugrel, ticagrelor, ticlopidine, warfarin, acenocoumarol, dicumarol, phenprocoumon, heparain, low molecular weight heparin, fondaparinux, and idraparinux.

In selected embodiments, the invention provides a method of treating a cancer in a human sensitive to platelet-mediated thrombosis, comprising the step of administering a therapeutically effective dose of a BTK inhibitor, wherein the BTK inhibitor is Formula (XVIII), and wherein the cancer is selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophogeal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

In selected embodiments, the invention provides a method of treating a cancer in a human sensitive to platelet-mediated thrombosis comprising the step of administering a therapeutically effective dose of a BTK inhibitor, or a pharmaceutically-acceptable salt, cocrystal, hydrate, solvate, or prodrug thereof. In selected embodiments, the invention provides a method of treating a cancer in a human sensitive to platelet-mediated thrombosis, method of treating a cancer in a human with a history of thrombosis, comprising the step of administering a therapeutically effective dose of a BTK inhibitor, wherein the BTK inhibitor is a compound of Formula (XVIII) or a pharmaceutically-acceptable salt, cocrystal, hydrate, solvate, or prodrug thereof.

In selected embodiments, the BTK inhibitor and the anticoagulent or the antiplatelet agent are administered sequentially. In selected embodiments, the BTK inhibitor and the anticoagulent or the antiplatelet agent are administered concomittently. In selected embodiments, the BTK inhibitor is administered before the anticoagulent or the antiplatelet agent. In selected embodiments, the BTK inhibitor is administered after the anticoagulent or the antiplatelet agent.

Preferred anti-platelet and anticoagulent agents for use in the methods of the present invention include, but are not limited to, cyclooxygenase inhibitors (e.g., aspirin), adenosine diphosphate (ADP) receptor inhibitors (e.g., clopidogrel and ticlopidine), phosphodiesterase inhibitors (e.g., cilostazol), glycoprotein IIb/IIIa inhibitors (e.g., abciximab, eptifibatide, and tirofiban), adenosine reuptake inhibitors (e.g., dipyridamole), and acetylsalicylic acid (aspirin). In other embodiments, examples of anti-platelet agents for use in the methods of the present invention include anagrelide, aspirin/extended-release dipyridamole, cilostazol, clopidogrel, dipyridamole, prasugrel, ticagrelor, ticlopidine, vorapaxar, tirofiban HCl, eptifibatide, abciximab, argatroban, bivalirudin, dalteparin, desirudin, enoxaparin, fondaparinux, heparin, lepirudin, apixaban, dabigatran etexilate mesylate, rivaroxaban, and warfarin.

Combinations of BTK Inhibitors, PI3K Inhibitors, JAK-2 Inhibitors, and/or BCL-2 Inhibitors with Anti-CD20 Antibodies The BTK inhibitors of the present invention and combinations of the BTK inhibitors with PI3K inhibitors, JAK-2 inhibitors, and/or BCL-2 inhibitors may also be safely co-administered with immunotherapeutic antibodies such as the anti-CD20 antibodies rituximab, obinutuzumab, ofatumumab, veltuzumab, tositumomab, and ibritumomab, and or antigen-binding fragments, derivatives, conjugates, variants, and radioisotope-labeled complexes thereof, which may be given alone or with conventional chemotherapeutic active pharmaceutical ingredients such as those described herein. The CD20 antigen (also called human B-lymphocyte-restricted differentiation antigen, Bp35, or $B_1$) is found on the surface of normal "pre-B" and mature B lymphocytes, including malignant B lymphocytes. Nadler, et al., *J. Clin. Invest.* 1981, 67, 134-40; Stashenko, et al., *J. Immunol.* 1980, 139, 3260-85. The CD20 antigen is a glycosylated integral membrane protein with a molecular weight of approximately 35 kD. Tedder, et al., *Proc. Natl. Acad. Sci. USA*, 1988, 85, 208-12. CD20 is also expressed on most B cell non-Hodgkin's lymphoma cells, but is not found on hematopoietic stem cells, pro-B cells, normal plasma cells, or other normal tissues. Anti-CD20 antibodies are currently used as therapies for many hematological malignancies, including indolent NHL, aggressive NHL, and CLL/SLL. Lim, et. al., *Haematologica* 2010, 95, 135-43; Beers, et. al., *Sem. Hematol.* 2010, 47, 107-14; and Klein, et al., *mAbs* 2013, 5, 22-33.

In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an anti-CD20 antibody, wherein the anti-CD20 antibody is a monoclonal antibody or an antigen-binding fragment, derivative, conjugate, variant, or radioisotope-labeled complex thereof. In an embodiment, the anti-CD20 antibody is selected from a chimeric antibody, a humanized antibody and a human antibody or an antigen-binding fragment, derivative, conjugate, variant or radiolabelled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an anti-CD20 antibody, wherein the anti-CD20 antibody is an anti-CD20 monoclonal antibody or an antigen-binding fragment, derivative, conjugate, variant, or radioisotope-labeled complex thereof, and wherein the anti-CD20 antibody specifically binds to human CD20 with a $K_D$ selected from the group consisting of $1\times10^{-7}$ M or less, $5\times10^{-8}$ M or less, $1\times10^{-8}$ M or less, and $5\times10^{-9}$ M or less. Anti-CD20 monoclonal antibodies are classified as Type I or Type II, as described in Klein, et al., mAbs 2013, 5, 22-33. Type I anti-CD20 monoclonal antibodies are characterized by binding to the Class I epitope, localization of CD20 to lipid rafts, high complement-dependent cytotoxicity, full binding capacity, weak homotypic aggregation, and moderate cell death induction. Type II anti-CD20 monoclonal antibodies are characterized by binding to the Class I epitope, a lack of localization of CD20 to lipid rafts, low complement-dependent cytotoxicity, half binding capacity, homotypic aggregation, and strong cell death induction. Both Type I and Type II anti-CD20 monoclonal antibodies exhibit antibody-dependent cytotoxicity (ADCC) and are thus useful with BTK inhibitors described herein. Type I anti-CD20 monoclonal antibodies include but are not limited to rituximab, ocrelizumab, and ofatumumab. Type II anti-CD20 monoclonal antibodies include but are not limited to obinutuzumab and tositumomab.

In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an anti-CD20 antibody, wherein the anti-CD20 antibody is a monoclonal antibody or an antigen-binding fragment, derivative, conjugate, variant, or radioisotope-labeled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an anti-CD20 antibody, wherein the anti-CD20 antibody is an anti-CD20 monoclonal antibody or an antigen-binding fragment, derivative, conjugate, variant, or radioisotope-labeled complex thereof, and wherein the anti-CD20 antibody specifically binds to human CD20 with a $K_D$ selected from the group consisting of $1\times10^{-7}$ M or less, $5\times10^{-8}$ M or less, $1\times10^{-8}$ M or less, and $5\times10^{-9}$ M or less.

In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an Type I anti-CD20 antibody, or an antigen-binding fragment, derivative, conjugate, variant, or radioisotope-labeled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering an Type II anti-CD20 antibody, or an antigen-binding fragment, derivative, conjugate, variant, or radioisotope-labeled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and a BCL-2 inhibitor or a pharmaceutically acceptable salt or ester, prodrug, cocrystal, solvate or hydrate thereof, and further comprising the step of administering an Type I anti-CD20 antibody, or an antigen-binding fragment, derivative, conjugate, variant, or radioisotope-labeled complex thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and a BCL-2 inhibitor or a pharmaceutically acceptable salt or ester, prodrug, cocrystal, solvate or hydrate thereof, and further comprising the step of administering an Type II anti-CD20 antibody, or an antigen-binding fragment, derivative, conjugate, variant, or radioisotope-labeled complex thereof.

In selected embodiments, the BTK inhibitors of the present invention and combinations of the BTK inhibitors with PI3K inhibitors, JAK-2 inhibitors, and/or BCL-2 inhibitors and the anti-CD20 monoclonal antibody are administered sequentially. In selected embodiments, the BTK inhibitors of the present invention and combinations of the BTK inhibitors with PI3K inhibitors, JAK-2 inhibitors, and/or BCL-2 inhibitors and the anti-CD20 monoclonal antibody are administered concomitantly. In selected embodiments, the BTK inhibitors of the present invention and combinations of the BTK inhibitors with PI3K inhibitors, JAK-2 inhibitors, and/or BCL-2 inhibitors is administered before the anti-CD20 monoclonal antibody. In selected embodiments, the BTK inhibitors of the present invention and combinations of the BTK inhibitors with PI3K inhibitors, JAK-2 inhibitors, and/or BCL-2 inhibitors is administered after the anticoagulant or the antiplatelet active pharmaceutical ingredient. In selected embodiments, the BTK inhibitors of the present invention and combinations of the BTK inhibitors with PI3K inhibitors, JAK-2 inhibitors, and/or BCL-2 inhibitors and the anti-CD20 monoclonal antibody are administered over the same time period, and the BTK inhibitor administration continues after the anti-CD20 monoclonal antibody administration is completed.

In an embodiment, the anti-CD20 monoclonal antibody is rituximab, or an antigen-binding fragment, derivative, conjugate, variant, or radioisotope-labeled complex thereof. Rituximab is a chimeric murine-human monoclonal antibody directed against CD20, and its structure comprises an IgG1 kappa immunoglobulin containing murine light- and heavy-chain variable region sequences and human constant region sequences. Rituximab is composed of two heavy chains of 451 amino acids and two light chains of 213 amino acids. The amino acid sequence for the heavy chains of rituximab is set forth in SEQ ID NO:1. The amino acid sequence for the light chains of rituximab is set forth in SEQ ID NO:2. Rituximab is commercially available, and its properties and use in cancer and other diseases is described in more detail in Rastetter, et al., *Ann. Rev. Med.* 2004, 55, 477-503, and in Plosker and Figgett, Drugs, 2003, 63, 803-43. In an embodiment, the anti-CD20 monoclonal antibody is an anti-CD20 biosimilar monoclonal antibody approved by one or more drug regulatory authority with reference to rituximab. In an embodiment, the anti-CD20 monoclonal antibody has a heavy chain sequence identity of greater than 90% to SEQ ID NO:1. In an embodiment, the anti-CD20 monoclonal antibody has a light chain sequence identity of greater than 90% to SEQ ID NO:2. In an embodiment, the anti-CD20 monoclonal antibody has a heavy chain sequence identity of greater than 95% to SEQ ID NO:1. In an embodiment, the anti-CD20 monoclonal antibody has a light chain sequence identity of greater than 95% to SEQ ID NO:2. In an embodiment, the anti-CD20 monoclonal antibody has a heavy chain sequence identity of greater than 98% to SEQ ID NO:1. In an embodiment, the anti-CD20 monoclonal antibody has a light chain sequence identity of greater than 98% to SEQ ID NO:2. In an embodiment, the anti-CD20 monoclonal antibody has a heavy chain sequence identity of greater than 99% to SEQ ID NO:1. In an embodiment, the anti-CD20 monoclonal antibody has a light chain sequence identity of greater than 99% to SEQ ID NO:2.

In an embodiment, the anti-CD20 monoclonal antibody is obinutuzumab, or an antigen-binding fragment, derivative, conjugate, variant, or radioisotope-labeled complex thereof. Obinutuzumab is also known as afutuzumab or GA-101. Obinutuzumab is a humanized monoclonal antibody directed against CD20. The amino acid sequence for the heavy chains of obinutuzumab is set forth in SEQ ID NO:3. The amino acid sequence for the light chains of obinutuzumab is set forth in SEQ ID NO:4. Obinutuzumab is commercially available, and its properties and use in cancer and other diseases is described in more detail in Robak, *Curr. Opin. Investig. Drugs* 2009, 10, 588-96. In an embodiment, the anti-CD20 monoclonal antibody is an anti-CD20 biosimilar monoclonal antibody approved by one or more drug regulatory authority with reference to obinutuzumab. In an embodiment, the anti-CD20 monoclonal antibody has a heavy chain sequence identity of greater than 90% to SEQ ID NO:3. In an embodiment, the anti-CD20 monoclonal antibody has a light chain sequence identity of greater than 90% to SEQ ID NO:4. In an embodiment, the anti-CD20 monoclonal antibody has a heavy chain sequence identity of greater than 95% to SEQ ID NO:3. In an embodiment, the anti-CD20 monoclonal antibody has a light chain sequence identity of greater than 95% to SEQ ID NO:4. In an embodiment, the anti-CD20 monoclonal antibody has a heavy chain sequence identity of greater than 98% to SEQ ID NO:3. In an embodiment, the anti-CD20 monoclonal antibody has a light chain sequence identity of greater than 98% to SEQ ID NO:4. In an embodiment, the anti-CD20 monoclonal antibody has a heavy chain sequence identity of greater than 99% to SEQ ID NO:3. In an embodiment, the anti-CD20 monoclonal antibody has a light chain sequence identity of greater than 99% to SEQ ID NO:4. In an embodiment, the anti-CD20 monoclonal antibody obinutuzumab is an immunoglobulin G1, anti-(human B-lymphocyte antigen CD20 (membrane-spanning 4-domains subfamily A member 1, B-lymphocyte surface antigen $B_1$, Leu-16 or Bp35)), humanized mouse monoclonal obinutuzumab des-CH3107-K-γ1 heavy chain (222-219')-disulfide with humanized mouse monoclonal obinutuzumab κ light chain dimer (228-228":231-231")-bisdisulfide antibody.

In an embodiment, the anti-CD20 monoclonal antibody is ofatumumab, or an antigen-binding fragment, derivative, conjugate, variant, or radioisotope-labeled complex thereof. Ofatumumab is described in Cheson, *J. Clin. Oncol.* 2010, 28, 3525-30. The crystal structure of the Fab fragment of ofatumumab has been reported in Protein Data Bank reference 3GIZ and in Du, et al., *Mol. Immunol.* 2009, 46, 2419-2423. Ofatumumab is commercially available, and its preparation, properties, and use in cancer and other diseases are described in more detail in U.S. Pat. No. 8,529,202 $B_2$, the disclosure of which is incorporated herein by reference. In an embodiment, the anti-CD20 monoclonal antibody is an anti-CD20 biosimilar monoclonal antibody approved by one or more drug regulatory authority with reference to ofatumumab. In an embodiment, the anti-CD20 monoclonal antibody has a variable heavy chain sequence identity of greater than 90% to SEQ ID NO:5. In an embodiment, the anti-CD20 monoclonal antibody has a variable light chain sequence identity of greater than 90% to SEQ ID NO:6. In an embodiment, the anti-CD20 monoclonal antibody has a variable heavy chain sequence identity of greater than 95% to SEQ ID NO:5. In an embodiment, the anti-CD20 monoclonal antibody has a variable light chain sequence identity of greater than 95% to SEQ ID NO:6. In an embodiment, the anti-CD20 monoclonal antibody has a variable heavy chain sequence identity of greater than 98% to SEQ ID NO:5. In an embodiment, the anti-CD20 monoclonal antibody has a variable light chain sequence identity of greater than 98% to SEQ ID NO:6. In an embodiment, the anti-CD20 monoclonal antibody has a variable heavy chain sequence identity of greater than 99% to SEQ ID NO:5. In an embodiment, the anti-CD20 monoclonal antibody has a variable light chain sequence identity of greater than 99% to SEQ ID NO:6. In an embodiment, the anti-CD20 monoclonal antibody has a Fab fragment heavy chain sequence identity of greater than 90% to SEQ ID NO:7. In an embodiment, the anti-CD20 monoclonal antibody has a Fab fragment light chain sequence identity of greater than 90% to SEQ ID NO:8. In an embodiment, the anti-CD20 monoclonal antibody has a Fab fragment heavy chain sequence identity of greater than 95% to SEQ ID NO:7. In an embodiment, the anti-CD20 monoclonal antibody has a Fab fragment light chain sequence identity of greater than 95% to SEQ ID NO:8. In an embodiment, the anti-CD20 monoclonal antibody has a Fab fragment heavy chain sequence identity of greater than 98% to SEQ ID NO:7. In an embodiment, the anti-CD20 monoclonal antibody has a Fab fragment light chain sequence identity of greater than 98% to SEQ ID NO:8. In an embodiment, the anti-CD20 monoclonal antibody has a Fab fragment heavy chain sequence identity of greater than 99% to SEQ ID NO:7. In an embodiment, the anti-CD20 monoclonal antibody has a Fab fragment light chain sequence identity of greater than 99% to SEQ ID NO:8. In an embodiment, the anti-CD20 monoclonal antibody ofatumumab is an immunoglobulin G1, anti-(human B-lymphocyte antigen CD20 (membrane-spanning 4-domains subfamily A member 1, B-lymphocyte surface antigen $B_1$, Leu-16 or Bp35)); human monoclonal ofatumumab-CD20 yl heavy chain (225-214')-disulfide with human monoclonal ofatumumab-CD20κ light chain, dimer (231-231":234-234")-bisdisulfide antibody.

In an embodiment, the anti-CD20 monoclonal antibody is veltuzumab, or an antigen-binding fragment, derivative, conjugate, variant, or radioisotope-labeled complex thereof. Veltuzumab is also known as hA20. Veltuzumab is described in Goldenberg, et al., *Leuk. Lymphoma* 2010, 51, 747-55. In an embodiment, the anti-CD20 monoclonal antibody is an anti-CD20 biosimilar monoclonal antibody approved by one or more drug regulatory authority with reference to veltuzumab. In an embodiment, the anti-CD20 monoclonal antibody has a heavy chain sequence identity of greater than 90% to SEQ ID NO:9. In an embodiment, the anti-CD20 monoclonal antibody has a light chain sequence identity of greater than 90% to SEQ ID NO:10. In an embodiment, the anti-CD20 monoclonal antibody has a heavy chain sequence identity of greater than 95% to SEQ ID NO:9. In an embodiment, the anti-CD20 monoclonal antibody has a light chain sequence identity of greater than 95% to SEQ ID NO:10. In an embodiment, the anti-CD20 monoclonal antibody has a heavy chain sequence identity of greater than 98% to SEQ ID NO:9. In an embodiment, the anti-CD20 monoclonal antibody has a light chain sequence identity of greater than 98% to SEQ ID NO:10. In an embodiment, the anti-CD20 monoclonal antibody has a heavy chain sequence identity of greater than 99% to SEQ ID NO:9. In an embodiment, the anti-CD20 monoclonal antibody has a light chain sequence identity of greater than 99% to SEQ ID NO:10. In an embodiment, the anti-CD20 monoclonal antibody ofatumumab is an immunoglobulin G1, anti-(human B-lymphocyte antigen CD20 (membrane-spanning 4-domains subfamily A member 1, Leu-16, Bp35)); [218-arginine,360-glutamic acid,362-methionine]humanized mouse monoclonal hA20 yl heavy chain (224-213')-disulfide with humanized mouse monoclonal hA20κ light chain (230-230":233-233")-bisdisulfide dimer In an embodiment, the anti-CD20 monoclonal antibody is tositumomab, or an antigen-binding fragment, derivative, conjugate, variant, or radioisotope-labeled complex thereof. In an embodiment, the anti-CD20 monoclonal antibody is $^{131}$I-labeled tositumomab. In an embodiment, the anti-CD20 monoclonal antibody is an anti-CD20 biosimilar monoclonal antibody approved by one or more drug regulatory authority with reference to tositumomab. In an embodiment, the anti-CD20 monoclonal antibody has a heavy chain sequence identity of greater than 90% to SEQ ID NO:11. In an embodiment, the anti-CD20 monoclonal antibody has a light chain sequence identity of greater than 90% to SEQ ID NO:12. In an embodiment, the anti-CD20 monoclonal antibody has a heavy chain sequence identity of greater than 95% to SEQ ID NO:11. In an embodiment, the anti-CD20 monoclonal antibody has a light chain sequence identity of greater than 95% to SEQ ID NO:12. In an embodiment, the anti-CD20 monoclonal antibody has a heavy chain sequence identity of greater than 98% to SEQ ID NO:11. In an embodiment, the anti-CD20 monoclonal antibody has a light chain sequence identity of greater than 98% to SEQ ID NO:12. In an embodiment, the anti-CD20 monoclonal antibody has a heavy chain sequence identity of greater than 99% to SEQ ID NO:11. In an embodiment, the anti-CD20 monoclonal antibody has a light chain sequence identity of greater than 99% to SEQ ID NO:12.

In an embodiment, the anti-CD20 monoclonal antibody is ibritumomab, or an antigen-binding fragment, derivative, conjugate, variant, or radioisotope-labeled complex thereof. The active form of ibritumomab used in therapy is ibritumomab tiuxetan. When used with ibritumomab, the chelator tiuxetan (diethylene triamine pentaacetic acid) is complexed with a radioactive isotope such as $^{90}$Y or $^{111}$In. In an embodiment, the anti-CD20 monoclonal antibody is ibritumomab tiuxetan, or radioisotope-labeled complex thereof. In an embodiment, the anti-CD20 monoclonal antibody is an anti-CD20 biosimilar monoclonal antibody approved by one or more drug regulatory authority with reference to ibritumomab and/or ibritumomab tiuxetan. In an embodiment, the anti-CD20 monoclonal antibody has a heavy chain sequence identity of greater than 90% to SEQ ID NO:13. In an embodiment, the anti-CD20 monoclonal antibody has a light chain sequence identity of greater than 90% to SEQ ID NO:14. In an embodiment, the anti-CD20 monoclonal antibody has a heavy chain sequence identity of greater than 95% to SEQ ID NO:13. In an embodiment, the anti-CD20 monoclonal antibody has a light chain sequence identity of greater than 95% to SEQ ID NO:14. In an embodiment, the anti-CD20 monoclonal antibody has a heavy chain sequence identity of greater than 98% to SEQ ID NO:13. In an embodiment, the anti-CD20 monoclonal antibody has a light chain sequence identity of greater than 98% to SEQ ID NO:14. In an embodiment, the anti-CD20 monoclonal antibody has a heavy chain sequence identity of greater than 99% to SEQ ID NO:13. In an embodiment, the anti-CD20 monoclonal antibody has a light chain sequence identity of greater than 99% to SEQ ID NO:14.

In an embodiment, an anti-CD20 antibody selected from the group consisting of obinutuzumab, ofatumumab, veltuzumab, tositumomab, and ibritumomab, and/or antigen-binding fragments, derivatives, conjugates, variants, and radioisotope-labeled complexes thereof, is administered to a subject by infusion in a dose selected from the group consisting of about 10 mg, about 20 mg, about 25 mg, about 50 mg, about 75 mg, 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, and about 2000 mg. In an embodiment, the anti-CD20 antibody is administered weekly. In an embodiment, the anti-CD20 antibody is administered every two weeks. In an embodiment, the anti-CD20 antibody is administered every three weeks. In an embodiment, the anti-CD20 antibody is administered monthly. In an embodiment, the anti-CD20 antibody is administered at a lower initial dose, which is escalated when administered at subsequent intervals administered monthly. For example, the first infusion can deliver 300 mg of anti-CD20 antibody, and subsequent weekly doses could deliver 2,000 mg of anti-CD20 antibody for eight weeks, followed by monthly doses of 2,000 mg of anti-CD20 antibody. During any of the foregoing embodiments, the BTK inhibitors of embodiments of the present invention and combinations of the BTK inhibitors with PI3K inhibitors, JAK-2 inhibitors, and/or BCL-2 inhibitors may be administered daily, twice daily, or at different intervals as described above, at the dosages described above.

In an embodiment, the invention provides a kit comprising a composition comprising a BTK inhibitors of the present invention and combinations of the BTK inhibitors with PI3K inhibitors, JAK-2 inhibitors, and/or BCL-2 inhibitors and a composition comprising an anti-CD20 antibody selected from the group consisting of rituximab, obinutuzumab, ofatumumab, veltuzumab, tositumomab, and ibritumomab, or an antigen-binding fragment, derivative, conjugate, variant, or radioisotope-labeled complex thereof, for use in the treatment of CLL or SLL, hematological malignancies, B cell malignancies or, or any of the other diseases described herein. The compositions are typically both pharmaceutical compositions. The kit is for use in co-administration of the anti-CD20 antibody and the BTK inhibitor, either simultaneously or separately, in the treatment of CLL or SLL, hematological malignancies, B cell malignancies, or any of the other diseases described herein.

The anti-CD20 antibody sequences referenced in the foregoing are summarized in

TABLE 1

Anti-CD20 antibody sequences.

| Identifier | Sequence (One-Letter Amino Acid Symbols) | |
|---|---|---|
| SEQ ID NO: 1<br>rituximab<br>heavy chain | QVQLQQPGAE LVKPGASVKM SCKASGYTFT SYNMHWVKQT PGRGLEWIGA IYPGNGDTSY | 60 |
| | NQKFKGKATL TADKSSSTAY MQLSSLTSED SAVYYCARST YYGGDWYFNV WGAGTTVTVS | 120 |
| | AASTKGPSVF PLAPSSKSTS GGTAALGCLV KDYFPEPVTV SWNSGALTSG VHTFPAVLQS | 180 |
| | SGLYSLSSVV TVPSSSLGTQ TYICNVNHKP SNTKVDKKVE PKSCDKTHTC PPCPAPELLG | 240 |
| | GPSVFLFPPK PKDTLMISRT PEVTCVVVDV SHEDPEVKFN WYVDGVEVHN AKTKPREEQY | 300 |
| | NSTYRVVSVL TVLHQDWLNG KEYKCKVSNK ALPAPIEKTI SKAKGQPREP QVYTLPPSRD | 360 |
| | ELTKNQVSLT CLVKGFYPSD IAVEWESNGQ PENNYKTTPP VLDSDGSFFL YSKLTVDKSR | 420 |
| | WQQGNVFSCS VMHEALHNHY TQKSLSLSPG K | 451 |
| SEQ ID NO: 2<br>rituximab<br>light chain | QIVLSQSPAI LSASPGEKVT MTCRASSSVS YIHWFQQKPG SSPKPWIYAT SNLASGVPVR | 60 |
| | FSGSGSGTSY SLTISRVEAE DAATYYCQQW TSNPPTFGGG TKLEIKRTVA APSVFIFPPS | 120 |
| | DEQLKSGTAS VVCLLNNFYP REAKVQWKVD NALQSGNSQE SVTEQDSKDS TYSLSSTLTL | 180 |
| | SKADYEKHKV YACEVTHQGL SSPVTKSFNR GEC | 213 |
| SEQ ID NO: 3<br>obinutuzumab<br>heavy chain | QVQLVQSGAE VKKPGSSVKV SCKASGYAFS YSWINWVRQA PGQGLEWMGR IFPGDGDTDY | 60 |
| | NGKFKGRVTI TADKSTSTAY MELSSLRSED TAVYYCARNV FDGYWLVYWG QGTLVTVSSA | 120 |
| | STKGPSVFPL APSSKSTSGG TAALGCLVKD YFPEPVTVSW NSGALTSGVH TFPAVLQSSG | 180 |
| | LYSLSSVVTV PSSSLGTQTY ICNVNHKPSN TKVDKKVEPK SCDKTHTCPP CPAPELLGGP | 240 |
| | SVFLFPPKPK DTLMISRTPE VTCVVVDVSH EDPEVKFNWY VDGVEVHNAK TKPREEQYNS | 300 |
| | TYRVVSVLTV LHQDWLNGKE YKCKVSNKAL PAPIEKTISK AKGQPREPQV YTLPPSRDEL | 360 |
| | TKNQVSLTCL VKGFYPSDIA VEWESNGQPE NNYKTTPPVL DSDGSFFLYS KLTVDKSRWQ | 420 |
| | QGNVFSCSVM HEALHNHYTQ KSLSLSPGK | 449 |
| SEQ ID NO: 4<br>obinutuzumab<br>light chain | DIVMTQTPLS LPVTPGEPAS ISCRSSKSLL HSNGITYLYW YLQKPGQSPQ LLIYQMSNLV | 60 |
| | SGVPDRFSGS GSGTDFTLKI SRVEAEDVGV YYCAQNLELP YTFGGGTKVE IKRTVAAPSV | 120 |
| | FIFPPSDEQL KSGTASVVCL LNNFYPREAK VQWKVDNALQ SGNSQESVTE QDSKDSTYSL | 180 |
| | SSTLTLSKAD YEKHKVYACE VTHQGLSSPV TKSFNRGEC | 219 |
| SEQ ID NO: 5<br>ofatumumab<br>variable<br>heavy chain | EVQLVESGGG LVQPGRSLRL SCAASGFTFN DYAMHWVRQA PGKGLEWVST ISWNSGSIGY | 60 |
| | ADSVKGRFTI SRDNAKKSLY LQMNSLRAED TALYYCAKDI QYGNYYYGMD VWGQGTTVTV | 120 |
| | SS | 122 |
| SEQ ID NO: 6<br>ofatumumab<br>variable<br>light chain | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPITFGQ GTRLEIK | 107 |
| SEQ ID NO: 7<br>ofatumumab<br>Fab fragment<br>heavy chain | EVQLVESGGG LVQPGRSLRL SCAASGFTFN DYAMHWVRQA PGKGLEWVST ISWNSGSIGY | 60 |
| | ADSVKGRFTI SRDNAKKSLY LQMNSLRAED TALYYCAKDI QYGNYYYGMD VWGQGTTVTV | 120 |
| | SSASTKGPSV FPLAPGSSKS TSGTAALGCL VKDYFPEPVT VSWNSGALTS GVHTFPAVLQ | 180 |
| | SSGLYSLSSV VTVPSSSLGT QTYICNVNHK PSNTKVDKKV EP | 222 |
| SEQ ID NO: 8<br>ofatumumab<br>Fab fragment<br>light chain | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPITFGQ GTRLEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN R | 211 |
| SEQ ID NO: 9<br>veltuzumab<br>heavy chain | QVQLQQSGAE VKKPGSSVKV SCKASGYTFT SYNMHWVKQA PGQGLEWIGA IYPGMGDTSY | 60 |
| | NQKFKGKATL TADESTNTAY MELSSLRSED TAFYYCARST YYGGDWYFDV WGQGTTVTVS | 120 |
| | SASTKGPSVF PLAPSSKSTS GGTAALGCLV KDYFPEPVTV SWNSGALTSG VHTFPAVLQS | 180 |
| | SGLYSLSSVV TVPSSSLGTQ TYICNVNHKP SNTKVDKRVE PKSCDKTHTC PPCPAPELLG | 240 |
| | GPSVFLFPPK PKDTLMISRT PEVTCVVVDV SHEDPEVKFN WYVDGVEVHN AKTKPREEQY | 300 |
| | NSTYRVVSVL TVLHQDWLNG KEYKCKVSNK ALPAPIEKTI SKAKGQPREP QVYTLPPSRE | 360 |

TABLE 1-continued

Anti-CD20 antibody sequences.

| Identifier | Sequence (One-Letter Amino Acid Symbols) | |
|---|---|---|
| | EMTKNQVSLT CLVKGFYPSD IAVEWESNGQ PENNYKTTPP VLDSDGSFFL YSKLTVDKSR | 420 |
| | WQQGNVFSCS VMHEALHNHY TQKSLSLSPG K | 451 |
| SEQ ID NO: 10<br>veltuzumab<br>light chain | DIQLTQSPSS LSASVGDRVT MTCRASSSVS YIHWFQQKPG KAPKPWIYAT SNLASGVPVR<br>FSGSGSGTDY TFTISSLQPE DIATYYCQQW TSNPPTFGGG TKLEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |
| SEQ ID NO: 11<br>tositumomab<br>heavy chain | QAYLQQSGAE LVRPGASVKM SCKASGYTFT SYNMHWVKQT PRQGLEWIGA IYPGNGDTSY<br>NQKFKGKATL TVDKSSSTAY MQLSSLTSED SAVYFCARVV YYSNSYWYFD VWGTGTTVTV<br>SGPSVFPLAP SSKSTSGGTA ALGCLVKDYF PEPVTVSWNS GALTSGVHTF PAVLQSSGLY<br>SLSSVVTVPS SSLGTQTYIC NVNHKPSNTK VDKKAEPKSC DKTHTCPPCP APELLGGPSV<br>FLFPPKPKDT LMISRTPEVT CVVVDVSHED PEEQYNWYVD GVEVHNAKTK PREEQYNSTY<br>RVVSVLTVLH QDWLNGKEYK CKVSNKALPA PIEKTISKAK GQPREPQVYT LPPSRDELTK<br>NQVSLTCLVK GFYPSDIAVE WESNGQPENN YKTTPPVLDS DGSFFLYSKL TVDKSRWQQG<br>NVFSCSVMHE ALHNHYTQKS LSLSPGK | 60<br>120<br>180<br>240<br>300<br>360<br>420<br>447 |
| SEQ ID NO: 12<br>tositumomab<br>light chain | QIVLSQSPAI LSASPGEKVT MTCRASSSVS YMHWYQQKPG SSPKPWIYAP SNLASGVPAR<br>FSGSGSGTSY SLTISRVEAE DAATYYCQQW SFNPPTFGAG TKLELKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR | 60<br>120<br>180<br>210 |
| SEQ ID NO: 13<br>ibritumomab<br>heavy chain | QAYLQQSGAE LVRPGASVKM SCKASGYTFT SYNMHWVKQT PRQGLEWIGA IYPGNGDTSY<br>NQKFKGKATL TVDKSSSTAY MQLSSLTSED SAVYFCARVV YYSNSYWYFD VWGTGTTVTV<br>SAPSVYPLAP VCGDTTGSSV TLGCLVKGYF PEPVTLTWNS GSLSSGVHTF PAVLQSDLYT<br>LSSSVTVTSS TWPSQSITCN VAHPASSTKV DKKIEPRGPT IKPCPPCKCP APNLLGGPSV<br>FIFPPKIKDV LMISLSPIVT CVVVDVSEDD PDVQISWFVN NVEVHTAQTQ THREDYNSTL<br>RVVSALPIQH QDWMSGKEFK CKVNNKDLPA PIERTISKPK GSVRAPQVYV LPPPEEEMTK<br>KQVTLTCMVT DFMPEDIYVE WTNNGKTELN YKNTEPVLDS DGSYFMYSKL RVEKKNWVER<br>NSYSCSVVHE GLHNHHTTKS FSR | 60<br>120<br>180<br>240<br>300<br>360<br>420<br>443 |
| SEQ ID NO: 14<br>ibritumomab<br>light chain | QIVLSQSPAI LSASPGEKVT MTCRASSSVS YMHWYQQKPG SSPKPWIYAP SNLASGVPAR<br>FSGSGSGTSY SLTISRVEAE DAATYYCQQW SFNPPTFGAG TKLELKRADA APTVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFN | 60<br>120<br>180<br>209 |

Combinations of BTK Inhibitors, PI3K Inhibitors, JAK-2 Inhibitors, and/or BCL-2 Inhibitors with Chemotherapeutic Active Pharmaceutical Ingredients The combinations of the BTK inhibitors with PI3K inhibitors, JAK-2 inhibitors, and/or BCL-2 inhibitors may also be safely co-administered with chemotherapeutic active pharmaceutical ingredients such as gemcitabine and albumin-bound paclitaxel (nab-paclitaxel). In an embodiment, the invention provides a method of treating a hematological malignancy or a solid tumor cancer in a human comprising the step of administering to said human a BTK inhibitors, a PI3K inhibitor, a JAK-2 inhibitor, and/or a BCL-2 inhibitor, and further comprising the step of administering a therapeutically-effective amount of gemcitabine, or a pharmaceutically acceptable salt or ester, prodrug, cocrystal, solvate or hydrate thereof. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering a therapeutically-effective amount of gemcitabine, or a pharmaceutically acceptable salt or ester, prodrug, cocrystal, solvate or hydrate thereof. In an embodiment, the solid tumor cancer in any of the foregoing embodiments is pancreatic cancer.

In an embodiment, the invention provides a method of treating a hematological malignancy or a solid tumor cancer in a human comprising the step of administering to said human a BTK inhibitor, a PI3K inhibitor, and/or a BCL-2 inhibitor, and further comprising the step of administering a therapeutically-effective amount of a combination of fludarabine, cyclophosphamide, and rituximab (which collectively may be referred to as "FCR" or "FCR chemotherapy"). In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering a therapeutically-effective amount of FCR chemotherapy. In an embodiment, the invention provides a hematological malignancy or a solid tumor cancer comprising the step of administering to said human a BTK inhibitor and a BCL-2 inhibitor, and further comprising the step of administering a therapeutically-effective amount of FCR chemotherapy. FCR chemotherapy has been shown to improve survival in patients with cancer, as described in Hallek, et al., *Lancet.* 2010, 376, 1164-1174.

In an embodiment, the invention provides a method of treating a hematological malignancy or a solid tumor cancer in a human comprising the step of administering to said human a BTK inhibitor, a PI3K inhibitor, and/or a BCL-2 inhibitor, and further comprising the step of administering a therapeutically-effective amount of a combination of rituximab, cyclophosphamide, doxorubicin hydrochloride (also referred to as hydroxydaunomycin), vincristine sulfate (also referred to as oncovin), and prednisone (which collectively may be referred to as "R-CHOP" or "R-CHOP chemotherapy"). In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering a therapeutically-effective amount of R-CHOP chemotherapy. In an embodiment, the invention provides a hematological malignancy or a solid tumor cancer comprising the step of administering to said human a BTK inhibitor and/or a BCL-2 inhibitor, and further comprising the step of administering a therapeutically-effective amount of R-CHOP therapy. R-CHOP chemotherapy has been shown to improve the 10-year progression-free and overall survival rates for patients with cancer, as described in Sehn, *Blood,* 2010, 116, 2000-2001.

In an embodiment, the invention provides a method of treating a hematological malignancy or a solid tumor cancer in a human comprising the step of administering to said human a BTK inhibitors, a PI3K inhibitor, a JAK-2 inhibitor, and/or a BCL-2 inhibitor, and further comprising the step of administering a therapeutically-effective amount of nab-paclitaxel. In an embodiment, the invention provides a method of treating a hematological malignancy or a solid tumor cancer in a human comprising the step of administering to said human a BTK inhibitor of Formula (XVIII), or a pharmaceutically acceptable salt or ester, prodrug, cocrystal, solvate or hydrate thereof, and further comprising the step of administering a therapeutically-effective amount of nab-paclitaxel. In an embodiment, the solid tumor cancer in any of the foregoing embodiments is pancreatic cancer.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Synergistic Combination of a BTK Inhibitor and a PI3K-δ Inhibitor

Ficoll purified mantle cell lymphoma (MCL) cells ($2 \times 10^5$) isolated from bone marrow or peripheral blood were treated with each drug alone and with six equimolar concentrations of a BTK inhibitor (Formula XVIII) and a PI3K-δ inhibitor (Formula IX) ranging from 0.01 nM to 10 µM on 96-well plates in triplicate. Plated cells were then cultured in HS-5 conditioned media at 37° C. with 5% $CO_2$. After 72 hours of culture, cell viability was determined using an (3-(4,5-dimethylthiazol-2-yl)-5-(3-carboxymethoxyphenyl)-2-(4-sulfophenyl)-2H-tetrazolium) (MTS) assay (Cell Titer 96, Promega). Viability data were used to generate cell viability curves for each drug alone and in combination for each sample. The potential synergy of the combination of the BTK inhibitor of Formula XVIII and the PI3K-δ inhibitor of Formula IX at a given equimolar concentration was determined using the median effect model as described in Chou TC, Talalay P. Quantitative analysis of dose-effect relationships: the combined effects of multiple drugs or enzyme inhibitors. *Adv Enzyme Regul.* 1984; 22: 27-55. The statistical modeling was run in R using a script that utilizes the median effect model as described in Lee, et al., Interaction index and different methods for determining drug interaction in combination therapy. *J Biopharm Stat.* 2007, 17(3), 461-80. A value of 1, less than 1, and greater than 1 using R defines an additive interaction, a synergistic interaction, and an antagonistic interaction, respectively. The Lee et al. method calculates a 95% confidence interval for each data point. For each viability curve, to be considered synergistic, a data point must have an interaction index below 1 and the upper confidence interval must also be below 1. In order to summarize and demonstrate collective synergy results, an interaction dot blot was generated for the primary patient samples.

A similar approach was utilized to study diffuse large B cell lymphoma (DLBCL) (TMD8) and MCL (MINO) cell lines. Cells were treated with each drug alone and with six equimolar concentrations of the BTK inhibitor of Formula XVIII and the PI3K-δ inhibitor of Formula IX ranging from 0.003 nM to 1.0 µM (for TMD8) or 0.03 nM to 10 µM (for MINO) on 96-well plates in triplicate. Plated cells were then cultured in standard conditioned media plus FBS at 37° C. with 5% $CO_2$. After 72 hours of culture, viability was determined using an MTS assay (Cell Titer 96, Promega). Viability data were used to generate cell viability curves for each drug alone and in combination for each sample. The results of the experiments described in this example are shown in FIG. 1, FIG. 2, FIG. 3, and FIG. 4.

Example 2—Synergistic Combination of a BTK Inhibitor and a PI3K-δ Inhibitor

Combination experiments were performed to determine the synergistic, additive, or antagonistic behavior of drug combinations using the Chou/Talalay method/algorithm by defining combination indexes for drug combinations. Information about experimental design for evaluation of synergy is described in e.g. Chou TC, Talalay P. Quantitative analysis of dose-effect relationships: the combined effects of multiple drugs or enzyme inhibitors. *Adv. Enzyme Regul.* 1984, 22, 27-55 and more generally in e.g.: Greco, W. R., Bravo, G., Parsons, J. C. The search for synergy: a critical review from a response surface perspective. *Pharmacol. Rev.* 1995, 47, 331-385. The study was performed using the BTK inhibitor of Formula XVIII and the PI3K-inhibitor of Formula IX. Single agent activities were first determined in the various cell lines and subsequently, the combination indexes were established using equimolar ratios taking the single agent drug EC50s into consideration. For individual agents that displayed no single agent activity, equimolar ratios were used at fixed concentrations to establish combination indexes. The readout from 72 hour proliferation assays using Cell TiterGlo (ATP content of remaining cells) determined the fraction of cells that were effected as compared to untreated cells (Fa=fraction affected=(1−((cells+inhibitor)−background signal)/((cells+DMSO)−background signal))).

The combination index obtained was ranked according to Table 2.

TABLE 2

Combination Index (CI) Ranking Scheme

| Range of CI | Description |
| --- | --- |
| <0.1 | Very strong synergism |
| 0.1-0.3 | Strong synergism |
| 0.3-0.7 | Synergism |
| 0.7-0.85 | Moderate synergism |
| 0.85-0.9 | Slight synergism |
| 0.9-1.1 | Nearly additive |
| 1.1-1.2 | Slight antagonism |
| 1.2-1.45 | Moderate antagonism |
| 1.45-3.3 | Antagonism |

TABLE 2-continued

Combination Index (CI) Ranking Scheme

| Range of CI | Description |
|---|---|
| 3.3-10 | Strong antagonism |
| >10 | Very strong antagonism |

The detailed results of the cell line studies for the BTK inhibitor of Formula XVIII and the PI3K-δ inhibitor of Formula IX are given in FIG. 5 to FIG. 37. The results of the cell line studies are summarized in Table 3.

TABLE 3

Summary of results of the combination of a BTK inhibitor with a PI3K-δ inhibitor (S = synergistic, A = additive, X = no effect).

| Cell Line | Indication | ED25 | ED50 | ED75 | ED90 |
|---|---|---|---|---|---|
| Raji | Burkitts | S | S | S | S |
| Ramos | Burkitts | X | X | X | X |
| Daudi | Burkitts | S | S | S | S |
| Mino | MCL | S | S | S | S |
| Pfeiffer | iNHL | S | S | S | S |
| DOHH | iNHL | S | S | S | S |
| REC-1 | iNHL | S | S | A | A |
| U937 | Myeloid | S | S | S | S |
| K562 | CML | X | X | X | X |
| SU-DHL-1 | ABC | S | A | X | X |
| SU-DHL-2 | ABC | S | S | S | S |
| HBL-1 | ABC | S | S | S | S |
| TMD8 | ABC | S | S | S | S |
| LY19 | GCB | X | X | X | X |
| LY7 | GCB | S | S | S | S |
| LY1 | GCB | X | X | X | X |
| SU-DHL-6 | GCB | S | S | S | S |
| SupB15 | B-ALL | S | S | S | S |
| CCRF | B-ALL | S | A/S | X | X |

Example 3—Synergistic Combination of a BTK Inhibitor and the JAK-2 Inhibitor Ruxolitinib Combination experiments were performed to determine the synergistic, additive, or antagonistic behavior of drug combinations using the methods described above in Example 2. The study was performed using the BTK inhibitor of Formula XVIII and the JAK-2 inhibitor of Formula XXX (ruxolitinib).

The detailed results of the cell line studies for the BTK inhibitor of Formula XVIII and the JAK-2 inhibitor of Formula XXX (ruxolitinib) are given in FIG. 38 to FIG. 65. The results of the cell line studies are summarized in Table 4.

TABLE 4

Summary of results of the combination of a BTK inhibitor with a JAK-2 inhibitor (S = synergistic, A = additive, X = no effect).

| Cell Line | Indication | ED25 | ED50 | ED75 | ED90 |
|---|---|---|---|---|---|
| Raji | Burkitt's | S | S | S | S |
| Ramos | Burkitt's | S | S | S | S |
| Daudi | Burkitt's | S | S | S | S |
| Mino | MCL | S | S | S | S |
| Pfeiffer | iNHL | S | S | S | S |
| DOHH | iNHL | S | S | S | S |
| REC-1 | iNHL | S | S | S | S |
| JVM-2 | CLL like | S | S | S | X |
| U937 | Myeloid | X | X | X | X |

TABLE 4-continued

Summary of results of the combination of a BTK inhibitor with a JAK-2 inhibitor (S = synergistic, A = additive, X = no effect).

| Cell Line | Indication | ED25 | ED50 | ED75 | ED90 |
|---|---|---|---|---|---|
| K562 | CML | X | X | X | X |
| SU-DHL-1 | ABC | S | S | S | S |
| SU-DHL-2 | ABC | S | S | S | X |
| HBL-1 | ABC | S | S | S | S |
| TMD8 | ABC | S | S | S | S |
| LY19 | GCB | X | X | X | X |
| LY7 | GCB | X | X | X | X |
| LY1 | GCB | X | X | X | X |
| SU-DHL-6 | GCB | S | S | X | X |
| SupB15 | B-ALL | X | X | X | X |
| CCRF | B-ALL | X | X | A | A |

Example 4—Synergistic Combination of a BTK Inhibitor and the JAK-2 Inhibitor Pacritinib Combination experiments were performed to determine the synergistic, additive, or antagonistic behavior of drug combinations using the methods described above in Example 2. The study was performed using the BTK inhibitor of Formula (XVIII) and the JAK-2 inhibitor of Formula LIV (pacritinib).

The detailed results of the cell line studies for the BTK inhibitor of Formula (XVIII) and the JAK-2 inhibitor of Formula LIV (pacritinib) are given in FIG. 66 to FIG. 94. The results of the cell line studies are summarized in Table 5.

TABLE 5

Summary of results of the combination of a BTK inhibitor with the JAK-2 inhibitor of Formula LIV (pacritinib) (S = synergistic, A = additive, X = no effect).

| Cell Line | Indication | ED25 | ED50 | ED75 | ED90 |
|---|---|---|---|---|---|
| Mino | MCL | S | S | S | S |
| JVM-2 | prolymphocytic leukemia | S | S | S | S |
| Maver-1 | B-ALL, MCL | S | S | S | S |
| Raji | B-ALL, Burkitt's | S | S | S | S |
| Daudi | Burkitt's | S | S | S | S |
| Rec-1 | FL | X | S | S | S |
| CCRF | B-ALL | S | S | S | S |
| Sup-B15 | B-ALL | S | S | A | A |
| SU-DHL-4 | DLBCL-ABC | S | S | S | S |
| EB3 | B-ALL, Burkitt's | S | S | S | S |
| CA46 | B-ALL, Burkitt's | S | S | S | S |
| Pfeiffer | FL | S | S | S | S |
| DB | B-ALL, MCL | S | S | S | S |
| DOHH2 | FL | S | S | S | S |
| Namalwa | B-ALL, Burkitt's | S | S | S | S |
| JVM-13 | B-ALL, MCL | S | S | S | S |
| SU-DHL-1 | DLBCL-ABC | S | S | S | S |
| SU-DHL-2 | DLBCL-ABC | S | S | S | X |
| Ramos | Burkitt's | S | S | S | S |
| SU-DHL-6 | DLBCL-GCB | S | S | S | A |
| TMD-8 | DLBCL-ABC | X | X | S | S |
| SU-DHL-10 | DLBCL-GCB | S | S | S | S |
| HBL-1 | DLBCL-ABC | S | S | S | X |
| OCI-Ly3 | DLBCL-ABC | S | S | S | S |
| OCI-Ly7 | DLBCL-ABC | S | S | S | S |
| Jeko | B-ALL, MCL | S | S | S | S |

Example 5—Synergistic Combination of a BCL-2 Inhibitor and the BTK Inhibitor of Formula (XVIII)

Combination experiments were performed to determine the synergistic, additive, or antagonistic behavior of drug combinations using the methods described above in Example 2. The study was performed using the BTK inhibitor of Formula (XVIII) and the BCL-2 inhibitor of Formula (LXVI) (venetoclax).

The detailed results of the cell line studies for the BTK inhibitor of Formula (XVIII) and the BCL-2 inhibitor of Formula (LXVI) (venetoclax) are given in FIG. 95 to FIG. 115. The results of the cell line studies are summarized in Table 6.

TABLE 6

Summary of results of the combination of a BTK inhibitor with a BCL-2 inhibitor (S = synergistic, A = additive, X = no effect).

| Cell Line | Indication | ED25 | ED50 | ED75 | ED90 |
| --- | --- | --- | --- | --- | --- |
| Mino | MCL | A | S | S | S |
| U937 | Myeloid | S | S | S | S |
| JVM-13 | Mantle | S | S | S | S |
| K562 | CML | X | X | X | X |
| REC-1 | iNHL | X | S | S | S |
| EB3 | Burkitt's | X | S | S | S |
| CA46 | Burkitt's | X | X | X | X |
| DB | DLBCL | X | A | A | A |
| Namalwa | Burkitts | X | S | S | S |
| HBL-1 | ABC | X | S | S | S |
| SU-DHL-10 | GCB | X | A | S | S |
| Maver-1 | Mantle | S | S | S | S |
| SU-DHL-1 | ABC | X | S | S | S |
| Pfeiffer | iNHL | X | S | S | X |
| SU-DHL-2 | ABC | X | X | X | X |
| TMD-8 | ABC | S | S | A | X |
| Raji | Burkitt's | X | X | X | X |
| Jeko | Mantle | S | S | S | S |

Example 6—Synergistic Combination of a BCL-2 Inhibitor and the BTK Inhibitor Ibrutinib Combination experiments were performed to determine the synergistic, additive, or antagonistic behavior of drug combinations using the methods described above in Example 2. The study was performed using the BTK inhibitor of Formula (XX-A) (ibrutinib) and the BCL-2 inhibitor of Formula (LXVI) (venetoclax). Proliferation was again determined with MTS (CellTiter 96 AQueous, Promega). Incubations were performed for 96 hours.

The detailed results of the cell line studies for the BTK inhibitor of Formula (XX-A) (ibrutinib) and the BCL-2 inhibitor of Formula (LXVI) (venetoclax) are given in FIG. 116 to FIG. 120. The results of the cell line studies are summarized in Table 7.

TABLE 7

Summary of results of the combination of a BTK inhibitor with a BCL-2 inhibitor (S = synergistic, A = additive, X = no effect).

| Cell Line | Indication | ED25 | ED50 | ED75 | ED90 |
| --- | --- | --- | --- | --- | --- |
| TMD-8 | DLBCL-ABC | S | S | S | S |
| RI-1 | NHL | A | A | A | S |
| Mino | MCL | A | S | S | S |
| SU-DHL-6 | DLBCL-GCB and/or PTCL | A | S | S | S |

Example 7—Effects of BTK Inhibitors on Thrombosis

Clinical studies have shown that targeting the BCR signaling pathway by inhibiting BTK produces significant clinical benefit (Byrd, et al., *N. Engl. J. Med.* 2013, 369(1), 32-42, Wang, et al., *N. Engl. J. Med.* 2013, 369(6), 507-16). However, in these studies, bleeding has been reported in up to 50% of ibrutinib-treated patients. Most bleeding events were of grade 1-2 (spontaneous bruising or petechiae) but, in 5% of patients, they were of grade 3 or higher after trauma. These results are reflected in the prescribing information for ibrutinib, where bleeding events of any grade, including bruising and petechiae, were reported in approximately half of patients treated with ibrutinib (IMBRUVICA package insert and prescribing information, revised July 2014, U.S. Food and Drug Administration).

Constitutive or aberrant activation of the BCR signaling cascade has been implicated in the propagation and maintenance of a variety of B cell malignancies. Small molecule inhibitors of BTK, a protein early in this cascade and specifically expressed in B cells, have emerged as a new class of targeted agents. There are several BTK inhibitors, including Formula XXVII (CC-292), and Formula (XX-A) (PCI-32765, ibrutinib), in clinical development. Importantly, early stage clinical trials have found ibrutinib to be particularly active in chronic lymphocytic leukemia (CLL) and mantle cell lymphoma (MCL), suggesting that this class of inhibitors may play a significant role in various types of cancers (Aalipour and Advani, *Br. J. Haematol.* 2013, 163, 436-43). However, their effects are not limited to leukemia or lymphomas as platelets also rely on the Tec kinases family members BTK and Tec for signal transduction in response to various thrombogenic stimuli (Oda, et al., *Blood* 2000, 95(5), 1663-70; Atkinson, et al. *Blood* 2003, 102(10), 3592-99). In fact, both Tec and BTK play an important role in the regulation of phospholipase Cy2 (PLCy2) downstream of the collagen receptor glycoprotein VI (GPVI) in human platelets. In addition, BTK is activated and undergoes tyrosine phosphorylation upon challenge of the platelet thrombin receptor, which requires the engagement of $\alpha IIb\beta 3$ integrin and PI3K activity (Laffargue, et al., *FEBS Lett.* 1999, 443(1), 66-70). It has also been implicated in GPIbα-dependent thrombus stability at sites of vascular injury (Liu, et al., *Blood* 2006, 108(8), 2596-603). Thus, BTK and Tec are involved in several processes important in supporting the formation of a stable hemostatic plug, which is critical for preventing significant blood loss in response to vascular injury. Hence, the effects of the BTK inhibitor of Formula (XVIII) and ibrutinib were evaluated on human platelet-mediated thrombosis by utilizing the in vivo human thrombus formation in the VWF HA1 mice model described in Chen, et al. *Nat. Biotechnol.* 2008, 26(1), 114-19.

Administration of anesthesia, insertion of venous and arterial catheters, fluorescent labeling and administration of human platelets ($5 \times 10^8$/ml), and surgical preparation of the cremaster muscle in mice have been previously described (Chen, et al. *Nat Biotechnol.* 2008, 26(1), 114-19). Injury to the vessel wall of arterioles (~40-65 mm diameter) was performed using a pulsed nitrogen dye laser (440 nm, Photonic Instruments) applied through a 20x water-immersion Olympus objective (LUMPlanFl, 0.5 numerical aperature (NA)) of a Zeiss Axiotech vario microscope. Human platelet and wall interactions were visualized by fluorescence microscopy using a system equipped with a Yokogawa CSU-22 spinning disk confocal scanner, iXON EM camera, and 488 nm and 561 nm laser lines to detect BCECF-labeled and rhodamine-labeled platelets, respectively (Revolution XD, Andor Technology). The extent of thrombus formation was assessed for 2 minutes after injury and the area ($\mu m^2$) of coverage determined (Image IQ, Andor Technology). For the Formula (XVIII), Formula (XXVII) (CC-292), and Formula (XX-A) (ibrutinib) inhibition studies, the BTK inhibitors were were added to purified human platelets for 30 minutes before administration.

The in vivo throbus effects of the BTK inhibitors, Formula (XVIII), Formula (XXVII) (CC-292), and Formula (XX-A) (ibrutinib), were evaluated on human platelet-mediated thrombosis by utilizing the in vivo human thrombus formation in the VWF HA1 mice model, which has been previously described (Chen, et al. *Nat Biotechnol.* 2008, 26(1), 114-19). Purified human platelets were preincubated with various concentrations of the BTK inhibitors (0.1 uM, 0.5 uM, or 1 uM) or DMSO and then administered to VWF HA1 mice, followed by laser-induced thrombus formation. The BTK inhibitor-treated human platelets were fluorescently labeled and infused continuously through a catheter inserted into the femoral artery. Their behavior in response to laser-induced vascular injury was monitored in real time using two-channel confocal intravital microscopy (Furie and Furie, *J. Clin. Invest.* 2005, 115(12), 2255-62).

The objective of this study was to evaluate in vivo thrombus formation in the presence of BTK inhibitors. In vivo testing of novel antiplatelet agents requires informative biomarkers. By utilizing a genetic modified mouse von Willebrand factor (VWFR1326H) model that supports human but not mouse platelet-mediated thrombosis, we evaluated the effects of Formula (XVIII), Formula XXVII (CC-292), and Formula (XX-A) (ibrutinib) on thrombus formation. These results show that Formula (XVIII) had no significant effect on human platelet-mediated thrombus formation while Formula (XX-A) (ibrutinib) was able to limit this process, resulting in a reduction in maximal thrombus size by 61% compared with control. Formula XXVII (CC-292) showed an effect similar to Formula (XX-A) (ibrutinib). These results, which show reduced thrombus formation for ibrutinib at physiologically relevant concentrations, may provide some mechanistic background for the Grade ≥3 bleeding events (eg, subdural hematoma, gastrointestinal bleeding, hematuria and postprocedural hemorrhage) that have been reported in ≤6% of patients treated with Formula (XX-A) (ibrutinib).

GPVI platelet aggregation was measured for Formula (XVIII) and Formula (XX-A) (ibrutinib). Blood was obtained from untreated humans, and platelets were purified from plasma-rich protein by centrifugation. Cells were resuspended to a final concentration of 350,000/μL in buffer containing 145 mmol/L NaCl, 10 mmol/L HEPES, 0.5 mmol/L $Na_2HPO_4$, 5 mmol/L KCl, 2 mmol/L $MgCl_2$, 1 mmol/L $CaCl_2$), and 0.1% glucose, at pH 7.4. Stock solutions of Convulxin (CVX) GPVI were prepared on the day of experimentation and added to platelet suspensions 5 minutes (37° C., 1200 rpm) before the induction of aggregation. Aggregation was assessed with a Chronolog Lumi-Aggregometer (model 540 VS; Chronolog, Havertown, Pa.) and permitted to proceed for 6 minutes after the addition of agonist. The results are reported as maximum percent change in light transmittance from baseline with platelet buffer used as a reference. The results are shown in FIG. 122.

In FIG. 123, the results of CVX-induced (250 ng/mL) human platelet aggregation results before and 15 minutes after administration of the BTK inhibitors to 6 healthy individuals are shown.

The results depicted in FIG. 122 and FIG. 123 indicate that the BTK inhibitor of Formula (XX-A) (ibrutinib) significantly inhibits GPVI platelet aggregation, while the BTK inhibitor of Formula (XVIII) does not, further illustrating the surprising benefits of the latter compound.

Example 8—Study of a BTK Inhibitor and a Combination of a BTK Inhibitor and a PI3K Inhibitor in Canine Lymphoma Canine B cell lymphoma exists as a pathological entity that is characterized by large anaplastic, centroblastic or immunoblastic lymphocytes with high proliferative grade, significant peripheral lymphadenopathy and an aggressive clinical course. While some dogs respond initially to prednisone, most canine lymphomas progress quickly and must be treated with combination therapies, including cyclophosphamide, vincristine, doxorubicin, and prednisone (CHOP), or other cytotoxic agents. In their histopathologic features, clinical course, and high relapse rate after initial treatment, canine B cell lymphomas resemble diffuse large B cell lymphoma (DLBCL) in humans. Thus, responses of canine B cell lymphomas to experimental treatments are considered to provide proof of concept for therapeutic candidates in DLBCL.

In this example, companion dogs with newly diagnosed or relapsed/refractory B cell lymphoma were enrolled on a veterinary clinical trial of the BTK inhibitor of Formula (XVIII) ("Arm 1") or the BTK inhibitor of Formula (XVIII) and the PI3K-δ inhibitor of Formula (IX) ("Arm 2"). Enrollment has completed for both arms. The results show that combined treatment with the BTK inhibitor of Formula (XVIII) and the PI3K-δ inhibitor of Formula (IX) may have greater efficacy than treatment with the BTK inhibitor of Formula (XVIII) alone in aggressive lymphomas.

Twenty-one dogs were treated in Arm 1 with the BTK inhibitor of Formula (XVIII) at dosages of 2.5 mg/kg once daily to 20 mg/kg twice daily. Intra-subject dose escalation was allowed. Six of the 11 dogs that initiated at 2.5 or 5 mg/kg once daily were escalated and completed the study with dosages of 10 mg/kg twice daily. Among all the dose cohorts, 8 dogs had shrinkage of target lesions >20%; the best tumor responses were between 45-49% reduction in the sum of target lesions in two dogs. Complete responses ("CR", disappearance of all evidence of disease per evaluator judgment; and absence of new lesions) were not observed in Arm 1. CR were defined as disappearance of all evidence of disease per evaluator judgment, and absence of new lesions. Vali, et al., *Vet. Comp. Oncol.* 2010, 8, 28-37.

In the combination phase of the study (Arm 2), 10 dogs were treated with 10 mg/kg the BTK inhibitor of Formula (XVIII) and the PI3K-δ inhibitor of Formula (IX) at 2.5 or 3.5 mg/kg, on a twice daily schedule. Of these, 7 dogs had shrinkage of target lesions >20%, providing evidence of biological activity for the combination; four of these dogs achieved a PR. The best tumor responses were between 58-65% reduction in the sum of target lesions, with one sustained CR observed among the 10 dogs treated. The initial reductions in the sum of target lesions continued to deepen during the course of therapy in 7 of the 10 dogs. A summary of the results is presented in Table 8.

TABLE 8

Summary of the results of the canine lymphoma study.

| Response Metric | Formula (XVIII) and Formula (IX) | Formula (XVIII) monotherapy |
| --- | --- | --- |
| Sum $LD^a$ decreased by ≥20% | 7/10 (70%) | 8/21 (38.1%) |
| Sum $LD^a$ decreased by ≥30% (PR) | 4/10 (40%) | 6/21 (28.6%) |

TABLE 8-continued

Summary of the results of the canine lymphoma study.

| Response Metric | Formula (XVIII) and Formula (IX) | Formula (XVIII) monotherapy |
|---|---|---|
| CR by investigator evaluation | 1/10 (10%) | 0/21 (0%) |
| Median time on study | 23 days | 24 days |
| Median time to best response | 18 days | 7 days |

[a]LD, longest diameter of up to 5 target lesions.

These data suggest that in companion dogs with naturally occurring B cell lymphomas, treatment with the combination of the BTK inhibitor of Formula (XVIII) and the PI3K-δ inhibitor of Formula (IX) may provide increased biological activity (tumor shrinkage and stable disease) and may possibly lead to deeper responses than treatment with the BTK inhibitor of Formula (XVIII) alone. The higher rate of biological responses and extended response duration (median time to best response), along with the observation of a CR in this aggressive disease setting, provide evidence of synergy between Formula (XVIII) and Formula (IX).

Example 9—Preclinical Characteristics of BTK Inhibitors

The BTK inhibitor ibrutinib ((1-[(3R)-3-[4-amino-3-(4-phenoxyphenyl)-1H-pyrazolo[3,4-d]pyrimidin-1-yl]piperidin-1-yl]prop-2-en-1-one) is a first-generation BTK inhibitor. In clinical testing as a monotherapy in subjects with hematologic malignancies, ibrutinib was generally well tolerated at dose levels through 840 mg (the highest dose tested). Advani, et al., J. Clin. Oncol. 2013, 31, 88-94; Byrd, et al., N. Engl. J. Med. 2013, 369, 32-42; Wang, et al., N. Engl. J. Med. 2013, 369, 507-16. No maximum tolerated dose (MTD) was apparent within the tested dose range. Furthermore, subjects typically found the drug tolerable over periods extending to >2 years. No subject had tumor lysis syndrome. No overt pattern of myelosuppression was associated with ibrutinib treatment. No drug-related reductions in circulating CD4$^+$ T cells or serum immunoglobulins were noted. Adverse events with an apparent relationship to study drug included diarrhea and rash.

In subjects with heavily pretreated non-Hodgkin lymphoma (NHL), ibrutinib showed substantial antitumor activity, inducing durable regressions of lymphadenopathy and splenomegaly in most subjects. Improvements in disease-associated anemia and thrombocytopenia were observed. The pattern of changes in subjects with CLL was notable. Single-active pharmaceutical ingredient ibrutinib caused rapid and substantial reductions in lymph node size concomitant with a redistribution of malignant sites into the peripheral blood. An asymptomatic absolute lymphocyte count (ALC) increase was observed that was maximal during the first few months of treatment and generally decreased thereafter but could be persistent in some subjects or could be seen repeatedly in subjects who had interruption and resumption of drug therapy.

Collectively, these data with ibrutinib support the potential benefits of selective BTK inhibition in the treatment of subjects with relapsed lymphoid cancers. However, while highly potent in inhibiting BTK, ibrutinib has also shown in vitro activity against other kinases with a cysteine in the same position as Cys481 in BTK to which the drug covalently binds. For example, ibrutinib inhibits epidermal growth factor receptor (EGFR), which may be the cause of ibrutinib-related diarrhea and rash. In addition, it is a substrate for both cytochrome P450 (CYP) enzymes 3A4/5 and 2D6, which increases the possibility of drug-drug interactions. These liabilities support the development of alternative BTK inhibitors for use in the therapy of lymphoid cancer.

The preclinical selectivity and potency characteristics of the second-generation BTK inhibitor of Formula (XVIII) were compared to the first-generation BTK inhibitor ibrutinib. In Table 9, a kinome screen (performed Life Technologies or based on literature data) is shown that compares these compounds.

TABLE 9

Kinome Screen for BTK Inhibitors (IC$_{50}$, nM)

| 3F-Cys Kinase | Formula (XVIII) | Ibrutinib (Formula (XX-A)) |
|---|---|---|
| Btk | 3.1 | 0.5 |
| Tec | 29 | 78 |
| Bmx | 39 | 0.80 |
| Itk | >1000 | 10.7 |
| Txk | 291 | 2.0 |
| EGFR | >1000 | 5.6 |
| ErbB2 | 912 | 9.4 |
| ErbB4 | 13.2 | 2.7 |
| Blk | >1000 | 0.5 |
| JAK-3 | >1000 | 16.1 |

The results shown in Table 9 are obtained from a 10 point biochemical assay generated from 10 point concentration curves. The BTK inhibitor of Formula (XVIII) shows much greater selectivity for BTK compared to other kinases than ibrutinib.

A comparison of the in vivo potency results for the BTK inhibitors of Formula (XVIII) and ibrutinib is shown in FIG. 124. CD86 and CD69 are cell surface proteins that are BCR activation markers. To obtain the in vivo potency results, mice were gavaged at increasing drug concentration and sacrificed at one time point (3 h post-dose). BCR was stimulated with IgM and the expression of activation marker CD69 and CD86 are monitored by flow cytometry and to determine EC$_{50}$ values.

In vitro and in vivo safety pharmacology studies with Formula (XVIII) have demonstrated a favorable nonclinical safety profile. When screened at 10 μM in binding assays evaluating interactions with 80 known pharmacologic targets such as G-protein-coupled receptors, nuclear receptors, proteases, and ion channels, Formula (XVIII) shows significant activity only against the A3 adenosine receptor; follow-up dose-response experiments indicated a IC50 of 2.711M, suggesting a low clinical risk of off-target effects. Formula (XVIII) at 10 μM showed no inhibition of in vitro EGFR phosphorylation in an A431 human epidermoid cancer cell line whereas ibrutinib had an IC50 of 66 nM. The in vitro effect of Formula (XVIII) on human ether-a-go-go-related gene (hERG) channel activity was investigated in vitro in human embryonic kidney cells stably transfected with hERG. Formula (XVIII) inhibited hERG channel activity by 25% at 10 μM, suggesting a low clinical risk that Formula (XVIII) would induce clinical QT prolongation as predicted by this assay. Formula (XVIII) was well tolerated in standard in vivo Good Laboratory Practices (GLP) studies of pharmacologic safety. A functional observation battery in rats at doses of through 300 mg/kg (the highest dose level) revealed no adverse effects on neurobehavioral effects or body temperature at any dose level. A study of respiratory function in rats also indicated no treatment-related adverse effects at doses through 300 mg/kg (the highest dose level). In a cardiovascular function study in awake telemeterized male beagle dogs, single doses of Formula (XVIII) at dose levels through 30 mg/kg (the highest dose level) induced no meaningful changes in body temperature, cardiovascular, or electrocardiographic (ECG) (including QT interval) parameters. The results suggest that Formula (XVIII) is unlikely to cause serious off-target effects or adverse effects on critical organ systems.

The drug-drug interaction potential of Formula (XVIII) was also evaluated. In vitro experiments evaluating loss of parent drug as catalyzed by CYPs indicated that Formula (XVIII) is metabolized by CYP3A4. In vitro metabolism studies using mouse, rat, dog, rabbit, monkey, and human hepatocytes incubated with $^{14}$C-labeled Formula (XVIII) indicated two mono-oxidized metabolites and a glutathione conjugate. No unique human metabolite was identified. Preliminary evaluations of metabolism in the plasma, bile, and urine of rats, dogs, and monkeys indicated metabolic processes of oxidation, glutathione binding, and hydrolysis. It was shown that Formula (XVIII) binds to glutathione but does not deplete glutathione in vitro. Nonclinical CYP interaction studies data indicate that Formula (XVIII) is very unlikely to cause clinical drug-drug interactions through alteration of the metabolism of drugs that are substrates for CYP enzymes.

Example 10—Clinical Study of a BTK Inhibitor in Leukemia/Lymphoma and Effects on Bone Marrow and Lymphoid Microenvironments Clinical studies have shown that targeting the BCR signaling pathway by inhibiting BTK produces significant clinical benefit in patients with non-Hodgkin's lymphoma (NHL). The second generation BTK inhibitor, Formula (XVIII), achieves significant oral bioavailability and potency, and has favorable preclinical characteristics, as described above. The purpose of this study is to evaluate the safety and efficacy of the second generation BTK inhibitor of Formula (XVIII) in treating subjects with chronic lymphocytic leukemia (CLL) and small lymphocytic lymphoma (SLL).

The design and conduct of this study is supported by an understanding of the history and current therapies for subjects with lymphoid cancers; knowledge of the activity and safety of a first-generation BTK inhibitor, ibrutinib, in subjects with hematologic cancers; and the available nonclinical information regarding Formula (XVIII). The collective data support the following conclusions. BTK expression plays an important role in the biology of lymphoid neoplasms, which represent serious and life-threatening disorders with continuing unmet medical need. Clinical evaluation of Formula (XVIII) as a potential treatment for these disorders has sound scientific rationale based on observations that the compound selectively abrogates BTK activity and shows activity in nonclinical models of lymphoid cancers. These data are supported by clinical documentation that ibrutinib, a first-generation BTK inhibitor, is clinically active in these diseases. Ibrutinib clinical data and Formula (XVIII) nonclinical safety pharmacology and toxicology studies support the safety of testing Formula (XVIII) in subjects with B cell malignancies.

The primary objectives of the clinical study are as follows: (1) establish the safety and the MTD of orally administered Formula (XVIII) in subjects with CLL/SLL; (2) determine pharmacokinetics (PK) of orally administered Formula (XVIII) and identification of its major metabolite(s); and (3) measure pharmacodynamic (PD) parameters including drug occupancy of BTK, the target enzyme, and effect on biologic markers of B cell function.

The secondary objective of the clinical study is to evaluate tumor responses in patients treated with Formula (XVIII).

This study is a multicenter, open-label, nonrandomized, sequential group, dose escalation study. The following dose cohorts will be evaluated:
Cohort 1: 100 mg/day for 28 days (=1 cycle)
Cohort 2: 175 mg/day for 28 days (=1 cycle)
Cohort 3: 250 mg/day for 28 days (=1 cycle)
Cohort 4: 350 mg/day for 28 days (=1 cycle)
Cohort 5: 450 mg/day for 28 days (=1 cycle)
Cohort 6: To be determined amount in mg/day for 28 days (=1 cycle)

Each cohort will be enrolled sequentially with 6 subjects per cohort. If ≤1 dose-limiting toxicity (DLT) is observed in the cohort during Cycle 1, escalation to the next cohort will proceed. Subjects may be enrolled in the next cohort if 4 of the 6 subjects enrolled in the cohort completed Cycle 1 without experiencing a DLT, while the remaining 2 subjects are completing evaluation. If ≥2 DLTs are observed during Cycle 1, dosing at that dose and higher will be suspended and the MTD will be established as the previous cohort. The MTD is defined as the largest daily dose for which fewer than 33% of the subjects experience a DLT during Cycle 1. Dose escalation will end when either the MTD is achieved or at 3 dose levels above full BTK occupancy, whichever occurs first. Full BTK occupancy is defined as Formula (XVIII) active-site occupancy of ≥80% (average of all subjects in cohort) at 24 hours postdose. Should escalation to Cohort 6 be necessary, the dose will be determined based on the aggregate data from Cohorts 1 to 5, which includes safety, efficacy, and PK/PD results. The dose for Cohort 6 will not exceed 900 mg/day.

Treatment with Formula (XVIII) may be continued for >28 days until disease progression or an unacceptable drug-related toxicity occurs. Subjects with disease progression will be removed from the study. All subjects who discontinue study drug will have a safety follow-up visit 30 (±7) days after the last dose of study drug unless they have started another cancer therapy within that timeframe. Radiologic tumor assessment will be done at screening and at the end of Cycle 2, Cycle 4, and Cycle 12 and at investigator discretion. Confirmation of complete response (CR) will require bone marrow analysis and radiologic tumor assessment. For subjects who remain on study for >11 months, a mandatory bone marrow aspirate and biopsy is required in Cycle 12 concurrent with the radiologic tumor assessment.

All subjects will have standard hematology, chemistry, and urinalysis safety panels done at screening. This study also includes pancreatic function assessment (serum amylase and serum lipase) due to the pancreatic findings in the 28-day GLP rat toxicity study. Once dosing commences, all subjects will be evaluated for safety once weekly for the first 4 weeks, every other week for Cycle 2, and monthly thereafter. Blood samples will be collected during the first week of treatment for PK/PD assessments. ECGs will be done at screening, and on Day 1-2, 8, 15, 22, 28 of Cycle 1, Day 15 and 28 of Cycle 2, and monthly thereafter through Cycle 6. ECGs are done in triplicate for screening only. Thereafter, single ECG tests are done unless a repeat ECG testing is required.

Dose-limiting toxicity is defined as any of the following events (if not related to disease progression): (1) any Grade ≥3 non-hematologic toxicity (except alopecia) persisting despite receipt of a single course of standard outpatient symptomatic therapy (e.g., Grade 3 diarrhea that responds to a single, therapeutic dose of Imodium® would not be considered a DLT); (2) grade ≥3 prolongation of the corrected QT interval (QTc), as determined by a central ECG laboratory overread; (3) grade 4 neutropenia (absolute neutrophil count [ANC]<500/µL) lasting >7 days after discontinuation of therapy without growth factors or lasting >5 days after discontinuation of therapy while on growth factors (i.e., Grade 4 neutropenia not lasting as long as specified will not be considered a DLT), (4) grade 4 thrombocytopenia (platelet count <20,000/µL) lasting >7 days after discontinuation of therapy or requiring transfusion (i.e., Grade 4 thrombocytopenia not lasting as long as specified will not be considered a DLT), and (5) dosing delay due to toxicity for >7 consecutive days.

The efficacy parameters for the study include overall response rate, duration of response, and progression-free survival (PFS). The safety parameters for the study include DLTs and MTD, frequency, severity, and attribution of adverse events (AEs) based on the Common Terminology Criteria for Adverse Events (CTCAE v4.03) for non-hematologic AEs. Hallek, et al., *Blood* 2008, 111, 5446-5456.

The schedule of assessments is as follows, with all days stated in the following meaning the given day or +/−2 days from the given day. A physical examination, including vital signs and weight, are performed at screening, during cycle 1 at 1, 8, 15, 22, and 28 days, during cycle 2 at 15 and 28 days, during cycles 3 to 24 at 28 days, and at follow up (after the last dose). The screening physical examination includes, at a minimum, the general appearance of the subject, height (screening only) and weight, and examination of the skin, eyes, ears, nose, throat, lungs, heart, abdomen, extremities, musculoskeletal system, lymphatic system, and nervous system. Symptom-directed physical exams are done thereafter. Vital signs (blood pressure, pulse, respiratory rate, and temperature) are assessed after the subject has rested in the sitting position. Eastern Cooperative Oncology Group (ECOG) status is assessed at screening, during cycle 1 at 1, 8, 15, 22, and 28 days, during cycle 2 at 15 and 28 days, during cycles 3 to 24 at 28 days, and at follow up, using the published ECOG performance status indications described in Oken, et al., *Am. J. Clin. Oncol.* 1982, 5, 649-655. ECG testing is performed at screening, during cycle 1 at 1, 2, 8, 15, 22, and 28 days, during cycle 2 at 15 and 28 days, during cycles 3 to 24 at 28 days, and at follow up. The 12-lead ECG test will be done in triplicate (>1 minute apart) at screening. The calculated QTc average of the 3 ECGs must be <480 ms for eligibility. On cycle 1, day 1 and cycle 1, day 8, single ECGs are done predose and at 1, 2, 4, and 6 h postdose. The single ECG on Cycle 1 Day 2 is done predose. On cycle 1, day 15, day 22, and day 28, a single ECG is done 2 hours post-dose. Starting with cycle 2, a single ECG is done per visit. Subjects should be in supine position and resting for at least 10 minutes before study-related ECGs. Two consecutive machine-read QTc >500 ms or >60 ms above baseline require central ECG review. Hematology, including complete blood count with differential and platelet and reticulocyte counts, is assessed at screening, during cycle 1 at 1, 8, 15, 22, and 28 days, during cycle 2 at 15 and 28 days, during cycles 3 to 24 at 28 days, and at follow up. Serum chemistry is assessed at screening, during cycle 1 at 1, 8, 15, 22, and 28 days, during cycle 2 at 15 and 28 days, during cycles 3 to 24 at 28 days, and at follow up. Serum chemistry includes albumin, alkaline phosphatase, ALT, AST, bicarbonate, blood urea nitrogen (BUN), calcium, chloride, creatinine, glucose, lactate dehydrogenase (LDH), magnesium, phosphate, potassium, sodium, total bilirubin, total protein, and uric acid. Cell counts and serum immunoglobulin are performed at screening, at cycle 2, day 28, and at every 6 months thereafter until last dose and include T/B/NK/monocyte cell counts (CD3, CD4, CD8, CD14, CD19, CD19, CD16/56, and others as needed) and serum immunoglobulin (IgG, IgM, IgA, and total immunoglobulin). Bone marrow aspirates are performed at cycle 12. Pharmacodynamics samples are drawn during cycle 1 at 1, 2, and 8 days, and at follow up. On days 1 and 8, pharmacodynamic samples are drawn pre-dose and 4 hours (±10 minutes) post-dose, and on day 2, pharmacodynamic samples are drawn pre-dose. Pharmacokinetics samples are drawn during cycle 1 at 1, 2, 8, 15, 22, and 28 days. Pharmacokinetic samples for Cycle 1 Day 1 are drawn pre-dose and at 0.5, 1, 2, 4, 6 and 24 hours (before dose on Day 2) post-dose. Samples for Cycle 1 Day 8 are drawn pre-dose and at 0.5, 1, 2, 4, and 6 hours post-dose. On Cycle 1 Day 15, 22, and 28, a PK sample is drawn pre-dose and the second PK sample must be drawn before (up to 10 minutes before) the ECG acquisition, which is 2 hours postdose. Pretreatment radiologic tumor assessments are performed within 30 days before the first dose. A computed tomography (CT) scan (with contrast unless contraindicated) is required of the chest, abdomen, and pelvis. In addition, a positron emission tomography (PET) or PET/CT must done for subjects with SLL. Radiologic tumor assessments are mandatory at the end of Cycle 2 (~7 days), Cycle 4 (~7 days), and Cycle 12 (~7 days). Otherwise, radiologic tumor assessments are done at investigator discretion. A CT (with contrast unless contraindicated) scan of the chest, abdomen, and pelvis is required for subjects with CLL. In addition, a PET/CT is required in subjects with SLL. Bone marrow and radiologic assessments are both required for confirmation of a complete response (CR). Clinical assessments of tumor response should be done at the end of Cycle 6 and every 3 months thereafter. Molecular markers are measured at screening, and include interphase cytogenetics, stimulated karyotype, IgHV mutational status, Zap-70 methylation, and beta-2 microglobulin levels. Urinalysis is performed at screening, and includes pH, ketones, specific gravity, bilirubin, protein, blood, and glucose. Other assessments, including informed consent, eligibility, medical history, and pregnancy test are done at the time of screening.

The investigator rates the subject's response to treatment based on recent guidelines for CLL, as given in Hallek, et al., *Blood* 2008, 111, 5446-56, and for SLL, as given in Cheson, et al., *J. Clin. Oncol.* 2007, 25, 579-586. The response assessment criteria for CLL are summarized in Table 10.

TABLE 10

Response Assessment Criteria for CLL.

| Response | Peripheral Blood | Bone Marrow (if performed) | Nodes, Liver, and Spleen[a] |
|---|---|---|---|
| CR | Lymphocytes <4 × $10^9$/L<br>ANC >1.5 × $10^9$/L[b]<br>Platelets >100 × $10^9$/L[b]<br>Hemoglobin >11.0 g/dL (untransfused)[b] | Normocellular <30% lymphocytes<br>No B-lymphoid nodules | Normal (e.g., no lymph nodes >1.5 cm) |
| CRi | Lymphocytes <4 × $10^9$/L<br>Persistent anemia, thrombocytopenia, or neutropenia related to drug toxicity | Hypocellular <30% lymphocytes | Normal (e.g., no lymph nodes >1.5 cm) |

TABLE 10-continued

Response Assessment Criteria for CLL.

| Response | Peripheral Blood | Bone Marrow (if performed) | Nodes, Liver, and Spleen[a] |
|---|---|---|---|
| PR | Lymphocytes ≥50% decrease from baseline ANC >1.5 × 10$^9$/L or Platelets >100 × 10$^9$/L or 50% improvement over baseline[b] or Hemoglobin >11.0 g/dL or 50% improvement over baseline (untransfused)[b] | Not assessed | ≥50% reduction in lymphadenopathy[c] and/or in spleen or liver enlargement |

Abbreviations: ANC = absolute neutrophil count; CR = complete remission; CRi = CR with incomplete blood count recovery; PR = partial remission.
[a]Computed tomography (CT) scan of abdomen, pelvis, and chest is required for this evaluation
[b]Without need for exogenous growth factors
[c]In the sum products of ≤6 lymph nodes or in the largest diameter of the enlarged lymph node(s) detected before therapy and no increase in any lymph node or new enlarged lymph nodes The response assessment criteria for SLL are summarized in Table 11.

TABLE 11

Response Assessment Criteria for SLL.

| Response | Definition | Nodal Masses | Spleen, Liver | Bone Marrow |
|---|---|---|---|---|
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | If infiltrate present at screening, infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes (a) FDG-avid or PET positive prior to therapy; ≥1 PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or progressive disease | (a) FDG-avid or PET positive prior to therapy; PET positive at prior sites of disease, and no new sites on CT or PET (b) Variably FDG avid or PET negative; no change in size of previous lesions on CT | | |

Abbreviations: CR = complete remission, CT = computed tomography, FDG = [$^{18}$F]fluorodeoxyglucose, PET = positron-emission tomography, PR = partial remission, SD = stable disease, SPD = sum of the product of the diameters.

The PK parameters of the study are as follows. The plasma PK of Formula (XVIII) and a metabolite is characterized using noncompartmental analysis. The following PK parameters are calculated, whenever possible, from plasma concentrations of Formula (XVIII):

$AUC_{(0-t)}$: Area under the plasma concentration-time curve calculated using linear trapezoidal summation from time 0 to time t, where t is the time of the last measurable concentration (Ct), $AUC_{(0-24)}$: Area under the plasma concentration-time curve from 0 to 24 hours, calculated using linear trapezoidal summation, $AUC_{(0-\infty)}$: Area under the plasma concentration-time curve from 0 to infinity, calculated using the formula: $AUC_{(0-\infty)} = AUC_{(0-t)} + Ct/\lambda z$, where $\lambda z$ is the apparent terminal elimination rate constant, $C_{max}$: Maximum observed plasma concentration, $T_{max}$: Time of the maximum plasma concentration (obtained without interpolation), $t_{1/2}$: Terminal elimination half-life (whenever possible), $\lambda z$: Terminal elimination rate constant (whenever possible), Cl/F: Oral clearance.

The PD parameters of the study are as follows. The occupancy of BTK by Formula (XVIII) are measured in peripheral blood mononuclear cells (PBMCs) with the aid of a biotin-tagged Formula (XVIII) analogue probe. The effect of Formula (XVIII) on biologic markers of B cell function will also be evaluated.

The statistical analysis used in the study is as follows. No formal statistical tests of hypotheses are performed. Descriptive statistics (including means, standard deviations, and medians for continuous variables and proportions for discrete variables) are used to summarize data as appropriate.

The following definitions are used for the safety and efficacy analysis sets: Safety analysis set: All enrolled subjects who receive ≥1 dose of study drug; Per-protocol (PP) analysis set: All enrolled subjects who receive ≥1 dose of study drug and with ≥1 tumor response assessment after treatment. The safety analysis set will be used for evaluating the safety parameters in this study. The PP analysis sets will be analyzed for efficacy parameters in this study.

No imputation of values for missing data is performed except for missing or partial start and end dates for adverse events and concomitant medication will be imputed according to prespecified, conservative imputation rules. Subjects lost to follow-up (or drop out) will be included in statistical analyses to the point of their last evaluation.

The safety endpoint analysis was performed as follows. Safety summaries will include summaries in the form of tables and listings. The frequency (number and percentage) of treatment emergent adverse events will be reported in each treatment group by Medical Dictionary for Regulatory Activities (MedDRA) System Organ Class and Preferred Term. Summaries will also be presented by the severity of the adverse event and by relationship to study drug. Laboratory shift tables containing counts and percentages will be prepared by treatment assignment, laboratory parameter, and time. Summary tables will be prepared for each laboratory parameter. Figures of changes in laboratory parameters over time will be generated. Vital signs, ECGs, and physical exams will be tabulated and summarized.

Additional analyses include summaries of subject demographics, baseline characteristics, compliance, and concurrent treatments. Concomitant medications will be coded according to the World Health Organization (WHO) Drug Dictionary and tabulated.

The analysis of efficacy parameters was performed as follows. The point estimate of the overall response rate will be calculated for the PP analysis set. The corresponding 95% confidence interval also will be derived. The duration of overall response is measured from the time measurement criteria are met for CR or PR (whichever is first recorded) until the first date that recurrent or progressive disease is objectively documented (taking as reference for progressive disease the smallest measurements recorded since the treatment started). Kaplan-Meier methodology will be used to estimate event-free curves and corresponding quantiles (including the median). Progression-free survival is measured from the time of first study drug administration until the first date that recurrent or progressive disease is objectively documented (taking as reference for progressive disease the smallest measurements recorded since the treatment started). Kaplan-Meier methodology will be used to estimate the event-free curves and corresponding quantiles (including the median).

The study scheme is a sequential cohort escalation. Each cohort consists of six subjects. The sample size of the study is 24 to 36 subjects, depending on dose escalation into subsequent cohorts. Cohort 1 (N=6) consists of Formula (XVIII), 100 mg QD for 28 days. Cohort 2 (N=6) consists of Formula (XVIII), 175 mg QD for 28 days. Cohort 3 (N=6) consists of Formula (XVIII), 250 mg QD for 28 days. Cohort 4 (N=6) consists of Formula (XVIII), 350 mg QD for 28 days. Cohort 5 (N=6) consists of Formula (XVIII), 450 mg QD for 28 days. Cohort 6 (N=6) consists of Formula (XVIII), at a dose to be determined QD for 28 days. The dose level for Cohort 6 will be determined based on the safety and efficacy of Cohorts 1 to 5, and will not exceed 900 mg/day. Escalation will end with either the MTD cohort or three levels above full BTK occupancy, whichever is observed first. An additional arm of the study will explore 100 mg BID dosing. Treatment with oral Formula (XVIII) may be continued for greater than 28 days until disease progression or an unacceptable drug-related toxicity occurs.

The inclusion criteria for the study are as follows: (1) men and women ≥18 years of age with a confirmed diagnosis of CLL/SLL, which has relapsed after, or been refractory to, ≥2 previous treatments for CLL/SLL; however, subjects with 17p deletion are eligible if they have relapsed after, or been refractory to, 1 prior treatment for CLL/SLL; (2) body weight ≥60 kg, (3) ECOG performance status of ≤2; (4) agreement to use contraception during the study and for 30 days after the last dose of study drug if sexually active and able to bear children; (5) willing and able to participate in all required evaluations and procedures in this study protocol including swallowing capsules without difficulty; or (6) ability to understand the purpose and risks of the study and provide signed and dated informed consent and authorization to use protected health information (in accordance with national and local subject privacy regulations).

The dosage form and strength of Formula (XVIII) used in the clinical study is a hard gelatin capsules prepared using standard pharmaceutical grade excipients (microcrystalline cellulose) and containing 25 mg of Formula (XVIII) each. The color of the capsules is Swedish orange. The route of administration is oral (per os, or PO). The dose regimen is once daily or twice daily, as defined by the cohort, on an empty stomach (defined as no food 2 hours before and 30 minutes after dosing).

The baseline characteristics for the patients enrolled in the clinical study are given in Table 12.

TABLE 12

Relapsed/refractory CLL baseline characteristics.

| Characteristic | CLL (N = 44) |
| --- | --- |
| Patient Demographics | |
| Age (years), median (range) | 62 (45-84) |
| Sex, men (%) | 33 (75) |
| Prior therapies, median (range), n | 3 (1-10) |
| ≥3 prior therapies, n (%) | 26 (59) |
| Clinical Details | |
| ECOG performance status ≥1 (%) | 28 (63) |
| Rai stage III/IV | 16 (36) |
| Bulky disease ≥5 cm, n (%) | 15 (34) |
| Cytopenia at baseline | 33 (75) |
| Cytogenic Status | |
| Chromosome 11q22.3 deletion (Del 11q), n (%) | 18 (41) |
| Chromosome 17p13.1 (Del 17p), n (%) | 19 (34) |
| IgV$_H$ status (unmutated), n (%) | 28 (64) |

The results of the clinical study in relapsed/refractory CLL patients are summarized in Table 13.

TABLE 13

Activity of Formula (XVIII) in relapsed/refractory CLL.

| n (%) | All Cohorts (N = 31)† | 100 mg QD (N = 8) | 175 mg QD (N = 8) | 250 mg QD (N = 7) | 100 mg BID (N = 3) | 400 mg QD (N = 5) |
|---|---|---|---|---|---|---|
| PR | 22 (71) | 7 (88) | 5 (63) | 5 (71) | 3 (100) | 2 (40) |
| PR + L | 7 (23) | 0 (0) | 3 (37) | 2 (29) | 0 (0) | 2 (40) |
| SD | 2 (6) | 1 (12) | 0 (0) | 0 (0) | 0 (0) | 1 (20) |
| PD | 0 (0) | 0 (0) | 0 (0) | 0 (0) | 0 (0) | 0 (0) |
| Median (range) Cycles | | | | | | |
| | 7.3 (3.0-10.8) | 10.0 (9.0-10.8) | 8.6 (3.0-8.8) | 7.0 (7.0-7.3) | 5.2 (4.7-5.5) | 5.0 (4.8-5.5) |

(PR = partial response; PR + L = partial response with lymphocytosis; SD = stable disease; PD = progressive disease.)

FIG. 125 shows the median % change in ALC and SPD from baseline in the clinical study of Formula (XVIII), plotted in comparison to the results reported for ibrutinib in FIG. 1A of Byrd, et al., N. Engl. J. Med. 2013, 369, 32-42. The results show that Formula (XVIII) leads to a more rapid patient response in CLL than corresponding treatment with ibrutinib. This effect is illustrated, for example, by the median % change in SPD, which achieved the same status in the present study at 7 months of treatment with Formula (XVIII) as compared to 18 months for ibrutinib. The % change in SPD observed in the different cohorts (i.e. by dose and dosing regimen) is shown in FIG. 126, and in all cases shows significant responses.

A Kaplan-Meier curve showing PFS from the clinical CLL study of Formula (XVIII) is shown in FIG. 127. A comparison of survival curves was performed using the Log-Rank (Mantle-Cox) test, with a p-value of 0.0206 indicating that the survival curves are different. The number of patients at risk is shown in FIG. 128. Both FIG. 127 and FIG. 128 show the results for Formula (XVIII) in comparison to the results reported for ibrutinib in Byrd, et al., N. Engl. J. Med. 2013, 369, 32-42. An improvement in survival and a reduction in risk are observed in CLL patients treated with Formula (XVIII) in comparison to patients treated with ibrutinib.

Based on the data and comparisons shown in FIG. 125 to FIG. 128, the CLL study with Formula (XVIII) showed that the efficacy of Formula (XVIII) was surprisingly superior to that of ibrutinib.

In the literature study of ibrutinib, increased disease progression was associated with patients with high-risk cytogenetic lesions (17p13.1 deletion or 11q22.3 deletion), as shown in FIG. 3A in Byrd, et al., N. Engl. J. Med. 2013, 369, 32-42, which shows ibrutinib PFS including PFS broken down by genetic abnormality. The 17p and 11q deletions are validated high-risk characteristics of CLL, and the 17p deletion is the highest risk. In FIG. 129, the PFS is shown for Formula (XVIII) in patients with the 17p deletion in comparison to the results obtained for ibrutinib in Byrd, et al., N. Engl. J. Med. 2013, 369, 32-42. A p-value of 0.0696 was obtained. In FIG. 130, the number of patients at risk with the 17p deletion is compared. To date, no 17p patients have progressed on Formula (XVIII).

The adverse events observed in the clinical study in relapsed/refractory CLL are given in Table 14. No DLTs were observed. The MTD was not reached. No treatment-related serious adverse events (SAEs) were observed. No prophylactic antivirals or antibiotics were needed.

TABLE 14

Treatment-related adverse events reported in the clinical study of Formula (XVIII) in relapsed/refractory CLL. (Reported in ≥5% of patients.)

| Adverse Events (Treatment-Related), n (%) | Grade | All (N = 44) |
|---|---|---|
| Headache | 1/2 | 7 (16) |
| Increased tendency to bruise | 1 | 6 (14) |
| Diarrhea | 1 | 4 (9) |
| Petechiae | 1 | 3 (7) |

The clinical study of Formula (XVIII) thus showed other unexpectedly superior results compared to ibrutinib therapy. A lack of lymphocytosis was observed in the study. Furthermore, only grade 1 AEs were observed, and these AEs were attributable to the high BTK selectivity of Formula (XVIII).

BTK target occupancy was measured for relapsed/refractory CLL patients with the results shown in FIG. 131. For 200 mg QD dosing of the BTK inhibitor of Formula (XVIII), approximately 94%-99% BTK occupancy was observed, with superior 24 hour coverage and less inter-patient variability also observed. For 420 mg and 840 mg QD of the BTK inhibitor ibrutinib, 80%-90% BTK occupancy was observed, with more inter-patient variability and capped occupancy. These results indicate that the BTK inhibitor of Formula (XVIII) achieves superior BTK occupancy in CLL patients than ibrutinib.

The effects of Formula (XVIII) on cell subset percentages were also evaluated using flow cytometry analysis of peripheral blood, with the results shown in FIG. 132, FIG. 133, FIG. 134, FIG. 135, FIG. 136, and FIG. 137. PBMC samples from CLL patient samples drawn prior to (predose) and after 28 days of dosing with Formula (XVIII) were compared for potential changes in cell subsets. PBMCs were stained with monoclonal antibodies conjugated to fluorescent tags (flourochromes) to identify cell subsets via flow cytometry. Non-viable cells were excluded from the analysis using the dye 7-aminoactinomycin D (7-AAD). To produce the metric of percent change, the following steps were taken. First, each cell subset was defined by hierarchical flow cytometry gating. Then, the change in frequency (between day 1 and day 28) was calculated for each cell subset. MDSC subsets were measured as a % of all myeloid cells. T cell subsets were measured as a % of all CD3$^+$ cells, and NK cells were measured as a % of all live CD45$^+$ cells. In FIG. 132 and FIG. 133, the results show the % change in MDSC (monocytic) level over 28 days versus % ALC change at cycle 1 day 28 (C1D28) and at cycle 2 day 28 (C₂D28). A cycle is 28 days. A trend is observed wherein patients with decreasing ALC % had increasing MDSC (monocytic) %. This may include patients who had quickly resolving lymphocytosis and those with no initial lymphocytosis. This provides evidence that treatment with Formula (XVIII) mobilizes MDSCs and thus affects the CLL tumor microenvironment in marrow and lymph nodes, which is an unexpected indication of superior efficacy. In FIG. 134 and FIG. 135, the results show the % change in NK cell level over 28 days versus % ALC change, measured at C₁D28 or C₂D28, and similar trends are observed wherein patients with decreasing ALC % had increasing NK cell %. This may include patients who had quickly resolving lymphocytosis and those having no initial lymphocytosis. The effects in FIG. 132 to FIG. 135 are observed in multiple cohorts, at doses including 100 mg BID, 200 mg QD, and 400 mg QD. In FIG. 136 and FIG. 137, the effects on NK cells and MDSC cells are compared to a number of other markers versus % change in ALC at C₁D28 and C₂D28. These other markers include CD4+ T cells, CD8+ T cells, CD4+/CD8+ T cell ratio, NK-T cells, PD-1+CD4+ T cells, and PD-1+CD8+ T cells. The effects on NK cells and MDSC cells are observed to be much more pronounced than on any of these other markers.

These results indicate that after Formula (XVIII) administration, the CLL microenvironment undergoes a change wherein NK cells and monocytic MDSC subsets increase in frequency in the peripheral blood in patients with falling ALC counts, an important clinical parameter in CLL. The NK cell increase may reflect an overall increase in cytolytic activity against B-CLL resulting in the ALC % to drop. The increase in MDSC % in the blood may be due to a movement of these cells out of the lymph nodes, spleen, and bone marrow, which are all possible sites of CLL proliferation. Fewer MDSCs at the CLL proliferation centers would likely result in a reduced immunosuppressive microenvironment leading to an increase in cell-mediated immunity against the tumor, decreased tumor proliferation, and eventually lower ALC % in the circulation.

Clinical results from the CLL study are shown in FIG. 138 to FIG. 143. FIG. 138 shows an update of the data presented in FIG. 125. FIG. 139 shows an update of the data presented in FIG. 131, and includes BID dosing results. Formula (XVIII) 200 mg QD dosing resulted in 94%-99% BTK occupancy, 24 hour coverage, and less inter-patient variability. Ibrutinib 420 mg and 840 mg QD dosing resulted in 80%-90% BTK occupancy, more inter-patient variability, and capped occupancy. Formula (XVIII) 100 mg BID dosing resulted in 97%-99% BTK occupancy, complete BTK coverage, and less inter-patient variability. The PFS for patients with 17p deletions and 11q deletions are illustrated in FIG. 140, FIG. 141, and FIG. 142. Updated SPD results are illustrated in FIG. 143.

Treatment of CLL patients with Formula (XVIII) also resulted in increased apoptotis, as illustrated in FIG. 144. Apoptotic B-CLL was defined by flow cytometry as having cleaved PARP⁺, Caspase 3⁺, CD19⁺, and CD5⁺phenotypes. 82% of samples tested had a baseline change greater than 25%. Treatment of CLL patients also showed that Formula (XVIII) decreased plasma chemokines associated with MDSC homing and retention. A significant decrease in CXCL12 and CCL2 levels has been observed in patients treated with Formula (XVIII), as shown in FIG. 145 and FIG. 146, respectively.

Overall, Formula (XVIII) shows superior efficacy to first generation BTK inhibitors such as ibrutinib, or to monotherapy with PI3K-δ inhibitors such as idelalisib. Formula (XVIII) has better target occupancy and better pharmacokinetic and metabolic parameters than ibrutinib, leading to improved B cell apoptosis. Furthermore, unlike treatment with ibrutinib and PI3K-δ inhibitors, treatment with Formula (XVIII) does not affect NK cell function. Finally, treatment with Formula (XVIII) leads to a CLL tumor microenvironmental effect by excluding MDSC cells from the marrow and lymph nodes and reducing their number.

Example 11—Clinical Study of a BTK Inhibitor in Leukemia/Lymphoma in Combination with Obinutuzumab (GA-101)

The primary objectives of the study are (1) to determine the overall response rate (ORR) at 12 months with the combination of Formula (XVIII) and obinutuzumab in patients with relapsed or refractory CLL, (2) to determine the ORR at 12 months with the combination of Formula (XVIII) and obinutuzumab in patients with treatment-naive CLL, and (3) to establish the safety and feasibility of the combination of Formula (XVIII) and obinutuzumab.

The secondary objectives of this study are: (1) to determine the complete response (CR) rate and MRD-negative CR rate in previously untreated and relapsed and refractory CLL with this regimen; (2) to determine the progression-free survival (PFS), time to next treatment (TTNT), and overall survival (OS) with this regimen, (3) to perform baseline analysis of patients enrolled on this trial including fluorescence in situ hybridization (FISH), stimulated karyotype, Zap-70 methylation, and IgV$_H$ mutational status and describe relationships between these biomarkers and ORR or PFS for patients treated with this regimen; (4) to determine pharmacokinetics (PK) of orally administered Formula (XVIII); (5) to measure pharmacodynamic (PD) parameters including drug occupancy of BTK, change in miR and gene expression on day 8 and 29 of therapy of Formula (XVIII); (6) to determine the influence of Formula (XVIII) on NK cell and T cell function in vivo; (7) to assess for serial development of resistance by baseline and longitudinal assessment of mutations of BTK and PLCG2 at regular follow up intervals and by examining diagnosis to relapse samples by whole exome sequencing; (8) to determine the influence of Formula (XVIII) on emotional distress and quality of life in CLL patients; and (9) to determine trajectory of psychological and behavioral responses to Formula (XVIII) and covariation with response to therapy.

CLL is the most prevalent form of adult leukemia and has a variable clinical course, where many patients do not require treatment for years and have survival equal to age matched controls. Other patients, however, exhibit aggressive disease and have a poor prognosis despite appropriate therapy. Byrd, et al., Chronic lymphocytic leukemia. Hematology Am. *Soc. Hematol. Educ. Program.* 2004, 163-183. While patients with early disease have not been shown to have a survival advantage with early treatment, most patients will eventually require therapy for their disease with the onset of symptoms or cytopenias, and despite the relatively long life expectancy for early stage disease, CLL remains an incurable disease. Patients diagnosed with or progressing to advanced disease have a mean survival of 18 months to 3 years. Unfortunately these patients with advanced disease are also more refractory to conventional therapy.

The treatment of CLL has progressed significantly over the previous decades. While alkylator therapy was used in the past, randomized trials have demonstrated a higher response rate and longer progression free survival (PFS)

with fludarabine and subsequently with fludarabine- and cyclophosphamide-based combinations. O'Brien, et al., Advances in the biology and treatment of B-cell chronic lymphocytic leukemia. *Blood* 1995, 85, 307-18; Rai, et al., Fludarabine compared with chlorambucil as primary therapy for chronic lymphocytic leukemia. *N. Engl. J. Med.* 2000, 343, 1750-57; Johnson, et al., Multicentre prospective randomised trial of fludarabine versus cyclophosphamide, doxorubicin, and prednisone (CAP) for treatment of advanced-stage chronic lymphocytic leukaemia. The French Cooperative Group on CLL. *Lancet* 1996, 347, 1432-38; Leporrier, et al., Randomized comparison of fludarabine, CAP, and ChOP in 938 previously untreated stage B and C chronic lymphocytic leukemia patients. *Blood* 2001, 98, 2319-25; Catovsky, et al., Assessment of fludarabine plus cyclophosphamide for patients with chronic lymphocytic leukaemia (the LRF CLL4 Trial): A randomised controlled trial. *Lancet* 2007, 370, 230-239; Eichhorst, et al., Fludarabine plus cyclophosphamide versus fludarabine alone in first-line therapy of younger patients with chronic lymphocytic leukemia. *Blood* 2006, 107, 885-91. At the same time, the chimeric anti-CD20 monoclonal antibody rituximab was introduced for the treatment of CLL. At high doses or with dose intensive treatment, single agent rituximab has shown efficacy; however complete responses and extended remissions are very rare. O'Brien, et al. Rituximab dose-escalation trial in chronic lymphocytic leukemia. *J. Clin. Oncol.* 2001, 19, 2165-70; Byrd, et al., Rituximab using a thrice weekly dosing schedule in B-cell chronic lymphocytic leukemia and small lymphocytic lymphoma demonstrates clinical activity and acceptable toxicity. *Clin. Oncol.* 2001, 19, 2153-64. The efficacy of rituximab has been improved by combining it with traditional cytotoxic agents such as fludarabine or fludarabine and cyclophosphamide, which have produced high CR rates and extended progression free survival (PFS) compared to historical controls. Indeed, a large randomized clinical trial reported by the German CLL study group has shown a benefit of the addition of antibody therapy with rituximab to fludarabine and cyclophosphamide in the prolongation of PFS and OS in patients with untreated CLL. Hallek, et al., Addition of rituximab to fludarabine and cyclophosphamide in patients with chronic lymphocytic leukaemia: a randomised, open-label, phase 3 trial. *Lancet* 2010, 376, 1164-74. This encouraging progress in therapy and our understanding of the disease has resulted in significantly improved response rates and PFS.

While fludarabine based chemoimmunotherapy is standard for younger patients, the therapy for older patients is less well defined. In the large Phase 2 and 3 trials outlined previously, median ages were typically in the early-60s, while the average age of patients diagnosed with CLL is 72, which calls into question whether these results are generalizable to the entire CLL population. In fact, the one randomized Phase 3 trial investigating primary CLL therapy in older patients demonstrated that in patients >65 years old, fludarabine is not superior to chlorambucil. Eichhorst, et al., First-line therapy with fludarabine compared with chlorambucil does not result in a major benefit for elderly patients with advanced chronic lymphocytic leukemia. *Blood* 2009, 114, 3382-91. This finding was corroborated by a large retrospective study of front-line trials performed by the Alliance for Clinical Trials in Oncology, which demonstrated again that fludarabine is not superior to chlorambucil in older patients, but also showed that the addition of rituximab to chemotherapy was beneficial regardless of age. Woyach, et al., Impact of age on outcomes after initial therapy with chemotherapy and different chemoimmunotherapy regimens in patients with chronic lymphocytic leukemia: Results of sequential cancer and leukemia group B studies. *J. Clin. Oncol.* 2013, 31, 440-7. Two studies have evaluated the combination of rituximab with chlorambucil, showing that this combination is safe and moderately effective. Hillmen, et al., rituximab plus chlorambucil in patients with CD20-positive B-cell chronic lymphocytic leukemia (CLL): Final response analysis of an open-label Phase II Study, *ASH Annual Meeting Abstracts*, Blood 2010, 116, 697; Foa, et al., A Phase II study of chlorambucil plus rituximab followed by maintenance versus observation in elderly patients with previously untreated chronic lymphocytic leukemia: Results of the first interim analysis, *ASH Annual Meeting Abstracts*, Blood 2010, 116, 2462.

Recently, the type II glycoengineered CD20 monoclonal antibody obinutuzumab was introduced. In a Phase 1 trial of previously treated CLL as monotherapy, this antibody has a 62% response rate including 1 MRD-negative complete response, suggesting that alone this antibody may be more active in CLL than rituximab. Morschhauser, et al., Phase I study of R05072759 (GA101) in relapsed/refractory chronic lymphocytic leukemia, ASH Annual Meeting Abstracts. *Blood,* 2009, 114, 884. The German CLL Study Group (GCLLSG) recently completed a Phase 3 trial of rituximab and chlorambucil or obinutuzumab and chlorambucil vs chlorambucil alone in patients with untreated CLL and significant comorbidities. In this population, obinutuzumab and chlorambucil (but not rituximab and chlorambucil) improved OS over chlorambucil alone (hazard ratio 0.41, p=0.002), and obinutuzumab and chlorambucil improved PFS over rituximab and chlorambucil (median PFS 26.7 months vs 14.9 months, p<0.001). Goede, et al., Obinutuzumab plus chlorambucil in patients with CLL and coexisting conditions, *N. Engl. J. Med.* 2014, 370, 1101-10. On the basis of these favorable data, the combination of obinutuzumab and chlorambucil is FDA approved as frontline therapy for CLL patients.

Many older patients are also treated with the combination of bendamustine plus rituximab (BR). Although BR has not been compared directly with chlorambucil and rituximab, results of a recent Phase 2 trial show an ORR of 88% with a median event free survival of 33.9 months and 90.5% OS at 27 months. Fischer, et al., Bendamustine in combination with rituximab for previously untreated patients with chronic lymphocytic leukemia: A multicenter phase II trial of the German Chronic Lymphocytic Leukemia Study Group. *J. Clin. Oncol.* 2012, 30, 3209-16. These results held for patients >70 years old, and compare favorably with results published for chlorambucil and rituximab. While results with this regimen appear to be improved over historical controls, outcomes are not as good as those observed in younger patients with chemoimmunotherapy. Therefore, the optimal therapy for older patients remains an unmet need in clinical trials.

Additionally, most patients eventually relapse with their disease and are frequently refractory to existing agents. Patients who relapse after combined chemoimmunotherapy have a poor outcome with subsequent standard therapies. While options for these patients include alemtuzumab, bendamustine, high dose corticosteroids, ofatumumab, and combination based approaches, none of these therapies produces durable remissions that exceed that observed with first line chemoimmunotherapy. Keating, et al., Therapeutic role of alemtuzumab (Campath-1H) in patients who have failed fludarabine: results of a large international study. *Blood* 2002, 99, 3554-61; Bergmann, et al., Efficacy of bendamustine in patients with relapsed or refractory chronic lymphocytic leukemia: results of a phase I/II study of the German CLL Study Group. *Haematologica* 2005, 90, 1357-64; Thornton PD, Matutes E, Bosanquet A G, et al. High dose methylprednisolone can induce remissions in CLL patients with p53 abnormalities. *Ann. Hematology* 2003, 82, 759-65; Coiffier, et al., Safety and efficacy of ofatumumab, a fully human monoclonal anti-CD20 antibody, in patients with relapsed or refractory B-cell chronic lymphocytic leukemia: A phase 1-2 study. *Blood* 2008, 111, 1094-1100; Tsimberidou, et al., Phase I-II study of oxaliplatin, fludarabine, cytarabine, and rituximab combination therapy in patients with Richter's syndrome or fludarabine-refractory chronic lymphocytic leukemia. *J. Clin. Oncol.* 2008, 26, 196-203. Several of these therapies including alemtuzumab and high dose steroids are also associated with significant toxicities and sustained immunosuppression. Lozanski G, Heerema NA, Flinn 1W, et al. Alemtuzumab is an effective therapy for chronic lymphocytic leukemia with p53 mutations and deletions. *Blood* 2004, 103, 3278-81; Osuji, et al., The efficacy of alemtuzumab for refractory chronic lymphocytic leukemia in relation to cytogenetic abnormalities of p53. *Haematologica* 2005, 90, 1435-36; Thornton, et al., High dose methyl prednisolone in refractory chronic lymphocytic leukaemia. *Leuk. Lymphoma* 1999, 34, 167-70; Bowen, et al. Methylprednisolone-rituximab is an effective salvage therapy for patients with relapsed chronic lymphocytic leukemia including those with unfavorable cytogenetic features. *Leuk Lymphoma* 2007, 48, 2412-17; Castro, et al., Rituximab in combination with high-dose methylprednisolone for the treatment of fludarabine refractory high-risk chronic lymphocytic leukemia. *Leukemia* 2008, 22, 2048-53.

In an ongoing Phase Ib/2 study, the BTK inhibitor ibrutinib has shown activity in patients with relapsed or refractory CLL. In patients with relapsed or refractory CLL and measurable lymphadenopathy, the rate of lymph node shrinkage >50% is 89%. With a median follow-up of 4 months, ORR was 48% due to asymptomatic lymphocytosis, and with longer follow-up of 26 months in patients receiving the 420 mg dose, has improved to 71%, with an additional 20% of patients achieving a partial response with lymphocytosis (PR-L). Byrd, et al., Activity and tolerability of the Bruton's tyrosine kinase (Btk) inhibitor PCI-32765 in patients with chronic lymphocytic leukemia/small lymphocytic lymphoma (CLL/SLL): Interim results of a phase Ib/II study. *J. Clin. Oncol.* ASCO Annual Meeting Abstracts, 2011, 29, Abstract 6508; Byrd, et al. Targeting BTK with ibrutinib in relapsed chronic lymphocytic leukemia. *N. Engl. J. Med.* 2013, 369, 32-42. This lymphocytosis is likely related to B cell release from lymph node, spleen and marrow microenvironment due to disruption of homing signals or chemoattractants that are relevant to usual lymphocyte circulation dynamics. Lymphocytosis with ibrutinib is seen within 1-2 weeks of starting therapy, reaches plateau within the first 2-3 cycles, and has resolved over time in virtually all patients. The duration of lymphocytosis does not appear to be related to the depth of eventual response nor to response duration. Woyach, et al., Prolonged lymphocytosis during ibrutinib therapy is associated with distinct molecular characteristics and does not indicate a suboptimal response to therapy. *Blood* 2014, 123, 1810-7. Response to ibrutinib occurs independently of high-risk genomic features including IgVH mutational status and del(17p13.1). Responses to this drug have been durable as well, with an estimated 26 month PFS of 76% and OS of 83% for these relapsed and refractory patients. This study also included a cohort of 31 previously untreated patients. With 16.6 months of follow-up, ORR is 71%, with an additional 10% of patients having persistent lymphocytosis; estimated 22 month PFS is 96%. This agent is currently in Phase 3 trials in treatment-naïve disease and is currently FDA approved for the treatment of relapsed CLL. These data with ibrutinib support the potential benefits of selective BTK inhibition in CLL. However, while highly potent in inhibiting BTK, ibrutinib has also shown in vitro activity against other kinases (e.g., epidermal growth factor receptor), which may be the cause of ibrutinib-related diarrhea and rash. Honigberg, et al., The Bruton tyrosine kinase inhibitor PCI-32765 blocks B-cell activation and is efficacious in models of autoimmune disease and B-cell malignancy. *Proc. Natl. Acad. Sci. USA* 2010, 107, 13075-13080. In addition, it is a substrate for both cytochrome P450 (CYP) enzymes 3A4/5, which increases the possibility of drug-drug interactions. Finally, the inhibition of ITK that is seen with ibrutinib has the potential to abrogate NK cell ADCC, which makes combination with monoclonal antibodies less effective. Kohrt, et al., Ibrutinib antagonizes rituximab-dependent NK cell-mediated cytotoxicity. *Blood* 2014, 123, 1957-60. These liabilities support the development of alternative BTK inhibitors for use in the therapy of lymphoid cancers.

In this Phase 1B study, two cohorts (relapsed/refractory and treatment-naïve) will be evaluated with slightly staggered enrollment. First, 6 subjects with R/R CLL will be enrolled into Cohort 1. Once the safety has been evaluated, the R/R cohort will be expanded to 26 subjects and enrollment of 6 treatment-naïve subjects can begin in Cohort 2. Once safety is established for Cohort 2, then the cohort will be expanded to 19 subjects.

Formula (XVIII) will be administered starting cycle 1 day 1 and will be administered twice daily (100 mg BID) until disease progression. Obinutuzumab will be given in the standard dosing fashion starting on cycle 2 day 1. On cycle 2 day 1, patients will receive 100 mg IV. On cycle 2 day 2, patients will receive 900 mg. On cycle 2 days 8 and 15, patients will receive 1000 mg IV. On cycles 3-7, patients will receive 1000 mg on day 1 of each cycle. For patients treated at dose level −1, 100 mg will be given on Day 1 and 650 mg on Day 2 of Cycle 2. On cycle 2 day 8 and 15, patients will receive 750 mg IV and during cycles 3-7, patients will receive 750 mg on Day 1 of each cycle. It is acceptable for cycles to begin <a 24-hour (1 business day) window before and after the protocol-defined date for Day 1 of a new cycle.

The inclusion criteria for patient eligibility are as follows: (1) Patients with a diagnosis of intermediate or high risk CLL (or variant immunophenotype), SLL, or B-PLL by IWCLL 2008 criteria" who have: (a) COHORT 1: Previously received at least one therapy for their disease; (b) COHORT 2: Previously untreated disease and >65 years old OR under 65 years old and refuse or are ineligible for chemoimmunotherapy; (2) Patients on Cohort 1 may have received previous ibrutinib (or another BTK inhibitor) as long as discontinuation was for a reason other than "on-treatment" disease progression; (3) All patients must satisfy one of the following criteria for active disease requiring therapy: (a) Evidence of marrow failure as manifested by the development or worsening of anemia or thrombocytopenia (not attributable to autoimmune hemolytic anemia or thrombocytopenia); (b) Massive (>6 cm below the costal margin), progressive or symptomatic splenomegaly; (c) Massive nodes (>10 cm) or progressive or symptomatic lymphadenopathy; (d) Constitutional symptoms, which include any of the following: Unintentional weight loss of 10% or more within 6 months, Significant fatigue limiting activity, Fevers >100.5 degrees F. for 2 weeks or more without evidence of infection, Night sweats >1 month without evidence of infection; (4) Measurable nodal disease by computed tomography (CT). Measurable nodal disease is defined as >1 lymph node >1.5 cm in the longest diameter in a site; (5) Patients with a history of Richter's syndrome are eligible if they now have evidence of CLL only, with <10% large cells in the bone marrow; (6) Subjects must have adequate organ function, defined as creatinine <2.5 times the upper limit of normal (ULN), ALT and AST <3.0×ULN, and bilirubin <2.5×ULN; (7) Platelets >50×10$^9$/L. In subjects with CLL involvement of the marrow, >30×10$^9$/L; (8) ANC >750/mm$^3$ In subjects with CLL involvement of the marrow, ANC >500/mm$^3$; (9) Subject must have an ECOG performance status <2; (10) Subject must not have secondary cancers that result in a life expectancy of <2 years or that would confound assessment of toxicity in this study; (11) Subjects must be >18 years of age; (12) Subject must provide written informed consent. A signed copy of the consent form will be retained in the patient's chart; (13) Subject must be able to receive outpatient treatment and follow-up at the treating institution; (14) Subject must have completed all CLL therapies >4 weeks prior to first study dose. Palliative steroids are allowed, but must be at a dose equivalent of <20 mg prednisone daily for at least 1 week prior to treatment initiation; (15) Subjects capable of reproduction and male subjects who have partners capable of reproduction must agree to use an effective contraceptive method during the course of the study and for 2 months following the completion of their last treatment. Females of childbearing potential must have a negative β-hCG pregnancy test result within 3 days of first study dose. Female patients who are surgically sterilized or who are >45 years old and have not experienced menses for >2 years may have ther3-hCG pregnancy test waived; (16) Subjects must be able to swallow whole capsules.

The exclusion criteria for patient eligibility are as follows: (1) For cohort 1, previous therapy for CLL. Treatment of autoimmune complications of CLL with steroids or rituximab is allowed, however, CD20 must have returned on 10% of the CLL cells if rituximab was recently administered. Palliative steroids are acceptable at doses <20 mg prednisone equivalent daily; (2) Any life-threatening illness, medical condition, or organ dysfunction which, in the investigator's opinion, could compromise the patients' safety, interfere with the absorption or metabolism of Formula (XVIII), or put the study outcomes at undue risk; (3) Female subjects who are pregnant or breastfeeding; (4) Subjects with active cardiovascular disease not medically controlled or those who have had myocardial infarction in the past 6 months, or QTc >480 ms; (5) Malabsorption syndrome, disease significantly affecting gastrointestinal function, or resection of the stomach or small bowel or gastric bypass, ulcerative colitis, symptomatic inflammatory bowel disease, or partial or complete bowel obstruction; (6) Grade 2 toxicity (other than alopecia) continuing from prior anticancer therapy including radiation; (7) Major surgery within 4 weeks before first dose of study drug; (8) History of a bleeding diathesis (e.g., hemophilia, von Willebrand disease); (9) Uncontrolled autoimmune hemolytic anemia or idiopathic thrombocytopenia purpura; (10) History of stroke or intracranial hemorrhage within 6 months before the first dose of study drug; (11) Requires or receiving anticoagulation with warfarin or equivalent vitamin K antagonists (eg, phenprocoumon) within 28 days of first dose of study drug; (12) Requires treatment with long-acting proton pump inhibitors (e.g., omeprazole, esomeprazole, lansoprazole, dexlansoprazole, rabeprazole, or pantoprazole); (13) Subjects with active infections requiring IV antibiotic/antiviral therapy are not eligible for entry onto the study until resolution of the infection. Patients on prophylactic antibiotics or antivirals are acceptable; (14) Subjects with history of or ongoing drug-induced pneumonitis; (15) Subjects with human immunodeficiency virus (HIV) or active infection with hepatitis C virus (HCV) or hepatitis B virus (HBV) or any uncontrolled active systemic infection; (16) Subjects who are known to have Hepatitis B infection or who are hepatitis B core antibody or surface antigen positive. Patients receiving prophylactic WIG may have false positive hepatitis serologies. Patients who are on WIG who have positive hepatitis serologies must have a negative hepatitis B DNA to be eligible; (17) Subjects with substance abuse or other medical or psychiatric conditions that, in the opinion of the investigator, would confound study interpretation or affect the patient's ability to tolerate or complete the study; (18) Subjects cannot concurrently participate in another therapeutic clinical trial; (19) Subjects who have received a live virus vaccination within 1 month of starting study drug.

In this study, Formula (XVIII) is administered 100 mg BID, with the second dose 11-13 hours after the first. Obinutuzumab is administered by IV infusion as an absolute (flat) dose. Obinutuzumab is administered in a single day, with the exception of the first administration when patients receive their first dose of obinutuzumab over two consecutive days (split dose) in Cycle 2: 100 mg on Day 1 and 900 mg on Day 2. For patients treated at dose level −1 (750 mg obinutuzumab), −100 mg will be given on Day 1 and 650 mg on Day 2. On days when both Formula (XVIII) and obinutuzumab are given, the order of study treatment administration will be Formula (XVIII) followed at least 1 hour later by obinutuzumab. The full dosing schedule is given in Table 15.

TABLE 15

Dosing of obinutuzumab during 6 treatment cycles each of 28 days duration.

| Day of Treatment Cycle | | Dose of Obinutuzumab | Rate of Infusion (In the absence of infusion reactions/hypersensitivity during previous infusions) |
|---|---|---|---|
| Cycle 2 (loading doses) | Day 1 | 100 mg | Administer at 25 mg/hr over 4 hours. Do not increase the infusion rate. |
| | Day 2 | 900 mg | Administer at 50 mg/hr. The rate of the infusion can be escalated in increments of 50 mg/hr every 30 minutes to a maximum rate of 400 mg/hr. |
| | Day 8 | 1000 mg | Infusions can be started |
| | Day 15 | 1000 mg | at a rate of 100 mg/hr |
| Cycles 3-7 | Day 1 | 1000 mg | and increased by 100 mg/hr increments every 30 minutes to a maximum of 400 mg/hr. |

Anti-CD20 antibodies have a known safety profile, which include infusion related reactions (IRR). Anti-CD20 antibodies, and in particular obinutuzumab, can cause severe and life threatening infusion reactions. Sequelae of the infusion reactions include patient discontinuations from antibody treatment leading to suboptimal efficacy or increased medical resource utilization, such as hospitalization for hypotension or prolonged antibody infusion time. In the initial study of obinutuzumab in relapsed/refractory CLL patients (Cartron, et al., *Blood* 2014, 124, 2196), all patients (n=13) in the Phase 1 portion experienced IRRs (15% Grade 3, no Grade 4, and 100% patients experienced all grade AE), with hypotension and pyrexia the most common symptoms. In the Phase 2 portion of the study, 95% of patients developed IRR, with 60% of cases developing symptoms of hypotension; of those, 25% were Grade 3 reactions. In the pivotal trial of obinutuzumab and chlorambucil in previously untreated patients, 69% developed infusion related reactions, of which 21% were grade 3-4.

The results of the Phase 1b study described in this example for Formula (XVIII) in combination with obinutuzumab for patients with relapsed/refractory or untreated CLL/SLL/PLL are as follows. 6 patients have been treated in the study to date with the combination of Formula (XVIII) and obinutuzumab. Patients are first treated with a month run-in of Formula (XVIII) alone, then on cycle 2, day 1, patients are given obinutuzumab. To date, 41 doses of obinutuzumab have been administered to 6 patients. Lymphocyte counts immediately prior to treatment with obinutuzumab have ranged from 8 to $213 \times 10^9$/L. No cases of serious or Grade 3-4 IRRs have been reported. Only 2 patients have had obinutuzumab temporarily held for chills and arthralgias/slurred, respectively, and were able to complete the planned infusion. An additional 3 patients had adverse events within 24 hours of the infusion, all grade 1 (terms: flushing, palpitations in one patient, rash, and restlessness and headache). Consequently, there has been a substantial decrease in serious or Grade 3-4 IRRs with the one month lead-in of Formula (XVIII), which could potentially lead to higher efficacy for the combination as well as better tolerability, leading to a decrease in medical resource utilization.

Example 12—BTK Inhibitory Effects on MDSCs in the Solid Tumor Microenvironment A molecular probe assay was used to calculate the percent irreversible occupancy of total BTK. MDSCs were purified from tumor bearing PDA mice (as described previously) dosed at 15 mg/kg BID of Formula (XVIII). Complete BTK occupancy is observed for both the granulocytic and monocytic MDSC compartment on Day 8 at 4 hours post dose (N=5). The results are shown in FIG. 147.

Example 13—BTK Inhibitory Effects on Solid Tumor Microenvironment in a Non-Small Cell Lung Cancer (NSCLC) Model A genetic tumor model of NSCLC (KrasLA2) was studied as a model for lung cancer using the treatment schema shown in FIG. 148. The model is designed to have sporadic expression in single cells of G12D mutant Kras off its own promoter triggered by spontaneous intrachromosomal recombination. Johnson, et al. *Nature* 2001, 410, 1111-16. While the mutant Kras protein is expressed in a few cells in all tissues, tumor development is seen only in the lung at high penetrance. Mice treated with Formula (XVIII) showed a significant decrease in tumor volumes versus vehicle (FIG. 169) and fewer overall tumors with dosing of 15 mg/kg. The effects on TAMs (FIG. 170), MDSCs (FIG. 171), Tregs (FIG. 172), and CD8+ cells (FIG. 173) were consistent with suppression of the solid tumor microenviroment as demonstrated previously.

Example 14—Additional Preclinical Characteristics of BTK Inhibitors

The in vitro potency in whole blood of Formula (XVIII), ibrutinib and CC-292 in inhibiting signals through the B cell receptor was also assessed. Blood from four healthy donors was incubated for 2 hours with the compounds shown over a concentration range, and then stimulated with anti-human IgD [10 μg/mL] for 18 hours. The mean fluorescent intensity (MFI) of CD69 (and CD86, data not shown) on gated CD19+B cells was measured by flow cytometry. MFI values were normalized so that 100% represents CD69 level in stimulated cells without inhibitor, while 0% represents the unstimulated/no drug condition. The results are shown in FIG. 149. The $EC_{50}$ values obtained were 8.2 nM (95% confidence interval: 6.5-10.3), 6.1 nM (95% confidence interval: 5.2-7.2), and 121 nM (95% confidence interval: 94-155) for Formula (XVIII), ibrutinib, and CC-292, respectively.

The EGF receptor phosphorylation in vitro was also determined for Formula (XVIII) and ibrutinib. Epidermoid carcinoma A431 cells were incubated for 2h with a dose titration of Formula (XVIII) or ibrutinib, before stimulation with EGF (100 ng/mL) for 5 min to induce EGFR phosphorylation (p-EGFR). Cells were fixed with 1.6% paraformaldehyde and permeabilized with 90% MeOH. Phosphoflow cytometry was performed with p-EGFR (Y1069). MFI values were normalized so that 100% represents the p-EGFR level in stimulated cells without inhibitor, while 0% represents the unstimulated/no drug condition. The results are shown in FIG. 150. EGF-induced p-EGFR inhibition was determined to be 7% at 10 μM for Formula (XVIII), while ibrutinib has an $EC_{50}$ of 66 nM. The much more potent inhibition of EGF-induced p-EGFR by ibrutinib may be associated with increased side effects including diarrhea and rash.

Example 15—Synergistic Combination of a BTK Inhibitor and a PI3K-δ Inhibitor A study was also performed using the approach described above in Example 2 with the BTK inhibitor of Formula (XXVIII-R) (ONO-4059) and the PI3K-δ inhibitor of Formula (XVI) (idelalisib). Proliferation was again determined with MTS (CellTiter 96 AQueous, Promega). Incubations were performed for 96 hours. The detailed results of the additional cell line studies for the BTK inhibitor of Formula (XXVIII-R) and the PI3K-δ inhibitor of Formula (XVI) are given in FIG. 151 to FIG. 156. The results of these combination studies are summarized in Table 16.

TABLE 16

Summary of results of the combination of a BTK inhibitor with a PI3K-δ inhibitor (S = synergistic, A = additive, X = no effect).

| Cell Line | Indication | ED25 | ED50 | ED75 | ED90 |
|---|---|---|---|---|---|
| TMD-8 | DLBCL-ABC | A | S | S | S |
| Mino | MCL | S | S | S | S |
| RI-1 | NHL | A/X | S | S | S |
| DOHH-2 | FL | A | A | A | S |
| SU-DHL-6 | DLBCL-GCB | X | X | A | S |

Synergistic effects of the combination of the BTK inhibitor of Formula (XXVIII-R) with the PI3K-δ inhibitor of Formula (XVI) are observed in cell lines that are representative of a number of clinically-significant B cell malignancies.

Example 16—Blood-Brain Barrier Penetration of BTK Inhibitors in Rats

P-glycoprotein substrates may have relatively low brain exposure, due to activity of efflux pumps including P-glycoprotein at the blood-brain barrier (BBB). In a biodistribution study using radiolabeled Formula (XVIII), low relative concentrations (3% to 4% of plasma concentrations) were observed in the brain. Preliminary brain PK experiments were performed to evaluate the potential for Formula (XVIII) to cross the blood brain barrier, with results illustrated in FIG. 157. Four Sprague-Dawley rats per group were treated by oral gavage with 5 or 30 mg/kg/day Formula (XVIII) and tissues were collected at 30 minutes after dosing—the approximate time of $C_{max}$—on Days 1, 3 and 5. Two vehicle treated rats were sacrificed on each sampling day for comparison. Cerebral spinal fluid (CSF) was collected; and the brains were flushed with heparinized saline prior to collection and snap frozen for analysis of Formula (XVIII). Bioanalytical methods specific to CSF and brain tissue were used to measure Formula (XVIII) concentrations in these matrices. Results (FIG. 157) showed low but detectable levels of Formula (XVIII) in the brain and CSF samples. Penetration of Formula (XVIII) into the brain was surprising because of the efflux ratio observed with in vitro studies in Caco-2 cells. However, the ratio of Formula (XVIII) in the flushed brains, compared with matched plasma concentrations, showed that brain extracts had ~3-4% of the observed plasma concentrations, consistent with the results from the biodistribution study. The ratios observed in clean CSF samples from rats treated with 5 and 30 mg/kg/day were between 1-2% of the plasma levels. The results indicate that Formula (XVIII) can penetrate the BBB, and because of the covalent binding of Formula (XVIII) and low BTK resynthesis rates, high levels of BTK occupancy in tumor cells in the brain (such as infiltrating lymphocytes and microglia) as well as in cells of the solid tumor microenvironment in order to treat cancers such as gliomas and primary central nervous system lymphoma (Schideman, et al., *J. Neurosci. Res.* 2006, 83(8), 1471-84).

While preferred embodiments of the invention are shown and described herein, such embodiments are provided by way of example only and are not intended to otherwise limit the scope of the invention. Various alternatives to the described embodiments of the invention may be employed in practicing the invention.

---

We claim:

1. A method of treating a hematological malignancy, comprising administering, to a human subject in need thereof, therapeutically effective amounts of (1) a B-cell lymphoma 2 (BCL-2) inhibitor of the formula:

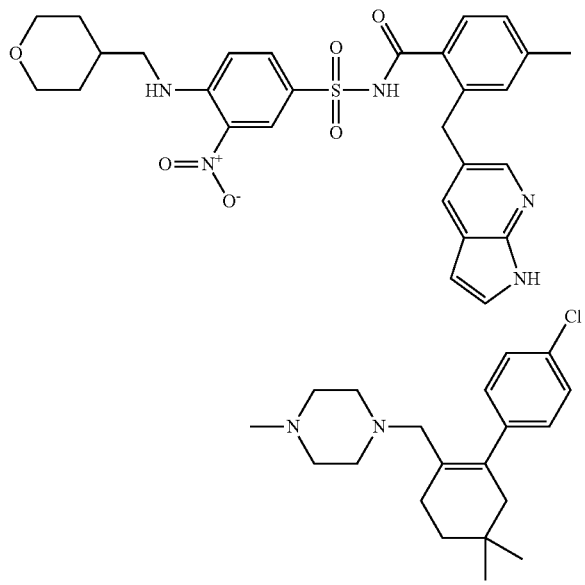

or a pharmaceutically acceptable salt thereof, and (2) a Bruton's tyrosine kinase (BTK) inhibitor of the formula:

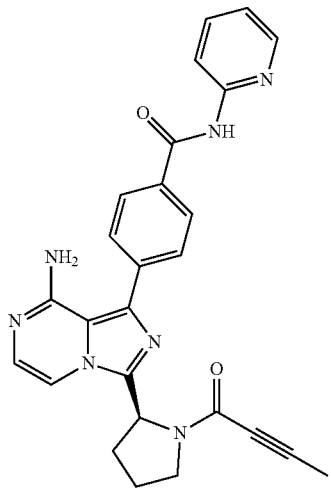 [SMILES: CC#CC(=O)N1CCC[C@H]1c1nc(-c2ccc(C(=O)Nc3ccccn3)cc2)c2c(N)nccn12]

or a pharmaceutically acceptable salt thereof; wherein the hematological malignancy is chronic lymphocytic leukemia or small lymphocytic leukemia.

2. The method of claim 1, wherein the BCL-2 inhibitor is administered before administration of the BTK inhibitor.

3. The method of claim 1, wherein the BCL-2 inhibitor is administered concurrently with the administration of the BTK inhibitor.

4. The method of claim 1, wherein the BCL-2 inhibitor is administered to the subject after administration of the BTK inhibitor.

5. The method of claim 1, wherein the method further comprises the step of administering to the human a therapeutically effective amount of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof.

6. The method of claim 1, wherein the therapeutically effective amount of the BTK inhibitor is 100 mg.

7. The method of claim 1, wherein the therapeutically effective amount of the BTK inhibitor is 100 mg administered twice per day.

8. The method of claim 1, wherein the therapeutically effective amount of the BCL-2 inhibitor is 400 mg.

9. The method of claim 1, wherein the hematological malignancy is chronic lymphocytic leukemia.

10. The method of claim 9, wherein the chronic lymphocytic leukemia is relapsed or refractory chronic lymphocytic leukemia.

11. The method of claim 10, wherein the human subject is a human subject with a 17p chromosomal deletion.

12. The method of claim 10, wherein the human subject is a human subject with an 11q chromosomal deletion.

13. The method of claim 10, wherein the relapsed or refractory chronic lymphocytic leukemia is due to a 17p chromosomal deletion in the human subject.

14. The method of claim 10, wherein the relapsed or refractory chronic lymphocytic leukemia is due to an 11q chromosomal deletion in the human subject.

15. The method of claim 1, wherein the free form of the BCL-2 inhibitor is administered.

16. The method of claim 1, wherein the pharmaceutically acceptable salt of the BCL-2 inhibitor is administered.

17. The method of claim 1, wherein the free form of the BTK inhibitor is administered.

18. The method of claim 1, wherein the pharmaceutically acceptable salt of the BTK inhibitor is administered.

* * * * *